(12) United States Patent
Alam et al.

(10) Patent No.: US 9,683,221 B2
(45) Date of Patent: Jun. 20, 2017

(54) LIGNIN DEGRADING ENZYMES FROM MACROPHOMINA PHASEOLINA AND USES THEREOF

(71) Applicant: Bangladesh Jute Research Institute, Dhaka (BD)

(72) Inventors: Masqsudul Alam, Honolulu, HI (US); Mohammed S. Islam, Dhaka (BD); Mohammed M. Hossen, Dhaka (BD); Mohammed S. Haque, Dhaka (BD); Mohammed M. Alam, Dhaka (BD)

(73) Assignee: Bangladesh Jute Research Institute, Dacca (BD)

( * ) Notice: Subject to any disclaimer, the term of this patent is extended or adjusted under 35 U.S.C. 154(b) by 0 days.

(21) Appl. No.: 14/421,739

(22) PCT Filed: Aug. 15, 2013

(86) PCT No.: PCT/US2013/055199
§ 371 (c)(1),
(2) Date: Feb. 13, 2015

(87) PCT Pub. No.: WO2014/028773
PCT Pub. Date: Feb. 20, 2014

(65) Prior Publication Data
US 2015/0291937 A1    Oct. 15, 2015

Related U.S. Application Data

(60) Provisional application No. 61/683,913, filed on Aug. 16, 2012.

(51) Int. Cl.
| | |
|---|---|
| C12N 9/08 | (2006.01) |
| C12N 9/02 | (2006.01) |
| C12N 1/00 | (2006.01) |
| C12N 15/00 | (2006.01) |
| C12P 21/06 | (2006.01) |
| C12P 19/34 | (2006.01) |
| C07H 21/04 | (2006.01) |
| C07K 1/00 | (2006.01) |

(52) U.S. Cl.
CPC ......... *C12N 9/0061* (2013.01); *C12N 9/0065* (2013.01)

(58) Field of Classification Search
CPC ............................ C12N 9/0061; C12N 9/0065
USPC ..... 435/192, 189, 254.11, 320.1, 69.1, 91.1; 536/23.1, 23.2; 530/350
See application file for complete search history.

(56) References Cited

U.S. PATENT DOCUMENTS

| | | |
|---|---|---|
| 7,423,195 B2 | 9/2008 | Sticklen et al. |
| 2001/0041666 A1 | 11/2001 | Svendsen et al. |
| 2006/0051305 A1 | 3/2006 | Belinky et al. |

FOREIGN PATENT DOCUMENTS

| | | |
|---|---|---|
| CN | 1293708 A | 5/2001 |
| CN | 1747712 A | 3/2006 |
| WO | WO 91/18090 A1 | 11/1991 |
| WO | WO-97/09431 A1 | 3/1997 |
| WO | WO-2009/055564 A1 | 4/2009 |
| WO | WO-2009/108941 A2 | 9/2009 |
| WO | WO-2011/104339 A1 | 9/2011 |
| WO | WO-2012/027262 A1 | 3/2012 |
| WO | WO-2012/027282 A2 | 3/2012 |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Seffernick et al., Melamine deaminase and Atrazine chlorohydrolase: 98 percent identical but functionally different. J. Bacteriol., 2001, vol. 183 (8): 2405-2410.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Guo et al., Protein tolerance to random amino acid change. PNAS., 2004, vol. 101 (25): 9205-9210.*
Akbar, M. T. et al., "An Insight into the Lignin Peroxidase of *Macrophomina phaseolina*, ," Bioinformation, 9(14):730-735 (2013).
Barnett, P. et al., "Isolation, Characterization, and Primary Structure of the Vanadium Chloroperoxidase from the Fungus *Embellisia didymospora*," J. of Biol Chem, 273(36):23381-23387 (1998).
Islam, M.S. et al., "Tools to Kill: Genome of one of the Most Destructive Plant Pathogenic Fungi *Macrophomina phaseolina*," BMC Genomics, 13:493 (2012).

(Continued)

*Primary Examiner* — Ganapathirama Raghu
(74) *Attorney, Agent, or Firm* — Foley Hoag LLP

(57) ABSTRACT

The present invention relates to the field of plant breeding and disease resistance in respect of lignin degradation by *Macrophomina phaseolina* ("*M. phaseolina*"). Disclosed are isolated polynucleotides encoding the lignin degrading enzymes produced by *Macrophomina phaseolina*, or the complement of such sequences. Also disclosed are isolated polypeptides encoded by various polynucleotide sequences; a recombinant gene construct comprising a polynucleotide; a transformant and a transgenic fungus comprising the recombinant gene construct, having enhanced production of lignin degrading enzyme. Further disclosed are polypeptides having an oligomerase activity, e.g., enzymes that convert recalcitrant soluble oligomerase to fermentable sugar in saccharification process of biomass.

20 Claims, 18 Drawing Sheets

(56) References Cited

OTHER PUBLICATIONS

Larrondo, L.F. et al., "Characterization of a Multicopper Oxidase Gene Cluster in *Phanerochaete chrysosporium* and Evidence of Altered Splicing of the *mco* Transcripts," Microbiology, 150:2775-2783 (2004).
Ruiz-Dueñas, F.J. et al., "Molecular Characterization of a Novel Peroxidase Isolated from the Ligninolytic Fungus *Pleurotus eryngii*," Molecular Microbiology, 31(1):223-235 (1999).
Schalch, H. et al., "Molecular Cloning and Sequences of Lignin Peroxidase Genes of *Phanerochaete chrysosporium*," Molecular and Cellular Biology, pp. 2743-2747 (1989).
International Search Report completed on Feb. 10, 2014.
Supplementary European Search Report Completed on Nov. 26, 2015.
XP002751445, Database Accession No. K2RG38, May 29, 2013.
XP002751446, Database Accession No. K2SCB4, May 29, 2013.
XP002751447 Database Accession No. K2SCI0, May 29, 2013.
GenBank Accession No. EKG20024, "Fungal lignin peroxidase [Macrophomina phaseolina MS6]," Oct. 3, 2012.

* cited by examiner 1935 bp 2033 bp 1703 bp 1873 bp

SEQUENCE LISTING

```
<160> NUMBER OF SEQ ID NOS: 185

<210> SEQ ID NO 1
<211> LENGTH: 1379
<212> TYPE: DNA
<213> ORGANISM: M. phaseolina

<400> SEQUENCE: 1
ctgctcagca gatcttatcc ctccagagcc agagcatctt taactgacca gcttgccttc      60
gtcccatcgt ttgcattttt ttacacttga ccagtcaagg ccctcttcc ttctttgaga      120 ccgctacacc caccccttcg tactgtcaaa atgttattct caaagtcttc catctttctc      180
ctctccactg cggccagtgt gcaagcactc agcctctccg atgtctcctc tgccgcctcg      240
gtcctgaagc gtgaagcttc cggcttgggg aacaaccttc tatctctcgt tcaccgtcgg      300
gactcttgcc ctgatgtttg gcagaaagtc gcatccgagc tgaagggctg gttcttggat      360
ggttccgtgt gcagtgacga cgcacgcgct gccatccgcc tctctttcca cgactgcttt      420
tccggcggct gcgatgggtc catcatcctt gcccacgagt acacccgctc cgacaacgct      480
```

```
ggcttagcag actttgctat gaagctagcg cctctcgcgg accagtacga ggtcggaaca    540
gctgacctga tccaattcgc tggcggtaag ccttatctat ccaccttaaa acaaaaaaaa    600
aaaaggaaaa aaagactatc tctaacacct acctcgacca gccctcgcca cggccacctg    660 tccctcggc ccccgcatag ccgtcaaagt cggccgccag gactcgtcaa cgccctcggc    720
agagggacag ctcccctcgt cgcgatcctc ggcctccgtc ctgatcgacc agttcgcggc    780
gaaggggttc tctgagatag acctcgtcgc cctcgtcggt gcccacagca ctgccaagca    840
gttcttcgat cagcccgaca aggccggcca agcctcgac tccaccccg gcacttggga    900 caccaacttt taccgccaga cgacgctcgg cactgcgccc gttaccctcg agagcgataa    960
gaacctcgcc acggatctga ggaccgcggt gcagtggacg gcgtttaatg cccagggcgt   1020
gtgggccgcg gcgtatgtga gcgcgtaagt agtgcatcat atgtttcttc tctgctctca   1080
gattgttgag aactaatggt caatgtagga tgaacaagat gaccgttttg ggcaatgatg   1140
tcagcagctt gacggattgc acgagtgtta tcagtgcggc aacgagcaag cgcgacatca   1200
aggccgcacc tattgcggat aggatttgag ctatgcaagc agttctgggt gagcgaggtc   1260
gtagtgcggt gactggagtt ctgtttttttt tttttttctt aattggtaat gtctgctctt   1320
gtttgatacc tgccagtatt cgcgatttat tcatcgggaa gagtttagag aaggggca    1379
```

<210> SEQ ID NO 2
<211> LENGTH: 939
<212> TYPE: DNA
<213> ORGANISM: M. phaseolina

<400> SEQUENCE: 2

```
atgttattct caaagtcttc catctttctc ctctccactg cggccagtgt gcaagcactc     60
agcctctccg atgtctcctc tgccgcctcg gtcctgaagc gtgaagcttc cggcttgggg    120
aacaaccttc tatctctcgt tcaccgtcgg gactcttgcc ctgatgtttg gcagaaagtc    180
gcatccgagc tgaagggctg gttcttggat ggttccgtgt gcagtgacga cgcacgcgct    240
gccatccgcc tctctttcca cgactgcttt tccggcggct gcgatgggtc catcatcctt    300
gcccacgagt acacccgctc cgacaacgct ggcttagcag actttgctat gaagctagcg    360
cctctcgcgg accagtacga ggtcggaaca gctgacctga tccaattcgc tggcgccctc    420
gccacggcca cctgtcccct cggccccgc atagccgtca aagtcggccg ccaggactcg    480
tcaacgccct cggcagaggg acagctcccc tcgtcgcgat cctcggcctc cgtcctgatc    540
gaccagttcg cggcgaaggg gttctctgag atagacctcg tcgccctcgt cggtgcccac    600
agcactgcca agcagttctt cgatcagccc gacaaggccg ccaaagcct cgactccacc    660 cccggcactt gggacaccaa cttttaccgc cagacgacgc tcggcactgc gcccgttacc    720
ctcgagagcg ataagaacct cgccacggat ctgaggaccg cggtgcagtg gacggcgttt    780
aatgcccagg gcgtgtgggc cgcggcgtat gtgagcgcga tgaacaagat gaccgttttg    840
ggcaatgatg tcagcagctt gacggattgc acgagtgtta tcagtgcggc aacgagcaag    900
cgcgacatca aggccgcacc tattgcggat aggatttga                           939
```

<210> SEQ ID NO 3
<211> LENGTH: 312
<212> TYPE: PRT
<213> ORGANISM: M. phaseolina

<400> SEQUENCE: 3

```
Met Leu Phe Ser Lys Ser Ser Ile Phe Leu Ser Thr Ala Ala Ser
1               5                   10                  15

Val Gln Ala Leu Ser Leu Ser Asp Val Ser Ser Ala Ala Ser Val Leu
        20                  25                  30

Lys Arg Glu Ala Ser Gly Leu Gly Asn Asn Leu Leu Ser Leu Val His
            35                  40                  45

Arg Arg Asp Ser Cys Pro Asp Val Trp Gln Lys Val Ala Ser Glu Leu
50                  55                  60

Lys Gly Trp Phe Leu Asp Gly Ser Val Cys Ser Asp Asp Ala Arg Ala
65                  70                  75                  80

Ala Ile Arg Leu Ser Phe His Asp Cys Phe Ser Gly Gly Cys Asp Gly
                85                  90                  95

Ser Ile Ile Leu Ala His Glu Tyr Thr Arg Ser Asp Asn Ala Gly Leu
            100                 105                 110

Ala Asp Phe Ala Met Lys Leu Ala Pro Leu Ala Asp Gln Tyr Glu Val
        115                 120                 125

Gly Thr Ala Asp Leu Ile Gln Phe Ala Gly Ala Leu Ala Thr Ala Thr
    130                 135                 140

Cys Pro Leu Gly Pro Arg Ile Ala Val Lys Val Gly Arg Gln Asp Ser
145                 150                 155                 160

Ser Thr Pro Ser Ala Glu Gly Gln Leu Pro Ser Ser Arg Ser Ser Ala
                165                 170                 175

Ser Val Leu Ile Asp Gln Phe Ala Ala Lys Gly Phe Ser Glu Ile Asp
            180                 185                 190

Leu Val Ala Leu Val Gly Ala His Ser Thr Ala Lys Gln Phe Phe Asp
        195                 200                 205

Gln Pro Asp Lys Ala Gly Gln Ser Leu Asp Ser Thr Pro Gly Thr Trp
    210                 215                 220

Asp Thr Asn Phe Tyr Arg Gln Thr Thr Leu Gly Thr Ala Pro Val Thr
225                 230                 235                 240

Leu Glu Ser Asp Lys Asn Leu Ala Thr Asp Leu Arg Thr Ala Val Gln
                245                 250                 255

Trp Thr Ala Phe Asn Ala Gln Gly Val Trp Ala Ala Tyr Val Ser
            260                 265                 270

Ala Met Asn Lys Met Thr Val Leu Gly Asn Asp Val Ser Ser Leu Thr
        275                 280                 285

Asp Cys Thr Ser Val Ile Ser Ala Ala Thr Ser Lys Arg Asp Ile Lys
    290                 295                 300

Ala Ala Pro Ile Ala Asp Arg Ile
305                 310

<210> SEQ ID NO 4
<211> LENGTH: 1416
<212> TYPE: DNA
<213> ORGANISM: M. phaseolina

<400> SEQUENCE: 4
tctatatctt gcccttcgcc tgttcgcttc aggagaaccc aacgccaaca ttcattctca      60
acctcctctt tgagttacaa tcgctactct gggaaatttg tcccagcctt tcattcaaca    120
actgtttctg tttcaaacca atccgacgcc atgaagttct ccacagtcat ctcgagcgtt    180
gctctcactt ctctactcca gcccgcccct gcctaccctg gcatggcaaa tgtcgtctcg    240
gagatcaagg cccgtcaaaa caccaataat gatggtgact caaatcccga gatgattggc    300
gatctcgcca ccaccggccc aaccacccct gtgggccaaa gcatatacaa catcctgatg    360
```

```
gggaccgagt cggccgagac caagcaggct ggctacatcc cccctcttat cggcaccaac    420
gcctgcaaga gggacacctg ctgcatctgg gcctacatcg ccgccgaact gaccctcaat    480
ttcaagggca tcacgggccg ctgcaacaag aacgcgcgtg ccgccattcg gctcggcttc    540
cacgacgcgg ggacttggtc caagagcagc aacggcggcg cgcggacgg ctcgatcgcg     600 ctgtcgggca cggagatcaa caaggccgag aacaacgggc tgcaggacat catcggcaag    660
atgatcacgt ggcagaagcg gtacggggtg ggcatggcgg atctgatcca gttcgcggcc    720
atccacgccg tggtgacgtg cccgctgggg ccgcgcatcc gcttcttcgt cgggcgcaag    780
gacagcaaaa cggccaacga cgtcagcctg ctgccgggcg tcaacgattc ggccgacaag    840
ctgatcgcgc tcttccagga caagaccatc acgccgcacg agctcgccgc cctgctcggc    900
gcccacacca cctcacagca gttcttcgtc gacaccaccc gcgccggcgc ccccaggac     960 agcacccccg gcgtctggga cacccgcttc tacaaccaaa ccacctccga ccaagttccc    1020
aagaaggtct ccgcttcgc cagcgacgtt gtgctggcca aggacccgcg tatgagtgat    1080
gagtgggccg ccttcgccga ccccgtcaag ggccagaacc actggaatga ggattacgcc    1140
accgcctata cccgcctcag cctgctcggc gtcaacaaca tcaataactt gactgagtgc    1200
agcaaggtgc tgccgtgggc gcaaccgaag ttccccgatg cctggaacct gttcttggac    1260
cagtagagtg tagtttcttc ttaatatctg gcgttcttgg gggtttggtc aaaaaggaga    1320
aagatattat tgtcgatatt tggtataccc taatgttggg aactatacat acgtatacag    1380
gcttcttgta attactcggg catcttttgc acagag                              1416

<210> SEQ ID NO 5
<211> LENGTH: 1116
<212> TYPE: DNA
<213> ORGANISM: M. phaseolina

<400> SEQUENCE: 5
atgaagttct ccacagtcat ctcgagcgtt gctctcactt ctctactcca gcccgcccctt    60 gcctaccctg gcatggcaaa tgtcgtctcg gagatcaagg cccgtcaaaa caccaataat    120
gatggtgact caaatcccga gatgattggc gatctcgcca ccaccggccc aaccaccct     180 gtgggccaaa gcatatacaa catcctgatg gggaccgagt cggccgagac caagcaggct    240
ggctacatcc cccctcttat cggcaccaac gcctgcaaga gggacacctg ctgcatctgg    300
gcctacatcg ccgccgaact gaccctcaat ttcaagggca tcacgggccg ctgcaacaag    360
aacgcgcgtg ccgccattcg gctcggcttc cacgacgcgg ggacttggtc caagagcagc    420
aacggcggcg cgcggacgg ctcgatcgcg ctgtcgggca cggagatcaa caaggccgag     480
aacaacgggc tgcaggacat catcggcaag atgatcacgt ggcagaagcg gtacggggtg    540
ggcatggcgg atctgatcca gttcgcggcc atccacgccg tggtgacgtg cccgctgggg    600
ccgcgcatcc gcttcttcgt cgggcgcaag gacagcaaaa cggccaacga cgtcagcctg    660
ctgccgggcg tcaacgattc ggccgacaag ctgatcgcgc tcttccagga caagaccatc    720
acgccgcacg agctcgccgc cctgctcggc gcccacacca cctcacagca gttcttcgtc    780
gacaccaccc gcgccggcgc ccccaggac agcacccccg gcgtctggga cacccgcttc     840
tacaaccaaa ccacctccga ccaagttccc aagaaggtct ccgcttcgc cagcgacgtt    900 gtgctggcca aggacccgcg tatgagtgat gagtgggccg ccttcgccga ccccgtcaag    960
ggccagaacc actggaatga ggattacgcc accgcctata cccgcctcag cctgctcggc    1020
```

```
gtcaacaaca tcaataactt gactgagtgc agcaaggtgc tgccgtgggc gcaaccgaag      1080
ttccccgatg cctggaacct gttcttggac cagtag                                1116
```

<210> SEQ ID NO 6
<211> LENGTH: 371
<212> TYPE: PRT
<213> ORGANISM: M. phaseolina

<400> SEQUENCE: 6

```
Met Lys Phe Ser Thr Val Ile Ser Ser Val Ala Leu Thr Ser Leu Leu
1               5                   10                  15

Gln Pro Ala Leu Ala Tyr Pro Gly Met Ala Asn Val Val Ser Glu Ile
            20                  25                  30

Lys Ala Arg Gln Asn Thr Asn Asn Asp Gly Asp Ser Asn Pro Glu Met
        35                  40                  45

Ile Gly Asp Leu Ala Thr Thr Gly Pro Thr Thr Pro Val Gly Gln Ser
    50                  55                  60

Ile Tyr Asn Ile Leu Met Gly Thr Glu Ser Ala Glu Thr Lys Gln Ala
65                  70                  75                  80

Gly Tyr Ile Pro Pro Leu Ile Gly Thr Asn Ala Cys Lys Arg Asp Thr
                85                  90                  95

Cys Cys Ile Trp Ala Tyr Ile Ala Ala Glu Leu Thr Leu Asn Phe Lys
            100                 105                 110

Gly Ile Thr Gly Arg Cys Asn Lys Asn Ala Arg Ala Ala Ile Arg Leu
        115                 120                 125

Gly Phe His Asp Ala Gly Thr Trp Ser Lys Ser Ser Asn Gly Gly Gly
    130                 135                 140

Ala Asp Gly Ser Ile Ala Leu Ser Gly Thr Glu Ile Asn Lys Ala Glu
145                 150                 155                 160

Asn Asn Gly Leu Gln Asp Ile Ile Gly Lys Met Ile Thr Trp Gln Lys
                165                 170                 175

Arg Tyr Gly Val Gly Met Ala Asp Leu Ile Gln Phe Ala Ala Ile His
            180                 185                 190

Ala Val Val Thr Cys Pro Leu Gly Pro Arg Ile Arg Phe Phe Val Gly
        195                 200                 205

Arg Lys Asp Ser Lys Thr Ala Asn Asp Val Ser Leu Leu Pro Gly Val
    210                 215                 220

Asn Asp Ser Ala Asp Lys Leu Ile Ala Leu Phe Gln Asp Lys Thr Ile
225                 230                 235                 240

Thr Pro His Glu Leu Ala Ala Leu Leu Gly Ala His Thr Thr Ser Gln
                245                 250                 255

Gln Phe Phe Val Asp Thr Thr Arg Ala Gly Ala Pro Gln Asp Ser Thr
            260                 265                 270

Pro Gly Val Trp Asp Thr Arg Phe Tyr Asn Gln Thr Thr Ser Asp Gln
        275                 280                 285

Val Pro Lys Lys Val Phe Arg Phe Ala Ser Asp Val Leu Ala Lys
    290                 295                 300

Asp Pro Arg Met Ser Asp Glu Trp Ala Ala Phe Ala Asp Pro Val Lys
305                 310                 315                 320

Gly Gln Asn His Trp Asn Glu Asp Tyr Ala Thr Ala Tyr Thr Arg Leu
                325                 330                 335

Ser Leu Leu Gly Val Asn Asn Ile Asn Asn Leu Thr Glu Cys Ser Lys
            340                 345                 350

Val Leu Pro Trp Ala Gln Pro Lys Phe Pro Asp Ala Trp Asn Leu Phe
```

```
                355               360               365
Leu Asp Gln
   370

<210> SEQ ID NO 7
<211> LENGTH: 1323
<212> TYPE: DNA
<213> ORGANISM: M. phaseolina

<400> SEQUENCE: 7
tcgagatggc ggctctctcg cagacgtaaa tctataaagc cttgccgcga ctttcttttg    60
tgtatctcat cagcatcgag ttccacaaga gcttgcttcc tctcctcact gagcctagcg   120
aggagcatca ctcagaaccc tccaatcaca atgcggacct catccctgtt ccttgcttcc   180
gcatgcggaa catctgctta cactctcgtc tcgctcgact ctctgccaag cactcttcat   240
gacataacct cccgcaccat ctccaacctc gaccccgca  acctcctctc cgcgcgcaag   300
acgcccgact gccggccat  ctggaggacc atctcagccg acctgaccaa gagcttcctc   360
gccaacggcg agtgcaccga cctcgcccgc gccgccatcc gctacgcctt ccacgacgcg   420
ggcaccttct cgctcaagct gcccacctac gcgccggcct ccggcggcgc cgacggctcg   480
ctgctgctcg tcgattcgga gatccagcgg cccgagaaca cgggctgca  ggcgtacaac   540 gacttcatca aggccaagta cagcacgtac aagtcctcgg gcgtcggcgc cgccgacctg   600
atccagttcg ccggcaacca cgccgtggtg acgtgcccgg gcgggcccac ggtcaagacg   660
ctcgtcggcc gcggcgacag cacgaccgcg tcgccgctga acgtgatgcc gccggggttc   720
ggcgcgggca gcgaccacga ctcgctgctc cagctcttcc aggacaaggg gttcagcgcc   780
gtcgacctgg ccgcgctgat cggcgcccac accacctcca cgaacatcgc ggaggcgcag   840
atccccgtcg gcgcgccgca ggacagcacg ccgggcaggt gggacgtcaa gtactacgcc   900
gagacgtacg ccccgcccgc gggcgtctcc cgcttcgcct ccgacatcaa cctctccgac   960
ccgacgaaag cggtcggcaa agagttccag ggattcgtca acaaccaggg taagtggacg  1020
ggcaagtttg ccgacgccat gttccgtctg agtgtgttgg catcccgcc  ggcgacgtac  1080 aagaatttcg cggactgcac cgctgcgctg cccaagggca cgagcgccaa gcgggacatc  1140
cgcagcgccc cgatcaacga ccgcgcaagg tagaggaggg gaaaagaaag gaagaaaaga  1200
aaataaaaag cgcagcgagg atgaatcggt tggggcaggg cgtttcggtt gaggttgttt  1260
gtttgctcgc ctgccttttt ttttttttta atccctctca tgatccatcg aatgagaaca  1320
ctt                                                                1323

<210> SEQ ID NO 8
<211> LENGTH: 1023
<212> TYPE: DNA
<213> ORGANISM: M. phaseolina

<400> SEQUENCE: 8
atgcggacct catccctgtt ccttgcttcc gcatgcggaa catctgctta cactctcgtc    60
tcgctcgact ctctgccaag cactcttcat gacataacct cccgcaccat ctccaacctc   120 gaccccgca  acctcctctc cgcgcgcaag acgcccgact gccggccat  ctggaggacc   180 atctcagccg acctgaccaa gagcttcctc gccaacggcg agtgcaccga cctcgcccgc   240
gccgccatcc gctacgcctt ccacgacgcg ggcaccttct cgctcaagct gcccacctac   300
gcgccggcct ccggcggcgc cgacggctcg ctgctgctcg tcgattcgga gatccagcgg   360
```

```
cccgagaaca acgggctgca ggcgtacaac gacttcatca aggccaagta cagcacgtac    420
aagtcctcgg gcgtcggcgc cgccgacctg atccagttcg ccggcaacca cgccgtggtg    480
acgtgcccgg gcgggcccac ggtcaagacg ctcgtcggcc gcggcgacag cacgaccgcg    540
tcgccgctga acgtgatgcc gccggggttc ggcgcgggca cgaccacga ctcgctgctc     600 cagctcttcc aggacaaggg gttcagcgcc gtcgacctgg ccgcgctgat cggcgcccac    660
accacctcca cgaacatcgc ggaggcgcag atccccgtcg cgcgccgcca ggacagcacg    720
ccgggcaggt gggacgtcaa gtactacgcc gagacgtacg ccccgcccgc gggcgtctcc    780
cgcttcgcct ccgacatcaa cctctccgac ccgacgaaag cggtcggcaa agagttccag    840
ggattcgtca caaccaggg taagtggacg ggcaagtttg ccgacgccat gttccgtctg    900
agtgtgttgg gcatcccgcc ggcgacgtac aagaatttcg cggactgcac cgctgcgctg    960
cccaagggca cgagcgccaa gcgggacatc cgcagcgccc cgatcaacga ccgcgcaagg    1020
tag                                                                  1023
```

<210> SEQ ID NO 9
<211> LENGTH: 340
<212> TYPE: PRT
<213> ORGANISM: M. phaseolina

<400> SEQUENCE: 9

```
Met Arg Thr Ser Ser Leu Phe Leu Ala Ser Ala Cys Gly Thr Ser Ala
1               5                   10                  15

Tyr Thr Leu Val Ser Leu Asp Ser Leu Pro Ser Thr Leu His Asp Ile
            20                  25                  30

Thr Ser Arg Thr Ile Ser Asn Leu Asp Pro Arg Asn Leu Leu Ser Ala
        35                  40                  45

Arg Lys Thr Pro Asp Cys Pro Ala Ile Trp Arg Thr Ile Ser Ala Asp
    50                  55                  60

Leu Thr Lys Ser Phe Leu Ala Asn Gly Glu Cys Thr Asp Leu Ala Arg
65                  70                  75                  80

Ala Ala Ile Arg Tyr Ala Phe His Asp Ala Gly Thr Phe Ser Leu Lys
                85                  90                  95

Leu Pro Thr Tyr Ala Pro Ala Ser Gly Gly Ala Asp Gly Ser Leu Leu
            100                 105                 110

Leu Val Asp Ser Glu Ile Gln Arg Pro Glu Asn Asn Gly Leu Gln Ala
        115                 120                 125

Tyr Asn Asp Phe Ile Lys Ala Lys Tyr Ser Thr Tyr Lys Ser Ser Gly
    130                 135                 140

Val Gly Ala Ala Asp Leu Ile Gln Phe Ala Gly Asn His Ala Val Val
145                 150                 155                 160

Thr Cys Pro Gly Gly Pro Thr Val Lys Thr Leu Val Gly Arg Gly Asp
                165                 170                 175

Ser Thr Thr Ala Ser Pro Leu Asn Val Met Pro Gly Phe Gly Ala
            180                 185                 190

Gly Ser Asp His Asp Ser Leu Leu Gln Leu Phe Gln Asp Lys Gly Phe
        195                 200                 205

Ser Ala Val Asp Leu Ala Ala Leu Ile Gly Ala His Thr Thr Ser Thr
    210                 215                 220

Asn Ile Ala Glu Ala Gln Ile Pro Val Gly Ala Pro Gln Asp Ser Thr
225                 230                 235                 240

Pro Gly Arg Trp Asp Val Lys Tyr Tyr Ala Glu Thr Tyr Ala Pro Pro
                245                 250                 255
```

```
Ala Gly Val Ser Arg Phe Ala Ser Asp Ile Asn Leu Ser Asp Pro Thr
        260                 265                 270

Lys Ala Val Gly Lys Glu Phe Gln Gly Phe Val Asn Asn Gln Gly Lys
            275                 280                 285

Trp Thr Gly Lys Phe Ala Asp Ala Met Phe Arg Leu Ser Val Leu Gly
        290                 295                 300

Ile Pro Pro Ala Thr Tyr Lys Asn Phe Ala Asp Cys Thr Ala Ala Leu
305                 310                 315                 320

Pro Lys Gly Thr Ser Ala Lys Arg Asp Ile Arg Ser Ala Pro Ile Asn
            325                 330                 335

Asp Arg Ala Arg
        340

<210> SEQ ID NO 10
<211> LENGTH: 1930
<212> TYPE: DNA
<213> ORGANISM: M. phaseolina

<400> SEQUENCE: 10
gagcacggca ggtaggttgc atccgagagg tcgtggtagg taggtatata ttgctgcctc     60
cgctctgtcg ctctatagag gcaggtcttg gacatctgtg aacaggttac cttctcataa    120
tttgatccat tggcgaagat atactcaaga atgccgtcta cctggatgat tgcattgggc    180
gcactcaccc ttgccggcca gtccgcagcc tttcctgctg tggcagaaca atacgctgct    240
cagacatctc acaaggagaa aagagtaaat gcaattagcc ccgggttcaa tgcggcggca    300
cagaggattg acgtctcggg agctcacact ttcgtgcccc ctggcccggg tgaccagaga    360
gggccctgcc cgggtctgaa tgccttagcg aaccagtaag tgctctgcaa gtctcacagg    420
tcttcttgta ctgacaaagt gtagcaacta tttgccccag tgagttctcc acaacttcat    480
tcccgaaacc ttgtcactga ttgtcttcag caatggcgtc gcaacaatca cgcagttcgt    540
ccaggccaca aaccagggtt agtacagcat caccgccacg gaagctacta cgtcagctga    600
accacatacg cagtatacgg catgggtctc gaccttggca cgttcctgtc cgtctacggc    660
gcggtaatgg atggcgacgg cctcagctgg tccatcggcg cgcgcccag taccgcaaac    720
ctactcaacc tccttactca gccgcaaggc ctctcaggtt cgcacaacaa gtacgagaca    780
gatgcatcgc ctacgcgcgg agacctgtac caatagtgcg tctatcccct tcttctgcct    840
cccgccactc cgctgacctg caccgcagtg gcgacaactc ccgggtcgtc atttcgcaat    900
gggacgccct cttcgcgaag caagcggcac tgcccaatga ccagtccaat tatggcctag    960
gtgtgctgac cgacttccga gtcgagcgtt ccagcagag cgtcgatgaa accccctact   1020
tcttcaacgc gccctttttc ggtgtgctcg tgcagcctgc cgcgtacaca ttcatctacc   1080
gcttcatggg caacaagagc gccgagaaac ccgagggtgt gctgacgaaa gaggtgctga   1140
agagcttctt cggcttcact gggcctgacg acgacatgac atacgtgagt cccatcccgc   1200
cgcctttctc atttcttccc actcgagtct cccacatccc ccccccccc ccccccccc    1260
ccaccatttg ttgtcgccct tccctccagc cacgccactg cccacaacgc caccgtctga   1320
cccaccgcag aaccccggcc acgagcgcat ccccgaaaac tggtacaagc gcgccccgg    1380
cgacgaatac acgatcccct tctacgcact tgacctcaac gccgcggcgc tgcagcaccc   1440
gcaattcctg tccgtcggcg gcaacacggg caccaccaac tccttcgccg gcgtcgacct   1500
gcaggacctg agcggcggcc tgtacaacgc cgccagcctg ctcgagggca acaacctcgc   1560
```

| ctgcttcggt ttccaggcgg ccgtccaatt cgcgccggac ctgttgaaag ggctggtgag | 1620 |
| cgatttgacc aagccgttgg gtgtcctggg agatgcgttg gcgagtgcgt tgaatggatt | 1680 |
| agggtgtccg cagttaggcg gccaggcgtg ggatgatagc gcgctggcgc agtttccggg | 1740 |
| gtatgctagg ctgagggcgg atgggacgta cgggaagtaa tggacgcgga gaagtagtgt | 1800 |
| ggcagaggcg acatggtgcg catggtggac tgcggcttca acgacaatgc agagatgatg | 1860 |
| gtatgaggaa actgcacagc agtctgcatg gatttgctag actagacgaa ttttatgatt | 1920 |
| ttgaatgaac | 1930 |

<210> SEQ ID NO 11
<211> LENGTH: 1260
<212> TYPE: DNA
<213> ORGANISM: M. phaseolina

<400> SEQUENCE: 11

| atgccgtcta cctggatgat tgcattgggc gcactcaccc ttgccggcca gtccgcagcc | 60 |
| tttcctgctg tggcagaaca atacgctgct cagacatctc acaaggagaa aagagtaaat | 120 |
| gcaattagcc ccgggttcaa tgcggcggca cagaggattg acgtctcggg agctcacact | 180 |
| ttcgtgcccc ctggccccgg tgaccagaga gggccctgcc cgggtctgaa tgccttagcg | 240 |
| aaccacaatg gcgtcgcaac aatcacgcag ttcgtccagg ccacaaacca ggtatacggc | 300 |
| atgggtctcg accttggcac gttcctgtcc gtctacggcg cggtaatgga tggcgacggc | 360 |
| ctcagctggt ccatcggcgg cgcgcccagt accgcaaacc tactcaacct ccttactcag | 420 |
| ccgcaaggcc tctcaggttc gcacaacaag tacgagacga atgcatcgcc tacgcgcgga | 480 |
| gacctgtacc aatatggcga caactcccgg gtcgtcattt cgcaatggga cgccctcttc | 540 |
| gcgaagcaag cggcactgcc caatgaccag tccaattatg cctaggtgt gctgaccgac | 600 |
| ttccgagtcg agcgtttcca gcagagcgtc gatgaaaacc cctacttctt caacgcgccc | 660 |
| ttttccggtg tgctcgtgca gcctgccgcg tacacattca tctaccgctt catgggcaac | 720 |
| aagagcgccg agaaacccga gggtgtgctg acgaaagagg tgctgaagag cttcttcggc | 780 |
| ttcactgggc ctgacgacga catgacatac aaccccggcc acgagcgcat ccccgaaaac | 840 |
| tggtacaagc gcgcccccgg cgacgaatac acgatcccct tctacgcact tgacctcaac | 900 |
| gccgcggcgc tgcagcaccc gcaattcctg tccgtcggcg gcaacacggg caccaccaac | 960 |
| tccttcgccg gcgtcgacct gcaggacctg agcggcggcc tgtacaacgc cgccagcctg | 1020 |
| ctcgagggca caaccctcgc ctgcttcggt ttccaggcgg ccgtccaatt cgcgccggac | 1080 |
| ctgttgaaag ggctggtgag cgatttgacc aagccgttgg gtgtcctggg agatgcgttg | 1140 |
| gcgagtgcgt tgaatggatt agggtgtccg cagttaggcg gccaggcgtg ggatgatagc | 1200 |
| gcgctggcgc agtttccggg gtatgctagg ctgagggcgg atgggacgta cgggaagtaa | 1260 |

<210> SEQ ID NO 12
<211> LENGTH: 419
<212> TYPE: PRT
<213> ORGANISM: M. phaseolina

<400> SEQUENCE: 12

Met Pro Ser Thr Trp Met Ile Ala Leu Gly Ala Leu Thr Leu Ala Gly
1               5                   10                  15

Gln Ser Ala Ala Phe Pro Ala Val Ala Glu Gln Tyr Ala Ala Gln Thr
            20                  25                  30

Ser His Lys Glu Lys Arg Val Asn Ala Ile Ser Pro Gly Phe Asn Ala

```
              35                  40                  45
Ala Ala Gln Arg Ile Asp Val Ser Gly Ala His Thr Phe Val Pro Pro
 50                  55                  60

Gly Pro Gly Asp Gln Arg Gly Pro Cys Pro Gly Leu Asn Ala Leu Ala
 65                  70                  75                  80

Asn His Asn Gly Val Ala Thr Ile Thr Gln Phe Val Gln Ala Thr Asn
                 85                  90                  95

Gln Val Tyr Gly Met Gly Leu Asp Leu Gly Thr Phe Leu Ser Val Tyr
                100                 105                 110

Gly Ala Val Met Asp Gly Asp Gly Leu Ser Trp Ser Ile Gly Gly Ala
                115                 120                 125

Pro Ser Thr Ala Asn Leu Leu Asn Leu Leu Thr Gln Pro Gln Gly Leu
130                 135                 140

Ser Gly Ser His Asn Lys Tyr Glu Thr Asp Ala Ser Pro Thr Arg Gly
145                 150                 155                 160

Asp Leu Tyr Gln Tyr Gly Asp Asn Ser Arg Val Val Ile Ser Gln Trp
                165                 170                 175

Asp Ala Leu Phe Ala Lys Gln Ala Ala Leu Pro Asn Asp Gln Ser Asn
                180                 185                 190

Tyr Gly Leu Gly Val Leu Thr Asp Phe Arg Val Glu Arg Phe Gln Gln
                195                 200                 205

Ser Val Asp Glu Asn Pro Tyr Phe Phe Asn Ala Pro Phe Ser Gly Val
210                 215                 220

Leu Val Gln Pro Ala Ala Tyr Thr Phe Ile Tyr Arg Phe Met Gly Asn
225                 230                 235                 240

Lys Ser Ala Glu Lys Pro Glu Gly Val Leu Thr Lys Glu Val Leu Lys
                245                 250                 255

Ser Phe Phe Gly Phe Thr Gly Pro Asp Asp Met Thr Tyr Asn Pro
                260                 265                 270

Gly His Glu Arg Ile Pro Glu Asn Trp Tyr Lys Arg Ala Pro Gly Asp
                275                 280                 285

Glu Tyr Thr Ile Pro Phe Tyr Ala Leu Asp Leu Asn Ala Ala Ala Leu
                290                 295                 300

Gln His Pro Gln Phe Leu Ser Val Gly Gly Asn Thr Gly Thr Thr Asn
305                 310                 315                 320

Ser Phe Ala Gly Val Asp Leu Gln Asp Leu Ser Gly Gly Leu Tyr Asn
                325                 330                 335

Ala Ala Ser Leu Leu Glu Gly Asn Asn Leu Ala Cys Phe Gly Phe Gln
                340                 345                 350

Ala Ala Val Gln Phe Ala Pro Asp Leu Leu Lys Gly Leu Val Ser Asp
                355                 360                 365

Leu Thr Lys Pro Leu Gly Val Leu Gly Asp Ala Leu Ala Ser Ala Leu
                370                 375                 380

Asn Gly Leu Gly Cys Pro Gln Leu Gly Gly Gln Ala Trp Asp Ser
385                 390                 395                 400

Ala Leu Ala Gln Phe Pro Gly Tyr Ala Arg Leu Arg Ala Asp Gly Thr
                405                 410                 415

Tyr Gly Lys

<210> SEQ ID NO 13
<211> LENGTH: 1108
<212> TYPE: DNA
<213> ORGANISM: M. phaseolina
```

<400> SEQUENCE: 13

```
ctgatggtat gtactttggt aagcacgcca ttaactactc gctccatcgc ctcgagttac      60
cctgttggag cagcaaccac aacttgagcg aacaaattcg gccattaata ccatcgtacg     120
aagaaggctt aaccgcttta cctgccagcc atgaatccaa tctgcttttt atccctgctc     180
acggccatgc taggcatggc catgggcggt ggaaaccctc tgaaccatgc tgaaccttt      240
gatcccacga acagcttgtg ggtgtgactg atgcgcatga gcccattctt cctgatatca     300
ccaacgctcg cagcccctgt cccggcctta acacgttggc gaaccaggaa gctcattcgc     360
cccccttgcta tgaagaaaac ctggaattta cgctcctccc ggtggcttcg acggtgtcgc    420
gaactacgat gaacttgtta aggctctggt tgatagtgtg ttgcttttga tcggggtca     480
ccaccttcg gttgacgaga acatcacgat tccgcctaat aatttcacac gcagcctcag    540
cggcacacaa atctccctag attctgaggc ctcgcctaca cgccacgacg cgtacgaccc    600
tcgggcctac tccggctcga gcagcatcga aatgaagtgg aacttcttca aacagctgta    660
cgagaagcag gccgggatcc cacgcgatgc ggttaacttt gcactggatg ttcttgctca    720
aaacatgttg gagctggtgg tggtcagcat caagaacaac ccgaacttct tcctgagccc    780
aacgcacatc gcattcggac catcgacggc ccacatgtgc attcccaact tgttcgcgaa    840
ccacagcact gagcattggc tgacctctct cctgaataga gagggagggt ctcgccattc    900
attccatgct caaactatga cgctttgtag tcttcagctc agattgtcac caatctgaag    960
gcgagatccc acttctatac tcagattaaa gacctaataa tacaatcgta tactcagcga   1020
gagaagcacg agaaggaccg agccaacatt cacctcatcc ttcacacaac acactcctga   1080
gcaccgaccc caattctaaa tcagcccc                                       1108
```

<210> SEQ ID NO 14
<211> LENGTH: 690
<212> TYPE: DNA
<213> ORGANISM: M. phaseolina

<400> SEQUENCE: 14

```
atgaatccaa tctgcttttt atccctgctc acggccatgc taggcatggc catgggcggt      60
ggaaaccctc tgaaccatgc tgaaccttt gatcccacga acagcttaaa acctggaatt     120
tacgctcctc ccggtggctt cgacggtgtc gcgaactacg atgaacttgt taaggctctg     180
gttgatagtg tgttgctttt gatcggggt caccaccttt cggttgacga gaacatcacg     240
attccgccta ataatttcac acgcagcctc agcggcacac aaatctcccct agattctgag    300
gcctcgccta cacgccacga cgcgtacgac cctcgggcct actccggctc gagcagcatc    360
gaaatgaagt ggaacttctt caaacagctg tacgagaagc aggccgggat cccacgcgat    420
gcggttaact ttgcactgga tgttcttgct caaaacatgt tggagctggt ggtggtcagc    480
atcaagaaca cccgaactt cttcctgagc ccaacgcaca tcgcattcgg accatcgacg    540
gcccacatgt gcattcccaa cttgttcgcg aaccacagca ctgagcattg gctgacctct    600
ctcctgaata gagagggagg gtctcgccat tcattccatg ctcaaactat gacgctttgt    660
agtcttcagc tcagattgtc accaatctga                                     690
```

<210> SEQ ID NO 15
<211> LENGTH: 229
<212> TYPE: PRT
<213> ORGANISM: M. phaseolina

<400> SEQUENCE: 15

```
Met Asn Pro Ile Cys Phe Leu Ser Leu Leu Thr Ala Met Leu Gly Met
1               5                   10                  15

Ala Met Gly Gly Gly Asn Pro Leu Asn His Ala Glu Pro Phe Asp Pro
                20                  25                  30

Thr Asn Ser Leu Lys Pro Gly Ile Tyr Ala Pro Pro Gly Gly Phe Asp
            35                  40                  45

Gly Val Ala Asn Tyr Asp Glu Leu Val Lys Ala Leu Val Asp Ser Val
        50                  55                  60

Leu Leu Leu Ile Gly Gly His His Leu Ser Val Asp Glu Asn Ile Thr
65                  70                  75                  80

Ile Pro Pro Asn Asn Phe Thr Arg Ser Leu Ser Gly Thr Gln Ile Ser
                85                  90                  95

Leu Asp Ser Glu Ala Ser Pro Thr Arg His Asp Ala Tyr Asp Pro Arg
            100                 105                 110

Ala Tyr Ser Gly Ser Ser Ser Ile Glu Met Lys Trp Asn Phe Phe Lys
        115                 120                 125

Gln Leu Tyr Glu Lys Gln Ala Gly Ile Pro Arg Asp Ala Val Asn Phe
    130                 135                 140

Ala Leu Asp Val Leu Ala Gln Asn Met Leu Glu Leu Val Val Val Ser
145                 150                 155                 160

Ile Lys Asn Asn Pro Asn Phe Phe Leu Ser Pro Thr His Ile Ala Phe
                165                 170                 175

Gly Pro Ser Thr Ala His Met Cys Ile Pro Asn Leu Phe Ala Asn His
            180                 185                 190

Ser Thr Glu His Trp Leu Thr Ser Leu Leu Asn Arg Glu Gly Gly Ser
        195                 200                 205

Arg His Ser Phe His Ala Gln Thr Met Thr Leu Cys Ser Leu Gln Leu
    210                 215                 220

Arg Leu Ser Pro Ile
225

<210> SEQ ID NO 16
<211> LENGTH: 1554
<212> TYPE: DNA
<213> ORGANISM: M. phaseolina

<400> SEQUENCE: 16
aagccttgct ggatcgacct ttttcaattc cggcagatac acccaagtca ttgaacatcg      60
aaacagtact tgccttcgtc aaatatgcgg tcactcttcc ttgcttcctt attactttct     120
gcggcgtccg ctttcccttt cgtggcagat atgccagagg tagactcttc tctcttccgt     180
gaagcacccg tacgtaggca acaacctggc ggcaaccaac ctggcggagc ggcgacttgc     240
cctttcaatg ccaaccacgt ccccgctgcg ccagtgacag ctcgatttcc ctataacaac     300
gcaaagaacg gagttcccgg caacggaaag ggcggttacc aggttccagc gcctggtgac     360
acggctcatc agttcattgc accaacagcg cacgatatcc gtgggccttg cccgggcctg     420
aacgctgcgg ccaatcacgg cgtgagtctt tcctgtagtc cccattcgag tttcaagtct     480
cctgacggtg accctaaaca gttcctcgcg cgcgacggca tagtgacctt caacgaactg     540
gtcgacgccc agcagaatgt ctacaatgtc ggctacgacc tctctgtgct gctcgccgtc     600
ctcggcctca cgctcaccga cggtgacccc atcacccaaa aactgtctat cggctgcgac     660
gcaacgacac gcacatctgt ggcccccctg ctgactggca gtcagcccgg tctggatggc     720
cacaacaagt tcgaagcgga cacgtcgctc acacgcaacg actacttcct ggcgggcggc     780
```

-continued

```
gacaacttca acttcaacgg cacgctcttc ggcatgatgg tggatacgtg ccagggcaac      840
ttcaaccgtg agaacctggc gctgtaccgc aagcagcgct acgaccagag cctacgcgac      900
aacgagaact tctacttcgg cccgctaagc ctgctgctgt tcggcgccgc cagcttcctt      960
tacgagctga tgcccagcgg cacgcacaac tacgcgcccg atctcgacac catctcgtcc     1020
ttcttcggcg ccgagcaggc gcccgatggc tcctggcgct tcaccgccga gcgtatcccg     1080
gacaactgga ccaaccgtgt gctgccgtac accaatgagg acgtgacgcg cgaaatcctg     1140
gctatgtacc tcctcaaccc tgtgctattt ggcggcgcca caggcgacgg cggcttcaac     1200
acgctgccga agtttggctc catccaggac ggcaagatcg ttgaggcacc caatacgctg     1260
tgcctgctgt accagctgtc gacgcagagc gtgccgagct cgctgaatgg catcatcacg     1320
ccgactgtgg atgcgctgaa cctggtcgcg gataagctag cgccgcagtt caagaacttg     1380
gggtgcccga atccgttgac ttgaatgagt gatggccgtg tagagcctct gctcgcggtg     1440
cgaaggaaaa gaaaaaagtg agggattttt tggcgagaaa tgaaattcac gaagatactg     1500
cccggatggt agagggaaac ttggtcatgc atgtgcatgc gaaggcgttg atat           1554
```

<210> SEQ ID NO 17
<211> LENGTH: 1194
<212> TYPE: DNA
<213> ORGANISM: M. phaseolina

<400> SEQUENCE: 17

```
atgccagagg tagactcttc tctcttccgt gaagcacccg tacgtaggca acaacctggc       60
ggcaaccaac ctggcggagc ggcgacttgc cctttcaatg ccaaccacgt ccccgctgcg      120
ccagtgacag ctcgatttcc ctataacaac gcaaagaacg gagttcccgg caacggaaag      180
ggcggttacc aggttccagc gcctggtgac acggctcatc agttcattgc accaacagcg      240
cacgatatcc gtgggccttg cccgggcctg aacgctgcgg ccaatcacgg cttcctcgcg      300
cgcgacggca tagtgacctt caacgaactg gtcgacgccc agcagaatgt ctacaatgtc      360
ggctacgacc tctctgtgct gctcgccgtc ctcggcctca cgctcaccga cggtgacccc      420
atcacccaaa aactgtctat cggctgcgac gcaacgacac gcacatctgt ggcccccctg      480
ctgactggca gtcagcccgg tctggatggc cacaacaagt tcgaagcgga cacgtcgctc      540
acacgcaacg actacttcct ggcgggcggc gacaacttca acttcaacgg cacgctcttc      600
ggcatgatgg tggatacgtg ccagggcaac ttcaaccgtg agaacctggc gctgtaccgc      660
aagcagcgct acgaccagag cctacgcgac aacgagaact tctacttcgg cccgctaagc      720
ctgctgctgt tcggcgccgc cagcttcctt tacgagctga tgcccagcgg cacgcacaac      780
tacgcgcccg atctcgacac catctcgtcc ttcttcggcg ccgagcaggc gcccgatggc      840
tcctggcgct tcaccgccga gcgtatcccg gacaactgga ccaaccgtgt gctgccgtac      900
accaatgagg acgtgacgcg cgaaatcctg gctatgtacc tcctcaaccc tgtgctattt      960
ggcggcgcca caggcgacgg cggcttcaac acgctgccga agtttggctc catccaggac     1020
ggcaagatcg ttgaggcacc caatacgctg tgcctgctgt accagctgtc gacgcagagc     1080
gtgccgagct cgctgaatgg catcatcacg ccgactgtgg atgcgctgaa cctggtcgcg     1140
gataagctag cgccgcagtt caagaacttg gggtgcccga atccgttgac ttga           1194
```

<210> SEQ ID NO 18
<211> LENGTH: 397
<212> TYPE: PRT

```
<213> ORGANISM: M. phaseolina

<400> SEQUENCE: 18

Met Pro Glu Val Asp Ser Ser Leu Phe Arg Glu Ala Pro Val Arg Arg
1               5                   10                  15

Gln Gln Pro Gly Gly Asn Gln Pro Gly Gly Ala Ala Thr Cys Pro Phe
            20                  25                  30

Asn Ala Asn His Val Pro Ala Ala Pro Val Thr Ala Arg Phe Pro Tyr
        35                  40                  45

Asn Asn Ala Lys Asn Gly Val Pro Gly Asn Gly Lys Gly Gly Tyr Gln
50                  55                  60

Val Pro Ala Pro Gly Asp Thr Ala His Gln Phe Ile Ala Pro Thr Ala
65                  70                  75                  80

His Asp Ile Arg Gly Pro Cys Pro Gly Leu Asn Ala Ala Ala Asn His
                85                  90                  95

Gly Phe Leu Ala Arg Asp Gly Ile Val Thr Phe Asn Glu Leu Val Asp
            100                 105                 110

Ala Gln Gln Asn Val Tyr Asn Val Gly Tyr Asp Leu Ser Val Leu Leu
        115                 120                 125

Ala Val Leu Gly Leu Thr Leu Thr Asp Gly Asp Pro Ile Thr Gln Lys
130                 135                 140

Leu Ser Ile Gly Cys Asp Ala Thr Thr Arg Thr Ser Val Ala Pro Leu
145                 150                 155                 160

Leu Thr Gly Ser Gln Pro Gly Leu Asp Gly His Asn Lys Phe Glu Ala
                165                 170                 175

Asp Thr Ser Leu Thr Arg Asn Asp Tyr Phe Leu Ala Gly Gly Asp Asn
            180                 185                 190

Phe Asn Phe Asn Gly Thr Leu Phe Gly Met Met Val Asp Thr Cys Gln
        195                 200                 205

Gly Asn Phe Asn Arg Glu Asn Leu Ala Leu Tyr Arg Lys Gln Arg Tyr
210                 215                 220

Asp Gln Ser Leu Arg Asp Asn Glu Asn Phe Tyr Phe Gly Pro Leu Ser
225                 230                 235                 240

Leu Leu Leu Phe Gly Ala Ala Ser Phe Leu Tyr Glu Leu Met Pro Ser
                245                 250                 255

Gly Thr His Asn Tyr Ala Pro Asp Leu Asp Thr Ile Ser Ser Phe Phe
            260                 265                 270

Gly Ala Glu Gln Ala Pro Asp Gly Ser Trp Arg Phe Thr Ala Glu Arg
        275                 280                 285

Ile Pro Asp Asn Trp Thr Asn Arg Val Leu Pro Tyr Thr Asn Glu Asp
290                 295                 300

Val Thr Arg Glu Ile Leu Ala Met Tyr Leu Leu Asn Pro Val Leu Phe
305                 310                 315                 320

Gly Gly Ala Thr Gly Asp Gly Phe Asn Thr Leu Pro Lys Phe Gly
                325                 330                 335

Ser Ile Gln Asp Gly Lys Ile Val Glu Ala Pro Asn Thr Leu Cys Leu
            340                 345                 350

Leu Tyr Gln Leu Ser Thr Gln Ser Val Pro Ser Ser Leu Asn Gly Ile
        355                 360                 365

Ile Thr Pro Thr Val Asp Ala Leu Asn Leu Val Ala Asp Lys Leu Ala
370                 375                 380

Pro Gln Phe Lys Asn Leu Gly Cys Pro Asn Pro Leu Thr
385                 390                 395
```

<210> SEQ ID NO 19
<211> LENGTH: 1792
<212> TYPE: DNA
<213> ORGANISM: M. phaseolina

<400> SEQUENCE: 19

| | | | | | |
|---|---|---|---|---|---|
| accgaccacc | atccattcgc | tctttcgctg | gcggctggcg | tccaaggctc | actctcactc | 60 |
| tagtcactct | ttgcaatctc | tgaattcccg | cgagcccttg | gtctgcgttg | ttaaggattt | 120 |
| gttgtccggg | catcccctct | cttttccgca | atgaagttct | cgtccgccct | tctcctgctc | 180 |
| tcctcgagct | cccttgtcgt | cgatgccttc | cccgccctcg | gtgcgcagaa | ccttgagggc | 240 |
| ctcactccgg | aaaggttgac | cgctgccctc | aagacggtcg | agaagtacag | gaaggagaag | 300 |
| cgccttatca | tcgactccag | caagcctatc | gataccaccg | gcgaccacgc | tttccagcca | 360 |
| cccagcgaaa | ccgaccagcg | cggccctgt | cctggcttga | cgccctggc | caaccatggc | 420 |
| tacatctctc | gcgacggcat | caccagcttc | gccgaggttg | tcaccgccat | taaccaaggt | 480 |
| tcgtcgtgga | ttcgtcgaga | aaggcgtgg | cttggcactg | acaaggatgt | gaagtgatgg | 540 |
| gcatgggcat | cgagctctct | ctgattctcg | gtgttatggg | taccgtgtgg | acgggtaacc | 600 |
| cgctttcgct | ggaccctggc | ttctctatcg | gtgggaccgc | cccggtgat | ggctccgaca | 660 |
| acattctggg | caaccttgtc | ggcctgctcg | gtacgtaact | gtccctcatc | ggagccacgc | 720 |
| cgccgcagct | aagctgagac | gtctgcaggt | gaccctcgtg | gtctgcaagg | ctcccacaac | 780 |
| tggattgagt | ctgactcctc | tctgacgcgt | gatgatctgt | acctcaccgg | agatgcctgg | 840 |
| acgatgaaca | tgacgctctt | ccgcgacatc | tacgaccgcg | cggatgagga | tggcgtcatc | 900 |
| tccatggatc | tgctcgccga | ccaggccgcc | cgtcgctggg | agtacagcat | cggccacaac | 960 |
| cccaacttct | actacggccc | tgtcaccggc | atggtcagcc | gtaatgccgg | ctacttttc | 1020 |
| ctcggccgcc | tgctgtcaaa | ccacaccgat | gaacatccgg | acggaattct | cactcaagaa | 1080 |
| gttttcaaga | agttcttcgc | cgtctacgag | gacgagcagg | gcaacatgga | ataccgcaag | 1140 |
| ggccacgaga | ccttcccgga | caactggtac | cgcaagccgg | tcgagtatgg | cctggtcccg | 1200 |
| ctcaacttgg | acctcgttgg | ctgggtcttg | aagcaccctg | agctgggaag | gtacgtcgtc | 1260 |
| ccttctcacc | ccaagatggg | aaggcatgtg | aactgactcg | gcttcccaca | gcatcggcgg | 1320 |
| taacactggc | accgtcaact | ccttctccgg | cctcgatctg | cacagcatca | ccggcggcgt | 1380 |
| cctcaatgcc | acttcgctcc | tcgagaacaa | caacctgctg | tgttttgtct | ttgaagttct | 1440 |
| caagaccttc | gcccccaact | ccctctcccc | gctcctgtcg | acgctcgaag | tgccgctcaa | 1500 |
| gcttatcgcc | gacaccctgg | ccaccccgct | cttgagcctg | gctgccctg | cctggaagga | 1560 |
| tatgaccgac | ggtggcgagc | cgctgtggga | tggcattcag | aacaggttcc | ctggcgcgag | 1620 |
| caaggccgga | tcgagtttgt | agagttgctc | gagaggacac | aggacgtctg | gagcatgacg | 1680 |
| tctgggtgaa | cgtactgcgt | ggaagaagag | caaaggaacc | agcgagggcg | agaaatgatg | 1740 |
| tagttagcgt | cttgattcta | attcgatacc | atttacattc | ttcgccttat | cc | 1792 |

<210> SEQ ID NO 20
<211> LENGTH: 1317
<212> TYPE: DNA
<213> ORGANISM: M. phaseolina

<400> SEQUENCE: 20

| | | | | | |
|---|---|---|---|---|---|
| atgaagttct | cgtccgccct | tctcctgctc | tcctcgagct | cccttgtcgt | cgatgccttc | 60 |
| cccgccctcg | gtgcgcagaa | ccttgagggc | ctcactccgg | aaaggttgac | cgctgccctc | 120 |

```
aagacggtcg agaagtacag gaaggagaag cgccttatca tcgactccag caagcctatc    180
gataccaccg gcgaccacgc tttccagcca cccagcgaaa ccgaccagcg cggcccctgt    240
cctggcttga acgccctggc caaccatggc tacatctctc gcgacggcat caccagcttc    300
gccgaggttg tcaccgccat taaccaagtg atgggcatgg gcatcgagct ctctctgatt    360
ctcggtgtta tgggtaccgt gtggacgggt aacccgcttt cgctggaccc tggcttctct    420
atcggtggga ccgcccccgg tgatggctcc gacaacattc tgggcaacct tgtcggcctg    480
ctcggtgacc ctcgtggtct gcaaggctcc cacaactgga ttgagtctga ctcctctctg    540
acgcgtgatg atctgtacct caccggagat gcctggacga tgaacatgac gctcttccgc    600
gacatctacg accgcgcgga tgaggatggc gtcatctcca tggatctgct cgccgaccag    660
gccgcccgtc gctgggagta cagcatcggc cacaacccca acttctacta cggccctgtc    720
accggcatgg tcagccgtaa tgccggctac ttttttcctcg gccgcctgct gtcaaaccac    780
accgatgaac atccggacgg aattctcact caagaagttt tcaagaagtt cttcgccgtc    840
tacgaggacg agcagggcaa catggaatac cgcaagggcc acgagacctt cccggacaac    900
tggtaccgca agccggtcga gtatggcctg gtcccgctca acttggacct cgttggctgg    960
gtcttgaagc accctgagct gggaagcatc ggcggtaaca ctggcaccgt caactccttc   1020
tccggcctcg atctgcacag catcaccggc ggcgtcctca atgccacttc gctcctcgag   1080
aacaacaacc tgctgtgttt tgtctttgaa gttctcaaga ccttcgcccc caactccctc   1140
tccccgctcc tgtcgacgct cgaagtgccg ctcaagctta tcgccgacac cctggccacc   1200
ccgctcttga gcctggcctg ccctgcctgg aaggatatga ccgacggtgg cgagccgctg   1260
tgggatggca ttcagaacag gttccctggc gcgagcaagg ccggatcgag tttgtag      1317
```

<210> SEQ ID NO 21
<211> LENGTH: 438
<212> TYPE: PRT
<213> ORGANISM: M. phaseolina

<400> SEQUENCE: 21

```
Met Lys Phe Ser Ser Ala Leu Leu Leu Ser Ser Ser Ser Leu Val
1               5                   10                  15

Val Asp Ala Phe Pro Ala Leu Gly Ala Gln Asn Leu Glu Gly Leu Thr
            20                  25                  30

Pro Glu Arg Leu Thr Ala Ala Leu Lys Thr Val Glu Lys Tyr Arg Lys
        35                  40                  45

Glu Lys Arg Leu Ile Ile Asp Ser Ser Lys Pro Ile Asp Thr Thr Gly
    50                  55                  60

Asp His Ala Phe Gln Pro Pro Ser Glu Thr Asp Gln Arg Gly Pro Cys
65                  70                  75                  80

Pro Gly Leu Asn Ala Leu Ala Asn His Gly Tyr Ile Ser Arg Asp Gly
                85                  90                  95

Ile Thr Ser Phe Ala Glu Val Val Thr Ala Ile Asn Gln Val Met Gly
            100                 105                 110

Met Gly Ile Glu Leu Ser Leu Ile Leu Gly Val Met Gly Thr Val Trp
        115                 120                 125

Thr Gly Asn Pro Leu Ser Leu Asp Pro Gly Phe Ser Ile Gly Gly Thr
    130                 135                 140

Ala Pro Gly Asp Gly Ser Asp Asn Ile Leu Gly Asn Leu Val Gly Leu
145                 150                 155                 160
```

Leu Gly Asp Pro Arg Gly Leu Gln Gly Ser His Asn Trp Ile Glu Ser
              165                 170                 175

Asp Ser Ser Leu Thr Arg Asp Asp Leu Tyr Leu Thr Gly Asp Ala Trp
            180                 185                 190

Thr Met Asn Met Thr Leu Phe Arg Asp Ile Tyr Asp Arg Ala Asp Glu
        195                 200                 205

Asp Gly Val Ile Ser Met Asp Leu Leu Ala Asp Gln Ala Ala Arg Arg
    210                 215                 220

Trp Glu Tyr Ser Ile Gly His Asn Pro Asn Phe Tyr Gly Pro Val
225                 230                 235                 240

Thr Gly Met Val Ser Arg Asn Ala Gly Tyr Phe Phe Leu Gly Arg Leu
                245                 250                 255

Leu Ser Asn His Thr Asp Glu His Pro Asp Gly Ile Leu Thr Gln Glu
            260                 265                 270

Val Phe Lys Lys Phe Phe Ala Val Tyr Glu Asp Glu Gln Gly Asn Met
        275                 280                 285

Glu Tyr Arg Lys Gly His Glu Thr Phe Pro Asp Asn Trp Tyr Arg Lys
    290                 295                 300

Pro Val Glu Tyr Gly Leu Val Pro Leu Asn Leu Asp Leu Val Gly Trp
305                 310                 315                 320

Val Leu Lys His Pro Glu Leu Gly Ser Ile Gly Gly Asn Thr Gly Thr
                325                 330                 335

Val Asn Ser Phe Ser Gly Leu Asp Leu His Ser Ile Thr Gly Gly Val
            340                 345                 350

Leu Asn Ala Thr Ser Leu Leu Glu Asn Asn Asn Leu Leu Cys Phe Val
        355                 360                 365

Phe Glu Val Leu Lys Thr Phe Ala Pro Asn Ser Leu Ser Pro Leu Leu
    370                 375                 380

Ser Thr Leu Glu Val Pro Leu Lys Leu Ile Ala Asp Thr Leu Ala Thr
385                 390                 395                 400

Pro Leu Leu Ser Leu Ala Cys Pro Ala Trp Lys Asp Met Thr Asp Gly
                405                 410                 415

Gly Glu Pro Leu Trp Asp Gly Ile Gln Asn Arg Phe Pro Gly Ala Ser
            420                 425                 430

Lys Ala Gly Ser Ser Leu
        435

<210> SEQ ID NO 22
<211> LENGTH: 1391
<212> TYPE: DNA
<213> ORGANISM: M. phaseolina

<400> SEQUENCE: 22
atactaacgc cgtgcaaccc ccgggcagcg caggtcttgt tgatcgatat aaatgttttg    60
tttcgcgccg ctattgaaat tggacactcc aactgttttc catacattca tctttcccta   120
ttgatcaatt gctgcaaaaa acattccatc atgaagctca ccgtctgtgc cacgacccct   180
tgcttcgctt tggtttatgg acaaggctcc tacgaggggt ggaagccagc tgggccagac   240
gactgtatgt tcagtggaat ttctacgttt cctttgattt gcgctgatgt acatctacag   300
ttcgcggccc ttgccctatg atgaatacct tggccaacca tggctttctc ccccacgatg   360
gcaggaatat cacgaaagcc aacgcaatcc acgctctcaa cacagctatc aacttcaaca   420
cttccctcgc tgctatcatg tgggagcagg ctatcattgc aaacccggag cccaatgcta   480
cgttcttcac tctgtacgtg acttcaagca agcgtctttt gagctaccct gagtaggggg   540

```
ctgctccgaa aggcgactta tctaaacctc ctctttccac tatgtgaagc tctgacatta    600
actaatattg aacagtgacc atcttaatcg tcacaacgtc ttggagcacg atgccagctt    660
gaggtgagtg aagccgcct ttctccagcc tattccaaca atctcctga ccaacactcc      720 tcttcagccg atccgacgcc ttcttcggca acaaccacgt cttcaaccaa actatcttcg    780
acgtctctcg cgcgtggtgg acggaggaaa ccgtagacgc caagatgctg gccaacagca    840
agttgttccg gcagatcgag tcgcgagccg ccaacccgaa ttacaccttc acccaaacta    900
ccgaggcctt tagcttgggc gaggtggctg ctcccatcat cgtcttcggc gaccacgcgg    960
ccggcaccgt caacaggagt ctggtcgagt acttcttcgg tgagccaaga cctcagagac    1020
tttggtctgc aagggttcaa aattactaat tatggggtgg tcttgcagag aacgaacgcc    1080
tcccgaccga gttgggctgg actaagcagg ctaatgatgt gtctctggag gtcatcctgg    1140
agatccagga cctcgtccgc aacgcgacca acctgatcac cgatgccccg ctgccggcag    1200
cgcctcacaa gcgggacctg cacgccccctt acagcctcta gatacgaata taaagctggc    1260
atgaagatca ccaggggttt ttgagaattg tgtcttcggc gggacgggag tggtagattg    1320
agccttgttg ggcttcaggt gtctgggca tggtttgctt tggtccttt acatgatttc      1380 cctagcacgc c                                                         1391
```

<210> SEQ ID NO 23
<211> LENGTH: 780
<212> TYPE: DNA
<213> ORGANISM: M. phaseolina

<400> SEQUENCE: 23

```
atgaagctca ccgtctgtgc cacgacccctt tgcttcgctt tggtttatgg acaaggctcc    60
tacgaggggt ggaagccagc tgggccagac gactttcgcg gcccttgccc tatgatgaat    120
accttggcca accatggctt tctcccccac gatggcagga atatcacgaa agccaacgca    180
atccacgctc tcaacacagc tatcaacttc aacacttccc tcgctgctat catgtgggag    240
caggctatca ttgcaaaccc ggagcccaat gctacgttct tcactcttga ccatcttaat    300
cgtcacaacg tcttggagca cgatgccagc ttgagccgat ccgacgcctt cttcggcaac    360
aaccacgtct tcaaccaaac tatcttcgac gtctctcgcg cgtggtggac ggaggaaacc    420
gtagacgcca agatgctggc caacagcaag ttgttccggc agatcgagtc gcgagccgcc    480
aacccgaatt acaccttcac ccaaactacc gaggccttta gcttgggcga ggtggctgct    540
cccatcatcg tcttcggcga ccacgcggcc ggcaccgtca acaggagtct ggtcgagtac    600 ttcttcggaga acgaacgcct cccgaccgag ttgggctgga ctaagcaggc taatgatgtg    660
tctctggagg tcatcctgga gatccaggac ctcgtccgca acgcgaccaa cctgatcacc    720
gatgccccgc tgccggcagc gcctcacaag cgggacctgc acgccccctta cagcctctag    780
```

<210> SEQ ID NO 24
<211> LENGTH: 259
<212> TYPE: PRT
<213> ORGANISM: M. phaseolina

<400> SEQUENCE: 24

```
Met Lys Leu Thr Val Cys Ala Thr Thr Leu Cys Phe Ala Leu Val Tyr
1               5                   10                  15

Gly Gln Gly Ser Tyr Glu Gly Trp Lys Pro Ala Gly Pro Asp Asp Phe
            20                  25                  30
```

```
Arg Gly Pro Cys Pro Met Met Asn Thr Leu Ala Asn His Gly Phe Leu
            35                  40                  45
Pro His Asp Gly Arg Asn Ile Thr Lys Ala Asn Ala Ile His Ala Leu
 50                  55                  60
Asn Thr Ala Ile Asn Phe Asn Thr Ser Leu Ala Ala Ile Met Trp Glu
 65                  70                  75                  80
Gln Ala Ile Ile Ala Asn Pro Glu Pro Asn Ala Thr Phe Phe Thr Leu
                 85                  90                  95
Asp His Leu Asn Arg His Asn Val Leu Glu His Asp Ala Ser Leu Ser
                100                 105                 110
Arg Ser Asp Ala Phe Phe Gly Asn Asn His Val Phe Asn Gln Thr Ile
            115                 120                 125
Phe Asp Val Ser Arg Ala Trp Trp Thr Glu Thr Val Asp Ala Lys
        130                 135                 140
Met Leu Ala Asn Ser Lys Leu Phe Arg Gln Ile Glu Ser Arg Ala Ala
145                 150                 155                 160
Asn Pro Asn Tyr Thr Phe Thr Gln Thr Thr Glu Ala Phe Ser Leu Gly
                165                 170                 175
Glu Val Ala Ala Pro Ile Ile Val Phe Gly Asp His Ala Ala Gly Thr
            180                 185                 190
Val Asn Arg Ser Leu Val Glu Tyr Phe Phe Glu Asn Glu Arg Leu Pro
        195                 200                 205
Thr Glu Leu Gly Trp Thr Lys Gln Ala Asn Asp Val Ser Leu Glu Val
210                 215                 220
Ile Leu Glu Ile Gln Asp Leu Val Arg Asn Ala Thr Asn Leu Ile Thr
225                 230                 235                 240
Asp Ala Pro Leu Pro Ala Ala Pro His Lys Arg Asp Leu His Ala Pro
                245                 250                 255
Tyr Ser Leu

<210> SEQ ID NO 25
<211> LENGTH: 1314
<212> TYPE: DNA
<213> ORGANISM: M. phaseolina

<400> SEQUENCE: 25
ggcccccgaa agggagacaa aatacgagat tctcctatta cgcgcccaag aatcgacaac     60
accgcccatc agctaccgcc gccttcgttt acgtcgtccg cagcagcaac gcccgacgct    120
acagtcagtc aacagcctcc agccgccacg atgcccaacg cagtgcatct gtcaatgctc    180
gtcctcacgc atgcggtgcc gatcgcgggt tatccgggct gggaagcgca gcaagttgtc    240
gcagaagcgc cctccaagca ccacaacgac ctctacgtgc ccaacccaag ccatccggtg    300
ccggggaaag tgccgtacat cccggacgag gaagagcact actttgagaa gcaggtaaac    360
ggctccggca atggctacta ccggcggtcg tcctgcccgg cagtcaacat catggcgaac    420
agggctaca tcagccgctc gggccgggac atcagctacg aggagatagc gatggcatcg    480
cgggagctgt tcaacttcgg cgacgacaac gtgagcagcg cccctgcag accggcaaag    540
taagcgggct caccaacaat tccttcttga cagatcatga tcgtgctggg gcccagcttc    600
gcggcgcacc cgggccgcga gcgcatcgac ctcgacatgc tggccgacga cgcggtgcag    660
cacatcacca actgccctgc ggcgccgacg cggacggacc gcgcgctggg cgacaacgtg    720
aacctgaaca cgacgctgct ggagcagctg ctggcgacgt ccaaggacgg cgtcacgctg    780
acgctcgaag acgcagccga gcaccaccac ctgcggcaca accagtcgct ggccgagaac    840
```

```
cccggcttcc gcttcagcaa ctccgacgcc atctgctcgc ttgcgcagta cgccaacctg    900
ttcggtatcc tgggccggca gggcaagcat gggctcaaca cgctgtatgt ggaagacgtc    960
aagaccctgt tcgtcgacga agacctgccg gacggatacg gccggaggga gctgccgtat   1020
ttctcgaccg aggcgaacaa ctacatcgac cgtatggccc accacatcgg cttcgagatc   1080
gagcggccgt tcccggccaa cgacgccgac ctgaaggaca tcgagccggt gcaagccaga   1140
tttgaagtgg tggacggatg ctgagcggtg caaaatttaa aaaaaaattt tttttaggca   1200
gaagtcaagc atttaatcgg gctatacaca catcattccg tgcaaacaaa atcatttcta   1260
cagctgtacc gcctcggaaa agaataacgg agatttaaaa aaaaaaaaa aaac          1314
```

<210> SEQ ID NO 26
<211> LENGTH: 951
<212> TYPE: DNA
<213> ORGANISM: M. phaseolina

<400> SEQUENCE: 26

```
atgcccaacg cagtgcatct gtcaatgctc gtcctcacgc atgcggtgcc gatcgcgggt    60
tatccgggct gggaagcgca gcaagttgtc gcagaagcgc cctccaagca ccacaacgac   120
ctctacgtgc ccaacccaag ccatccggtg ccggggaaag tgccgtacat cccggacgag   180
gaagagcact actttgagaa gcaggtaaac ggctccggca atggctacta ccggcggtcg   240
tcctgcccgg cagtcaacat catggcgaac aggggctaca tcagccgctc gggccgggac   300
atcagctacg aggagatagc gatggcatcg cgggagctgt tcaacttcgg cgacgacaac   360
atcatgatcg tgctggggcc cagcttcgcg gcgcacccgg gccgcgagcg catcgacctc   420
gacatgctgg ccgacgacgc ggtgcagcac atcaccaact gccctgcggc gccgacgcgg   480
acggaccgcg cgctgggcga caacgtgaac ctgaacacga cgctgctgga gcagctgctg   540
gcgacgtcca aggacggcgt cacgctgacg ctcgaagacg cagccgagca ccaccacctg   600
cggcacaacc agtcgctggc cgagaacccc ggcttccgct tcagcaactc cgacgccatc   660
tgctcgcttg cgcagtacgc caacctgttc ggtatcctgg gccggcaggg caagcatggg   720
ctcaacacgc tgtatgtgga agacgtcaag accctgttcg tcgacgaaga cctgccggac   780
ggatacggcc ggagggagct gccgtatttc tcgaccgagg cgaacaacta catcgaccgt   840
atggcccacc acatcggctt cgagatcgag cggccgttcc cggccaacga cgccgacctg   900
aaggacatcg agccggtgca agccagattt gaagtggtgg acggatgctg a            951
```

<210> SEQ ID NO 27
<211> LENGTH: 316
<212> TYPE: PRT
<213> ORGANISM: M. phaseolina

<400> SEQUENCE: 27

```
Met Pro Asn Ala Val His Leu Ser Met Leu Val Leu Thr His Ala Val
1               5                   10                  15

Pro Ile Ala Gly Tyr Pro Gly Trp Glu Ala Gln Gln Val Val Ala Glu
            20                  25                  30

Ala Pro Ser Lys His His Asn Asp Leu Tyr Val Pro Asn Pro Ser His
        35                  40                  45

Pro Val Pro Gly Lys Val Pro Tyr Ile Pro Asp Glu Glu His Tyr
    50                  55                  60

Phe Glu Lys Gln Val Asn Gly Ser Gly Asn Gly Tyr Tyr Arg Arg Ser
65                  70                  75                  80
```

```
Ser Cys Pro Ala Val Asn Ile Met Ala Asn Arg Gly Tyr Ile Ser Arg
                85                  90                  95

Ser Gly Arg Asp Ile Ser Tyr Glu Glu Ile Ala Met Ala Ser Arg Glu
            100                 105                 110

Leu Phe Asn Phe Gly Asp Asp Asn Ile Met Ile Val Leu Gly Pro Ser
        115                 120                 125

Phe Ala Ala His Pro Gly Arg Glu Arg Ile Asp Leu Asp Met Leu Ala
    130                 135                 140

Asp Asp Ala Val Gln His Ile Thr Asn Cys Pro Ala Ala Pro Thr Arg
145                 150                 155                 160

Thr Asp Arg Ala Leu Gly Asp Asn Val Asn Leu Asn Thr Thr Leu Leu
                165                 170                 175

Glu Gln Leu Leu Ala Thr Ser Lys Asp Gly Val Thr Leu Thr Leu Glu
            180                 185                 190

Asp Ala Ala Glu His His His Leu Arg His Asn Gln Ser Leu Ala Glu
        195                 200                 205

Asn Pro Gly Phe Arg Phe Ser Asn Ser Asp Ala Ile Cys Ser Leu Ala
    210                 215                 220

Gln Tyr Ala Asn Leu Phe Gly Ile Leu Gly Arg Gln Gly Lys His Gly
225                 230                 235                 240

Leu Asn Thr Leu Tyr Val Glu Asp Val Lys Thr Leu Phe Val Asp Glu
                245                 250                 255

Asp Leu Pro Asp Gly Tyr Gly Arg Arg Glu Leu Pro Tyr Phe Ser Thr
            260                 265                 270

Glu Ala Asn Asn Tyr Ile Asp Arg Met Ala His His Ile Gly Phe Glu
        275                 280                 285

Ile Glu Arg Pro Phe Pro Ala Asn Asp Ala Asp Leu Lys Asp Ile Glu
    290                 295                 300

Pro Val Gln Ala Arg Phe Glu Val Val Asp Gly Cys
305                 310                 315

<210> SEQ ID NO 28
<211> LENGTH: 1480
<212> TYPE: DNA
<213> ORGANISM: M. phaseolina

<400> SEQUENCE: 28
atctggcttt tcctctcttc tctgtcgggc gtcccttgcg caacagatac cccattcatc     60
ccttcagtgc ttcttcttat ctcttcgcgc gctttccccc aaccacagcc tcttatcgcc    120
tgtgctcaca ccacgtttcc cgcacaccca atggcttcca ccgccaggtc cgtcttcgcc    180
cgcagcgcgc ttctgcgctc cgccccggcc tccatcaagt cgaatgccgc ccgctcatct    240
cgcttcgccg tccctacccc agcattccgc cagcagtctc gccgcggcta ctcttccgag    300
gccggctcca gtctaacgg ccccaacccc gccatctgga ttggtgctct cgccgtcctg    360
ggtggcgccg ggtactatgc ctacagctcg ggtgccggcg cccagatcgc ctccaaggaa    420
cccttcaccc ccaagcccga ggactaccag aaggtctacg acgccatcgc caaggccctc    480
gaagagcacg acgactacga cgacggcagc tacggccctg tcctgctgag actggcttgg    540
cacgccagcg gaacgtgagt gacttcccca acacttccag cccaccattg aaccacgcac    600
tgacgccctc cctcacagct acgacaagga aaccggcacc ggcggctcca acggcgccac    660
gatgcgcttc gcgcccgagg cggaccacgg cgccaacgcc ggcctcaagg cggcccgcga    720
cttcctcgag cccatcaagc agcagttccc gtggattacg tactcggacc tgtggacgct    780
```

| | | |
|---|---|---|
| ggcaggcgtc gctgcgatcc aggagatgca gggccccaag gtgccgtggc gccccggccg | 840 | |
| cagcgatcgc gacgtctcct tctgcacgcc cgacggccgc ctgcccgacg cctccaagga | 900 | |
| ccagaaccac ctccgcgcca tcttcggccg catgggttgg aatgaccagg agatcgtggc | 960 | |
| gctgtcgggc gcgcatgcgc tggggaggtg ccatacggat aggagtggat tcgatgcccc | 1020 | |
| gtggaccttc agcccgacga cgctgacgaa cgattatttc aagttgttga tcgacgagaa | 1080 | |
| gtggcagtgg cggaagtggg atggacctaa gcagttggag acaagaaga cgaagagcct | 1140 | |
| gatgatgctg ccgacggatt acgcgttggt gcaggacaag aagtttaagc cctgggtcga | 1200 | |
| gaggtacgcg aaggatcagg atgccttctt caaggacttc tcgaacgtgg ttatgaggtt | 1260 | |
| gttcgagctg ggcgtgccgt tccagagtgg tgaggactcg aggattgtgt taagagcag | 1320 | |
| cttcgactag gcgtgcttgg cggacgttaa ttctgatcga cggggtttga tgggaagttg | 1380 | |
| taaaaggttc tatgacgatc agtaaagaag ggttgttttt gcttttgagt ttcgaggact | 1440 | |
| aaagactaag acaagagtag cgcaaaggtg ggaaagaata | 1480 | |

<210> SEQ ID NO 29
<211> LENGTH: 1116
<212> TYPE: DNA
<213> ORGANISM: M. phaseolina

<400> SEQUENCE: 29

| | | |
|---|---|---|
| atggcttcca ccgccaggtc cgtcttcgcc cgcagcgcgc ttctgcgctc cgccccggcc | 60 | |
| tccatcaagt cgaatgccgc ccgctcatct cgcttcgccg tccctaccca agcattccgc | 120 | |
| cagcagtctc gccgcggcta ctcttccgag gccggctcca agtctaacgg ccccaacccc | 180 | |
| gccatctgga ttggtgctct cgccgtcctg ggtggcgccg gtactatgc ctacagctcg | 240 | |
| ggtgccggcg cccagatcgc ctccaaggaa cccttcaccc caagcccga ggactaccag | 300 | |
| aaggtctacg acgccatcgc caaggccctc gaagagcacg acgactacga cgacggcagc | 360 | |
| tacggccctg tcctgctgag actggcttgg cacgccagcg gaacctacga caaggaaacc | 420 | |
| ggcaccggcg gctccaacgg cgccacgatg cgcttcgcgc ccgaggcgga ccacggcgcc | 480 | |
| aacgccggcc tcaaggcggc ccgcgacttc ctcgagccca tcaagcagca gttcccgtgg | 540 | |
| attacgtact cggacctgtg gacgctggca ggcgtcgctg cgatccagga gatgcagggc | 600 | |
| cccaaggtgc cgtggcgccc cggccgcagc gatcgcgacg tctccttctg cacgcccgac | 660 | |
| ggccgcctgc ccgacgcctc caaggaccag aaccacctcc gcgccatctt cggccgcatg | 720 | |
| ggttggaatg accaggagat cgtggcgctg tcgggcgcgc atgcgctggg gaggtgccat | 780 | |
| acggatagga gtggattcga tgcccgtgg accttcagcc cgacgacgct gacgaacgat | 840 | |
| tatttcaagt tgttgatcga cgagaagtgg cagtggcgga agtgggatgg acctaagcag | 900 | |
| ttggaggaca agaagacgaa gagcctgatg atgctgccga cggattacgc gttggtgcag | 960 | |
| gacaagaagt ttaagccctg gtcgagagg tacgcgaagg atcaggatgc cttcttcaag | 1020 | |
| gacttctcga acgtggttat gaggttgttc gagctgggcg tgccgttcca gagtggtgag | 1080 | |
| gactcgagga ttgtgtttaa gagcagcttc gactag | 1116 | |

<210> SEQ ID NO 30
<211> LENGTH: 371
<212> TYPE: PRT
<213> ORGANISM: M. phaseolina

<400> SEQUENCE: 30

-continued

```
Met Ala Ser Thr Ala Arg Ser Val Phe Ala Arg Ser Ala Leu Leu Arg
1               5                   10                  15

Ser Ala Pro Ala Ser Ile Lys Ser Asn Ala Ala Arg Ser Ser Arg Phe
            20                  25                  30

Ala Val Pro Thr Gln Ala Phe Arg Gln Gln Ser Arg Arg Gly Tyr Ser
                35                  40                  45

Ser Glu Ala Gly Ser Lys Ser Asn Gly Pro Asn Pro Ala Ile Trp Ile
 50                  55                  60

Gly Ala Leu Ala Val Leu Gly Gly Ala Gly Tyr Tyr Ala Tyr Ser Ser
 65                  70                  75                  80

Gly Ala Gly Ala Gln Ile Ala Ser Lys Glu Pro Phe Thr Pro Lys Pro
                85                  90                  95

Glu Asp Tyr Gln Lys Val Tyr Asp Ala Ile Ala Lys Ala Leu Glu Glu
                100                 105                 110

His Asp Tyr Asp Asp Gly Ser Tyr Gly Pro Val Leu Leu Arg Leu
                115                 120                 125

Ala Trp His Ala Ser Gly Thr Tyr Asp Lys Glu Thr Gly Thr Gly Gly
 130                 135                 140

Ser Asn Gly Ala Thr Met Arg Phe Ala Pro Glu Ala Asp His Gly Ala
145                 150                 155                 160

Asn Ala Gly Leu Lys Ala Ala Arg Asp Phe Leu Glu Pro Ile Lys Gln
                165                 170                 175

Gln Phe Pro Trp Ile Thr Tyr Ser Asp Leu Trp Thr Leu Ala Gly Val
                180                 185                 190

Ala Ala Ile Gln Glu Met Gln Gly Pro Lys Val Pro Trp Arg Pro Gly
                195                 200                 205

Arg Ser Asp Arg Asp Val Ser Phe Cys Thr Pro Asp Gly Arg Leu Pro
 210                 215                 220

Asp Ala Ser Lys Asp Gln Asn His Leu Arg Ala Ile Phe Gly Arg Met
225                 230                 235                 240

Gly Trp Asn Asp Gln Glu Ile Val Ala Leu Ser Gly Ala His Ala Leu
                245                 250                 255

Gly Arg Cys His Thr Asp Arg Ser Gly Phe Asp Gly Pro Trp Thr Phe
                260                 265                 270

Ser Pro Thr Thr Leu Thr Asn Asp Tyr Phe Lys Leu Leu Ile Asp Glu
                275                 280                 285

Lys Trp Gln Trp Arg Lys Trp Asp Gly Pro Lys Gln Leu Glu Asp Lys
                290                 295                 300

Lys Thr Lys Ser Leu Met Met Leu Pro Thr Asp Tyr Ala Leu Val Gln
305                 310                 315                 320

Asp Lys Lys Phe Lys Pro Trp Val Glu Arg Tyr Ala Lys Asp Gln Asp
                325                 330                 335

Ala Phe Phe Lys Asp Phe Ser Asn Val Val Met Arg Leu Phe Glu Leu
                340                 345                 350

Gly Val Pro Phe Gln Ser Gly Glu Asp Ser Arg Ile Val Phe Lys Ser
                355                 360                 365

Ser Phe Asp
    370

<210> SEQ ID NO 31
<211> LENGTH: 1981
<212> TYPE: DNA
<213> ORGANISM: M. phaseolina

<400> SEQUENCE: 31
```

```
tagaaggcgc atggagtcgc acgcagggac catgcgcaac acggtgcctg cagagaggcg      60
aaagcccatg catatcacat tgatttttaa agaaggaagt gcaagaagca ttgagacatc     120
gcactcaccc ttcaacaccg ctatcgcgcg atgaaagcca tcagcatcgc cgtgttcgcc     180
gcgtcagtgg tacctcacac tctggcagac tatgtttggc cctcgcaaca tgacttgttg     240
gaggatatgt tggccatcca acaaggctat attcgcatgg gcttcactga ctgtatgtcg     300
acattcactt gagcctgaag taatgtctcc ctactaaagc atcgtcgaag tggttgttcc     360
ttgcggtcac ggcagcaaca ggcccggagt aaacaacgcg gcacaatgga ttcggacggg     420
tttccacgac ttcgccaccc acgactcggc cgctgggacc ggcggcctcg atgcctccct     480
cctctacgag gtcgaacggc ccgagaacga gggctcagcc tttaacgaca ccttcgccga     540
catgcacgac tttatcaatc cccgatcaag cgcctcggat ctgatagcgc tggccgtcgt     600
cgcatcggtt gcggcttgcg gcggacccaa gatcccctg cgagcgggac gaattgatgc      660
tgtggaggcg ggcccggccg gcgttcccaa gcccgacgac tcactggaga gcacgatcga     720
tgcattcgcg cggacggggt caacaccag cgacatgatc gccctcgttg cctgtggcca      780
taccgtcggc ggcgtgcaca gcgtagattt ccccgagatc accggcggcg agaaagacgt     840
cctggacgtg ccgcaatttg acagcagcgg caccatcttc gacaccgcag tcgtggacga     900
atacctcgac agcaacggcg ccaacccccct cgtcttcgga gccaacgaca ccacgaactc    960
ggacaagcgc gtcttcagcg ccgacggcaa cagcaccatg gccaagctca agacccccgc    1020
cacattcaaa gccacctgcg ccgccctctt cgagcgtatg atcaacaccg tcccctcatc    1080
cgtcacccct cagcgaaccca tcgagctggc cgacatcaag ccctacatcg acaagctcga   1140
gctcacaccc aacgcctccg ccctcgcctt cgaaggccgc atccggctgc gcacctcccc    1200
cgtcaccggc cgcgacgccg agggcaccag catcgccctc aatgtcaccg accgcgctgg    1260
cgggcgcaag ctggtgccgg cgccgcgcgc cgtgttgcgc ggcggcacct cgtacggctt    1320
cttcgacgag cagttcagct ggttcgaatt tgcgacgcag ctcgacgtcg cagccggcat    1380
ccaggccttt gatatccagc tcacgacgga ggcgaccgga cacgtggaga cgttcgacaa    1440
cgctggcacc ggcggctatc ctagtctcga cgacttgcta tacttgcagt cgcaatcgtg    1500
catggacacg actgccacgg aggggaatat aacggtgacg gttgcggcgg cggtgcgcga    1560
ggatgcggcg aaggcgggtg cggcgccagt ggtgaggatg cgcataaggt tcagcagat    1620 gggtgtgatg ttgccgaagc ttgtcgtaga ggcagtgcca atggagaggt caaacgtttc    1680
gcagggcggg tatgtattgt acgaggtgga catcccaatc gatgccgctg ctgagcac     1740 gaagttcgat gttgtgttga cggctggggg agacgagatt gtgtctggcc tgcacgggac    1800
cagcgatctt accacatgtt cgggaaactg accggttgat gggcttgggg acttgccctg    1860
agtagcatag catcggcgtg ttttgggttt gtttacaggt gtggaagatc agatgaagga    1920
agaaccaaca ggtgattgaa cctatgtcgc aagtcagcaa tgcagtgatg gtctcggcgt    1980
c                                                                  1981
```

<210> SEQ ID NO 32
<211> LENGTH: 1623
<212> TYPE: DNA
<213> ORGANISM: M. phaseolina

<400> SEQUENCE: 32

```
atgaaagcca tcagcatcgc cgtgttcgcc gcgtcagtgg tacctcacac tctggcagac      60
```

```
tatgtttggc cctcgcaaca tgacttgttg gaggatatgt tggccatcca acaaggctat    120
attcgcatgg gcttcactga cttggttgtt ccttgcggtc acggcagcaa caggcccgga    180
gtaaacaacg cggcacaatg gattcggacg ggtttccacg acttcgccac ccacgactcg    240
gccgctggga ccggcggcct cgatgcctcc ctcctctacg aggtcgaacg gcccgagaac    300
gagggctcag cctttaacga caccttcgcc gacatgcacg actttatcaa tccccgatca    360
agcgcctcgg atctgatagc gctggccgtc gtcgcatcgg ttgcggcttg cggcggaccc    420
aagatccccc tgcgagcggg acgaattgat gctgtggagg cgggcccggc cggcgttccc    480
aagcccgacg actcactgga gagcacgatc gatgcattcg cgcggacggg gttcaacacc    540
agcgacatga tcgccctcgt tgcctgtggc cataccgtcg gcggcgtgca cagcgtagat    600
ttccccgaga tcaccggcgg cgagaaagac gtcctggacg tgccgcaatt tgacagcagc    660
ggcaccatct tcgacaccgc agtcgtggac gaatacctcg acagcaacgg cgccaacccc    720
ctcgtcttcg gagccaacga caccacgaac tcggacaagc gcgtcttcag cgccgacggc    780
aacagcacca tggccaagct caaagacccc gccacattca aagccacctg cgccgccctc    840
ttcgagcgta tgatcaacac cgtcccctca tccgtcaccc tcagcgaacc catcgagctg    900
gccgacatca agccctacat cgacaagctc gagctcacac ccaacgcctc cgccctcgcc    960
ttcgaaggcc gcatccggct gcgcacctcc cccgtcaccg gccgcgacgc cgagggcacc   1020
agcatcgccc tcaatgtcac cgaccgcgct ggcgggcgca agctggtgcc ggcgccgcgc   1080
gccgtgttgc gcggcggcac ctcgtacggc ttcttcgacg agcagttcag ctggttcgaa   1140
tttgcgacgc agctcgacgt cgcagccggc atccaggcct ttgatatcca gctcacgacg   1200
gaggcgaccg acacgtggga cgttcgac aacgctggca ccggcggcta tcctagtctc   1260
gacgacttgc tatacttgca gtcgcaatcg tgcatggaca cgactgccac ggaggggaat   1320
ataacggtga cggttgcggc ggcggtgcgc gaggatgcgg cgaaggcggg tgcggcgcca   1380
gtggtgagga tggcgcataa ggttcagcag atgggtgtga tgttgccgaa gcttgtcgta   1440
gaggcagtgc caatggagag gtcaaacgtt tcgcagggcg gtatgtatt gtacgaggtg   1500 gacatcccaa tcgatgccgc tggctggagc acgaagttcg atgttgtgtt gacggctggg   1560
ggagacgaga ttgtgtctgg cctgcacggg accagcgatc ttaccacatg ttcgggaaac   1620
tga                                                                  1623
```

<210> SEQ ID NO 33
<211> LENGTH: 540
<212> TYPE: PRT
<213> ORGANISM: M. phaseolina

<400> SEQUENCE: 33

```
Met Lys Ala Ile Ser Ile Ala Val Phe Ala Ala Ser Val Val Pro His
1               5                   10                  15

Thr Leu Ala Asp Tyr Val Trp Pro Ser Gln His Asp Leu Leu Glu Asp
            20                  25                  30

Met Leu Ala Ile Gln Gln Gly Tyr Ile Arg Met Gly Phe Thr Asp Leu
        35                  40                  45

Val Val Pro Cys Gly His Gly Ser Asn Arg Pro Gly Val Asn Asn Ala
    50                  55                  60

Ala Gln Trp Ile Arg Thr Gly Phe His Asp Phe Ala Thr His Asp Ser
65                  70                  75                  80

Ala Ala Gly Thr Gly Gly Leu Asp Ala Ser Leu Leu Tyr Glu Val Glu
                85                  90                  95
```

```
Arg Pro Glu Asn Glu Gly Ser Ala Phe Asn Asp Thr Phe Ala Asp Met
                100                 105                 110

His Asp Phe Ile Asn Pro Arg Ser Ala Ser Asp Leu Ile Ala Leu
            115                 120                 125

Ala Val Val Ala Ser Val Ala Ala Cys Gly Gly Pro Lys Ile Pro Leu
130                 135                 140

Arg Ala Gly Arg Ile Asp Ala Val Glu Ala Gly Pro Ala Gly Val Pro
145                 150                 155                 160

Lys Pro Asp Asp Ser Leu Glu Ser Thr Ile Asp Ala Phe Ala Arg Thr
                165                 170                 175

Gly Phe Asn Thr Ser Asp Met Ile Ala Leu Val Ala Cys Gly His Thr
            180                 185                 190

Val Gly Gly Val His Ser Val Asp Phe Pro Glu Ile Thr Gly Gly Glu
        195                 200                 205

Lys Asp Val Leu Asp Val Pro Gln Phe Asp Ser Ser Gly Thr Ile Phe
210                 215                 220

Asp Thr Ala Val Val Asp Glu Tyr Leu Asp Ser Asn Gly Ala Asn Pro
225                 230                 235                 240

Leu Val Phe Gly Ala Asn Asp Thr Thr Asn Ser Asp Lys Arg Val Phe
                245                 250                 255

Ser Ala Asp Gly Asn Ser Thr Met Ala Lys Leu Lys Asp Pro Ala Thr
            260                 265                 270

Phe Lys Ala Thr Cys Ala Ala Leu Phe Glu Arg Met Ile Asn Thr Val
        275                 280                 285

Pro Ser Ser Val Thr Leu Ser Glu Pro Ile Glu Leu Ala Asp Ile Lys
        290                 295                 300

Pro Tyr Ile Asp Lys Leu Glu Leu Thr Pro Asn Ala Ser Ala Leu Ala
305                 310                 315                 320

Phe Glu Gly Arg Ile Arg Leu Arg Thr Ser Pro Val Thr Gly Arg Asp
                325                 330                 335

Ala Glu Gly Thr Ser Ile Ala Leu Asn Val Thr Asp Arg Ala Gly Gly
            340                 345                 350

Arg Lys Leu Val Pro Ala Pro Arg Ala Val Leu Arg Gly Gly Thr Ser
        355                 360                 365

Tyr Gly Phe Phe Asp Glu Gln Phe Ser Trp Phe Glu Phe Ala Thr Gln
        370                 375                 380

Leu Asp Val Ala Ala Gly Ile Gln Ala Phe Asp Ile Gln Leu Thr Thr
385                 390                 395                 400

Glu Ala Thr Gly His Val Glu Thr Phe Asp Asn Ala Gly Thr Gly Gly
                405                 410                 415

Tyr Pro Ser Leu Asp Asp Leu Leu Tyr Leu Gln Ser Gln Ser Cys Met
            420                 425                 430

Asp Thr Thr Ala Thr Glu Gly Asn Ile Thr Val Thr Ala Ala Ala
        435                 440                 445

Val Arg Glu Asp Ala Ala Lys Ala Gly Ala Ala Pro Val Val Arg Met
        450                 455                 460

Ala His Lys Val Gln Gln Met Gly Val Met Leu Pro Lys Leu Val Val
465                 470                 475                 480

Glu Ala Val Pro Met Glu Arg Ser Asn Val Ser Gln Gly Gly Tyr Val
                485                 490                 495

Leu Tyr Glu Val Asp Ile Pro Ile Asp Ala Ala Gly Trp Ser Thr Lys
            500                 505                 510
```

```
Phe Asp Val Val Leu Thr Ala Gly Gly Asp Glu Ile Val Ser Gly Leu
    515                 520                 525

His Gly Thr Ser Asp Leu Thr Thr Cys Ser Gly Asn
    530                 535                 540
```

<210> SEQ ID NO 34
<211> LENGTH: 2012
<212> TYPE: DNA
<213> ORGANISM: M. phaseolina

<400> SEQUENCE: 34

```
gggggaggcc aatgcatgtc agcaaaatac ctgtggctac ccctgttatg gccacatcca     60
gcccattttg aatggacggt ataaaatctc ttctgaaacc ttcagaaaat taaggcaggg    120
actattgaag gttttgccgt atctgccaaa atgcggtttc tcgggggctt ctatctactc    180
cttgctgcca ctcgccacac acctacggcc agagctgcgc tgcactaccc aaatgccctc    240
atttctcgca tggaacacct gctggttgat acggacggct cattcaggtc tggtttcaag    300
gacgccatca acccctgcac gaactacatt tcaggtgccc aaacgctggg gcggcagacc    360
tctgcacagt ggctccgagt tgccttccat gatttcgtca cggcccacgt cgacgagggc    420
actggcggga tcgacgcgtc catcggcttc gaaactctcc gagcagaaga ttccgggtcc    480
gcattcaatg acagtttcgc cttctttgct ccgttcgtgg atgcgcaaac ttccagtatc    540
acccatcgag ccttccccgt cgagggccgt ggcatgcgct gacgtccttg cagtggccga    600
cctcgtagcc ctctctgtgg tgacttctct gggccactgc ggtggtctgc atgtcccata    660
tcgagcgggc cgtatcgatg ctacgggcgg agggccgttc ggcgttcccg aacccgagac    720
aagcctggaa gagaccctgg aagagtttgc caatgctggt ttcaatgctg aagatgccat    780
tggattaacg gcgtgcgggc attctctcgg ccgcgtccat cacggcgggt tccccaacgt    840
cgtgcccgaa tcggccatag caccaaacaa caccgcgggc ggcgtgaacc tggactccac    900
acgggataaa ttcgacatca gcattgtcaa agaatacctc ggcaactatg gcagcgcgg    960
cggacctctc gttaccagtg acaacgtgac tgtccgctcg gatcttcggc tgtacgaaag   1020
cgatcagaac aggacaatgc aagctctcgg tcagtcaaaa gaatacttct ttagcacctg   1080
tggaaatcta tttgagagga tgatcaacac cgttccgcgc gaggtcactt tgtcagatgt   1140
catccatccg atgacggtgc agccggtgaa tttcacgttc gatatcatca atgaccaggc   1200
gctgaggtta tcaggagtag tgcgggtgag cttccaaata gagctgtttc ggtctgcacg   1260
caactgaccg agccccgcag tatttgccct cagataatgc tgcaccgtcg acgctcgagg   1320
tctcactcgc cgacaaagcc ggaaagacta tggcatccat tacagcaagg gttattgaag   1380
agaaagggaa tagtttctgg ggggccacag cttactaccc ggtcgttttt gacataaacc   1440
ttgctgggat tgcttctcgc aacaatcttc ctgggaagct ccaggttcgc acagcatctc   1500
ctcagacatt tgagctgcaa ccggagctgt ttttcatacc atcccgttct agccctggca   1560
cggggataag tgtgggggct gccataggtg ctgctgcgcg tcccgcaac tcgactctga   1620
gtgtagagag tgtggaagcc gtggtcagtg tgccggtatc ccagacggga acactggcac   1680
cgaaggtcga gaagcatgag ttgaatctcg aaagagatca agatattggt ttgtactcta   1740
tattcaaggg gaacctaagc gatgatttgg ctttcaacct gcagacgacc gttgatatca   1800
cggcaacttt ttcagacggc actgtctggc aagatagtta caacagattt gcagtgccgt   1860
agagcatcct gaaaatgtct tcgtcaaaat gccttcatag ggccagcaac aaattttcag   1920
gcagatatgt agctagagag tcattcaaat acaaatgtct tggttgtcga acaagttcgt   1980
```

```
gagacgctgc tcatgcacaa tacaagtgag cc                                   2012
```

<210> SEQ ID NO 35
<211> LENGTH: 1599
<212> TYPE: DNA
<213> ORGANISM: M. phaseolina

<400> SEQUENCE: 35

```
atgcggtttc tcgggggctt ctatctactc cttgctgcca ctcgccacac acctacggcc      60
agagctgcgc tgcactaccc aaatgccctc atttctcgca tggaacacct gctggttgat     120
acggacggct cattcaggtc tggtttcaag gacgccatca cccctgcac gaactacatt      180
tcaggtgccc aaacgctggg gcggcagacc tctgcacagt ggctccgagt tgccttccat     240
gatttcgtca cggcccacgt cgacgagggc actggcggga tcgacgcgtc catcggcttc     300
gaaactctcc gagcagaaga ttccgggtcc gcattcaatg acagtttcgc cttctttgct     360
ccgttcgtgg atgcgcaaac ttccatggcc gacctcgtag ccctctctgt ggtgacttct     420
ctgggccact gcggtggtct gcatgtccca tatcgagcgg gccgtatcga tgctacgggc     480
ggagggccgt tcggcgttcc cgaacccgag acaagcctgg aagagaccct ggaagagttt     540
gccaatgctg gtttcaatgc tgaagatgcc attggattaa cggcgtgcgg gcattctctc     600
ggccgcgtcc atcacggcgg gttcccccaac gtcgtgcccg aatcggccat agcaccaaac     660
aacaccgcgg gcggcgtgaa cctggactcc acacgggata aattcgacat cagcattgtc     720
aaagaatacc tcggcaacta tgggcagcgc ggcggacctc tcgttaccag tgacaacgtg     780
actgtccgct cggatcttcg gctgtacgaa agcgatcaga caggacaat gcaagctctc     840
ggtcagtcaa aagaatactt ctttagcacc tgtggaaatc tatttgagag atgatcaac     900
accgttccgc gcgaggtcac tttgtcagat gtcatccatc cgatgacggt gcagccggtg     960
aatttcacgt tcgatatcat caatgaccag gcgctgaggt tatcaggagt agtgcggtat    1020
ttgccctcag ataatgctgc accgtcgacg ctcgaggtct cactcgccga caaagccgga    1080
aagactatgg catccattac agcaagggtt attgaagaga aagggaatag tttctggggg    1140
gccacagctt actaccggt cgttttgac ataaaccttg ctgggattgc ttctcgcaac    1200
aatcttcctg ggaagctcca ggttcgcaca gcatctcctc agacatttga gctgcaaccg    1260
gagctgtttt tcataccatc ccgttctagc cctggcacgg gataagtgt gggggctgcc    1320
ataggtgctg ctgcgcggtc ccgcaactcg actctgagtg tagagagtgt ggaagccgtg    1380
gtcagtgtgc cggtatccca gacgggaaca ctggcaccga aggtcgagaa gcatgagttg    1440
aatctcgaaa gagatcaaga tattggtttg tactctatat tcaaggggaa cctaagcgat    1500
gatttggctt tcaacctgca gacgaccgtt gatatcacgg caacttttc agacggcact    1560
gtctggcaag atagttacaa cagatttgca gtgccgtag                           1599
```

<210> SEQ ID NO 36
<211> LENGTH: 532
<212> TYPE: PRT
<213> ORGANISM: M. phaseolina

<400> SEQUENCE: 36

```
Met Arg Phe Leu Gly Gly Phe Tyr Leu Leu Leu Ala Ala Thr Arg His
1               5                   10                  15

Thr Pro Thr Ala Arg Ala Ala Leu His Tyr Pro Asn Ala Leu Ile Ser
            20                  25                  30
```

```
Arg Met Glu His Leu Leu Val Asp Thr Asp Gly Ser Phe Arg Ser Gly
         35                  40                  45

Phe Lys Asp Ala Ile Asn Pro Cys Thr Asn Tyr Ile Ser Gly Ala Gln
     50                  55                  60

Thr Leu Gly Arg Gln Thr Ser Ala Gln Trp Leu Arg Val Ala Phe His
 65                  70                  75                  80

Asp Phe Val Thr Ala His Val Asp Glu Gly Thr Gly Gly Ile Asp Ala
                 85                  90                  95

Ser Ile Gly Phe Glu Thr Leu Arg Ala Glu Asp Ser Gly Ser Ala Phe
             100                 105                 110

Asn Asp Ser Phe Ala Phe Phe Ala Pro Phe Val Asp Ala Gln Thr Ser
         115                 120                 125

Met Ala Asp Leu Val Ala Leu Ser Val Val Thr Ser Leu Gly His Cys
130                 135                 140

Gly Gly Leu His Val Pro Tyr Arg Ala Gly Arg Ile Asp Ala Thr Gly
145                 150                 155                 160

Gly Gly Pro Phe Gly Val Pro Glu Pro Glu Thr Ser Leu Glu Glu Thr
                 165                 170                 175

Leu Glu Glu Phe Ala Asn Ala Gly Phe Asn Ala Glu Asp Ala Ile Gly
             180                 185                 190

Leu Thr Ala Cys Gly His Ser Leu Gly Arg Val His His Gly Gly Phe
         195                 200                 205

Pro Asn Val Val Pro Glu Ser Ala Ile Ala Pro Asn Asn Thr Ala Gly
     210                 215                 220

Gly Val Asn Leu Asp Ser Thr Arg Asp Lys Phe Asp Ile Ser Ile Val
225                 230                 235                 240

Lys Glu Tyr Leu Gly Asn Tyr Gly Gln Arg Gly Gly Pro Leu Val Thr
                 245                 250                 255

Ser Asp Asn Val Thr Val Arg Ser Asp Leu Arg Leu Tyr Glu Ser Asp
             260                 265                 270

Gln Asn Arg Thr Met Gln Ala Leu Gly Gln Ser Lys Glu Tyr Phe Phe
         275                 280                 285

Ser Thr Cys Gly Asn Leu Phe Glu Arg Met Ile Asn Thr Val Pro Arg
     290                 295                 300

Glu Val Thr Leu Ser Asp Val Ile His Pro Met Thr Val Gln Pro Val
305                 310                 315                 320

Asn Phe Thr Phe Asp Ile Ile Asn Asp Gln Ala Leu Arg Leu Ser Gly
                 325                 330                 335

Val Val Arg Tyr Leu Pro Ser Asp Asn Ala Ala Pro Ser Thr Leu Glu
             340                 345                 350

Val Ser Leu Ala Asp Lys Ala Gly Lys Thr Met Ala Ser Ile Thr Ala
         355                 360                 365

Arg Val Ile Glu Glu Lys Gly Asn Ser Phe Trp Gly Ala Thr Ala Tyr
     370                 375                 380

Tyr Pro Val Val Phe Asp Ile Asn Leu Ala Gly Ile Ala Ser Arg Asn
385                 390                 395                 400

Asn Leu Pro Gly Lys Leu Gln Val Arg Thr Ala Ser Pro Gln Thr Phe
                 405                 410                 415

Glu Leu Gln Pro Glu Leu Phe Phe Ile Pro Ser Arg Ser Ser Pro Gly
             420                 425                 430

Thr Gly Ile Ser Val Gly Ala Ala Ile Gly Ala Ala Ala Arg Ser Arg
         435                 440                 445

Asn Ser Thr Leu Ser Val Glu Ser Val Glu Ala Val Val Ser Val Pro
```

```
                450              455              460
Val Ser Gln Thr Gly Thr Leu Ala Pro Lys Val Glu Lys His Glu Leu
465                 470                 475                 480

Asn Leu Glu Arg Asp Gln Asp Ile Gly Leu Tyr Ser Ile Phe Lys Gly
                485                 490                 495

Asn Leu Ser Asp Asp Leu Ala Phe Asn Leu Gln Thr Thr Val Asp Ile
            500                 505                 510

Thr Ala Thr Phe Ser Asp Gly Thr Val Trp Gln Asp Ser Tyr Asn Arg
        515                 520                 525

Phe Ala Val Pro
    530

<210> SEQ ID NO 37
<211> LENGTH: 2401
<212> TYPE: DNA
<213> ORGANISM: M. phaseolina

<400> SEQUENCE: 37
```

| | | | | | |
|---|---|---|---|---|---|
| ttttaatata | ttctgccgct | aaaacgttcg | ccatgtgctc | ctgattttc | tcgaccgcca | 60 |
| tttctcgcct | ccgcatcggc | tccctgcttc | ggcgcgctcg | tcgctagcat | ccagtttcgc | 120 |
| cagtccttcc | gtttctcccg | ctcttgaacc | atggcaaggc | atcccggcct | gaccctggtg | 180 |
| tgggtcgcag | gcgtggtcta | ccacgccatt | ggcaccgctg | ctgccccgac | atggccatct | 240 |
| tccatggatg | aactggagga | catcatggtc | ctcaacaccg | gctaccgcgc | ccgcagcttc | 300 |
| gcagtgcccg | tcacacctg | cggcttctcg | tcgcaaggcc | ccggacgcgt | ccaagctgcc | 360 |
| gaatggatac | gaaccgcctt | ccacgacatg | gctcccggca | gcgtgtatac | cggcgtcgga | 420 |
| ggactggacg | catcgatagc | ttacgaaaca | cggagcttgg | aaaatctcgg | ccccgccttc | 480 |
| aacaccacac | tagctaccta | cgcgccgtat | ctgacaagca | gatcttccat | ggctgacatc | 540 |
| attgcgctag | gagtctacac | ggcggtgcgg | tcatgcggag | gtccaatcgt | gcctatccgg | 600 |
| acaggcagag | tagacgcaaa | ggcagcaggc | ccgcaaggtg | tgcctctgcc | gcagaattct | 660 |
| atcggaactt | ttcaaaacca | gtttctccgt | actggcttca | acacgacgga | gatgatccaa | 720 |
| gtggtggcgt | gtggccacac | tctgggcggc | gtgcacgcat | ctgccaaccc | ggagatcgtg | 780 |
| cccgtgggt | cggcggagga | cggcgtcgtc | aagttcgaca | cgacggacgc | gtttgacaac | 840 |
| aaggttgtca | ccgagtacct | ctcgaataca | accaagaact | cgcttgttgt | gggccctct | 900 |
| actgcgaacg | gccggaactc | ggacgctcgt | gtctttgcgg | cggatggaaa | tgctacggtc | 960 |
| agggctctgg | ctgaccctga | tacgttcaac | agtgtttgcg | ctaggatgct | gcagaagatg | 1020 |
| attgatgttg | ttccaacggg | cgtggtgctc | actgacccga | tttcaatcta | tgatgtcaaa | 1080 |
| cccagtgggc | tgcagctgac | attgcttggt | ggaggagagt | cggtaaagct | tacgggagat | 1140 |
| atccgtgtta | ggactacgga | gcgctctgcg | agccagattg | agaaggtcga | gcttgtctac | 1200 |
| aaggaccgcg | aggggccga | atcctcgaca | gctttgagca | ccgaatcctc | aggttcggcc | 1260 |
| tctgggttcg | atgacagctt | cgaggtataa | ctcatcctaa | gccctgttg | ggatgccaca | 1320 |
| ctaacggccg | agaaagttct | acggggtctc | cgcaaacatc | cccaccgact | ccggcatctc | 1380 |
| ctcattcaac | gtcctcatca | ccctcaccag | cggcgaaacc | gaacttcacg | acaataatgg | 1440 |
| cagcggtttc | ccctccaag | acaccgtcat | cttcaaagc | ccgcagagct | gcctcagcgg | 1500 |
| caccaccatg | accgtcgccg | ccgccgtcct | caataccgcc | tcctccgccc | caccctcag | 1560 |
| cgtcacccctc | aaggtcccca | actcccgctc | cgtcctcccc | gtcctccagg | tcagcacagt | 1620 |

| | |
|---|---:|
| cgccatgacg aagagctcgt ctgtcggccc gtacgacctc tactcaacca catacacgct | 1680 |
| aacctccgcc caactcgccg acacgcgctt tgacgtcaag ctcggcgctg ccgccgccga | 1740 |
| cgccttcaag tcctccgccg acctcggtga tgcctgccag gacctgagcc ccgaaccgcc | 1800 |
| cacttcttcc agcgcgccta gctcctcgag cacggctgcg ccgccggcct cgtcctcctc | 1860 |
| tgccgcacca agctcctctg acctcccggc cccctccccc agcacaacac ccacgtcctc | 1920 |
| ccacccaatc tcctcatcta caacattagc atcatcgacc accccaacgc ccacaacact | 1980 |
| cgcctgcccc gccgctgacg gcgccacctg gacgctatcc ggcggccaga agttcgccgt | 2040 |
| caagtgcggc aaggactacc aggccggcca gatcggcgtc acgtggacgg ccagcttcga | 2100 |
| ggcctgtctg caggcgtgcg tggatacgga cacgtgccag gcggtcgcat tcgtggggag | 2160 |
| tgcagaggcg ggcgggcagt gctacttgaa ggaccagagc gcgggcagtg tggatgttga | 2220 |
| gggggtgtgg gggggcggttc tggaaagctg agcggtcggg cgatggagta ggggatagag | 2280 |
| ggtttgggct gggggtaat gaattacttc tgatgagctt ctactactgc aggtggcaca | 2340 |
| aatcatggcc tctcatggac ctccgacgcc gcatgctgcc cgcgtttcaa ggtattcttg | 2400 |
| g | 2401 |

<210> SEQ ID NO 38
<211> LENGTH: 2049
<212> TYPE: DNA
<213> ORGANISM: M. phaseolina

<400> SEQUENCE: 38

| | |
|---|---:|
| atggcaaggc atcccggcct gaccctggtg tgggtcgcag gcgtggtcta ccacgccatt | 60 |
| ggcaccgctg ctgccccgac atggccatct tccatggatg aactggagga catcatggtc | 120 |
| ctcaacaccg ctaccgcgc ccgcagcttc gcagtgcccg tcacaccctg cggcttctcg | 180 |
| tcgcaaggcc ccggacgcgt ccaagctgcc gaatggatac gaaccgcctt ccacgacatg | 240 |
| gctcccggca gcgtgtatac cggcgtcgga ggactgacg catcgatagc ttacgaaaca | 300 |
| cggagcttgg aaaatctcgg ccccgccttc aacaccacac tagctaccta cgcgccgtat | 360 |
| ctgacaagca gatcttccat ggctgacatc attgcgctag gagtctacac ggcggtgcgg | 420 |
| tcatgcggag gtccaatcgt gcctatccgg acaggcagag tagacgcaaa ggcagcaggc | 480 |
| ccgcaaggtg tgcctctgcc gcagaattct atcggaactt ttcaaaacca gtttctccgt | 540 |
| actggcttca acacgacgga gatgatccaa gtggtggcgt gtggccacac tctgggcggc | 600 |
| gtgcacgcat ctgccaaccc ggagatcgtg cccgtggggt cggcggagga cggcgtcgtc | 660 |
| aagttcgaca cgacggacgc gtttgacaac aaggttgtca ccgagtacct ctcgaataca | 720 |
| accaagaact cgcttgttgt gggcccctct actgcgaacg gccggaactc ggacgctcgt | 780 |
| gtctttgcgg cggatggaaa tgctacggtc agggctctgg ctgaccctga tacgttcaac | 840 |
| agtgtttgcg ctaggatgct gcagaagatg attgatgttg ttccaacggg cgtggtgctc | 900 |
| actgacccga tttcaatcta tgatgtcaaa cccagtgggc tgcagctgac attgcttggt | 960 |
| ggaggagagt cggtaaagct tacgggagat atccgtgtta ggactacgga gcgctctgcg | 1020 |
| agccagattg agaaggtcga gcttgtctac aaggaccgcg aggggccgga atcctcgaca | 1080 |
| gctttgagca ccgaatcctc aggttcggcc tctgggttcg atgacagctt cgagttctac | 1140 |
| ggggtctccg caaacatccc caccgactcc ggcatctcct cattcaacgt cctcatcacc | 1200 |
| ctcaccagcg gcgaaaccga acttcacgac aataatggca gcggtttccc cctccaagac | 1260 |
| accgtcatct ttcaaagccc gcagagctgc ctcagcggca ccaccatgac cgtcgccgcc | 1320 |

```
gccgtcctca ataccgcctc ctccgccccc accctcagcg tcaccctcaa ggtccccaac    1380
tcccgctccg tcctccccgt cctccaggtc agcacagtcg ccatgacgaa gagctcgtct    1440
gtcggcccgt acgacctcta ctcaaccaca tacacgctaa cctccgccca actcgccgac    1500
acgcgctttg acgtcaagct cggcgctgcc gccgccgacg ccttcaagtc ctccgccgac    1560
ctcggtgatg cctgccagga cctgagcccc gaaccgccca cttcttccag cgcgcctagc    1620
tcctcgagca cggctgcgcc gccggcctcg tcctcctctg ccgcaccaag ctcctctgac    1680
ctcccggccc cctcccccag cacaacaccc acgtcctccc acccaatctc ctcatctaca    1740
acattagcat catcgaccac cccaacgccc acaacactcg cctgccccgc cgctgacggc    1800
gccacctgga cgctatccgg cggccagaag ttcgccgtca agtgcggcaa ggactaccag    1860
gccggccaga tcggcgtcac gtggacggcc agcttcgagg cctgtctgca ggcgtgcgtg    1920
gatacggaca cgtgccaggc ggtcgcattc gtggggagtg cagaggcggg cgggcagtgc    1980
tacttgaagg accagagcgc gggcagtgtg gatgttgagg gggtgtgggg ggcggttctg    2040
gaaagctga                                                            2049
```

<210> SEQ ID NO 39
<211> LENGTH: 682
<212> TYPE: PRT
<213> ORGANISM: M. phaseolina

<400> SEQUENCE: 39

```
Met Ala Arg His Pro Gly Leu Thr Leu Val Trp Val Ala Gly Val Val
1               5                   10                  15

Tyr His Ala Ile Gly Thr Ala Ala Pro Thr Trp Pro Ser Ser Met
                20                  25                  30

Asp Glu Leu Glu Asp Ile Met Val Leu Asn Thr Gly Tyr Arg Ala Arg
        35                  40                  45

Ser Phe Ala Val Pro Val Thr Pro Cys Gly Phe Ser Ser Gln Gly Pro
    50                  55                  60

Gly Arg Val Gln Ala Ala Glu Trp Ile Arg Thr Ala Phe His Asp Met
65                  70                  75                  80

Ala Pro Gly Ser Val Tyr Thr Gly Val Gly Leu Asp Ala Ser Ile
                85                  90                  95

Ala Tyr Glu Thr Arg Ser Leu Glu Asn Leu Gly Pro Ala Phe Asn Thr
            100                 105                 110

Thr Leu Ala Thr Tyr Ala Pro Tyr Leu Thr Ser Arg Ser Ser Met Ala
        115                 120                 125

Asp Ile Ile Ala Leu Gly Val Tyr Thr Ala Val Arg Ser Cys Gly Gly
    130                 135                 140

Pro Ile Val Pro Ile Arg Thr Gly Arg Val Asp Ala Lys Ala Ala Gly
145                 150                 155                 160

Pro Gln Gly Val Pro Leu Pro Gln Asn Ser Ile Gly Thr Phe Gln Asn
                165                 170                 175

Gln Phe Leu Arg Thr Gly Phe Asn Thr Thr Glu Met Ile Gln Val Val
            180                 185                 190

Ala Cys Gly His Thr Leu Gly Gly Val His Ala Ser Ala Asn Pro Glu
        195                 200                 205

Ile Val Pro Val Gly Ser Ala Glu Asp Gly Val Val Lys Phe Asp Thr
    210                 215                 220

Thr Asp Ala Phe Asp Asn Lys Val Val Thr Glu Tyr Leu Ser Asn Thr
225                 230                 235                 240
```

-continued

```
Thr Lys Asn Ser Leu Val Val Gly Pro Ser Thr Ala Asn Gly Arg Asn
            245                 250                 255

Ser Asp Ala Arg Val Phe Ala Ala Asp Gly Asn Ala Thr Val Arg Ala
        260                 265                 270

Leu Ala Asp Pro Asp Thr Phe Asn Ser Val Cys Ala Arg Met Leu Gln
    275                 280                 285

Lys Met Ile Asp Val Val Pro Thr Gly Val Val Leu Thr Asp Pro Ile
290                 295                 300

Ser Ile Tyr Asp Val Lys Pro Ser Gly Leu Gln Leu Thr Leu Leu Gly
305                 310                 315                 320

Gly Gly Glu Ser Val Lys Leu Thr Gly Asp Ile Arg Val Arg Thr Thr
                325                 330                 335

Glu Arg Ser Ala Ser Gln Ile Glu Lys Val Glu Leu Val Tyr Lys Asp
            340                 345                 350

Arg Glu Gly Ala Glu Ser Ser Thr Ala Leu Ser Thr Glu Ser Ser Gly
        355                 360                 365

Ser Ala Ser Gly Phe Asp Asp Ser Phe Glu Phe Tyr Gly Val Ser Ala
    370                 375                 380

Asn Ile Pro Thr Asp Ser Gly Ile Ser Ser Phe Asn Val Leu Ile Thr
385                 390                 395                 400

Leu Thr Ser Gly Glu Thr Glu Leu His Asp Asn Asn Gly Ser Gly Phe
                405                 410                 415

Pro Leu Gln Asp Thr Val Ile Phe Gln Ser Pro Gln Ser Cys Leu Ser
            420                 425                 430

Gly Thr Thr Met Thr Val Ala Ala Val Leu Asn Thr Ala Ser Ser
        435                 440                 445

Ala Pro Thr Leu Ser Val Thr Leu Lys Val Pro Asn Ser Arg Ser Val
    450                 455                 460

Leu Pro Val Leu Gln Val Ser Thr Val Ala Met Thr Lys Ser Ser Ser
465                 470                 475                 480

Val Gly Pro Tyr Asp Leu Tyr Ser Thr Thr Tyr Leu Thr Ser Ala
                485                 490                 495

Gln Leu Ala Asp Thr Arg Phe Asp Val Lys Leu Gly Ala Ala Ala
            500                 505                 510

Asp Ala Phe Lys Ser Ser Ala Asp Leu Gly Asp Ala Cys Gln Asp Leu
        515                 520                 525

Ser Pro Glu Pro Pro Thr Ser Ser Ala Pro Ser Ser Ser Thr
    530                 535                 540

Ala Ala Pro Pro Ala Ser Ser Ser Ala Ala Pro Ser Ser Ser Asp
545                 550                 555                 560

Leu Pro Ala Pro Ser Pro Ser Thr Thr Pro Thr Ser Ser His Pro Ile
                565                 570                 575

Ser Ser Ser Thr Thr Leu Ala Ser Ser Thr Thr Pro Thr Pro Thr Thr
            580                 585                 590

Leu Ala Cys Pro Ala Ala Asp Gly Ala Thr Trp Thr Leu Ser Gly Gly
        595                 600                 605

Gln Lys Phe Ala Val Lys Cys Gly Lys Asp Tyr Gln Ala Gly Gln Ile
    610                 615                 620

Gly Val Thr Trp Thr Ala Ser Phe Glu Ala Cys Leu Gln Ala Cys Val
625                 630                 635                 640

Asp Thr Asp Thr Cys Gln Ala Val Ala Phe Val Gly Ser Ala Glu Ala
                645                 650                 655
```

```
Gly Gly Gln Cys Tyr Leu Lys Asp Gln Ser Ala Gly Ser Val Asp Val
            660                 665                 670

Glu Gly Val Trp Gly Ala Val Leu Glu Ser
        675                 680

<210> SEQ ID NO 40
<211> LENGTH: 2004
<212> TYPE: DNA
<213> ORGANISM: M. phaseolina

<400> SEQUENCE: 40
```

| | | | | |
|---|---|---|---|---|
| ccttcctgaa | atttcatggc | cagcttctcg | gtctttctaa | tgaattataa ggctatcttc | 60 |
| ctgcagcttg | tcgtctgcac | gttctaggat | tcaaccaccc | gtcattcctt ctcaaaatct | 120 |
| cagtccagtc | gttacagcta | atcacttaat | atgaagcccg | ccgctcttgc aggcattggc | 180 |
| ctgcttaatg | tcctacccat | taccgccgaa | tacgtctggc | cttctaaata cgactatttg | 240 |
| gaagacctgc | tttaccttca | atccggttat | ctgcgtgagg | gatttgtcga cggtatgcat | 300 |
| atatgaacaa | ctgctggtgt | cccccaacta | atggctttta | ggtgtggctc cttgttcgtt | 360 |
| ttcctccgct | ggacctggcc | gtcaaaccgc | agcggaatgg | gtccgcactg cataccatga | 420 |
| tatgccact | catgatgccg | atgctggcac | tggtggcttg | gacgcctcta tcatgtttga | 480 |
| gaccgagcgg | gacgaaaacg | tgggcgatgc | gttcaatggt | accttcggct ttacaaacaa | 540 |
| ctactacaac | atcaaagcat | ccgctgctga | tcttcttgca | ctctccactg tcatcgccgt | 600 |
| tggaaactgc | ggtggcccga | agattccttt | ccgtgtcggt | cgcgtggacg ccacggaggc | 660 |
| tggccctctg | ggtgttccca | agccggatca | agacgttgat | acgcacattc aaatttttgc | 720 |
| caaggcaggc | tttaacacca | gtaggccttg | aattacctga | ggtccaccta ccagccgctg | 780 |
| actagaatag | gcgacatgat | caccatggtg | gcctgcggcc | acacccttgg tggcgtccat | 840 |
| ggcaaggact | ccccgagat | cactttcaac | gacacggaga | ccaatttcgt caagttcgaa | 900 |
| ggcaacaact | ccttctccaa | cttttgataac | ccgtcgtga | ccgagtatct tggcggaaac | 960 |
| cccccaacc | ccctcgtcac | cggcaagaac | gagaccaaca | acagcgataa gcgcgtcttt | 1020 |
| ggtgccgaca | caacgccac | aatgcactcc | ctgtcggacc | cctccgtctt ccagtcctcc | 1080 |
| tgccaagaca | tcctcgcccg | catgatcgac | accgtccct | ccaacgtcgc tctcaccgag | 1140 |
| cctctcgacc | caatcctcat | caagcccctac | atccaaacct | tctccctcgt caacgccacc | 1200 |
| cacctcaccc | tgaccggccg | catccgcgtc | cgtaccgact | gggacagcta caccgaccag | 1260 |
| tcagtccacc | tcacctacaa | cccgcgcaca | gcgcccgccc | agaatgcgac cctcaacacc | 1320 |
| accatcccca | ccaccgcgc | caccttccag | ggcggcacct | ccagcggcat ctttggtgaa | 1380 |
| gtcttcgcct | ggcacgagtt | ctccgccacc | ctccccacat | ccagctcgat taccggcttc | 1440 |
| actgtcaccg | tcacgcgcgg | ctccacgggc | gaatccacca | cctacgacaa cgccggcagc | 1500 |
| acgaacggct | acgcgctcga | cgacacgctg | ctctaccaga | gcgcgcagtc gtgccgcgac | 1560 |
| gtcggcacca | caaccatcac | cgctgctgtg | cgcaaggact | cctcgcccg aggtgcaaag | 1620 |
| gtcgccgtcg | agatggtgaa | cagggtgccg | cgccagggcg | tgtacgtgcc ggcgctagag | 1680 |
| gtcgaaccgt | gggggcgga | gacggtcaag | gaggtcggcg | agtgggtcat cgtgcaggct | 1740 |
| aagggtgagt | tgacgatgga | gagcttgagc | acaacgtttg | acgtcgttgc gggcgagaaa | 1800 |
| agggtcgagt | tccaaaggac | gaatgtgctg | ggggaggagt | gtgcggctct gtgaggcgta | 1860 |
| acttaaaaaa | aaaaaaaaag | gaaggatata | tcagttctg | gtacatactt cgaatgaaag | 1920 |
| tctatgattc | gtatgtccat | aacattactc | taggcttgaa | acaacaatgc tgaatgtgct | 1980 | ttattgtgag ataaagagtg tcct                                           2004

<210> SEQ ID NO 41
<211> LENGTH: 1605
<212> TYPE: DNA
<213> ORGANISM: M. phaseolina

<400> SEQUENCE: 41
atgaagcccg ccgctcttgc aggcattggc ctgcttaatg tcctacccat taccgccgaa    60
tacgtctggc cttctaaata cgactatttg gaagacctgc tttaccttca atccggttat   120
ctgcgtgagg gatttgtcga cggtgtggct ccttgttcgt tttcctccgc tggacctggc   180
cgtcaaaccg cagcggaatg ggtccgcact gcataccatg atatggccac tcatgatgcc   240
gatgctggca ctggtggctt ggacgcctct atcatgtttg agaccgagcg ggacgaaaac   300
gtgggcgatg cgttcaatgg taccttcggc tttacaaaca actactacaa catcaaagca   360
tccgctgctg atcttcttgc actctccact gtcatcgccg ttggaaactg cggtggcccg   420
aagattcctt tccgtgtcgg tcgcgtggac gccacggagg ctggccctct gggtgttccc   480
aagccggatc aagacgttga tacgcacatt caaattttttg ccaaggcagg ctttaacacc   540
agcgacatga tcaccatggt ggcctgcggc cacacccttg gtggcgtcca tggcaaggac   600
ttccccgaga tcactttcaa cgacacggag accaatttcg tcaagttcga aggcaacaac   660
tccttctcca actttgataa caccgtcgtg accgagtatc ttggcggaaa cccccccaac   720
cccctcgtca ccggcaagaa cgagaccaac aacagcgata gcgcgtcttt ggtgccgac    780
aacaacgcca caatgcactc cctgtcggac cctccgtct  tccagtcctc ctgccaagac   840
atcctcgccc gcatgatcga caccgtcccc tccaacgtcg ctctcaccga gcctctcgac   900
ccaatcctca tcaagcccta catccaaacc ttctccctcg tcaacgccac ccacctcacc   960
ctgaccggcc gcatccgcgt ccgtaccgac tgggacagct acaccgacca gtcagtccac  1020
ctcacctaca acccgcgcac agcgcccgcc cagaatgcga ccctcaacac caccatcccc  1080
accacccgcg ccaccttcca gggcggcacc tccagcggca tctttggtga agtcttcgcc  1140
tggcacgagt tctccgccac cctccccaca tccagctcga ttaccggctt cactgtcacc  1200
gtcacgcgcg gctccacggg cgaatccacc acctacgaca acgccggcag cacgaacggc  1260
tacgcgctcg acgacacgct gctctaccag agcgcgcagt cgtgccgcga cgtcggcacc  1320
acaaccatca ccgctgctgt gcgcaaggac ttcctcgccc gaggtgcaaa ggtcgccgtc  1380
gagatggtga cagggtgcc gcgccagggc gtgtacgtgc cggcgctaga ggtcgaaccg  1440
tgggggcgg agacggtcaa ggaggtcggc gagtgggtca tcgtgcaggc taagggtgag  1500
ttgacgatga gagcttgag cacaacgttt gacgtcgttg cgggcgagaa aagggtcgag  1560
ttccaaagga cgaatgtgct ggggaggag tgtgcggctc tgtga                   1605

<210> SEQ ID NO 42
<211> LENGTH: 534
<212> TYPE: PRT
<213> ORGANISM: M. phaseolina

<400> SEQUENCE: 42

Met Lys Pro Ala Ala Leu Ala Gly Ile Gly Leu Leu Asn Val Leu Pro
 1               5                  10                  15

Ile Thr Ala Glu Tyr Val Trp Pro Ser Lys Tyr Asp Tyr Leu Glu Asp
            20                  25                  30

-continued

```
Leu Leu Tyr Leu Gln Ser Gly Tyr Leu Arg Glu Gly Phe Val Asp Gly
             35                  40                  45

Val Ala Pro Cys Ser Phe Ser Ala Gly Pro Gly Arg Gln Thr Ala
 50                  55                  60

Ala Glu Trp Val Arg Thr Ala Tyr His Asp Met Ala Thr His Asp Ala
 65                  70                  75                  80

Asp Ala Gly Thr Gly Gly Leu Asp Ala Ser Ile Met Phe Glu Thr Glu
                 85                  90                  95

Arg Asp Glu Asn Val Gly Asp Ala Phe Asn Gly Thr Phe Gly Phe Thr
                100                 105                 110

Asn Asn Tyr Tyr Asn Ile Lys Ala Ser Ala Ala Asp Leu Leu Ala Leu
                115                 120                 125

Ser Thr Val Ile Ala Val Gly Asn Cys Gly Gly Pro Lys Ile Pro Phe
    130                 135                 140

Arg Val Gly Arg Val Asp Ala Thr Glu Ala Gly Pro Leu Gly Val Pro
145                 150                 155                 160

Lys Pro Asp Gln Asp Val Asp Thr His Ile Gln Ile Phe Ala Lys Ala
                165                 170                 175

Gly Phe Asn Thr Ser Asp Met Ile Thr Met Val Ala Cys Gly His Thr
                180                 185                 190

Leu Gly Gly Val His Gly Lys Asp Phe Pro Glu Ile Thr Phe Asn Asp
    195                 200                 205

Thr Glu Thr Asn Phe Val Lys Phe Glu Gly Asn Asn Ser Phe Ser Asn
    210                 215                 220

Phe Asp Asn Thr Val Val Thr Glu Tyr Leu Gly Gly Asn Pro Pro Asn
225                 230                 235                 240

Pro Leu Val Thr Gly Lys Asn Glu Thr Asn Asn Ser Asp Lys Arg Val
                245                 250                 255

Phe Gly Ala Asp Asn Asn Ala Thr Met His Ser Leu Ser Asp Pro Ser
                260                 265                 270

Val Phe Gln Ser Ser Cys Gln Asp Ile Leu Ala Arg Met Ile Asp Thr
    275                 280                 285

Val Pro Ser Asn Val Ala Leu Thr Glu Pro Leu Asp Pro Ile Leu Ile
    290                 295                 300

Lys Pro Tyr Ile Gln Thr Phe Ser Leu Val Asn Ala Thr His Leu Thr
305                 310                 315                 320

Leu Thr Gly Arg Ile Arg Val Arg Thr Asp Trp Ser Tyr Thr Asp
                325                 330                 335

Gln Ser Val His Leu Thr Tyr Asn Pro Arg Thr Ala Pro Ala Gln Asn
                340                 345                 350

Ala Thr Leu Asn Thr Thr Ile Pro Thr Thr Arg Ala Thr Phe Gln Gly
    355                 360                 365

Gly Thr Ser Ser Gly Ile Phe Gly Glu Val Phe Ala Trp His Glu Phe
    370                 375                 380

Ser Ala Thr Leu Pro Thr Ser Ser Ile Thr Gly Phe Thr Val Thr
385                 390                 395                 400

Val Thr Arg Gly Ser Thr Gly Glu Ser Thr Thr Tyr Asp Asn Ala Gly
                405                 410                 415

Ser Thr Asn Gly Tyr Ala Leu Asp Asp Thr Leu Leu Tyr Gln Ser Ala
                420                 425                 430

Gln Ser Cys Arg Asp Val Gly Thr Thr Thr Ile Thr Ala Ala Val Arg
    435                 440                 445

Lys Asp Phe Leu Ala Arg Gly Ala Lys Val Ala Val Glu Met Val Asn
```

```
                     450              455              460
Arg Val Pro Arg Gln Gly Val Tyr Val Pro Ala Leu Glu Val Glu Pro
465                 470                 475                 480

Trp Gly Ala Glu Thr Val Lys Glu Val Gly Glu Trp Val Ile Val Gln
                485                 490                 495

Ala Lys Gly Glu Leu Thr Met Glu Ser Leu Ser Thr Thr Phe Asp Val
                500                 505                 510

Val Ala Gly Glu Lys Arg Val Glu Phe Gln Arg Thr Asn Val Leu Gly
            515                 520                 525

Glu Glu Cys Ala Ala Leu
        530

<210> SEQ ID NO 43
<211> LENGTH: 1414
<212> TYPE: DNA
<213> ORGANISM: M. phaseolina

<400> SEQUENCE: 43
agcttgcctc ttcttctgtc tttctgcccc cttcttctcc agactccttt cgccgtagat      60
ttctgccttt tggacctcgt tttctgccct ccaccaatag caagccaaga gattagatta    120
gacatcgcca tcccatcgcc gactccaaca atgcccagca acccaggcga ctacgacgcc    180
gtccgccacg acgtcaagaa cctcctgcac cagcccgagt acgacgacgg ttccgccggg    240
cccgtcctcg tccgtctcgc atggtatgtt acggctaccc gcatcctcca gcccaatccg    300
ccgtttatct gctgttcgtg gctctgccat cttctctcca ggggcagcaa gtttcccgag    360
cctttttttt ttgtcttacg aacggcatct cgaacagccc gctgacaacc acaccaggca    420
ttccgcaggg acctacgacg cccactctga cacaggaggc agcaacggtg caggcatgcg    480
ctacgaggct gaaggcggcg accccgccaa tgccggcctg cagcacgccc gcgtcttcct    540
cgagcccatc aaggccgcgc acccctggat aacctactct gatctgtgga cgctggcggg    600
cgtggtcgcc atcaaggaga tgggcggccc ggacatcccg tggcagcccg gccgcaccga    660
cttcgtcgac gacagcaagc tgccgccgcg gggccgcctg ccggacgccg cgcagggcgc    720
tgaccacatc cgctggattt tctaccgcat gggcttcaac gatcaggaaa ttgtcgccct    780
cagcggcgcc acaacctcg gccgctgcca cgccgaccgc tccggcttcg acggcgcctg    840
ggtcaacaac cccacccgct ctccaaccca gtacttaag ctcctgacct cggtcgagtg    900
gaaagagaag accctcccca gcggcatcaa gcagttcgcc tactatgatg aggactcgga    960
ggaggagctc atgatgctgc ccaccgatat cgctctcttg cacgacccct ccttccggcc    1020
gtgggtcgag aagtatgccg aggacaagga tgcctttttc gcagacttct caaaggtctt    1080
tgccaagctg attgagctgg gcatagtcag agatgagagc ggtgcggtaa tcaacactga    1140
taacgtcaag ggcggctaca tctctgcgcc caagaagagt gagctgcctg gtgctccggg    1200
taaggctaat gaggaggctg agccgctcat gaaagagaat gagaggttca gggcacgtct    1260
gtaagctggt tggtttagat ttccttttttt tttttttttc aagaccgtta gactgcgcaa    1320
gctagagggg acggatagat ggacgatacc acctagattc ctatgcctta agaggagaaa    1380
gatagtgcct agagttttca tagagaatgc aaac                                  1414

<210> SEQ ID NO 44
<211> LENGTH: 960
<212> TYPE: DNA
<213> ORGANISM: M. phaseolina
```

<400> SEQUENCE: 44

```
atgcccagca acccaggcga ctacgacgcc gtccgccacg acgtcaagaa cctcctgcac      60
cagcccgagt acgacgacgg ttccgccggg cccgtcctcg tccgtctcgc atggcattcc     120
gcagggacct acgacgccca ctctgacaca ggaggcagca acggtgcagg catgcgctac     180
gaggctgaag gcggcgaccc cgccaatgcc ggcctgcagc acgcccgcgt cttcctcgag     240
cccatcaagg ccgcgcaccc ctggataacc tactctgatc tgtggacgct ggcgggcgtg     300
gtcgccatca aggagatggg cggcccggac atcccgtggc agcccggccg caccgacttc     360
gtcgacgaca gcaagctgcc gccgcggggc cgcctgccgg acgccgcgca gggcgctgac     420
cacatccgct ggattttcta ccgcatgggc ttcaacgatc aggaaattgt cgccctcagc     480
ggcgcccaca acctcggccg ctgccacgcc gaccgctccg gcttcgacgg cgcctgggtc     540
aacaacccca cccgcttctc caaccagtac tttaagctcc tgacctcggt cgagtggaaa     600
gagaagaccc tccccagcgg catcaagcag ttcgcctact atgatgagga ctcggaggag     660
gagctcatga tgctgcccac cgatatcgct ctcttgcacg acccctcctt ccggccgtgg     720
gtcgagaagt atgccgagga caaggatgcc ttttttcgcag acttctcaaa ggtctttgcc     780
aagctgattg agctgggcat agtcagagat gagagcggtg cggtaatcaa cactgataac     840
gtcaagggcg gctacatctc tgcgcccaag aagagtgagc tgcctggtgc tccgggtaag     900
gctaatgagg aggctgagcc gctcatgaaa gagaatgaga ggttcagggc acgtctgtaa     960
```

<210> SEQ ID NO 45
<211> LENGTH: 319
<212> TYPE: PRT
<213> ORGANISM: M. phaseolina

<400> SEQUENCE: 45

```
Met Pro Ser Asn Pro Gly Asp Tyr Asp Ala Val Arg His Asp Val Lys
  1               5                  10                  15

Asn Leu Leu His Gln Pro Glu Tyr Asp Asp Gly Ser Ala Gly Pro Val
             20                  25                  30

Leu Val Arg Leu Ala Trp His Ser Ala Gly Thr Tyr Asp Ala His Ser
         35                  40                  45

Asp Thr Gly Gly Ser Asn Gly Ala Gly Met Arg Tyr Glu Ala Glu Gly
     50                  55                  60

Gly Asp Pro Ala Asn Ala Gly Leu Gln His Ala Arg Val Phe Leu Glu
 65                  70                  75                  80

Pro Ile Lys Ala Ala His Pro Trp Ile Thr Tyr Ser Asp Leu Trp Thr
                 85                  90                  95

Leu Ala Gly Val Val Ala Ile Lys Glu Met Gly Gly Pro Asp Ile Pro
            100                 105                 110

Trp Gln Pro Gly Arg Thr Asp Phe Val Asp Asp Ser Lys Leu Pro Pro
        115                 120                 125

Arg Gly Arg Leu Pro Asp Ala Ala Gln Gly Ala Asp His Ile Arg Trp
    130                 135                 140

Ile Phe Tyr Arg Met Gly Phe Asn Asp Gln Glu Ile Val Ala Leu Ser
145                 150                 155                 160

Gly Ala His Asn Leu Gly Arg Cys His Ala Asp Arg Ser Gly Phe Asp
                165                 170                 175

Gly Ala Trp Val Asn Asn Pro Thr Arg Phe Ser Asn Gln Tyr Phe Lys
            180                 185                 190

Leu Leu Thr Ser Val Glu Trp Lys Glu Lys Thr Leu Pro Ser Gly Ile
```

|  |  | 195 |  |  | 200 |  |  | 205 |  |  |  |
|--|--|--|--|--|--|--|--|--|--|--|--|

Lys Gln Phe Ala Tyr Tyr Asp Glu Asp Ser Glu Glu Leu Met Met
    210                          215                      220

Leu Pro Thr Asp Ile Ala Leu Leu His Asp Pro Ser Phe Arg Pro Trp
225                         230                     235                  240

Val Glu Lys Tyr Ala Glu Asp Lys Asp Ala Phe Phe Ala Asp Phe Ser
              245                        250                     255

Lys Val Phe Ala Lys Leu Ile Glu Leu Gly Ile Val Arg Asp Glu Ser
        260                        265                     270

Gly Ala Val Ile Asn Thr Asp Asn Val Lys Gly Gly Tyr Ile Ser Ala
              275                        280                     285

Pro Lys Lys Ser Glu Leu Pro Gly Ala Pro Gly Lys Ala Asn Glu Glu
    290                        295                     300

Ala Glu Pro Leu Met Lys Glu Asn Glu Arg Phe Arg Ala Arg Leu
305                       310                     315

<210> SEQ ID NO 46
<211> LENGTH: 2160
<212> TYPE: DNA
<213> ORGANISM: M. phaseolina

<400> SEQUENCE: 46

| | | | | | |
|---|---|---|---|---|---|
| caactctttg | gatcattcgc | agttctgcag | attagactac | tcttttctcg | ctccacaatg | 60 |
| aagcttgcat | catggctgct | cctccctcaa | gtactggcag | cgctgggcgg | gcaggtacgt | 120 |
| gaatataact | tgactcttga | ggcaagctgg | atggctcaag | gtagatgtcc | ccgaagaaac | 180 |
| aaagtgatag | tatctctgct | aacatggaca | gacgggaacc | ctcgcggtgt | cttaactatc | 240 |
| aacggccaga | cacctggtcc | attgatctgg | ggatatgaag | gagacacact | tcgcgtcact | 300 |
| gtgaccaata | aaatgtttat | tgaggctact | atgcattggt | cagagtgaag | tctgtctgga | 360 |
| ctggagaat | caactaacgg | aaagcaggca | cggtgtctat | caggtcgaca | agtactggaa | 420 |
| cgacggagta | cctggcgtga | ctcaatggcc | cattgaatcc | agggattcgt | atacttacga | 480 |
| gtttactctc | accaaccaaa | ctggaagcta | cttctaccat | ggccactttg | gacccgcatt | 540 |
| cgcggacggc | caacgaggcc | cgctgtggat | tgcaccggcc | cctggagac | ccgtccgta | 600 |
| tgagcttgcg | tctgatgacc | cggcagaggt | tgcagcaatg | cgcgcggccg | aagacaatcc | 660 |
| gagacacctc | atggtttccg | actggaacta | tgagggaatg | gaagtgctga | ttgtgggctt | 720 |
| cagagatgca | ggcattgctc | cggcatgttc | tgcgtccctc | gtgacaaatg | gaaagggcag | 780 |
| gacaacttgc | ctcggcccag | atgatatcaa | gaaatacgat | cccgagggtc | ggaggaattc | 840 |
| acttgggtgc | cttcctcctc | cagtcggcgc | tgagttcacc | aacaagagag | aatgccgcga | 900 |
| gactaccacc | gacttcgaga | tcattcaggc | cgaagaaggg | gagaagtata | tctacatgaa | 960 |
| ctttatccac | cctggagccc | accatgaact | gcgaatcgcg | gtggacgagc | acgacatgat | 1020 |
| catcgtggca | gctgacgggg | attttgtcat | gccgaaaaaa | gtccaggtac | gttaatgcga | 1080 |
| gaacttgcac | tgagcggtgc | tgacctatgg | ctgcaggcaa | taaacctcaa | catgggcgac | 1140 |
| aggatcagtg | tcctggtacc | gctagacaag | aagccggggg | aatacgccat | ccgcctgtcg | 1200 |
| tccatttccg | aggagcaatt | gattacgggc | ttgagcatct | tgcgctaccc | cggtgtgcag | 1260 |
| gagcgccgca | aagacggtat | tatgctggca | ccggaaacaa | aaccccatat | tgatctgttg | 1320 |
| gggcggatgg | tcactgaagg | aggtgtcatg | atggatgaaa | tgaccgattt | tggccccttt | 1380 |
| ccgccgcgct | cacccccagc | gacgtctgat | cacacgtttc | ggttttatc | aaaccgcacc | 1440 |

| | |
|---|---|
| ggcccgagca catggatgct gtcgagcgag ccacaccaag gcttccgcca gcagatgcct | 1500 |
| cctattatgt ggaacgaaga gtctcgtggc cctacaacca ttcagggdat gaagaatgga | 1560 |
| tccaccgtag acatcatctt cgagagccgc gcatacgcca tgcacccttt ccacaaacac | 1620 |
| aatcacaagg cctggattat tggtagagga aagggctact tccgttggcc agatgttgct | 1680 |
| actgccatct cggaagctcc agagaatttc aacctgatca acccgccgtt gcgagatggt | 1740 |
| gcccggctcg aagcggaaga gggatcctgg acggtgatcc gttacaccat caccttttcct | 1800 |
| gccatgagca tgctgcactg ccatcgtatt cagcactttg cggtaagtgt gtgatctagc | 1860 |
| caccaaacga atggtcactg attgaaacag gctggacaac agatagtcct tttggagggg | 1920 |
| caggatgtga tgcaaagccc tcctgagtac atcaaaaaaa tgacgcatgc gagctttgtg | 1980 |
| ccgccactcc gatacggccc ccttgactga gagttcccat gcgaggccag agcacggaat | 2040 |
| tgggtagttg aagttaaaac ctgccacata aaaaatagct cgaataacag gattttgcta | 2100 |
| gctcatggaa ctagccactt gttcctttgc gttcagtcta atggctgcgg tgaaagcgaa | 2160 |

<210> SEQ ID NO 47
<211> LENGTH: 1713
<212> TYPE: DNA
<213> ORGANISM: M. phaseolina

<400> SEQUENCE: 47

| | |
|---|---|
| atggctcaag gtagatgtcc ccgaagaaac aaagtgatag tatctctgct aacatggaca | 60 |
| gacgggaacc ctcgcggtgt cttaactatc aacggccaga cacctggtcc attgatctgg | 120 |
| ggatatgaag gagacacact tcgcgtcact gtgaccaata aaatgtttat tgaggctact | 180 |
| atgcattggc acggtgtcta tcaggtcgac aagtactgga cgacggagt acctggcgtg | 240 |
| actcaatggc ccattgaatc cagggattcg tatacttacg agtttactct caccaaccaa | 300 |
| actggaagct acttctacca tggccacttt ggacccgcat cgcggacgg ccaacgaggc | 360 |
| ccgctgtgga ttgcaccggc cccctggaga ccccgtccgt atgagcttgc gtctgatgac | 420 |
| ccggcagagg ttgcagcaat gcgcgcggcc gaagacaatc cgagacacct catggttttcc | 480 |
| gactggaact atgagggaat ggaagtgctg attgtgggct tcagagatgc aggcattgct | 540 |
| ccggcatgtt ctgcgtccct cgtgacaaat ggaaagggca ggacaacttg cctcggccca | 600 |
| gatgatatca agaaatacga tcccgagggt cggaggaatt cacttgggtg ccttcctcct | 660 |
| ccagtcggcg ctgagttcac caacaagaga gaatgccgcg agactaccac cgacttcgag | 720 |
| atcattcagg ccgaagaagg ggagaagtat atctacatga actttatcca ccctggagcc | 780 |
| caccatgaac tgcgaatcgc ggtggacgag cacgacatga tcatcgtggc agctgacggg | 840 |
| gattttgtca tgccgaaaaa agtccaggca ataaacctca acatgggcga caggatcagt | 900 |
| gtcctggtac cgctagacaa gaagccgggg gaatacgcca tccgcctgtc gtccatttcc | 960 |
| gaggagcaat tgattacggg cttgagcatc ttgcgctacc ccggtgtgca ggagcgccgc | 1020 |
| aaagacggta ttatgctggc accggaaaca aaaccccata ttgatctgtt ggggcggatg | 1080 |
| gtcactgaag gaggtgtcat gatggatgaa atgaccgatt tggccccctt tccgccgcgc | 1140 |
| tcacccccag cgacgtctga tcacacgttt cggttttttat caaaccgcac cggcccgagc | 1200 |
| acatggatgc tgtcgagcga gccacaccaa ggcttccgcc agcagatgcc tcctattatg | 1260 |
| tggaacgaag agtctcgtgg ccctacaacc attcagggga tgaagaatgg atccaccgta | 1320 |
| gacatcatct tcgagagccg cgcatacgcc atgcaccctt tccacaaaca caatcacaag | 1380 |
| gcctggatta ttggtagagg aaagggctac ttccgttggc cagatgttgc tactgccatc | 1440 |

```
tcggaagctc cagagaattt caacctgatc aacccgccgt tgcgagatgg tgcccggctc    1500
gaagcggaag agggatcctg gacggtgatc cgttacacca tcacctttcc tgccatgagc    1560
atgctgcact gccatcgtat tcagcacttt gcggctggac aacagatagt cctttggag     1620 gggcaggatg tgatgcaaag ccctcctgag tacatcaaaa aaatgacgca tgcgagcttt    1680
gtgccgccac tccgatacgg cccccttgac tga                                 1713
```

<210> SEQ ID NO 48
<211> LENGTH: 570
<212> TYPE: PRT
<213> ORGANISM: M. phaseolina

<400> SEQUENCE: 48

```
Met Ala Gln Gly Arg Cys Pro Arg Arg Asn Lys Val Ile Val Ser Leu
1               5                   10                  15

Leu Thr Trp Thr Asp Gly Asn Pro Arg Gly Val Leu Thr Ile Asn Gly
            20                  25                  30

Gln Thr Pro Gly Pro Leu Ile Trp Gly Tyr Glu Gly Asp Thr Leu Arg
        35                  40                  45

Val Thr Val Thr Asn Lys Met Phe Ile Glu Ala Thr Met His Trp His
    50                  55                  60

Gly Val Tyr Gln Val Asp Lys Tyr Trp Asn Asp Gly Val Pro Gly Val
65                  70                  75                  80

Thr Gln Trp Pro Ile Glu Ser Arg Asp Ser Tyr Thr Tyr Glu Phe Thr
                85                  90                  95

Leu Thr Asn Gln Thr Gly Ser Tyr Phe Tyr His Gly His Phe Gly Pro
            100                 105                 110

Ala Phe Ala Asp Gly Gln Arg Gly Pro Leu Trp Ile Ala Pro Ala Pro
        115                 120                 125

Trp Arg Pro Arg Pro Tyr Glu Leu Ala Ser Asp Asp Pro Ala Glu Val
    130                 135                 140

Ala Ala Met Arg Ala Ala Glu Asp Asn Pro Arg His Leu Met Val Ser
145                 150                 155                 160

Asp Trp Asn Tyr Glu Gly Met Glu Val Leu Ile Val Gly Phe Arg Asp
                165                 170                 175

Ala Gly Ile Ala Pro Ala Cys Ser Ala Ser Leu Val Thr Asn Gly Lys
            180                 185                 190

Gly Arg Thr Thr Cys Leu Gly Pro Asp Asp Ile Lys Lys Tyr Asp Pro
        195                 200                 205

Glu Gly Arg Arg Asn Ser Leu Gly Cys Leu Pro Pro Val Gly Ala
    210                 215                 220

Glu Phe Thr Asn Lys Arg Glu Cys Arg Glu Thr Thr Thr Asp Phe Glu
225                 230                 235                 240

Ile Ile Gln Ala Glu Glu Gly Glu Lys Tyr Ile Tyr Met Asn Phe Ile
                245                 250                 255

His Pro Gly Ala His His Glu Leu Arg Ile Ala Val Asp Glu His Asp
            260                 265                 270

Met Ile Ile Val Ala Ala Asp Gly Asp Phe Val Met Pro Lys Lys Val
        275                 280                 285

Gln Ala Ile Asn Leu Asn Met Gly Asp Arg Ile Ser Val Leu Val Pro
    290                 295                 300

Leu Asp Lys Lys Pro Gly Glu Tyr Ala Ile Arg Leu Ser Ser Ile Ser
305                 310                 315                 320
```

Glu Glu Gln Leu Ile Thr Gly Leu Ser Ile Leu Arg Tyr Pro Gly Val
            325                 330                 335

Gln Glu Arg Arg Lys Asp Gly Ile Met Leu Ala Pro Glu Thr Lys Pro
        340                 345                 350

His Ile Asp Leu Leu Gly Arg Met Val Thr Glu Gly Gly Val Met Met
    355                 360                 365

Asp Glu Met Thr Asp Leu Ala Pro Phe Pro Arg Ser Pro Pro Ala
370                 375                 380

Thr Ser Asp His Thr Phe Arg Phe Leu Ser Asn Arg Thr Gly Pro Ser
385                 390                 395                 400

Thr Trp Met Leu Ser Ser Glu Pro His Gln Gly Phe Arg Gln Gln Met
                405                 410                 415

Pro Pro Ile Met Trp Asn Glu Ser Arg Gly Pro Thr Thr Ile Gln
            420                 425                 430

Gly Met Lys Asn Gly Ser Thr Val Asp Ile Ile Phe Glu Ser Arg Ala
        435                 440                 445

Tyr Ala Met His Pro Phe His Lys His Asn His Lys Ala Trp Ile Ile
    450                 455                 460

Gly Arg Gly Lys Gly Tyr Phe Arg Trp Pro Asp Val Ala Thr Ala Ile
465                 470                 475                 480

Ser Glu Ala Pro Glu Asn Phe Asn Leu Ile Asn Pro Pro Leu Arg Asp
                485                 490                 495

Gly Ala Arg Leu Glu Ala Glu Gly Ser Trp Thr Val Ile Arg Tyr
            500                 505                 510

Thr Ile Thr Phe Pro Ala Met Ser Met Leu His Cys His Arg Ile Gln
        515                 520                 525

His Phe Ala Ala Gly Gln Gln Ile Val Leu Leu Glu Gly Gln Asp Val
    530                 535                 540

Met Gln Ser Pro Pro Glu Tyr Ile Lys Lys Met Thr His Ala Ser Phe
545                 550                 555                 560

Val Pro Pro Leu Arg Tyr Gly Pro Leu Asp
                565                 570

<210> SEQ ID NO 49
<211> LENGTH: 2269
<212> TYPE: DNA
<213> ORGANISM: M. phaseolina

<400> SEQUENCE: 49
agtatgtgcg ttgatcccgc tgtctattcg agcaccagag cactgtccag ccaccttgag     60
ctatctcaag gggctatctc atctggtcat cttcgctggg gcatcggttg ccttctcaac    120
ccttctcaat tcccctcacg cttctgcaac atgttcttcg gctccctcca cttgggcatc    180
ggcgccctat tggttgccgg cactcttgct ggcgacgaca agtggcttag ccccgtctac    240
aagaactttt acgagttccc cctacctaag ccaccaatca aggaagcgaa agcgtaagtc    300
aactgatatt tctctcgctc gtcatttgca tgcctaatct tcgcaggaaa tataccaacc    360
cgactaccgg tgctgtgatc aactactacg aaatcaccat ctcacccctg cagcaacagg    420
tttatcctgg ccttggcaag gcaaacctcg ttggctacga tggtatctct cccggtccca    480
cttttaagat ggagagggga gaagaggctg tcgttcgttt catcaacaag gcctccattc    540
ccaattccgt ccatcttcac ggctcctact cctttgcccc cttcgatggc tgggcggagg    600
atacgaccag cccaggccaa tacaaggact actactaccc caatgcccag tctgcccgta    660
ccctctggta ccacgaccat gccgtcttcc acactgccga gaacgcctac tacggtcagg    720

```
caggtttcta catcctgcac gactcggctg aggatagtct gggtctcccg tctggagact    780
acgacatccc gctcggtctg agctcgaagc aataccagtc caacggtgac cttttcagcc    840
cgaatggcga gacggatagc cttttggcg atgttatcca tgtcaacggc cagccctggc     900
cgtacctcaa ggtcgagccc aggaagtacc gcttccgcct gcttgataca agcatttccc    960
gtgccttcca gctgtcactc caagacgata agagcaagaa gattgacttt aacgtcatcg   1020
cctccgatgc cggcctcctg tccagccctg ttccgaccaa cctgctacac atttccatgg   1080
ccgaacgctg ggaaattgtc gtcgacttct cccagtacgc tggcaagaac atcaccatga   1140
agaacgagcg tgacgtgcag gccgatgaag actacaacag cactgacaag gtcatgcgct   1200
tcgtagtagg caacaaggtt acctcgactg ccaacaacaa cctgcctggc agcctccgca   1260
gcgtgccttt cccgccgaat aagtctggtg ttgacaggag cttcaagttc gagcgcaaag   1320
gcggtgaatg gactatcaac ggcgttacct tgccgacgt cgagaaccgt attctaggca    1380
agccccaacg cggacaggtt gaggtctggg agctcgagaa ctcttccggc ggctggtctc   1440
accccgttca catccatctc atcgacttcc aggttatttc tcgcactggt ggcaagcgtg   1500
atgtcctgcc ttacgagaag aacggtctca agatgtcgt cttgcttggc gtgaacgaga   1560
aggtcagagt tgtcgctcgc ttccagccct gggaaggtgt ctacatgttc cattgccaca   1620
acctgatcca cgaggaccac gatatggtgc gctcccagca ttcctctgat tactcgcaac   1680
aaagactgac aaataattac agatggccgc tttcaatgta tccaccctt cagactacgg    1740
ctacgaccag aaggagaccc ttttcatcga cccgatggag tccgctggc gcgcaaagga    1800
tgtcaagacc gaagacttca caaccgatgc catccagtcg aagcttgccg cttcgctga    1860
aataaatcgc tacaaggacg ttgcgaagat cgaaagtgct cttgaaaatt attggaagac   1920
cgctcccacc gggttcaaga ttagcaccac ctcctcaact ccgagctcaa ccgccgccac   1980
ctccaccgct tccagcagtg gctcaaacac ctctattacc gccccattc agtcccggc    2040
cactacttca cccgcgacca cttcgaccaa ggcggatgac aagggcaagg ctaagacttc   2100
tacgaccaaa acgaagtaac gaaatggctt ttagatcacg ctcattatag ataaaacttg   2160
ggagaatttg ggtcggtgtt tttggatagt ttggttcgga ggagcgctct ctgtaaatat   2220
gggcctcgcg aactctgtgg atatttgttt ctcggtgtct gttaatatc               2269
```

<210> SEQ ID NO 50
<211> LENGTH: 1860
<212> TYPE: DNA
<213> ORGANISM: M. phaseolina

<400> SEQUENCE: 50

```
atgttcttcg gctccctcca cttgggcatc ggcgccctat tggttgccgg cactcttgct     60
ggcgacgaca agtggcttag ccccgtctac aagaactttt acgagttccc cctacctaag   120
ccaccaatca aggaagcgaa agcgaaatat accaacccga ctaccggtgc tgtgatcaac   180
tactacgaaa tcaccatctc accctgcag caacaggttt atcctggcct tggcaaggca    240
aacctcgttg gctacgatgg tatctctccc ggtcccactt ttaagatgga gaggggagaa   300
gaggctgtcg ttcgtttcat caacaaggcc tccattccca attccgtcca tcttcacggc   360
tcctactcct ttgccccctt cgatggctgg gcggaggata cgaccagccc aggccaatac   420
aaggactact actaccccaa tgcccagtct gcccgtaccc tctggtacca cgaccatgcc   480
gtcttccaca ctgccgagaa cgcctactac ggtcaggcag gtttctacat cctgcacgac   540
```

```
tcggctgagg atagtctggg tctcccgtct ggagactacg catcccgct cggtctgagc    600
tcgaagcaat accagtccaa cggtgacctt ttcagcccga atggcgagac ggatagcctt    660
tttggcgatg ttatccatgt caacggccag ccctggccgt acctcaaggt cgagcccagg    720
aagtaccgct tccgcctgct tgatacaagc atttcccgtg ccttccagct gtcactccaa    780
gacgataaga gcaagaagat tgactttaac gtcatcgcct ccgatgccgg cctcctgtcc    840
agccctgttc cgaccaacct gctacacatt tccatggccg aacgctggga aattgtcgtc    900
gacttctccc agtacgctgg caagaacatc accatgaaga cgagcgtga cgtgcaggcc    960
gatgaagact acaacagcac tgacaaggtc atgcgcttcg tagtaggcaa caaggttacc   1020
tcgactgcca acaacaacct gcctggcagc ctccgcagcg tgccttcc gccgaataag   1080
tctggtgttg acaggagctt caagttcgag cgcaaaggcg gtgaatggac tatcaacggc   1140
gttacctttg ccgacgtcga gaaccgtatt ctaggcaagc cccaacgcgg acaggttgag   1200
gtctgggagc tcgagaactc ttccggcggc tggtctcacc ccgttcacat ccatctcatc   1260
gacttccagg ttatttctcg cactggtggc aagcgtgatg tcctgcctta cgagaagaac   1320
ggtctcaaag atgtcgtctt gcttggcgtg aacgagaagg tcagagttgt cgctcgcttc   1380
cagccctggg aaggtgtcta catgttccat tgccacaacc tgatccacga ggaccacgat   1440
atgatggccg ctttcaatgt atccacccctt tcagactacg gctacgacca aaggagacc   1500
cttttcatcg acccgatgga gtcccgctgg cgcgcaaagg atgtcaagac cgaagacttc   1560
acaaccgatg ccatccagtc gaagcttgcc gctttcgctg aaataaatcg ctacaaggac   1620
gttgcgaaga tcgaaagtgc tcttgaaaat tattggaaga ccgctcccac cgggttcaag   1680
attagcacca cctcctcaac tccgagctca accgccgcca cctccaccgc ttccagcagt   1740
ggctcaaaca cctctattac cgcccccatt cagtccccgg ccactacttc acccgcgacc   1800
acttcgacca aggcggatga caagggcaag gctaagactt ctacgaccaa aacgaagtaa   1860
```

<210> SEQ ID NO 51
<211> LENGTH: 619
<212> TYPE: PRT
<213> ORGANISM: M. phaseolina

<400> SEQUENCE: 51

```
Met Phe Phe Gly Ser Leu His Leu Gly Ile Gly Ala Leu Leu Val Ala
1               5                   10                  15

Gly Thr Leu Ala Gly Asp Asp Lys Trp Leu Ser Pro Val Tyr Lys Asn
            20                  25                  30

Phe Tyr Glu Phe Pro Leu Pro Lys Pro Ile Lys Glu Ala Lys Ala
        35                  40                  45

Lys Tyr Thr Asn Pro Thr Thr Gly Ala Val Ile Asn Tyr Tyr Glu Ile
50                  55                  60

Thr Ile Ser Pro Leu Gln Gln Gln Val Tyr Pro Gly Leu Gly Lys Ala
65                  70                  75                  80

Asn Leu Val Gly Tyr Asp Gly Ile Ser Pro Gly Pro Thr Phe Lys Met
                85                  90                  95

Glu Arg Gly Glu Glu Ala Val Val Arg Phe Ile Asn Lys Ala Ser Ile
            100                 105                 110

Pro Asn Ser Val His Leu His Gly Ser Tyr Ser Phe Ala Pro Phe Asp
        115                 120                 125

Gly Trp Ala Glu Asp Thr Thr Ser Pro Gly Gln Tyr Lys Asp Tyr Tyr
    130                 135                 140
```

-continued

Tyr Pro Asn Ala Gln Ser Ala Arg Thr Leu Trp Tyr His Asp His Ala
145                 150                 155                 160

Val Phe His Thr Ala Glu Asn Ala Tyr Tyr Gly Gln Ala Gly Phe Tyr
                165                 170                 175

Ile Leu His Asp Ser Ala Glu Asp Ser Leu Gly Leu Pro Ser Gly Asp
            180                 185                 190

Tyr Asp Ile Pro Leu Gly Leu Ser Ser Lys Gln Tyr Gln Ser Asn Gly
        195                 200                 205

Asp Leu Phe Ser Pro Asn Gly Glu Thr Asp Ser Leu Phe Gly Asp Val
    210                 215                 220

Ile His Val Asn Gly Gln Pro Trp Pro Tyr Leu Lys Val Glu Pro Arg
225                 230                 235                 240

Lys Tyr Arg Phe Arg Leu Leu Asp Thr Ser Ile Ser Arg Ala Phe Gln
                245                 250                 255

Leu Ser Leu Gln Asp Asp Lys Ser Lys Lys Ile Asp Phe Asn Val Ile
            260                 265                 270

Ala Ser Asp Ala Gly Leu Leu Ser Ser Pro Val Pro Thr Asn Leu Leu
        275                 280                 285

His Ile Ser Met Ala Glu Arg Trp Glu Ile Val Asp Phe Ser Gln
290                 295                 300

Tyr Ala Gly Lys Asn Ile Thr Met Lys Asn Glu Arg Asp Val Gln Ala
305                 310                 315                 320

Asp Glu Asp Tyr Asn Ser Thr Asp Lys Val Met Arg Phe Val Val Gly
                325                 330                 335

Asn Lys Val Thr Ser Thr Ala Asn Asn Asn Leu Pro Gly Ser Leu Arg
            340                 345                 350

Ser Val Pro Phe Pro Pro Asn Lys Ser Gly Val Asp Arg Ser Phe Lys
        355                 360                 365

Phe Glu Arg Lys Gly Gly Glu Trp Thr Ile Asn Gly Val Thr Phe Ala
    370                 375                 380

Asp Val Glu Asn Arg Ile Leu Gly Lys Pro Gln Arg Gly Gln Val Glu
385                 390                 395                 400

Val Trp Glu Leu Glu Asn Ser Ser Gly Gly Trp Ser His Pro Val His
                405                 410                 415

Ile His Leu Ile Asp Phe Gln Val Ile Ser Arg Thr Gly Gly Lys Arg
            420                 425                 430

Asp Val Leu Pro Tyr Glu Lys Asn Gly Leu Lys Asp Val Val Leu Leu
        435                 440                 445

Gly Val Asn Glu Lys Val Arg Val Val Ala Arg Phe Gln Pro Trp Glu
    450                 455                 460

Gly Val Tyr Met Phe His Cys His Asn Leu Ile His Glu Asp His Asp
465                 470                 475                 480

Met Met Ala Ala Phe Asn Val Ser Thr Leu Ser Asp Tyr Gly Tyr Asp
                485                 490                 495

Gln Lys Glu Thr Leu Phe Ile Asp Pro Met Glu Ser Arg Trp Arg Ala
            500                 505                 510

Lys Asp Val Lys Thr Glu Asp Phe Thr Thr Asp Ala Ile Gln Ser Lys
        515                 520                 525

Leu Ala Ala Phe Ala Glu Ile Asn Arg Tyr Lys Asp Val Ala Lys Ile
    530                 535                 540

Glu Ser Ala Leu Glu Asn Tyr Trp Lys Thr Ala Pro Thr Gly Phe Lys
545                 550                 555                 560

Ile Ser Thr Thr Ser Ser Thr Pro Ser Ser Thr Ala Ala Thr Ser Thr 565                 570                 575
Ala Ser Ser Ser Gly Ser Asn Thr Ser Ile Thr Ala Pro Ile Gln Ser
                580                 585                 590
Pro Ala Thr Thr Ser Pro Ala Thr Thr Ser Lys Ala Asp Asp Lys
            595                 600                 605
Gly Lys Ala Lys Thr Ser Thr Thr Lys Thr Lys
        610                 615

<210> SEQ ID NO 52
<211> LENGTH: 2423
<212> TYPE: DNA
<213> ORGANISM: M. phaseolina

<400> SEQUENCE: 52
aaaggccttt ggctcccgcc aaaattgttc atcctcacgc tcactcctgc gctcttccct    60
acagaccttt tgcctgtagc tttagcttca cggtcttttc attccccttc tctggcattc   120
atcccaccgc gggaagcctc aattaccaca atggtgtccc ttaagcaaat cggtgccact   180
ctgttggcac tgactgctca aaccttcgct gctgccatcc ctgaggccga accggtggac   240
ctcgtcgccc gtcaagccac gaccactacg tccaccacct cctcaaccac ctcgagggtt   300
cccgattccc gatgtacttg gggcccttcg agcaggggtt gctggaagaa cggcttcagc   360
attgccactg actttgacac gaagtggcca tctactggca agactgtctc atatcgcttg   420
gaagttacga atgtcaccaa ctgcgaggac tatcaaagca agggaattgg agatggcttc   480
tgcaggccga tgctgctcat caacaatcag ttcccagggc ctaccagtca gttttttccct   540
cctcgatgcc gggtgacaag ggcgctaatg actcgtactt tccagtcaat gcggaatggg   600
gagacaacct tgagattact gttgtcaata gtatgcaaga caacggcacc tcattccact   660
ggcacggcat tcgtcagctg aactcatgcc aaaacgatgg tgccaacggc gtcaccgagt   720
gccctattcc tcccggcgga agcttcactt ataagttcaa ggctacacag tatggtgagt   780
cttttgcctt c tcttctacct ttt ccatttc atgcaagcat cttcatgtgc gttctgttga   840
gttttgaggc ggaaatactc ttgagcttgc cccgttccgt ttgtgagcca cgtgcaaggc   900
cacctgctcc caccct t gtc ataatactga ccggcccttc caggaacaac atggtaccat   960
agccatcact ctgctcagta cggcgatggg atccaaggtg ccatcgtgat caatggcccg  1020
gcaaccgcca attcgacga ggatttaggc cccgttgccc tcaccgaaac ctacgatgag  1080
acggcatgga cgaagaactg gctggcgctg cacgtggcat tccctcctca gcccctcaac  1140
attctcttca atggctccat ggtcaacagc accggcggcg ccgctacaa caccatctca  1200
gtcaagcaag gcaagactta ccggctgcgc ctgattaaca tgagcgtcga cactttcttc  1260
gtattctcca tggacgggca cgagttccag atcatcacgg ccgacctcgt ccccgtgcac  1320
ccttacaatg cgacctcgat catgatcggc atcgccagc gctacgacat cgtcttcaag  1380
gccaaccagc ccgctgccaa ctactggctg cgtaccgaga tcgccagctg cagtgccaac  1440
gccatcacgg ccgaagccga catcgtcccc ggcggcatcc tgaactacga caccatcgac  1500
aagacggatc tgccagtctc caccaagtcc gttatcgaga cgaccgactg cgccgccgag  1560
ccctacgaca agctggtccc ctggtgggag acgcaggtcc ccaaggacca gttcctgacc  1620
cagctcgagg gcatcgacct gacgttcgcg gcgggcgcca cggtcggcag cgagactggt  1680
cttgtgcagt ggtacctgaa cgacagcgcc atggtcgtcg actgggccaa accgactctg  1740
gagtacttct ccgagggaga cactaactat acgtcttcaa tgaacgtttt ccagatgccc  1800

| | |
|---|---|
| gcggagggga agtggtcgtt ctggatcatc cacaacaacg cggccgctct gctcgaccac | 1860 |
| ccgatccatc tccacggcca cgactttttc cacctgggcg ccggcaccgg cacctgggac | 1920 |
| ggcaacgtgg actccttgat cttcgacaat cctatgcgca gggacgtgat gatcttgccc | 1980 |
| acaggatggc ttattatcgc cttttccagcg gacaaccccg cgcgcgtggtt gatgcattgc | 2040 |
| cacatcgtaa gtacccaaca agccccatct ctctctctct ctctcatcaa agatgacggc | 2100 |
| aactgacaag caaccaggca tggcacgtta ccgacgggct ttccttgcag ttcgttgaaa | 2160 |
| acccaggctc attcacgcag gacctctcgg gcatgaagag caactgcgcc gcctggaaag | 2220 |
| agtacgagga gaaggcttac tatgagaagg aggttggcga ttccggcttg taaaaccgtg | 2280 |
| acggcgggga tgaggagttt atgacgagat gttcacttta taccttctac caccaccacc | 2340 |
| acccttttcc tctttctttt accgacgtag ggctgcacta tctggcgcgt ctgtggtctg | 2400 |
| cttttgcatat gcataaatac ctt | 2423 |

<210> SEQ ID NO 53
<211> LENGTH: 1824
<212> TYPE: DNA
<213> ORGANISM: M. phaseolina

<400> SEQUENCE: 53

| | |
|---|---|
| atggtgtccc ttaagcaaat cggtgccact ctgttggcac tgactgctca aaccttcgct | 60 |
| gctgccatcc ctgaggccga accggtggac ctcgtcgccc gtcaagccac gaccactacg | 120 |
| tccaccacct cctcaaccac ctcgagggtt cccgattccc gatgtacttg ggcccttcg | 180 |
| agcaggggtt gctggaagaa cggcttcagc attgccactg actttgacac gaagtggcca | 240 |
| tctactggca agactgtctc atatcgcttg gaagttacga atgtcaccaa ctgcgaggac | 300 |
| tatcaaagca agggaattgg agatggcttc tgcaggccga tgctgctcat caacaatcag | 360 |
| ttcccagggc ctaccatcaa tgcggaatgg ggagacaacc ttgagattac tgttgtcaat | 420 |
| agtatgcaag acaacggcac ctcattccac tggcacggca ttcgtcagct gaactcatgc | 480 |
| caaaacgatg gtgccaacgg cgtcaccgag tgccctattc ctcccggcgg aagcttcact | 540 |
| tataagttca aggctacaca gtatggaaca acatggtacc atagccatca ctctgctcag | 600 |
| tacggcgatg ggatccaagg tgccatcgtg atcaatggcc cggcaaccgc caattacgac | 660 |
| gaggatttag gccccgttgc cctcaccgaa acctacgatg agacggcatg gacgaagaac | 720 |
| tggctggcgc tgcacgtggc attccctcct cagcccctca acattctctt caatggctcc | 780 |
| atggtcaaca gcaccggcgg cggccgctac aacaccatct cagtcaagca aggcaagact | 840 |
| taccggctgc gcctgattaa catgagcgtc gacactttct tcgtattctc catggacggg | 900 |
| cacgagttcc agatcatcac ggccgacctc gtccccgtgc accttacaa tgcgacctcg | 960 |
| atcatgatcg gcatcggcca cgctacgac atcgtcttca aggccaacca gcccgctgcc | 1020 |
| aactactggc tgcgtaccga gatcgccagc tgcagtgcca acgccatcac ggccgaagcc | 1080 |
| gacatcgtcc ccggcggcat cctgaactac gacaccatcg acaagacgga tctgccagtc | 1140 |
| tccaccaagt ccgttatcga gacgaccgac tgcgccgccg agccctacga caagctggtc | 1200 |
| ccctggtggg agacgcaggt ccccaaggac cagttcctga cccagctcga gggcatcgac | 1260 |
| ctgacgttcg cggcgggcgc cacggtcggc agcgagactg gtcttgtgca gtggtacctg | 1320 |
| aacgacagcg ccatggtcgt cgactgggcc aaaccgactc tggagtactt ctccgaggga | 1380 |
| gacactaact atacgtcttc aatgaacgtt ttccagatgc ccgcggaggg gaagtggtcg | 1440 |
| ttctggatca tccacaacaa cgcggccgct ctgctcgacc acccgatcca tctccacggc | 1500 |

```
cacgactttt tccacctggg cgccggcacc ggcacctggg acggcaacgt ggactccttg    1560
atcttcgaca atcctatgcg cagggacgtg atgatcttgc ccacaggatg gcttattatc    1620
gcctttccag cggacaaccc cggcgcgtgg ttgatgcatt gccacatcgc atggcacgtt    1680
accgacgggc tttccttgca gttcgttgaa aacccaggct cattcacgca ggacctctcg    1740
ggcatgaaga gcaactgcgc cgcctggaaa gagtacgagg agaaggctta ctatgagaag    1800
gaggttggcg attccggctt gtaa                                          1824
```

<210> SEQ ID NO 54
<211> LENGTH: 607
<212> TYPE: PRT
<213> ORGANISM: M. phaseolina

<400> SEQUENCE: 54

```
Met Val Ser Leu Lys Gln Ile Gly Ala Thr Leu Leu Ala Leu Thr Ala
1               5                   10                  15

Gln Thr Phe Ala Ala Ile Pro Glu Ala Glu Pro Val Asp Leu Val
            20                  25                  30

Ala Arg Gln Ala Thr Thr Thr Thr Ser Thr Thr Ser Ser Thr Thr Ser
        35                  40                  45

Arg Val Pro Asp Ser Arg Cys Thr Trp Gly Pro Ser Ser Arg Gly Cys
    50                  55                  60

Trp Lys Asn Gly Phe Ser Ile Ala Thr Asp Phe Asp Thr Lys Trp Pro
65                  70                  75                  80

Ser Thr Gly Lys Thr Val Ser Tyr Arg Leu Glu Val Thr Asn Val Thr
                85                  90                  95

Asn Cys Glu Asp Tyr Gln Ser Lys Gly Ile Gly Asp Gly Phe Cys Arg
            100                 105                 110

Pro Met Leu Leu Ile Asn Asn Gln Phe Pro Gly Pro Thr Ile Asn Ala
        115                 120                 125

Glu Trp Gly Asp Asn Leu Glu Ile Thr Val Val Asn Ser Met Gln Asp
    130                 135                 140

Asn Gly Thr Ser Phe His Trp His Gly Ile Arg Gln Leu Asn Ser Cys
145                 150                 155                 160

Gln Asn Asp Gly Ala Asn Gly Val Thr Glu Cys Pro Ile Pro Pro Gly
                165                 170                 175

Gly Ser Phe Thr Tyr Lys Phe Lys Ala Thr Gln Tyr Gly Thr Thr Trp
            180                 185                 190

Tyr His Ser His His Ser Ala Gln Tyr Gly Asp Gly Ile Gln Gly Ala
        195                 200                 205

Ile Val Ile Asn Gly Pro Ala Thr Ala Asn Tyr Asp Glu Asp Leu Gly
    210                 215                 220

Pro Val Ala Leu Thr Glu Thr Tyr Asp Glu Thr Ala Trp Thr Lys Asn
225                 230                 235                 240

Trp Leu Ala Leu His Val Ala Phe Pro Pro Gln Pro Leu Asn Ile Leu
                245                 250                 255

Phe Asn Gly Ser Met Val Asn Ser Thr Gly Gly Gly Arg Tyr Asn Thr
            260                 265                 270

Ile Ser Val Lys Gln Gly Lys Thr Tyr Arg Leu Arg Leu Ile Asn Met
        275                 280                 285

Ser Val Asp Thr Phe Phe Val Phe Ser Met Asp Gly His Glu Phe Gln
    290                 295                 300

Ile Ile Thr Ala Asp Leu Val Pro Val His Pro Tyr Asn Ala Thr Ser
```

|  |  |  |  |  |  |  |  |  |  |  |  |
|---|---|---|---|---|---|---|---|---|---|---|---|
| 305 | | | 310 | | | 315 | | | 320 | | |
| Ile | Met | Ile | Gly | Ile | Gly | Gln | Arg | Tyr | Asp | Ile | Val | Phe | Lys | Ala | Asn |

Ile Met Ile Gly Ile Gly Gln Arg Tyr Asp Ile Val Phe Lys Ala Asn
305                 310                 315                 320

Gln Pro Ala Ala Asn Tyr Trp Leu Arg Thr Glu Ile Ala Ser Cys Ser
            325                 330                 335

Ala Asn Ala Ile Thr Ala Glu Ala Asp Ile Val Pro Gly Gly Ile Leu
        340                 345                 350

Asn Tyr Asp Thr Ile Asp Lys Thr Asp Leu Pro Val Ser Thr Lys Ser
    355                 360                 365

Val Ile Glu Thr Thr Asp Cys Ala Ala Glu Pro Tyr Asp Lys Leu Val
370                 375                 380

Pro Trp Trp Glu Thr Gln Val Pro Lys Asp Gln Phe Leu Thr Gln Leu
385                 390                 395                 400

Glu Gly Ile Asp Leu Thr Phe Ala Ala Gly Ala Thr Val Gly Ser Glu
            405                 410                 415

Thr Gly Leu Val Gln Trp Tyr Leu Asn Asp Ser Ala Met Val Val Asp
        420                 425                 430

Trp Ala Lys Pro Thr Leu Glu Tyr Phe Ser Glu Gly Asp Thr Asn Tyr
    435                 440                 445

Thr Ser Ser Met Asn Val Phe Gln Met Pro Ala Glu Gly Lys Trp Ser
450                 455                 460

Phe Trp Ile Ile His Asn Asn Ala Ala Ala Leu Leu Asp His Pro Ile
465                 470                 475                 480

His Leu His Gly His Asp Phe Phe His Leu Gly Ala Gly Thr Gly Thr
            485                 490                 495

Trp Asp Gly Asn Val Asp Ser Leu Ile Phe Asp Asn Pro Met Arg Arg
        500                 505                 510

Asp Val Met Ile Leu Pro Thr Gly Trp Leu Ile Ile Ala Phe Pro Ala
    515                 520                 525

Asp Asn Pro Gly Ala Trp Leu Met His Cys His Ile Ala Trp His Val
530                 535                 540

Thr Asp Gly Leu Ser Leu Gln Phe Val Glu Asn Pro Gly Ser Phe Thr
545                 550                 555                 560

Gln Asp Leu Ser Gly Met Lys Ser Asn Cys Ala Ala Trp Lys Glu Tyr
            565                 570                 575

Glu Glu Lys Ala Tyr Tyr Glu Lys Glu Val Gly Asp Ser Gly Leu
        580                 585                 590

595                 600                 605

<210> SEQ ID NO 55
<211> LENGTH: 2147
<212> TYPE: DNA
<213> ORGANISM: M. phaseolina

<400> SEQUENCE: 55
gccacggctc catttggatc gtcactcacc accaccacca caaccactct ctactcacct      60
cttcaccagc cccctctttc tcctcactgg catccattcg ttgaagtcgc tgtcccgttt     120
tcttgtcttt cgtcttcttc caccgtcaga atgagggctt cttacctctc tgcggctgcc     180
ttcctgggcc tctcggctgc cgcgccgcaa gccgccagca cttcttcttc ctctgcttca     240
gccaacgcca gttccaccag ctcagcagct acttccactt gcactggcaa cactgccgac     300
gaccgcactg tgtggtgcga ctacgacatc agcaccgact actacaacga cggacccgac     360 acggggggtca cccgcgagta ctacttcgtc gtcagcgacg tgaccgtctc gcccgatggc     420
atctcgcgct ccgctatggc ggtgaacggc agcatccccg ccccaccat tttcgccgac     480

```
tggggtgaca cagtgaaagt tactgtctac aacgacctca ccacgagcgg caacggctct      540
tccatccatt ggcacggtat ccggcagaac tacacgaacc agaatgatgg tgtggtgtct      600
attacgcaat gcccgattgc ggtcggcgag acctacacct acgagtggaa ggccacgcag      660
tacggctctt cctggtacca ctctcacatt ggcctgcagg cctgggaggg tgttttcggt      720
ggtatcatta tcaacggtcc cgctactgca aattacgacg aggacctcgg catcatgttt      780
ctcaatgatt gggatcactc gactgttgac gagctctacg attcagctca gagcagcggt      840
cctcctacgc ttgacaccgg tctcattaac ggaaccaaca tctacaatga ctccggaaca      900
gttactggat ctcgctggga ggccagcctg accgagggta ccagctaccg gctccgtctt      960
gtcaacgctg ctgtagactc gcacttcaaa ttttcgatcg ataaccacac cctccaggtt     1020
atcgccatgg acctggtccc cattgagccc tacgagacta ctgttctgga cattggcatg     1080
ggtcagcgct acgacgtcat tgttacggca gaccaggctt ctgttgcttc tgatttctgg     1140
cttcgcgcaa ttccccagac cgcctgctcg gacaacgata cgcagatgat atcaagggc     1200 ataatccact acggatcatc aactggtact ccggaaacca ctgcttagta agttccgatg     1260
tccacatctt ccgagctctc cgctaatgat tcaacagtga ttacactgat gcctgtgtcg     1320
atgaggacag ctctgatctc gtaagtgctc gagattcacg gtcgtctgga aagagtaggc     1380
gcgctgactg tgatctttag gtcccgtatg tctctaagac tgccacctcc ggtacctccc     1440
tggccgaggc tgtttccgtc ggctacaact cggacaacct cttccgctgg tacatgaacg     1500
agacctctat ggaggtcgag tgggagaatc caacccttct gcaggtctac aacgacaatc     1560
tgacgttcac tgacacatcg ggtgttgttc aacttgacac cgcagaccaa tggtacttct     1620
tcgtcatcga accgacaac gctgtgccac acccaatcca tcttcacggc cacgacttct     1680
tcgtcctggc tgcgggcacc ggctcttaca gttcagacgt tactctgact ctggataacc     1740
ctccccgccg cgacacggct atgcttgact cctctggcta cttggtcctg gctttcgaga     1800
ccgacaaccc aggtgcgtgg ttgatgcact gccacatcgg ctggcacacc agcgagggct     1860
ttgcccttca gatcttggag cgctacaccg agatccagga tagcctgatc gactacgacg     1920
tcctcaatga cacctgctcg acttggtcta cttactccga ggcaaactcg atcgaggagg     1980
aggactctgg tgtgtaagga aaactctgag tgacaatccg tctatggcag gtgtgcgggg     2040
cgctttggag ctctctctat ctctgtgaaa gatcttgtat ataacgtgat gccagcctct     2100
ccctgacatt tggtgcttcg gttgatctac atatatttcc ttatttta                 2147
```

<210> SEQ ID NO 56
<211> LENGTH: 1737
<212> TYPE: DNA
<213> ORGANISM: M. phaseolina

<400> SEQUENCE: 56

```
atgagggctt cttacctctc tgcggctgcc ttcctgggcc tctcggctgc cgcgccgcaa       60
gccgccagca cttcttcttc ctctgcttca gccaacgcca gttccaccag ctcagcagct      120
acttccactt gcactggcaa cactgccgac gaccgcactg tgtggtgcga ctacgacatc      180
agcaccgact actacaacga cggacccgac acgggggtca cccgcgagta ctacttcgtc      240
gtcagcgacg tgaccgtctc gcccgatggc atctcgcgct ccgctatggc ggtgaacggc      300
agcatccccg gccccaccat tttcgccgac tggggtgaca cagtgaaagt tactgtctac      360
aacgacctca ccacgagcgg caacggctct tccatccatt ggcacggtat ccggcagaac      420
```

```
tacacgaacc agaatgatgg tgtggtgtct attacgcaat gcccgattgc ggtcggcgag      480
acctacacct acgagtggaa ggccacgcag tacggctctt cctggtacca ctctcacatt      540
ggcctgcagg cctgggaggg tgttttcggt ggtatcatta tcaacggtcc cgctactgca      600
aattacgacg aggacctcgg catcatgttt ctcaatgatt gggatcactc gactgttgac      660
gagctctacg attcagctca gagcagcggt cctcctacgc ttgacaccgg tctcattaac      720
ggaaccaaca tctacaatga ctccggaaca gttactggat ctcgctggga ggccagcctg      780
accgagggta ccagctaccg gctccgtctt gtcaacgctg ctgtagactc gcacttcaaa      840
ttttcgatcg ataaccacac cctccaggtt atcgccatgg acctggtccc cattgagccc      900
tacgagacta ctgttctgga cattggcatg ggtcagcgct acgacgtcat tgttacggca      960
gaccaggctt ctgttgcttc tgatttctgg cttcgcgcaa ttccccagac cgcctgctcg     1020
gacaacgata acgcagatga tatcaagggc ataatccact acggatcatc aactggtact     1080
ccggaaacca ctgcttatga ttacactgat gcctgtgtcg atgaggacag ctctgatctc     1140
gtcccgtatg tctctaagac tgccacctcc ggtacctccc tggccgaggc tgtttccgtc     1200
ggctacaact cggacaacct cttccgctgg tacatgaacg agacctctat ggaggtcgag     1260
tgggagaatc caacccttct gcaggtctac aacgacaatc tgacgttcac tgacacatcg     1320
ggtgttgttc aacttgacac cgcagaccaa tggtacttct tcgtcatcga accgacaac      1380 gctgtgccac acccaatcca tcttcacggc acgacttctc tcgtcctggc tgcgggcacc     1440
ggctcttaca gttcagacgt tactctgact ctggataacc ctccccgccg cgacacggct     1500
atgcttgact cctctggcta cttggtcctg gctttcgaga ccgacaaccc aggtgcgtgg     1560
ttgatgcact gccacatcgg ctggcacacc agcgagggct tgcccttca  gatcttggag     1620 cgctacaccg agatccagga tagcctgatc gactacgacg tcctcaatga cacctgctcg     1680
acttggtcta cttactccga ggcaaactcg atcgaggagg aggactctgg tgtgtaa        1737
```

<210> SEQ ID NO 57
<211> LENGTH: 578
<212> TYPE: PRT
<213> ORGANISM: M. phaseolina

<400> SEQUENCE: 57

```
Met Arg Ala Ser Tyr Leu Ser Ala Ala Ala Phe Leu Gly Leu Ser Ala
1               5                   10                  15

Ala Ala Pro Gln Ala Ala Ser Thr Ser Ser Ser Ala Ser Ala Asn
                20                  25                  30

Ala Ser Ser Thr Ser Ser Ala Ala Thr Ser Thr Cys Thr Gly Asn Thr
            35                  40                  45

Ala Asp Asp Arg Thr Val Trp Cys Asp Tyr Asp Ile Ser Thr Asp Tyr
        50                  55                  60

Tyr Asn Asp Gly Pro Asp Thr Gly Val Thr Arg Glu Tyr Tyr Phe Val
65                  70                  75                  80

Val Ser Asp Val Thr Val Ser Pro Asp Gly Ile Ser Arg Ser Ala Met
                85                  90                  95

Ala Val Asn Gly Ser Ile Pro Gly Pro Thr Ile Phe Ala Asp Trp Gly
            100                 105                 110

Asp Thr Val Lys Val Thr Val Tyr Asn Asp Leu Thr Thr Ser Gly Asn
        115                 120                 125

Gly Ser Ser Ile His Trp His Gly Ile Arg Gln Asn Tyr Thr Asn Gln
    130                 135                 140
```

```
Asn Asp Gly Val Val Ser Ile Thr Gln Cys Pro Ile Ala Val Gly Glu
145                 150                 155                 160

Thr Tyr Thr Tyr Glu Trp Lys Ala Thr Gln Tyr Gly Ser Ser Trp Tyr
            165                 170                 175

His Ser His Ile Gly Leu Gln Ala Trp Glu Gly Val Phe Gly Gly Ile
        180                 185                 190

Ile Ile Asn Gly Pro Ala Thr Ala Asn Tyr Asp Glu Asp Leu Gly Ile
    195                 200                 205

Met Phe Leu Asn Asp Trp Asp His Ser Thr Val Asp Glu Leu Tyr Asp
210                 215                 220

Ser Ala Gln Ser Ser Gly Pro Pro Thr Leu Asp Thr Gly Leu Ile Asn
225                 230                 235                 240

Gly Thr Asn Ile Tyr Asn Asp Ser Gly Thr Val Thr Gly Ser Arg Trp
            245                 250                 255

Glu Ala Ser Leu Thr Glu Gly Thr Ser Tyr Arg Leu Arg Leu Val Asn
            260                 265                 270

Ala Ala Val Asp Ser His Phe Lys Phe Ser Ile Asp Asn His Thr Leu
        275                 280                 285

Gln Val Ile Ala Met Asp Leu Val Pro Ile Glu Pro Tyr Glu Thr Thr
290                 295                 300

Val Leu Asp Ile Gly Met Gly Gln Arg Tyr Asp Val Ile Val Thr Ala
305                 310                 315                 320

Asp Gln Ala Ser Val Ala Ser Asp Phe Trp Leu Arg Ala Ile Pro Gln
            325                 330                 335

Thr Ala Cys Ser Asp Asn Asp Asn Ala Asp Asp Ile Lys Gly Ile Ile
            340                 345                 350

His Tyr Gly Ser Ser Thr Gly Thr Pro Glu Thr Thr Ala Tyr Asp Tyr
        355                 360                 365

Thr Asp Ala Cys Val Asp Glu Asp Ser Ser Asp Leu Val Pro Tyr Val
        370                 375                 380

Ser Lys Thr Ala Thr Ser Gly Thr Ser Leu Ala Glu Ala Val Ser Val
385                 390                 395                 400

Gly Tyr Asn Ser Asp Asn Leu Phe Arg Trp Tyr Met Asn Glu Thr Ser
            405                 410                 415

Met Glu Val Glu Trp Glu Asn Pro Thr Leu Leu Gln Val Tyr Asn Asp
            420                 425                 430

Asn Leu Thr Phe Thr Asp Thr Ser Gly Val Val Gln Leu Asp Thr Ala
        435                 440                 445

Asp Gln Trp Tyr Phe Phe Val Ile Glu Thr Asp Asn Ala Val Pro His
450                 455                 460

Pro Ile His Leu His Gly His Asp Phe Phe Val Leu Ala Ala Gly Thr
465                 470                 475                 480

Gly Ser Tyr Ser Ser Asp Val Thr Leu Thr Leu Asp Asn Pro Pro Arg
            485                 490                 495

Arg Asp Thr Ala Met Leu Asp Ser Gly Tyr Leu Val Leu Ala Phe
        500                 505                 510

Glu Thr Asp Asn Pro Gly Ala Trp Leu Met His Cys His Ile Gly Trp
        515                 520                 525

His Thr Ser Glu Gly Phe Ala Leu Gln Ile Leu Glu Arg Tyr Thr Glu
        530                 535                 540

Ile Gln Asp Ser Leu Ile Asp Tyr Asp Val Leu Asn Asp Thr Cys Ser
545                 550                 555                 560

Thr Trp Ser Thr Tyr Ser Glu Ala Asn Ser Ile Glu Glu Glu Asp Ser
```

Gly Val

<210> SEQ ID NO 58
<211> LENGTH: 2302
<212> TYPE: DNA
<213> ORGANISM: M. phaseolina

<400> SEQUENCE: 58

```
tgcgcccctc ccgcgtgctg ggcactcttt tataaaggca gctctccact cctgccctgt      60
gaatgcttgc tcaagggcgc tcaggcatag gtaagtaggg taagtattga ggcgtctggc     120
tttgcggcga atcttgggac gatttcagcc atgactcgcc ttccgttcgt cctcgggctc     180
gtggctacgg ctttggccaa gacggtcact gttgactggg acattggctg ggtttccagg     240
gctcccgatg gattcgagcg gcctgtcatc gcaatcaacg ccaatggcc gctccctgtg      300
ctggaggccg acgtcaacga caccatcatc gccactgtcc acaattctct tggcaacgaa     360
acgaccagca tccactggca cggcatgtgg cagagaggca cgcccgagca agacggcggg     420
gctggcgtca cgcagtgtcc gatcccgcct ggcgagactt tcacgtacga gttcaaagca     480
tacccggccg gtactttctg gtaccactcg catgacatgg ccagtatccc gatggcctg      540
cgcgcaccca tgatcatcca tgaccccgac tccgaaaccc agaagagcag tgatggtgaa     600
gtcgtgctct atgtgtccga ctggtaccac gaccagatgc cgccgcttat ccacagcttc     660
ctgaccaccc ccaatttcaa cggcgcgatg cccaacccga actccagctt gatcaacgat     720
cagcagtcca cgtccatcaa catccgtccc ggcgagaaga aatacgtgcg catcatcaac     780
acgtccgccc tcgccacgta ctacctgcag tttggtgggt ccgcttcag ccaccctcc      840
cctgcggaag tgactgacga tttcagacca acacaacatc accgttgtcg caattgacgg     900
tgttgacggt ccgtactacc cctgtcgctt atgctgtggc ttcgtgcata cccgtcggca     960
gcttccgcc gttgcatgcc cgaggcgata caaggtttta gtgctgaccg tagtcgtgca    1020
gtcgaaccgc agagctggaa ggccctggag atcgtccccg ccagcggta cgacttcatc    1080
atcgaaggtc tcgagaaccc cacaaggaac tacgcattca tcaacaagat ggctgttctc    1140
ggtctgcaga acgtcaacag cctggtctac gacgagtcct tcggcgagcc ggagtcgttc    1200
agcctgagct ctggcgatct cggaagtgat tcaccctgg tgcctctaga tcacgagcct    1260
ctcttggaat ccgtggacca ccatcacg atggaggtca ataatttgaa cattgatggc    1320
gttggctttc ggtacggctg atcccgtggc cgggagaaat cttgctcaca tgtgccacag    1380
catcactcaa ggcccggacc cgtacatttc accccgcacg cctaccctgt acacagccct    1440
cagcaccggc ttcaacgcca ccgacccaga atctacggc caggtgaacc cctacgtcgt    1500
caacgccggt gaagtcgtcc ggctcgtcgt caacagcaac gatctcgtca ccgccaacaa    1560
ctctggccgc gggcaccca tgcatctgca cggccacgtt ttccaggtgg tcggtcagtt    1620
ctccgagcac tgggacggca acacctcgtc cttccccgcc acgccatga agcgtgacac    1680
caccgtccta ttcgctggcg gcagcctggt gctccagttc cgtgccgaca accccggtgt    1740
ttggctgtgt aagtattttt ttttccgatg cccatggtgc ctggacgtga gctgatgagg    1800
atgggccttg cagttcactg ccatattgag tggcacctag acgccggcat gtccgctaca    1860
atcatcgagg cgccgctcga cttgcagcgc gagggcatca agatccccca gcagcatctt    1920
gaatcgtgca gagccttgaa cttgaccact caaggcaatt gcgccggcaa caccgccaac    1980
ctggatgaca ctgccgcctg cagggtctac gacaccgatc catgggggta ggtcatatcg    2040
```

```
gagtttaatt gagcttgaag gacatgtgct gaccgttgcg tttagtgcgc ttatcacgga   2100
tgacggtggt ggaaatagta ccctgaacgg aaccacttat aagagaattt agtgtgtaat   2160
cttaatacgt cttcacatgt acacaaccta tgcattgtat tcaaattcta cataagcact   2220
tcgacagtag tctgagttga ctgactaggc tcgtggacgg aggacgccgt ttcctcgtct   2280
ttgcctgcta aattttcgcg at                                           2302
```

<210> SEQ ID NO 59
<211> LENGTH: 1665
<212> TYPE: DNA
<213> ORGANISM: M. phaseolina

<400> SEQUENCE: 59

```
atgactcgcc ttccgttcgt cctcgggctc gtggctacgg ctttggccaa gacggtcact     60
gttgactggg acattggctg ggtttccagg gctcccgatg gattcgagcg gcctgtcatc    120
gcaatcaacg gccaatggcc gctccctgtg ctggaggccg acgtcaacga caccatcatc    180
gccactgtcc acaattctct tggcaacgaa acgaccagca tccactggca cggcatgtgg    240
cagagaggca cgcccgagca agacggcggg gctggcgtca cgcagtgtcc gatcccgcct    300
ggcgagactt tcacgtacga gttcaaagca tacccggccg gtactttctg gtaccactcg    360
catgacatgg gccagtatcc cgatggcctg cgcgcaccca tgatcatcca tgaccccgac    420
tccgaaaccc agaagagcag tgatggtgaa gtcgtgctct atgtgtccga ctggtaccac    480
gaccagatgc cgccgcttat ccacagcttc ctgaccaccc ccaatttcaa cggcgcgatg    540
cccaacccga actccagctt gatcaacgat cagcagtcca cgtccatcaa catccgtccc    600
ggcgagaaga aatacgtgcg catcatcaac acgtccgccc tcgccacgta ctacctgcag    660
tttgaccaac acaacatcac cgttgtcgca attgacggtg ttgacgtcga accgcagagc    720
tggaaggccc tggagatcgt ccccggccag cggtacgact tcatcatcga aggtctcgag    780
aaccccacaa ggaactacgc attcatcaac aagatggctg ttctcggtct gcagaacgtc    840
aacagcctgg tctacgacga gtccttcggc gagccggagt cgttcagcct gagctctggc    900
gatctcggaa gtgatttcac cctggtgcct ctagatcacg agcctctctt ggaatccgtg    960
gaccacacca tcacgatgga ggtcaataat ttgaacattg atggcgttgg ctttcgcatc   1020
actcaaggcc cggacccgta catttcaccc cgcacgccta ccctgtacac agccctcagc   1080
accggcttca cgccaccgga cccagaaatc tacggccagg tgaaccccta cgtcgtcaac   1140
gccggtgaag tcgtccggct cgtcgtcaac agcaacgatc tcgtcaccgc caacaactct   1200
ggccgcgggc accccatgca tctgcacggc cacgttttcc aggtggtcgg tcagttctcc   1260
gagcactggg acgcaacac ctcgtccttc ccgccacgc ccatgaagcg tgacaccacc    1320
gtcctattcg ctggcggcag cctggtgctc cagttccgtg ccgacaaccc cggtgtttgg   1380
ctgtttcact gccatattga gtggcaccta gacgccggca tgtccgctac aatcatcgag   1440
gcgccgctcg acttgcagcg cgagggcatc aagatccccc agcagcatct tgaatcgtgc   1500
agagccttga acttgaccac tcaaggcaat tgcgccggca acaccgccaa cctggatgac   1560
actgccgcct gcagggtcta cgacaccgat ccatggggtg cgcttatcac ggatgacggt   1620
ggtggaaata gtaccctgaa cggaaccact tataagagaa tttag                  1665
```

<210> SEQ ID NO 60
<211> LENGTH: 554
<212> TYPE: PRT

<213> ORGANISM: M. phaseolina

<400> SEQUENCE: 60

```
Met Thr Arg Leu Pro Phe Val Leu Gly Leu Val Ala Thr Ala Leu Ala
1               5                   10                  15

Lys Thr Val Thr Val Asp Trp Asp Ile Gly Trp Val Ser Arg Ala Pro
            20                  25                  30

Asp Gly Phe Glu Arg Pro Val Ile Ala Ile Asn Gly Gln Trp Pro Leu
        35                  40                  45

Pro Val Leu Glu Ala Asp Val Asn Asp Thr Ile Ile Ala Thr Val His
    50                  55                  60

Asn Ser Leu Gly Asn Glu Thr Thr Ser Ile His Trp His Gly Met Trp
65                  70                  75                  80

Gln Arg Gly Thr Pro Glu Gln Asp Gly Gly Ala Gly Val Thr Gln Cys
                85                  90                  95

Pro Ile Pro Pro Gly Glu Thr Phe Thr Tyr Glu Phe Lys Ala Tyr Pro
            100                 105                 110

Ala Gly Thr Phe Trp Tyr His Ser His Asp Met Gly Gln Tyr Pro Asp
        115                 120                 125

Gly Leu Arg Ala Pro Met Ile Ile His Asp Pro Asp Ser Glu Thr Gln
    130                 135                 140

Lys Ser Ser Asp Gly Glu Val Val Leu Tyr Val Ser Asp Trp Tyr His
145                 150                 155                 160

Asp Gln Met Pro Pro Leu Ile His Ser Phe Leu Thr Thr Pro Asn Phe
                165                 170                 175

Asn Gly Ala Met Pro Asn Pro Asn Ser Ser Leu Ile Asn Asp Gln Gln
            180                 185                 190

Ser Thr Ser Ile Asn Ile Arg Pro Gly Glu Lys Lys Tyr Val Arg Ile
        195                 200                 205

Ile Asn Thr Ser Ala Leu Ala Thr Tyr Tyr Leu Gln Phe Asp Gln His
    210                 215                 220

Asn Ile Thr Val Val Ala Ile Asp Gly Val Asp Val Glu Pro Gln Ser
225                 230                 235                 240

Trp Lys Ala Leu Glu Ile Val Pro Gly Gln Arg Tyr Asp Phe Ile Ile
                245                 250                 255

Glu Gly Leu Glu Asn Pro Thr Arg Asn Tyr Ala Phe Ile Asn Lys Met
            260                 265                 270

Ala Val Leu Gly Leu Gln Asn Val Asn Ser Leu Val Tyr Asp Glu Ser
        275                 280                 285

Phe Gly Glu Pro Glu Ser Phe Ser Leu Ser Ser Gly Asp Leu Gly Ser
    290                 295                 300

Asp Phe Thr Leu Val Pro Leu Asp His Glu Pro Leu Leu Glu Ser Val
305                 310                 315                 320

Asp His Thr Ile Thr Met Glu Val Asn Leu Asn Ile Asp Gly Val
                325                 330                 335

Gly Phe Arg Ile Thr Gln Gly Pro Asp Pro Tyr Ile Ser Pro Arg Thr
            340                 345                 350

Pro Thr Leu Tyr Thr Ala Leu Ser Thr Gly Phe Asn Ala Thr Asp Pro
        355                 360                 365

Glu Ile Tyr Gly Gln Val Asn Pro Tyr Val Val Asn Ala Gly Glu Val
    370                 375                 380

Val Arg Leu Val Val Asn Ser Asn Asp Leu Val Thr Ala Asn Asn Ser
385                 390                 395                 400
```

Gly Arg Gly His Pro Met His Leu His Gly His Val Phe Gln Val Val
            405                 410                 415

Gly Gln Phe Ser Glu His Trp Asp Gly Asn Thr Ser Ser Phe Pro Ala
        420                 425                 430

Thr Pro Met Lys Arg Asp Thr Thr Val Leu Phe Ala Gly Gly Ser Leu
        435                 440                 445

Val Leu Gln Phe Arg Ala Asp Asn Pro Gly Val Trp Leu Phe His Cys
    450                 455                 460

His Ile Glu Trp His Leu Asp Ala Gly Met Ser Ala Thr Ile Ile Glu
465                 470                 475                 480

Ala Pro Leu Asp Leu Gln Arg Glu Gly Ile Lys Ile Pro Gln Gln His
                485                 490                 495

Leu Glu Ser Cys Arg Ala Leu Asn Leu Thr Thr Gln Gly Asn Cys Ala
            500                 505                 510

Gly Asn Thr Ala Asn Leu Asp Asp Thr Ala Ala Cys Arg Val Tyr Asp
        515                 520                 525

Thr Asp Pro Trp Gly Ala Leu Ile Thr Asp Gly Gly Gly Asn Ser
    530                 535                 540

Thr Leu Asn Gly Thr Thr Tyr Lys Arg Ile
545                 550

<210> SEQ ID NO 61
<211> LENGTH: 2460
<212> TYPE: DNA
<213> ORGANISM: M. phaseolina

<400> SEQUENCE: 61

```
ctccgtatct actgctgact tcacatccac agcatgcaag gactcgaggg cttctgattt      60
aacgagcact cacttggctt ttgtctgcgt tttcttttcg ttttcctact atttcatctt     120
gatccattcg ttctcgccgt cgctttccag atgtctttcg tttcgaaaat tttcacaggc     180
ctcatcgctt ttaccgctgg cttaggccaa gatgagacta atgggtgagt atgctgaacc     240
ttgcgcagga tatctgaata atagttgtag ggtttcgaaa tggggcacgt tcgatgcacc     300
gaggctccag aagtttctgg atcgggtgag gttattctga acattactg agctcggcac      360
tgattggtcg gcagggtcat ggcattccct ggggcggtat gacttgtacc aacgccaacc     420
cgtatactga gtaggactcg gcccgtggtc cacaatcttc tctgcgctga cgttcggaaa     480
gagctccaga cacaggacag actgtgcggt atgatttcac agtccagcgg catccggtgt     540
ctccggacgg ctacaagaag aacgttttgc ttgtgaacgg gcaatttcca ggcccgctca     600
tggaagctaa ctggggagac acaattgaag gtaggatgag agtaaatacg ggcagcaaca     660
actgctgaca gatacagtga ctgtgcacaa caacatagcc ggacctgagg aaggcacaca     720
aatccactgg cacggcttca cgcagagagg gacgccgttc atggatggta tcccttccgt     780
atcaagctgc cccattgcgc ccaacaatac ctttgtgtat accttcaagg cagacccttta    840
cggcactggc tggtaccact tcattactc tgggcaatcc accggcggcc tcctcggccc     900
aatcgtcgtc catggtccca gtgcgcttga ctatgatatt gaccttggcc ctgtgttttt     960
gaatgactgg taccacaagg actacttgca gctattgac ggtggtgaga ctttcccgta    1020
ggtcaaaggg ctcgatagct gaaacctcca acagtcgtcg gaacggaccc cagcctatgg    1080
catcccaagg cggacaacaa catgataaac gggaagatgg actacgattg ctcccttgtc    1140
actgacggca cgccttgcgt ctctaatgcc ggcttggcca cgttcagctt caccaagggc    1200
gccacgcacc gtctcaggct cataaacgga ggatccgcct ccctgcagca cttcagtatc    1260
```

```
gatggacacg agatgacagt catttccaat gacttcgtag ccgtagagcc ataccagacg    1320
aagacagtga ctcttgcagt aagccgcccg attttccag atatcccaca ttactaacac     1380
ccaccaggtc ggccagcgga cagacgtcct cgtcacggcc aacggcgacg ccaccggcgc    1440
ctactggatg cgcagcaccg tcgcggacga tgaatcctgc aactggtcca accagcccgc    1500
cgcgctcgcc gcagtctact acgacgcggc aaaccccacc gtcaagccca acagcaccgg    1560
ctggcccccc gtcgccaacc agcaaggcag ctgcgacaac gacccgctta cccaaaccat    1620
ccccctcttc cccatccccg cggaccccag ccctcaacg acgcttgagc tcgacttcgg     1680
ctggacgcaa aacgcaaccg gacaccaagt ctggacggtc aacgaccgcg gcttccgcgg    1740
caactacaac cgccccgtgc tgcagctcgc cgcgggctcg acaccgcgt cgtccgcgta     1800 cgcgtgggag cccgaatgga acgtctacga cacgggccgc aaccgcaccg tccgcatcgt    1860
catgcacaac aactcctcca tgtaccacgt acgtgagccc ttgtctcccc cccccccccc    1920
cctcccctct cgctaatgga aagacacatg cagcccatgc acctcacgg gcacaacgcg     1980 cagatcctcg ccgcgggcgc caacggcccc tgggacggcc gcaccgtcgc gcgccccgcc    2040
aacccggccc gccgcgacgt ctaccagctc ccgccgaacg ggcacctggt gatccagtac    2100
gcgcaggaca acccgggcgt gtggccgctg cactgccaca tcgcgtggca cgcgagcgcg    2160
ggcatgtttg cgagcgtgct ggagcgggcg ggggacattg tggggagcag cggggccggc    2220
gggtggaggg aggagatggc gggcgtgtgt gccgggtggg aggcgtacac gcggatgaac    2280
gtggtggagc aggtggacag tggggtgtga gttgggagca aggaggggg tttgagatgc     2340 gcgtatatgg taagcggttg gggttcttgt ttgactcgat ttgctctgca ggcggtgtct    2400
cttttcgact gtggcgcgtg caatctcgtt tcgtgcatcc tgggtggata gggagcggcg    2460
```

<210> SEQ ID NO 62
<211> LENGTH: 1803
<212> TYPE: DNA
<213> ORGANISM: M. phaseolina

<400> SEQUENCE: 62

```
atgtctttcg tttcgaaaat tttcacaggc ctcatcgctt ttaccgctgg cttaggccaa     60
gatgagacta atggggtttc gaaatggggc acgttcgatg caccgaggct ccagaagttt    120
ctggatcggg gtcatggcat tccctggggc ggtatgactt gtaccaacgc caacccgtat    180
actgaagctc cagacacagg acagactgtg cggtatgatt tcacagtcca gcggcatccg    240
gtgtctccgg acggctacaa gaagaacgtt ttgcttgtga acgggcaatt tccaggcccg    300
ctcatggaag ctaactgggg agacacaatt gaagtgactg tgcacaacaa catagccgga    360
cctgaggaag gcacacaaat ccactggcac ggcttcacgc agagagggac gccgttcatg    420
gatggtatcc cttccgtatc aagctgcccc attgcgccca acaataccct tgtgtatacc    480
ttcaaggcag accttacgg cactggctgg taccactctc attactctgg caatccacc      540 ggcggcctcc tcggcccaat cgtcgtccat ggtcccagtg cgcttgacta tgatattgac    600
cttggccctg tgtttttgaa tgactggtac cacaaggact acttgcagct tattgacggt    660
gtcgtcggaa cggaccccag cctatggcat cccaaggcgg acaacaacat gataaacggg    720
aagatggact acgattgctc ccttgtcact gacggcacgc cttgcgtctc taatgccggc    780
ttggccacgt tcagcttcac caagggcgcc acgcaccgtc tcaggctcat aaacggagga    840
tccgcctccc tgcagcactt cagtatcgat ggacacgaga tgacagtcat tccaatgac    900
```

```
ttcgtagccg tagagccata ccagacgaag acagtgactc ttgcagtcgg ccagcggaca    960
gacgtcctcg tcacggccaa cggcgacgcc accggcgcct actggatgcg cagcaccgtc   1020
gcggacgatg aatcctgcaa ctggtccaac cagcccgccg cgctcgccgc agtctactac   1080
gacgcggcaa accccaccgt caagcccaac agcaccggct ggccccccgt cgccaaccag   1140
caaggcagct gcgacaacga cccgcttacc caaaccatcc ccctcttccc catcccgcg    1200 gaccccagcc cctcaacgac gcttgagctc gacttcggct ggacgcaaaa cgcaaccgga   1260
caccaagtct ggacggtcaa cgaccgcggc ttccgcggca actacaaccg ccccgtgctg   1320
cagctcgccg cgggctcgga caccgcgtcg tccgcgtacg cgtgggagcc cgaatggaac   1380
gtctacgaca cgggccgcaa ccgcaccgtc cgcatcgtca tgcacaacaa ctcctccatg   1440
taccacccca tgcacctcca cgggcacaac gcgcagatcc tcgccgcggg cgccaacggc   1500
ccctgggacg gccgcaccgt cgcgcgcccc gccaacccgg ccgccgcga cgtctaccag    1560 ctcccgccga acgggcacct ggtgatccag tacgcgcagg acaacccggg cgtgtggccg   1620
ctgcactgcc acatcgcgtg gcacgcgagc gcgggcatgt tgcgagcgt gctggagcgg    1680 gcggggggaca ttgtggggag cagcggggcc ggcgggtgga gggaggagat ggcgggcgtg   1740
tgtgccgggt gggaggcgta cacgcggatg aacgtggtgg agcaggtgga cagtggggtg   1800
tga                                                                 1803
```

<210> SEQ ID NO 63
<211> LENGTH: 600
<212> TYPE: PRT
<213> ORGANISM: M. phaseolina

<400> SEQUENCE: 63

```
Met Ser Phe Val Ser Lys Ile Phe Thr Gly Leu Ile Ala Phe Thr Ala
 1               5                   10                  15

Gly Leu Gly Gln Asp Glu Thr Asn Gly Val Ser Lys Trp Gly Thr Phe
             20                  25                  30

Asp Ala Pro Arg Leu Gln Lys Phe Leu Asp Arg Gly His Gly Ile Pro
         35                  40                  45

Trp Gly Gly Met Thr Cys Thr Asn Ala Asn Pro Tyr Thr Glu Ala Pro
     50                  55                  60

Asp Thr Gly Gln Thr Val Arg Tyr Asp Phe Thr Val Gln Arg His Pro
 65                  70                  75                  80

Val Ser Pro Asp Gly Tyr Lys Lys Asn Val Leu Leu Val Asn Gly Gln
                 85                  90                  95

Phe Pro Gly Pro Leu Met Glu Ala Asn Trp Gly Asp Thr Ile Glu Val
            100                 105                 110

Thr Val His Asn Asn Ile Ala Gly Pro Glu Glu Gly Thr Gln Ile His
        115                 120                 125

Trp His Gly Phe Thr Gln Arg Gly Thr Pro Phe Met Asp Gly Ile Pro
    130                 135                 140

Ser Val Ser Ser Cys Pro Ile Ala Pro Asn Asn Thr Phe Val Tyr Thr
145                 150                 155                 160

Phe Lys Ala Asp Leu Tyr Gly Thr Gly Trp Tyr His Ser His Tyr Ser
                165                 170                 175

Gly Gln Ser Thr Gly Gly Leu Leu Gly Pro Ile Val Val His Gly Pro
            180                 185                 190

Ser Ala Leu Asp Tyr Asp Ile Asp Leu Gly Pro Val Phe Leu Asn Asp
        195                 200                 205
```

```
Trp Tyr His Lys Asp Tyr Leu Gln Leu Ile Asp Gly Val Val Gly Thr
    210                 215                 220
Asp Pro Ser Leu Trp His Pro Lys Ala Asp Asn Asn Met Ile Asn Gly
225                 230                 235                 240
Lys Met Asp Tyr Asp Cys Ser Leu Val Thr Asp Gly Thr Pro Cys Val
                245                 250                 255
Ser Asn Ala Gly Leu Ala Thr Phe Ser Phe Thr Lys Gly Ala Thr His
            260                 265                 270
Arg Leu Arg Leu Ile Asn Gly Gly Ser Ala Ser Leu Gln His Phe Ser
        275                 280                 285
Ile Asp Gly His Glu Met Thr Val Ile Ser Asn Asp Phe Val Ala Val
    290                 295                 300
Glu Pro Tyr Gln Thr Lys Thr Val Thr Leu Ala Val Gly Gln Arg Thr
305                 310                 315                 320
Asp Val Leu Val Thr Ala Asn Gly Asp Ala Thr Gly Ala Tyr Trp Met
                325                 330                 335
Arg Ser Thr Val Ala Asp Asp Glu Ser Cys Asn Trp Ser Asn Gln Pro
            340                 345                 350
Ala Ala Leu Ala Ala Val Tyr Tyr Asp Ala Ala Asn Pro Thr Val Lys
        355                 360                 365
Pro Asn Ser Thr Gly Trp Pro Val Ala Asn Gln Gln Gly Ser Cys
    370                 375                 380
Asp Asn Asp Pro Leu Thr Gln Thr Ile Pro Leu Phe Pro Ile Pro Ala
385                 390                 395                 400
Asp Pro Ser Pro Ser Thr Thr Leu Glu Leu Asp Phe Gly Trp Thr Gln
                405                 410                 415
Asn Ala Thr Gly His Gln Val Trp Thr Val Asn Asp Arg Gly Phe Arg
            420                 425                 430
Gly Asn Tyr Asn Arg Pro Val Leu Gln Leu Ala Ala Gly Ser Asp Thr
        435                 440                 445
Ala Ser Ser Ala Tyr Ala Trp Glu Pro Glu Trp Asn Val Tyr Asp Thr
    450                 455                 460
Gly Arg Asn Arg Thr Val Arg Ile Val Met His Asn Asn Ser Ser Met
465                 470                 475                 480
Tyr His Pro Met His Leu His Gly His Asn Ala Gln Ile Leu Ala Ala
                485                 490                 495
Gly Ala Asn Gly Pro Trp Asp Gly Arg Thr Val Ala Arg Pro Ala Asn
            500                 505                 510
Pro Ala Arg Arg Asp Val Tyr Gln Leu Pro Pro Asn Gly His Leu Val
        515                 520                 525
Ile Gln Tyr Ala Gln Asp Asn Pro Gly Val Trp Pro Leu His Cys His
    530                 535                 540
Ile Ala Trp His Ala Ser Ala Gly Met Phe Ala Ser Val Leu Glu Arg
545                 550                 555                 560
Ala Gly Asp Ile Val Gly Ser Ser Gly Ala Gly Gly Trp Arg Glu Glu
                565                 570                 575
Met Ala Gly Val Cys Ala Gly Trp Glu Ala Tyr Thr Arg Met Asn Val
            580                 585                 590
Val Glu Gln Val Asp Ser Gly Val
        595                 600

<210> SEQ ID NO 64
<211> LENGTH: 2285
<212> TYPE: DNA
```

<213> ORGANISM: M. phaseolina

<400> SEQUENCE: 64

```
tgaagccctc tctgacgcag gtatctattt tattaaacca gtttcaccct ccggtcgggt      60
aagtatttgc tcaaacaaac ttgtccaagt gtcagttagg taagctagga ggctcacgaa     120
ttcaagagac tctccagaga tatcttcgcc atgattcgcc tttctctcgt gctcggcttc     180
atggccacga cactggccaa gaccgtcact cttaactggg atattgggtg ggtttctgcg     240
gctccagatg gatttacacg gcccgtcatt ggcatcaacg gggagtggcc gccccccgtt     300
ttggaagccg acgtcaacga cactattata gtaattacgc ggaacctcct gcgtaacgag     360
acgacgagct tgcactggca tggtatgtgg cactataact cgacccacat ggacggcgga     420
gccaggattt cacagtgtga aatccctccg gggggacat tcacgtacaa gttcaaggcg      480
tacccggccg gcaccttttg gtatcattct cacgatatgg gccaatatcc cgacggcctg     540
cgcgccccaa tgatcattca cgaccctaag gctgccgcgg agcgggacac tgataaggag     600
tacgtactta cggtctccga ctggtaccgt gaccagatgc cgtcacttat ccaccgctac     660
ttgacaactt ccacttataa tagtactatg ccaaatccaa actcgagctt gatcaacgat     720
cagcagtcta caacgctaaa catccgcccc gggcagaaga tatatgttcg gattattaac     780
atgtcagccc tcgcaacgta ctatctacag ttcggtaggt gtatccatat ggccctgtta     840
cacggacgaa gctaacgatt aagatcaaca ccacttgact gttattgcca ttgacggtgt     900
cgacggttgg taactctatt acctattctg cgctaagatg catgtcggca tatgtgccgt     960
tagctgcatg caaacgcgtt acaaggttaa gtgctaacaa cggcagtcg atccccagac    1020
ttgggaggct ctggagatta tccctggaca gcggtacgac gtcattatca ccggcctaga    1080
gaacccccgaa aggaactatg catttatcaa caagatggct actcttggct tccagaacaa    1140
taacgtcctt agttacgatt cgtcctggcc tgtcccggag ccgttgaacg tgggcagctt    1200
caatcttaga agcgatttca acctgaccc ggcttgatgag gagctactac tggagcccgt    1260
ggaccacacc ttcaccatgg aggtcaataa cgtgaacgtc gacggcgtag gctcccggtg    1320
agatattccc taccccccgg gccccggggg cgggtcccga agtcggtatg aggcttactc    1380
actccaatcc gcagcatcac gcagggaccg gaccctttaca tcgcccccgcg tacgcccacc    1440
ctatacacca ccctgagcac cggctctaat gctattaacc ccgccatata cggccaggcg    1500
aacgcttacg tagtggaagc cggcgatatt gtccagcttg tcgtcaatag taacgaaccc    1560
gtcactacca acacttccgg tcgtgggcac cctatgcact tgcacggcca caccttccaa    1620
gtggttggcc aatatggcag cccttgggac ggcgatgcct ctaaattccc tgctgttcct    1680
atgaagcggg ataccactgt tctgtttact ggcgggagct tggtgatccg gttccgcgcg    1740
gacaatcctg gagtttggat gtgtacggct ccgctttgct cgaagacccg cgtttgaaag    1800
cgttgactga cctgtaactc gcagtccatt gccacaacga atggcacctt gacgccggca    1860
tggctggaac gattatcgaa gcgccactcg agcttcaaca aagcggtctg acgattccgc    1920
cgcagcacct cgcgtcgtgc agggcgttaa acttaacgac ccggggcaat tgtgccggta    1980
atactgcgaa cctagaggat acggctgcat gcagagtcta cgacactgag ccttgggggt    2040
gagttactcc attattgttt tgttgttata accttgctg atgacaatac ttctctagtg    2100
cacttatcaa gagagatgag gaaacagcat attaaatagc acgctggcat agcacctgta    2160
gatgtagact gatttctagt atttattacc tgtgtacact tgaagaaat tgttgtaaaa    2220
tgatatgtcc ccatgcaact gaacatggcc tacgtggcga gagtttatca ggcgccttct    2280
```

```
gctcc                                                          2285
```

<210> SEQ ID NO 65
<211> LENGTH: 1635
<212> TYPE: DNA
<213> ORGANISM: M. phaseolina

<400> SEQUENCE: 65

```
atgattcgcc tttctctcgt gctcggcttc atggccacga cactggccaa gaccgtcact    60
cttaactggg atattgggtg ggtttctgcg gctccagatg gatttacacg gcccgtcatt   120
ggcatcaacg gggagtggcc gcccccgtt ttggaagccg acgtcaacga cactattata   180
gtaattacgc ggaacctcct gcgtaacgag acgacgagct tgcactggca tggtatgtgg   240
cactataact cgacccacat ggacggcgga gccaggattt cacagtgtga aatccctccg   300
gggggacat tcacgtacaa gttcaaggcg tacccggccg gcacctttg gtatcattct    360
cacgatatgg ccaatatcc cgacggcctg cgcgcccaa tgatcattca cgaccctaag   420
gctgccgcgg agcgggacac tgataaggag tacgtactta cggtctccga ctggtaccgt   480
gaccagatgc cgtcacttat ccaccgctac ttgacaactt ccacttataa tagtactatg   540
ccaaatccaa actcgagctt gatcaacgat cagcagtcta caacgctaaa catccgcccc   600
gggcagaaga tatatgttcg gattattaac atgtcagccc tcgcaacgta ctatctacag   660
ttcgatcaac accacttgac tgttattgcc attgacggtg tcgacgtcga tccccagact   720
tgggaggctc tggagattat ccctggacag cggtacgacg tcattatcac cggcctagag   780
aaccccgaaa ggaactatgc atttatcaac aagatggcta ctcttggctt ccagaacaat   840
aacgtcctta gttacgattc gtcctggcct gtcccggagc cgttgaacgt gggcagcttc   900
aatcttagaa gcgatttcaa cctgaccccg cttgatgagg agctactact ggagcccgtg   960
gaccacacct tcaccatgga ggtcaataac gtgaacgtcg acggcgtagg ctcccgcatc  1020
acgcagggac cggacccta catcgccccg cgtacgccca ccctatacac caccctgagc  1080
accggctcta atgctattaa ccccgccata tacggccagg cgaacgctta cgtagtggaa  1140
gccggcgata ttgtccagct tgtcgtcaat agtaacgaac ccgtcactac caacacttcc  1200
ggtcgtgggc accctatgca cttgcacggc cacaccttcc aagtggttgg ccaatatggc  1260
agcccttggg acgcgatgc ctctaaattc cctgctgttc ctatgaagcg ggataccact  1320
gttctgttta ctggcgggag cttggtgatc cggttccgcg cggacaatcc tggagtttgg  1380
atgttccatt gccacaacga atggcacctt gacgccggca tggctggaac gattatcgaa  1440
gcgccactcg agcttcaaca aagcggtctg acgattccgc cgcagcacct cgcgtcgtgc  1500
agggcgttaa acttaacgac ccggggcaat tgtgccggta atactgcgaa cctagaggat  1560
acggctgcat gcagagtcta cgacactgag ccttggggtg cacttatcaa gagagatgag  1620
gaaacagcat attaa                                                  1635
```

<210> SEQ ID NO 66
<211> LENGTH: 544
<212> TYPE: PRT
<213> ORGANISM: M. phaseolina

<400> SEQUENCE: 66

```
Met Ile Arg Leu Ser Leu Val Leu Gly Phe Met Ala Thr Thr Leu Ala
1               5                  10                  15

Lys Thr Val Thr Leu Asn Trp Asp Ile Gly Trp Val Ser Ala Ala Pro
```

```
                    20                  25                  30
Asp Gly Phe Thr Arg Pro Val Ile Gly Ile Asn Gly Glu Trp Pro Pro
                35                  40                  45
Pro Val Leu Glu Ala Asp Val Asn Asp Thr Ile Ile Val Ile Thr Arg
         50                  55                  60
Asn Leu Leu Arg Asn Glu Thr Thr Ser Leu His Trp His Gly Met Trp
 65                  70                  75                  80
His Tyr Asn Ser Thr His Met Asp Gly Gly Ala Arg Ile Ser Gln Cys
                 85                  90                  95
Glu Ile Pro Pro Gly Thr Phe Thr Tyr Lys Phe Lys Ala Tyr Pro
                100                 105                 110
Ala Gly Thr Phe Trp Tyr His Ser His Asp Met Gly Gln Tyr Pro Asp
                115                 120                 125
Gly Leu Arg Ala Pro Met Ile Ile His Asp Pro Lys Ala Ala Ala Glu
                130                 135                 140
Arg Asp Thr Asp Lys Glu Tyr Val Leu Thr Val Ser Asp Trp Tyr Arg
145                 150                 155                 160
Asp Gln Met Pro Ser Leu Ile His Arg Tyr Leu Thr Thr Ser Thr Tyr
                165                 170                 175
Asn Ser Thr Met Pro Asn Pro Asn Ser Ser Leu Ile Asn Asp Gln Gln
                180                 185                 190
Ser Thr Thr Leu Asn Ile Arg Pro Gly Gln Lys Ile Tyr Val Arg Ile
                195                 200                 205
Ile Asn Met Ser Ala Leu Ala Thr Tyr Tyr Leu Gln Phe Asp Gln His
                210                 215                 220
His Leu Thr Val Ile Ala Ile Asp Gly Val Asp Val Asp Pro Gln Thr
225                 230                 235                 240
Trp Glu Ala Leu Glu Ile Ile Pro Gly Gln Arg Tyr Asp Val Ile Ile
                245                 250                 255
Thr Gly Leu Glu Asn Pro Glu Arg Asn Tyr Ala Phe Ile Asn Lys Met
                260                 265                 270
Ala Thr Leu Gly Phe Gln Asn Asn Asn Val Leu Ser Tyr Asp Ser Ser
                275                 280                 285
Trp Pro Val Pro Glu Pro Leu Asn Val Gly Ser Phe Asn Leu Arg Ser
                290                 295                 300
Asp Phe Asn Leu Thr Pro Leu Asp Glu Glu Leu Leu Leu Glu Pro Val
305                 310                 315                 320
Asp His Thr Phe Thr Met Glu Val Asn Val Asn Val Asp Gly Val
                325                 330                 335
Gly Ser Arg Ile Thr Gln Gly Pro Asp Pro Tyr Ile Ala Pro Arg Thr
                340                 345                 350
Pro Thr Leu Tyr Thr Thr Leu Ser Thr Gly Ser Asn Ala Ile Asn Pro
                355                 360                 365
Ala Ile Tyr Gly Gln Ala Asn Ala Tyr Val Val Glu Ala Gly Asp Ile
                370                 375                 380
Val Gln Leu Val Val Asn Ser Asn Glu Pro Val Thr Thr Asn Thr Ser
385                 390                 395                 400
Gly Arg Gly His Pro Met His Leu His Gly His Thr Phe Gln Val Val
                405                 410                 415
Gly Gln Tyr Gly Ser Pro Trp Asp Gly Asp Ala Ser Lys Phe Pro Ala
                420                 425                 430
Val Pro Met Lys Arg Asp Thr Thr Val Leu Phe Thr Gly Gly Ser Leu
                435                 440                 445
```

```
Val Ile Arg Phe Arg Ala Asp Asn Pro Gly Val Trp Met Phe His Cys
    450                 455                 460

His Asn Glu Trp His Leu Asp Ala Gly Met Ala Gly Thr Ile Ile Glu
465                 470                 475                 480

Ala Pro Leu Glu Leu Gln Gln Ser Gly Leu Thr Ile Pro Pro Gln His
                485                 490                 495

Leu Ala Ser Cys Arg Ala Leu Asn Leu Thr Thr Arg Gly Asn Cys Ala
                500                 505                 510

Gly Asn Thr Ala Asn Leu Glu Asp Thr Ala Ala Cys Arg Val Tyr Asp
                515                 520                 525

Thr Glu Pro Trp Gly Ala Leu Ile Lys Arg Asp Glu Glu Thr Ala Tyr
                530                 535                 540

<210> SEQ ID NO 67
<211> LENGTH: 2412
<212> TYPE: DNA
<213> ORGANISM: M. phaseolina

<400> SEQUENCE: 67
gggagacgat ctggaagtgt tgttcagaa tgatttggcc gttgaaacca ccattcattg      60
gcacggtcgg tatccatggt atacttttta cgaaggctag tcagctgaag gagaagttcg     120
gcaggcatcc ttcagcaagg aacaccacac atggacggag ttccgggagt aacacaggtt     180
ggttgatgac cttctatcgg gatgactagg gcctaacttt tggcgcagga gccgatccca     240
ccaggaggaa acttcacgta ccgcttctcg ctcaaaaacg aatacggctt ctactggtat     300
cactcgcatt tccgagcata ctcggacgac gccatccgcg gaccactagt catccatcca     360
tcctcacaac gcccccggcc atacgagact ctcgcgagga accagactga gcttactgct     420
ttgcaagaag ctgaacgcga agcggtgcct atcctcctat ctgactggta ccatcgcgtt     480
tcggacgaca tcttcaacga atacctaaca acaggcgcgt tccccagttg cgtggacagt     540
ctcctcgcca atggatacgg aagggtgcgg tgtctaccgg aatacattct ggcagccgga     600
gctgggctag gcatggagcc tgcacctgtc aatgctaccg cgactagcat cggcacaacg     660
cccatgtctt ccatggcgat gggtacaaag tacatggaga ccaataccaa ggagtcgatg     720
cgtatggagt ctatggcact agacactacg tccatggagc atcacatgcg acgcatggat     780
tccatgtcag cggaggatat gtccatgaat acgatgactg ctcattctac gcctgcggct     840
gcgcccgact caggcatgcc gatgggctcc atgtcaatgg cttctctacc cgtatcaggc     900
atatcgggca cgtcgggcct gtcgggcatg tcaaatatgg cgagcggtcc ccttggtcct     960
cgcggctgca gtgctcccat gatgttcaga ccgggctaca acatcagctc tctcccgcca    1020
gagacttgca cagacacgtc agcgccgctg ctgactgtcg atgcaaacta tacgcgaggc    1080
tggcttgcat taaacctagt caactccggt tcagtaacca agctcagcgt ctcactagac    1140
gcccattcga tgtttgtcta tgcggccgac ggattctttg tgaaacccca agaagtagaa    1200
gtaagttgca cctcccccta acttgtcgtc ggaagactta ccgcgtctag gtattacaaa    1260
tctcaatcgg gcaacggtac tcagtaatga tcaaacttaa tcaacggccc ggaaactaca    1320
ctctacggtt tgcgtcgtat ccctacggcg atatgcaaca ggttatcgaa ggccaagcga    1380
ccgtctcata taggtaagc agcaagcttt tcccccactc ggtatagaac taacttcgtt    1440
aggttgatgc cgcagaggac attatgccgg tggacttgac aaacgaccct actgcaacgt    1500
ggatgcttgt caacggttcg gcaaagtcga acgcttctga attgaagacg gacatgctcg    1560
```

| | |
|---|---|
| ccccgttcga ggcaattgcg ccgccatccc aagcggatat aacttacgac ttcacgatca | 1620 |
| gtcagacaga gatcgtaact tgggtgttaa acggatatcc ctattcggaa ccttcgacgc | 1680 |
| ctattatcta cggcaatgcg tcggaagcgt ggaacgcaaa tactacaatc cgcattcctt | 1740 |
| ccaactcgac cgtagacatt ataatgcgga ttgccaacga ctcaatggat acggcaagtt | 1800 |
| gcagtccagg ccgccgtcaa aacgcctgca taagctaacc cgataatgcc gtagatgggt | 1860 |
| catcctatgc accttcacgg ccaccggttc ttcgccctcg gctctggatc gggctccttc | 1920 |
| ccatatcaga acgccgtcga cgcgcctcca tccctcatta acctcgaaaa ccctccgtac | 1980 |
| cgggacacaa ccgatttacc accttcaggc tgggcagtca ttcgctatgt agccaacaat | 2040 |
| ccaggcgcat ggatgtttca ctgccacatc cagtggcacc tcgtgagcgg catggcattg | 2100 |
| gtgtttgtcg aaggagaaga gcagctgcct ggtttggtgg gtgcggctgc gaacggaaca | 2160 |
| agcaatgcga atagcgcgtc accggcgcgt agcactcgag agcatgcggc ctttgccgtt | 2220 |
| gttgctaccc taagcactgt tttcttcgcg tatggctact aatgcgcgaa gcgccatgta | 2280 |
| agagcgcgcc tgaggtaata aaggtggcga ctgcaaaaag ctcatgtccc gcgaatgatg | 2340 |
| ggagttcttt ggagattctg aatcaaagac gtcgatattc tgggtccagt cggtgcagaa | 2400 |
| cagaccccat gg | 2412 |

<210> SEQ ID NO 68
<211> LENGTH: 1743
<212> TYPE: DNA
<213> ORGANISM: M. phaseolina

<400> SEQUENCE: 68

| | |
|---|---|
| atggacggag ttccgggagt aacacaggag ccgatcccac caggaggaaa cttcacgtac | 60 |
| cgcttctcgc tcaaaaacga atacggcttc tactggtatc actcgcattt ccagagcatac | 120 |
| tcggacgacg ccatccgcgg accactagtc atccatccat cctcacaacg cccccggcca | 180 |
| tacgagactc tcgcgaggaa ccagactgag cttactgctt tgcaagaagc tgaacgcgaa | 240 |
| gcggtgccta tcctcctatc tgactggtac catcgcgttt cggacgacat cttcaacgaa | 300 |
| tacctaacaa caggcgcgtt ccccagttgc gtggacagtc tcctcgccaa tggatacgga | 360 |
| agggtgcggt gtctaccgga atacattctg gcagccggag ctgggctagg catggagcct | 420 |
| gcacctgtca atgctaccgc gactagcatc ggcacaacgc ccatgtcttc catggcgatg | 480 |
| ggtacaaagt acatggagac caataccaag gagtcgatgc gtatggagtc tatggcacta | 540 |
| gacactacgt ccatggagca tcacatgcga cgcatggatt ccatgtcagc ggaggatatg | 600 |
| tccatgaata cgatgactgc tcattctacg cctgcggctg cgcccgactc aggcatgccg | 660 |
| atgggctcca tgtcaatggc ttctctaccc gtatcaggca tatcgggcac gtcgggcctg | 720 |
| tcgggcatgt caaatatggc gagcggtccc cttggtcctc gcggctgcag tgctcccatg | 780 |
| atgttcagac cgggctacaa catcagctct ctcccgccag agacttgcac agacacgtca | 840 |
| gcgccgctgc tgactgtcga tgcaaactat acacagaggct ggcttgcatt aaacctagtc | 900 |
| aactccggtt cagtaaccaa gctcagcgtc tcactagacg cccattcgat gtttgtctat | 960 |
| gcggccgacg gattctttgt gaaaccccaa gaagtagaag tattacaaat ctcaatcggg | 1020 |
| caacggtact cagtaatgat caaacttaat caacggcccg gaaactacac tctacggttt | 1080 |
| gcgtcgtatc cctacggcga tatgcaacag gttatcgaag gccaagcgac cgtctcatat | 1140 |
| aaggttgatg ccgcagagga cattatgccg gtggacttga caaacgaccc tactgcaacg | 1200 |
| tggatgcttg tcaacggttc ggcaaagtcg aacgcttctg aattgaagac ggacatgctc | 1260 |

```
gccccgttcg aggcaattgc gccgccatcc caagcggata taacttacga cttcacgatc    1320
agtcagacag agatcatggg tcatcctatg caccttcacg gccaccggtt cttcgccctc    1380
ggctctggat cgggctcctt cccatatcag aacgccgtcg acgcgcctcc atccctcatt    1440
aacctcgaaa accctccgta ccgggacaca accgatttac caccttcagg ctgggcagtc    1500
attcgctatg tagccaacaa tccaggcgca tggatgtttc actgccacat ccagtggcac    1560
ctcgtgagcg gcatggcatt ggtgtttgtc gaaggagaag agcagctgcc tggtttggtg    1620
ggtgcggctg cgaacggaac aagcaatgcg aatagcgcgt caccggcgcg tagcactcga    1680
gagcatgcgg cctttgccgt tgttgctacc ctaagcactg ttttcttcgc gtatggctac    1740
taa                                                                  1743
```

<210> SEQ ID NO 69
<211> LENGTH: 580
<212> TYPE: PRT
<213> ORGANISM: M. phaseolina

<400> SEQUENCE: 69

```
Met Asp Gly Val Pro Gly Val Thr Gln Glu Pro Ile Pro Pro Gly Gly
1               5                   10                  15

Asn Phe Thr Tyr Arg Phe Ser Leu Lys Asn Glu Tyr Gly Phe Tyr Trp
            20                  25                  30

Tyr His Ser His Phe Arg Ala Tyr Ser Asp Asp Ala Ile Arg Gly Pro
        35                  40                  45

Leu Val Ile His Pro Ser Ser Gln Arg Pro Arg Pro Tyr Glu Thr Leu
    50                  55                  60

Ala Arg Asn Gln Thr Glu Leu Thr Ala Leu Gln Glu Ala Glu Arg Glu
65                  70                  75                  80

Ala Val Pro Ile Leu Leu Ser Asp Trp Tyr His Arg Val Ser Asp Asp
                85                  90                  95

Ile Phe Asn Glu Tyr Leu Thr Thr Gly Ala Phe Pro Ser Cys Val Asp
            100                 105                 110

Ser Leu Leu Ala Asn Gly Tyr Gly Arg Val Arg Cys Leu Pro Glu Tyr
        115                 120                 125

Ile Leu Ala Ala Gly Ala Gly Leu Gly Met Glu Pro Ala Pro Val Asn
    130                 135                 140

Ala Thr Ala Thr Ser Ile Gly Thr Thr Pro Met Ser Ser Met Ala Met
145                 150                 155                 160

Gly Thr Lys Tyr Met Glu Thr Asn Thr Lys Glu Ser Met Arg Met Glu
                165                 170                 175

Ser Met Ala Leu Asp Thr Thr Ser Met Glu His His Met Arg Arg Met
            180                 185                 190

Asp Ser Met Ser Ala Glu Asp Met Ser Met Asn Thr Met Thr Ala His
        195                 200                 205

Ser Thr Pro Ala Ala Ala Pro Asp Ser Gly Met Pro Met Gly Ser Met
    210                 215                 220

Ser Met Ala Ser Leu Pro Val Ser Gly Ile Ser Gly Thr Ser Gly Leu
225                 230                 235                 240

Ser Gly Met Ser Asn Met Ala Ser Gly Pro Leu Gly Pro Arg Gly Cys
                245                 250                 255

Ser Ala Pro Met Met Phe Arg Pro Gly Tyr Asn Ile Ser Ser Leu Pro
            260                 265                 270

Pro Glu Thr Cys Thr Asp Thr Ser Ala Pro Leu Leu Thr Val Asp Ala
```

```
                275                 280                 285
Asn Tyr Thr Arg Gly Trp Leu Ala Leu Asn Leu Val Asn Ser Gly Ser
290                 295                 300
Val Thr Lys Leu Ser Val Ser Leu Asp Ala His Ser Met Phe Val Tyr
305                 310                 315                 320
Ala Ala Asp Gly Phe Val Lys Pro Gln Glu Val Glu Val Leu Gln
                325                 330                 335
Ile Ser Ile Gly Gln Arg Tyr Ser Val Met Ile Lys Leu Asn Gln Arg
            340                 345                 350
Pro Gly Asn Tyr Thr Leu Arg Phe Ala Ser Tyr Pro Tyr Gly Asp Met
            355                 360                 365
Gln Gln Val Ile Glu Gly Gln Ala Thr Val Ser Tyr Lys Val Asp Ala
370                 375                 380
Ala Glu Asp Ile Met Pro Val Asp Leu Thr Asn Asp Pro Thr Ala Thr
385                 390                 395                 400
Trp Met Leu Val Asn Gly Ser Ala Lys Ser Asn Ala Ser Glu Leu Lys
                405                 410                 415
Thr Asp Met Leu Ala Pro Phe Glu Ala Ile Ala Pro Pro Ser Gln Ala
            420                 425                 430
Asp Ile Thr Tyr Asp Phe Thr Ile Ser Gln Thr Glu Ile Met Gly His
            435                 440                 445
Pro Met His Leu His Gly His Arg Phe Phe Ala Leu Gly Ser Gly Ser
450                 455                 460
Gly Ser Phe Pro Tyr Gln Asn Ala Val Asp Ala Pro Pro Ser Leu Ile
465                 470                 475                 480
Asn Leu Glu Asn Pro Pro Tyr Arg Asp Thr Thr Asp Leu Pro Pro Ser
                485                 490                 495
Gly Trp Ala Val Ile Arg Tyr Val Ala Asn Asn Pro Gly Ala Trp Met
            500                 505                 510
Phe His Cys His Ile Gln Trp His Leu Val Ser Gly Met Ala Leu Val
            515                 520                 525
Phe Val Glu Gly Glu Glu Gln Leu Pro Gly Leu Val Gly Ala Ala Ala
530                 535                 540
Asn Gly Thr Ser Asn Ala Asn Ser Ala Ser Pro Ala Arg Ser Thr Arg
545                 550                 555                 560
Glu His Ala Ala Phe Ala Val Val Ala Thr Leu Ser Thr Val Phe Phe
                565                 570                 575
Ala Tyr Gly Tyr
            580

<210> SEQ ID NO 70
<211> LENGTH: 2242
<212> TYPE: DNA
<213> ORGANISM: M. phaseolina

<400> SEQUENCE: 70
agtccaccct tcctatttc tttcctcacg tcacattcag atacccgggc tcctttcaac      60
tgccaaattt ccttttccc gggactcatt ccctccccg actctcttac tcttctctca     120
atttcctacc acccaccgct cgctctcaca atgtctttcg ttgccaggtc cgtagtaagc    180
ggcctcgcca gcagagccgc ctttactaat ggatcatgga ccggtgcctg ggagactcat    240
ggctccaccc aaggttccat ctcaccgcaa ctacgcaacg gtacgtacca ggttcagttg    300
tttaaatccc aaatttgact gatctttgtt gcaggcggcg ggcctcttgg taccttggac    360
```

```
gctccaaact tgcctggctg tattggttct ccaccgtggg gcaaccatga ctctcatgac    420
cctttcggca tgcctgatac tggcattact cgggagtatg actttactct cacttatcaa    480
gacatcgctc ccgatggcgt cactaagagg ggcgtcgttg tcaatggtca atatcccggg    540
cccacgatcg aggccaactg gtgcgtacat cactacatca cgcacatgac atcaggctaa    600
cacttcgttc agggggcgact ggatccaggt cacggtccac aacggtctag gcgaggacga    660
aggtgagggt accgcgatgc actggcacgg cttttttgcag aaggagagcc agtggatgga    720
tggtgtcccc ggtgttcaac aatgtcctat tcctcccgga gagagcttca cctaccgctt    780
ccgcgctgag cagtatggca cttcttggta ccacagccac tacagcgcgc agtactcggg    840
cggtgctgct ggtcctctca tcgtatacgg tccggacagc cagagttacg acgttgacct    900
cggtcccgtc atggtatctg actggtacca ctcgcaatac tacgatattg tcaagcagac    960
catgcaggcc gaccccacgg gcaccacccc tccgccgccg cctcagtccg acaacaacct   1020
gatccagggc tttggcgaat cgactgctc gctgacgacg aagccctgca ttcctgacgc   1080
cggtgtagcc aagttcaagt tcacttccgg caagaagcat cgcctcaggc tcatcaactc   1140
cggctccgag gcgatgcaga ggttctctat cgacggccac accatgaaga tcatcgcaca   1200
cgacttcgtc ccgatcgagc cctacgaggt cacggccctg acccttggcg tcggacagcg   1260
ggccgacgtg gttgtcgaag ccacgggcaa gccctcggac gcgtactgga tgcgctcaga   1320
gatcgggctc aacaagtgca acgtcttcaa tgcgaacgcc tccgaggccc tcgccgtcat   1380
cctctacgag gatgcagacc tgctggccgt gcccagctcc tccgcccagc ccgatgcgga   1440
gctgacatcg tgcaccaacg acgacatctc cgtcggcctg ccgctccagc acatcctgcc   1500
cgaccccaac ccgtccgtca cgaccgagct gcacatcgag aacaagtaca acggcacgca   1560
ctggctctgg cacttcggcg gccccagcta ccgcgccgac ttcaacgacg ccctcctcta   1620
ccagctccaa cagggcacgc ccgacttcgg cccgcagtcc aacgtgcacg acttcggcgc   1680
caacaaatcc gtccgcttcg tcgtctacaa ccacgtcccg gctcagcatc ccatgcactt   1740
gcatggccac aacttctggg tcctcgccga cggcgtcggc acctgggacg gcgccatcgc   1800
caacccgcag aaccccagc gccgcgacgt gcacgtcctt cagcccgccc agggcagcac   1860
cccgtcgtac atggtcgtac agattgagct ggacaacccg ggcctgtggc cgttccactg   1920
ccacatcgcg tggcacgtct cggcgggggtt gtatttgaac gtgctggagc gcccggacga   1980
catcaaggcg ctgcagattc cggccgcggt tggtgatcag tgcagggcgt gggcggacta   2040
cacggcaaag aatacggtgg atcagatcga ctcgggggttg aagaaggagt agaaggcgtg   2100
atagtttgct attgttcttt ctctctctct cttttttttt tttttttac accttccctt   2160 cttgatacca gcatgttttt gggcgttatt tacggtcctt ctgcgcattt ccaaggcgtt   2220
atgtctttcc cttgcggata ag                                           2242
```

<210> SEQ ID NO 71
<211> LENGTH: 1836
<212> TYPE: DNA
<213> ORGANISM: M. phaseolina

<400> SEQUENCE: 71

```
atgtctttcg ttgccaggtc cgtagtaagc ggcctcgcca gcagagccgc ctttactaat     60
ggatcatgga ccggtgcctg ggagactcat ggctccaccc aaggttccat ctcaccgcaa    120
ctacgcaacg gcggcgggcc tcttggtacc ttggacgctc caaacttgcc tggctgtatt    180
ggttctccac cgtggggcaa ccatgactct catgacccct tcggcatgcc tgatactggc    240
```

```
attactcggg agtatgactt tactctcact tatcaagaca tcgctcccga tggcgtcact    300 aagagggcg tcgttgtcaa tggtcaatat cccgggccca cgatcgaggc caactggggc    360
gactggatcc aggtcacggt ccacaacggt ctaggcgagg acgaaggtga gggtaccgcg    420
atgcactggc acggcttttt gcagaaggag agccagtgga tggatggtgt ccccggtgtt    480
caacaatgtc ctattcctcc cggagagagc ttcacctacc gcttccgcgc tgagcagtat    540
ggcacttctt ggtaccacag ccactacagc gcgcagtact cgggcggtgc tgctggtcct    600
ctcatcgtat acgtccgga cagccagagt tacgacgttg acctcggtcc cgtcatggta    660
tctgactggt accactcgca atactacgat attgtcaagc agaccatgca ggccgacccc    720
acgggcacca cccctccgcc gccgcctcag tccgacaaca acctgatcca gggctttggc    780
gaattcgact gctcgctgac gacgaagccc tgcattcctg acgccggtgt agccaagttc    840
aagttcactt ccggcaagaa gcatcgcctc aggctcatca actccggctc cgaggcgatg    900
cagaggttct ctatcgacgg ccacaccatg aagatcatcg cacgacttc gtcccgatc    960 gagccctacg aggtcacggc cctgacccttt ggcgtcggac agcgggccga cgtggttgtc   1020
gaagccacgg gcaagccctc ggacgcgtac tggatgcgct cagagatcgg gctcaacaag   1080
tgcaacgtct tcaatgcgaa cgcctccgag gccctcgccg tcatcctcta cgaggatgca   1140
gacctgctgg ccgtgcccag ctcctccgcc cagcccgatg cggagctgac atcgtgcacc   1200
aacgacgaca tctccgtcgg cctgccgctc cagcacatcc tgcccgaccc caacccgtcc   1260
gtcacgaccg agctgcacat cgagaacaag tacaacggca cgcactggct ctggcacttc   1320
ggcggcccca gctaccgcgc cgacttcaac gacgccctcc tctaccagct ccaacagggc   1380
acgcccgact cggcccgca gtccaacgtg cacgacttcg cgccaacaa atccgtccgc   1440 ttcgtcgtct acaaccacgt cccggctcag catcccatgc acttgcatgg ccacaacttc   1500
tgggtcctcg ccgacggcgt cggcacctgg gacggcgcca tcgccaaccc gcagaacccc   1560
cagcgccgcg acgtgcacgt ccttcagccc gcccagggca gcaccccgtc gtacatggtc   1620
gtacagattg agctggacaa cccgggcctg tggccgttcc actgccacat cgcgtggcac   1680
gtctcggcgg ggttgtattt gaacgtgctg gagcgcccgg acgacatcaa ggcgctgcag   1740
attccggccg cggttggtga tcagtgcagg gcgtgggcgg actacacggc aaagaatacg   1800
gtggatcaga tcgactcggg gttgaagaag gagtag                              1836
```

<210> SEQ ID NO 72
<211> LENGTH: 611
<212> TYPE: PRT
<213> ORGANISM: M. phaseolina

<400> SEQUENCE: 72

Met Ser Phe Val Ala Arg Ser Val Val Ser Gly Leu Ala Ser Arg Ala
1               5                   10                  15

Ala Phe Thr Asn Gly Ser Trp Thr Gly Ala Trp Glu Thr His Gly Ser
            20                  25                  30

Thr Gln Gly Ser Ile Ser Pro Gln Leu Arg Asn Gly Gly Pro Leu
        35                  40                  45

Gly Thr Leu Asp Ala Pro Asn Leu Pro Gly Cys Ile Gly Ser Pro Pro
    50                  55                  60

Trp Gly Asn His Asp Ser His Asp Pro Phe Gly Met Pro Asp Thr Gly
65                  70                  75                  80

Ile Thr Arg Glu Tyr Asp Phe Thr Leu Thr Tyr Gln Asp Ile Ala Pro

-continued

```
                85                  90                  95
Asp Gly Val Thr Lys Arg Gly Val Val Asn Gly Gln Tyr Pro Gly
                100                 105                 110
Pro Thr Ile Glu Ala Asn Trp Gly Asp Trp Ile Gln Val Thr Val His
                115                 120                 125
Asn Gly Leu Gly Glu Asp Glu Gly Gly Thr Ala Met His Trp His
                130                 135                 140
Gly Phe Leu Gln Lys Glu Ser Gln Trp Met Asp Gly Val Pro Gly Val
145                 150                 155                 160
Gln Gln Cys Pro Ile Pro Pro Gly Glu Ser Phe Thr Tyr Arg Phe Arg
                165                 170                 175
Ala Glu Gln Tyr Gly Thr Ser Trp Tyr His Ser His Tyr Ser Ala Gln
                180                 185                 190
Tyr Ser Gly Gly Ala Ala Gly Pro Leu Ile Val Tyr Gly Pro Asp Ser
                195                 200                 205
Gln Ser Tyr Asp Val Asp Leu Gly Pro Val Met Val Ser Asp Trp Tyr
                210                 215                 220
His Ser Gln Tyr Tyr Asp Ile Val Lys Gln Thr Met Gln Ala Asp Pro
225                 230                 235                 240
Thr Gly Thr Thr Pro Pro Pro Pro Gln Ser Asp Asn Asn Leu Ile
                245                 250                 255
Gln Gly Phe Gly Glu Phe Asp Cys Ser Leu Thr Thr Lys Pro Cys Ile
                260                 265                 270
Pro Asp Ala Gly Val Ala Lys Phe Lys Phe Thr Ser Gly Lys Lys His
                275                 280                 285
Arg Leu Arg Leu Ile Asn Ser Gly Ser Glu Ala Met Gln Arg Phe Ser
                290                 295                 300
Ile Asp Gly His Thr Met Lys Ile Ile Ala His Asp Phe Val Pro Ile
305                 310                 315                 320
Glu Pro Tyr Glu Val Thr Ala Leu Thr Leu Gly Val Gly Gln Arg Ala
                325                 330                 335
Asp Val Val Val Glu Ala Thr Gly Lys Pro Ser Asp Ala Tyr Trp Met
                340                 345                 350
Arg Ser Glu Ile Gly Leu Asn Lys Cys Asn Val Phe Asn Ala Asn Ala
                355                 360                 365
Ser Glu Ala Leu Ala Val Ile Leu Tyr Glu Asp Ala Asp Leu Leu Ala
                370                 375                 380
Val Pro Ser Ser Ser Ala Gln Pro Asp Ala Glu Leu Thr Ser Cys Thr
385                 390                 395                 400
Asn Asp Asp Ile Ser Val Gly Leu Pro Leu Gln His Ile Leu Pro Asp
                405                 410                 415
Pro Asn Pro Ser Val Thr Thr Glu Leu His Ile Glu Asn Lys Tyr Asn
                420                 425                 430
Gly Thr His Trp Leu Trp His Phe Gly Gly Pro Ser Tyr Arg Ala Asp
                435                 440                 445
Phe Asn Asp Ala Leu Leu Tyr Gln Leu Gln Gln Gly Thr Pro Asp Phe
                450                 455                 460
Gly Pro Gln Ser Asn Val His Asp Phe Gly Ala Asn Lys Ser Val Arg
465                 470                 475                 480
Phe Val Val Tyr Asn His Val Pro Ala Gln His Pro Met His Leu His
                485                 490                 495
Gly His Asn Phe Trp Val Leu Ala Asp Gly Val Gly Thr Trp Asp Gly
                500                 505                 510
```

```
Ala Ile Ala Asn Pro Gln Asn Pro Gln Arg Arg Asp Val His Val Leu
        515                 520                 525
Gln Pro Ala Gln Gly Ser Thr Pro Ser Tyr Met Val Val Gln Ile Glu
        530                 535                 540
Leu Asp Asn Pro Gly Leu Trp Pro Phe His Cys His Ile Ala Trp His
545                 550                 555                 560
Val Ser Ala Gly Leu Tyr Leu Asn Val Leu Glu Arg Pro Asp Asp Ile
                565                 570                 575
Lys Ala Leu Gln Ile Pro Ala Ala Val Gly Asp Gln Cys Arg Ala Trp
                580                 585                 590
Ala Asp Tyr Thr Ala Lys Asn Thr Val Asp Gln Ile Asp Ser Gly Leu
        595                 600                 605
Lys Lys Glu
    610

<210> SEQ ID NO 73
<211> LENGTH: 1048
<212> TYPE: DNA
<213> ORGANISM: M. phaseolina

<400> SEQUENCE: 73
ggaccgttgc ggcgttactg atcttcgggt gaacgtctct cttcgtacca ggaagccgcc      60
aacgccgaag aaagggagaa atacgtgtgg ctcaactta tccaccctgg cgcccatcat     120
gagctgcgga tctccgttga cgagcacgac atgtggattg cggccgcaga tggagacttc     180
gtaaaaccaa agaaagtcca agtaagtttc cacgtctcgg tttcgagcac gcgctgacaa     240
tctcaaggcc atcaatgtca acatgggcga aggataagc gtccttattc ctcttaccca     300
aagtcctgga gagtacgcca tccgcatggt ctctctcgcg gaagagcagc tcatctgggg     360
cttgggaatt ctccggtacc ccggtgttca agagagacga gatgagaatg cataatgat     420
cctgccagaa agccagccac acattgatgt tcaggataac ctgttgactg acggaattgt     480
gatggacgaa atgaccgacc tgatcccgtt tcccgcgcgc cgtcctccag ccaaggccga     540
ccacaccttt cgcttcgcca tcaagcggcc gaatccaagc acgtggattt tggcatcgga     600
gccgcatcaa ggattcagac aacagcttcc gccggtgctt tggaacaagg attcccgtgg     660
ccctacgacg ttcggcggaa tgaagaacgg ctcggttgtg acatcatttt atgaaaacgg     720
agcatttggg atgcatccgt ttcaccagtg gatgaacgaa tcgcatcaca gtatggcaac     780
tgctgacatt tcatgcacaa ccacaaagcg ttcatcatcg gcatggggga tgggttcttc     840
cggtggccag acgttgcctc ggccctcaag gaggcccctg aaaactttaa catggtgaac     900
cctcctctcc gtgacggagc acggctggca aagggagaag gatcgtggac tgtaatccgc     960
taccagatca cctctcccgc aatgtccatg ttacactgta agcagctctc tgcaaagtgc    1020
ctgacggtgt aagcactgac gacctctc                                        1048

<210> SEQ ID NO 74
<211> LENGTH: 702
<212> TYPE: DNA
<213> ORGANISM: M. phaseolina

<400> SEQUENCE: 74
atgtggattg cggccgcaga tggagacttc gtaaaaccaa agaaagtcca agccatcaat      60
gtcaacatgg gcgagaggat aagcgtcctt attcctctta cccaaagtcc tggagagtac     120
gccatccgca tggtctctct cgcggaagag cagctcatct ggggcttggg aattctccgg     180
```

```
taccccggtg ttcaagagag acgagatgag aatggcataa tgatcctgcc agaaagccag    240
ccacacattg atgttcagga taacctgttg actgacggaa ttgtgatgga cgaaatgacc    300
gacctgatcc cgtttcccgc gcgccgtcct ccagccaagg ccgaccacac ctttcgcttc    360
gccatcaagc ggccgaatcc aagcacgtgg attttggcat cggagccgca tcaaggattc    420
agacaacagc ttccgccggt gctttggaac aaggattccc gtggccctac gacgttcggc    480
ggaatgaaga acggctcggt tgtggacatc atttatgaaa acggagcatt tgggatgcat    540
ccgtttcacc agtggatgaa cgaatcgcat cacagtatgg caactgctga catttcatgc    600
acaaccacaa agcgttcatc atcggcatgg gggatgggtt cttccggtgg ccagacgttg    660
cctcggccct caaggaggcc cctgaaaact ttaacatggt ga    702
```

<210> SEQ ID NO 75
<211> LENGTH: 233
<212> TYPE: PRT
<213> ORGANISM: M. phaseolina

<400> SEQUENCE: 75

```
Met Trp Ile Ala Ala Asp Gly Asp Phe Val Lys Pro Lys Lys Val
1               5                   10                  15

Gln Ala Ile Asn Val Asn Met Gly Glu Arg Ile Ser Val Leu Ile Pro
                20                  25                  30

Leu Thr Gln Ser Pro Gly Glu Tyr Ala Ile Arg Met Val Ser Leu Ala
            35                  40                  45

Glu Glu Gln Leu Ile Trp Gly Leu Gly Ile Leu Arg Tyr Pro Gly Val
50                  55                  60

Gln Glu Arg Arg Asp Glu Asn Gly Ile Met Ile Leu Pro Glu Ser Gln
65                  70                  75                  80

Pro His Ile Asp Val Gln Asp Asn Leu Leu Thr Asp Gly Ile Val Met
                85                  90                  95

Asp Glu Met Thr Asp Leu Ile Pro Phe Pro Ala Arg Arg Pro Pro Ala
            100                 105                 110

Lys Ala Asp His Thr Phe Arg Phe Ala Ile Lys Arg Pro Asn Pro Ser
        115                 120                 125

Thr Trp Ile Leu Ala Ser Glu Pro His Gln Gly Phe Arg Gln Gln Leu
    130                 135                 140

Pro Pro Val Leu Trp Asn Lys Asp Ser Arg Gly Pro Thr Thr Phe Gly
145                 150                 155                 160

Gly Met Lys Asn Gly Ser Val Val Asp Ile Ile Tyr Glu Asn Gly Ala
                165                 170                 175

Phe Gly Met His Pro Phe His Gln Trp Met Asn Glu Ser His His Ser
            180                 185                 190

Met Ala Thr Ala Asp Ile Ser Cys Thr Thr Lys Arg Ser Ser Ser
        195                 200                 205

Ala Trp Gly Met Gly Ser Gly Gly Gln Thr Leu Pro Arg Pro Ser
    210                 215                 220

Arg Arg Pro Leu Lys Thr Leu Thr Trp
225                 230
```

<210> SEQ ID NO 76
<211> LENGTH: 2269
<212> TYPE: DNA
<213> ORGANISM: M. phaseolina

<400> SEQUENCE: 76

```
gctgcgaggc attcgagagg attaccgagt attggagagg ccgcgtgaag gcagcagagc      60
attaaatacg tgctttggag cacgcgaatt actttcaagt tgaacaagat atcacctgtc     120
ttgcacgacg ttgcaagctc cgccgcagcc atgaagtgtg caactctttg gagctatctt     180
gcctctgtcc tgaccgtcgg cgcttctgcg aggtattcca ttcagcatag acttcaaaca     240
ttacctaaat gctgacaact catttacaga agcttgacgc ggtccttgcc tcagcacaag     300
accaacggag gtccaattg gggaactttg gactgtccaa agttaccga ttttttgacc       360
tcgaacccgc tgcccggcgg cttccgtgg ggtgacagaa gcggcctaag caacgatccc      420
tacactgatg tgccgaacac cggggtgacg aggtactacg atttcagcgt cgcacgtggc     480
tatctcgctc cagatggcta aacaaaagt ggcatcttca tcaacggcga gttccctggg     540
cctgccattg aggccaattg gggcgacatg attgaagtac gagtgcacaa caacatcgtc     600
ggccctgaag aaggcactgc gttccactgg catggcatta ctcagaaggg cacgcaatgg     660
tttgacggcg ttcccggcgt gtcccaatgc cccattgccc ctggatcctc ttttacctac     720
cgcttccgtg ccgacgtcta cggcacttct tggtggcact cgcacttctc tgcgcaatat     780
accgctggtg cttttgggcc cctcattatc tacggcccca agcatgttcc ttacgatgtt     840
gatgtcggcc ctgtaattct cggtgattac taccaccgtg actactttga tgttctggag     900
gatgctgcca gcaacaccac tgacttcaac atctacgtcc cttggtccga caacaatctg     960
atcaatggca agaacaacta taattgctcc atggtagctg aaaactctac gagcttcgcc    1020
aacgctacaa gctcctcgaa cgccacgtgc ttctccaacg ctggccttgc ccagttccgt    1080
ttcgagccag gcaaagtgca ccgcctgcgt ctgatgaacg tgggcgcagc agcactgctg    1140
cacttctcaa tcgacgggca caaaatgcaa gtcatcgccc acgacttcga acctgttgtc    1200
ccgtacgagg cagacgtcat cacgctgggc gccgcccaac gcaccgacat cctcgtcact    1260
gcagatgcca accccaacga gacatactgg atccgctcca ccatctcgct caactgctct    1320
gtctcgcaca acaccaacgc gctggccgtt ctctcctacg aaggcaatga ccacatagaa    1380
gagccacgca gccgcattag cgccgccgcg gccgctgctg acgagaagag cttcctctgc    1440
aagaacgacg acctgtccca gacggtgccc ttcttcccca gcccgtcgc cgagcccgat    1500
gtgaccgaga cgatcgaagt cgacctcttc accaatgcga ccggccacca tgtgtggatc    1560
atgaacaacc gcacgcagcg cacgaactac aacgagcccg tcttgctgct cgccaaccag    1620
ggcaacagca ccttcccgga cgagtggaac gtttacgact ttgggcgcaa caagaccatc    1680
cgcatcgtcc tcaacaccgt ctaccagtcc gcccacccga tgcacttgca cggccactct    1740
ttcgtaagac ccttcatccc ttcgccacgc atgtgtgccc actctgacct cttcctcgca    1800
gcaagtcctc gccgaaggcc ccggcgcctg gacggcacg accatcacca acccatccaa    1860
tcccgcccgc cgcgacacgc acatgcagcg ccggtacggg cacctggtaa tccagttcga    1920
ggccgacaac ccgggcgcgt ggagctacca ctgccacatc gcctggcacg ccagcatggg    1980
ctacaacatc gagatcctcg agcgcggcga cgagctggcg gccgccggcg ctattcctat    2040
ggtcatgcag cagacgtgtg atgattggaa ggagtggagc ggcaggaatg tggtcaatca    2100
gatcgacgcg ggcatttaga ttatcggcga cttctatgcc cgatggtata atgtttttac    2160
cgagcgtggg atgatgtggg tttggggtcg gaatttgtag atatgggcgg gggattgcct    2220
gcacaaaata gaccgatgca catgtttata aagcaaaaac tcttcccat                2269
```

<210> SEQ ID NO 77

```
<211> LENGTH: 1854
<212> TYPE: DNA
<213> ORGANISM: M. phaseolina

<400> SEQUENCE: 77
atgaagtgtg caactctttg gagctatctt gcctctgtcc tgaccgtcgg cgcttctgcg        60
agaagcttga cgcggtcctt gcctcagcac aagaccaacg gagggtccaa ttggggaact      120
ttggactgtc caaagttacc cgattttttg acctcgaacc cgctgcccgg cggcttcccg      180
tggggtgaca gaagcggcct aagcaacgat ccctacactg atgtgccgaa caccggggtg      240
acgaggtact acgatttcag cgtcgcacgt ggctatctcg ctccagatgg ctacaacaaa      300
agtggcatct tcatcaacgg cgagttccct gggcctgcca ttgaggccaa ttggggcgac      360
atgattgaag tacgagtgca caacaacatc gtcggccctg aagaaggcac tgcgttccac      420
tggcatggca ttactcagaa gggcacgcaa tggtttgacg gcgttcccgg cgtgtcccaa      480
tgccccattg ccctggatc ctcttttacc taccgcttcc gtgccgacgt ctacggcact      540
tcttggtggc actcgcactt ctctgcgcaa ataccgctg gtgcttttgg gcccctcatt      600
atctacggcc caagcatgt tccttacgat gttgatgtcg gccctgtaat tctcggtgat      660
tactaccacc gtgactactt tgatgttctg gaggatgctg ccagcaacac cactgacttc      720
aacatctacg tcccttggtc cgacaacaat ctgatcaatg gcaagaacaa ctataattgc      780
tccatggtag ctggaaactc tacgagcttc gccaacgcta caagctcctc gaacgccacg      840
tgcttctcca cgctggcct tgcccagttc cgtttcgagc caggcaaagt gcaccgcctg      900
cgtctgatga acgtgggcgc agcagcactg ctgcacttct caatcgacgg cacaaaatg      960
caagtcatcg cccacgactt cgaacctgtt gtcccgtacg aggcagacgt catcacgctg     1020
ggcgccgccc aacgcaccga catcctcgtc actgcagatg ccaacccaa cgagacatac     1080
tggatccgct ccaccatctc gctcaactgc tctgtctcgc acaacaccaa cgcgctggcc     1140
gttctctcct acgaaggcaa tgaccacata gaagagccac gcagccgcat tagcgccgcc     1200
gcggccgctg ctgacgagaa gagcttcctc tgcaagaacg acgacctgtc ccagacggtg     1260
cccttcttcc ccaagcccgt cgccgagccc gatgtgaccg agacgatcga agtcgacctc     1320
ttcaccaatg cgaccggcca ccatgtgtgg atcatgaaca accgcacgca gcgcacgaac     1380
tacaacgagc ccgtcttgct gctcgccaac cagggcaaca gcaccttccc ggacgagtgg     1440
aacgtttacg actttgggcg caacaagacc atccgcatcg tcctcaacac cgtctaccag     1500
tccgcccacc cgatgcactt gcacggccac tctttccaag tcctcgccga aggcccccggc     1560
gcctgggacg gcacgaccat caccaaccca tccaatcccg cccgccgcga cacgcacatg     1620
cagcgccggt acgggcacct ggtaatccag ttcgaggccg acaacccggg cgcgtggagc     1680
taccactgcc acatcgcctg gcacgccagc atgggctaca acatcgagat cctcgagcgc     1740
ggcgacgagc tggcggccgc cggcgctatt cctatggtca tgcagcagac gtgtgatgat     1800
tggaaggagt ggagcggcag gaatgtggtc aatcagatcg acgcgggcat ttag           1854

<210> SEQ ID NO 78
<211> LENGTH: 617
<212> TYPE: PRT
<213> ORGANISM: M. phaseolina

<400> SEQUENCE: 78

Met Lys Cys Ala Thr Leu Trp Ser Tyr Leu Ala Ser Val Leu Thr Val
1               5                   10                  15
```

Gly Ala Ser Ala Arg Ser Leu Thr Arg Ser Leu Pro Gln His Lys Thr
            20                  25                  30

Asn Gly Gly Ser Asn Trp Gly Thr Leu Asp Cys Pro Lys Leu Pro Asp
        35                  40                  45

Phe Leu Thr Ser Asn Pro Leu Pro Gly Gly Phe Pro Trp Gly Asp Arg
    50                  55                  60

Ser Gly Leu Ser Asn Asp Pro Tyr Thr Asp Val Pro Asn Thr Gly Val
65                  70                  75                  80

Thr Arg Tyr Tyr Asp Phe Ser Val Ala Arg Gly Tyr Leu Ala Pro Asp
                85                  90                  95

Gly Tyr Asn Lys Ser Gly Ile Phe Ile Asn Gly Glu Phe Pro Gly Pro
            100                 105                 110

Ala Ile Glu Ala Asn Trp Gly Asp Met Ile Glu Val Arg Val His Asn
        115                 120                 125

Asn Ile Val Gly Pro Glu Glu Gly Thr Ala Phe His Trp His Gly Ile
    130                 135                 140

Thr Gln Lys Gly Thr Gln Trp Phe Asp Gly Val Pro Gly Val Ser Gln
145                 150                 155                 160

Cys Pro Ile Ala Pro Gly Ser Ser Phe Thr Tyr Arg Phe Arg Ala Asp
                165                 170                 175

Val Tyr Gly Thr Ser Trp Trp His Ser His Phe Ser Ala Gln Tyr Thr
            180                 185                 190

Ala Gly Ala Phe Gly Pro Leu Ile Ile Tyr Gly Pro Lys His Val Pro
        195                 200                 205

Tyr Asp Val Asp Val Gly Pro Val Ile Leu Gly Asp Tyr Tyr His Arg
    210                 215                 220

Asp Tyr Phe Asp Val Leu Glu Asp Ala Ala Ser Asn Thr Thr Asp Phe
225                 230                 235                 240

Asn Ile Tyr Val Pro Trp Ser Asp Asn Asn Leu Ile Asn Gly Lys Asn
                245                 250                 255

Asn Tyr Asn Cys Ser Met Val Ala Gly Asn Ser Thr Ser Phe Ala Asn
            260                 265                 270

Ala Thr Ser Ser Ser Asn Ala Thr Cys Phe Ser Asn Ala Gly Leu Ala
        275                 280                 285

Gln Phe Arg Phe Glu Pro Gly Lys Val His Arg Leu Arg Leu Met Asn
    290                 295                 300

Val Gly Ala Ala Ala Leu Leu His Phe Ser Ile Asp Gly His Lys Met
305                 310                 315                 320

Gln Val Ile Ala His Asp Phe Glu Pro Val Pro Tyr Glu Ala Asp
                325                 330                 335

Val Ile Thr Leu Gly Ala Ala Gln Arg Thr Asp Ile Leu Val Thr Ala
            340                 345                 350

Asp Ala Asn Pro Asn Glu Thr Tyr Trp Ile Arg Ser Thr Ile Ser Leu
        355                 360                 365

Asn Cys Ser Val Ser His Asn Thr Asn Ala Leu Ala Val Leu Ser Tyr
    370                 375                 380

Glu Gly Asn Asp His Ile Glu Glu Pro Arg Ser Arg Ile Ser Ala Ala
385                 390                 395                 400

Ala Ala Ala Ala Asp Glu Lys Ser Phe Leu Cys Lys Asn Asp Asp Leu
                405                 410                 415

Ser Gln Thr Val Pro Phe Phe Pro Lys Pro Val Ala Glu Pro Asp Val
            420                 425                 430

Thr Glu Thr Ile Glu Val Asp Leu Phe Thr Asn Ala Thr Gly His His

```
                435                 440                 445
Val Trp Ile Met Asn Asn Arg Thr Gln Arg Thr Asn Tyr Asn Glu Pro
450                     455                     460

Val Leu Leu Leu Ala Asn Gln Gly Asn Ser Thr Phe Pro Asp Glu Trp
465                     470                     475                 480

Asn Val Tyr Asp Phe Gly Arg Asn Lys Thr Ile Arg Ile Val Leu Asn
                    485                     490                     495

Thr Val Tyr Gln Ser Ala His Pro Met His Leu His Gly His Ser Phe
                500                     505                     510

Gln Val Leu Ala Glu Gly Pro Gly Ala Trp Asp Gly Thr Thr Ile Thr
                515                     520                     525

Asn Pro Ser Asn Pro Ala Arg Arg Asp Thr His Met Gln Arg Arg Tyr
530                     535                     540

Gly His Leu Val Ile Gln Phe Glu Ala Asp Asn Pro Gly Ala Trp Ser
545                     550                     555                 560

Tyr His Cys His Ile Ala Trp His Ala Ser Met Gly Tyr Asn Ile Glu
                    565                     570                     575

Ile Leu Glu Arg Gly Asp Glu Leu Ala Ala Ala Gly Ala Ile Pro Met
                580                     585                     590

Val Met Gln Gln Thr Cys Asp Asp Trp Lys Glu Trp Ser Gly Arg Asn
                595                     600                     605

Val Val Asn Gln Ile Asp Ala Gly Ile
    610                     615

<210> SEQ ID NO 79
<211> LENGTH: 2373
<212> TYPE: DNA
<213> ORGANISM: M. phaseolina

<400> SEQUENCE: 79
gacaatccct ccgctaaatc cgacatccgg tactctcgcc tcccggatcc cgagcggaca      60
cacagcttcg cctgtatacc actttcaccg gagtcgcctt cccacccct ataattcttt     120
tcctgttgag tctactccgc gcgcggtatc atgatagata ccaagagcac agggtccggc     180
gcagacggcg gtcgttacgc cgccttaagg caagacgagt cagagctata cgagcagaaa     240
gaacatacgc agtgtacaca gccctccggc gccgcgtacc tcggtggaaa tggcagagaa     300
gaagccctgg gattgatcga cgaaaatgtc gtcgctcgaa caaaaagacg ctgtggaccc     360
acccggcggt actctgtctt ccttgaattt gccatcctcg gtctggtact cataatcgct     420
ctactcggcg ctctcgcttg gtccagaggc tctcatcatc ataccgaccc ggtatctggc     480
agttcacaac catcgtccaa gggtcgccgc ggaaagtatg tcctggaccc tgcctgggat     540
ttcgctgcac cgccgcaggt ccgcaaatac cactggacga tcaggacat cgagcttcgc     600
ccagacggcg tgaagcggcc gctgatcacc atcaataacg agttcccggg gccgaccatc     660
gaatgcaacc aggggggatac cgtgcgggtt gaggttcata cgaagccgt caattcaact     720
tcctttcact ggcacggcat ttaccagaac ggaaccacgt acatggatgg cacggtcggc     780
atcagccagt gtcctatcac gtctgggtct agcatgacat atgagttcaa agtcgacaga     840
gaatccggca cctattggta tcatgcgcac atggctatgc agggctcaga tggtcttttt     900
ggtcctctga tcgtccattc gaaaaatgag cggaagctgc agcaactcga atatgcctcc     960
gatcaagtca tcatggtcca cgattactac acgatctga ccagcgcgct gataccacac    1020
tacttagcgc cggataacga gaacacagag cctgtccctg acggaggtct catcaacgga    1080
```

```
atgaataaga gaaattgcga gctcctccgt ggtcgagact gtgatgccac tgatgcacag      1140
cttgccacat tcggcctcga accgaacaag aaccaccgtc ttcgaattat caatactgga      1200
gcatttgctg aattccaggt gaagattgac gagcacacgt tcgctgtgac ggaggtggat      1260
gggaccgaag ttgctcccgc ctactaccac aggctcaaca tcaatcccgg acagcgctac      1320
agcatcgtaa taaacaccaa tgtcacggat cgtgactcct tctggctgag agctaagatg      1380
attgaggcct gtttcgctga ggagaaccca aatctggatc cgaagtgcg cgccattatc       1440
caatatactc gcaaggacga ggatacccag cccaaggaac cttcgagcag agactgggac      1500
gacatcgtgg acatgcagtg tctcgacatg aacgtgacag agctccagcc cgtagagaag      1560
gcaacacctc cacctgcaga caccacacta tacctccgct ccaacttcga gatcggcaac      1620
tggcgtctga ccgcggctt cttcaacagc tcgtcctggc gtccaacact ctcatcccca       1680
agcctgcacc gcatgatcga cggcctccac agccaaaacg ccagcttcct ccccgaccga      1740
gcgtacccct tccagatcaa ctcggccggc ttcgacactg ggcccgagct ggtctaccag      1800
accagcggca tccgcaccat cgacatcctc gtttccaact tcgacgacgg caaccacccg      1860
ctccacctgc acggctacaa gtacttcgtc cttgcgtcgg gccacggcta cccgcccgcc      1920
gacctctacg cgcatctcga catctcgaac ccgctgcgcc gcgacaccgc ctcgatcgag      1980
gcgttcggct ggatcctact gcgtctcgtc gccgacaacc cgggcgtctg ggccttccac      2040
tgccacatcg gctggcacac cgaggccggc atgctgatgc agttcgccac gcgcgtcgac      2100
gtgctcgcat ccagccaaat cccggatacg cacctcgcgc tctgcgcggc cgacgggctc      2160
gaccgcggcg cgtcgccgcc agactcgacg tggtttgggg attttgggga tctagatcct      2220
tgaaaagttc tggagaggag tgggagtttc acctggcatg caagcgtctc cgtttcttca      2280
ggccaggctg accccacttcc cgcgcacgcc gatctcgtac tgcagcccgt cgccttccat      2340
gtttaggtcc cacctgcggt actcatcttc gac                                   2373
```

<210> SEQ ID NO 80
<211> LENGTH: 2073
<212> TYPE: DNA
<213> ORGANISM: M. phaseolina

<400> SEQUENCE: 80

```
atgatagata ccaagagcac agggtccggc gcagacggcg gtcgttacgc cgccttaagg       60
caagacgagt cagagctata cgagcagaaa gaacatacgc agtgtacaca gccctccggc      120
gccgcgtacc tcggtggaaa tgcagagaa gaagccctgg gattgatcga cgaaaatgtc       180
gtcgctcgaa caaaaagacg ctgtggaccc accggcggt actctgtctt ccttgaattt       240
gccatcctcg gtctggtact cataatcgct ctactcggcg ctctcgcttg gtccagaggc      300
tctcatcatc ataccgaccc ggtatctggc agttcacaac catcgtccaa gggtcgccgc      360
ggaaagtatg tcctggaccc tgcctgggat ttcgctgcac cgccgcaggt ccgcaaatac      420
cactggacga tcagggacat cgagcttcgc ccagacggcg tgaagcggcc gctgatcacc      480
atcaataacg agttcccggg gccgaccatc gaatgcaacc aggggatac cgtgcgggtt       540
gaggttcata cgaagccgt caattcaact tcctttcact ggcacggcat ttaccagaac       600
ggaaccacgt acatggatgg cacggtcggc atcagccagt gtcctatcac gtctgggtct      660
agcatgacat atgagttcaa agtgacagag aatccggca cctattggta tcatgcgcac      720
atggctatgc agggctcaga tggtcttttt ggtcctctga tcgtccattc gaaaaatgag       780
cggaagctgc agcaactcga atatgcctcc gatcaagtca tcatggtcca cgattactac      840
```

```
cacgatctga ccagcgcgct gataccacac tacttagcgc cggataacga gaacacagag    900
cctgtccctg acggaggtct catcaacgga atgaataaga gaaattgcga gctcctccgt    960
ggtcgagact gtgatgccac tgatgcacag cttgccacat tcggcctcga accgaacaag   1020
aaccaccgtc ttcgaattat caatactgga gcatttgctg aattccaggt gaagattgac   1080
gagcacacgt tcgctgtgac ggaggtggat gggaccgaag ttgctcccgc ctactaccac   1140
aggctcaaca tcaatcccgg acagcgctac agcatcgtaa taaacaccaa tgtcacggat   1200
cgtgactcct tctggctgag agctaagatg attgaggcct gtttcgctga ggagaaccca   1260
aatctggatc ccgaagtgcg cgccattatc caatatactc gcaaggacga ggatacccag   1320
cccaaggaac cttcgagcag agactgggac gacatcgtgg acatgcagtg tctcgacatg   1380
aacgtgacag agctccagcc cgtagagaag gcaacacctc cacctgcaga caccacacta   1440
tacctccgct ccaacttcga gatcggcaac tggcgtctga gccgcggctt cttcaacagc   1500
tcgtcctggc gtccaacact ctcatcccca agcctgcacc gcatgatcga cggcctccac   1560
agccaaaacg ccagcttcct ccccgaccga gcgtacccct tccagatcaa ctcggccggc   1620
ttcgacactg ggcccgagct ggtctaccag accagcggca tccgcaccat cgacatcctc   1680
gtttccaact tcgacgacgg caaccacccg ctccacctgc acggctacaa gtacttcgtc   1740
cttgcgtcgg gccacggcta cccgcccgcc gacctctacg cgcatctcga catctcgaac   1800
ccgctgcgcc gcgacaccgc ctcgatcgag gcgttcggct ggatcctact gcgtctcgtc   1860
gccgacaacc cgggcgtctg ggccttccac tgccacatcg gctggcacac cgaggccggc   1920
atgctgatgc agttcgccac gcgcgtcgac gtgctcgcat ccagccaaat cccggatacg   1980
cacctcgcgc tctgcgcggc cgacgggctc gaccgcggcg cgtcgccgcc agactcgacg   2040
tggtttgggg attttgggga tctagatcct tga                                2073
```

<210> SEQ ID NO 81
<211> LENGTH: 690
<212> TYPE: PRT
<213> ORGANISM: M. phaseolina

<400> SEQUENCE: 81

Met Ile Asp Thr Lys Ser Thr Gly Ser Gly Ala Asp Gly Gly Arg Tyr
1               5                   10                  15

Ala Ala Leu Arg Gln Asp Glu Ser Glu Leu Tyr Glu Gln Lys Glu His
                20                  25                  30

Thr Gln Cys Thr Gln Pro Ser Gly Ala Ala Tyr Leu Gly Gly Asn Gly
            35                  40                  45

Arg Glu Glu Ala Leu Gly Leu Ile Asp Glu Asn Val Val Ala Arg Thr
        50                  55                  60

Lys Arg Arg Cys Gly Pro Thr Arg Arg Tyr Ser Val Phe Leu Glu Phe
65                  70                  75                  80

Ala Ile Leu Gly Leu Val Leu Ile Ile Ala Leu Leu Gly Ala Leu Ala
                85                  90                  95

Trp Ser Arg Gly Ser His His Thr Asp Pro Val Ser Gly Ser Ser
                100                 105                 110

Gln Pro Ser Ser Lys Gly Arg Arg Gly Lys Tyr Val Leu Asp Pro Ala
            115                 120                 125

Trp Asp Phe Ala Ala Pro Pro Gln Val Arg Lys Tyr His Trp Thr Ile
        130                 135                 140

Arg Asp Ile Glu Leu Arg Pro Asp Gly Val Lys Arg Pro Leu Ile Thr

```
145                 150                 155                 160
Ile Asn Asn Glu Phe Pro Gly Pro Thr Ile Glu Cys Asn Gln Gly Asp
                165                 170                 175
Thr Val Arg Val Glu Val His Asn Glu Ala Val Asn Ser Thr Ser Phe
                180                 185                 190
His Trp His Gly Ile Tyr Gln Asn Gly Thr Thr Tyr Met Asp Gly Thr
                195                 200                 205
Val Gly Ile Ser Gln Cys Pro Ile Thr Ser Gly Ser Ser Met Thr Tyr
210                 215                 220
Glu Phe Lys Val Asp Arg Glu Ser Gly Thr Tyr Trp Tyr His Ala His
225                 230                 235                 240
Met Ala Met Gln Gly Ser Asp Gly Leu Phe Gly Pro Leu Ile Val His
                245                 250                 255
Ser Lys Asn Glu Arg Lys Leu Gln Gln Leu Glu Tyr Ala Ser Asp Gln
                260                 265                 270
Val Ile Met Val His Asp Tyr Tyr His Asp Leu Thr Ser Ala Leu Ile
                275                 280                 285
Pro His Tyr Leu Ala Pro Asp Asn Glu Asn Thr Glu Pro Val Pro Asp
                290                 295                 300
Gly Gly Leu Ile Asn Gly Met Asn Lys Arg Asn Cys Glu Leu Leu Arg
305                 310                 315                 320
Gly Arg Asp Cys Asp Ala Thr Asp Ala Gln Leu Ala Thr Phe Gly Leu
                325                 330                 335
Glu Pro Asn Lys Asn His Arg Leu Arg Ile Ile Asn Thr Gly Ala Phe
                340                 345                 350
Ala Glu Phe Gln Val Lys Ile Asp Glu His Thr Phe Ala Val Thr Glu
                355                 360                 365
Val Asp Gly Thr Glu Val Ala Pro Ala Tyr Tyr His Arg Leu Asn Ile
                370                 375                 380
Asn Pro Gly Gln Arg Tyr Ser Ile Val Ile Asn Thr Asn Val Thr Asp
385                 390                 395                 400
Arg Asp Ser Phe Trp Leu Arg Ala Lys Met Ile Glu Ala Cys Phe Ala
                405                 410                 415
Glu Glu Asn Pro Asn Leu Asp Pro Glu Val Arg Ala Ile Ile Gln Tyr
                420                 425                 430
Thr Arg Lys Asp Glu Asp Thr Gln Pro Lys Glu Pro Ser Ser Arg Asp
                435                 440                 445
Trp Asp Asp Ile Val Asp Met Gln Cys Leu Asp Met Asn Val Thr Glu
                450                 455                 460
Leu Gln Pro Val Glu Lys Ala Thr Pro Pro Ala Asp Thr Thr Leu
465                 470                 475                 480
Tyr Leu Arg Ser Asn Phe Glu Ile Gly Asn Trp Arg Leu Ser Arg Gly
                485                 490                 495
Phe Phe Asn Ser Ser Ser Trp Arg Pro Thr Leu Ser Ser Pro Ser Leu
                500                 505                 510
His Arg Met Ile Asp Gly Leu His Ser Gln Asn Ala Ser Phe Leu Pro
                515                 520                 525
Asp Arg Ala Tyr Pro Phe Gln Ile Asn Ser Ala Gly Phe Asp Thr Gly
                530                 535                 540
Pro Glu Leu Val Tyr Gln Thr Ser Gly Ile Arg Thr Ile Asp Ile Leu
545                 550                 555                 560
Val Ser Asn Phe Asp Asp Gly Asn His Pro Leu His Leu His Gly Tyr
                565                 570                 575
```

```
Lys Tyr Phe Val Leu Ala Ser Gly His Gly Tyr Pro Pro Ala Asp Leu
            580                 585                 590

Tyr Ala His Leu Asp Ile Ser Asn Pro Leu Arg Arg Asp Thr Ala Ser
        595                 600                 605

Ile Glu Ala Phe Gly Trp Ile Leu Leu Arg Leu Val Ala Asp Asn Pro
610                 615                 620

Gly Val Trp Ala Phe His Cys His Ile Gly Trp His Thr Glu Ala Gly
625                 630                 635                 640

Met Leu Met Gln Phe Ala Thr Arg Val Asp Val Leu Ala Ser Ser Gln
                645                 650                 655

Ile Pro Asp Thr His Leu Ala Leu Cys Ala Ala Asp Gly Leu Asp Arg
            660                 665                 670

Gly Ala Ser Pro Pro Asp Ser Thr Trp Phe Gly Asp Phe Gly Asp Leu
        675                 680                 685

Asp Pro
    690

<210> SEQ ID NO 82
<211> LENGTH: 2372
<212> TYPE: DNA
<213> ORGANISM: M. phaseolina

<400> SEQUENCE: 82
tatatgttcc tccgtcctca acggaaatcc ggcagtgcgc aagacgagcc ccctttcct      60 tctgcttcgc ctgcttttcg tagtctcgtc ctccgcccta cgtcgtct tctcagacaa     120 tttgctcaaa tccctctca cctcgccgcc atgcgcttcg cgagcctcgc cgtggcatgg     180
ctcacaacgt gcgttgtcca atcacttgcc aacgagccca tcccgttcga caggatcctc     240
tggggtgaga atggccccgc cggtaaccat atggtgaagc gtcaggccag ctccagctcc     300
cctgcctcat ccaccacaag ggccccggat tccgcctgca caaacggccc ttgacgagg     360 agctgctggt ccaatggctt ttccatagcc actgactttg acgccaagtg gcccaatacc     420
ggaaagaccg tccatgtaag cgcgcctgca gatatgcatc cgtcctgctg ctgacgtgca     480
gcccatagta tgacctgacc atcaacaacg ccacctgcag ccccgacggc gggcccagcc     540
gcccgtgcct gatgttcaac aacaagatcc ctgggcctac gctttacgcc aattggggcg     600
acatgatctc cgttaccatc accaacaaga tgcccaacaa cggcaccagc gtgcactggc     660
atggtctgcg tcagtacaat acaaacaccc aggatggcgt caacggaatc acggaatgcc     720
ctctggctcc cggcgattcc aagacctacc tattccaggc tacacagttc ggcacgacct     780
ggttccacag ccatttctct gcgcagtatg gcgacggtgc cgtcggccag ctcatcatca     840
atggccccgc ctcggcgaat tacgatttcg atctcggcac ctacactatg accgactggt     900
actacagcac tgcgttccag gtcgaagatc aatttgatgc cgcccttcag aggaaggccc     960
ccggcccgcc aggtgacacc atcctggtga acggtacgat gaagtctccg gatggctctg    1020
ctggtagcta cagccaagtc aagggccttg tcaagggaaa gaagtaccgc ctgcgtctca    1080
tcaacaccct cggtggacaa catccgcg tctcgctgga caaccaccca ttcaccgtcg    1140
tcacttccga cttcgtcccg agcaagcctt ggactactga ctggcttctc ttagccatcg    1200
gccagcgcta cgatgtcatc ttcacggcca atcaaccgc ggccaattat tggttccgtg    1260
cagaagttgc caccgcatgt gctagcgcca acaagtaccg cggccgcggt atattcagct    1320
acgttggtgc cgatggcagc gctcccccag agaccgccgt gactgttcca ggtggctgta    1380
```

| | |
|---|---|
| ccgagcctct gcctgcgcct ttcgtcgcaa accaggttcc aagccaagtc ttcctcgacc | 1440 |
| aagtgaagac ccttagcgtc gatgtttatg cggcaaacgt ctcgaccaac cagaagaaca | 1500 |
| ttgtcttctg gggcatcaac atgactgcca ttgacattga ttgggagaag ccgacgctgg | 1560 |
| aatacgtcag gacaaaaaat accagctacc cccacgttta caacttgatc gagttgccca | 1620 |
| cagagaacat tgtaagcgga gttaagcttc aaccccgaga atgttatta acgatcgcaa | 1680 |
| cagtggacct actggatcat ccaagaaact cccggcactc ccccaattcc gcatccaatt | 1740 |
| cacttgcacg gtaagctgca ggtctcaacc ttgcaacccc gtagagatac tgatggtcgc | 1800 |
| ctctgtccag gccacgactt ctacatcctc ggaaccggct ctggtgcctt cgaccgcagc | 1860 |
| acctcgccgt cctccctcaa tttcaataac cccacccggc gcgacgtcgc actggttccc | 1920 |
| ggcggcggtt ggttggccat tgccttcccg accgacaacc caggcgcttg gctcatgcac | 1980 |
| tgccatatcg taagtttacc tatctctccg actacgatca attgtgtata ttcatgcgca | 2040 |
| cggcgctgac acgtggattt ccctcgccac aggcttggca cattagcgaa ggtctcggag | 2100 |
| ttcagttcct cgagggcaag gataagatca atcttcccga cgctgcgtgg gagacgacct | 2160 |
| gctcgaattg ggacaagtac tgggacacca ctatctaccc caagcaggat tccggtctct | 2220 |
| gaggggtggc cggtttttttt tcttctttac gggcctgagt ttaagggggg tttgatgttt | 2280 |
| tgctgaaaaa agacccgtag tgattcttgt attatacttt tcgttttatt catattgata | 2340 |
| ggaagcaacc tgatcgcact tcgtaaaccg ca | 2372 |

<210> SEQ ID NO 83
<211> LENGTH: 1824
<212> TYPE: DNA
<213> ORGANISM: M. phaseolina

<400> SEQUENCE: 83

| | |
|---|---|
| atgcgcttcg cgagcctcgc cgtggcatgg ctcacaacgt gcgttgtcca atcacttgcc | 60 |
| aacgagccca tccgttcga caggatcctc tggggtgaga atggccccgc cggtaaccat | 120 |
| atggtgaagc gtcaggccag ctccagctcc cctgcctcat ccaccacaag ggccccggat | 180 |
| tccgcctgca caaacggccc tttgacgagg agctgctggt ccaatggctt ttccatagcc | 240 |
| actgactttg acgccaagtg gcccaatacc ggaaagaccg tccattatga cctgaccatc | 300 |
| aacaacgcca cctgcagccc cgacggcggg cccagccgcc cgtgcctgat gttcaacaac | 360 |
| aagatccctg ggcctacgct ttacgccaat tggggcgaca tgatctccgt taccatcacc | 420 |
| aacaagatgc ccaacaacgg caccagcgtg cactggcatg gtctgcgtca gtacaataca | 480 |
| aacacccagg atggcgtcaa cggaatcacg gaatgccctc tggctcccgg cgattccaag | 540 |
| acctacctat tccaggctac acagttcggc acgacctggt tccacagcca tttctctgcg | 600 |
| cagtatggcg acggtgccgt cggccagctc atcatcaatg gccccgcctc ggcgaattac | 660 |
| gatttcgatc tcggcaccta cactatgacc gactggtact acagcactgc gttccaggtc | 720 |
| gaagatcaat ttgatgccgc ccttcagagg aaggcccccg gccgccagg tgacaccatc | 780 |
| ctggtgaacg gtacgatgaa gtctccggat ggctctgctg gtagctacag ccaagtcaag | 840 |
| ggccttgtca aggaaagaa gtaccgcctg cgtctcatca cacctcggt ggacaacaac | 900 |
| atccgcgtct cgctggacaa ccacccattc accgtcgtca cttccgactt cgtcccgagc | 960 |
| aagccttgga ctactgactg gcttctctta gccatcggcc agcgctacga tgtcatcttc | 1020 |
| acggccaatc aacccgcggc caattattgg ttccgtgcag aagttgccac cgcatgtgct | 1080 |
| agcgccaaca agtaccgcgg ccgcggtata ttcagctacg ttggtgccga tggcagcgct | 1140 |

-continued

```
cccccagaga ccgccgtgac tgttccaggt ggctgtaccg agcctctgcc tgcgcctttc    1200
gtcgcaaacc aggttccaag ccaagtcttc ctcgaccaag tgaagaccct tagcgtcgat    1260
gtttatgcgg caaacgtctc gaccaaccag aagaacattg tcttctgggg catcaacatg    1320
actgccattg acattgattg ggagaagccg acgctggaat acgtcaggac aaaaaatacc    1380
agctaccccc acgtttacaa cttgatcgag ttgcccacag agaacatttg gacctactgg    1440
atcatccaag aaactcccgg cactcccca attccgcatc caattcactt gcacggccac    1500
gacttctaca tcctcggaac cggctctggt gccttcgacc gcagcacctc gccgtcctcc    1560
ctcaatttca ataaccccac ccggcgcgac gtcgcactgg ttcccggcgg cggttggttg    1620
gccattgcct tcccgaccga acccaggc gcttggctca tgcactgcca tatcgcttgg    1680
cacattagcg aaggtctcgg agttcagttc ctcgagggca aggataagat caatcttccc    1740
gacgctgcgt gggagacgac ctgctcgaat tgggacaagt actgggacac cactatctac    1800
cccaagcagg attccggtct ctga                                          1824
```

<210> SEQ ID NO 84
<211> LENGTH: 607
<212> TYPE: PRT
<213> ORGANISM: M. phaseolina

<400> SEQUENCE: 84

```
Met Arg Phe Ala Ser Leu Ala Val Ala Trp Leu Thr Thr Cys Val Val
1               5                   10                  15

Gln Ser Leu Ala Asn Glu Pro Ile Pro Phe Asp Arg Ile Leu Trp Gly
            20                  25                  30

Glu Asn Gly Pro Ala Gly Asn His Met Val Lys Arg Gln Ala Ser Ser
        35                  40                  45

Ser Ser Pro Ala Ser Ser Thr Thr Arg Ala Pro Asp Ser Ala Cys Thr
    50                  55                  60

Asn Gly Pro Leu Thr Arg Ser Cys Trp Ser Asn Gly Phe Ser Ile Ala
65                  70                  75                  80

Thr Asp Phe Asp Ala Lys Trp Pro Asn Thr Gly Lys Thr Val His Tyr
                85                  90                  95

Asp Leu Thr Ile Asn Asn Ala Thr Cys Ser Pro Asp Gly Gly Pro Ser
            100                 105                 110

Arg Pro Cys Leu Met Phe Asn Asn Lys Ile Pro Gly Pro Thr Leu Tyr
        115                 120                 125

Ala Asn Trp Gly Asp Met Ile Ser Val Thr Ile Thr Asn Lys Met Pro
    130                 135                 140

Asn Asn Gly Thr Ser Val His Trp His Gly Leu Arg Gln Tyr Asn Thr
145                 150                 155                 160

Asn Thr Gln Asp Gly Val Asn Gly Ile Thr Glu Cys Pro Leu Ala Pro
                165                 170                 175

Gly Asp Ser Lys Thr Tyr Leu Phe Gln Ala Thr Gln Phe Gly Thr Thr
            180                 185                 190

Trp Phe His Ser His Phe Ser Ala Gln Tyr Gly Asp Gly Ala Val Gly
        195                 200                 205

Gln Leu Ile Ile Asn Gly Pro Ala Ser Ala Asn Tyr Asp Phe Asp Leu
    210                 215                 220

Gly Thr Tyr Thr Met Thr Asp Trp Tyr Ser Thr Ala Phe Gln Val
225                 230                 235                 240

Glu Asp Gln Phe Asp Ala Ala Leu Gln Arg Lys Ala Pro Gly Pro Pro
```

```
            245                 250                 255
Gly Asp Thr Ile Leu Val Asn Gly Thr Met Lys Ser Pro Asp Gly Ser
    260                 265                 270

Ala Gly Ser Tyr Ser Gln Val Lys Gly Leu Val Lys Gly Lys Lys Tyr
        275                 280                 285

Arg Leu Arg Leu Ile Asn Thr Ser Val Asp Asn Asn Ile Arg Val Ser
    290                 295                 300

Leu Asp Asn His Pro Phe Thr Val Val Thr Ser Asp Phe Val Pro Ser
305                 310                 315                 320

Lys Pro Trp Thr Thr Asp Trp Leu Leu Leu Ala Ile Gly Gln Arg Tyr
                325                 330                 335

Asp Val Ile Phe Thr Ala Asn Gln Pro Ala Ala Asn Tyr Trp Phe Arg
                340                 345                 350

Ala Glu Val Ala Thr Ala Cys Ala Ser Ala Asn Lys Tyr Arg Gly Arg
            355                 360                 365

Gly Ile Phe Ser Tyr Val Gly Ala Asp Gly Ser Ala Pro Pro Glu Thr
    370                 375                 380

Ala Val Thr Val Pro Gly Gly Cys Thr Glu Pro Leu Pro Ala Pro Phe
385                 390                 395                 400

Val Ala Asn Gln Val Pro Ser Gln Val Phe Leu Asp Gln Val Lys Thr
                405                 410                 415

Leu Ser Val Asp Val Tyr Ala Ala Asn Val Ser Thr Asn Gln Lys Asn
            420                 425                 430

Ile Val Phe Trp Gly Ile Asn Met Thr Ala Ile Asp Ile Asp Trp Glu
        435                 440                 445

Lys Pro Thr Leu Glu Tyr Val Arg Thr Lys Asn Thr Ser Tyr Pro His
    450                 455                 460

Val Tyr Asn Leu Ile Glu Leu Pro Thr Glu Asn Ile Trp Thr Tyr Trp
465                 470                 475                 480

Ile Ile Gln Glu Thr Pro Gly Thr Pro Pro Ile Pro His Pro Ile His
                485                 490                 495

Leu His Gly His Asp Phe Tyr Ile Leu Gly Thr Gly Ser Gly Ala Phe
            500                 505                 510

Asp Arg Ser Thr Ser Pro Ser Ser Leu Asn Phe Asn Asn Pro Thr Arg
        515                 520                 525

Arg Asp Val Ala Leu Val Pro Gly Gly Trp Leu Ala Ile Ala Phe
    530                 535                 540

Pro Thr Asp Asn Pro Gly Ala Trp Leu Met His Cys His Ile Ala Trp
545                 550                 555                 560

His Ile Ser Glu Gly Leu Gly Val Gln Phe Leu Glu Gly Lys Asp Lys
                565                 570                 575

Ile Asn Leu Pro Asp Ala Ala Trp Glu Thr Thr Cys Ser Asn Trp Asp
            580                 585                 590

Lys Tyr Trp Asp Thr Thr Ile Tyr Pro Lys Gln Asp Ser Gly Leu
        595                 600                 605

<210> SEQ ID NO 85
<211> LENGTH: 3008
<212> TYPE: DNA
<213> ORGANISM: M. phaseolina

<400> SEQUENCE: 85
gagaagagct ttcgaagcc atgtcagcag gattagctcc tgagacagcc ctgccccaaa    60
gtcccgtatt tctatggccg cagttctctc tcctcgccga accaaagcct cctccagtac   120
```

```
tttcttctca aacctgctca tacaagtgca atggggttct tcaatgcctg ctgggacttg    180
ctgctccacc tcccttcctt tgctccgcgg ggcggcggct tcgagcggga tcgctcgcag    240
cttccgatct cctccggtcc gagtggcggc gtagtcatcc acccggagaa tgcttcccct    300
ggcttcacct gctcttaccc gagcatggaa gggtgggaaa gctgcaactc acccgacgac    360
aggagctgct ggcttaaaga tgggagggcg agtcagcctt acttctctca atacgatatc    420
cacacagact gtaagtcctc gatatggttg cccgcattgc atgctttcag ctttaccagg    480
ccttcgtgct aaatttatga agacgagacc gtctggcctc agggtgtaac cagagaagta    540
agtgtggaaa atcaaagccc tggggcgcgg ggaacccggc ctctgagcct tcatctatgg    600
cagcccgtac acatcgagag acgaagtatt tatcgcgaag agaatgcccc tgatctcttt    660
aagcacatac atctgcatga atatttcaat tccccttgtc atcagggatg atcaaggggc    720
catgccgtta ccaaaatgtc tgggcagagt cccttctttt cacgctgcag cagatttgct    780
tactcggtgt ttactgaaca tttgcagtac tggatcaacc tcaaggacca agtggtaagt    840
gctgccattc ccttgagtcc gctgtagctg ctcatacgcc cagcttttcc ccgacggtta    900
ttccaagcct tatggcaaag taatcaacga cacctaccca ggtcctttaa tcgaggcttg    960
ctggggcgat gaagtagttg ttcatgtgac aaactacctg cagacgaatg cactacgta    1020
ttcacacgtc tatatcagtt gtgccgcggt atgagctgat gatggggcag tattcactgg    1080
cacggtgtga gacagcagtt cagcaacgaa atggacggag tcaacggttt gttctgcaag    1140
atccactat ttacctcctc ggctcacgtc atgtaggtat tacacagtgt cctatcgctt    1200
atggtgacac cttcacctac cgctttcgtg ttactcaata tggaactacg tgtaagtgtt    1260
tccgactcct gatctggtct cagccattga cacggaagta gggtaccatt cacactactc    1320
gctccaatac ccagatggcg ttgctggccc tctcgtattt cacggcccta cagcagccga    1380
ttggatgaa gagtgggaga ccccgctgat gatcactgat tgggttcacg attcggcttt    1440
tggggtcttc tcccaggaac tcctcgcgtc ggatcctgcc aaccggaacg tcacaccacc    1500
cgtgggggac agcattctgc ttaacggaca cggacattac aactgcagcc tttctcagga    1560
ccaaaaccgc tgcgcgccgg gatatggatc ttactacacg caaagattcc aaaagggtaa    1620
aaggtacttg atcaggctaa ttaactcctc agctggagca gcatttatct tctccataga    1680
cggacacaaa atgaaggtca tctccacgga tctcgttccc attgagccgt acgagacaaa    1740
tgcagtgctc ctcaacatag gtatatagcg tttggtgctc gtcctagcat gtctcccaga    1800
cactaacttc ccgcaggcca acgctacaac atcatcgtcg aagccaacgc cgaacccggc    1860
gactactgga tccgtaccga gatacccggc gggccaggcg gctgtggcag cgtgcacgac    1920
cgggccggta acgtgacggg catcctgcgc tacgacggac gcagtaccgc gctaccgacc    1980
tcatcgaaga atgactaccc gtcggactgc cacgatgagc cagcggagct gctgcaccca    2040
atcctgccgt ggacggtgga tccgcacccg cagaacgacg tacacaacaa cacgtacgag    2100
gtcggcattt cagacgccca gttccacaag gccttccgct gggacctgac cgacacgccc    2160
atgtggctcg acttctcaaa cccgaccatc ctcaacctgt acaacaccac ctggaacccg    2220
gagtacgccg tcatcgactg tgagttgtcc ttcttacctc ccgttctccc caaaaaacac    2280
tagcaacgag tggatgaaga ctgacaggta cgaaaacaga caactatgac cgcggcttcg    2340
tctacctcgt catcacggcc aacctgacac ggctgggcga caacaagcgc gagatccccg    2400
ccggccaccc catccacctg cacggccacg acttcgccgt cctcgcccag tccaactcga    2460
```

```
cctatgacga gcgctccgac ccgctcaatt tcaccctcgc caacccgccg cgccgcgatg   2520
tcgtcttcct gccgagcaac ggctacgtcg cgctggcgtt caagccggac aatcccggca   2580
tatggttggt gcattgccat atcgcttggc atgccagttc tggtgagtgt tttctttttt   2640 tcttttggt  aactttgttt tctgtggctt ttttaaaagt gtgtgaatgc atgctgatga   2700
tttttatacg atgcacaggc ctggcactgc agattctgga gaggcagcca gatatcctgg   2760
attcgattgg cacgctcgag gcgacgaata agacgtgtgc tggatgggat acgtacgaga   2820
gggcgcatcc gatcgagcaa gacgacagcg gtatctgatt agacgtacct ctgcgtcaga   2880
tccgacgagt tgggagtgaa tgatgccctc tggaaggatt gtgaaggatg gggtgagctc   2940
tttctcctgt gcattttctc tcatgttgag gagctctgtt cgtagctgga gtacgctcat   3000
ttatttcc                                                            3008
```

<210> SEQ ID NO 86
<211> LENGTH: 1932
<212> TYPE: DNA
<213> ORGANISM: M. phaseolina

<400> SEQUENCE: 86

```
atggggttct tcaatgcctg ctgggacttg ctgctccacc tcccttttctt tgctccgcgg    60 ggcggcggct tcgagcggga tcgctcgcag cttccgatct cctccggtcc gagtggcggc   120
gtagtcatcc acccggagaa tgcttcccct ggcttcacct gctcttaccc gagcatggaa   180
gggtgggaaa gctgcaactc acccgacgac aggagctgct ggcttaaaga tgggagggcg   240
agtcagcctt acttctctca atacgatatc cacacagact acgagaccgt ctggcctcag   300
ggtgtaacca gagaatactg gatcaacctc aaggaccaag tgcttttccc cgacggttat   360
tccaagcctt atggcaaagt aatcaacgac acctacccag gtcctttaat cgaggcttgc   420
tggggcgatg aagtagttgt tcatgtgaca aactacctgc agacgaatgg cactactatt   480
cactggcacg gtgtgagaca gcagttcagc aacgaaatgg acggagtcaa cggtattaca   540
cagtgtccta tcgcttatgg tgacaccttc acctaccgct ttcgtgttac tcaatatgga   600
actacgtggt accattcaca ctactcgctc caatacccag atggcgttgc tggccctctc   660
gtatttcacg gccctacagc agccgattgg gatgaagagt gggagacccc gctgatgatc   720
actgattggg ttcacgattc ggcttttggg gtcttctccc aggaactcct cgcgtcggat   780
cctgccaacc ggaacgtcac accaccgtg  ggggacagca ttctgcttaa cggacacgga   840
cattacaact gcagcctttc tcaggaccaa aaccgctgcg cgccgggata tggatcttac   900
tacacgcaaa gattccaaaa gggtaaaagg tacttgatca ggctaattaa ctcctcagct   960
ggagcagcat ttatcttctc catagacgga cacaaaatga aggtcatctc cacggatctc  1020
gttcccattg agccgtacga gacaaatgca gtgctcctca acataggcca acgctacaac  1080
atcatcgtcg aagccaacgc cgaacccggc gactactgga tccgtaccga gatacccggc  1140
gggccaggcg gctgtggcag cgtgcacgac cgggccggta cgtgacgggc atcctgcgc  1200 tacgacggac gcagtaccgc gctaccgacc tcatcgaaga tgactacccc gtcggactgc  1260
cacgatgagc cagcggagct gctgcaccca atcctgccgt ggacggtgga tccgcacccg  1320
cagaacgacg tacacaacaa cacgtacgag gtcggcattt cagacgccca gttccacaag  1380
gccttccgct gggacctgac cgacacgccc atgtggctcg acttctcaaa cccgaccatc  1440
ctcaacctgt acaacaccac ctggaacccg gagtacgccg tcatcgacta caactatgac  1500
cgcggcttcg tctacctcgt catcacggcc aacctgacac ggctgggcga caacaagcgc  1560
```

```
gagatccccg ccggccaccc catccacctg cacggccacg acttcgccgt cctcgcccag   1620
tccaactcga cctatgacga gcgctccgac ccgctcaatt tcaccctcgc caacccgccg   1680
cgccgcgatg tcgtcttcct gccgagcaac ggctacgtcg cgctggcgtt caagccggac   1740
aatcccggca tatggttggt gcattgccat atcgcttggc atgccagttc tggcctggca   1800
ctgcagattc tggagaggca gccagatatc ctggattcga ttggcacgct cgaggcgacg   1860
aataagacgt gtgctggatg ggatacgtac gagagggcgc atccgatcga gcaagacgac   1920
agcggtatct ga                                                       1932
```

<210> SEQ ID NO 87  
<211> LENGTH: 643  
<212> TYPE: PRT  
<213> ORGANISM: M. phaseolina

<400> SEQUENCE: 87

```
Met Gly Phe Phe Asn Ala Cys Trp Asp Leu Leu His Leu Pro Phe
1               5                   10                  15

Phe Ala Pro Arg Gly Gly Phe Glu Arg Asp Arg Ser Gln Leu Pro
            20                  25                  30

Ile Ser Ser Gly Pro Ser Gly Val Val Ile His Pro Glu Asn Ala
        35                  40                  45

Ser Pro Gly Phe Thr Cys Ser Tyr Pro Ser Met Glu Gly Trp Glu Ser
50                  55                  60

Cys Asn Ser Pro Asp Asp Arg Ser Cys Trp Leu Lys Asp Gly Arg Ala
65                  70                  75                  80

Ser Gln Pro Tyr Phe Ser Gln Tyr Asp Ile His Thr Asp Tyr Glu Thr
            85                  90                  95

Val Trp Pro Gln Gly Val Thr Arg Glu Tyr Trp Ile Asn Leu Lys Asp
        100                 105                 110

Gln Val Leu Phe Pro Asp Gly Tyr Ser Lys Pro Tyr Gly Lys Val Ile
            115                 120                 125

Asn Asp Thr Tyr Pro Gly Pro Leu Ile Glu Ala Cys Trp Gly Asp Glu
130                 135                 140

Val Val Val His Val Thr Asn Tyr Leu Gln Thr Asn Gly Thr Thr Ile
145                 150                 155                 160

His Trp His Gly Val Arg Gln Gln Phe Ser Asn Glu Met Asp Gly Val
                165                 170                 175

Asn Gly Ile Thr Gln Cys Pro Ile Ala Tyr Gly Asp Thr Phe Thr Tyr
            180                 185                 190

Arg Phe Arg Val Thr Gln Tyr Gly Thr Thr Trp Tyr His Ser His Tyr
        195                 200                 205

Ser Leu Gln Tyr Pro Asp Gly Val Ala Gly Pro Leu Val Phe His Gly
    210                 215                 220

Pro Thr Ala Ala Asp Trp Asp Glu Glu Trp Glu Thr Pro Leu Met Ile
225                 230                 235                 240

Thr Asp Trp Val His Asp Ser Ala Phe Gly Val Phe Ser Gln Glu Leu
                245                 250                 255

Leu Ala Ser Asp Pro Ala Asn Arg Asn Val Thr Pro Val Gly Asp
            260                 265                 270

Ser Ile Leu Leu Asn Gly His Gly His Tyr Asn Cys Ser Leu Ser Gln
        275                 280                 285

Asp Gln Asn Arg Cys Ala Pro Gly Tyr Gly Ser Tyr Tyr Thr Gln Arg
    290                 295                 300
```

Phe Gln Lys Gly Lys Arg Tyr Leu Ile Arg Leu Ile Asn Ser Ser Ala
305                 310                 315                 320

Gly Ala Ala Phe Ile Phe Ser Ile Asp Gly His Lys Met Lys Val Ile
            325                 330                 335

Ser Thr Asp Leu Val Pro Ile Glu Pro Tyr Glu Thr Asn Ala Val Leu
        340                 345                 350

Leu Asn Ile Gly Gln Arg Tyr Asn Ile Ile Val Glu Ala Asn Ala Glu
    355                 360                 365

Pro Gly Asp Tyr Trp Ile Arg Thr Glu Ile Pro Gly Pro Gly Gly
370                 375                 380

Cys Gly Ser Val His Asp Arg Ala Gly Asn Val Thr Gly Ile Leu Arg
385                 390                 395                 400

Tyr Asp Gly Arg Ser Thr Ala Leu Pro Thr Ser Ser Lys Asn Asp Tyr
                405                 410                 415

Pro Ser Asp Cys His Asp Glu Pro Ala Glu Leu Leu His Pro Ile Leu
            420                 425                 430

Pro Trp Thr Val Asp Pro His Pro Gln Asn Asp Val His Asn Asn Thr
        435                 440                 445

Tyr Glu Val Gly Ile Ser Asp Ala Gln Phe His Lys Ala Phe Arg Trp
    450                 455                 460

Asp Leu Thr Asp Thr Pro Met Trp Leu Asp Phe Ser Asn Pro Thr Ile
465                 470                 475                 480

Leu Asn Leu Tyr Asn Thr Thr Trp Asn Pro Glu Tyr Ala Val Ile Asp
                485                 490                 495

Tyr Asn Tyr Asp Arg Gly Phe Val Tyr Leu Val Ile Thr Ala Asn Leu
            500                 505                 510

Thr Arg Leu Gly Asp Asn Lys Arg Glu Ile Pro Ala Gly His Pro Ile
        515                 520                 525

His Leu His Gly His Asp Phe Ala Val Leu Ala Gln Ser Asn Ser Thr
    530                 535                 540

Tyr Asp Glu Arg Ser Asp Pro Leu Asn Phe Thr Leu Ala Asn Pro Pro
545                 550                 555                 560

Arg Arg Asp Val Val Phe Leu Pro Ser Asn Gly Tyr Val Ala Leu Ala
                565                 570                 575

Phe Lys Pro Asp Asn Pro Gly Ile Trp Leu Val His Cys His Ile Ala
            580                 585                 590

Trp His Ala Ser Ser Gly Leu Ala Leu Gln Ile Leu Glu Arg Gln Pro
    595                 600                 605

Asp Ile Leu Asp Ser Ile Gly Thr Leu Glu Ala Thr Asn Lys Thr Cys
610                 615                 620

Ala Gly Trp Asp Thr Tyr Glu Arg Ala His Pro Ile Glu Gln Asp Asp
625                 630                 635                 640

Ser Gly Ile

<210> SEQ ID NO 88
<211> LENGTH: 2404
<212> TYPE: DNA
<213> ORGANISM: M. phaseolina

<400> SEQUENCE: 88
aaatgccatg gacagctcgc ccgggatcga tgtcctttct ccccgagccc ccgtcgcccg     60
tccaggagag ataaaccttc tcatagggcc tcattcctac tctctccttc ccttttcgt    120 taccctcccc gaccgcggtc caccttcgac atgtggtggt tggcattgtt ctcattgctt   180

-continued

```
gtggccgcca cggcctgggc caaggagccc tacctcaagg tccacgatga tacctttatt    240
ccagatgccg tgttgcgggt aacagaggag agtgcctcca ttggttgcat cgagaggacc    300
tccgccgtgg tcaacggcac agttccgggg ccgattttgg aattccaatc cggcagcgtg    360
gtatgggttc gtgtttacaa tgatatggca gacaaaaacc tcaccatggt aagcccgac     420
gatatgcctg cggtgaatca gactagtcaa ttaacttctc ggtccacagc attggcatgg    480
cctcaccatg gcagccgctc cattcgccga cggttccgtt gcagccagcc agtgggcgat    540
cgagccgttc aaattcttcg actacgagct caacctattc gacatcaagc ctgggacgta    600
tttctaccac tcccatgtcg gattccaggc aattactgcc acgggtcccc tgctcattac    660
caaaaagccg ggagaggagc cgccgtatga gtacgaggag aacgcatcg tcctcttttc     720
cgacctttac aacacgacgg accacgacat tgaaaccgga ctggtagcca gcccttcaa     780
atggagcggt gaggtcggag acgtcctcgt caacggatat ggcatatcgc agtacccggc    840
cacgaacgac gccgagagtt gcaaccttgc acagattccc gtggaagctg gaagacgta     900
ccgtttgcgt ttcattggtg ccactgccct ttctttcctc tccgttggct ttgagaagca    960
caatcttacc atcatcgagg cggatggcca ctacacggaa cctgcagaaa tcagcttcct   1020
tcaaatcggc ggcggccaac ggtattctgc tctcctaaag acatggactt gcgaggagct   1080
cgccgccaag actgctggtc gaaaccagtt ctacatccaa atcgagactc gtgacaggcc   1140
caagaacctc accacctacg ccattctgga ctacagcgac agctgcgcca ccaatagcat   1200
cagcgtcgag gccaccatcg gcaaggactc aacatcgccc ccttcctacg ccctccttc    1260
gctcagcaaa cccggcaaca caacaaaaa caacaacaac accacgctct cccgcaagac    1320
gccgccaag accccaccgc tgcacctccc gcccaccgtg caaggctggc tcgaccatga    1380
cctccacccg ctcgaaacct acacggactt cccgacggcg gacgaggtca cgcgcaccgt   1440
ctacatggac atcttccagc tagggcagga cggctacgtc aagtgggcgc agaacaacct   1500
gtcgtggtac gagcacacgc ccaaggttcc ctacctcgtc gcgctctaca ccaacagcac   1560
gcagtacctg cccgactacg actatgccgt cgcatcgggg acgggccacg acgaccgcgt   1620
cggtgcctgg cccgccaaga tgggcgaggt gctcgagatc atcgtcgtca acacgggcag   1680
ctacagcggc ggcatggacg tgcatcccat gcacctgcac ggcgcgcacc cgttctattt   1740
ggggagtggg aagggcacgt acaacagaga ggagaacgag aagaagttgg cggggagggt   1800
gccggtcacg agggattcga tgatgctgta tcggtatggc gagaaggagg agccgcacaa   1860
ggataatagc tggattgcgc tgaggataag ggtgacgcag ccggggtgt ggatgttcca    1920
ttgccatacg ctggcgcata tgattatggg tgagtttgac cctttttccc tttttttttt   1980
ttttttcctt attgcgcatg ttggtttgat gaaaaccatg gtgctgatgt gatttggaac   2040
aggtatgcaa acggtctggg tgtttggcga ttcgaaggat atcctcacgc tgccgctgcc   2100
gatggtggaa ggttacttgg tgcctggcgg agatgtgttc ggtgatgatg atcatgatcc   2160
ggtggtggtg cacttctttg acctggacga cgacgacgac gatgatgatg atgccaataa   2220
gaccgacggg aacggcggga agaatggccg gtagatgggg ggaggagagt tacttgattc   2280
gcaatggaag aggttactgc ggaggggatt tgtaatgcat gctacagttt ttatgttata   2340
tgccaggtat aaccagaagg aaagccggat gattaatcgt ggaaacaaga gaaagaagca   2400
ttta                                                                 2404
```

<210> SEQ ID NO 89

<211> LENGTH: 1950
<212> TYPE: DNA
<213> ORGANISM: M. phaseolina

<400> SEQUENCE: 89

```
atgtggtggt tggcattgtt ctcattgctt gtggccgcca cggcctgggc caaggagccc      60
tacctcaagg tccacgatga tacctttatt ccagatgccg tgttgcgggt aacagaggag     120
agtgcctcca ttggttgcat cgagaggacc tccgccgtgg tcaacggcac agttccgggg     180
ccgattttgg aattccaatc cggcagcgtg gtatgggttc gtgtttacaa tgatatggca     240
gacaaaaacc tcaccatgca ttggcatggc ctcaccatgg cagccgctcc attcgccgac     300
ggttccgttg cagccagcca gtgggcgatc gagccgttca aattcttcga ctacgagctc     360
aacctattcg acatcaagcc tgggacgtat ttctaccact cccatgtcgg attccaggca     420
attactgcca cgggtcccct gctcattacc aaaaagccgg gagaggagcc gccgtatgag     480
tacgaggagg aacgcatcgt cctctttttcc gacctttaca acacgacgga ccacgacatt     540
gaaaccggac tggtagccag cccttttcaaa tggagcggtg aggtcggaga cgtcctcgtc     600
aacggatatg gcatatcgca gtaccngggcc acgaacgacg ccgagagttg caaccttgca     660
cagattcccg tggaagctgg gaagacgtac cgtttgcgtt tcattggtgc cactgccctt     720
tctttcctct ccgttggctt tgagaagcac aatcttacca tcatcgaggc ggatggccac     780
tacacgaacc tgcagaaaat cagcttcctt caaatcggcg cggccaacg gtattctgct     840
ctcctaaaga catggacttg cgaggagctc gccgccaaga ctgctggtcg aaaccagttc     900
tacatccaaa tcgagactcg tgacaggccc aagaacctca ccacctacgc cattctggac     960
tacagcgaca gctgcgccac caatagcatc agcgtcgagg ccaccatcgg caaggactca    1020
acatcgcccc cttcctacgc ccctccttcg ctcagcaaac ccggcaacaa caacaaaaac    1080
aacaacaaca ccacgctctc ccgcaagacg ccgcccaaga ccccaccgct gcacctcccg    1140
cccaccgtgc aaggctggct cgaccatgac ctccacccgc tcgaaaccta cacgacttc    1200
ccgacggcgg acgaggtcac gcgcaccgtc tacatggaca tcttccagct agggcaggac    1260
ggctacgtca gtgggcgca gaacaacctg tcgtggtacg agcacacgcc caaggttccc    1320
tacctcgtcg cgctctacac caacagcacg cagtacctgc ccgactacga ctatgccgtc    1380
gcatcgggga cgggccacga cgaccgcgtc ggtgcctggc ccgccaagat gggcgaggtg    1440
ctcgagatca tcgtcgtcaa cacgggcagc tacagcggcg gcatggacgt gcatcccatg    1500
cacctgcacg gcgcgcaccc gttctatttg gggagtggga agggcacgta caacagagag    1560
gagaacgaga agaagttggc ggggagggtg ccggtcacga gggattcgat gatgctgtat    1620
cggtatggcg agaaggagga gccgcacaag gataatagct ggattgcgct gaggataagg    1680
gtgacgcagc cgggggtgtg gatgttccat tgccatacgc tggcgcatat gattatgggt    1740
atgcaaacgg tctgggtgtt tggcgattcg aaggatatcc tcacgctgcc gctgccgatg    1800
gtggaaggtt acttggtgcc tggcggagat gtgttcggtg atgatgatca tgatccggtg    1860
gtggtgcact tctttgacct ggacgacgac gacgacgatg atgatgatgc caataagacc    1920
gacgggaacg gcgggaagaa tggccggtag                                      1950
```

<210> SEQ ID NO 90
<211> LENGTH: 649
<212> TYPE: PRT
<213> ORGANISM: M. phaseolina

<400> SEQUENCE: 90

-continued

```
Met Trp Trp Leu Ala Leu Phe Ser Leu Leu Ala Ala Thr Ala Trp
1               5                   10                  15

Ala Lys Glu Pro Tyr Leu Lys Val His Asp Asp Thr Phe Ile Pro Asp
            20                  25                  30

Ala Val Leu Arg Val Thr Glu Glu Ser Ala Ser Ile Gly Cys Ile Glu
            35                  40                  45

Arg Thr Ser Ala Val Val Asn Gly Thr Val Pro Gly Pro Ile Leu Glu
    50                  55                  60

Phe Gln Ser Gly Ser Val Val Trp Val Arg Val Tyr Asn Asp Met Ala
65                  70                  75                  80

Asp Lys Asn Leu Thr Met His Trp His Gly Leu Thr Met Ala Ala Ala
                85                  90                  95

Pro Phe Ala Asp Gly Ser Val Ala Ala Ser Gln Trp Ala Ile Glu Pro
            100                 105                 110

Phe Lys Phe Phe Asp Tyr Glu Leu Asn Leu Phe Asp Ile Lys Pro Gly
        115                 120                 125

Thr Tyr Phe Tyr His Ser His Val Gly Phe Gln Ala Ile Thr Ala Thr
    130                 135                 140

Gly Pro Leu Leu Ile Thr Lys Lys Pro Gly Glu Glu Pro Pro Tyr Glu
145                 150                 155                 160

Tyr Glu Glu Arg Ile Val Leu Phe Ser Asp Leu Tyr Asn Thr Thr
                165                 170                 175

Asp His Asp Ile Glu Thr Gly Leu Val Ala Ser Pro Phe Lys Trp Ser
            180                 185                 190

Gly Glu Val Gly Asp Val Leu Val Asn Gly Tyr Gly Ile Ser Gln Tyr
        195                 200                 205

Pro Ala Thr Asn Asp Ala Glu Ser Cys Asn Leu Ala Gln Ile Pro Val
    210                 215                 220

Glu Ala Gly Lys Thr Tyr Arg Leu Arg Phe Ile Gly Ala Thr Ala Leu
225                 230                 235                 240

Ser Phe Leu Ser Val Gly Phe Glu Lys His Asn Leu Thr Ile Ile Glu
                245                 250                 255

Ala Asp Gly His Tyr Thr Glu Pro Ala Glu Ile Ser Phe Leu Gln Ile
            260                 265                 270

Gly Gly Gly Gln Arg Tyr Ser Ala Leu Leu Lys Thr Trp Thr Cys Glu
        275                 280                 285

Glu Leu Ala Ala Lys Thr Ala Gly Arg Asn Gln Phe Tyr Ile Gln Ile
    290                 295                 300

Glu Thr Arg Asp Arg Pro Lys Asn Leu Thr Thr Tyr Ala Ile Leu Asp
305                 310                 315                 320

Tyr Ser Asp Ser Cys Ala Thr Asn Ser Ile Ser Val Glu Ala Thr Ile
                325                 330                 335

Gly Lys Asp Ser Thr Ser Pro Ser Tyr Ala Pro Ser Leu Ser
            340                 345                 350

Lys Pro Gly Asn Asn Asn Lys Asn Asn Asn Thr Thr Leu Ser Arg
                355                 360                 365

Lys Thr Pro Pro Lys Thr Pro Leu His Leu Pro Pro Thr Val Gln
    370                 375                 380

Gly Trp Leu Asp His Asp Leu His Pro Leu Glu Thr Tyr Thr Asp Phe
385                 390                 395                 400

Pro Thr Ala Asp Glu Val Thr Arg Thr Val Tyr Met Asp Ile Phe Gln
                405                 410                 415
```

Leu Gly Gln Asp Gly Tyr Val Lys Trp Ala Gln Asn Asn Leu Ser Trp
            420                 425                 430

Tyr Glu His Thr Pro Lys Val Pro Tyr Leu Val Ala Leu Tyr Thr Asn
        435                 440                 445

Ser Thr Gln Tyr Leu Pro Asp Tyr Asp Tyr Ala Val Ala Ser Gly Thr
    450                 455                 460

Gly His Asp Asp Arg Val Gly Ala Trp Pro Ala Lys Met Gly Glu Val
465                 470                 475                 480

Leu Glu Ile Ile Val Asn Thr Gly Ser Tyr Ser Gly Gly Met Asp
                485                 490                 495

Val His Pro Met His Leu His Gly Ala His Pro Phe Tyr Leu Gly Ser
            500                 505                 510

Gly Lys Gly Thr Tyr Asn Arg Glu Glu Asn Glu Lys Lys Leu Ala Gly
        515                 520                 525

Arg Val Pro Val Thr Arg Asp Ser Met Met Leu Tyr Arg Tyr Gly Glu
    530                 535                 540

Lys Glu Glu Pro His Lys Asp Asn Ser Trp Ile Ala Leu Arg Ile Arg
545                 550                 555                 560

Val Thr Gln Pro Gly Val Trp Met Phe His Cys His Thr Leu Ala His
                565                 570                 575

Met Ile Met Gly Met Gln Thr Val Trp Val Phe Gly Asp Ser Lys Asp
            580                 585                 590

Ile Leu Thr Leu Pro Leu Pro Met Val Glu Gly Tyr Leu Val Pro Gly
        595                 600                 605

Gly Asp Val Phe Gly Asp Asp His Asp Pro Val Val His Phe
610                 615                 620

Phe Asp Leu Asp Asp Asp Asp Asp Asp Asp Ala Asn Lys Thr
625                 630                 635                 640

Asp Gly Asn Gly Gly Lys Asn Gly Arg
                645

<210> SEQ ID NO 91
<211> LENGTH: 2569
<212> TYPE: DNA
<213> ORGANISM: M. phaseolina

<400> SEQUENCE: 91
cgcccgattc acaccattcc tctgacactc tcctccggag ctcgcatcag ggcgctctct      60
cgccctcctg accttccgtc cggcgccgat atcgtcgtgt tccgtatatg agggtaatc     120 gcgacggtgc tcccgcccac actctcagcc atggcccagt ctctgttcct cctgcttgct    180
gctgccctgt gcagccgcgc tgccacagtc acgtatgact taacgtgac ctgggtcacc     240 gccaaccctg atgctgcttt tcgtcgcact accattggca tcaatggcca gtggccgctc    300
cctgcaatcg acgtcaccaa gggcgaccgc gttgtcatca cgtcaacaa ccagctggaa     360 acggagagta ccagtttgca tttccatgga atctacatga atggcaccaa ccacatggat    420
ggcccgactg gcgtgaccca gtgcgagata ccgcccggga gctcattcac atacaatttt    480
acggtatagc acgatcccac cccttgttta cttatagcta accgcacgca ggtcgaccaa    540
ccgggaactt actggtgagt agccagctgt tggcgtcaag actgggaaag ctgacgtagc    600
ttcaggtatc attctcacaa ccgcggccag tatcccgatg gattgcgagg cctttttatt    660
gtcagagacc ccgacaatcc gttcaaggat gactatgatg aggaagtcgt cctgacattc    720
tccgactggt accacgaccg gatccccacc ctcatgaaga gtttcattag tgtcacaaac    780

| | |
|---|---|
| cccaccggcg cggagcctgt cccgaacgcg gcactgatga atgacactca gaacctcacc | 840 |
| ttccagatga ctcccgggcg gagatacatg ttccgactaa taaacattgg tgcatttgct | 900 |
| gctcaatacg tctggttcga aggccatacc atgcgtatcg tagaagtcga cggcgtgtac | 960 |
| accgaagccg cagatgcaga gcgaatttac atgactgccg ctcaacgcta cagcgtaatc | 1020 |
| atcaccgcaa agaacgaatc tacctcaaac ttcgcctttg ttggaagcat ggatcaggtc | 1080 |
| agctatcctt ttactgggcc gacattttcc ttcttctaac ataatgcagg atctctttga | 1140 |
| tactattcca gcaggcctta ataataacgt gaccgggtgg cttgtctaca atcaacagaa | 1200 |
| cggcttgttg ccacctttag ctatcgggga ctacgatccg ttcgatgact tcacacttgt | 1260 |
| gcctcaagat ggtatggagc tctacgatca cgtcgatcat ccatcaccc tcgatatgaa | 1320 |
| gatggacaat ctcggggacg gagcaaatta gtatgttgac tgtagttgac aacggccaaa | 1380 |
| tgccatgact gacgagcgca gtgccttttt caacgacgtg acctacgtcg agcccaaggt | 1440 |
| gccgactctg tacacggtgt tgtctactgg caataatgcc acagactcga gaatctacgg | 1500 |
| tagcaacacc aacagcttca tattggctaa ggacgaagtc gtcgagatca tcctcaacaa | 1560 |
| caatgatccg ggaaagcacc cttttccatct gcatgggcac gcattccaag caatcgttcg | 1620 |
| ctccgaagaa gaagccggcg cgtacgtggc aaacgaaacc ttcccccaga cgccaatgcg | 1680 |
| ccgcgataca attcttgtcc ggcccaatgg caatatagta ctgagattca aggctgacaa | 1740 |
| tcctggtgtc tggctgttcc attgtcatat tgaatggtat gctccttggt atctttatc | 1800 |
| ctagctctac tgacctctta ctgttaggca tgttgcgtcg ggccttattg ccaccatgat | 1860 |
| agaggcaccg cttgacctgc aatcttctct cggcaacagc attcctgctg atcactggcg | 1920 |
| agcttgtgcc gccgccggca cacctactgc aggcaacgca gcaggcaaca cgattgatta | 1980 |
| tcttgacctg actggtgaaa acaagagccc cggcccgctt ccctctggct ttgaagcgaa | 2040 |
| aggcattgtc gcgcttgtct tcagttgtat tgctgctgtc ttgggcatgg cagccatcgt | 2100 |
| atggtacggg atggcgcctc tgacagatgg aactggtcag caacaacacg ttgtggatca | 2160 |
| acagccgcaa ggacgctccg cacaagttgg cgtcatgccc ctagcggtcg cggcaaaacg | 2220 |
| tgagcaaagg atggccagcc ggactgattt ggaggcagag atgcggcaag aaaagagcgg | 2280 |
| agaaattacc atggtggagc agaggaggag cagccgtggg tcatcgaaca tgctggatgt | 2340 |
| caggaggagt agccgcggtt cgtctaacat gctagagacc agaagaagca gtcgtggcag | 2400 |
| tgagcagatg ctgtcatgag gaccaacatc atggtagcaa ggtaagtgga aatcggctgt | 2460 |
| gaagaaatac agggtcagtt gtgagaggga aagctatcac gaatggctga agagctttgg | 2520 |
| gccttgttac gatgtaatgt tgtccggaaa tgttgtggta attattgta | 2569 |

<210> SEQ ID NO 92
<211> LENGTH: 2016
<212> TYPE: DNA
<213> ORGANISM: M. phaseolina

<400> SEQUENCE: 92

| | |
|---|---|
| atggcccagt ctctgttcct cctgcttgct gctgccctgt gcagccgcgc tgccacagtc | 60 |
| acgtatgact ttaacgtgac ctgggtcacc gccaaccctg atgctgcttt cgtcgcact | 120 |
| accattggca tcaatggcca gtggccgctc cctgcaatcg acgtcaccaa gggcgaccgc | 180 |
| gttgtcatca cgtcaacaa ccagctggaa acggagagta ccagtttgca tttccatgga | 240 |
| atctacatga atggcaccaa ccacatggat ggcccgactg gcgtgaccca gtgcgagata | 300 |
| ccgcccggga gctcattcac atacaatttt acggtcgacc aaccgggaac ttactggtat | 360 |

```
cattctcaca accgcggcca gtatcccgat ggattgcgag ggccttttat tgtcagagac    420
cccgacaatc cgttcaagga tgactatgat gaggaagtcg tcctgacatt ctccgactgg    480
taccacgacc ggatccccac cctcatgaag agtttcatta gtgtcacaaa ccccaccggc    540
gcggagcctg tcccgaacgc ggcactgatg aatgacactc agaacctcac cttccagatg    600
actcccgggc ggagatacat gttccgacta ataaacattg gtgcatttgc tgctcaatac    660
gtctggttcg aaggccatac catgcgtatc gtagaagtcg acggcgtgta caccgaagcc    720
gcagatgcag agcgaattta catgactgcc gctcaacgct acagcgtaat catcaccgca    780
aagaacgaat ctacctcaaa cttcgccttt gttggaagca tggatcagga tctctttgat    840
actattccag caggccttaa taataacgtg accgggtggc ttgtctacaa tcaacagaac    900
ggcttgttgc cacctttagc tatcggggac tacgatccgt tcgatgactt cacacttgtg    960
cctcaagatg gtatggagct ctacgatcac gtcgatcatt ccatcaccct cgatatgaag   1020
atggacaatc tcggggacgg agcaaattat gccttttttca cgacgtgac ctacgtcgag   1080
cccaaggtgc cgactctgta cacggtgttg tctactggca ataatgccac agactcgaga   1140
atctacggta gcaacaccaa cagcttcata ttggctaagg acgaagtcgt cgagatcatc   1200
ctcaacaaca atgatccggg aaagcaccct ttccatctgc atgggcacgc attccaagca   1260
atcgttcgct ccgaagaaga agccggcgcg tacgtggcaa acgaaacctt cccccagacg   1320
ccaatgcgcc gcgatacaat tcttgtccgg cccaatggca atatagtact gagattcaag   1380
gctgacaatc ctggtgtctg gctgttccat tgtcatattg aatggcatgt tgcgtcgggc   1440
cttattgcca ccatgataga ggcaccgctt gacctgcaat cttctctcgg caacagcatt   1500
cctgctgatc actggcgagc ttgtgccgcc gccggcacac ctactgcagg caacgcagca   1560
ggcaacacga ttgattatct tgacctgact ggtgaaaaca agagccccgg cccgcttccc   1620
tctggctttg aagcgaaagg cattgtcgcg cttgtcttca gttgtattgc tgctgtcttg   1680
ggcatggcag ccatcgtatg gtacgggatg gcgcctctga cagatggaac tggtcagcaa   1740
caacacgttg tggatcaaca gccgcaagga cgctcccgca agttggcgt catgccccta   1800
gcggtcgcgg caaaacgtga gcaaaggatg gccagccgga ctgatttgga ggcagagatg   1860
cggcaagaaa agagcggaga aattaccatg gtggagcaga ggaggagcag ccgtgggtca   1920
tcgaacatgc tggatgtcag gaggagtagc cgcggttcgt ctaacatgct agagaccaga   1980
agaagcagtc gtggcagtga gcagatgctg tcatga                             2016
```

<210> SEQ ID NO 93
<211> LENGTH: 671
<212> TYPE: PRT
<213> ORGANISM: M. phaseolina
<400> SEQUENCE: 93

```
Met Ala Gln Ser Leu Phe Leu Leu Ala Ala Ala Leu Cys Ser Arg
1               5                   10                  15

Ala Ala Thr Val Thr Tyr Asp Phe Asn Val Thr Trp Val Thr Ala Asn
                20                  25                  30

Pro Asp Ala Ala Phe Arg Arg Thr Thr Ile Gly Ile Asn Gly Gln Trp
            35                  40                  45

Pro Leu Pro Ala Ile Asp Val Thr Lys Gly Asp Arg Val Val Ile Asn
        50                  55                  60

Val Asn Asn Gln Leu Glu Thr Glu Ser Thr Ser Leu His Phe His Gly
65                  70                  75                  80
```

```
Ile Tyr Met Asn Gly Thr Asn His Met Asp Gly Pro Thr Gly Val Thr
                85                  90                  95

Gln Cys Glu Ile Pro Pro Gly Ser Ser Phe Thr Tyr Asn Phe Thr Val
            100                 105                 110

Asp Gln Pro Gly Thr Tyr Trp Tyr His Ser His Asn Arg Gly Gln Tyr
        115                 120                 125

Pro Asp Gly Leu Arg Gly Pro Phe Ile Val Arg Asp Pro Asp Asn Pro
    130                 135                 140

Phe Lys Asp Asp Tyr Asp Glu Glu Val Val Leu Thr Phe Ser Asp Trp
145                 150                 155                 160

Tyr His Asp Arg Ile Pro Thr Leu Met Lys Ser Phe Ile Ser Val Thr
                165                 170                 175

Asn Pro Thr Gly Ala Glu Pro Val Pro Asn Ala Ala Leu Met Asn Asp
            180                 185                 190

Thr Gln Asn Leu Thr Phe Gln Met Thr Pro Gly Arg Arg Tyr Met Phe
        195                 200                 205

Arg Leu Ile Asn Ile Gly Ala Phe Ala Ala Gln Tyr Val Trp Phe Glu
    210                 215                 220

Gly His Thr Met Arg Ile Val Glu Val Asp Gly Val Tyr Thr Glu Ala
225                 230                 235                 240

Ala Asp Ala Glu Arg Ile Tyr Met Thr Ala Ala Gln Arg Tyr Ser Val
                245                 250                 255

Ile Ile Thr Ala Lys Asn Glu Ser Thr Ser Asn Phe Ala Phe Val Gly
            260                 265                 270

Ser Met Asp Gln Asp Leu Phe Asp Thr Ile Pro Ala Gly Leu Asn Asn
        275                 280                 285

Asn Val Thr Gly Trp Leu Val Tyr Asn Gln Gln Asn Gly Leu Leu Pro
    290                 295                 300

Pro Leu Ala Ile Gly Asp Tyr Asp Pro Phe Asp Phe Thr Leu Val
305                 310                 315                 320

Pro Gln Asp Gly Met Glu Leu Tyr Asp His Val Asp His Ser Ile Thr
                325                 330                 335

Leu Asp Met Lys Met Asp Asn Leu Gly Asp Gly Ala Asn Tyr Ala Phe
            340                 345                 350

Phe Asn Asp Val Thr Tyr Val Glu Pro Lys Val Pro Thr Leu Tyr Thr
        355                 360                 365

Val Leu Ser Thr Gly Asn Asn Ala Thr Asp Ser Arg Ile Tyr Gly Ser
    370                 375                 380

Asn Thr Asn Ser Phe Ile Leu Ala Lys Asp Glu Val Val Glu Ile Ile
385                 390                 395                 400

Leu Asn Asn Asn Asp Pro Gly Lys His Pro Phe His Leu His Gly His
                405                 410                 415

Ala Phe Gln Ala Ile Val Arg Ser Glu Glu Glu Ala Gly Ala Tyr Val
            420                 425                 430

Ala Asn Glu Thr Phe Pro Gln Thr Pro Met Arg Arg Asp Thr Ile Leu
        435                 440                 445

Val Arg Pro Asn Gly Asn Ile Val Leu Arg Phe Lys Ala Asp Asn Pro
    450                 455                 460

Gly Val Trp Leu Phe His Cys His Ile Glu Trp His Val Ala Ser Gly
465                 470                 475                 480

Leu Ile Ala Thr Met Ile Glu Ala Pro Leu Asp Leu Gln Ser Ser Leu
                485                 490                 495
```

Gly Asn Ser Ile Pro Ala Asp His Trp Arg Ala Cys Ala Ala Ala Gly
            500                 505                 510

Thr Pro Thr Ala Gly Asn Ala Ala Gly Asn Thr Ile Asp Tyr Leu Asp
        515                 520                 525

Leu Thr Gly Glu Asn Lys Ser Pro Gly Pro Leu Pro Ser Gly Phe Glu
    530                 535                 540

Ala Lys Gly Ile Val Ala Leu Val Phe Ser Cys Ile Ala Ala Val Leu
545                 550                 555                 560

Gly Met Ala Ala Ile Val Trp Tyr Gly Met Ala Pro Leu Thr Asp Gly
                565                 570                 575

Thr Gly Gln Gln Gln His Val Val Asp Gln Gln Pro Gln Gly Arg Ser
            580                 585                 590

Ala Gln Val Gly Val Met Pro Leu Ala Val Ala Ala Lys Arg Glu Gln
        595                 600                 605

Arg Met Ala Ser Arg Thr Asp Leu Glu Ala Glu Met Arg Gln Glu Lys
    610                 615                 620

Ser Gly Glu Ile Thr Met Val Glu Gln Arg Arg Ser Ser Arg Gly Ser
625                 630                 635                 640

Ser Asn Met Leu Asp Val Arg Arg Ser Ser Arg Gly Ser Ser Asn Met
                645                 650                 655

Leu Glu Thr Arg Arg Ser Ser Arg Gly Ser Glu Gln Met Leu Ser
            660                 665                 670

<210> SEQ ID NO 94
<211> LENGTH: 3063
<212> TYPE: DNA
<213> ORGANISM: M. phaseolina

<400> SEQUENCE: 94

```
acgcctcgcc aacctcatct tcgtcgaaca ggcttaggta tcaagcctcc tttgcaatca      60
cttacgcggc cctctctacc tcctgctcat gtttgaacaa atcacacctc tttgaaacgc     120
tagaaacaca ctgtttctat accgtcgaga atggcctgga cctcagctct agatcgatcc     180
tcgtggcttg ccccagcttc cccaccaagg gggtttggta agtcgtaaaa gtttcctcac     240
agttcgcaaa ttcagagtac cggttcagcc tctgatcttt gccactgtca cggcggcagc     300
tgaagccgcg tgtacgtcga attctcccct gaatacgtat gtgccggact tgtatttctt     360
catacccagc cgtctaggat cgttcggtat cggtctctgc aacgactacc actacgacca     420
ctgggaaatc ctccacgttc tctacgctga ccagcacttc atcttcgtct acagcgaaga     480
ctagctcggc cagctcggca tcgctttcac gcactactcc ttcacctgcc agctcttctt     540
ccgtgagctc ttcgtcgatc agatcctctt ctggcggatc ttcatctgct ggtacttctt     600
ctgcccgctc atcatatgtc agctcttctt tgagctcgcg ttctgctgtt cttccctag     660 tgaccagcat atcctcttct ctcacctcaa ctggcacggt atcgtcctcg cccgcttcga     720
agagctccag ctcttcatct tccactcttt cagcctcttc aaccacaaag gttgctactg     780
gtaccccgtg tgctggaaac actgcggctt ccaggacagc ctggtgcgat cacaccattg     840
acgatgacta ctatcccatt atcccagata ccggagtcac acgcgaatac tggttcgacc     900
ttgtcgaggt gactgttgcc cctgatggca ttgagagagc tgccatggcg gtcaacggca     960
gcatccctgg acccaccatt gaggcggatt ggggcgatat cgccgtcatg catgtgacca    1020
acagcttgat ctcgagcaag aacggcacta gcattcattt ccacggtatc cagcagaact    1080
tcacaaatca aacggacggt gttatttcca tcactcagtg ccctaccgct cctggcgaga    1140
```

| | |
|---|---|
| actacacgta tacctggagg gctgagcagt acggaactac atggtgagct tgatccgagg | 1200 |
| atacagatgt aaaggagatg ctaagatatc acaggtacca ttctcacttt gcgcttcaag | 1260 |
| cttgggaagg tgtctttgga ggtacataca tccccgctcc aggacctcca acatttatta | 1320 |
| acgaagccct gcaggtatca agatcaatgg tccggcgagt gccaactacg attacgatct | 1380 |
| tggccatgtc ttcctgtgag tttcgacgcc ccttttccac tcattgtata aagtaagctt | 1440 |
| atgcgacaaa agccaacgat ggagccacg agacttcgag ctctctcgag atcgtttctg | 1500 |
| caattcgagg tccgccaaca cttgagaatg cccttatcaa cggtaccaac gtgtacaaca | 1560 |
| actcgggaac cataacgggc tctcgttttg agacaacatt tgaggaaggc aaatcctaca | 1620 |
| ggttgaggtt ggtcagcggc gccatcgaca cgcatttcaa ggtgtcattg ggtaagttga | 1680 |
| gccaaaacat tgagatttcc tgagatctaa agctgattgt gttgcagata accacagcat | 1740 |
| gcttgtcata gccaacgacc ttgtacccat cgtgccgtac aacacgaccg tcctgaacat | 1800 |
| cggaatgggt catccacttt ctatcaggaa ctggccatca aactgacact gaaccccagg | 1860 |
| ccaacgctac gatgtaatca tcaccgccaa ccaagccgta gtcgccaccg acttctggct | 1920 |
| gcgtgccgtc ccgcagacgg cctgctccaa taacgccaac ccagacaata tcaaaggaat | 1980 |
| aatccggtac agcacctcca cctccgccta cgactgacg aacgaatgcg tcgacgaggc | 2040 |
| cctcaccaac ctcgtgccat gggtgactaa gaacgcggcc tcgggcacga gtctatctga | 2100 |
| agtggtgacg ctgggtcgca acgttgacaa cctcaaccgc tggatgatga acagcacatc | 2160 |
| gatggttgtc gagtggaatg atccctcgtt gctgcaggtt tggaataatg ataccaattt | 2220 |
| cacgatacg agcggcgtgg tcaggcttgg tacggcggac gagtgggtca tgtttgttat | 2280 |
| cgagatgacg ctgccgattc cgcgtcccat ccatcttcac gggcatgatg tagatttctt | 2340 |
| ccagccgccc cccccccccc cctttttttt gggctctact tcctagaata ccggacggag | 2400 |
| tcgttgcgga gcgcgccttc gccgactttt gcgttccgat gtctcaagaa aggtgtccat | 2460 |
| gttgtaatgt gtatcccaga ggcttccgg ctgacttgtt ttgtcaacac agttcaacat | 2520 |
| cctcgcccaa gggaccggca cgtacgattc atccgtgtcg ctcaccctgt caaacccgcc | 2580 |
| gcggagggac gttgcgctgc tgcccgcagc cgggtacttg tgattgcat cgccaccga | 2640 |
| taaccctgga gcctgtgagg acttctcttt ttcttgtgca tccctggatg tcatccttgc | 2700 |
| tgtgaaattt ttggctgacg cattcgtctc aatgcagggc tcatgcactg ccacatcggc | 2760 |
| cggcgcacta cggagggctt cgcaatccag atcctcgagc gctgggacga gatctcgccg | 2820 |
| cttatcgact acgagacgct tgaaggcaac tgcaacagat gggacgcgta cgtgtcggtc | 2880 |
| agcgatgtcg tacaggacga ttctggcgta tgagcaatga aggttagagt atttgcgacg | 2940 |
| tgttttatca tatatacaac cttttaatc gtagtcgctc cttaaccata atgttaatcc | 3000 |
| atcacttggg ccatccaagc accaacaaaa catttgagcc ttcccaatca ggactggcac | 3060 |
| aag | 3063 |

<210> SEQ ID NO 95
<211> LENGTH: 2085
<212> TYPE: DNA
<213> ORGANISM: M. phaseolina

<400> SEQUENCE: 95

| | |
|---|---|
| atggcctgga cctcagctct agatcgatcc tcgtggcttg ccccagcttc cccaccaagg | 60 |
| gggtttgcta agccgcgtg tacgtcgaat ctctccctga atacgtatgt gccggacttg | 120 |
| tatttcttca tacccagccg tctaggatcg ttcggtatcg gtctctgcaa cgactaccac | 180 |

```
tacgaccact gggaaatcct ccacgttctc tacgctgacc agcacttcat cttcctcttc    240
ttccgtgagc tcttcgtcga tcagatcctc ttctggcgga tcttcatctg ctggtacttc    300
ttctgcccgc tcatcatatg tcagctcttc tttgagctcg cgttctgctg tttcttccct    360
agtgaccagc atatcctctt ctctcacctc aactggcacg gtatcgtcct cgcccgcttc    420
gaagagctcc agctcttcat cttccactct ttcagcctct caaccacaa agcctggtgc     480 gatcacacca ttgacgatga ctactatccc attatcccag ataccggagt cacacgcgaa    540
tactggttcg accttgtcga ggtgactgtt gcccctgatg gcattgagag agctgccatg    600
gcggtcaacg gcagcatccc tgacccacc attgaggcgg attggggcga tatcgccgtc     660
atgcatgtga ccaacagctt gatctcgagc aagaacggca ctagcattca tttccacggt    720
atccagcaga acttcacaaa tcaaacggac ggtgttattt ccatcactca gtgccctacc    780
gctcctggcg agaactacac gtatacctgg agggctgagc agtacggaac tacatggtac    840
cattctcact ttgcgcttca agcttgggaa ggtgtctttg gaggtacata catccccgct    900
ccaggacctc caacatttat taacgaagcc ctgcaggtat caagatcaat ggtccggcga    960
gtgccaacta cgattacgat cttggccatg tcttcctcca acgattggag ccacgagact   1020
tcgagctctc tcgagatcgt ttctgcaatt cgaggtccgc caacacttga aatgcccttt   1080
atcaacggta ccaacgtgta caacaactcg ggaaccataa cgggctctcg tttgagaca   1140 acatttgagg aaggcaaatc ctacaggttg aggttggtca gcggcgccat cgacacgcat   1200
ttcaaggtgt cattggataa ccacagcatg cttgtcatag ccaacgacct tgtacccatc   1260
gtgccgtaca acacgaccgt cctgaacatc ggaatgggcc aacgctacga tgtaatcatc   1320
accgccaacc aagccgtagt cgccaccgac ttctggctgc gtgccgtccc gcagacggcc   1380
tgctccaata cgccaacccc agacaatatc aaaggaataa tccggtacag cacctccacc   1440
tccgcctacg actggacgaa cgaatgcgtc gacgaggccc tcaccaacct cgtgccatgg   1500
gtgactaaga acgcggcctc gggcacgagt ctatctgaag tggtgacgct gggtcgcaac   1560
gttgacaacc tcaaccgctg gatgatgaac agcacatcga tggttgtcga gtggaatgat   1620
ccctcgttgc tgcaggtttg gaataatgat accaatttca cggatacgag cggcgtggtc   1680
aggcttggta cggcggacga gtgggtcatg tttgttatcg agatgacgct gccgattccg   1740
cgtcccatcc atcttcacgg gcatgatttc aacatcctcg cccaagggac cggcacgtac   1800
gattcatccg tgtcgctcac cctgtcaaac ccgccgcgga gggacgttgc gctgctgccc   1860
gcagccgggt acttggtgat tgcattcgcc accgataacc ctggagcctg gctcatgcac   1920
tgccacatcg gccggcgcac tacggagggc ttcgcaatcc agatcctcga gcgctgggac   1980
gagatctcgc cgcttatcga ctacgagacg cttgaaggca actgcaacag atgggacgcg   2040
tacgtgtcgg tcagcgatgt cgtacaggac gattctggcg tatga                    2085
```

<210> SEQ ID NO 96  
<211> LENGTH: 694  
<212> TYPE: PRT  
<213> ORGANISM: M. phaseolina

<400> SEQUENCE: 96

Met Ala Trp Thr Ser Ala Leu Asp Arg Ser Ser Trp Leu Ala Pro Ala
1               5                   10                  15

Ser Pro Pro Arg Gly Phe Ala Glu Ala Ala Cys Thr Ser Asn Ser Pro
            20                  25                  30

```
Leu Asn Thr Tyr Val Pro Asp Leu Tyr Phe Ile Pro Ser Arg Leu
         35                  40                  45

Gly Ser Phe Gly Ile Gly Leu Cys Asn Asp Tyr His Tyr Asp His Trp
 50                  55                  60

Glu Ile Leu His Val Leu Tyr Ala Asp Gln His Phe Ile Phe Leu Phe
 65                  70                  75                  80

Phe Arg Glu Leu Phe Val Asp Gln Ile Leu Phe Trp Arg Ile Phe Ile
                 85                  90                  95

Cys Trp Tyr Phe Phe Cys Pro Leu Ile Ile Cys Gln Leu Phe Phe Glu
                100                 105                 110

Leu Ala Phe Cys Cys Phe Phe Pro Ser Asp Gln His Ile Leu Phe Ser
             115                 120                 125

His Leu Asn Trp His Gly Ile Val Leu Ala Arg Phe Glu Glu Leu Gln
 130                 135                 140

Leu Phe Ile Phe His Ser Phe Ser Leu Phe Asn His Lys Ala Trp Cys
145                 150                 155                 160

Asp His Thr Ile Asp Asp Tyr Tyr Pro Ile Ile Pro Asp Thr Gly
                165                 170                 175

Val Thr Arg Glu Tyr Trp Phe Asp Leu Val Glu Val Thr Val Ala Pro
             180                 185                 190

Asp Gly Ile Glu Arg Ala Ala Met Ala Val Asn Gly Ser Ile Pro Gly
             195                 200                 205

Pro Thr Ile Glu Ala Asp Trp Gly Asp Ile Ala Val Met His Val Thr
     210                 215                 220

Asn Ser Leu Ile Ser Ser Lys Asn Gly Thr Ser Ile His Phe His Gly
225                 230                 235                 240

Ile Gln Gln Asn Phe Thr Asn Gln Thr Asp Gly Val Ile Ser Ile Thr
                 245                 250                 255

Gln Cys Pro Thr Ala Pro Gly Glu Asn Tyr Thr Tyr Thr Trp Arg Ala
             260                 265                 270

Glu Gln Tyr Gly Thr Thr Trp Tyr His Ser His Phe Ala Leu Gln Ala
             275                 280                 285

Trp Glu Gly Val Phe Gly Gly Thr Tyr Ile Pro Ala Pro Gly Pro Pro
     290                 295                 300

Thr Phe Ile Asn Glu Ala Leu Gln Val Ser Arg Ser Met Val Arg Arg
305                 310                 315                 320

Val Pro Thr Thr Ile Thr Ile Leu Ala Met Ser Ser Ser Asn Asp Trp
                 325                 330                 335

Ser His Glu Thr Ser Ser Ser Leu Glu Ile Val Ser Ala Ile Arg Gly
             340                 345                 350

Pro Pro Thr Leu Glu Asn Ala Leu Ile Asn Gly Thr Asn Val Tyr Asn
             355                 360                 365

Asn Ser Gly Thr Ile Thr Gly Ser Arg Phe Glu Thr Thr Phe Glu Glu
 370                 375                 380

Gly Lys Ser Tyr Arg Leu Arg Leu Val Ser Gly Ala Ile Asp Thr His
385                 390                 395                 400

Phe Lys Val Ser Leu Asp Asn His Ser Met Leu Val Ile Ala Asn Asp
                 405                 410                 415

Leu Val Pro Ile Val Pro Tyr Asn Thr Val Leu Asn Ile Gly Met
             420                 425                 430

Gly Gln Arg Tyr Asp Val Ile Ile Thr Ala Asn Gln Ala Val Val Ala
             435                 440                 445

Thr Asp Phe Trp Leu Arg Ala Val Pro Gln Thr Ala Cys Ser Asn Asn
```

```
            450                 455                 460
Ala Asn Pro Asp Asn Ile Lys Gly Ile Ile Arg Tyr Ser Thr Ser Thr
465                 470                 475                 480

Ser Ala Tyr Asp Trp Thr Asn Glu Cys Val Asp Glu Ala Leu Thr Asn
                485                 490                 495

Leu Val Pro Trp Val Thr Lys Asn Ala Ala Ser Gly Thr Ser Leu Ser
                500                 505                 510

Glu Val Val Thr Leu Gly Arg Asn Val Asp Asn Leu Asn Arg Trp Met
            515                 520                 525

Met Asn Ser Thr Ser Met Val Val Glu Trp Asn Asp Pro Ser Leu Leu
        530                 535                 540

Gln Val Trp Asn Asn Asp Thr Asn Phe Thr Asp Thr Ser Gly Val Val
545                 550                 555                 560

Arg Leu Gly Thr Ala Asp Glu Trp Val Met Phe Val Ile Glu Met Thr
                565                 570                 575

Leu Pro Ile Pro Arg Pro Ile His Leu His Gly His Asp Phe Asn Ile
                580                 585                 590

Leu Ala Gln Gly Thr Gly Thr Tyr Asp Ser Ser Val Ser Leu Thr Leu
            595                 600                 605

Ser Asn Pro Pro Arg Arg Asp Val Ala Leu Leu Pro Ala Ala Gly Tyr
        610                 615                 620

Leu Val Ile Ala Phe Ala Thr Asp Asn Pro Gly Ala Trp Leu Met His
625                 630                 635                 640

Cys His Ile Gly Arg Arg Thr Thr Glu Gly Phe Ala Ile Gln Ile Leu
                645                 650                 655

Glu Arg Trp Asp Glu Ile Ser Pro Leu Ile Asp Tyr Glu Thr Leu Glu
                660                 665                 670

Gly Asn Cys Asn Arg Trp Asp Ala Tyr Val Ser Val Ser Asp Val Val
            675                 680                 685

Gln Asp Asp Ser Gly Val
        690

<210> SEQ ID NO 97
<211> LENGTH: 2449
<212> TYPE: DNA
<213> ORGANISM: M. phaseolina

<400> SEQUENCE: 97
gcgcaccccc gaatttcat gtggcacttt gctggtggcg atgcataaag tctcccaaac      60
ttgatcttca gcgtcgagag cagctcaacg tccgatccga ttttcgttc accgcgcttc     120 ttgtccctca agcccccaat acaattcaac atgtttctt tgtcgtcca gaagcctcaa      180 ctgccgctat ggctggactt tggccttca atatggtcaa tgttcggcgg aaacagtcaa     240
gactgcgtac actcgcccca gagcagacac tgctggcatg atgggttcga tatcaacacc     300
gattatgaag ctaagatacc gccagggaag ctcgtggagg taagataacc cagccacaga     360
cggctcaggc catcgcaact cacctccctt agtacgattt cactatctcg gaagcagtcc     420
ttgctccgga cggatacttg acgaatgtca ctctggtaaa tggagtattc cctggtccaa     480
ccctcgaagc tgaatgggga gatacgatca gtatgccttc ttcatatgaa atctttctgt     540 gtgcctttg acgtgattgc tgacattcc tgccagggat aacgatccac aacaacctca     600
caaaccacaa tggcacatcc atacattggc atggaattcg ccaattcgag accaattggc     660
ttgatggtgt tcccggcgtc actcaatgcc cgtcaaaggt actacggctg gtttgctttg     720
```

```
ggagagaaac aggggagcta agtgtcacca gcctggagac tcgcaagttg tcgaattccg    780
agcgatgcaa tatgggaccg catggtatca ttcacactac agtcttcagt gtcagtatca    840
atcacagagc tcttgagcgg cacttacgct aaccatgatt agatacaaac ggagttctcg    900
gtatttgcta tctcccttcc atacagttca aacctgtgg gctgatcccg ttgcaggacc    960
cattcacatc aagggaccct cgagcatgaa ctacgacgtg gatctcgggc cactgttgat   1020
cagtgattgg tatcaccacg atgccttcgg cctattccat tatgagatcg cttcaccgca   1080
cgcgccgctt ccggtcacaa ctatcttgaa tggcaaggga gtcttttgatt gcgatccagc   1140
cagcgatgct cgttgtacgg gagagcacca acggcacgag atagtgttcg aagagggtaa   1200
aagatacaaa attggactaa taaataccgg cagccttctg acatacaagt tctggatcga   1260
tggccataat tttacagttg tgcagacgga tttcgttccc atcaaaccat acgtcaccga   1320
cgttctgatc gtcgggatag gtatgttcag tgcctacaaa gaattggcgg taaactgatc   1380
attcccagct caacgatacg agatcattat cgaagcaaat gtgacattca cacgtggctc   1440
caacttctgg attcacgcaa cgtactgtga cgatgatgac atgttggact cgagagttgg   1500
catagtccgc tacgacggca gcgacggtcg tgatccgcac acgccgccca agagtgagca   1560
acaccccgga tacgggtgtc gtgatccagc cacgagaat cttgttccca tcgtgaagag   1620
ggaagtaggc aagagagtga acgggctcag ccctgctgat tacctcagga tcggcctgca   1680
gggctggccc aacatctcgg acacagattc gctcgtacac aaatgacac ttaccaacag   1740
aacccagtac attgattgga gggagccaac aatcaaggcg ctcacttcgg atgtcggggc   1800
tgattttgcg gatgagacat gccccatata cctggactac gagactggcg agtgggtgta   1860
cttcgtcatc gagaacaact acacgctgag cgacgccaac acgccccgca ccatcccccg   1920
ctcggtccat cccatccact tacacgggca tgacttcgtg atcctcgccc agggtgacgg   1980
catgttcgac cccgtcgacg tggtgccgaa cctccacaac ccaaccagga gggacgtggt   2040
caattgcccg attggcggct acgtatggat cgcattccag gtcaacaatc caggagcgtg   2100
gctgatgcat tgccatatcg cctggcatgc cagcgccgga ctctcactgc agttcattga   2160
gcaacctggc ctgatcaagg ggttaatgga gcaggcagga gccttgccgg agcttgctga   2220
tcgatgcgag gactggactg agtactacaa tactgtaaac ataccaaaag gcgcactgca   2280
agatgattcg ggcatatgag ttggtattga acttccggct gaaacgctc agccacggct   2340
acttgcttgg ccaagattga gggttggccg agaaatgagt agtgggggatt atcactttct   2400
tagaatgtgc acgaaagggt agtgttcggt catgtctctt agcttgaaa              2449
```

<210> SEQ ID NO 98
<211> LENGTH: 1821
<212> TYPE: DNA
<213> ORGANISM: M. phaseolina

<400> SEQUENCE: 98

```
atgttttctt ttgtcgtcca gaagcctcaa ctgccgctat ggctggactt tggcctttca    60
atatggtcaa tgttcggcgg aaacagtcaa gactgcgtac actcgcccca gagcagacac   120
tgctggcatg atgggttcga tatcaacacc gattatgaag ctaagatacc gccagggaag   180
ctcgtggagt acgatttcac tatctcggaa gcagtccttg ctccggacgg atacttgacg   240
aatgtcactc tggtaaatgg agtattccct ggtccaaccc tcgaagctga atggggagat   300
acgatcagga taacgatcca caacaacctc acaaaccaca atggcacatc catacattgg   360
catggaattc gccaattcga gaccaattgg cttgatggtg ttcccggcgt cactcaatgc   420
```

-continued

```
ccgtcaaagc ctggagactc gcaagttgtc gaattccgag cgatgcaata tgggaccgca    480
tggtatcatt cacactacag tcttcagtat acaaacggag ttctcggacc cattcacatc    540
aagggaccct cgagcatgaa ctacgacgtg gatctcgggc cactgttgat cagtgattgg    600
tatcaccacg atgccttcgg cctattccat tatgagatcg cttcaccgca cgcgccgctt    660
ccggtcacaa ctatcttgaa tggcaaggga gtctttgatt gcgatccagc cagcgatgct    720
cgttgtacgg gagagcacca acggcacgag atagtgttcg aagagggtaa agatacaaa     780 attggactaa taaataccgg cagccttctg acatacaagt tctggatcga tggccataat    840
tttacagttg tgcagacgga tttcgttccc atcaaaccat acgtcaccga cgttctgatc    900
gtcgggatag ctcaacgata cgagatcatt atcgaagcaa atgtgacatt cacacgtggc    960
tccaacttct ggattcacgc aacgtactgt gacgatgatg acatgttgga ctcgagagtt   1020
ggcatagtcc gctacgacgg cagcgacggt cgtgatccgc acacgccgcc caagagtgag   1080
caacaccccg gatacgggtg tcgtgatcca gccacggaga tcttgttcc catcgtgaag    1140 agggaagtag gcaagagagt gaacgggctc agccctgctg attacctcag gatcggcctg   1200
cagggctggc ccaacatctc ggacacagat tcgctcgtac acaaatggac acttaccaac   1260
agaacccagt acattgattg gagggagcca acaatcaagg cgctcacttc ggatgtcggg   1320
gctgattttg cggatgagac atgccccata tacctggact acgagactgg cgagtgggtg   1380
tacttcgtca tcgagaacaa ctacacgctg agcgacgcca acacgccccg caccatcccc   1440
cgctcggtcc atcccatcca cttacacggg catgacttcg tgatcctcgc ccagggtgac   1500
ggcatgttcg accccgtcga cgtggtgccg aacctccaca cccaaccag gagggacgtg    1560 gtcaattgcc cgattggcgg ctacgtatgg atcgcattcc aggtcaacaa tccaggagcg   1620
tggctgatgc attgccatat cgcctggcat gccagcgccg gactctcact gcagttcatt   1680
gagcaacctg gcctgatcaa ggggttaatg gagcaggcag gagccttgcc ggagcttgct   1740
gatcgatgcg aggactggac tgagtactac aatactgtaa acataccaaa aggcgcactg   1800
caagatgatt cgggcatatg a                                              1821
```

<210> SEQ ID NO 99
<211> LENGTH: 606
<212> TYPE: PRT
<213> ORGANISM: M. phaseolina

<400> SEQUENCE: 99

```
Met Phe Ser Phe Val Val Gln Lys Pro Gln Leu Pro Leu Trp Leu Asp
1               5                   10                  15

Phe Gly Leu Ser Ile Trp Ser Met Phe Gly Gly Asn Ser Gln Asp Cys
            20                  25                  30

Val His Ser Pro Gln Ser Arg His Cys Trp His Asp Gly Phe Asp Ile
        35                  40                  45

Asn Thr Asp Tyr Glu Ala Lys Ile Pro Pro Gly Lys Leu Val Glu Tyr
    50                  55                  60

Asp Phe Thr Ile Ser Glu Ala Val Leu Ala Pro Asp Gly Tyr Leu Thr
65                  70                  75                  80

Asn Val Thr Leu Val Asn Gly Val Phe Pro Gly Pro Thr Leu Glu Ala
                85                  90                  95

Glu Trp Gly Asp Thr Ile Arg Ile Thr Ile His Asn Asn Leu Thr Asn
            100                 105                 110

His Asn Gly Thr Ser Ile His Trp His Gly Ile Arg Gln Phe Glu Thr
```

-continued

```
            115                 120                 125
Asn Trp Leu Asp Gly Val Pro Gly Val Thr Gln Cys Pro Ser Lys Pro
130                 135                 140
Gly Asp Ser Gln Val Val Glu Phe Arg Ala Met Gln Tyr Gly Thr Ala
145                 150                 155                 160
Trp Tyr His Ser His Tyr Ser Leu Gln Tyr Thr Asn Gly Val Leu Gly
                165                 170                 175
Pro Ile His Ile Lys Gly Pro Ser Ser Met Asn Tyr Asp Val Asp Leu
            180                 185                 190
Gly Pro Leu Leu Ile Ser Asp Trp Tyr His His Asp Ala Phe Gly Leu
            195                 200                 205
Phe His Tyr Glu Ile Ala Ser Pro His Ala Pro Leu Pro Val Thr Thr
210                 215                 220
Ile Leu Asn Gly Lys Gly Val Phe Asp Cys Asp Pro Ala Ser Asp Ala
225                 230                 235                 240
Arg Cys Thr Gly Glu His Gln Arg His Glu Ile Val Phe Glu Glu Gly
                245                 250                 255
Lys Arg Tyr Lys Ile Gly Leu Ile Asn Thr Gly Ser Leu Leu Thr Tyr
            260                 265                 270
Lys Phe Trp Ile Asp Gly His Asn Phe Thr Val Val Gln Thr Asp Phe
            275                 280                 285
Val Pro Ile Lys Pro Tyr Val Thr Asp Val Leu Ile Val Gly Ile Ala
290                 295                 300
Gln Arg Tyr Glu Ile Ile Ile Glu Ala Asn Val Thr Phe Thr Arg Gly
305                 310                 315                 320
Ser Asn Phe Trp Ile His Ala Thr Tyr Cys Asp Asp Asp Met Leu
                325                 330                 335
Asp Ser Arg Val Gly Ile Val Arg Tyr Asp Gly Ser Asp Gly Arg Asp
            340                 345                 350
Pro His Thr Pro Pro Lys Ser Glu Gln His Pro Gly Tyr Gly Cys Arg
            355                 360                 365
Asp Pro Ala Thr Glu Asn Leu Val Pro Ile Val Lys Arg Glu Val Gly
370                 375                 380
Lys Arg Val Asn Gly Leu Ser Pro Ala Asp Tyr Leu Arg Ile Gly Leu
385                 390                 395                 400
Gln Gly Trp Pro Asn Ile Ser Thr Asp Ser Leu Val His Lys Trp
                405                 410                 415
Thr Leu Thr Asn Arg Thr Gln Tyr Ile Asp Trp Arg Glu Pro Thr Ile
            420                 425                 430
Lys Ala Leu Thr Ser Asp Val Gly Ala Asp Phe Ala Asp Glu Thr Cys
            435                 440                 445
Pro Ile Tyr Leu Asp Tyr Glu Thr Gly Glu Trp Tyr Phe Val Ile
450                 455                 460
Glu Asn Asn Tyr Thr Leu Ser Asp Ala Asn Thr Pro Arg Thr Ile Pro
465                 470                 475                 480
Arg Ser Val His Pro Ile His Leu His Gly His Asp Phe Val Ile Leu
                485                 490                 495
Ala Gln Gly Asp Gly Met Phe Asp Pro Val Asp Val Pro Asn Leu
            500                 505                 510
His Asn Pro Thr Arg Arg Asp Val Val Asn Cys Pro Ile Gly Gly Tyr
            515                 520                 525
Val Trp Ile Ala Phe Gln Val Asn Asn Pro Gly Ala Trp Leu Met His
530                 535                 540
```

Cys His Ile Ala Trp His Ala Ser Ala Gly Leu Ser Leu Gln Phe Ile
545                 550                 555                 560

Glu Gln Pro Gly Leu Ile Lys Gly Leu Met Glu Gln Ala Gly Ala Leu
            565                 570                 575

Pro Glu Leu Ala Asp Arg Cys Glu Asp Trp Thr Glu Tyr Tyr Asn Thr
        580                 585                 590

Val Asn Ile Pro Lys Gly Ala Leu Gln Asp Asp Ser Gly Ile
    595                 600                 605

<210> SEQ ID NO 100
<211> LENGTH: 2347
<212> TYPE: DNA
<213> ORGANISM: M. phaseolina

<400> SEQUENCE: 100

```
gatacaactc ttctccccgc ctctctttca caaactgtct atcgctcctt tgttttttctg     60
tccctcctta aggtcacata ctactgagac tattcgtgtc tcgtgcctct catttagttt    120
ttagttgatt catcttgccg ttgctgtaac atgccgtttt ctccacgcct aagtatatgc    180
cttttagcat tttgctctca cattgtgttc gcactttcga taccaaatgt aaaggatagg    240
accccccact taagcccgcg caattacgga tttcgtttcg gcaacctgtc ttggggcggg    300
gcggagcctt ccgacccact cgcacaaggt gcagaacgtt tggatgacat cagtctcccg    360
gccccctgaag atggctgtct tttctccaaa gatgctcgga actgctggcg cgataacttc    420
aacatcgaca ccgatttcga cgagcgcttc cccacgaccg ggaagacggt cactgtaagg    480
aatcatcgca cctcttggaa cccttacgct aataccgagg gcagtataat ctggagatca    540
caaacactac catggcccct gacggaatcg aacgcgtcgt catggccgtg aatggccaat    600
atcccggccc gaccctattt gctgattggg gggacacgat ggttatcaac gtcaagaata    660
gcctggacca caacggtacg ggtctccatt tccatggact cgccaatac aaaagcaacg    720
gcgccgatgg ggcgaacggt atcacagaat gcccaattgc ccccggcgag accaagacct    780
acacctttca atgtacccag cacggtagct cgtggtacca ctcgcattac tctgtccagt    840
actccgacgg cgttctcggc ggcattatca tcaacggccc cgccgacgcg cactacgacc    900
acgatcttgg tgtgtacatg ctttctgact ggtaccacac tccaatgttt gaactagccg    960
aagctgccag gcattcgaca aggggccac cgaaggcgga taacggactc atcaacggga   1020
cgatgaagag ccctgacggt tctcttggag cctatggcca gatccatgtg aagaagggtc   1080
tgcggtacag gattcgcgta atgaatgttg cactaacga ccactacctc ttctctgttg   1140
atgggcacaa cctcaccgtg atcgcaagtg atttcgtgcc ggtcgtgccc ttttcggcgt   1200
ccagcatttc cctcggtgtt ggtgagatat ccgatcttta tgttgttatt tcgctgctga   1260
ccgtcacttt aggacagagg tacgacgtga tccttatcgc cgaccaagac attgacaact   1320
actggatccg ctccgacccg gactctgcct gtagcgttaa cggcaacgcc ggcaacataa   1380
aagccatcct ctcgtatgac acggctcccg cggacgctca gccgaatagc acgcgccaca   1440
gcatctcctc gggctgcaag gacatggcag tcgtgccaag agttgctaat accgtgccct   1500
ctgatcgctt cgcggacgcc gtccagagcc tggcgatgag cgtcaatatc acgcagcaga   1560
acggcccgct cgtccagtgg tatatcaacg gctcggctat ggaggtcgac tggagctacc   1620
cgacggtcca atatgtccta gatgggaaca cgtcgtaccc cgtgagctg aacctagtcc   1680
agctggatga ggcggaccag tggtactact tcgtcatcca gaccgtgcaa ggcttgcgtg   1740
```

| | |
|---|---|
| tcaacctgcc gcacccaatt catcttcatg ccacgtacg ttccctcctt tcccttcctc | 1800 |
| cctaaacgaa acagtaaaag agggacaagt gaatgcgacg tactgatttg ttgtccaatt | 1860 |
| ggtccaggac ttctacatcc tcggcgccgg tcccggcgag tgggacggca acatcgatgg | 1920 |
| cctgcagttc gacaaccctc gcggcgcgca tacggcaatg ctacctgcgg gtggctacct | 1980 |
| catcctcgcc tttccggccg acaaccctgg cgcctggctc atgcattgcc acatcccgtt | 2040 |
| ccacgtccag cagggcttcg ggctgcagtt cttggagcgg ccggatgaga ttgagggcgt | 2100 |
| catgggcgat acgagcccgt tttacaacga gtgtgcggct tggaaggact actatggtgg | 2160 |
| gggccaggct tttcagcagt ccgattcggg cttgtaattg gtcgtggtgg cttgcgcaag | 2220 |
| agcaaagcgc cgtcggtgct ctggcggtga tttttagtgg cacggttttt gtactcatca | 2280 |
| actcctaatc actaagtcag ccaccctcgt ttccgcccac cctgtacagt cagcatcata | 2340 |
| acgtaac | 2347 |

<210> SEQ ID NO 101
<211> LENGTH: 1854
<212> TYPE: DNA
<213> ORGANISM: M. phaseolina

<400> SEQUENCE: 101

| | |
|---|---|
| atgccgtttt ctccacgcct aagtatatgc cttttagcat tttgctctca cattgtgttc | 60 |
| gcactttcga taccaaatgt aaaggatagg accccccact taagcccgcg caattacgga | 120 |
| tttcgtttcg gcaacctgtc ttggggcggg gcggagcctt ccgacccact cgcacaaggt | 180 |
| gcagaacgtt tggatgacat cagtctcccg gcccctgaag atggctgtct tttctccaaa | 240 |
| gatgctcgga actgctggcg cgataacttc aacatcgaca ccgatttcga cgagcgcttc | 300 |
| cccacgaccg ggaagacggt cacttataat ctggagatca caaacactac catggcccct | 360 |
| gacggaatcg aacgcgtcgt catggccgtg aatggccaat atcccggccc gacccttatt | 420 |
| gctgattggg gggacacgat ggttatcaac gtcaagaata gcctggacca caacggtacg | 480 |
| ggtctccatt tccatggact gcgccaatac aaaagcaacg cgccgatgg ggcgaacggt | 540 |
| atcacagaat gcccaattgc ccccggcgag accaagaccct acacctttca atgtacccag | 600 |
| cacggtagct cgtggtacca ctcgcattac tctgtccagt actccgacgg cgttctcggc | 660 |
| ggcattatca tcaacggccc cgccgacgcg cactacgacc acgatcttgg tgtgtacatg | 720 |
| ctttctgact ggtaccacac tccaatgttt gaactagccg aagctgccag gcattcgaca | 780 |
| aggggcccac cgaaggcgga taacggactc atcaacggga cgatgaagag ccctgacggt | 840 |
| tctcttggag cctatggcca gatccatgtg aagaagggtc tgcggtacag gattcgcgta | 900 |
| atgaatgttg gcactaacga ccactacctc ttctctgttg atgggcacaa cctcaccgtg | 960 |
| atcgcaagtg atttcgtgcc ggtcgtgccc tttttcggcgt ccagcatttc cctcggtgtt | 1020 |
| ggacagaggt acgacgtgat ccttatcgcc gaccaagaca ttgacaacta ctggatccgc | 1080 |
| tccgacccgg actctgcctg tagcgttaac ggcaacgccg gcaacataaa agccatcctc | 1140 |
| tcgtatgaca cggctcccgc ggacgctcag ccgaatagca cgcgccacag catctcctcg | 1200 |
| ggctgcaagg acatggcagt cgtgccaaga gttgctaata ccgtgccctc tgatcgcttc | 1260 |
| gcggacgccg tccagagcct ggcgatgagc gtcaatatca cgcagcagaa cggcccgctc | 1320 |
| gtccagtggt atatcaacgg ctcggctatg gaggtcgact ggagctaccc gacggtccaa | 1380 |
| tatgtcctag atgggaacac gtcgtacccg cgtgagctga acctagtcca gctgatgag | 1440 |
| gcggaccagt ggtactactt cgtcatccag accgtgcaag gcttgcgtgt caacctgccg | 1500 |

```
cacccaattc atcttcatgg ccacgacttc tacatcctcg gcgccggtcc cggcgagtgg    1560
gacggcaaca tcgatggcct gcagttcgac aaccctccgc ggcgcgatac ggcaatgcta    1620
cctgcgggtg gctacctcat cctcgccttt ccggccgaca accctggcgc ctggctcatg    1680
cattgccaca tcccgttcca cgtccagcag ggcttcgggc tgcagttctt ggagcggccg    1740
gatgagattg agggcgtcat gggcgatacg agcccgtttt acaacgagtg tgcggcttgg    1800
aaggactact atggtggggg ccaggctttt cagcagtccg attcgggctt gtaa          1854
```

<210> SEQ ID NO 102
<211> LENGTH: 617
<212> TYPE: PRT
<213> ORGANISM: M. phaseolina

<400> SEQUENCE: 102

```
Met Pro Phe Ser Pro Arg Leu Ser Ile Cys Leu Leu Ala Phe Cys Ser
1               5                   10                  15

His Ile Val Phe Ala Leu Ser Ile Pro Asn Val Lys Asp Arg Thr Pro
            20                  25                  30

His Leu Ser Pro Arg Asn Tyr Gly Phe Arg Phe Gly Asn Leu Ser Trp
        35                  40                  45

Gly Gly Ala Glu Pro Ser Asp Pro Leu Ala Gln Gly Ala Glu Arg Leu
    50                  55                  60

Asp Asp Ile Ser Leu Pro Ala Pro Glu Asp Gly Cys Leu Phe Ser Lys
65                  70                  75                  80

Asp Ala Arg Asn Cys Trp Arg Asp Asn Phe Asn Ile Asp Thr Asp Phe
                85                  90                  95

Asp Glu Arg Phe Pro Thr Thr Gly Lys Thr Val Thr Tyr Asn Leu Glu
            100                 105                 110

Ile Thr Asn Thr Thr Met Ala Pro Asp Gly Ile Glu Arg Val Val Met
        115                 120                 125

Ala Val Asn Gly Gln Tyr Pro Gly Pro Thr Leu Ile Ala Asp Trp Gly
    130                 135                 140

Asp Thr Met Val Ile Asn Val Lys Asn Ser Leu Asp His Asn Gly Thr
145                 150                 155                 160

Gly Leu His Phe His Gly Leu Arg Gln Tyr Lys Ser Asn Gly Ala Asp
                165                 170                 175

Gly Ala Asn Gly Ile Thr Glu Cys Pro Ile Ala Pro Gly Glu Thr Lys
            180                 185                 190

Thr Tyr Thr Phe Gln Cys Thr Gln His Gly Ser Ser Trp Tyr His Ser
        195                 200                 205

His Tyr Ser Val Gln Tyr Ser Asp Gly Val Leu Gly Gly Ile Ile Ile
    210                 215                 220

Asn Gly Pro Ala Asp Ala His Tyr Asp His Asp Leu Gly Val Tyr Met
225                 230                 235                 240

Leu Ser Asp Trp Tyr His Thr Pro Met Phe Glu Leu Ala Glu Ala Ala
                245                 250                 255

Arg His Ser Thr Arg Gly Pro Pro Lys Ala Asp Asn Gly Leu Ile Asn
            260                 265                 270

Gly Thr Met Lys Ser Pro Asp Gly Ser Leu Gly Ala Tyr Gly Gln Ile
        275                 280                 285

His Val Lys Lys Gly Leu Arg Tyr Arg Ile Arg Val Met Asn Val Gly
    290                 295                 300

Thr Asn Asp His Tyr Leu Phe Ser Val Asp Gly His Asn Leu Thr Val
```

```
            305                 310                 315                 320
Ile Ala Ser Asp Phe Val Pro Val Pro Phe Ser Ala Ser Ser Ile
                325                 330                 335

Ser Leu Gly Val Gly Gln Arg Tyr Asp Val Ile Leu Ile Ala Asp Gln
                340                 345                 350

Asp Ile Asp Asn Tyr Trp Ile Arg Ser Asp Pro Asp Ser Ala Cys Ser
                355                 360                 365

Val Asn Gly Asn Ala Gly Asn Ile Lys Ala Ile Leu Ser Tyr Asp Thr
            370                 375                 380

Ala Pro Ala Asp Ala Gln Pro Asn Ser Thr Arg His Ser Ile Ser Ser
385                 390                 395                 400

Gly Cys Lys Asp Met Ala Val Val Pro Arg Val Ala Asn Thr Val Pro
                405                 410                 415

Ser Asp Arg Phe Ala Asp Ala Val Gln Ser Leu Ala Met Ser Val Asn
                420                 425                 430

Ile Thr Gln Gln Asn Gly Pro Leu Val Gln Trp Tyr Ile Asn Gly Ser
                435                 440                 445

Ala Met Glu Val Asp Trp Ser Tyr Pro Thr Val Gln Tyr Val Leu Asp
            450                 455                 460

Gly Asn Thr Ser Tyr Pro Arg Glu Leu Asn Leu Val Gln Leu Asp Glu
465                 470                 475                 480

Ala Asp Gln Trp Tyr Tyr Phe Val Ile Gln Thr Val Gln Gly Leu Arg
                485                 490                 495

Val Asn Leu Pro His Pro Ile His Leu His Gly His Asp Phe Tyr Ile
                500                 505                 510

Leu Gly Ala Gly Pro Gly Glu Trp Asp Gly Asn Ile Asp Gly Leu Gln
                515                 520                 525

Phe Asp Asn Pro Pro Arg Arg Asp Thr Ala Met Leu Pro Ala Gly Gly
                530                 535                 540

Tyr Leu Ile Leu Ala Phe Pro Ala Asp Asn Pro Gly Ala Trp Leu Met
545                 550                 555                 560

His Cys His Ile Pro Phe His Val Gln Gln Gly Phe Gly Leu Gln Phe
                565                 570                 575

Leu Glu Arg Pro Asp Glu Ile Glu Gly Val Met Gly Asp Thr Ser Pro
                580                 585                 590

Phe Tyr Asn Glu Cys Ala Ala Trp Lys Asp Tyr Tyr Gly Gly Gly Gln
                595                 600                 605

Ala Phe Gln Gln Ser Asp Ser Gly Leu
    610                 615

<210> SEQ ID NO 103
<211> LENGTH: 2415
<212> TYPE: DNA
<213> ORGANISM: M. phaseolina

<400> SEQUENCE: 103
tcgagcaaga tgaatgtatc ctccgtggaa agtctttttt ctcagggcgg ccgtccgctt      60
tgacctctgc cctcttgctg gattatagaa tacccagacg cccatgtagt gcatggcctt     120
gtgaacttac ccaccacctc tctcgcgaag atgattggcc attctctcgt agctgtagca     180
ctcggcagcg cagccatggc actggctctt cctcagagcc acgtccccgc tgcttgcatg     240
aacggtccgc actctcggaa gtgctggggc aactactcca tcgacacgga ctggtacacc     300
gaaactccat acacgggcgt ggtgagagaa tactggttcc tggtcgagaa taccaccgta     360
```

-continued

```
gcaccagatg tacacgcccc tctgggttgc gccattggca acgcatggca ggctgacttg    420
gggtggcagg gatatgagac atgggctctc acggtaaacc gctcgattcc tggaccaaca    480
atcgaggcca actggggcga cgaaggtaaa gttgtttcga ctgggattcg ccggccgata    540
atgcttactg ctacgcagta atcgttcatg tcaccaatgg catggagcgg aatggtaccg    600
caatccattt ccacggccta aggcagctgg gagcccacga aatggatggt gtccctgggg    660
ttacgcagtg tcctatagta cgcccgtacc ctctctctct cgcactgctg cgcgcaagct    720
attgatactt ctcaggctcc cggacactcc tacacataca agtggcgagc tactcaatac    780
ggaacggtga atccccctc gaggcagaat cggccatact ttaactgacg ggtctgaaag     840
agctggtatc attcccactt cagcatgcaa tactcggtcg gtctacaggg cccgatcgtc    900
attcacggac ctgctacggc agactatgac gaggacctgg aacggtcgt cttgcaggac     960
tggagtcaca cctctccgtt cgccatgtgg tggtacgcac gtgtgccttc cggaccgccc   1020
tcgctctcaa actcgctcat caacggcaaa acgtcttct attgcgacag tacgaccgat    1080
tcgagatgct acgtaacgg cacacggtcg gagtggcgct tgagcaggg gaaaaagtat     1140
cgaatgaggc tcatcaatac aggcctctac tcaaacttcc gttttgccat tgacaaccac   1200
aacctcaccg ttattgcgac cgactttgtt cctatcaaac cctacaccac agataacgtg   1260
agtcaccaac cccttgcttt cgtgcactct aacgagacat ttctcccagg tggcaatttc   1320
aatgggcaa cgctacgaca tcgtcgttga ggcaaatcaa ccggaaggtg attactggct    1380
gcggtaaggc tctaatgaat tgatcagaca ttgaaaaaaa aggggggcgg ggggaacccc   1440
atcaactgac attcaaccct acctagggct atatggcaaa catcctgctg cccgaacgac   1500
tactcaaaca atacccttgg cataatccgc tacacagcaa actccactgc gaaccaaac    1560
acaacaagtc ctgcactatc ctacccggac acatgcggcg acgagccggc agcgagcctc   1620
gtgccgcacc tggccctcaa cgcgagcacg ccggccgtcg tgcgcaccta cgacctgtcc   1680
aaagtcacac tcgagctgcc aaagggcttc tctggacac tgaacgacac ctacctctgg    1740
atcaactggt cgtcgccaac gaacttgagg ctggccgagg gcggcgccgc cgctgcggcg   1800
agcctgcccg ccgaatatct cgccgtcgac agccgggccg gcaacgaggg acgctgggcg   1860
tatctcgtgt tcaacgacgt ctcccgcccgc aatcgctcgc acccgatgca cctgcacggc   1920
cacgacttct tcctgctcgg caccggcct ggctattttg agtacggcag caacagcagc    1980
agcctggcga tgctcaacct gcacaacccg cctcgtcgcg acacggcgac ctggcccgag   2040
tctggctgga tggtcgtcgc gttcctcatg acaacccgg ggagctggct gatccactgc    2100
cacatcgcct ggcactcgag cgagtcgctc ggcctgcagt tcctggagag ccctgagacg   2160
tatgtccctc gattggaagg ccagagattg cgggagacgt gcgaggcgtg ggatgcattc   2220
tggaatcgcc acgactcata cgagcaagag gatgcgggga tataagggcc gcgaggactg   2280
catgaacgca tgctttggtc ctgcatggag gcttcgtgaa ttggcgggaa agatgtgact   2340
aacttcttcc tcgcatgttc ttggctctct ccttctctac actctctaaa taatccgcaa   2400
atttccatgt gcgta                                                    2415
```

<210> SEQ ID NO 104
<211> LENGTH: 1815
<212> TYPE: DNA
<213> ORGANISM: M. phaseolina

<400> SEQUENCE: 104

```
atgattggcc attctctcgt agctgtagca ctcggcagcg cagccatggc actggctctt    60
```

-continued

```
cctcagagcc acgtccccgc tgcttgcatg aacggtccgc actctcggaa gtgctggggc       120
aactactcca tcgacacgga ctggtacacc gaaactccat acacgggcgt ggtgagagaa       180
tactggttcc tggtcgagaa taccaccgta gcaccagatg tacacgcccc tctgggttgc       240
gccattggca acgcatggca ggctgacttg gggtggcagg gatatgagac atgggctctc       300
acggtaaacc gctcgattcc tggaccaaca atcgaggcca actggggcga cgaagtaatc       360
gttcatgtca ccaatggcat ggagcggaat ggtaccgcaa tccatttcca cggcctaagg       420
cagctgggag cccacgaaat ggatggtgtc cctggggtta cgcagtgtcc tatagctccc       480
ggacactcct acacatacaa gtggcgagct actcaatacg gaacgagctg gtatcattcc       540
cacttcagca tgcaatactc ggtcggtcta cagggcccga tcgtcattca cggacctgct       600
acggcagact atgacgagga cctgggaacg gtcgtcttgc aggactggag tcacacctct       660
ccgttcgcca tgtggtggta cgcacgtgtg ccttccggac cgccctcgct ctcaaactcg       720
ctcatcaacg gcaaaaacgt cttctattgc gacagtacga ccgattcgag atgctacggt       780
aacggcacac ggtcggagtg gcgctttgag caggggaaaa gtatcgaat gaggctcatc       840 aatacaggcc tctactcaaa cttccgtttt gccattgaca accacaacct caccgttatt       900
gcgaccgact ttgttcctat caaaccctac accacagata acgtggcaat ttcaatgggg       960
caacgctacg acatcgtcgt tgaggcaaat caaccggaag gtgattactg gctgcgggct      1020
atatggcaaa catcctgctg cccgaacgac tactcaaaca ataccttgg cataatccgc      1080 tacacagcaa actccactgc cgaaccaaac acaacaagtc ctgcactatc ctacccggac      1140
acatgcggcg acgagccggc agcgagcctc gtgccgcacc tggccctcaa cgcgagcacg      1200
ccggccgtcg tgcgcaccta cgacctgtcc aaagtcacac tcgagctgcc aaagggcttc      1260
ctctggacac tgaacgacac ctacctctgg atcaactggt cgtcgccaac gaacttgagg      1320
ctggccgagg gcggcgccgc cgctgcggcg agcctgcccg ccgaatatct cgccgtcgac      1380
agccgggccg gcaacgaggg acgctgggcg tatctcgtgt caacgacgt ctccgcccgc      1440 aatcgctcgc acccgatgca cctgcacggc acgacttct tcctgctcgg caccggccct      1500
ggctattttg agtacggcag caacagcagc agcctggcga tgctcaacct gcacaacccg      1560
cctcgtcgcg acacgcgac ctggcccgag tctggctgga tggtcgtcgc gttcctcatg      1620
gacaacccgg ggagctggct gatccactgc cacatcgcct ggcactcgag cgagtcgctc      1680
ggcctgcagt tcctggagag ccctgagacg tatgtccctc gattggaagg ccagagattg      1740
cgggagacgt gcgaggcgtg ggatgcattc tggaatcgcc acgactcata cgagcaagag      1800
gatgcgggga tataa                                                      1815
```

<210> SEQ ID NO 105
<211> LENGTH: 604
<212> TYPE: PRT
<213> ORGANISM: M. phaseolina

<400> SEQUENCE: 105

```
Met Ile Gly His Ser Leu Val Ala Val Ala Leu Gly Ser Ala Ala Met
1               5                   10                  15

Ala Leu Ala Leu Pro Gln Ser His Val Pro Ala Ala Cys Met Asn Gly
            20                  25                  30

Pro His Ser Arg Lys Cys Trp Gly Asn Tyr Ser Ile Asp Thr Asp Trp
        35                  40                  45

Tyr Thr Glu Thr Pro Tyr Thr Gly Val Val Arg Glu Tyr Trp Phe Leu
```

-continued

```
            50                  55                  60
Val Glu Asn Thr Thr Val Ala Pro Asp Val His Ala Pro Leu Gly Cys
 65                  70                  75                  80

Ala Ile Gly Asn Ala Trp Gln Ala Asp Leu Gly Trp Gln Gly Tyr Glu
                 85                  90                  95

Thr Trp Ala Leu Thr Val Asn Arg Ser Ile Pro Gly Pro Thr Ile Glu
                100                 105                 110

Ala Asn Trp Gly Asp Glu Val Ile Val His Val Thr Asn Gly Met Glu
                115                 120                 125

Arg Asn Gly Thr Ala Ile His Phe His Gly Leu Arg Gln Leu Gly Ala
                130                 135                 140

His Glu Met Asp Gly Val Pro Gly Val Thr Gln Cys Pro Ile Ala Pro
145                 150                 155                 160

Gly His Ser Tyr Thr Tyr Lys Trp Arg Ala Thr Gln Tyr Gly Thr Ser
                165                 170                 175

Trp Tyr His Ser His Phe Ser Met Gln Tyr Ser Val Gly Leu Gln Gly
                180                 185                 190

Pro Ile Val Ile His Gly Pro Ala Thr Ala Asp Tyr Asp Glu Asp Leu
                195                 200                 205

Gly Thr Val Val Leu Gln Asp Trp Ser His Thr Ser Pro Phe Ala Met
210                 215                 220

Trp Trp Tyr Ala Arg Val Pro Ser Gly Pro Pro Ser Leu Ser Asn Ser
225                 230                 235                 240

Leu Ile Asn Gly Lys Asn Val Phe Tyr Cys Asp Ser Thr Thr Asp Ser
                245                 250                 255

Arg Cys Tyr Gly Asn Gly Thr Arg Ser Glu Trp Arg Phe Glu Gln Gly
                260                 265                 270

Lys Lys Tyr Arg Met Arg Leu Ile Asn Thr Gly Leu Tyr Ser Asn Phe
                275                 280                 285

Arg Phe Ala Ile Asp Asn His Asn Leu Thr Val Ile Ala Thr Asp Phe
                290                 295                 300

Val Pro Ile Lys Pro Tyr Thr Thr Asp Asn Val Ala Ile Ser Met Gly
305                 310                 315                 320

Gln Arg Tyr Asp Ile Val Glu Ala Asn Gln Pro Glu Gly Asp Tyr
                325                 330                 335

Trp Leu Arg Ala Ile Trp Gln Thr Ser Cys Cys Pro Asn Asp Tyr Ser
                340                 345                 350

Asn Asn Thr Leu Gly Ile Ile Arg Tyr Thr Ala Asn Ser Thr Ala Glu
                355                 360                 365

Pro Asn Thr Thr Ser Pro Ala Leu Ser Tyr Pro Asp Thr Cys Gly Asp
370                 375                 380

Glu Pro Ala Ala Ser Leu Val Pro His Leu Ala Leu Asn Ala Ser Thr
385                 390                 395                 400

Pro Ala Val Val Arg Thr Tyr Asp Leu Ser Lys Val Thr Leu Glu Leu
                405                 410                 415

Pro Lys Gly Phe Leu Trp Thr Leu Asn Asp Thr Tyr Leu Trp Ile Asn
                420                 425                 430

Trp Ser Pro Thr Asn Leu Arg Leu Ala Glu Gly Gly Ala Ala Ala
                435                 440                 445

Ala Ala Ser Leu Pro Ala Glu Tyr Leu Ala Val Asp Ser Arg Ala Gly
                450                 455                 460

Asn Glu Gly Arg Trp Ala Tyr Leu Val Phe Asn Asp Val Ser Ala Arg
465                 470                 475                 480
```

```
Asn Arg Ser His Pro Met His Leu His Gly His Asp Phe Phe Leu Leu
            485                 490                 495
Gly Thr Gly Pro Gly Tyr Phe Glu Tyr Gly Ser Asn Ser Ser Ser Leu
            500                 505                 510
Ala Met Leu Asn Leu His Asn Pro Pro Arg Arg Asp Thr Ala Thr Trp
            515                 520                 525
Pro Glu Ser Gly Trp Met Val Val Ala Phe Leu Met Asp Asn Pro Gly
            530                 535                 540
Ser Trp Leu Ile His Cys His Ile Ala Trp His Ser Ser Glu Ser Leu
545                 550                 555                 560
Gly Leu Gln Phe Leu Glu Ser Pro Glu Thr Tyr Val Pro Arg Leu Glu
            565                 570                 575
Gly Gln Arg Leu Arg Glu Thr Cys Glu Ala Trp Asp Ala Phe Trp Asn
            580                 585                 590
Arg His Asp Ser Tyr Glu Gln Glu Asp Ala Gly Ile
            595                 600
```

<210> SEQ ID NO 106
<211> LENGTH: 2275
<212> TYPE: DNA
<213> ORGANISM: M. phaseolina

<400> SEQUENCE: 106

```
tcgatgcatc cctctctgac gcagatctct tttataaaac cgactgtcat cctcgattga     60
gtcagtcttt gctcaaacgg acttattcaa aggtcagttg ggtgagttgg gaggctgatg    120
gattcaggat actctccggg cacgttcgcc atgattcgcc tttttctcgt gctcggcttt    180
gtggccacga cattggccaa gactgttact tttaactgga acatcggctg gtttctgcg     240
gctccagatg gatttacacg gcccgtcatc ggcatcaacg ggctgtggcc gcctcccgtc    300
ttagaagccg acgttaacga caccattatc gtaaccgcgc ataactcgct aggcaatgag    360
acgacgagct tgcactggca tggcatgtgg cagaacaact cgactcatat agacggcgga    420
agtagagtct cgcagtgcga aatccctcta gggggcaccct ttacgtacag gtttaaggca    480
tacccggcag gcactttttg gtaccattct cacgctatgg ccaatatcc cgacggccta    540
cgggccccga tgattattca cgaccctgat tctgctgcgg agcaggacgc cgatgagcag    600
catatactta cggtctcgga ctggtaccgt aaccagatgc cgccgcttat ccaccgctat    660
ctaactactc ctaactataa cggcgccatg ccgaaaccca actcgagctt agttaacgac    720
cagcagtcca agaggctaaa catccgcccg gggcagaaga gctatatccg cattattaat    780
atatcagcgc tagcaacgtt ctatctacag ttcggtaggt acatcccct tgttgtacag    840
acaaagctaa cgatttagat caacacaaca tgactgtcgt ttctatcgac gatgttaacg    900
gttggtaatc ctgttactta tgctacgcta agatgcatgt cggcatataa gccgtagtcg    960
tatgcaaaca cgtaagatta aagtgctaac gacaggtagt cgagcccag agttgggagg   1020
ccctagagat taccccccgga caacggtacg acgttatcat caccggtcta gagaacccc   1080
aaagaaacta tgcatttatc aataagatgg ccgttctcgg cttgcagaac aacaacatcc   1140
tcagttataa ttcgtcctgg cctgacccag agccattggc cgtgagtagg ttcaacctcg   1200
gaagcgatat caatctaact ccgcttgacc acgagccact gctggagccc gtggacaaaa   1260
ccttcaccat ggaggtcaac aacctcaaca tcgacgcgt aggctaccgg tgagattgcc   1320
ccgcggccct taatccgcat gccgcttgct aacttcgata cacagcatca cgcaaggccc   1380
```

```
gtacccctac attaccccgc gcacacccac tctgtacact gccctaacca ccggctttaa    1440
tgctaccaac cccgccatct acggccagac caactcttac atcgtagaag ccggcgatat    1500
cgtccagctc gttgtcaaca gcaacgacct tgtcacaact aacacctccg ccgcgggca    1560 ccccatgcac ttgcacggcc acaccttcca agtcgtgggc caatacggca cccactggga    1620
cggcgacacc gcaaaattcc ctaccgttcc aatgaagcgg gacacgaccg ttctcttcgc    1680
cggcgggagc ttggtcattc ggttccaggc gaacaatcct ggtgtctgga tgtgtacggc    1740
tctcctccac tttgcacgaa acccccagtc ccccggctgc ttgaaaagct tttttgaactg    1800 accttgtgag tcgcgcagtc cactgccata tcgaatggca tctcgacgcc ggcatggccg    1860
ccacaatcat cgaagcgccg ctcgagttcc agcgaagcgg tctgcggatc ccgccacagc    1920
acctcgcggc gtgccgggca ttaaacttaa cgacccgggg caattgtgcc ggcaacaccg    1980
ttaacctgga ggatacggct gcgtgcagaa tctacgacac tgatccttgg gggtgagttg    2040
ctctgatttc gcgttaacgc agcctttgct gacgactacc gctttctgca gtgcgcttat    2100
cggggaacgt gagacagcac gttgaataac acgctggcgt agcaccgtat tttgtataga    2160
ctacttttcc atgttaaatt tttctgtata cagttcgaaa tagattcatt tagggacaaa    2220
taccagaaac aggctcatcc gcaactcatg tgcaccctgc gtagatcgtt atgct         2275

<210> SEQ ID NO 107
<211> LENGTH: 1632
<212> TYPE: DNA
<213> ORGANISM: M. phaseolina

<400> SEQUENCE: 107
atgattcgcc ttttctcgt gctcggcttt gtggccacga cattggccaa gactgttact       60
tttaactgga acatcggctg ggtttctgcg gctccagatg gatttacacg gcccgtcatc     120
ggcatcaacg ggctgtggcc gcctcccgtc ttagaagccg acgttaacga caccattatc     180
gtaaccgcgc ataactcgct aggcaatgag acgacgagct tgcactggca tggcatgtgg     240
cagaacaact cgactcatat agacggcgga agtagagtct cgcagtgcga aatccctcta     300 gggggcaccct ttacgtacag gtttaaggca taccgggcag gcacttttg gtaccattct    360 cacgctatgg gccaatatcc cgacggccta cgggccccga tgattattca cgaccctgat     420
tctgctgcgg agcaggacgc cgatgagcag catatactta cggtctcgga ctggtaccgt     480
aaccagatgc cgccgcttat ccaccgctat ctaactactc ctaactataa cggcgccatg     540
ccgaaaccca actcgagctt agttaacgac cagcagtcca agaggctaaa catccgcccg     600
gggcagaaga gctatatccg cattattaat atatcagcgc tagcaacgtt ctatctacag     660
ttcgatcaac acaacatgac tgtcgtttct atcgacgatg ttaacgtcga gcccagagt      720 tgggaggccc tagagattac ccccggacaa cggtacgacg ttatcatcac cggtctagag     780 aaccccaaa gaactatgc atttatcaat aagatggccg ttctcggctt gcagaacaac      840
aacatcctca gttataattc gtcctggcct gacccagagc cattggccgt gagtaggttc     900
aacctcggaa gcgatatcaa tctaactccg cttgaccacg agccactgct ggagcccgtg    960
gacaaaacct tcaccatgga ggtcaacaac ctcaacatcg acggcgtagg ctaccgcatc    1020
acgcaaggcc cgtaccccta cattaccccg cgcacaccca ctctgtacac tgccctaacc   1080
accggcttta atgctaccaa cccgccatct tacggccaga ccaactctta catcgtagaa   1140
gccggcgata tcgtccagct cgttgtcaac agcaacgacc ttgtcacaac taacacctcc   1200
ggccgcgggc accccatgca cttgcacggc cacaccttcc aagtcgtggg ccaatacggc   1260
```

```
acccactggg acggcgacac cgcaaaattc cctaccgttc caatgaagcg ggacacgacc    1320
gttctcttcg ccggcgggag cttggtcatt cggttccagg cgaacaatcc tggtgtctgg    1380
atgttccact gccatatcga atggcatctc gacgccggca tggccgccac aatcatcgaa    1440
gcgccgctcg agttccagcg aagcggtctg cggatcccgc cacagcacct cgcggcgtgc    1500
cgggcattaa acttaacgac ccggggcaat tgtgccggca acaccgttaa cctggaggat    1560
acggctgcgt gcagaatcta cgacactgat ccttggggtg cgcttatcgg ggaacgtgag    1620
acagcacgtt ga                                                        1632
```

<210> SEQ ID NO 108
<211> LENGTH: 543
<212> TYPE: PRT
<213> ORGANISM: M. phaseolina

<400> SEQUENCE: 108

```
Met Ile Arg Leu Phe Leu Val Leu Gly Phe Val Ala Thr Thr Leu Ala
1               5                   10                  15

Lys Thr Val Thr Phe Asn Trp Asn Ile Gly Trp Val Ser Ala Ala Pro
            20                  25                  30

Asp Gly Phe Thr Arg Pro Val Ile Gly Ile Asn Gly Leu Trp Pro Pro
        35                  40                  45

Pro Val Leu Glu Ala Asp Val Asn Asp Thr Ile Ile Val Thr Ala His
    50                  55                  60

Asn Ser Leu Gly Asn Glu Thr Thr Ser Leu His Trp His Gly Met Trp
65                  70                  75                  80

Gln Asn Asn Ser Thr His Ile Asp Gly Gly Ser Arg Val Ser Gln Cys
                85                  90                  95

Glu Ile Pro Leu Gly Gly Thr Phe Thr Tyr Arg Phe Lys Ala Tyr Pro
            100                 105                 110

Ala Gly Thr Phe Trp Tyr His Ser His Ala Met Gly Gln Tyr Pro Asp
        115                 120                 125

Gly Leu Arg Ala Pro Met Ile Ile His Asp Pro Asp Ser Ala Ala Glu
    130                 135                 140

Gln Asp Ala Asp Glu Gln His Ile Leu Thr Val Ser Asp Trp Tyr Arg
145                 150                 155                 160

Asn Gln Met Pro Pro Leu Ile His Arg Tyr Leu Thr Thr Pro Asn Tyr
                165                 170                 175

Asn Gly Ala Met Pro Lys Pro Asn Ser Ser Leu Val Asn Asp Gln Gln
            180                 185                 190

Ser Lys Arg Leu Asn Ile Arg Pro Gly Gln Lys Ser Tyr Ile Arg Ile
        195                 200                 205

Ile Asn Ile Ser Ala Leu Ala Thr Phe Tyr Leu Gln Phe Asp Gln His
    210                 215                 220

Asn Met Thr Val Val Ser Ile Asp Asp Val Asn Val Glu Pro Gln Ser
225                 230                 235                 240

Trp Glu Ala Leu Glu Ile Thr Pro Gly Gln Arg Tyr Asp Val Ile Ile
                245                 250                 255

Thr Gly Leu Glu Asn Pro Gln Arg Asn Tyr Ala Phe Ile Asn Lys Met
            260                 265                 270

Ala Val Leu Gly Leu Gln Asn Asn Ile Leu Ser Tyr Asn Ser Ser
        275                 280                 285

Trp Pro Asp Pro Glu Pro Leu Ala Val Ser Arg Phe Asn Leu Gly Ser
    290                 295                 300
```

Asp Ile Asn Leu Thr Pro Leu Asp His Glu Pro Leu Leu Glu Pro Val
305                 310                 315                 320

Asp Lys Thr Phe Thr Met Glu Val Asn Asn Leu Asn Ile Asp Gly Val
            325                 330                 335

Gly Tyr Arg Ile Thr Gln Gly Pro Tyr Pro Tyr Ile Thr Pro Arg Thr
        340                 345                 350

Pro Thr Leu Tyr Thr Ala Leu Thr Thr Gly Phe Asn Ala Thr Asn Pro
    355                 360                 365

Ala Ile Tyr Gly Gln Thr Asn Ser Tyr Ile Val Glu Ala Gly Asp Ile
370                 375                 380

Val Gln Leu Val Val Asn Ser Asn Asp Leu Val Thr Thr Asn Thr Ser
385                 390                 395                 400

Gly Arg Gly His Pro Met His Leu His Gly His Thr Phe Gln Val Val
            405                 410                 415

Gly Gln Tyr Gly Thr His Trp Asp Gly Asp Thr Ala Lys Phe Pro Thr
        420                 425                 430

Val Pro Met Lys Arg Asp Thr Thr Val Leu Phe Ala Gly Gly Ser Leu
    435                 440                 445

Val Ile Arg Phe Gln Ala Asn Asn Pro Gly Val Trp Met Phe His Cys
450                 455                 460

His Ile Glu Trp His Leu Asp Ala Gly Met Ala Ala Thr Ile Ile Glu
465                 470                 475                 480

Ala Pro Leu Glu Phe Gln Arg Ser Gly Leu Arg Ile Pro Pro Gln His
            485                 490                 495

Leu Ala Ala Cys Arg Ala Leu Asn Leu Thr Thr Arg Gly Asn Cys Ala
        500                 505                 510

Gly Asn Thr Val Asn Leu Glu Asp Thr Ala Ala Cys Arg Ile Tyr Asp
    515                 520                 525

Thr Asp Pro Trp Gly Ala Leu Ile Gly Glu Arg Glu Thr Ala Arg
    530                 535                 540

<210> SEQ ID NO 109
<211> LENGTH: 2052
<212> TYPE: DNA
<213> ORGANISM: M. phaseolina

<400> SEQUENCE: 109
gcagcaacta catccgggta ggcatcaaac gcaaagatgg tacggaggga gcactgatgc    60
gcttttatag ctcatatcag cacagctgcg tgtagttgaa tgggaccgac cgagtttttt   120
tgtagcctca atctttccac gctccgaacc atgtcctcag attctcagaa gcatggcgct   180
gtgctccgta ggcgcagcat accacagcaa ccagaagaag aaaccccgcc ttcaacaacc   240
cggaagtcat cggaaaatcg acatagcgtt ctatcatggt ttctctttgt cctttcatgc   300
gccatcttcg cgacgtttat ttcctatctc aatagcgcaa cggcatacca aactgcgggg   360
tcttattaca caataactgg cctcaaggct tttctgtccc atgggaactc tgacaacaat   420
ttcgacagtc atcctggcaa gggcccatac ggcggatctc tgggccagaa cttgcatcct   480
cgagagcacg tggtccgtgc tcctagtgtc aggcactaca gttggaaggt taccaaggct   540
tttcgatacc cagatggggt gaaaaaggct gtttatctga ttaacgacgg ctttctggga   600
cccacagtcg aagctcgttc tggcgataga ctggtgattg aggtccaaaa tgcgttggaa   660
gacgaaggtc tctccttcca ctggcacggt ctttttaatga gaggtgccaa ctacatggac   720
ggtgccgtcg gatttacgca agacgccatt cacccgggcg ccaacttcac gtatgagttc   780

```
gatatcgcgg atgaccaagc cggcacattt tggtatcacg ctcatgacca agtgcagcgg      840
gcggatggcc tgttcggagg actgatcatc catcgcccgg aaaccgcaac tggagtcgcc      900
gatttggata gatatgggta cgatgaagag agattgctgc ttatcggaca ctggtaccat      960
cgttccgcac aagatgtcct agcgtggtac atcagtgctg ggtcctttgg aaatgagcct     1020
gtgccggatt cactcctcat caatggaatg ggagcattca attgctcaaa agctattcct     1080
gcgagacctg tggaatgcat taactttgaa ggaactgcca cacctaatct acagttcaac     1140
ttcaccagac gtcaccggct gagactcgtc aacactggta cattggctgg attcaccttg     1200
agcattccgg gtgcggccat gcaggtcatc gaagttgacg gcggcaatgc cgttaccagc     1260
gactctgaga acgacacttc agtagggagc ttatatccag ccaacgtgc cgacctaatc      1320 ctctcttggc cagaggatac tctagaagcc tcaaaaattt caatcaccct tgacggggag     1380
gacttcaagt accccaatcc agccctgact cgcactcagc acttctccat atttcgctct     1440
gcccctgtcc cgaaggaaaa gagcgaagcc tctgcctctt cggaacaagg caggccagaa     1500
agccacgcac cacaaaccct catcgacctc aatgcccttg tcagcgcaga tatcatcacc     1560
ccatcactgc cccctgccac tgaacacact ctcgttctat acgccaacac cctcaaactc     1620
tcccaccgcg gcaacaaacc ccacggctac atgaaccaaa ccagctggtc gccgcaatcc     1680
tctccgcccc gtccgctcat cgcgctgccg cgctcctctt gggacgccaa ccagttcgtc     1740
ccgcgcatcc ctcttcccaa cggcacctca gacgcgccct gggtcaccat cgtcctcaac     1800
aacctggacg acggctcgca ccccttccac ctacatggcc acgcgttctg ggtgctccaa     1860
acccacgccg cagggtgggg ctggggtcg tggaatccat gagcggagga gcagccgccg     1920
ggcggcccac tggagctgca gcgcgcggtg acgagggata cggtcatggt gccgcggagg     1980
gggtatgcgg tgctgcgatt tagagcggac aatgaggggc tctggatgct gcactgccac     2040
aatttgtggc at                                                          2052
```

<210> SEQ ID NO 110
<211> LENGTH: 1752
<212> TYPE: DNA
<213> ORGANISM: M. phaseolina

<400> SEQUENCE: 110

```
atgtcctcag attctcagaa gcatggcgct gtgctccgta ggcgcagcat accacagcaa       60
ccagaagaag aaaccccgcc ttcaacaacc cggaagtcat cggaaaatcg acatagcgtt      120
ctatcatggt ttctctttgt cctttcatgc gccatcttcg cgacgtttat ttcctatctc      180
aatagcgcaa cggcatacca aactgcgggg tcttattaca caataactgg cctcaaggct      240
tttctgtccc atgggaactc tgacaacaat ttcgacagtc atcctggcaa gggcccatac      300
ggcggatctc tgggccagaa cttgcatcct cgagagcacg tggtccgtgc tcctagtgtc      360
aggcactaca gttggaaggt taccaaggct tttcgatacc cagatgggt gaaaaaggct       420 gtttatctga ttaacgacgg ctttctggga cccacagtcg aagctcgttc tggcgataga      480
ctggtgattg aggtccaaaa tgcgttggaa gacgaaggtc tctccttcca ctggcacggt      540
cttttaatga gaggtgccaa ctacatggac ggtgccgtcg gatttacgca agacgccatt      600
cacccgggcg ccaacttcac gtatgagttc gatatcgcgg atgaccaagc cggcacattt      660
tggtatcacg ctcatgacca agtgcagcgg gcggatggcc tgttcggagg actgatcatc      720
catcgcccgg aaaccgcaac tggagtcgcc gatttggata gatatgggta cgatgaagag      780
```

```
agattgctgc ttatcggaca ctggtaccat cgttccgcac aagatgtcct agcgtggtac    840
atcagtgctg ggtcctttgg aaatgagcct gtgccggatt cactcctcat caatggaatg    900
ggagcattca attgctcaaa agctattcct gcgagacctg tggaatgcat taactttgaa    960
ggaactgcca cacctaatct acagttcaac ttcaccagac gtcaccggct gagactcgtc   1020
aacactggta cattggctgg attcaccttg agcattccgg gtgcggccat gcaggtcatc   1080
gaagttgacg gcggcaatgc cgttaccagc gactctgaga cgacacttc agtagggagc    1140 ttatatccag ccaacgtgc cgacctaatc ctctcttggc cagaggatac tctagaagcc    1200
tcaaaaattt caatcaccct tgacggggag gacttcaagt accccaatcc agccctgact   1260
cgcactcagc acttctccat atttcgctct gcccctgtcc gaaggaaaa gagcgaagcc    1320 tctgcctctt cggaacaagg caggccagaa agccacgcac cacaaaccct catcgacctc   1380 aatgccttg tcagcgcaga tatcatcacc ccatcactgc cccctgccac tgaacacact    1440
ctcgttctat acgccaacac cctcaaactc tcccaccgcg caacaaacc ccacggctac    1500 atgaaccaaa ccagctggtc gccgcaatcc tctccgcccc gtccgctcat cgcgctgccg   1560
cgctcctctt gggacgccaa ccagttcgtc ccgcgcatcc ctcttcccaa cggcacctca   1620
gacgcgccct gggtcaccat cgtcctcaac aacctggacg acggctcgca ccccttccac   1680
ctacatggcc acgcgttctg ggtgctccaa acccacgccg cagggtgggg ctggggtcg    1740 tggaatccat ga                                                       1752
```

<210> SEQ ID NO 111
<211> LENGTH: 583
<212> TYPE: PRT
<213> ORGANISM: M. phaseolina

<400> SEQUENCE: 111

Met Ser Ser Asp Ser Gln Lys His Gly Ala Val Leu Arg Arg Arg Ser
1               5                   10                  15

Ile Pro Gln Gln Pro Glu Glu Thr Pro Ser Thr Thr Arg Lys
            20                  25                  30

Ser Ser Glu Asn Arg His Ser Val Leu Ser Trp Phe Leu Phe Val Leu
        35                  40                  45

Ser Cys Ala Ile Phe Ala Thr Phe Ile Ser Tyr Leu Asn Ser Ala Thr
    50                  55                  60

Ala Tyr Gln Thr Ala Gly Ser Tyr Tyr Thr Ile Thr Gly Leu Lys Ala
65                  70                  75                  80

Phe Leu Ser His Gly Asn Ser Asp Asn Phe Asp Ser His Pro Gly
                85                  90                  95

Lys Gly Pro Tyr Gly Gly Ser Leu Gly Gln Asn Leu His Pro Arg Glu
            100                 105                 110

His Val Val Arg Ala Pro Ser Val Arg His Tyr Ser Trp Lys Val Thr
        115                 120                 125

Lys Ala Phe Arg Tyr Pro Asp Gly Val Lys Lys Ala Val Tyr Leu Ile
    130                 135                 140

Asn Asp Gly Phe Leu Gly Pro Thr Val Glu Ala Arg Ser Gly Asp Arg
145                 150                 155                 160

Leu Val Ile Glu Val Gln Asn Ala Leu Glu Asp Gly Leu Ser Phe
                165                 170                 175

His Trp His Gly Leu Leu Met Arg Gly Ala Asn Tyr Met Asp Gly Ala
            180                 185                 190

Val Gly Phe Thr Gln Asp Ala Ile His Pro Gly Ala Asn Phe Thr Tyr

-continued

```
            195                 200                 205
Glu Phe Asp Ile Ala Asp Asp Gln Ala Gly Thr Phe Trp Tyr His Ala
210                 215                 220
His Asp Gln Val Gln Arg Ala Asp Gly Leu Phe Gly Gly Leu Ile Ile
225                 230                 235                 240
His Arg Pro Glu Thr Ala Thr Gly Val Ala Asp Leu Asp Arg Tyr Gly
                245                 250                 255
Tyr Asp Glu Glu Arg Leu Leu Leu Ile Gly His Trp Tyr His Arg Ser
                260                 265                 270
Ala Gln Asp Val Leu Ala Trp Tyr Ile Ser Ala Gly Ser Phe Gly Asn
                275                 280                 285
Glu Pro Val Pro Asp Ser Leu Leu Ile Asn Gly Met Gly Ala Phe Asn
                290                 295                 300
Cys Ser Lys Ala Ile Pro Ala Arg Pro Val Glu Cys Ile Asn Phe Glu
305                 310                 315                 320
Gly Thr Ala Thr Pro Asn Leu Gln Phe Asn Phe Thr Arg Arg His Arg
                325                 330                 335
Leu Arg Leu Val Asn Thr Gly Thr Leu Ala Gly Phe Thr Leu Ser Ile
                340                 345                 350
Pro Gly Ala Ala Met Gln Val Ile Glu Val Asp Gly Gly Asn Ala Val
                355                 360                 365
Thr Ser Asp Ser Glu Asn Asp Thr Ser Val Gly Ser Leu Tyr Pro Gly
370                 375                 380
Gln Arg Ala Asp Leu Ile Leu Ser Trp Pro Glu Asp Thr Leu Glu Ala
385                 390                 395                 400
Ser Lys Ile Ser Ile Thr Leu Asp Gly Glu Asp Phe Lys Tyr Pro Asn
                405                 410                 415
Pro Ala Leu Thr Arg Thr Gln His Phe Ser Ile Phe Arg Ser Ala Pro
                420                 425                 430
Val Pro Lys Glu Lys Ser Glu Ala Ser Ala Ser Ser Glu Gln Gly Arg
                435                 440                 445
Pro Glu Ser His Ala Pro Gln Thr Leu Ile Asp Leu Asn Ala Leu Val
                450                 455                 460
Ser Ala Asp Ile Ile Thr Pro Ser Leu Pro Pro Ala Thr Glu His Thr
465                 470                 475                 480
Leu Val Leu Tyr Ala Asn Thr Leu Lys Leu Ser His Arg Gly Asn Lys
                485                 490                 495
Pro His Gly Tyr Met Asn Gln Thr Ser Trp Ser Pro Gln Ser Ser Pro
                500                 505                 510
Pro Arg Pro Leu Ile Ala Leu Pro Arg Ser Ser Trp Asp Ala Asn Gln
                515                 520                 525
Phe Val Pro Arg Ile Pro Leu Pro Asn Gly Thr Ser Asp Ala Pro Trp
                530                 535                 540
Val Thr Ile Val Leu Asn Asn Leu Asp Asp Gly Ser His Pro Phe His
545                 550                 555                 560
Leu His Gly His Ala Phe Trp Val Leu Gln Thr His Ala Ala Gly Trp
                565                 570                 575
Gly Trp Gly Ser Trp Asn Pro
                580

<210> SEQ ID NO 112
<211> LENGTH: 21
<212> TYPE: DNA
<213> ORGANISM: Artificial Sequence
```

```
<220> FEATURE:
<223> OTHER INFORMATION: Synthetic primer

<400> SEQUENCE: 112
gagaccgcta cacccacccc t                                              21

<210> SEQ ID NO 113
<211> LENGTH: 20
<212> TYPE: DNA
<213> ORGANISM: Artificial Sequence
<220> FEATURE:
<223> OTHER INFORMATION: Synthetic primer

<400> SEQUENCE: 113
caccgcacta cgacctcgct                                                20

<210> SEQ ID NO 114
<211> LENGTH: 20
<212> TYPE: DNA
<213> ORGANISM: Artificial Sequence
<220> FEATURE:
<223> OTHER INFORMATION: Synthetic primer

<400> SEQUENCE: 114
gtcgtcgcgt ggctgctaga                                                20

<210> SEQ ID NO 115
<211> LENGTH: 21
<212> TYPE: DNA
<213> ORGANISM: Artificial Sequence
<220> FEATURE:
<223> OTHER INFORMATION: Synthetic primer

<400> SEQUENCE: 115
ccaggcatcg gggaacttcg g                                              21

<210> SEQ ID NO 116
<211> LENGTH: 21
<212> TYPE: DNA
<213> ORGANISM: Artificial Sequence
<220> FEATURE:
<223> OTHER INFORMATION: Synthetic primer

<400> SEQUENCE: 116
ggcggctctc tcgcagacgt a                                              21

<210> SEQ ID NO 117
<211> LENGTH: 20
<212> TYPE: DNA
<213> ORGANISM: Artificial Sequence
<220> FEATURE:
<223> OTHER INFORMATION: Synthetic primer

<400> SEQUENCE: 117
gccctgcccc aaccgattca                                                20

<210> SEQ ID NO 118
<211> LENGTH: 20
<212> TYPE: DNA
<213> ORGANISM: Artificial Sequence
<220> FEATURE:
<223> OTHER INFORMATION: Synthetic primer

<400> SEQUENCE: 118
tgctgcctcc gctctgtcgc                                                20
```

```
<210> SEQ ID NO 119
<211> LENGTH: 20
<212> TYPE: DNA
<213> ORGANISM: Artificial Sequence
<220> FEATURE:
<223> OTHER INFORMATION: Synthetic primer

<400> SEQUENCE: 119
cgcaccatgt cgcctctgcc                                                        20

<210> SEQ ID NO 120
<211> LENGTH: 21
<212> TYPE: DNA
<213> ORGANISM: Artificial Sequence
<220> FEATURE:
<223> OTHER INFORMATION: Synthetic primer

<400> SEQUENCE: 120
aaccgcttta cctgccagcc a                                                      21

<210> SEQ ID NO 121
<211> LENGTH: 22
<212> TYPE: DNA
<213> ORGANISM: Artificial Sequence
<220> FEATURE:
<223> OTHER INFORMATION: Synthetic primer

<400> SEQUENCE: 121
attggggtcg gtgctcagga gt                                                     22

<210> SEQ ID NO 122
<211> LENGTH: 22
<212> TYPE: DNA
<213> ORGANISM: Artificial Sequence
<220> FEATURE:
<223> OTHER INFORMATION: Synthetic primer

<400> SEQUENCE: 122
acggagcaca tgaacaccgt cc                                                     22

<210> SEQ ID NO 123
<211> LENGTH: 20
<212> TYPE: DNA
<213> ORGANISM: Artificial Sequence
<220> FEATURE:
<223> OTHER INFORMATION: Synthetic primer

<400> SEQUENCE: 123
cttcgcaccg cgagcagagg                                                        20

<210> SEQ ID NO 124
<211> LENGTH: 20
<212> TYPE: DNA
<213> ORGANISM: Artificial Sequence
<220> FEATURE:
<223> OTHER INFORMATION: Synthetic primer

<400> SEQUENCE: 124
tcccgcgagc ccttggtctg                                                        20

<210> SEQ ID NO 125
<211> LENGTH: 21
<212> TYPE: DNA
<213> ORGANISM: Artificial Sequence
<220> FEATURE:
<223> OTHER INFORMATION: Synthetic primer
```

```
<400> SEQUENCE: 125
gccctcgctg gttcctttgc t                                              21

<210> SEQ ID NO 126
<211> LENGTH: 20
<212> TYPE: DNA
<213> ORGANISM: Artificial Sequence
<220> FEATURE:
<223> OTHER INFORMATION: Synthetic primer

<400> SEQUENCE: 126
atgttttgtt tcgcgccgct                                                20

<210> SEQ ID NO 127
<211> LENGTH: 21
<212> TYPE: DNA
<213> ORGANISM: Artificial Sequence
<220> FEATURE:
<223> OTHER INFORMATION: Synthetic primer

<400> SEQUENCE: 127
aatctaccac tcccgtcccg c                                              21

<210> SEQ ID NO 128
<211> LENGTH: 21
<212> TYPE: DNA
<213> ORGANISM: Artificial Sequence
<220> FEATURE:
<223> OTHER INFORMATION: Synthetic primer

<400> SEQUENCE: 128
accgccgcct tcgtttacgt c                                              21

<210> SEQ ID NO 129
<211> LENGTH: 20
<212> TYPE: DNA
<213> ORGANISM: Artificial Sequence
<220> FEATURE:
<223> OTHER INFORMATION: Synthetic primer

<400> SEQUENCE: 129
gcccgcttac tttgccggtc                                                20

<210> SEQ ID NO 130
<211> LENGTH: 20
<212> TYPE: DNA
<213> ORGANISM: Artificial Sequence
<220> FEATURE:
<223> OTHER INFORMATION: Synthetic primer

<400> SEQUENCE: 130
tcgcctgtgc tcacaccacg                                                20

<210> SEQ ID NO 131
<211> LENGTH: 20
<212> TYPE: DNA
<213> ORGANISM: Artificial Sequence
<220> FEATURE:
<223> OTHER INFORMATION: Synthetic primer

<400> SEQUENCE: 131
ttaacgtccg ccaagcacgc                                                20

<210> SEQ ID NO 132
```

```
<211> LENGTH: 21
<212> TYPE: DNA
<213> ORGANISM: Artificial Sequence
<220> FEATURE:
<223> OTHER INFORMATION: Synthetic primer

<400> SEQUENCE: 132
cgttcccaag cccgacgact c                                              21

<210> SEQ ID NO 133
<211> LENGTH: 21
<212> TYPE: DNA
<213> ORGANISM: Artificial Sequence
<220> FEATURE:
<223> OTHER INFORMATION: Synthetic primer

<400> SEQUENCE: 133
gggcaagtcc ccaagcccat c                                              21

<210> SEQ ID NO 134
<211> LENGTH: 20
<212> TYPE: DNA
<213> ORGANISM: Artificial Sequence
<220> FEATURE:
<223> OTHER INFORMATION: Synthetic primer

<400> SEQUENCE: 134
aatgcggttt ctcggggct                                                 20

<210> SEQ ID NO 135
<211> LENGTH: 23
<212> TYPE: DNA
<213> ORGANISM: Artificial Sequence
<220> FEATURE:
<223> OTHER INFORMATION: Synthetic primer

<400> SEQUENCE: 135
tgttgctggc cctatgaagg cat                                            23

<210> SEQ ID NO 136
<211> LENGTH: 20
<212> TYPE: DNA
<213> ORGANISM: Artificial Sequence
<220> FEATURE:
<223> OTHER INFORMATION: Synthetic primer

<400> SEQUENCE: 136
ccatggcaag gcatcccggc                                                20

<210> SEQ ID NO 137
<211> LENGTH: 20
<212> TYPE: DNA
<213> ORGANISM: Artificial Sequence
<220> FEATURE:
<223> OTHER INFORMATION: Synthetic primer

<400> SEQUENCE: 137
tgtggcatcc caacaggggc                                                20

<210> SEQ ID NO 138
<211> LENGTH: 20
<212> TYPE: DNA
<213> ORGANISM: Artificial Sequence
<220> FEATURE:
<223> OTHER INFORMATION: Synthetic primer

<400> SEQUENCE: 138
```
tggacctggc cgtcaaaccg                                              20

<210> SEQ ID NO 139
<211> LENGTH: 21
<212> TYPE: DNA
<213> ORGANISM: Artificial Sequence
<220> FEATURE:
<223> OTHER INFORMATION: Synthetic primer

<400> SEQUENCE: 139
gcctcacaga gccgcacact c                                            21

<210> SEQ ID NO 140
<211> LENGTH: 20
<212> TYPE: DNA
<213> ORGANISM: Artificial Sequence
<220> FEATURE:
<223> OTHER INFORMATION: Synthetic primer

<400> SEQUENCE: 140
caggcatgcg ctacgaggct                                              20

<210> SEQ ID NO 141
<211> LENGTH: 23
<212> TYPE: DNA
<213> ORGANISM: Artificial Sequence
<220> FEATURE:
<223> OTHER INFORMATION: Synthetic primer

<400> SEQUENCE: 141
accagcttac agacgtgccc tga                                          23

<210> SEQ ID NO 142
<211> LENGTH: 21
<212> TYPE: DNA
<213> ORGANISM: Artificial Sequence
<220> FEATURE:
<223> OTHER INFORMATION: Synthetic primer

<400> SEQUENCE: 142
tgggcgggca ggtacgtgaa t                                            21

<210> SEQ ID NO 143
<211> LENGTH: 20
<212> TYPE: DNA
<213> ORGANISM: Artificial Sequence
<220> FEATURE:
<223> OTHER INFORMATION: Synthetic primer

<400> SEQUENCE: 143
tccgtgctct ggcctcgcat                                              20

<210> SEQ ID NO 144
<211> LENGTH: 20
<212> TYPE: DNA
<213> ORGANISM: Artificial Sequence
<220> FEATURE:
<223> OTHER INFORMATION: Synthetic primer

<400> SEQUENCE: 144
gctggcgacg acaagtggct                                              20

<210> SEQ ID NO 145
<211> LENGTH: 20
<212> TYPE: DNA

```
<213> ORGANISM: Artificial Sequence
<220> FEATURE:
<223> OTHER INFORMATION: Synthetic primer

<400> SEQUENCE: 145
ccacagagtt cgcgaggccc                                        20

<210> SEQ ID NO 146
<211> LENGTH: 20
<212> TYPE: DNA
<213> ORGANISM: Artificial Sequence
<220> FEATURE:
<223> OTHER INFORMATION: Synthetic primer

<400> SEQUENCE: 146
catcccaccg cgggaagcct                                        20

<210> SEQ ID NO 147
<211> LENGTH: 20
<212> TYPE: DNA
<213> ORGANISM: Artificial Sequence
<220> FEATURE:
<223> OTHER INFORMATION: Synthetic primer

<400> SEQUENCE: 147
atccccgccg tcacggtttt                                        20

<210> SEQ ID NO 148
<211> LENGTH: 21
<212> TYPE: DNA
<213> ORGANISM: Artificial Sequence
<220> FEATURE:
<223> OTHER INFORMATION: Synthetic primer

<400> SEQUENCE: 148
tcgttgaagt cgctgtcccg t                                      21

<210> SEQ ID NO 149
<211> LENGTH: 20
<212> TYPE: DNA
<213> ORGANISM: Artificial Sequence
<220> FEATURE:
<223> OTHER INFORMATION: Synthetic primer

<400> SEQUENCE: 149
gccccgcaca cctgccatag                                        20

<210> SEQ ID NO 150
<211> LENGTH: 20
<212> TYPE: DNA
<213> ORGANISM: Artificial Sequence
<220> FEATURE:
<223> OTHER INFORMATION: Synthetic primer

<400> SEQUENCE: 150
tgcttgctca agggcgctca                                        20

<210> SEQ ID NO 151
<211> LENGTH: 25
<212> TYPE: DNA
<213> ORGANISM: Artificial Sequence
<220> FEATURE:
<223> OTHER INFORMATION: Synthetic primer

<400> SEQUENCE: 151
tcaactcaga ctactgtcga agtgc                                  25
```

```
<210> SEQ ID NO 152
<211> LENGTH: 20
<212> TYPE: DNA
<213> ORGANISM: Artificial Sequence
<220> FEATURE:
<223> OTHER INFORMATION: Synthetic primer

<400> SEQUENCE: 152
cactggcacg gcttcacgca                                               20

<210> SEQ ID NO 153
<211> LENGTH: 20
<212> TYPE: DNA
<213> ORGANISM: Artificial Sequence
<220> FEATURE:
<223> OTHER INFORMATION: Synthetic primer

<400> SEQUENCE: 153
ccgctacgcg gtcgactcct                                               20

<210> SEQ ID NO 154
<211> LENGTH: 20
<212> TYPE: DNA
<213> ORGANISM: Artificial Sequence
<220> FEATURE:
<223> OTHER INFORMATION: Synthetic primer

<400> SEQUENCE: 154
caccctccgg tcgggtaagt                                               20

<210> SEQ ID NO 155
<211> LENGTH: 22
<212> TYPE: DNA
<213> ORGANISM: Artificial Sequence
<220> FEATURE:
<223> OTHER INFORMATION: Synthetic primer

<400> SEQUENCE: 155
tacaggtgct atgccagcgt gc                                            22

<210> SEQ ID NO 156
<211> LENGTH: 21
<212> TYPE: DNA
<213> ORGANISM: Artificial Sequence
<220> FEATURE:
<223> OTHER INFORMATION: Synthetic primer

<400> SEQUENCE: 156
tagcatcggc acaacgccca t                                             21

<210> SEQ ID NO 157
<211> LENGTH: 21
<212> TYPE: DNA
<213> ORGANISM: Artificial Sequence
<220> FEATURE:
<223> OTHER INFORMATION: Synthetic primer

<400> SEQUENCE: 157
gaaccggtgg ccgtgaaggt g                                             21

<210> SEQ ID NO 158
<211> LENGTH: 20
<212> TYPE: DNA
<213> ORGANISM: Artificial Sequence
<220> FEATURE:
```

<223> OTHER INFORMATION: Synthetic primer

<400> SEQUENCE: 158
acccaccgct cgctctcaca                                               20

<210> SEQ ID NO 159
<211> LENGTH: 22
<212> TYPE: DNA
<213> ORGANISM: Artificial Sequence
<220> FEATURE:
<223> OTHER INFORMATION: Synthetic primer

<400> SEQUENCE: 159
tggaaatgcg cagaaggacc gt                                            22

<210> SEQ ID NO 160
<211> LENGTH: 21
<212> TYPE: DNA
<213> ORGANISM: Artificial Sequence
<220> FEATURE:
<223> OTHER INFORMATION: Synthetic primer

<400> SEQUENCE: 160
gcacgacatg tggattgcgg c                                             21

<210> SEQ ID NO 161
<211> LENGTH: 20
<212> TYPE: DNA
<213> ORGANISM: Artificial Sequence
<220> FEATURE:
<223> OTHER INFORMATION: Synthetic primer

<400> SEQUENCE: 161
ttgccagccg tgctccgtca                                               20

<210> SEQ ID NO 162
<211> LENGTH: 20
<212> TYPE: DNA
<213> ORGANISM: Artificial Sequence
<220> FEATURE:
<223> OTHER INFORMATION: Synthetic primer

<400> SEQUENCE: 162
acgacgttgc aagctccgcc                                               20

<210> SEQ ID NO 163
<211> LENGTH: 22
<212> TYPE: DNA
<213> ORGANISM: Artificial Sequence
<220> FEATURE:
<223> OTHER INFORMATION: Synthetic primer

<400> SEQUENCE: 163
ccatcgggca tagaagtcgc cg                                            22

<210> SEQ ID NO 164
<211> LENGTH: 21
<212> TYPE: DNA
<213> ORGANISM: Artificial Sequence
<220> FEATURE:
<223> OTHER INFORMATION: Synthetic primer

<400> SEQUENCE: 164
ttcaccggag tcgccttccc a                                             21

```
<210> SEQ ID NO 165
<211> LENGTH: 20
<212> TYPE: DNA
<213> ORGANISM: Artificial Sequence
<220> FEATURE:
<223> OTHER INFORMATION: Synthetic primer

<400> SEQUENCE: 165
cgacgggctg cagtacgaga                                                 20

<210> SEQ ID NO 166
<211> LENGTH: 21
<212> TYPE: DNA
<213> ORGANISM: Artificial Sequence
<220> FEATURE:
<223> OTHER INFORMATION: Synthetic primer

<400> SEQUENCE: 166
aatcccctct cacctcgccg c                                               21

<210> SEQ ID NO 167
<211> LENGTH: 21
<212> TYPE: DNA
<213> ORGANISM: Artificial Sequence
<220> FEATURE:
<223> OTHER INFORMATION: Synthetic primer

<400> SEQUENCE: 167
ggccacccct cagagaccgg a                                               21

<210> SEQ ID NO 168
<211> LENGTH: 21
<212> TYPE: DNA
<213> ORGANISM: Artificial Sequence
<220> FEATURE:
<223> OTHER INFORMATION: Synthetic primer

<400> SEQUENCE: 168
cgccgaacca aagcctcctc c                                               21

<210> SEQ ID NO 169
<211> LENGTH: 23
<212> TYPE: DNA
<213> ORGANISM: Artificial Sequence
<220> FEATURE:
<223> OTHER INFORMATION: Synthetic primer

<400> SEQUENCE: 169
gcacaggaga aagagctcac ccc                                             23

<210> SEQ ID NO 170
<211> LENGTH: 20
<212> TYPE: DNA
<213> ORGANISM: Artificial Sequence
<220> FEATURE:
<223> OTHER INFORMATION: Synthetic primer

<400> SEQUENCE: 170
tcgcccgtcc aggagagata                                                 20

<210> SEQ ID NO 171
<211> LENGTH: 20
<212> TYPE: DNA
<213> ORGANISM: Artificial Sequence
<220> FEATURE:
<223> OTHER INFORMATION: Synthetic primer
```

```
<400> SEQUENCE: 171
cccccatcta ccggccattc                                              20

<210> SEQ ID NO 172
<211> LENGTH: 20
<212> TYPE: DNA
<213> ORGANISM: Artificial Sequence
<220> FEATURE:
<223> OTHER INFORMATION: Synthetic primer

<400> SEQUENCE: 172
atgaggggta atcgcgacgg                                              20

<210> SEQ ID NO 173
<211> LENGTH: 21
<212> TYPE: DNA
<213> ORGANISM: Artificial Sequence
<220> FEATURE:
<223> OTHER INFORMATION: Synthetic primer

<400> SEQUENCE: 173
ccctctcaca actgaccctg t                                            21

<210> SEQ ID NO 174
<211> LENGTH: 22
<212> TYPE: DNA
<213> ORGANISM: Artificial Sequence
<220> FEATURE:
<223> OTHER INFORMATION: Synthetic primer

<400> SEQUENCE: 174
tcactcagtg ccctaccgct cc                                           22

<210> SEQ ID NO 175
<211> LENGTH: 20
<212> TYPE: DNA
<213> ORGANISM: Artificial Sequence
<220> FEATURE:
<223> OTHER INFORMATION: Synthetic primer

<400> SEQUENCE: 175
ccgcaacgac tccgtccggt                                              20

<210> SEQ ID NO 176
<211> LENGTH: 21
<212> TYPE: DNA
<213> ORGANISM: Artificial Sequence
<220> FEATURE:
<223> OTHER INFORMATION: Synthetic primer

<400> SEQUENCE: 176
tgggctgatc ccgttgcagg a                                            21

<210> SEQ ID NO 177
<211> LENGTH: 21
<212> TYPE: DNA
<213> ORGANISM: Artificial Sequence
<220> FEATURE:
<223> OTHER INFORMATION: Synthetic primer

<400> SEQUENCE: 177
gtagccgtgg ctgagcgtgt t                                            21

<210> SEQ ID NO 178
<211> LENGTH: 22
```

<212> TYPE: DNA
<213> ORGANISM: Artificial Sequence
<220> FEATURE:
<223> OTHER INFORMATION: Synthetic primer

<400> SEQUENCE: 178
tgccgttgct gtaacatgcc gt                                          22

<210> SEQ ID NO 179
<211> LENGTH: 20
<212> TYPE: DNA
<213> ORGANISM: Artificial Sequence
<220> FEATURE:
<223> OTHER INFORMATION: Synthetic primer

<400> SEQUENCE: 179
gacggcgctt tgctcttgcg                                             20

<210> SEQ ID NO 180
<211> LENGTH: 23
<212> TYPE: DNA
<213> ORGANISM: Artificial Sequence
<220> FEATURE:
<223> OTHER INFORMATION: Synthetic primer

<400> SEQUENCE: 180
agcatgcaat actcggtcgg tct                                         23

<210> SEQ ID NO 181
<211> LENGTH: 22
<212> TYPE: DNA
<213> ORGANISM: Artificial Sequence
<220> FEATURE:
<223> OTHER INFORMATION: Synthetic primer

<400> SEQUENCE: 181
cgggcagcag gatgtttgcc at                                          22

<210> SEQ ID NO 182
<211> LENGTH: 22
<212> TYPE: DNA
<213> ORGANISM: Artificial Sequence
<220> FEATURE:
<223> OTHER INFORMATION: Synthetic primer

<400> SEQUENCE: 182
ggatactctc cgggcacgtt cg                                          22

<210> SEQ ID NO 183
<211> LENGTH: 20
<212> TYPE: DNA
<213> ORGANISM: Artificial Sequence
<220> FEATURE:
<223> OTHER INFORMATION: Synthetic primer

<400> SEQUENCE: 183
atggcagtgg actgcgcgac                                             20

<210> SEQ ID NO 184
<211> LENGTH: 20
<212> TYPE: DNA
<213> ORGANISM: Artificial Sequence
<220> FEATURE:
<223> OTHER INFORMATION: Synthetic primer

<400> SEQUENCE: 184

-continued

```
ggagggagca ctgatgcgct                                                    20

<210> SEQ ID NO 185
<211> LENGTH: 20
<212> TYPE: DNA
<213> ORGANISM: Artificial Sequence
<220> FEATURE:
<223> OTHER INFORMATION: Synthetic primer

<400> SEQUENCE: 185
ggctgctcct ccgctcatgg                                                    20
```

LIGNIN DEGRADING ENZYMES FROM MACROPHOMINA PHASEOLINA AND USES THEREOF

RELATED APPLICATIONS

This application is a National Stage application of PCT/US2013/055199, filed Aug. 15, 2013, which claims the benefit of priority to U.S. Provisional Patent Application Ser. No. 61/683,913, filed Aug. 16, 2012.

SEQUENCE LISTING

The instant application contains a Sequence Listing which has been submitted via EFS-Web and is hereby incorporated by reference in its entirety. Said ASCII copy is named JGX 601 ST25.txt and is 352 kilobytes in size.

FIELD OF INVENTION

This invention relates to the lignin degrading proteins/enzymes and genes of M. phaseolina. More specifically, the present invention discloses nucleotide acid sequences of these proteins and facilitates the reduction lignin content of lignocellulosic materials. The present invention also relates to methods for selecting and isolating enzymes from M. phaseolina that are capable of degrading lignin, processes for cloning a gene segment from M. phaseolina, and methods of using the enzyme product of the gene segment. Particularly it can be used in the production or processing of pulps, woodpulps, methanol and textile.

BACKGROUND OF THE INVENTION

Lignin is the the second most abundant organic polymer, exceeded only by cellulose. It binds with cellulose fibres which make up approximately one-fourth of the weight of dry wood. This aromatic polymer is recalcitrant to degradation. Lignin is covalently associated with hemicelluloses in the cell wall via numerous types of linkage. Among the linkage, the most abundant lignin substructure is the β-aryl ether, which accounts for approximately 40% of the inter phenylpropane linkages (Higuchi T 1990. Lignin biochemistry: biosynthesis and biodegradation. Wood Sci. Technol. 24: 23-63). In addition lignin does not possess any repeating units like other biopolymer such as cellulose, protein, starch etc. Ether bonds are often prevalent, providing a variety of linkages to the numerous aromatic residues. These structural features dictate constraints on the degradation of the lignin. A portion of a typical structure is illustrated in FIG. 1 and that the arylglycerol β-aryl ether structure red color in the figure is quantitatively the most important linkage, constituting at least 40% of the polymer. But, biodegradation of lignin is a prerequisite for the processing of biofuel, and wood pulp from plant raw materials. The improving of lignin degradation would drive the output from biofuel processing to better gain or better efficiency factor.

Lignin is a component of lignocellulose, which must be degraded to allow efficient use of cellulosic material for saccharification, paper production, biofuel production or upgradation of fodder. Ligincellulose degradation is a multienzymatic process involving both hydrolytic and oxidative enzymes. In general lignin composed of three principal building blocks namely, p-coumaryl alcohol, coniferyl alcohol and sinapyl alcohol. In addition, grass and dicot lignin also contain large amounts of phenolic acids such as p-coumaric and ferulic acid, which are esterified to alcohol groups.

Lignin peroxidases (LiP), manganese peroxidases (MnPs) and laccases are three families of enzymes that are involved in the biological degradation of lignin. LiP oxidizes non-phenolic lignin substructures by abstracting one electron and generating cation radicals (Kirk T K, Tien M, Kersten P J, Mozuch M D and Kalyanaraman B 1986. Ligninase of *Phanerochaete chrysosporium*. Mechanism of its degradation of the non-phenolic arylglycerol β-aryl ether substructure of lignin. Biochem J 236: 279-287; Kirk T K and Farrell R L 1987. Enzymatic "combustion": The microbial degradation of lignin. Annu Rev Microbiol 41: 465-505) and MnP oxidizes phenolic rings to phenoxyl radicals which lead to decomposition of Lignin (Gold M H, Wariishi H and Valli K 1989. Extracellular peroxidases involved in lignin degradation by the white-rot basidiomycete *Phanerochaete chrysosporium*. In: Biocatalysis in Agricultural Biotechnology, pp. 127-140. Edited by Whitaker J R and Sonnet P E. American Chemical Society, Washington, D.C.). Whereas laccase is capable of oxidizing both phenolic and non-phenolic moieties of lignin but that the latter is dependent on the co-presence of primary laccase substrates (Bourbonnais R and Paice M G 1990. Oxidation of non-phenolic substrates. An expanded role for laccase in lignin biodegradation. FEBS Lett 267(1): 99-102). FIG. 2 showed a dimeric model compounds that represent the major arylglycerol β-aryl ether lignin structure undergo Cα-Cβ cleavage upon oxidation by LiP (Kirk et al. 1986. Ligninase of *Phanerochaete chrysosporium*. Mechanism of its degradation of the non-phenolic arylglycerol β-aryl ether substructure of lignin. Biochem J 236: 279-287). Research on lignin biodegradation has increased enormously in recent years. Especially since the discovery of the first lignocellulose degrading fungus *Phanerochaete chrysosporium* genome was sequenced due to the interest on biological degradation of lignin (Martinez et al. 2004. Genome sequence of the lignocellulose degrading fungus *Phanerochaete chrysosporium* strain RP78. Nature Biotehnol 22(6): 695-700). Perhaps the best studied, is the degradation of lignin in lignocellulose by white rot fungi, *Phanerochaete chrysosporium* (Aust S D 1995. Mechanisms of Degradation by White Rot Fungi. Environ Health Perspect 103:59-61; Leisola M S A, Ulmer D and Fiechter A 1984. Factors affecting lignin degradation in lignocellulose by *Phanerochaete chrysosporium*. Arch Microbiol 137: 171-175; Ulmer D, Leisola M, Puhakka J and Fiechter A 1983. *Phanerochaete chrysosporium:* Growth pattern and lignin degradation. Appl Microbiol Biotechnol 18: 153-157; Chua M G S, Chen C L, Chang H M and Kirk T K 1982. $^{13}$CNMR spectroscopic study of lignin degraded by *Phanerochaete chrysosporium*. I. New structures. Holzforschung 36: 165-172). White-rot fungi produce a range of extracellular lignolytic enzymes, including heme-dependent lignin peroxidases, manganese peroxidases, and versatile peroxidases and copper-dependent laccases (Sanchez C 2009. Lignocellulosic residues: biodegradation and bioconversion by fungi. Biotechnol Adv 27: 185-194; Ten Have R, Teunissen P J M 2001. Oxidative mechanisms involved in lignin degradation by white-rot fungi. Chem Rev 101: 3397-3413). With the aid of these extracellular peroxidase and laccase enzyme, white-rot fungi degrade lignin (Timothy D H B, Ahmad M, Hardiman E M and Rahmanpour R 2001. Pathways for degradation of lignin in bacteria and fungi. Nat. Prod. Rep 28: 1883-1896).

Increasing interest in the exploitation of plant biomass as a renewable resource has provided an impetus for research on microbial degradation of lignocellulose. Large quantity of biomass (mainly lignocellulosic materials) is generated from forestry, agriculture and food industry which are not used in byproduct processes. To effectively utilize this plant biomass as renewable resources, alternative means of degradation of lignocellulose need to be explored. It is desirable to identify new fungi capable of degrading lignin for use in the manufacture of cellulosic products from lignocellulosic materials.

In order to be efficient, the degradation of lignin requires several types of enzymes acting cooperatively. At least two categories of enzymes are necessary to degrade lignin: Lignin peroxidase that oxidizes nonphenolic lignin substructures and laccase that oxidize both phenolic and nonphenolic lignin substructure thus they can degrade cooperatively. To realize and commercialize the mentioned enzymes, stable supply of various lignin degrading proteins are needed. Therefore, it is desirable for the industry to completely identify these lignin degrading genes and their encoded proteins, thus utilizing the genetic information for degradation of lignin from lignocellulosic materials.

SUMMARY OF THE INVENTION

It has surprisingly been found that the fungus *M. phaseolina*, which are not closely related to either *Trichoderma reesi* or *Phanerochaete chrysoporium*, are capable of producing lignin degrading enzymes.

Accordingly, among other things, the present invention relates to the identification of and its corresponding use of lignin degrading enzyme which is derivable from *M. phaseolina*. The present invention also relates to the use of *M. phaseolina* fungi in the degradation of lignin content of cellulosic materials.

The primary object of the present invention is to disclose sets of nucleotides sequences encoding lignin peroxidase (SEQ ID Nos. 1, 2, 4, 5, 7, 8, and/or any mixtures/combinations thereof), chloroperoxidase (SEQ ID Nos. 10, 11, 13, 14, 16, 17, 19, 20, 22, 23, 25, 26, and/or any mixtures/combinations thereof) and haemperoxidase (SEQ ID Nos. 28, 29, 31, 32, 34, 35, 37, 38, 40, 41, 43, 44, and/or any mixtures/combinations thereof) of the fungi *M. phaseolina*.

The present invention also discloses sets of nucleotides sequences encoding multicopper oxidase (SEQ ID Nos. 46, 47, 49, 50, 52, 53, 55, 56, 58, 59, 61, 62, 64, 65, 67, 68, 70, 71, 73, 74, 76, 77, 79, 80, 82, 83, 85, 86, 88, 89, 91, 92, 94, 95, 97, 98, 100, 101, 103, 104, 106, 107, 109, 110, and/or any mixtures/combinations thereof) of the fungi *M. phaseolina*.

It is preferred that the isolated polynucleotide of the claimed invention consists and/or comprises of a nucleic acid sequence selected from the group comprising and/or consisting of SEQ ID Nos. 2, 5, 8, 11, 14, 17, 20, 23, 26, 29, 32, 35, 38, 41, 44, 47, 50, 53, 56, 59, 62, 65, 68, 71, 74, 77, 80, 83, 86, 89, 92, 95, 98, 101, 104, 107, 110, 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106 and 109, and/or any mixtures/combinations thereof, that codes for the polypeptide selected from the group comprising and/or consisting of SEQ ID Nos. 3, 6, 9, 12, 15, 18, 21, 24, 27, 30, 33, 36, 39, 42, 45, 48, 51, 54, 57, 60, 63, 66, 69, 72, 75, 78, 81, 84, 87, 90, 93, 96, 99, 102, 105, 108 and 111, and/or any mixtures/combinations thereof. The present invention also relates to an isolated polynucleotide consisting and/or comprising the complement of the nucleotide sequences described above.

Another object of the present invention is to provide the molecular biology and genetic information of the genes and enzymes set forth in the primary object to be utilized for the regulation and conversion of lignin degradation for the production of valuable products from lignocellulosic materials.

In another aspect, to facilitate in vitro production of the lignin degrading polypeptide, the present invention include an expression construct capable of expressing polypeptide containing at least 70% sequential amino acids as set forth in SEQ ID Nos. 3, 6, 9, 12, 15, 18, 21, 24, 27, 30, 33, 36, 39, 42, 45, 48, 51, 54, 57, 60, 63, 66, 69, 72, 75, 78, 81, 84, 87, 90, 93, 96, 99, 102, 105, 108 and 111. Preferably, the expression construct has inserted DNA or cDNA with sequential nucleotide as set forth in SEQ ID Nos. 2, 5, 8, 11, 14, 17, 20, 23, 26, 29, 32, 35, 38, 41, 44, 47, 50, 53, 56, 59, 62, 65, 68, 71, 74, 77, 80, 83, 86, 89, 92, 95, 98, 101, 104, 107, 110, 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106 and 109.

Yet another object of the present invention discloses a recombinant gene construct comprising a polynucleotide template having nucleotide sequence set forth in SEQ ID Nos. 2, 5, 8, 11, 14, 17, 20, 23, 26, 29, 32, 35, 38, 41, 44, 47, 50, 53, 56, 59, 62, 65, 68, 71, 74, 77, 80, 83, 86, 89, 92, 95, 98, 101, 104, 107, 110, 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106 and 109, wherein the polynucleotide template is expressible in a host cell to produce an enzyme which oxidize lignin from lignocellulosic materials. Preferably, the recombinant gene construct further comprises a promoter region operably-linked to enhance expression of the polynucleotide template.

In accordance with one of the preferred embodiments of the present invention, the fungus *M. phaseolina* strain ms6 isolated from infected jute plant. The isolated polypeptide is also preferably derived from this strain.

Still another object of the present invention is to provide a potential commercially feasible way to isolate lignin degrading enzyme from *M. phaseolina* in order to keep up with the increasing global demand on exploitation/utilization of plant biomass as a renewable resource for the manufacture of cellulosic products.

Further object of the invention is directed to utilization of the lignin degrading substances in animal feeds, biofuel, woodpulp, textile and paper industry.

One skilled in the art will readily appreciate that the present invention is well adapted to carry out the objects and obtain the ends and advantages mentioned, as well as those inherent therein. The embodiments described herein are not intended as limitations on the scope of the present invention.

BRIEF DESCRIPTION OF THE DRAWINGS

The accompanying drawings, which are incorporated in and form a part of the specification, illustrate the embodiments of the present invention and, together with the description, serve to explain the principles of the invention.

DETAILED DESCRIPTION OF THE INVENTION

Figure 1:
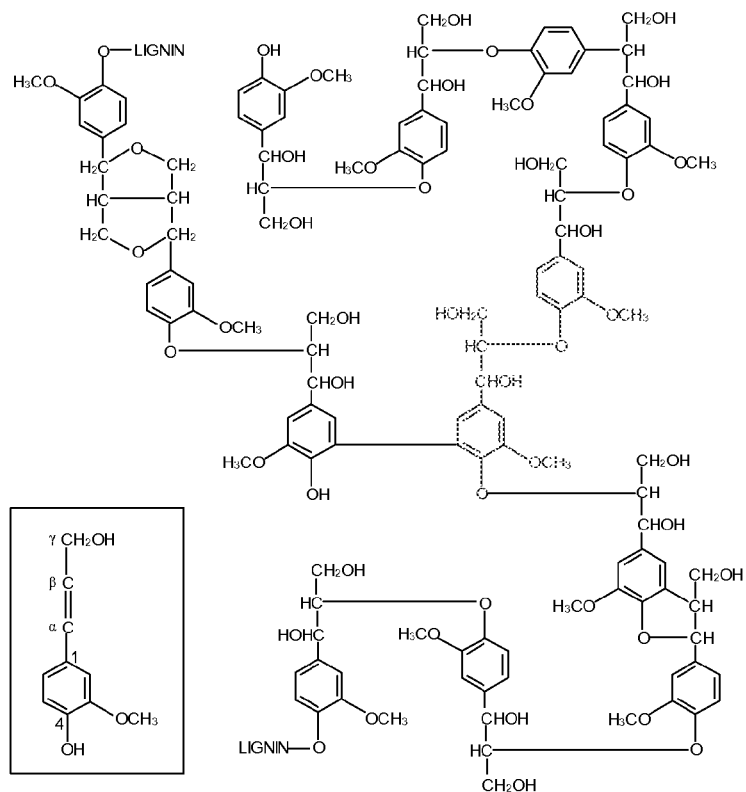
FIG. 1 Displays a common structure of softwood lignin. Major arylglyserol-β-aryl ether structure is shown in red color. The inset shows coniferyl alcohol, the phenylpropanoid building block of softwood lignin.
Figure 2:
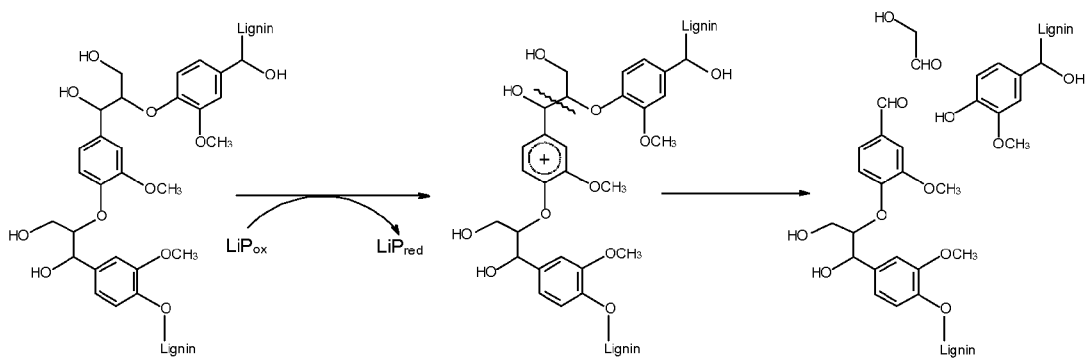
FIG. 2 Displays a cleavage of internal an non-phenolic arylglyserol-β-aryl ether lignin structure by oxidized lignin peroxidase.
Figure 3:
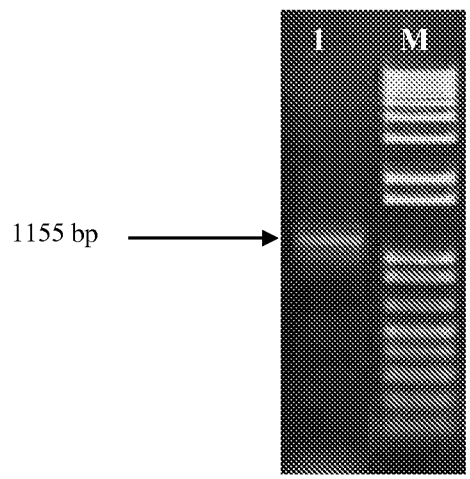
FIG. 3 is the electrophoresed agarose gel image showing the PCR amplification result in which lane 1 is polynucleotides of lignin peroxidase of SEQ ID NO. 1 and lane M is DNA molecular weight ladder.
Figure 4:
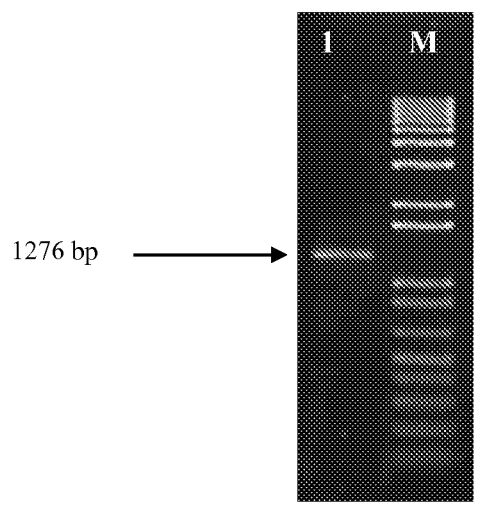
FIG. 4 is the electrophoresed agarose gel image showing the PCR amplification result in which lane 1 is polynucleotides of lignin peroxidase of SEQ ID NO. 4 and lane M is DNA molecular weight ladder.
Figure 5:
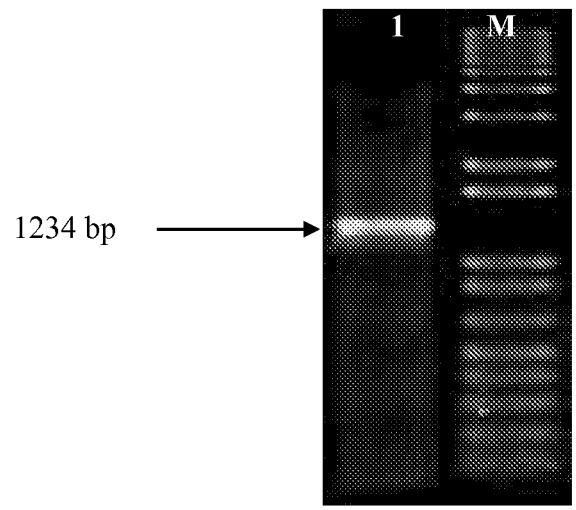
FIG. 5 is the electrophoresed agarose gel image showing the PCR amplification result in which lane 1 is polynucleotides of lignin peroxidase of SEQ ID NO. 7 and lane M is DNA molecular weight ladder.
Figure 6:
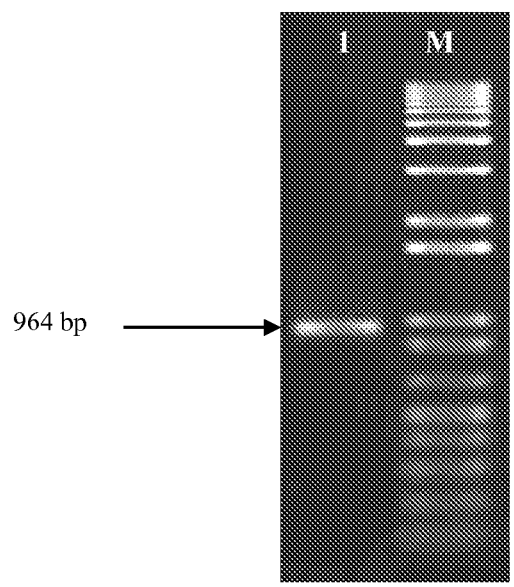
FIG. 6 is the electrophoresed agarose gel image showing the PCR amplification result in which lane 1 is polynucleotides of chloroperoxidase of SEQ ID NO. 13 and lane M is DNA molecular weight ladder.
Figure 7:
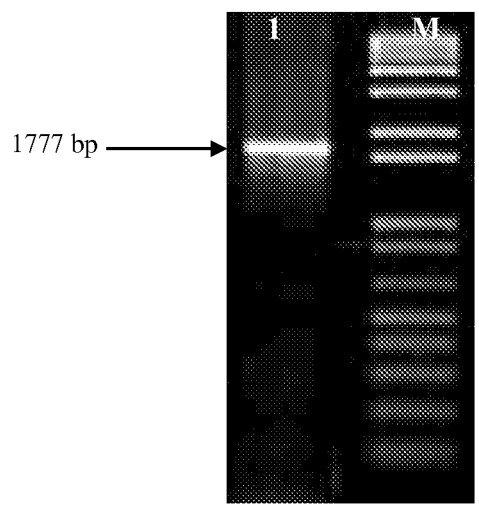
FIG. 7 is the electrophoresed agarose gel image showing the PCR amplification result in which lane 1 is polynucleotides of chloroperoxidase of SEQ ID NO. 16 and lane M is DNA molecular weight ladder.
Figure 8:
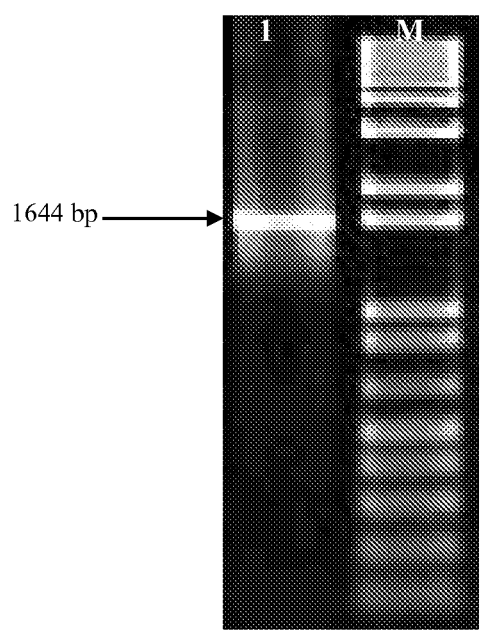
FIG. 8 is the electrophoresed agarose gel image showing the PCR amplification result in which lane 1 is polynucleotides of chloroperoxidase of SEQ ID NO. 19 and lane M is DNA molecular weight ladder.
Figure 9:
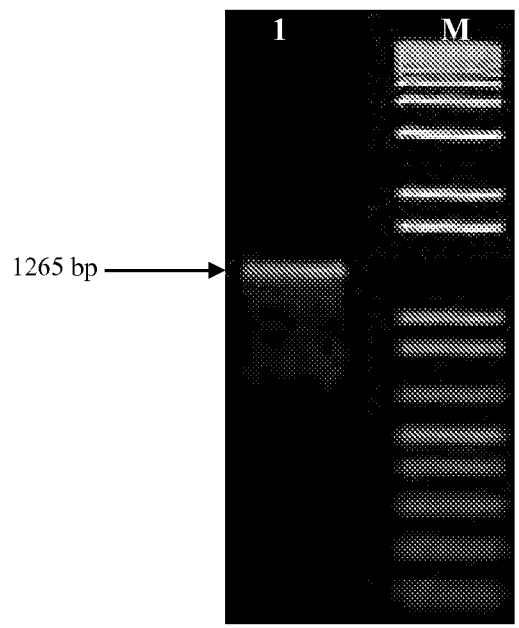
FIG. 9 is the electrophoresed agarose gel image showing the PCR amplification result in which lane 1 is polynucleotides of chloroperoxidase of SEQ ID NO. 22 and lane M is DNA molecular weight ladder.
Figure 10:
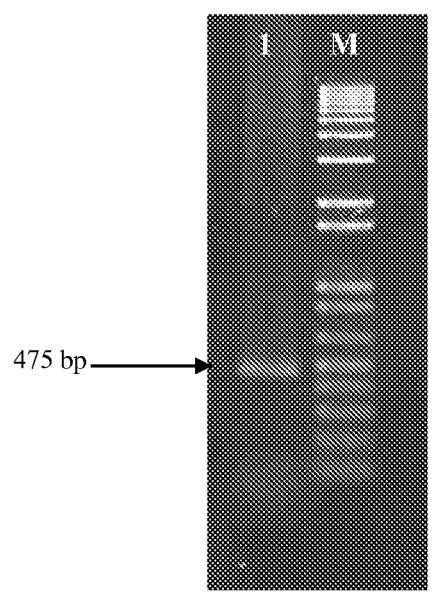
FIG. 10 is the electrophoresed agarose gel image showing the PCR amplification result in which lane 1 is polynucleotides of chloroperoxidase of SEQ ID NO. 25 and lane M is DNA molecular weight ladder.
Figure 11:
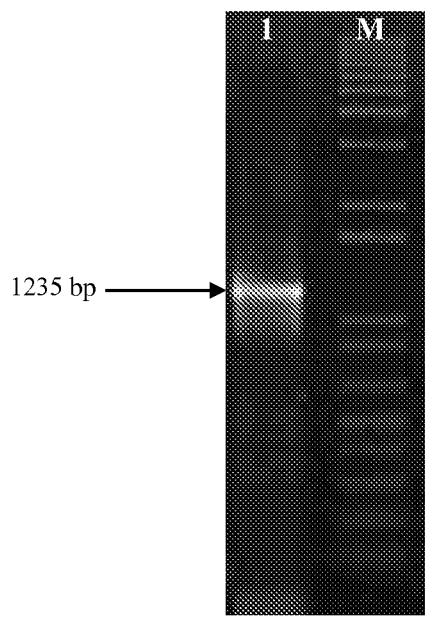
FIG. 11 is the electrophoresed agarose gel image showing the PCR amplification result in which lane 1 is polynucleotides of haemperoxidase of SEQ ID NO. 28 and lane M is DNA molecular weight ladder.
Figure 12:
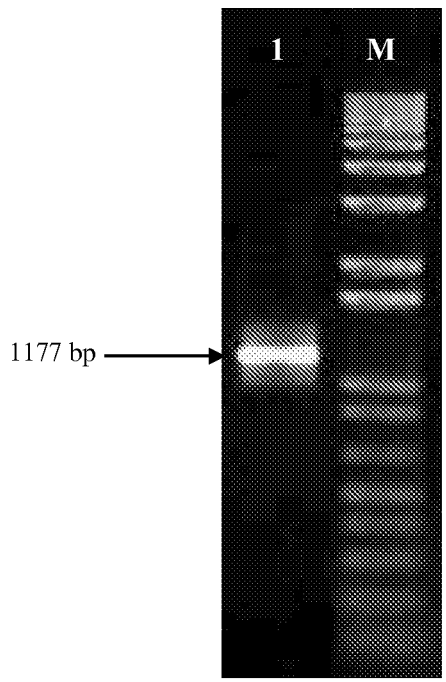
FIG. 12 is the electrophoresed agarose gel image showing the PCR amplification result in which lane 1 is polynucleotides of haemperoxidase of SEQ ID NO. 31 and lane M is DNA molecular weight ladder.
Figure 13:
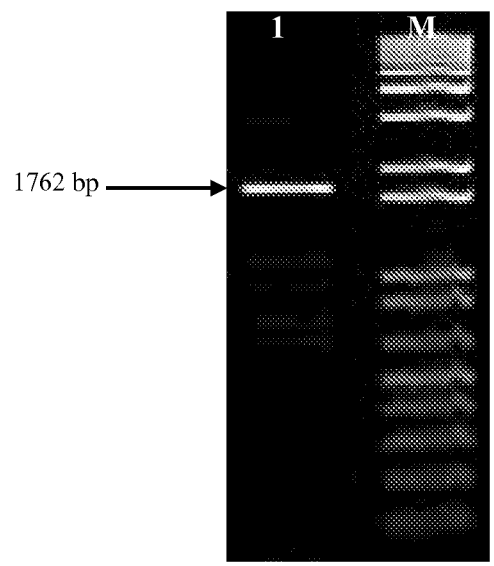
FIG. 13 is the electrophoresed agarose gel image showing the PCR amplification result in which lane 1 is polynucleotides of haemperoxidase of SEQ ID NO. 34 and lane M is DNA molecular weight ladder.
Figure 14:
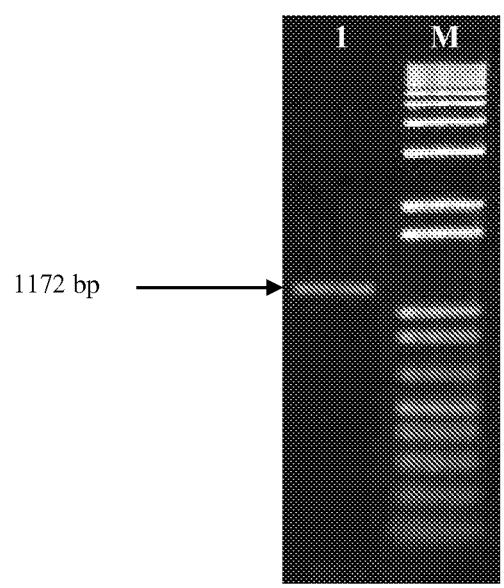
FIG. 14 is the electrophoresed agarose gel image showing the PCR amplification result in which lane 1 is polynucleotides of haemperoxidase of SEQ ID NO. 37 and lane M is DNA molecular weight ladder.
Figure 15:
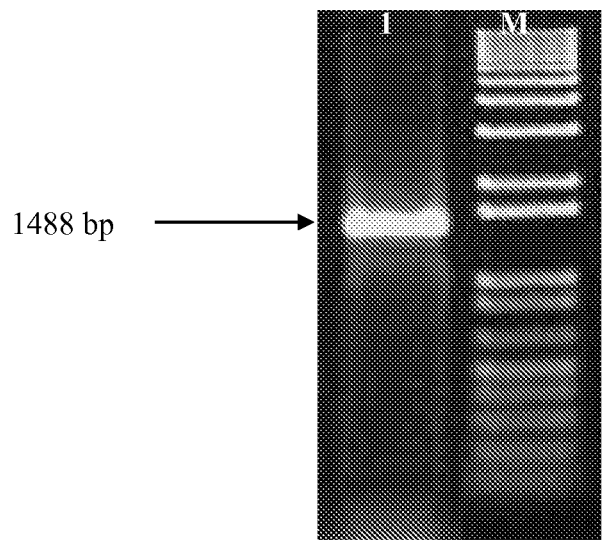
FIG. 15 is the electrophoresed agarose gel image showing the PCR amplification result in which lane 1 is polynucleotides of haemperoxidase of SEQ ID NO. 40 and lane M is DNA molecular weight ladder.
Figure 16:
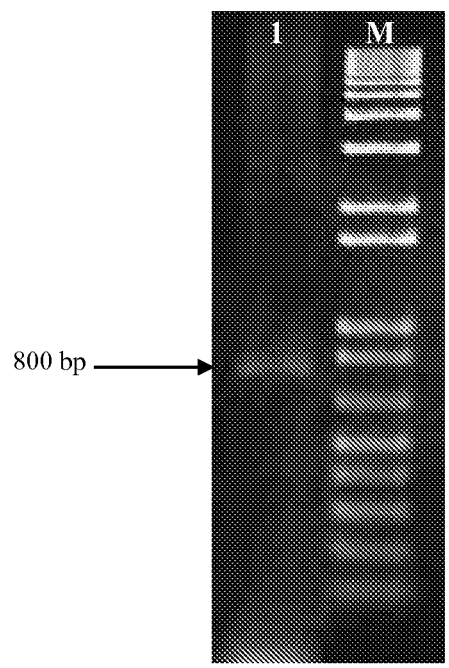
FIG. 16 is the electrophoresed agarose gel image showing the PCR amplification result in which lane 1 is polynucleotides of haemperoxidase of SEQ ID NO. 43 and lane M is DNA molecular weight ladder.
Figure 17:
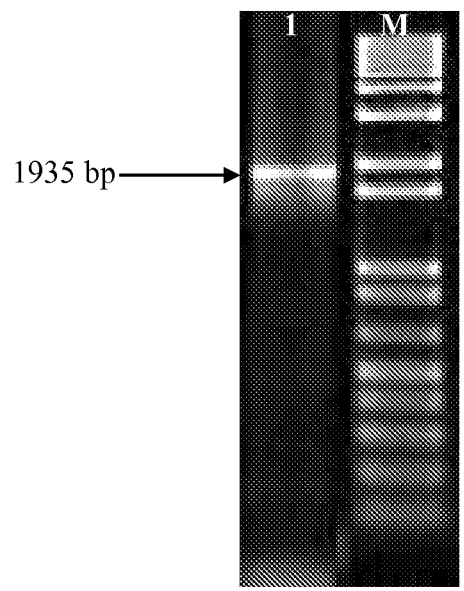
FIG. 17 is the electrophoresed agarose gel image showing the PCR amplification result in which lane 1 is polynucleotides of multicopper oxidase of SEQ ID NO. 46 and lane M is DNA molecular weight ladder.
Figure 18:
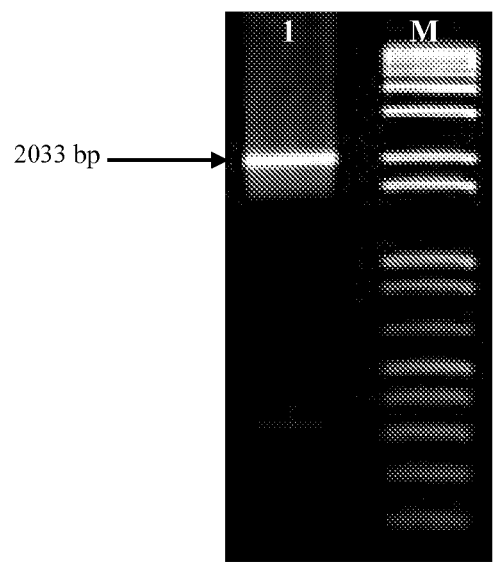
FIG. 18 is the electrophoresed agarose gel image showing the PCR amplification result in which lane 1 is polynucleotides of multicopper oxidase of SEQ ID NO. 49 and lane M is DNA molecular weight ladder.
Figure 19:
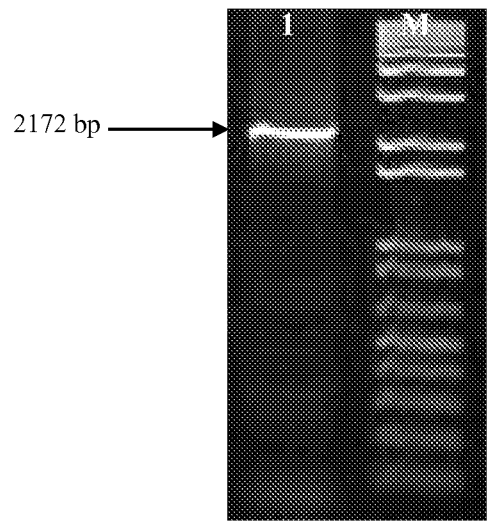
FIG. 19 is the electrophoresed agarose gel image showing the PCR amplification result in which lane 1 is polynucleotides of multicopper oxidase of SEQ ID NO. 52 and lane M is DNA molecular weight ladder.
Figure 20:
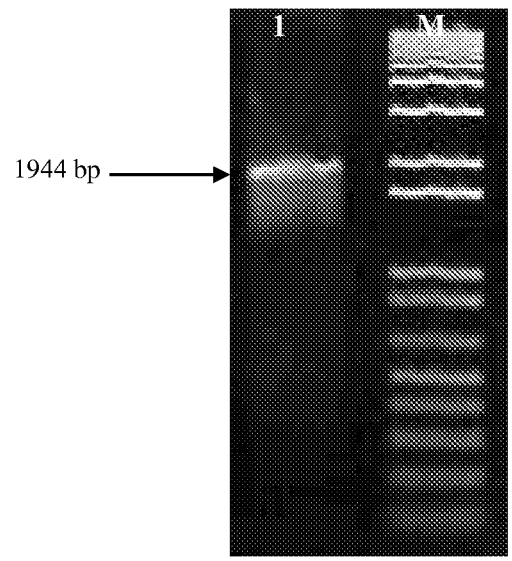
FIG. 20 is the electrophoresed agarose gel image showing the PCR amplification result in which lane 1 is polynucleotides of multicopper oxidase of SEQ ID NO. 55 and lane M is DNA molecular weight ladder.
Figure 21:
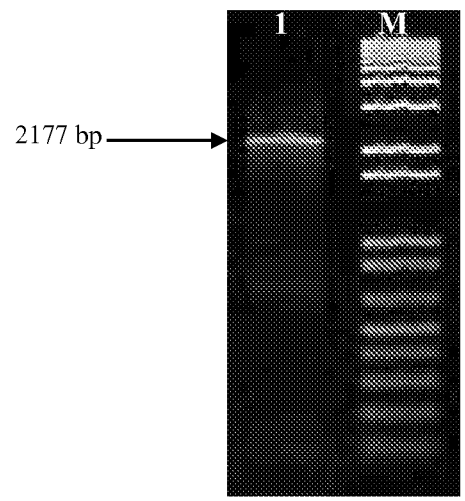
FIG. 21 is the electrophoresed agarose gel image showing the PCR amplification result in which lane 1 is polynucleotides of multicopper oxidase of SEQ ID NO. 58 and lane M is DNA molecular weight ladder.
Figure 22:
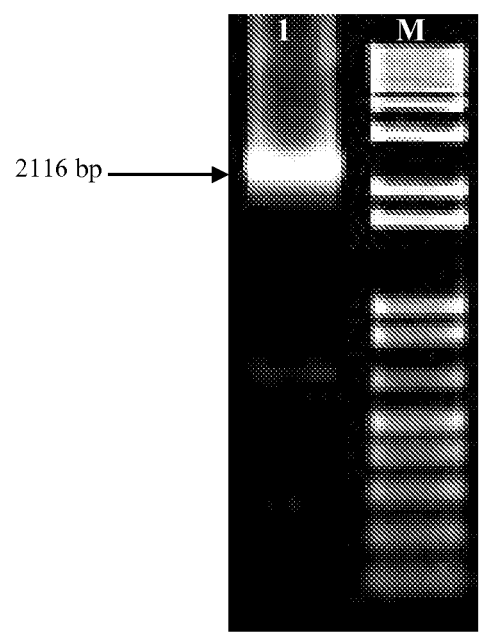
FIG. 22 is the electrophoresed agarose gel image showing the PCR amplification result in which lane 1 is polynucleotides of multicopper oxidase of SEQ ID NO. 64 and lane M is DNA molecular weight ladder.
Figure 23:
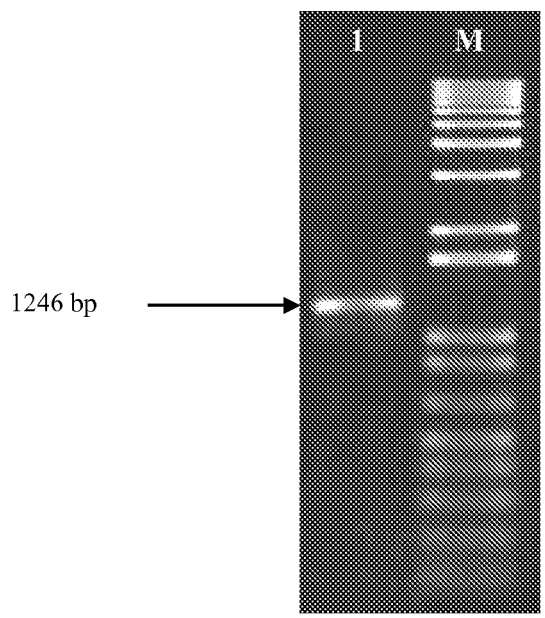
FIG. 23 is the electrophoresed agarose gel image showing the PCR amplification result in which lane 1 is polynucleotides of multicopper oxidase of SEQ ID NO. 67 and lane M is DNA molecular weight ladder.
Figure 24:
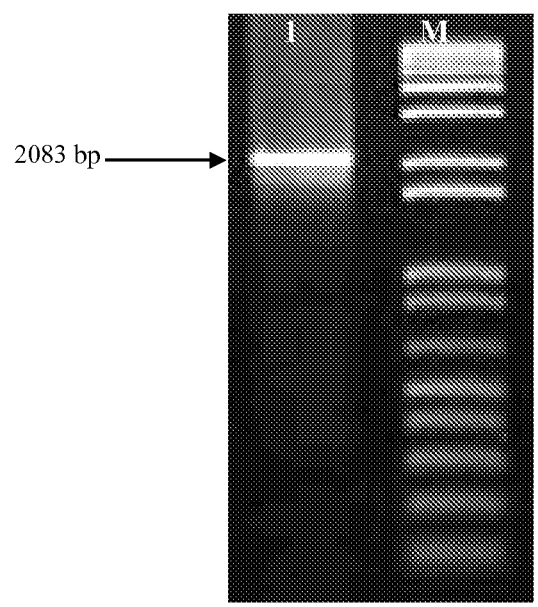
FIG. 24 is the electrophoresed agarose gel image showing the PCR amplification result in which lane 1 is polynucleotides of multicopper oxidase of SEQ ID NO. 70 and lane M is DNA molecular weight ladder.
Figure 25:
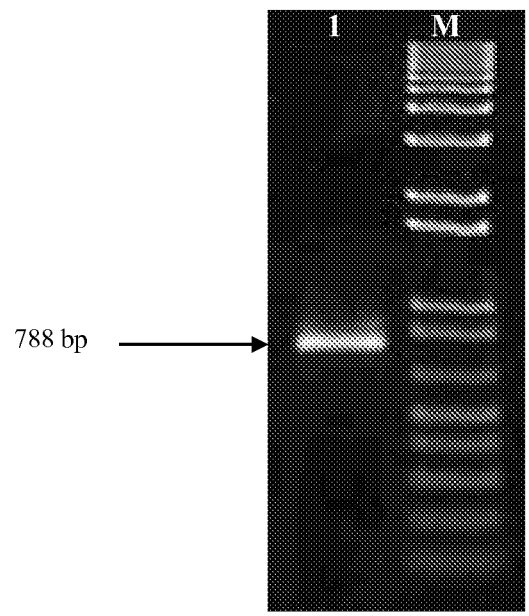
FIG. 25 is the electrophoresed agarose gel image showing the PCR amplification result in which lane 1 is polynucleotides of multicopper oxidase of SEQ ID NO. 73 and lane M is DNA molecular weight ladder.
Figure 26:
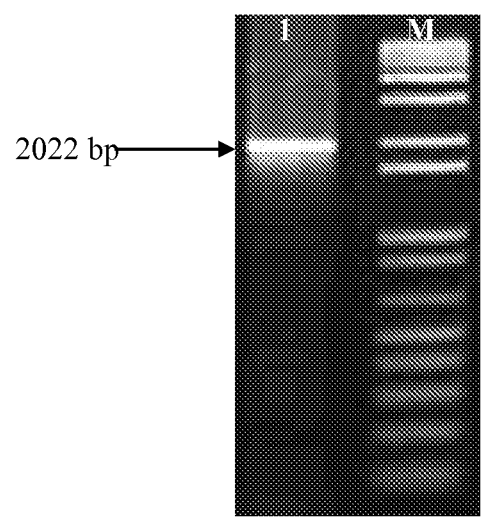
FIG. 26 is the electrophoresed agarose gel image showing the PCR amplification result in which lane 1 is polynucleotides of multicopper oxidase of SEQ ID NO. 76 and lane M is DNA molecular weight ladder.
Figure 27:
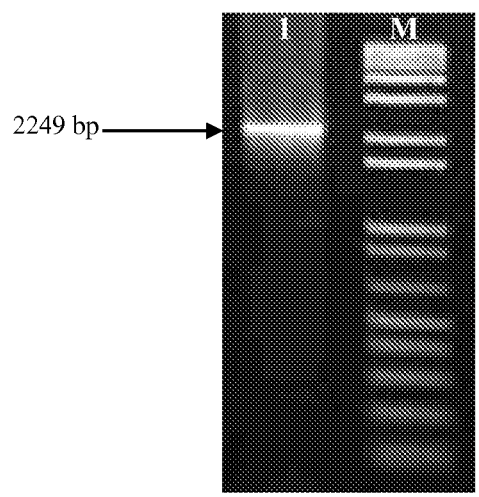
FIG. 27 is the electrophoresed agarose gel image showing the PCR amplification result in which lane 1 is polynucleotides of multicopper oxidase of SEQ ID NO. 79 and lane M is DNA molecular weight ladder.
Figure 28:
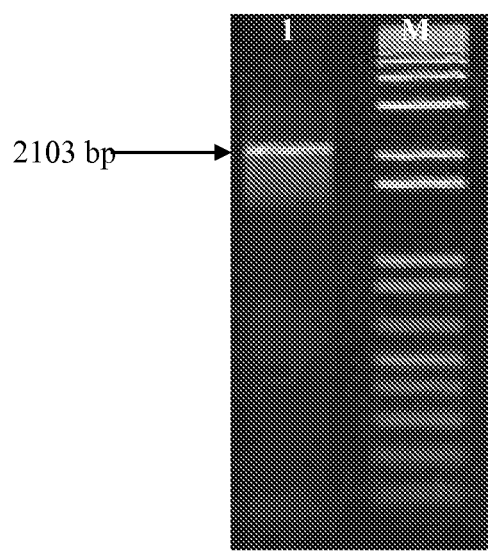
FIG. 28 is the electrophoresed agarose gel image showing the PCR amplification result in which lane 1 is polynucleotides of multicopper oxidase of SEQ ID NO. 82 and lane M is DNA molecular weight ladder.
Figure 29:
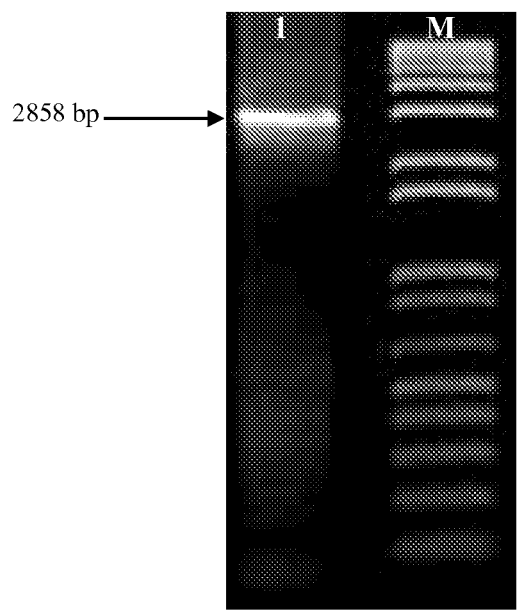
FIG. 29 is the electrophoresed agarose gel image showing the PCR amplification result in which lane 1 is polynucleotides of multicopper oxidase of SEQ ID NO. 85 and lane M is DNA molecular weight ladder.
Figure 30:
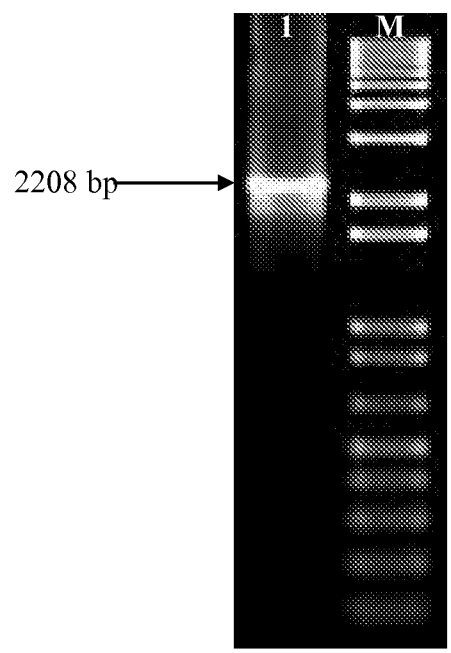
FIG. 30 is the electrophoresed agarose gel image showing the PCR amplification result in which lane 1 is polynucleotides of multicopper oxidase of SEQ ID NO. 88 and lane M is DNA molecular weight ladder.
Figure 31:
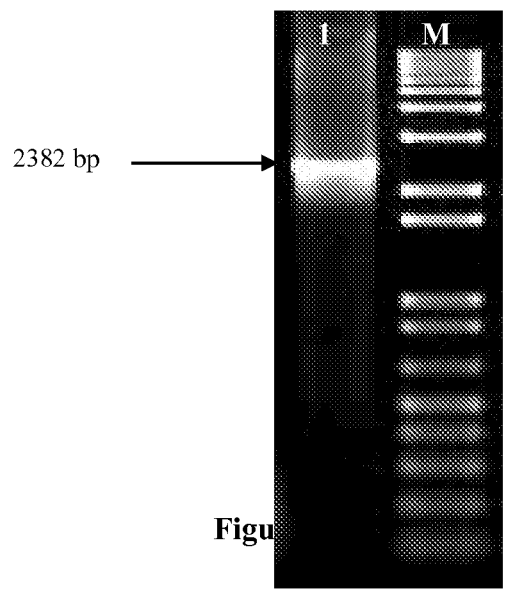
FIG. 31 is the electrophoresed agarose gel image showing the PCR amplification result in which lane 1 is polynucleotides of multicopper oxidase of SEQ ID NO. 91 and lane M is DNA molecular weight ladder.
Figure 32:
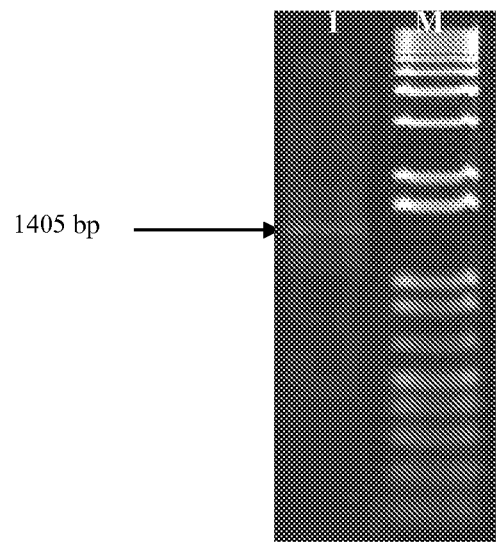
FIG. 32 is the electrophoresed agarose gel image showing the PCR amplification result in which lane 1 is polynucleotides of multicopper oxidase of SEQ ID NO. 97 and lane M is DNA molecular weight ladder.
Figure 33:
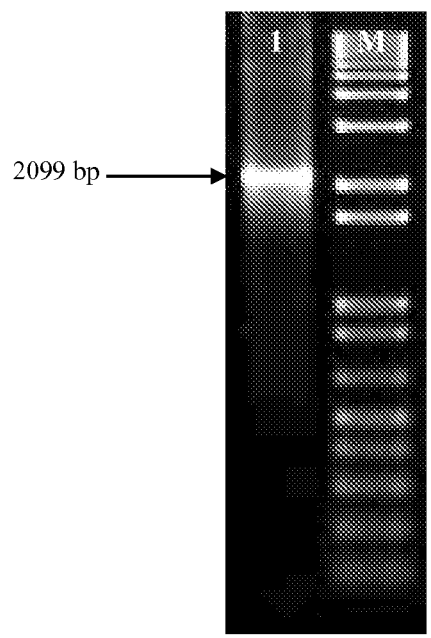
FIG. 33 is the electrophoresed agarose gel image showing the PCR amplification result in which lane 1 is polynucleotides of multicopper oxidase of SEQ ID NO. 100 and lane M is DNA molecular weight ladder.
Figure 34:
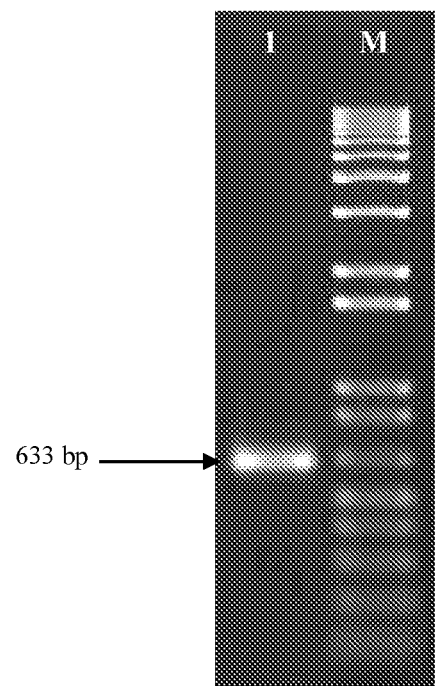
FIG. 34 is the electrophoresed agarose gel image showing the PCR amplification result in which lane 1 is polynucleotides of multicopper oxidase of SEQ ID NO. 103 and lane M is DNA molecular weight ladder.
Figure 35:
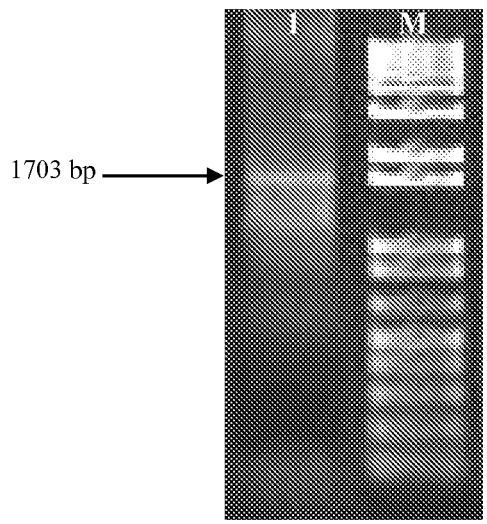
FIG. 35 is the electrophoresed agarose gel image showing the PCR amplification result in which lane 1 is polynucleotides of multicopper oxidase of SEQ ID NO. 106 and lane M is DNA molecular weight ladder.
Figure 36:
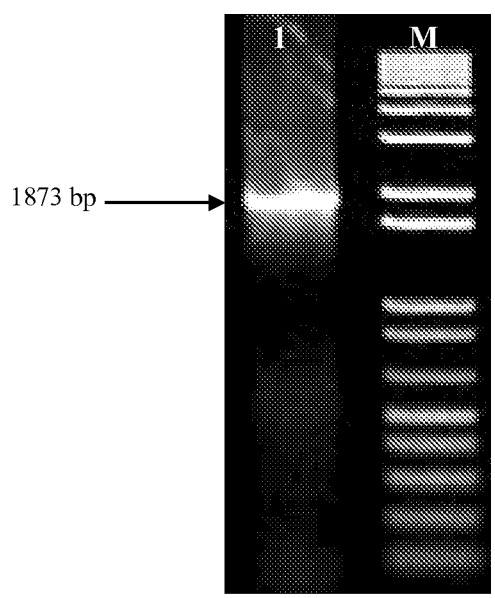
FIG. 36 is the electrophoresed agarose gel image showing the PCR amplification result in which lane 1 is polynucleotides of multicopper oxidase of SEQ ID NO. 109 and lane M is DNA molecular weight ladder.

The definitions and/or methods provided herein define the present invention and guide those of ordinary skill in the art in the practice of the present invention. Except where otherwise stated, terms are to be understood according to conventional usage by those of ordinary skill in the relevant art. To the extent to which any of the definitions and/or methods is found to be inconsistent with any of the definitions and/or methods provided in any patent or non-patent reference incorporated herein or in any reference found elsewhere, it is understood that the said definition and/or method which has been expressly provided/adopted in this application will be used herein. The singular terms "a," "an," and "the" include plural referents unless context clearly indicates otherwise. Similarly, the word "or" is intended to include "and" unless the context clearly indicates otherwise. Hence, "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below.

The present invention provides the nucleotide sequences of *M. phaseolina* encoded protein/enzyme involved in lignin degradation. The genes encode proteins with an enzyme activity that is either in use in an industry or of interest to an industry. The genomic sequences of the invention that encode the enzymes are identified primarily by comparison of nucleotide sequences of *M. phaseolina* genomic DNA and the nucleotide sequences of known enzyme genes of other microorganisms. Prior to this invention, the nucleotide sequences of these *M. phaseolina* genes, the reading frames, the positions of exons and introns, the structure of the enzymes, and their potential usefulness in various industries, such as those involved in the making of food and feed, beverages, textiles and detergents, were not known.

Analysis of the genome sequence of *M. phaseolina* reveals an abundance of genes coding for enzymes which degrade lignin in plant. The nucleotide sequences were initially annotated by software programs, such as Genescan and Glimmer M (The Institute of Genome Research, Rockville, N.M.), which can identify putative coding regions, introns, and splice junctions. Further automated and manual curation of the nucleotide sequences was performed to refine and establish precise characterization of the coding regions and other gene features.

Over 14000 cDNAs from *M. phaseolina* were partially or fully sequenced. Among them thirty-seven cDNAs encoding new enzymes with putative roles in lignin degradation were discovered.

Open reading frames (ORFS) are analyzed following full or partial sequencing of clones of cDNA libraries derived from *M. phaseolina* mRNA and are further analyzed using sequence analysis software, and by determining homology to known sequences in databases (public/private).

In the context of this disclosure, a number of terms used throughout the specification have the indicated meanings unless expressly indicated to have a different meaning.

As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least one of 150 contiguous nucleotides (both upstream and downstream) derived from SEQ ID No. 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106 and 109, or the complement of such sequences.

"Polypeptide" as used herein, is a single linear chain of amino acids bonded together by peptide bonds, and having usally a sequence greater than 100 amino acids in length.

"Isolated" means altered "by the hand of man" from the natural state. If a composition or substance occurs in nature, it has been "isolated" if it has been changed or removed from its original environment, or both. For example, a polynucleotide or a polypeptide naturally present in a living plant or animal is not "isolated," but the same polynucleotide or polypeptide separated from the coexisting materials of its natural state is "isolated", as the term is employed herein.

The term "gene", as used herein, is defined as the genomic sequences of the fungi *M. phaseolina*, particularly polynucleotide sequence encoding polypeptide of the series of enzymes involved in the lignin degradation pathway.

A "coding sequence" or "coding region" refers to a nucleic acid molecule having sequence information necessary to produce a gene product, such as an amino acid or polypeptide, when the sequence is expressed. The coding sequence may comprise untranslated sequences (e.g., introns or 5' or 3' untranslated regions) within translated regions, or may lack such intervening untranslated sequences (e.g., as in cDNA).

The term "primer" as used herein, is an oligonucleotide capable of binding to a target nucleic acid sequence and priming the nucleic acid synthesis. An amplification oligonucleotide as defined herein will preferably be 10 to 50, most preferably 15 to 25 nucleotides in length. While the amplification oligonucleotides of the present invention may be chemically synthesized and such oligonucleotides are not naturally occurring nucleic acids.

The abbreviation used throughout the specification to refer to nucleic acids comprising nucleotide sequences are the conventional one-letter abbreviations. Thus when included in a nucleic acid, the naturally occurring encoding nucleotides are abbreviated as follows: adenine (A), guanine (G), cytosine (C), thymine (T) and uracil (U). Also, unless otherwise specified, the nucleic acid sequences presented herein is the 5'-3'direction.

As used herein, the term "complementary" and derivatives thereof are used in reference to pairing of nucleic acids by the well-known rules that A pairs with T or U and C pairs with G. Complement can be "partial" or "complete". In partial complement, only some of the nucleic acid bases are matched according to the base pairing rules; while in complete or total complement, all the bases are matched according to the pairing rule. The degree of complement between the nucleic acid strands may have significant effects on the efficiency and strength of hybridization between nucleic acid strands as well known in the art. The efficiency and strength of said hybridization is depends upon in detection method.

The term "host cell", as used herein, includes any cell type which is susceptible to transformation, transfection, transduction, expression and the like with a nucleic acid construct or expression vector comprising a polynucleotide of the present invention.

The term "operably linked" denotes herein a configuration in which a control sequence is placed at an appropriate position relative to the coding sequence of the polynucleotide sequence such that the control sequence directs the expression of the coding sequence of a polypeptide.

A "vector" generally refers to a replicon, such as plasmid, phage, cosmid, yeast or virus to which another nucleic acid segment may be operably inserted so as to bring about the replication or expression of the segment. The term "vector" is also intended to refer to a nucleic acid molecule capable of transporting another nucleic acid to which it has been linked. One type of vector is a "plasmid," which refers to a circular double-stranded DNA loop into which additional DNA segments may be ligated. Another type of vector is a viral vector, where additional DNA segments may be ligated into the viral genome. Certain vectors are capable of autonomous replication in a host cell into which they are introduced (e.g., bacterial vectors having a bacterial origin of replication and episomal mammalian vectors). Other vectors can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "nucleic acid construct" or "DNA construct" is sometimes used to refer to a coding sequence or sequences operably linked to appropriate regulatory sequences and inserted into a vector for transforming a cell. This term may be used interchangeably with the term "transforming DNA" or "transgene."

The term "promoter" as used herein, refers to a nucleic acid sequence that functions to direct transcription of a downstream gene. The promoter will generally be appropriate to the host cell in which the target gene is being expressed. The promoter together with other transcriptional and translational regulatory nucleic acid sequences (also termed "control sequences") is necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

The term "in vitro" as used herein, refers to a biological reaction occurs in an artificial environment outside a living organism, which is usually conducted in a laboratory using components of an organism that have been isolated from their usual biological context in order to permit a more detailed or more convenient analysis to be performed.

The term "% homology" is used interchangeably herein with the term "% identity" herein and refers to the level of nucleic acid or amino acid sequence identity between the nucleic acid sequence that encodes any one of the inventive polypeptides or the inventive polypeptide's amino acid sequence, when aligned using a sequence alignment program.

For example, as used herein, 80% homology means the same thing as 80% sequence identity determined by a defined algorithm, and accordingly a homologue of a given sequence has greater than 80% sequence identity over a length of the given sequence. Exemplary levels of sequence identity include, but are not limited to, 80, 85, 90, 95, 98% or more sequence identity to a given sequence, e.g., the coding sequence for any one of the inventive polypeptides, as described herein.

Exemplary computer programs which can be used to determine identity between two sequences include, but are not limited to, the suite of BLAST programs, e.g., BLASTN, BLASTX, and TBLASTX, BLASTP and TBLASTN, publicly accessible at www.ncbi.nlm.nih.gov/BLAST.

Sequence searches are typically carried out using the BLASTN program, when evaluating a given nucleic acid sequence relative to nucleic acid sequences in the GenBank DNA Sequences and other public databases. The BLASTX program is preferred for searching nucleic acid sequences that have been translated in all reading frames against amino acid sequences in the GenBank Protein Sequences and other public databases.

A preferred alignment of selected sequences in order to determine "% identity" between two or more sequences is performed using for example, the CLUSTAL-W program.

As in setting forth, one embodiment of the present invention is an isolated polynucleotides encoding for lignin degrading polypeptide found in the fungi M. phaseolina comprising nucleotide sequence as setting forth in SEQ ID No. 2, 5, 8, 11, 14, 17, 20, 23, 26, 29, 32, 35, 38, 41, 44, 47, 50, 53, 56, 59, 62, 65, 68, 71, 74, 77, 80, 83, 86, 89, 92, 95, 98, 101, 104, 107, 110, 1, 4, 7, 10, 13, 16, 19, 22, 25, 28, 31, 34, 37, 40, 43, 46, 49, 52, 55, 58, 61, 64, 67, 70, 73, 76, 79, 82, 85, 88, 91, 94, 97, 100, 103, 106 and 109. Correspondingly, the respective lignin degrading polypeptide encoded by these nucleotide sequences shall possess amino acid sequence as setting forth in SEQ ID Nos. 3, 6, 9, 12, 15, 18, 21, 24, 27, 30, 33, 36, 39, 42, 45, 48, 51, 54, 57, 60, 63, 66, 69, 72, 75, 78, 81, 84, 87, 90, 93, 96, 99, 102, 105, 108 and 111.

In one embodiment, the 939 bp long polynucleotide illustrated in SEQ ID No. 2 is the full length cDNA clone encoded Lignin peroxidase protein exhibiting an open reading frame encoding a 312 amino acid polypeptide, as in SEQ ID No. 3, with a calculated molecular mass of about 32 kD. Through SMART analysis of SEQ ID No. 2, it reveals presence of Pfam peroxidase domain in the sequence. The protein family with the Pfam domain consists and/or comprises of secretory fungal peroxidases. These are monomeric glycoproteins involved in the degradation of lignin.

Preferably, the 1116 bp long polynucleotide illustrated in SEQ ID No. 5 is the full length cDNA clone encoded Lignin peroxidase protein exhibiting an open reading frame encoding a 371 amino acid polypeptide, as in SEQ ID No. 6, with a calculated molecular mass of about 40 kD. Through SMART analysis of SEQ ID No. 5, it reveals presence of Pfam peroxidase domain in the sequence. The protein family with the Pfam domain consists and/or comprises of secretory fungal peroxidases. These are monomeric glycoproteins involved in the degradation of lignin.

Similarly, another aspect, the 1023 bp long polynucleotide illustrated in SEQ ID No. 8 is the full length cDNA clone encoded Lignin peroxidase protein exhibiting an open reading frame encoding a 340 amino acid polypeptide, as in SEQ ID No. 9, with a calculated molecular mass of about 35 kD. Through SMART analysis of SEQ ID No. 8, it reveals presence of Pfam peroxidase domain in the sequence. The protein family with the Pfam domain consists and/or comprises of secretory fungal peroxidases. These are monomeric glycoproteins involved in the degradation of lignin.

In another aspect, polynucleotides encoding for chloroperoxidase has 1260 bp as illustrated in SEQ ID No. 11 while the encoded protein is a 419 amino acid polypeptide with a calculated molecular mass of about 45 kD as illustrated in SEQ ID No. 12. The SEQ ID No. 11 contains a Pfam domain, namely peroxidase_2. The said domain involved in the lignin degradation.

In another aspect, polynucleotides encoding for chloroperoxidase has 690 bp as illustrated in SEQ ID No. 14 while the encoded protein is a 229 amino acid polypeptide with a calculated molecular mass of about 25 kD as illustrated in SEQ ID No. 15. The SEQ ID No. 14 contains a Pfam domain, namely peroxidase_2. The said domain involved in the lignin degradation.

In another aspect, polynucleotides encoding for chloroperoxidase has 1194 bp as illustrated in SEQ ID No. 17 while the encoded protein is a 397 amino acid polypeptide with a calculated molecular mass of about 43 kD as illustrated in SEQ ID No. 18. The SEQ ID No. 17 contains a Pfam domain, namely peroxidase_2. The said domain involved in the lignin degradation.

In another aspect, polynucleotides encoding for chloroperoxidase has 1317 bp as illustrated in SEQ ID No. 20 while the encoded protein is a 438 amino acid polypeptide with a calculated molecular mass of about 47 kD as illustrated in SEQ ID No. 21. The SEQ ID No. 20 contains a Pfam domain, namely peroxidase_2. The said domain involved in the lignin degradation.

In another aspect, polynucleotides encoding for chloroperoxidase has 780 bp as illustrated in SEQ ID No. 23 while the encoded protein is a 259 amino acid polypeptide with a calculated molecular mass of about 29 kD as illustrated in SEQ ID No. 24. The SEQ ID No. 23 contains a Pfam domain, namely peroxidase_2. The said domain involved in the lignin degradation.

In another aspect, polynucleotides encoding for chloroperoxidase has 951 bp as illustrated in SEQ ID No. 26 while the encoded protein is a 316 amino acid polypeptide with a calculated molecular mass of about 35 kD as illustrated in SEQ ID No. 27. The SEQ ID No. 26 contains a Pfam domain, namely peroxidase_2. The said domain involved in the lignin degradation.

In another aspect, polynucleotides encoding for haemperoxidase has 1116 bp as illustrated in SEQ ID No. 29 while the encoded protein is a 371 amino acid polypeptide with a calculated molecular mass of about 41 kD as illustrated in SEQ ID No. 30. The SEQ ID No. 29 contains a Pfam domain, namely peroxidase. Haemperoxidases oxidize lignin subunits using extracellular hydrogen peroxide generated by unrelated oxidases as a co-substrate. The said domain involved in the lignin degradation.

In another aspect, polynucleotides encoding for haemperoxidase has 1623 bp as illustrated in SEQ ID No. 32 while the encoded protein is a 540 amino acid polypeptide with a calculated molecular mass of about 57 kD as illustrated in SEQ ID No. 33. The SEQ ID No. 32 contains a Pfam domain, namely peroxidase. Haemperoxidases oxidize lignin subunits using extracellular hydrogen peroxide generated by unrelated oxidases as a co-substrate. The said domain involved in the lignin degradation.

In another aspect, polynucleotides encoding for haemperoxidase has 1599 bp as illustrated in SEQ ID No. 35 while the encoded protein is a 532 amino acid polypeptide with a calculated molecular mass of about 57 kD as illustrated in SEQ ID No. 36. The SEQ ID No. 35 contains a Pfam domain, namely peroxidase. Haemperoxidases oxidize lignin subunits using extracellular hydrogen peroxide generated by unrelated oxidases as a co-substrate. The said domain involved in the lignin degradation.

In another aspect, polynucleotides encoding for haemperoxidase has 2049 bp as illustrated in SEQ ID No. 38 while the encoded protein is a 682 amino acid polypeptide with a calculated molecular mass of about 70 kD as illustrated in SEQ ID No. 39. The SEQ ID No. 38 contains a Pfam domain, namely peroxidase. Haemperoxidases oxidize lignin subunits using extracellular hydrogen peroxide generated by unrelated oxidases as a co-substrate. The said domain involved in the lignin degradation.

In another aspect, polynucleotides encoding for haemperoxidase has 1605 bp as illustrated in SEQ ID No. 41 while the encoded protein is a 534 amino acid polypeptide with a calculated molecular mass of about 57 kD as illustrated in SEQ ID No. 42. The SEQ ID No. 41 contains a Pfam domain, namely peroxidase. Haemperoxidases oxidize lignin subunits using extracellular hydrogen peroxide generated by unrelated oxidases as a co-substrate. The said domain involved in the lignin degradation.

In another aspect, polynucleotides encoding for haemperoxidase has 960 bp as illustrated in SEQ ID No. 44 while the encoded protein is a 319 amino acid polypeptide with a calculated molecular mass of about 35 kD as illustrated in SEQ ID No. 45. The SEQ ID No. 44 contains a Pfam domain, namely peroxidase. Haemperoxidases oxidize lignin subunits using extracellular hydrogen peroxide generated by unrelated oxidases as a co-substrate. The said domain involved in the lignin degradation.

In another aspect, polynucleotides encoding for multicopper oxidases (laccases) has 1713 bp as illustrated in SEQ ID No. 47 while the encoded protein is a 570 amino acid polypeptide with a calculated molecular mass of about 64 kD as illustrated in SEQ ID No. 48. The SEQ ID No. 47 contains a Pfam domain, namely multicopper oxidase. This multicopper oxidase (laccase) is extracellular, non-haem, copper containing proteins that catalyze the one-electron oxidation of phenols to phenoxy radicals.

In another aspect, polynucleotides encoding for multicopper oxidases (laccases) has 1860 bp as illustrated in SEQ ID No. 50 while the encoded protein is a 619 amino acid polypeptide with a calculated molecular mass of about 69 kD as illustrated in SEQ ID No. 51. The SEQ ID No. 50 contains a Pfam domain, namely multicopper oxidase. This multicopper oxidase (laccase) is extracellular, non-haem, copper containing proteins that catalyze the one-electron oxidation of phenols to phenoxy radicals.

In another aspect, polynucleotides encoding for multicopper oxidases (laccases) has 1824 bp as illustrated in SEQ ID No. 53 while the encoded protein is a 607 amino acid polypeptide with a calculated molecular mass of about 67 kD as illustrated in SEQ ID No. 54. The SEQ ID No. 53 contains a Pfam domain, namely multicopper oxidase. This multicopper oxidase (laccase) is extracellular, non-haem, copper containing proteins that catalyze the one-electron oxidation of phenols to phenoxy radicals.

In another aspect, polynucleotides encoding for multicopper oxidases (laccases) has 1737 bp as illustrated in SEQ ID No. 56 while the encoded protein is a 578 amino acid polypeptide with a calculated molecular mass of about 63 kD as illustrated in SEQ ID No. 57. The SEQ ID No. 56 contains a Pfam domain, namely multicopper oxidase. This multicopper oxidase (laccase) is extracellular, non-haem, copper containing proteins that catalyze the one-electron oxidation of phenols to phenoxy radicals.

In another aspect, polynucleotides encoding for multicopper oxidases (laccases) has 1665 bp as illustrated in SEQ ID No. 59 while the encoded protein is a 554 amino acid polypeptide with a calculated molecular mass of about 61 kD as illustrated in SEQ ID No. 60. The SEQ ID No. 59 contains a Pfam domain, namely multicopper oxidase. This multicopper oxidase (laccase) is extracellular, non-haem, copper containing proteins that catalyze the one-electron oxidation of phenols to phenoxy radicals.

In another aspect, polynucleotides encoding for multicopper oxidases (laccases) has 1803 bp as illustrated in SEQ ID No. 62 while the encoded protein is an 600 amino acid polypeptide with a calculated molecular mass of about 65 kD as illustrated in SEQ ID No. 63. The SEQ ID No. 62 contains a Pfam domain, namely multicopper oxidase. This multicopper oxidase (laccase) is extracellular, non-haem, copper containing proteins that catalyze the one-electron oxidation of phenols to phenoxy radicals.

In another aspect, polynucleotides encoding for multicopper oxidases (laccases) has 1635 bp as illustrated in SEQ ID No. 65 while the encoded protein is a 544 amino acid polypeptide with a calculated molecular mass of about 61 kD as illustrated in SEQ ID No. 66. The SEQ ID No. 65 contains a Pfam domain, namely multicopper oxidase. This multicopper oxidase (laccase) is extracellular, non-haem, copper containing proteins that catalyze the one-electron oxidation of phenols to phenoxy radicals.

In another aspect, polynucleotides encoding for multicopper oxidases (laccases) has 1743 bp as illustrated in SEQ ID No. 68 while the encoded protein is a 580 amino acid polypeptide with a calculated molecular mass of about 63 kD as illustrated in SEQ ID No. 69. The SEQ ID No. 68 contains a Pfam domain, namely multicopper oxidase. This multicopper oxidase (laccase) is extracellular, non-haem, copper containing proteins that catalyze the one-electron oxidation of phenols to phenoxy radicals.

In another aspect, polynucleotides encoding for multicopper oxidases (laccases) has 1836 bp as illustrated in SEQ ID No. 71 while the encoded protein is a 611 amino acid polypeptide with a calculated molecular mass of about 67 kD as illustrated in SEQ ID No. 72. The SEQ ID No. 71 contains a Pfam domain, namely multicopper oxidase. This multicopper oxidase (laccase) is extracellular, non-haem, copper containing proteins that catalyze the one-electron oxidation of phenols to phenoxy radicals.

In another aspect, polynucleotides encoding for multicopper oxidases (laccases) has 702 bp as illustrated in SEQ ID No. 74 while the encoded protein is a 233 amino acid polypeptide with a calculated molecular mass of about 26 kD as illustrated in SEQ ID No. 75. The SEQ ID No. 74 contains a Pfam domain, namely multicopper oxidase. This multicopper oxidase (laccase) is extracellular, non-haem, copper containing proteins that catalyze the one-electron oxidation of phenols to phenoxy radicals.

In another aspect, polynucleotides encoding for multicopper oxidases (laccases) has 1854 bp as illustrated in SEQ ID No. 77 while the encoded protein is a 617 amino acid polypeptide with a calculated molecular mass of about 68 kD as illustrated in SEQ ID No. 78. The SEQ ID No. 77 contains a Pfam domain, namely multicopper oxidase. This multicopper oxidase (laccase) is extracellular, non-haem, copper containing proteins that catalyze the one-electron oxidation of phenols to phenoxy radicals.

In another aspect, polynucleotides encoding for multicopper oxidases (laccases) has 2073 bp as illustrated in SEQ ID No. 80 while the encoded protein is a 690 amino acid polypeptide with a calculated molecular mass of about 77 kD as illustrated in SEQ ID No. 81. The SEQ ID No. 80 contains a Pfam domain, namely multicopper oxidase. This multicopper oxidase (laccase) is extracellular, non-haem, copper containing proteins that catalyze the one-electron oxidation of phenols to phenoxy radicals.

In another aspect, polynucleotides encoding for multicopper oxidases (laccases) has 1824 bp as illustrated in SEQ ID No. 83 while the encoded protein is a 607 amino acid polypeptide with a calculated molecular mass of about 67 kD as illustrated in SEQ ID No. 84. The SEQ ID No. 83 contains a Pfam domain, namely multicopper oxidase. This multicopper oxidase (laccase) is extracellular, non-haem, copper containing proteins that catalyze the one-electron oxidation of phenols to phenoxy radicals.

In another aspect, polynucleotides encoding for multicopper oxidases (laccases) has 1932 bp as illustrated in SEQ ID No. 86 while the encoded protein is a 643 amino acid polypeptide with a calculated molecular mass of about 72 kD as illustrated in SEQ ID No. 87. The SEQ ID No. 86 contains a Pfam domain, namely multicopper oxidase. This multicopper oxidase (laccase) is extracellular, non-haem, copper containing proteins that catalyze the one-electron oxidation of phenols to phenoxy radicals.

In another aspect, polynucleotides encoding for multicopper oxidases (laccases) has 1950 bp as illustrated in SEQ ID No. 89 while the encoded protein is a 649 amino acid polypeptide with a calculated molecular mass of about 72 kD as illustrated in SEQ ID No. 90. The SEQ ID No. 89 contains a Pfam domain, namely multicopper oxidase. This multicopper oxidase (laccase) is extracellular, non-haem, copper containing proteins that catalyze the one-electron oxidation of phenols to phenoxy radicals.

In another aspect, polynucleotides encoding for multicopper oxidases (laccases) has 2016 bp as illustrated in SEQ ID No. 92 while the encoded protein is a 671 amino acid polypeptide with a calculated molecular mass of about 74 kD as illustrated in SEQ ID No. 93. The SEQ ID No. 92 contains a Pfam domain, namely multicopper oxidase. This multicopper oxidase (laccase) is extracellular, non-haem, copper containing proteins that catalyze the one-electron oxidation of phenols to phenoxy radicals.

In another aspect, polynucleotides encoding for multicopper oxidases (laccases) has 2085 bp as illustrated in SEQ ID No. 95 while the encoded protein is a 694 amino acid polypeptide with a calculated molecular mass of about 78 kD as illustrated in SEQ ID No. 96. The SEQ ID No. 95 contains a Pfam domain, namely multicopper oxidase. This multicopper oxidase (laccase) is extracellular, non-haem, copper containing proteins that catalyze the one-electron oxidation of phenols to phenoxy radicals.

In another aspect, polynucleotides encoding for multicopper oxidases (laccases) has 1821 bp as illustrated in SEQ ID No. 98 while the encoded protein is a 606 amino acid polypeptide with a calculated molecular mass of about 68 kD as illustrated in SEQ ID No. 99. The SEQ ID No. 98 contains a Pfam domain, namely multicopper oxidase. This multicopper oxidase (laccase) is extracellular, non-haem, copper containing proteins that catalyze the one-electron oxidation of phenols to phenoxy radicals.

In another aspect, polynucleotides encoding for multicopper oxidases (laccases) has 1854 bp as illustrated in SEQ ID No. 101 while the encoded protein is a 617 amino acid polypeptide with a calculated molecular mass of about 68 kD as illustrated in SEQ ID No. 102. The SEQ ID No. 101 contains a Pfam domain, namely multicopper oxidase. This multicopper oxidase (laccase) is extracellular, non-haem, copper containing proteins that catalyze the one-electron oxidation of phenols to phenoxy radicals.

In another aspect, polynucleotides encoding for multicopper oxidases (laccases) has 1815 bp as illustrated in SEQ ID No. 104 while the encoded protein is a 604 amino acid polypeptide with a calculated molecular mass of about 67 kD as illustrated in SEQ ID No. 105. The SEQ ID No. 104 contains a Pfam domain, namely multicopper oxidase. This multicopper oxidase (laccase) is extracellular, non-haem, copper containing proteins that catalyze the one-electron oxidation of phenols to phenoxy radicals.

In another aspect, polynucleotides encoding for multicopper oxidases (laccases) has 1632 bp as illustrated in SEQ ID No. 107 while the encoded protein is a 543 amino acid polypeptide with a calculated molecular mass of about 61 kD as illustrated in SEQ ID No. 108. The SEQ ID No. 107 contains a Pfam domain, namely multicopper oxidase. This multicopper oxidase (laccase) is extracellular, non-haem, copper containing proteins that catalyze the one-electron oxidation of phenols to phenoxy radicals.

In another aspect, polynucleotides encoding for multicopper oxidases (laccases) has 1752 bp as illustrated in SEQ ID No. 110 while the encoded protein is a 583 amino acid polypeptide with a calculated molecular mass of about 64 kD as illustrated in SEQ ID No. 111. The SEQ ID No. 110 contains a Pfam domain, namely multicopper oxidase. This multicopper oxidase (laccase) is extracellular, non-haem, copper containing proteins that catalyze the one-electron oxidation of phenols to phenoxy radicals.

The sequences provided by the present invention can also be used as preparatory materials for the rational modification or design of novel enzymes with characteristics that enable the enzymes to perform better in demanding processes.

The present disclosure includes as contained in the appended claims, as well as that of the foregoing description. Although this invention has been described in its preferred form with a degree of particularity, it is understood that the present disclosure of the preferred form has been made only by way of example and that numerous changes in the details of construction and the combination and arrangements of parts may be resorted to without departing from the scope of the invention and claims.

Various references are cited herein, the disclosures of which are incorporated by reference in their entireties.

EXAMPLE

The following example is intended to further illustrate the invention, without any intent for the invention to be limited to the specific embodiments described therein.

Example 1

Designing and Synthesis of Primers

The primers used in the study were either designed from the manually curated transcriptome and the "gene models" predicted from the genomic sequences of *M. phaseolina* ms6, bp choosing the sequences manually with complete ORFs or using databases where similar genes have been successfully isolated from other plants. Comparative bioinformatic analysis of the nucleotide sequences obtained from transcriptome were carried out using NCBI BLAST, BLASTP, RPS-BLAST, BLASTX and PSI-BLAST to identify homologues of the related genes and for the proper identification of gene. Nucleotide sequence alignments were performed through clustalW version 1.82 whenever multiple sequences were found from the "gene pool". The alignment was then edited. Gene specific primers (both forward and reverse) were selected manually or through Primer 3 plus tool and the primers were custom synthesized.

All oligonucleotides used in this study were synthesized and HPLC purified by the supplier and procured from Integrated DNA Technologies (IDT). Stock solution of 100 pmol were prepared in autoclaved ddH$_2$O and stored at −20° C., in aliquots for use.

Oligonucleotides Sequences Used as Primers for PCR

| Gene name | SEQ ID No. | Primer Sequence | Amplified product (bp) |
|---|---|---|---|
| lignin peroxidase | 1 | Forward GAGACCGCTACACCCACCCCT<br>Reverse CACCGCACTACGACCTCGCT | 1155 |
| lignin peroxidase | 4 | Forward GTCGTCGCGTGGCTGCTAGA<br>Reverse CCAGGCATCGGGGAACTTCGG | 1276 |
| lignin peroxidase | 7 | Forward GGCGGCTCTCTCGCAGACGTA<br>Reverse GCCCTGCCCCAACCGATTCA | 1234 |
| Chloroperoxidase | 10 | Forward TGCTGCCTCCGCTCTGTCGC<br>Reverse CGCACCATGTCGCCTCTGCC | 1769 |
| Chloroperoxidase | 13 | Forward AACCGCTTTACCTGCCAGCCA<br>Reverse ATTGGGGTCGGTGCTCAGGAGT | 964 |
| Chloroperoxidase | 16 | Forward ACGGAGCACATGAACACCGTCC<br>Reverse CTTCGCACCGCGAGCAGAGG | 1777 |
| Chloroperoxidase | 19 | Forward TCCCGCGAGCCCTTGGTCTG<br>Reverse GCCCTCGCTGGTTCCTTTGCT | 1644 |
| Chloroperoxidase | 22 | Forward ATGTTTTGTTTCGCGCCGCT<br>Reverse AATCTACCACTCCCGTCCCGC | 1265 |

-continued

| Gene name | SEQ ID No. | Primer Sequence | Amplified product (bp) |
|---|---|---|---|
| Chloroperoxidase | 25 | Forward ACCGCCGCCTTCGTTTACGTC<br>Reverse GCCCGCTTACTTTGCCGGTC | 475 |
| Haem peroxidase | 28 | Forward TCGCCTGTGCTCACACCACG<br>Reverse TTAACGTCCGCCAAGCACGC | 1235 |
| Haem peroxidase | 31 | Forward CGTTCCCAAGCCCGACGACTC<br>Reverse GGGCAAGTCCCCAAGCCCATC | 1177 |
| Haem peroxidase | 34 | Forward AATGCGGTTTCTCGGGGGCT<br>Reverse TGTTGCTGGCCCTATGAAGGCAT | 1762 |
| Haem peroxidase | 37 | Forward CCATGGCAAGGCATCCCGGC<br>Reverse TGTGGCATCCCAACAGGGGC | 1172 |
| Haem peroxidase | 40 | Forward TGGACCTGGCCGTCAAACCG<br>Reverse GCCTCACAGAGCCGCACACTC | 1488 |
| Haem peroxidase | 43 | Forward CAGGCATGCGCTACGAGGCT<br>Reverse ACCAGCTTACAGACGTGCCCTGA | 800 |
| Multicopper oxidase | 46 | Forward TGGGCGGGCAGGTACGTGAAT<br>Reverse TCCGTGCTCTGGCCTCGCAT | 1935 |
| Multicopper oxidase | 49 | Forward GCTGGCGACGACAAGTGGCT<br>Reverse CCACAGAGTTCGCGAGGCCC | 2033 |
| Multicopper oxidase | 52 | Forward CATCCCACCGCGGGAAGCCT<br>Reverse ATCCCCGCCGTCACGGTTTT | 2172 |
| Multicopper oxidase | 55 | Forward TCGTTGAAGTCGCTGTCCCGT<br>Reverse GCCCCGCACACCTGCCATAG | 1944 |
| Multicopper oxidase | 58 | Forward TGCTTGCTCAAGGGCGCTCA<br>Reverse TCAACTCAGACTACTGTCGAAGTGC | 2177 |
| Multicopper oxidase | 61 | Forward CACTGGCACGGCTTCACGCA<br>Reverse CCGCTACGCGGTCGACTCCT | 4930 |
| Multicopper oxidase | 64 | Forward CACCCTCCGGTCGGGTAAGT<br>Reverse TACAGGTGCTATGCCAGCGTGC | 2116 |
| Multicopper oxidase | 67 | Forward TAGCATCGGCACAACGCCAT<br>Reverse GAACCGGTGGCCGTGAAGGTG | 1246 |
| Multicopper oxidase | 70 | Forward ACCCACCGCTCGCTCTCACA<br>Reverse TGGAAATGCGCAGAAGGACCGT | 2083 |
| Multicopper oxidase | 73 | Forward GCACGACATGTGGATTGCGGC<br>Reverse TTGCCAGCCGTGCTCCGTCA | 788 |
| Multicopper oxidase | 76 | Forward ACGACGTTGCAAGCTCCGCC<br>Reverse CCATCGGGCATAGAAGTCGCCG | 2022 |
| Multicopper oxidase | 79 | Forward TTCACCGGAGTCGCCTTCCCA<br>Reverse CGACGGGCTGCAGTACGAGA | 2249 |
| Multicopper oxidase | 82 | Forward AATCCCCTCTCACCTCGCCGC<br>Reverse GGCCACCCCTCAGAGACCGGA | 2103 |
| Multicopper oxidase | 85 | Forward CGCCGAACCAAAGCCTCCTCC<br>Reverse GCACAGGAGAAAGAGCTCACCCC | 2858 |
| Multicopper oxidase | 88 | Forward TCGCCCGTCCAGGAGAGATA<br>Reverse CCCCCATCTACCGGCCATTC | 2208 |
| Multicopper oxidase | 91 | Forward ATGAGGGGTAATCGCGACGG<br>Reverse CCCTCTCACAACTGACCCTGT | 2382 |
| Multicopper oxidase | 34 | Forward TCACTCAGTGCCCTACCGCTCC<br>Reverse CCGCAACGACTCCGTCCGGT | 1299 |
| Multicopper oxidase | 97 | Forward TGGGCTGATCCCGTTGCAGGA<br>Reverse GTAGCCGTGGCTGAGCGTGTT | 1405 |

-continued

| Gene name | SEQ ID No. | Primer Sequence | Amplified product (bp) |
|---|---|---|---|
| Multicopper oxidase | 100 | Forward TGCCGTTGCTGTAACATGCCGT<br>Reverse GACGGCGCTTTGCTCTTGCG | 2099 |
| Multicopper oxidase | 103 | Forward AGCATGCAATACTCGGTCGGTCT<br>Reverse CGGGCAGCAGGATGTTTGCCAT | 633 |
| Multicopper oxidase | 106 | Forward GGATACTCTCCGGGCACGTTCG<br>Reverse ATGGCAGTGGACTGCGCGAC | 1703 |
| Multicopper oxidase | 109 | Forward GGAGGGAGCACTGATGCGCT<br>Reverse GGCTGCTCCTCCGCTCATGG | 1873 |

Example 2

Amplification, Cloning and Sequencing of Lignin Peroxiclase, Chloroperoxidase, Haemperoxidase and Multicopper peroxidase from *M. phaseolina* ms6

Total RNA was isolated from three days old mycelium grown on liquid medium as previously described by Chomczynski P and Sacchi N, single-step method of RNA isolation by acid guanidinium thiocyanate-phenol-chloroform extraction, (Anal Biochem 1987, 162: 156-159). The quality or the integrity of the RNA was checked by agarose gel electrophoresis and was quantified using Thermo Scientific Nano Drop 2000 as per standard procedures. cDNA first strand was synthesised using Super Script III reverse transcriptase (Invitrogen) following the manufacturer's instructions. The gene was amplified from the cDNA by PCR using the gene specific primers. The PCR reaction (50 μL) contained 1 μL of cDNA, 20 pmoles of each primers, 5 μL of 10×PCR Buffer, 5 μL of 2.5 mM dNTP mix and 1.0 unit of PfuTaq DNA polymerase. PCR was carried out in Thermal Cycler (Applied Biosystems) using the following conditions: initial denaturation for 5 min at 95° C. followed by 35 cycles of denaturation at 95° C. for 30 sec, annealing at 59-61° C. for 30 sec and extension at 72° C. for 1 to 2.0 min depending on the length of the targeted gene, with a final extension at 72° C. for 7 min. The PCR product was analyzed by 1% agarose gel using 1×TAE buffer and the amplicon was eluted from the gel using QIAGEN gel extraction kit following the manufacturer's instructions. The purified PCR product was ligated into pCR®8/GW/TOPO® TA cloning kit (Invitrogen) and transformed into competent *E. coli* cells (Invitrogen). Plasmids were isolated from putative colonies using QIAprip Spin Miniprep Kit (QIAGEN) following the manufacturer's instructions. The presence of the insert was checked by using the gene specific primers and positive plasmids were subjected to Sequencing.

Example 3

Analysis of the Sequence

The nucleotide sequence and the amino acid sequence were analyzed by BLASTN and BLASTP programs respectively. The sequences reported from other plants were aligned with ClustalW. Phylogenetic analysis was carried out using the Neighbour Joining (NJ).

```
SEQ ID NO: 1
LENGTH: 1379 (including 150 bp 5' UTR and 150 bp 3' UTR)
TYPE: DNA
ORGANISM: M. phaseolina
CTGCTCAGCAGATCTTATCCCTCCAGAGCCAGAGCATCTTTAACTGACCAGCTTGCCTTCGTCCCAT

CGTTTGCATTTTTTTACACTTGACCAGTCAAGGCCCCTCTTCCTTCTTTGAGACCGCTACACCCACC

CCTTCGTACTGTCAAAATGTTATTCTCAAAGTCTTCCATCTTTCTCCTCTCCACTGCGGCCAGTGTG

CAAGCACTCAGCCTCTCCGATGTCTCCTCTGCCGCCTCGGTCCTGAAGCGTGAAGCTTCCGGCTTGG

GGAACAACCTTCTATCTCTCGTTCACCGTCGGGACTCTTGCCCTGATGTTTGGCAGAAAGTCGCATC

CGAGCTGAAGGGCTGGTTCTTGGATGGTTCCGTGTGCAGTGACGACGCACGCGCTGCCATCCGCCTC

TCTTTCCACGACTGCTTTTCCGGCGGCTGCGATGGGTCCATCATCCTTGCCCACGAGTACACCCGCT

CCGACAACGCTGGCTTAGCAGACTTTGCTATGAAGCTAGCGCCTCTCGCGGACCAGTACGAGGTCGG

AACAGCTGACCTGATCCAATTCGCTGGCGGTAAGCCTTATCTATCCACCTTAAAACAAAAAAAAAAA aGGAAAAAAaGACTATCTCTAACACCTACCTCGACCAGCCCTCGCCACGGCCACCTGTCCCCTCGGC

CCCCGCATAGCCGTCAAAGTCGGCCGCCAGGACTCGTCAACGCCCTCGGCAGAGGGACAGCTCCCCT

CGTCGCGATCCTCGGCCTCCGTCCTGATCGACCAGTTCGCGGCGAAGGGGTTCTCTGAGATAGACCT

CGTCGCCCTCGTCGGTGCCCACAGCACTGCCAAGCAGTTCTTCGATCAGCCCGACAAGGCCGGCCAA
```

```
AGCCTCGACTCCACCCCCGGCACTTGGGACACCAACTTTTACCGCCAGACGACGCTCGGCACTGCGC

CCGTTACCCTCGAGAGCGATAAGAACCTCGCCACGGATCTGAGGACCGCGGTGCAGTGGACGGCGTT

TAATGCCCAGGGCGTGTGGGCCGCGGCGTATGTGAGCGCGTAAGTAGTGCATCATATGTTTCTTCTC

TGCTCTCAGATTGTTGAGAACTAATGGTCAATGTAGGATGAACAAGATGACCGTTTTGGGCAATGAT

GTCAGCAGCTTGACGGATTGCACGAGTGTTATCAGTGCGGCAACGAGCAAGCGCGACATCAAGGCCG

CACCTATTGCGGATAGGATTTGAGCTATGCAAGCAGTTCTGGGTGAGCGAGGTCGTAGTGCGGTGAC

TGGAGTTCTGTTTTTTTTTTTTtCTTAATTGGTAATGTCTGCTCTTGTTTGATACCTGCCAGTATT

CGCGATTTATTCATCGGGAAGAGTTTAGAGAAGGGGGCA
```

```
SEQ ID NO: 2
LENGTH: 939
TYPE: DNA
ORGANISM: M. phaseolina
FEATURE NAME/KEY: CDS
LOCATION: (1) . . . (939)
atgttattctcaaagtcttccatctttctcctctccactgcggccagtgtgcaagcactc
 M  L  F  S  K  S  S  I  F  L  L  S  T  A  A  S  V  Q  A  L agcctctccgatgtctcctctgccgcctcggtcctgaagcgtgaagcttccggcttgggg
 S  L  S  D  V  S  S  A  A  S  V  L  K  R  E  A  S  G  L  G aacaaccttctatctctcgttcaccgtcgggactcttgccctgatgtttggcagaaagtc
 N  N  L  L  S  L  V  H  R  R  D  S  C  P  D  V  W  Q  K  V gcatccgagctgaagggctggttcttggatggttccgtgtgcagtgacgacgcacgcgct
 A  S  E  L  K  G  W  F  L  D  G  S  V  C  S  D  D  A  R  A gccatccgcctctcttccacgactgcttttccggcggctgcgatgggtccatcatcctt
 A  I  R  L  S  F  H  D  C  F  S  G  G  C  D  G  S  I  I  L gcccacgagtacaccgctccgacaacgctggcttagcagactttgctatgaagctagcg
 A  H  E  Y  T  R  S  D  N  A  G  L  A  D  F  A  M  K  L  A cctctcgcggaccagtacgaggtcggaacagctgacctgatccaattcgctggcgccctc
 P  L  A  D  Q  Y  E  V  G  T  A  D  L  I  Q  F  A  G  A  L gccacggccacctgtcccctcggcccccgcatagccgtcaaagtcggccgccaggactcg
 A  T  A  T  C  P  L  G  P  R  I  A  V  K  V  G  R  Q  D  S tcaacgccctcggcagagggacagctcccctcgtcgcgatcctcggcctccgtcctgatc
 S  T  P  S  A  E  G  Q  L  P  S  S  R  S  S  A  S  V  L  I gaccagttcgcggcgaaggggttctctgagatagacctcgtcgcctcgtcggtgcccac
 D  Q  F  A  A  K  G  F  S  E  I  D  L  V  A  L  V  G  A  H agcactgccaagcagttcttcgatcagcccgacaaggccggccaaagcctcgactccacc
 S  T  A  K  Q  F  F  D  Q  P  D  K  A  G  Q  S  L  D  S  T cccggcacttgggacaccaacttttaccgccagacgacgctcggcactgcgcccgttacc
 P  G  T  W  D  T  N  F  Y  R  Q  T  T  L  G  T  A  P  V  T ctcgagagcgataagaacctcgccacggatctgaggaccgcggtgcagtggacggcgttt
 L  E  S  D  K  N  L  A  T  D  L  R  T  A  V  Q  W  T  A  F aatgcccagggcgtgtgggccgcggcgtatgtgagcgcgatgaacaagatgaccgttttg
 N  A  Q  G  V  W  A  A  A  Y  V  S  A  M  N  K  M  T  V  L ggcaatgatgtcagcagcttgacggattgcacgagtgttatcagtgcggcaacgagcaag
 G  N  D  V  S  S  L  T  D  C  T  S  V  I  S  A  A  T  S  K cgcgacatcaaggccgcacctattgcggataggatttga
 R  D  I  K  A  A  P  I  A  D  R  I  -
```

```
SEQ ID NO: 3
LENGTH: 312
TYPE: PRT
ORGANISM: M. phaseolina
MLFSKSSIFLLSTAASVQALSLSDVSSAASVLKREASGLGNNLLSLVHRRDSCPDVWQKVASELKGW

FLDGSVCSDDARAAIRLSFHDCFSGGCDGSIILAHEYTRSDNAGLADFAMKLAPLADQYEVGTADLI

QFAGALATATCPLGPRIAVKVGRQDSSTPSAEGQLPSSRSSASVLIDQFAAKGFSEIDLVALVGAHS
```

TAKQFFDQPDKAGQSLDSTPGTWDTNFYRQTTLGTAPVTLESDKNLATDLRTAVQWTAFNAQGVWAA

AYVSAMNKMTVLGNDVSSLTDCTSVISAATSKRDIKAAPIADRI*

SEQ ID NO: 4
LENGTH: 1416 (including 150 bp 5' UTR and 150 bp 3' UTR)
TYPE: DNA
ORGANISM: M. phaseolina
TCTATATCTTGCCCTTCGCCTGTTCGCTTCAGGAGAACCCAACGCCAACATTCATTCTCAACCTCCT

CTTTGAGTTACAATCGCTACTCTGGGAAATTTGTCCCAGCCTTTCATTCAACAACTGTTTCTGTTTC

AAACCAATCCGACGCCATGAAGTTCTCCACAGTCATCTCGAGCGTTGCTCTCACTTCTCTACTCCAG

CCCGCCCTTGCCTACCCTGGCATGGCAAATGTCGTCTCGGAGATCAAGGCCCGTCAAAACACCAATA

ATGATGGTGACTCAAATCCCGAGATGATTGGCGATCTCGCCACCACCGGCCCAACCACCCCTGTGGG

CCAAAGCATATACAACATCCTGATGGGGACCGAGTCGGCCGAGACCAAGCAGGCTGGCTACATCCCC

CCTCTTATCGGCACCAACGCCTGCAAGAGGGACACCTGCTGCATCTGGGCCTACATCGCCGCCGAAC

TGACCCTCAATTTCAAGGGCATCACGGGCCGCTGCAACAAGAACGCGCGTGCCGCCATTCGGCTCGG

CTTCCACGACGCGGGGACTTGGTCCAAGAGCAGCAACGGCGGCGCGGACGGCTCGATCGCGCTG

TCGGGCACGGAGATCAACAAGGCCGAGAACAACGGGCTGCAGGACATCATCGGCAAGATGATCACGT

GGCAGAAGCGGTACGGGGTGGGCATGGCGGATCTGATCCAGTTCGCGGCCATCCACGCCGTGGTGAC

GTGCCCGCTGGGGCCGCGCATCCGCTTCTTCGTCGGGCGCAAGGACAGCAAAACGGCCAACGACGTC

AGCCTGCTGCCGGGCGTCAACGATTCGGCCGACAAGCTGATCGCGCTCTTCCAGGACAAGACCATCA

CGCCGCACGAGCTCGCCGCCCTGCTCGGCGCCCACACCACCTCACAGCAGTTCTTCGTCGACACCAC

CCGCGCCGGCGCCCCCAGGACAGCACCCCCGGCGTCTGGGACACCCGCTTCTACAACCAAACCACC

TCCGACCAAGTTCCCAAGAAGGTCTTCCGCTTCGCCAGCGACGTTGTGCTGGCCAAGGACCCGCGTA

TGAGTGATGAGTGGGCCGCCTTCGCCGACCCCGTCAAGGGCCAGAACCACTGGAATGAGGATTACGC

CACCGCCTATACCCGCCTCAGCCTGCTCGGCGTCAACAACATCAATAACTTGACTGAGTGCAGCAAG

GTGCTGCCGTGGGCGCAACCGAAGTTCCCCGATGCCTGGAACCTGTTCTTGGACCAGTAGAGTGTAG

TTTCTTCTTAATATCTGGCGTTCTTGGGGGTTTGGTCAAAAAGGAGAAAGATATTATTGTCGATATT

TGGTATACCCTAATGTTGGGAACTATACATACGTATACAGGCTTCTTGTAATTACTCGGGCATCTTT

TGCACAGAG

SEQ ID NO: 5
LENGTH: 1116
TYPE: DNA
ORGANISM: M. phaseolina
FEATURE NAME/KEY: CDS
LOCATION: (1) . . . (1116)
atgaagttctccacagtcatctcgagcgttgctctcacttctctactccagcccgcccectt
 M  K  F  S  T  V  I  S  S  V  A  L  T  S  L  L  Q  P  A  L gcctaccctggcatggcaaatgtcgtctcggagatcaaggcccgtcaaaacaccaataat
 A  Y  P  G  M  A  N  V  V  S  E  I  K  A  R  Q  N  T  N  N gatggtgactcaaatcccgagatgattggcgatctcgccaccaccggcccaaccacccct
 D  G  D  S  N  P  E  M  I  G  D  L  A  T  T  G  P  T  T  P gtgggccaaagcatatacaacatcctgatggggaccgagtcggccgagaccaagcaggct
 V  G  Q  S  I  Y  N  I  L  M  G  T  E  S  A  E  T  K  Q  A ggctacatccccctcttatcggcaccaacgcctgcaagagggacacctgctgcatctgg
 G  Y  I  P  P  L  I  G  T  N  A  C  K  R  D  T  C  C  I  W gcctacatcgccgccgaactgaccctcaatttcaagggcatcacgggccgctgcaacaag
 A  Y  I  A  A  E  L  T  L  N  F  K  G  I  T  G  R  C  N  K aacgcgcgtgccgccattcggctcggcttccacgacgcggggacttggtccaagagcagc
 N  A  R  A  A  I  R  L  G  F  H  D  A  G  T  W  S  K  S  S aacggcggcggcgcggacggctcgatcgcgctgtcgggcacggagatcaacaaggccgag
 N  G  G  G  A  D  G  S  I  A  L  S  G  T  E  I  N  K  A  E

```
aacaacgggctgcaggacatcatcggcaagatgatcacgtggcagaagcggtacggggtg
 N  N  G  L  Q  D  I  I  G  K  M  I  T  W  Q  K  R  Y  G  V ggcatggcggatctgatccagttcgcggccatccacgccgtggtgacgtgcccgctgggg
 G  M  A  D  L  I  Q  F  A  A  I  H  A  V  V  T  C  P  L  G ccgcgcatccgcttcttcgtcgggcgcaaggacagcaaaacggccaacgacgtcagcctg
 P  R  I  R  F  F  V  G  R  K  D  S  K  T  A  N  D  V  S  L ctgccgggcgtcaacgattcggccgacaagctgatcgcgctcttccaggacaagaccatc
 L  P  G  V  N  D  S  A  D  K  L  I  A  L  F  Q  D  K  T  I acgccgcacgagctcgccgccctgctcggcgcccacaccacctcacagcagttcttcgtc
 T  P  H  E  L  A  A  L  L  G  A  H  T  T  S  Q  Q  F  F  V gacaccacccgcgccggcgcccccaggacagcaccccggcgtctgggacacccgcttc
 D  T  T  R  A  G  A  P  Q  D  S  T  P  G  V  W  D  T  R  F tacaaccaaaccacctccgaccaagttcccaagaaggtcttccgcttcgccagcgacgtt
 Y  N  Q  T  T  S  D  Q  V  P  K  K  V  F  R  F  A  S  D  V gtgctggccaaggacccgcgtatgagtgatgagtgggccgccttcgccgaccccgtcaag
 V  L  A  K  D  P  R  M  S  D  E  W  A  A  F  A  D  P  V  K ggccagaaccactggaatgaggattacgccaccgcctataccgcctcagcctgctcggc
 G  Q  N  H  W  N  E  D  Y  A  T  A  Y  T  R  L  S  L  L  G gtcaacaacatcaataacttgactgagtgcagcaaggtgctgccgtgggcgcaaccgaag
 V  N  N  I  N  N  L  T  E  C  S  K  V  L  P  W  A  Q  P  K ttccccgatgcctggaacctgttcttggaccagtag
 F  P  D  A  W  N  L  F  L  D  Q  -

SEQ ID NO: 6
LENGTH: 371
TYPE: PRT
ORGANISM: M. phaseolina
MKFSTVISSVALTSLLQPALAYPGMANVVSEIKARQNTNNDGDSNPEMIGDLATTGPTTPVGQSIYN

ILMGTESAETKQAGYIPPLIGTNACKRDTCCIWAYIAAELTLNFKGITGRCNKNARAAIRLGFHDAG

TWSKSSNGGGADGSIALSGTEINKAENNGLQDIIGKMITWQKRYGVGMADLIQFAAIHAVVTCPLGP

RIRFFVGRKDSKTANDVSLLPGVNDSADKLIALFQDKTITPHELAALLGAHTTSQQFFVDTTRAGAP

QDSTPGVWDTRFYNQTTSDQVPKKVFRFASDVVLAKDPRMSDEWAAFADPVKGQNHWNEDYATAYTR

LSLLGVNNINNLTECSKVLPWAQPKFPDAWNLFLDQ*

SEQ ID NO: 7
LENGTH: 1323 (including 150 bp 5' UTR and 150 bp 3' UTR)
TYPE: DNA
ORGANISM: M. phaseolina
TCGAGATGGCGGCTCTCTCGCAGACGTAAATCTATAAAGCCTTGCCGCGACTTTCTTTTGTGTATCT

CATCAGCATCGAGTTCCACAAGAGCTTGCTTCCTCTCCTCACTGAGCCTAGCGAGGAGCATCACTCA

GAACCCTCCAATCACAATGCGGACCTCATCCCTGTTCCTTGCTTCCGCATGCGGAACATCTGCTTAC

ACTCTCGTCTCGCTCGACTCTCTGCCAAGCACTCTTCATGACATAACCTCCCGCACCATCTCCAACC

TCGACCCCGCAACCTCCTCTCCGCGCGCAAGACGCCCGACTGCCCGGCCATCTGGAGGACCATCTC

AGCCGACCTGACCAAGAGCTTCCTCGCCAACGGCGAGTGCACCGACCTCGCCCGCGCCGCCATCCGC

TACGCCTTCCACGACGCGGGCACCTTCTCGCTCAAGCTGCCCACCTACGCGCCGGCCTCCGGCGGCG

CCGACGGCTCGCTGCTGCTCGTCGATTCGGAGATCCAGCGGCCCGAGAACAACGGGCTGCAGGCGTA

CAACGACTTCATCAAGGCCAAGTACAGCACGTACAAGTCCTCGGGCGTCGGCGCCGCCGACCTGATC

CAGTTCGCCGGCAACCACGCCGTGGTGACGTGCCCGGGCGGGCCCACGGTCAAGACGCTCGTCGGCC

GCGGCGACAGCACGACCGCGTCGCCGCTGAACGTGATGCCGCCGGGGTTCGGCGCGGGCAGCGACCA

CGACTCGCTGCTCCAGCTCTTCCAGGACAAGGGGTTCAGCGCCGTCGACCTGGCCGCGCTGATCGGC

GCCCACACCACCTCCACGAACATCGCGGAGGCGCAGATCCCCGTCGGCGCGCCGCAGGACAGCACGC

CGGGCAGGTGGGACGTCAAGTACTACGCCGAGACGTACGCCCCGCCCGCGGGCGTCTCCCGCTTCGC
```

```
CTCCGACATCAACCTCTCCGACCCGACGAAAGCGGTCGGCAAAGAGTTCCAGGGATTCGTCAACAAC
CAGGGTAAGTGGACGGGCAAGTTTGCCGACGCCATGTTCCGTCTGAGTGTGTTGGGCATCCCGCCGG
CGACGTACAAGAATTTCGCGGACTGCACCGCTGCGCTGCCCAAGGGCACGAGCGCCAAGCGGGACAT
CCGCAGCGCCCCGATCAACGACCGCGCAAGGTAGAGGAGGGGAAAAGAAAGGAAGAAAAGAAAATAA
AAAGCGCAGCGAGGATGAATCGGTTGGGGCAGGGCGTTTCGGTTGAGGTTGTTTGTTTGCTCGCCTG
CCTTTTTTTTTTTTtAATCCCTCTCATGATCCATCGAATGAGAACACTT

SEQ ID NO: 8
LENGTH: 1023
TYPE: DNA
ORGANISM: M. phaseolina
FEATURE NAME/KEY: CDS
LOCATION: (1) . . . (1023)
atgcggacctcatccctgttccttgcttccgcatgcggaacatctgcttacactctcgtc
 M   R   T   S   S   L   F   L   A   S   A   C   G   T   S   A   Y   T   L   V tcgctcgactctctgccaagcactcttcatgacataacctcccgcaccatctccaacctc
 S   L   D   S   L   P   S   T   L   H   D   I   T   S   R   T   I   S   N   L gaccccgcaacctcctctccgcgcgcaagacgcccgactgcccggccatctggaggacc
 D   P   R   N   L   L   S   A   R   K   T   P   D   C   P   A   I   W   R   T atctcagccgacctgaccaagagcttcctcgccaacggcgagtgcaccgactcgcccgc
 I   S   A   D   L   T   K   S   F   L   A   N   G   E   C   T   D   L   A   R gccgccatccgctacgccttccacgacgcgggcaccttctcgctcaagctgcccacctac
 A   A   I   R   Y   A   F   H   D   A   G   T   F   S   L   K   L   P   T   Y gcgccggcctccggcggcgccgacggctcgctgctgctcgtcgattcggagatccagcgg
 A   P   A   S   G   G   A   D   G   S   L   L   L   V   D   S   E   I   Q   R cccgagaacaacgggctgcaggcgtacaacgacttcatcaaggccaagtacagcacgtac
 P   E   N   N   G   L   Q   A   Y   N   D   F   I   K   A   K   Y   S   T   Y aagtcctcgggcgtcggcgccgccgacctgatccagttcgccggcaaccacgccgtggtg
 K   S   S   G   V   G   A   A   D   L   I   Q   F   A   G   N   H   A   V   V acgtgcccgggcgggcccacggtcaagacgctcgtcggccgcggcgacagcacgaccgcg
 T   C   P   G   G   P   T   V   K   T   L   V   G   R   G   D   S   T   T   A tcgccgctgaacgtgatgccgccggggttcggcgcgggcagcgaccacgactcgctgctc
 S   P   L   N   V   M   P   P   G   F   G   A   G   S   D   H   D   S   L   L cagctcttccaggacaagggggttcagcgccgtcgacctggccgcgctgatcggcgcccac
 Q   L   F   Q   D   K   G   F   S   A   V   D   L   A   A   L   I   G   A   H accacctccacgaacatcgcggaggcgcagatccccgtcggcgcgccgcaggacagcacg
 T   T   S   T   N   I   A   E   A   Q   I   P   V   G   A   P   Q   D   S   T ccgggcaggtgggacgtcaagtactacgccgagacgtacgccccgcccgcgggcgtctcc
 P   G   R   W   D   V   K   Y   Y   A   E   T   Y   A   P   P   A   G   V   S cgcttcgcctccgacatcaacctctccgacccgacgaaagcggtcggcaaagagttccag
 R   F   A   S   D   I   N   L   S   D   P   T   K   A   V   G   K   E   F   Q ggattcgtcaacaaccagggtaagtggacgggcaagtttgccgacgccatgttccgtctg
 G   F   V   N   N   Q   G   K   W   T   G   K   F   A   D   A   M   F   R   L agtgtgttgggcatcccgccggcgacgtacaagaatttcgcggactgcaccgctgcgctg
 S   V   L   G   I   P   P   A   T   Y   K   N   F   A   D   C   T   A   A   L cccaagggcacgagcgccaagcgggacatccgcagcgccccgatcaacgaccgcgcaagg
 P   K   G   T   S   A   K   R   D   I   R   S   A   P   I   N   D   R   A   R tag
 -

SEQ ID NO: 9
LENGTH: 340
TYPE: PRT
ORGANISM: M. phaseolina
MRTSSLFLASACGTSAYTLVSLDSLPSTLHDITSRTISNLDPRNLLSARKTPDCPAIWRTISADLTK

SFLANGECTDLARAAIRYAFHDAGTFSLKLPTYAPASGGADGSLLLVDSEIQRPENNGLQAYNDFIK
```

-continued

AKYSTYKSSGVGAADLIQFAGNHAVVTCPGGPTVKTLVGRGDSTTASPLNVMPPGFGAGSDHDSLLQ

LFQDKGFSAVDLAALIGAHTTSTNIAEAQIPVGAPQDSTPGRWDVKYYAETYAPPAGVSRFASDINL

SDPTKAVGKEFQGFVNNQGKWTGKFADAMFRLSVLGIPPATYKNFADCTAALPKGTSAKRDIRSAPI

NDRAR*

SEQ ID NO: 10
LENGTH: 1930 (including 150 bp 5' UTR and 150 bp 3' UTR)
TYPE: DNA
ORGANISM: M. phaseolina
GAGCACGGCAGGTAGGTTGCATCCGAGAGGTCGTGGTAGGTAGGTATATATTGCTGCCTCCGCTCTG

TCGCTCTATAGAGGCAGGTCTTGGACATCTGTGAACAGGTTACCTTCTCATAATTTGATCCATTGGC

GAAGATATACTCAAGAATGCCGTCTACCTGGATGATTGCATTGGGCGCACTCACCcTTGCCGGCCAG

TCCGCAGCCTTTCCTGCTGTGGCAGAACAATACGCTGCTCAGACATCTCACAAGGAGAAAAGAGTAA

ATGCAATTAGCCCCGGGTTCAATGCGGCGGCACAGAGGATTGACGTCTCGGGAGCTCACACTTTCGT

GCCCCCTGGCCCCGGTGACCAGAGAGGGCCCTGCCCGGGTCTGAATGCCTTAGCGAACCAGTAAGTG

CTCTGCAAGTCTCACAGGTCTTCTTGTACTGACAAAGTGTAGCAACTATTTGCCCCAGTGAGTTCTC

CACAACTTCATTCCCGAAACCTTGTCACTGATTGTCTTCAGCAATGGCGTCGCAACAATCACGCAGT

TCGTCCAGGCCACAAACCAGGGTTAGTACAGCATCACCGCCACGGAAGCTACTACGTCAGCTGAACC

ACATACGCAGTATACGGCATGGGTCTCGACCTTGGCACGTTCCTGTCCGTCTACGGCGCGGTAATGG

ATGGCGACGGCCTCAGCTGGTCCATCGGCGGCGCGCCCAGTACCGCAAACCTACTCAACCTCCTTAC

TCAGCCGCAAGGCCTCTCAGGTTCGCACAACAAGTACGAGACAGATGCATCGCCTACGCGCGGAGAC

CTGTACCAATAGTGCGTCTATCCCCTTCTTCTGCCTCCCGCCACTCCGCTGACCTGCACCGCAGTGG

CGACAACTCCCGGGTCGTCATTTCGCAATGGGACGCCCTCTTCGCGAAGCAAGCGGCACTGCCCAAT

GACCAGTCCAATTATGGCCTAGGTGTGCTGACCGACTTCCGAGTCGAGCGTTTCCAGCAGAGCGTCG

ATGAAAACCCCTACTTCTTCAACGCGCCCTTTTCCGGTGTGCTCGTGCAGCCTGCCGCGTACACATT

CATCTACCGCTTCATGGGCAACAAGAGCGCCGAGAAACCCGAGGGTGTGCTGACGAAAGAGGTGCTG

AAGAGCTTCTTCGGCTTCACTGGGCCTGACGACGACATGACATACGTGAGTCCCATCCCGCCGCCTT

TCTCATTTCTTCCCACTCGAGTCTCCCACATCCCCCCCCCCCCCCCCCCCcACcATTTGTTG

TCGCCCTTCCCTCCAGCCACGCCACTGCCCACAACGCCACCGTCTGACCCACCGCAGAACCCCGGCC

ACGAGCGCATCCCCGAAAACTGGTACAAGCGCGCCCCCGGCGACGAATACACGATCCCCTTCTACGC

ACTTGACCTCAACGCCGCGGCGCTGCAGCACCCGCAATTCCTGTCCGTCGGCGGCAACACGGGCACC

ACCAACTCCTTCGCCGGCGTCGACCTGCAGGACCTGAGCGGCGGCCTGTACAACGCCGCCAGCCTGC

TCGAGGGCAACAACCTCGCCTGCTTCGGTTTCCAGGCGGCCGTCCAATTCGCGCCGGACCTGTTGAA

AGGGCTGGTGAGCGATTTGACCAAGCCGTTGGGTGTCCTGGGAGATGCGTTGGCGAGTGCGTTGAAT

GGATTAGGGTGTCCGCAGTTAGGCGGCCAGGCGTGGGATGATAGCGCGCTGGCGCAGTTTCCGGGGT

ATGCTAGGCTGAGGGCGGATGGGACGTACGGGAAGTAATGGACGCGGAGAAGTAGTGTGGCAGAGGC

GACATGGTGCGCATGGTGGACTGCGGCTTCAACGACAATGCAGAGATGATGGTATGAGGAAACTGCA

CAGCAGTCTGCATGGATTTGCTAGACTAGACGAATTTTATGATTTTGAATGAAC

SEQ ID NO: 11
LENGTH: 1260
TYPE: DNA
ORGANISM: M. phaseolina
FEATURE NAME/KEY: CDS
LOCATION: (1) . . . (1260)
atgccgtctacctggatgattgcattgggcgcactcacccttgccggccagtccgcagcc
 M  P  S  T  W  M  I  A  L  G  A  L  T  L  A  G  Q  S  A  A tttcctgctgtggcagaacaatacgctgctcagacatctcacaaggagaaaagagtaaat
 F  P  A  V  A  E  Q  Y  A  A  Q  T  S  H  K  E  K  R  V  N

```
gcaattagccccgggttcaatgcggcggcacagaggattgacgtctcgggagctcacact
 A  I  S  P  G  F  N  A  A  A  Q  R  I  D  V  S  G  A  H  T ttcgtgcccctggccccggtgaccagagagggccctgcccgggtctgaatgccttagcg
 F  V  P  P  G  P  G  D  Q  R  G  P  C  P  G  L  N  A  L  A aaccacaatggcgtcgcaacaatcacgcagttcgtccaggccacaaaccaggtatacggc
 N  H  N  G  V  A  T  I  T  Q  F  V  Q  A  T  N  Q  V  Y  G atgggtctcgaccttggcacgttcctgtccgtctacggcgcggtaatggatggcgacggc
 M  G  L  D  L  G  T  F  L  S  V  Y  G  A  V  M  D  G  D  G ctcagctggtccatcggcggcgcgcccagtaccgcaaacctactcaacctccttactcag
 L  S  W  S  I  G  G  A  P  S  T  A  N  L  L  N  L  L  T  Q ccgcaaggcctctcaggttcgcacaacaagtacgagacagatgcatcgcctacgcgcgga
 P  Q  G  L  S  G  S  H  N  K  Y  E  T  D  A  S  P  T  R  G gacctgtaccaatatggcgacaactcccgggtcgtcatttcgcaatgggacgccctcttc
 D  L  Y  Q  Y  G  D  N  S  R  V  V  I  S  Q  W  D  A  L  F gcgaagcaagcggcactgcccaatgaccagtccaattatggcctaggtgtgctgaccgac
 A  K  Q  A  A  L  P  N  D  Q  S  N  Y  G  L  G  V  L  T  D ttccgagtcgagcgtttccagcagagcgtcgatgaaaaccccctacttcttcaacgcgccc
 F  R  V  E  R  F  Q  Q  S  V  D  E  N  P  Y  F  F  N  A  P ttttccggtgtgctcgtgcagcctgccgcgtacacattcatctaccgcttcatgggcaac
 F  S  G  V  L  V  Q  P  A  A  Y  T  F  I  Y  R  F  M  G  N aagagcgccgagaaacccgagggtgtgctgacgaaagaggtgctgaagagcttcttcggc
 K  S  A  E  K  P  E  G  V  L  T  K  E  V  L  K  S  F  F  G ttcactgggcctgacgacgacatgacatacaaccccggccacgagcgcatccccgaaaac
 F  T  G  P  D  D  D  M  T  Y  N  P  G  H  E  R  I  P  E  N tggtacaagcgcgcccccggcgacgaatacacgatccccttctacgcacttgacctcaac
 W  Y  K  R  A  P  G  D  E  Y  T  I  P  F  Y  A  L  D  L  N gccgcggcgctgcagcacccgcaattcctgtccgtcggcggcaacacgggcaccaccaac
 A  A  A  L  Q  H  P  Q  F  L  S  V  G  G  N  T  G  T  T  N tccttcgccggcgtcgacctgcaggacctgagcggcggcctgtacaacgccgccagcctg
 S  F  A  G  V  D  L  Q  D  L  S  G  G  L  Y  N  A  A  S  L ctcgagggcaacaacctcgcctgcttcggttttccaggcggccgtccaattcgcgccggac
 L  E  G  N  N  L  A  C  F  G  F  Q  A  A  V  Q  F  A  P  D ctgttgaaagggctggtgagcgatttgaccaagccgttgggtgtcctgggagatgcgttg
 L  L  K  G  L  V  S  D  L  T  K  P  L  G  V  L  G  D  A  L gcgagtgcgttgaatggattagggtgtccgcagttaggcggccaggcgtgggatgatagc
 A  S  A  L  N  G  L  G  C  P  Q  L  G  G  Q  A  W  D  D  S gcgctggcgcagttccgggggtatgctaggctgagggcggatgggacgtacgggaagtaa
 A  L  A  Q  F  P  G  Y  A  R  L  R  A  D  G  T  Y  G  K  -
```

SEQ ID NO: 12
LENGTH: 419
TYPE: PRT
ORGANISM: M. phaseolina
MPSTWMIALGALTLAGQSAAFPAVAEQYAAQTSHKEKRVNAISPGFNAAAQRIDVSGAHTFVPPGPG

DQRGPCPGLNALANHNGVATITQFVQATNQVYGMGLDLGTFLSVYGAVMDGDGLSWSIGGAPSTANL

LNLLTQPQGLSGSHNKYETDASPTRGDLYQYGDNSRVVISQWDALFAKQAALPNDQSNYGLGVLTDF

RVERFQQSVDENPYFFNAPFSGVLVQPAAYTFIYRFMGNKSAEKPEGVLTKEVLKSFFGFTGPDDDM

TYNPGHERIPENWYKRAPGDEYTIPFYALDLNAAALQHPQFLSVGGNTGTTNSFAGVDLQDLSGGLY

NAASLLEGNNLACFGFQAAVQFAPDLLKGLVSDLTKPLGVLGDALASALNGLGCPQLGGQAWDDSAL

AQFPGYARLRADGTYGK*

SEQ ID NO: 13
LENGTH: 1108 (including 150 bp 5' UTR and 150 bp 3' UTR)
TYPE: DNA
ORGANISM: M. phaseolina
CTGATGGTATGTACTTTGGTAAGCACGCCATTAACTACTCGCTCCATCGCCTCGAGTTACCCTGTTG

```
GAGCAGCAACCACAACTTGAGCGAACAAATTCGGCCATTAATACCATCGTACGAAGAAGGCTTAACC

GCTTTACCTGCCAGCCATGAATCCAATCTGCTTTTTATCCCTGCTCACGGCCATGCTAGGCATGGCC

ATGGGCGGTGGAAACCCTCTGAACCATGCTGAACCTTTTGATCCCACGAACAGCTTGTGGGTGTGAC

TGATGCGCATGAGCCCATTCTTCCTGATATCACCAACGCTCGCAGCCCCTGTCCCGGCCTTAACACG

TTGGCGAACCAGGAAGCTCATTCGCCCCTTGCTATGAAGAAAACCTGGAATTTACGCTCCTCCCGG

TGGCTTCGACGGTGTCGCGAACTACGATGAACTTGTTAAGGCTCTGGTTGATAGTGTGTTGCTTTTG

ATCGGGGGTCACCACCTTTCGGTTGACGAGAACATCACGATTCCGCCTAATAATTTCACACGCAGCC

TCAGCGGCACACAAATCTCCCTAGATTCTGAGGCCTCGCCTACACGCCACGACGCGTACGACCCTCG

GGCCTACTCCGGCTCGAGCAGCATCGAAATGAAGTGGAACTTCTTCAAACAGCTGTACGAGAAGCAG

GCCGGGATCCCACGCGATGCGGTTAACTTTGCACTGGATGTTCTTGCTCAAAACATGTTGGAGCTGG

TGGTGGTCAGCATCAAGAACAACCCGAACTTCTTCCTGAGCCCAACGCACATCGCATTCGGACCATC

GACGGCCCACATGTGCATTCCCAACTTGTTCGCGAACCACAGCACTGAGCATTGGCTGACCTCTCTC

CTGAATAGAGAGGGAGGGTCTCGCCATTCATTCCATGCTCAAACTATGACGCTTTGTAGTCTTCAGC

TCAGATTGTCACCAATCTGAAGGCGAGATCCCACTTCTATACTCAGATTAAAGACCTAATAATACAA

TCGTATACTCAGCGAGAGAAGCACGAGAAGGACCGAGCCAACATTCACCTCATCCTTCACACAACAC

ACTCCTGAGCACCGACCCCAATTCTAAATCAGCCCC
```

```
SEQ ID NO: 14
LENGTH: 690
TYPE: DNA
ORGANISM: M. phaseolina
FEATURE NAME/KEY: CDS
LOCATION: (1)...(690)
atgaatccaatctgctttttatccctgctcacggccatgctaggcatggccatgggcggt
 M   N   P   I   C   F   L   S   L   L   T   A   M   L   G   M   A   M   G   G ggaaaccctctgaaccatgctgaaccttttgatcccacgaacagcttaaaacctggaatt
 G   N   P   L   N   H   A   E   P   F   D   P   T   N   S   L   K   P   G   I tacgctcctcccggtggcttcgacggtgtcgcgaactacgatgaacttgttaaggctctg
 Y   A   P   P   G   G   F   D   G   V   A   N   Y   D   E   L   V   K   A   L gttgatagtgtgttgcttttgatcgggggtcaccacctttcggttgacgagaacatcacg
 V   D   S   V   L   L   L   I   G   G   H   H   L   S   V   D   E   N   I   T attccgcctaataatttcacacgcagcctcagcggcacacaaatctccctagattctgag
 I   P   P   N   N   F   T   R   S   L   S   G   T   Q   I   S   L   D   S   E gcctcgcctacacgccacgacgcgtacgaccctcgggcctactccggctcgagcagcatc
 A   S   P   T   R   H   D   A   Y   D   P   R   A   Y   S   G   S   S   S   I gaaatgaagtggaacttcttcaaacagctgtacgagaagcaggccgggatcccacgcgat
 E   M   K   W   N   F   F   K   Q   L   Y   E   K   Q   A   G   I   P   R   D gcggttaactttgcactggatgttcttgctcaaaacatgttggagctggtggtggtcagc
 A   V   N   F   A   L   D   V   L   A   Q   N   M   L   E   L   V   V   V   S atcaagaacaacccgaacttcttcctgagcccaacgcacatcgcattcggaccatcgacg
 I   K   N   N   P   N   F   F   L   S   P   T   H   I   A   F   G   P   S   T gcccacatgtgcattcccaacttgttcgcgaaccacagcactgagcattggctgacctct
 A   H   M   C   I   P   N   L   F   A   N   H   S   T   E   H   W   L   T   S ctcctgaatagagagggagggtctcgccattcattccatgctcaaactatgacgctttgt
 L   L   N   R   E   G   G   S   R   H   S   F   H   A   Q   T   M   T   L   C agtcttcagctcagattgtcaccaatctga
 S   L   Q   L   R   L   S   P   I   -
```

```
SEQ ID NO: 15
LENGTH: 229
TYPE: PRT
ORGANISM: M. phaseolina
MNPICFLSLLTAMLGMAMGGNPLNHAEPFDPTNSLKPGIYAPPGGFDGVANYDELVKALVDSVLLL
```

-continued

IGGHHLSVDENITIPPNNFTRSLSGTQISLDSEASPTRHDAYDPRAYSGSSSIEMKWNFFKQLYEKQ

AGIPRDAVNFALDVLAQNMLELVVVSIKNNPNFFLSPTHIAFGPSTAHMCIPNLFANHSTEHWLTSL

LNREGGSRHSFHAQTMTLCSLQLRLSPI*

SEQ ID NO: 16
LENGTH: 1554 (including 150 bp 5' UTR and 150 bp 3' UTR)
TYPE: DNA
ORGANISM: M. phaseolina
AAGCCTTGCTGGATCGACCTTTTTCAATTCCGGCAGATACACCCAAGTCATTGAACATCGAAACAGT

ACTTGCCTTCGTCAAATATGCGGTCACTCTTCCTTGCTTCCTTATTACTTTCTGCGGCGTCCGCTTT

CCCTTTCGTGGCAGATATGCCAGAGGTAGACTCTTCTCTCTTCCGTGAAGCACCCGTACGTAGGCAA

CAACCTGGCGGCAACCAACCTGGCGGAGCGGCGACTTGCCCTTTCAATGCCAACCACGTCCCCGCTG

CGCCAGTGACAGCTCGATTTCCCTATAACAACGCAAAGAACGGAGTTCCCGGCAACGGAAAGGGCGG

TTACCAGGTTCCAGCGCCTGGTGACACGGCTCATCAGTTCATTGCACCAACAGCGCACGATATCCGT

GGGCCTTGCCCGGGCCTGAACGCTGCGGCCAATCACGGCGTGAGTCTTTCCTGTAGTCCCCATTCGA

GTTTCAAGTCTCCTGACGGTGACCCTAAACAGTTCCTCGCGCGCGACGGCATAGTGACCTTCAACGA

ACTGGTCGACGCCCAGCAGAATGTCTACAATGTCGGCTACGACCTCTCTGTGCTGCTCGCCGTCCTC

GGCCTCACGCTCACCGACGGTGACCCCATCACCCAAAAACTGTCTATCGGCTGCGACGCAACGACAC

GCACATCTGTGGCCCCCCTGCTGACTGGCAGTCAGCCCGGTCTGGATGGCCACAACAAGTTCGAAGC

GGACACGTCGCTCACACGCAACGACTACTTCCTGGCGGGCGGCGACAACTTCAACTTCAACGGCACG

CTCTTCGGCATGATGGTGGATACGTGCCAGGGCAACTTCAACCGTGAGAACCTGGCGCTGTACCGCA

AGCAGCGCTACGACCAGAGCCTACGCGACAACGAGAACTTCTACTTCGGCCCGCTAAGCCTGCTGCT

GTTCGGCGCCGCCAGCTTCCTTTACGAGCTGATGCCCAGCGGCACGCACAACTACGCGCCCGATCTC

GACACCATCTCGTCCTTCTTCGGCGCCGAGCAGGCGCCCGATGGCTCCTGGCGCTTCACCGCCGAGC

GTATCCCGGACAACTGGACCAACCGTGTGCTGCCGTACACCAATGAGGACGTGACGCGCGAAATCCT

GGCTATGTACCTCCTCAACCCTGTGCTATTTGGCGGCGCCACAGGCGACGGCGGCTTCAACACGCTG

CCGAAGTTTGGCTCCATCCAGGACGGCAAGATCGTTGAGGCACCCAATACGCTGTGCCTGCTGTACC

AGCTGTCGACGCAGAGCGTGCCGAGCTCGCTGAATGGCATCATCACGCCGACTGTGGATGCGCTGAA

CCTGGTCGCGGATAAGCTAGCGCCGCAGTTCAAGAACTTGGGGTGCCCGAATCCGTTGACTTGAATG

AGTGATGGCCGTGTAGAGCCTCTGCTCGCGGTGCGAAGGAAAAGAAAAAAGTGAGGGGATTTTTGGC

GAGAAATGAAATTCACGAAGATACTGCCCGGATGGTAGAGGGAAACTTGGTCATGCATGTGCATGCG

AAGGCGTTGATAT

SEQ ID NO: 17
LENGTH: 1194
TYPE: DNA
ORGANISM: M. phaseolina
FEATURE NAME/KEY: CDS
LOCATION: (1) . . . (1194)
atgccagaggtagactcttctctcttccgtgaagcacccgtacgtaggcaacaacctggc
 M  P  E  V  D  S  S  L  F  R  E  A  P  V  R  R  Q  Q  P  G ggcaaccaacctggcggagcggcgacttgccctttcaatgccaaccacgtccccgctgcg
 G  N  Q  P  G  G  A  A  T  C  P  F  N  A  N  H  V  P  A  A ccagtgacagctcgatttccctataacaacgcaaagaacggagttcccggcaacggaaag
 P  V  T  A  R  F  P  Y  N  N  A  K  N  G  V  P  G  N  G  K ggcggttaccaggttccagcgcctggtgacacggctcatcagttcattgcaccaacagcg
 G  G  Y  Q  V  P  A  P  G  D  T  A  H  Q  F  I  A  P  T  A cacgatatccgtgggccttgcccgggcctgaacgctgcggccaatcacggcttcctcgcg
 H  D  I  R  G  P  C  P  G  L  N  A  A  A  N  H  G  F  L  A cgcgacggcatagtgaccttcaacgaactggtcgacgcccagcagaatgtctacaatgtc
 R  D  G  I  V  T  F  N  E  L  V  D  A  Q  Q  N  V  Y  N  V

```
ggctacgacctctctgtgctgctcgccgtcctcggcctcacgctcaccgacggtgacccc
 G   Y   D   L   S   V   L   L   A   V   L   G   L   T   L   T   D   G   D   P atcacccaaaaactgtctatcggctgcgacgcaacgacacgcacatctgtggccccctg
 I   T   Q   K   L   S   I   G   C   D   A   T   T   R   T   S   V   A   P   L ctgactggcagtcagcccggtctggatggccacaacaagttcgaagcggacacgtcgctc
 L   T   G   S   Q   P   G   L   D   G   H   N   K   F   E   A   D   T   S   L acacgcaacgactacttcctggcgggcggcgacaacttcaacttcaacggcacgctcttc
 T   R   N   D   Y   F   L   A   G   G   D   N   F   N   F   N   G   T   L   F ggcatgatggtggatacgtgccagggcaacttcaaccgtgagaacctggcgctgtaccgc
 G   M   M   V   D   T   C   Q   G   N   F   N   R   E   N   L   A   L   Y   R aagcagcgctacgaccagagcctacgcgacaacgagaacttctacttcggcccgctaagc
 K   Q   R   Y   D   Q   S   L   R   D   N   E   N   F   Y   F   G   P   L   S ctgctgctgttcggcgccgccagcttcctttacgagctgatgcccagcggcacgcacaac
 L   L   L   F   G   A   A   S   F   L   Y   E   L   M   P   S   G   T   H   N tacgcgcccgatctcgacaccatctcgtccttcttcggcgccgagcaggcgcccgatggc
 Y   A   P   D   L   D   T   I   S   S   F   F   G   A   E   Q   A   P   D   G tcctggcgcttcaccgccgagcgtatcccggacaactggaccaaccgtgtgctgccgtac
 S   W   R   F   T   A   E   R   I   P   D   N   W   T   N   R   V   L   P   Y accaatgaggacgtgacgcgcgaaatcctggctatgtacctcctcaaccctgtgctattt
 T   N   E   D   V   T   R   E   I   L   A   M   Y   L   L   N   P   V   L   F ggcggcgccacaggcgacggcggcttcaacacgctgccgaagtttggctccatccaggac
 G   G   A   T   G   D   G   G   F   N   T   L   P   K   F   G   S   I   Q   D ggcaagatcgttgaggcacccaatacgctgtgcctgctgtaccagctgtcgacgcagagc
 G   K   I   V   E   A   P   N   T   L   C   L   L   Y   Q   L   S   T   Q   S gtgccgagctcgctgaatggcatcatcacgccgactgtggatgcgctgaacctggtcgcg
 V   P   S   S   L   N   G   I   I   T   P   T   V   D   A   L   N   L   V   A gataagctagcgccgcagttcaagaacttggggtgcccgaatccgttgacttga
 D   K   L   A   P   Q   F   K   N   L   G   C   P   N   P   L   T   -

SEQ ID NO: 18
LENGTH: 397
TYPE: PRT
ORGANISM: M. phaseolina
MPEVDSSLFREAPVRRQQPGGNQPGGAATCPFNANHVPAAPVTARFPYNNAKNGVPGNGKGGYQVPA

PGDTAHQFIAPTAHDIRGPCPGLNAAANHGFLARDGIVTFNELVDAQQNVYNVGYDLSVLLAVLGLT

LTDGDPITQKLSIGCDATTRTSVAPLLTGSQPGLDGHNKFEADTSLTRNDYFLAGGDNFNFNGTLFG

MMVDTCQGNFNRENLALYRKQRYDQSLRDNENFYFGPLSLLLFGAASFLYELMPSGTHNYAPDLDTI

SSFFGAEQAPDGSWRFTAERIPDNWTNRVLPYTNEDVTREILAMYLLNPVLFGGATGDGGFNTLPKF

GSIQDGKIVEAPNTLCLLYQLSTQSVPSSLNGIITPTVDALNLVADKLAPQFKNLGCPNPLT*

SEQ ID NO: 19
LENGTH: 1792 (including 150 bp 5' UTR and 150 bp 3' UTR)
TYPE: DNA
ORGANISM: M. phaseolina
ACCGACCACCATCCATTCGCTCTTTCGCTGGCGGCTGGCGTCCAAGGCTCACTCTCACTCTAGTCAC

TCTTTGCAATCTCTGAATTCCCGCGAGCCCTTGGTCTGCGTTGTTAAGGATTTGTTGTCCGGGCATC

CCCTCTCTTTTCCGCAATGAAGTTCTCGTCCGCCCTTCTCCTGCTCTCCTCGAGCTCCCTTGTCGTC

GATGCCTTCCCCGCCCTCGGTGCGCAGAACCTTGAGGGCCTCACTCCGGAAAGGTTGACCGCTGCCC

TCAAGACGGTCGAGAAGTACAGGAAGGAGAAGCGCCTTATCATCGACTCCAGCAAGCCTATCGATAC

CACCGGCGACCACGCTTTCCAGCCACCCAGCGAAACCGACCAGCGCGGCCCCTGTCCTGGCTTGAAC

GCCCTGGCCAACCATGGCTACATCTCTCGCGACGGCATCACCAGCTTCGCCGAGGTTGTCACCGCCA

TTAACCAAGGTTCGTCGTGGATTCGTCGAGAGAAGGCGTGGCTTGGCACTGACAAGGATGTGAAGTG

ATGGGCATGGGCATCGAGCTCTCTCTGATTCTCGGTGTTATGGGTACCGTGTGGACGGGTAACCCGC
```

```
TTTCGCTGGACCCTGGCTTCTCTATCGGTGGGACCGCCCCCGGTGATGGCTCCGACAACATTCTGGG

CAACCTTGTCGGCCTGCTCGGTACGTAACTGTCCCTCATCGGAGCCACGCCGCCGCAGCTAAGCTGA

GACGTCTGCAGGTGACCCTCGTGGTCTGCAAGGCTCCCACAACTGGATTGAGTCTGACTCCTCTCTG

ACGCGTGATGATCTGTACCTCACCGGAGATGCCTGGACGATGAACATGACGCTCTTCCGCGACATCT

ACGACCGCGCGGATGAGGATGGCGTCATCTCCATGGATCTGCTCGCCGACCAGGCCGCCCGTCGCTG

GGAGTACAGCATCGGCCACAACCCCAACTTCTACTACGGCCCTGTCACCGGCATGGTCAGCCGTAAT

GCCGGCTACTTTTTCCTCGGCCGCCTGCTGTCAAACCACACCGATGAACATCCGGACGGAATTCTCA

CTCAAGAAGTTTTCAAGAAGTTCTTCGCCGTCTACGAGGACGAGCAGGGCAACATGGAATACCGCAA

GGGCCACGAGACCTTCCCGGACAACTGGTACCGCAAGCCGGTCGAGTATGGCCTGGTCCCGCTCAAC

TTGGACCTCGTTGGCTGGGTCTTGAAGCACCCTGAGCTGGGAAGGTACGTCGTCCCTTCTCACCCCA

AGATGGGAAGGCATGTGAACTGACTCGGCTTCCCACAGCATCGGCGGTAACACTGGCACCGTCAACT

CCTTCTCCGGCCTCGATCTGCACAGCATCACCGGCGGCGTCCTCAATGCCACTTCGCTCCTCGAGAA

CAACAACCTGCTGTGTTTTGTCTTTGAAGTTCTCAAGACCTTCGCCCCCAACTCCCTCTCCCGCTC

CTGTCGACGCTCGAAGTGCCGCTCAAGCTTATCGCCGACACCCTGGCCACCCCGCTCTTGAGCCTGG

CCTGCCCTGCCTGGAAGGATATGACCGACGGTGGCGAGCCGCTGTGGGATGGCATTCAGAACAGGTT

CCCTGGCGCGAGCAAGGCCGGATCGAGTTTGTAGAGTTGCTCGAGAGGACACAGGACGTCTGGAGCA

TGACGTCTGGGTGAACGTACTGCGTGGAAGAAGAGCAAAGGAACCAGCGAGGGCGAGAAATGATGTA

GTTAGCGTCTTGATTCTAATTCGATACCATTTACATTCTTCGCCTTATCC

SEQ ID NO: 20
LENGTH: 1317
TYPE: DNA
ORGANISM: M. phaseolina
FEATURE NAME/KEY: CDS
LOCATION: (1) . . . (1317)
atgaagttctcgtccgcccttctcctgctctcctcgagctcccttgtcgtcgatgccttc
 M   K   F   S   S   A   L   L   L   L   S   S   S   S   L   V   V   D   A   F cccgccctcggtgcgcagaaccttgagggcctcactccggaaaggttgaccgctgccctc
 P   A   L   G   A   Q   N   L   E   G   L   T   P   E   R   L   T   A   A   L aagacggtcgagaagtacaggaaggagaagcgccttatcatcgactccagcaagcctatc
 K   T   V   E   K   Y   R   K   E   K   R   L   I   I   D   S   S   K   P   I gataccaccggcgaccacgcttttccagccacccagcgaaaccgaccagcgcggcccctgt
 D   T   T   G   D   H   A   F   Q   P   P   S   E   T   D   Q   R   G   P   C cctggcttgaacgccctggccaaccatggctacatctctcgcgacggcatcaccagcttc
 P   G   L   N   A   L   A   N   H   G   Y   I   S   R   D   G   I   T   S   F gccgaggttgtcaccgccattaaccaagtgatgggcatgggcatcgagctctctctgatt
 A   E   V   V   T   A   I   N   Q   V   M   G   M   G   I   E   L   S   L   I ctcggtgttatgggtaccgtgtggacgggtaacccgctttcgctggaccctggcttctct
 L   G   V   M   G   T   V   W   T   G   N   P   L   S   L   D   P   G   F   S atcggtgggaccgcccccggtgatggctccgacaacattctgggcaaccttgtcggcctg
 I   G   G   T   A   P   G   D   G   S   D   N   I   L   G   N   L   V   G   L ctcggtgaccctcgtggtctgcaaggctcccacaactggattgagtctgactcctctctg
 L   G   D   P   R   G   L   Q   G   S   H   N   W   I   E   S   D   S   S   L acgcgtgatgatctgtacctcaccggagatgcctggacgatgaacatgacgctcttccgc
 T   R   D   D   L   Y   L   T   G   D   A   W   T   M   N   M   T   L   F   R gacatctacgaccgcgcggatgaggatggcgtcatctccatggatctgctcgccgaccag
 D   I   Y   D   R   A   D   E   D   G   V   I   S   M   D   L   L   A   D   Q gccgcccgtcgctgggagtacagcatcggccacaaccccaacttctactacggccctgtc
 A   A   R   R   W   E   Y   S   I   G   H   N   P   N   F   Y   Y   G   P   V accggcatggtcagccgtaatgccggctacttttcctcggccgcctgctgtcaaaccac
 T   G   M   V   S   R   N   A   G   Y   F   F   L   G   R   L   L   S   N   H
```

-continued

```
accgatgaacatccggacggaattctcactcaagaagttttcaagaagttcttcgccgtc
 T  D  E  H  P  D  G  I  L  T  Q  E  V  F  K  K  F  F  A  V tacgaggacgagcagggcaacatggaataccgcaagggccacgagaccttcccggacaac
 Y  E  D  E  Q  G  N  M  E  Y  R  K  G  H  E  T  F  P  D  N tggtaccgcaagccggtcgagtatggcctggtcccgctcaacttggacctcgttggctgg
 W  Y  R  K  P  V  E  Y  G  L  V  P  L  N  L  D  L  V  G  W gtcttgaagcaccctgagctgggaagcatcggcggtaacactggcaccgtcaactccttc
 V  L  K  H  P  E  L  G  S  I  G  G  N  T  G  T  V  N  S  F tccggcctcgatctgcacagcatcaccggcggcgtcctcaatgccacttcgctcctcgag
 S  G  L  D  L  H  S  I  T  G  G  V  L  N  A  T  S  L  L  E aacaacaacctgctgtgttttgtctttgaagttctcaagaccttcgcccccaactccctc
 N  N  N  L  L  C  F  V  F  E  V  L  K  T  F  A  P  N  S  L tccccgctcctgtcgacgctcgaagtgccgctcaagcttatcgccgacaccctggccacc
 S  P  L  L  S  T  L  E  V  P  L  K  L  I  A  D  T  L  A  T ccgctcttgagcctggcctgccctgcctggaaggatatgaccgacggtggcgagccgctg
 P  L  L  S  L  A  C  P  A  W  K  D  M  T  D  G  G  E  P  L tgggatggcattcagaacaggttccctggcgcgagcaaggccggatcgagtttgtag
 W  D  G  I  Q  N  R  F  P  G  A  S  K  A  G  S  S  L  -
```

SEQ ID NO: 21
LENGTH: 438
TYPE: PRT
ORGANISM: M. phaseolina
MKFSSALLLLSSSSLVVDAFPALGAQNLEGLTPERLTAALKTVEKYRKEKRLIIDSSKPIDTTGDHA

FQPPSETDQRGPCPGLNALANHGYISRDGITSFAEVVTAINQVMGMGIELSLILGVMGTVWTGNPLS

LDPGFSIGGTAPGDGSDNILGNLVGLLGDPRGLQGSHNWIESDSSLTRDDLYLTGDAWTMNMTLFRD

IYDRADEDGVISMDLLADQAARRWEYSIGHNPNFYYGPVTGMVSRNAGYFFLGRLLSNHTDEHPDGI

LTQEVFKKFFAVYEDEQGNMEYRKGHETFPDNWYRKPVEYGLVPLNLDLVGWVLKHPELGSIGGNTG

TVNSFSGLDLHSITGGVLNATSLLENNNLLCFVFEVLKTFAPNSLSPLLSTLEVPLKLIADTLATPL

LSLACPAWKDMTDGGEPLWDGIQNRFPGASKAGSSL*

SEQ ID NO: 22
LENGTH: 1391 (including 150 bp 5' UTR and 150 bp 3' UTR)
TYPE: DNA
ORGANISM: M. phaseolina
ATACTAACGCCGTGCAACCCCCGGGCAGCGCAGGTCTTGTTGATCGATATAAATGTTTTGTTTCGCG

CCGCTATTGAAATTGGACACTCCAACTGTTTTCCATACATTCATCTTTCCCTATTGATCAATTGCTG

CAAAAAACATTCCATCATGAAGCTCACCGTCTGTGCCACGACCCTTTGCTTCGCTTTGGTTTATGGA

CAAGGCTCCTACGAGGGGTGGAAGCCAGCTGGGCCAGACGACTGTATGTTCAGTGGAATTTCTACGT

TTCCTTTGATTTGCGCTGATGTACATCTACAGTTCGCGGCCCTTGCCCTATGATGAATACCTTGGCC

AACCATGGCTTTCTCCCCCACGATGGCAGGAATATCACGAAAGCCAACGCAATCCACGCTCTCAACA

CAGCTATCAACTTCAACACTTCCCTCGCTGCTATCATGTGGGAGCAGGCTATCATTGCAAACCCGGA

GCCCAATGCTACGTTCTTCACTCTGTACGTGACTTCAAGCAAGCGTCTTTTGAGCTACCCTGAGTAG

GGGGCTGCTCCGAAAGGCGACTTATCTAAACCTCCTCTTTCCACTATGTGAAGCTCTGACATTAACT

AATATTGAACAGTGACCATCTTAATCGTCACAACGTCTTGGAGCACGATGCCAGCTTGAGGTGAGTG

GAAGCCGCCTTTCTCCAGCCTATTCCAACAAATCTCCTGACCAACACTCCTCTTCAGCCGATCCGAC

GCCTTCTTCGGCAACAACCACGTCTTCAACCAAACTATCTTCGACGTCTCTCGCGCGTGGTGGACGG

AGGAAACCGTAGACGCCAAGATGCTGGCCAACAGCAAGTTGTTCCGGCAGATCGAGTCGCGAGCCGC

CAACCCGAATTACACCTTCACCCAAACTACCGAGGCCTTTAGCTTGGGCGAGGTGGCTGCTCCCATC

ATCGTCTTCGGCGACCACGCGGCCGGCACCGTCAACAGGAGTCTGGTCGAGTACTTCTTCGGTGAGC

CAAGACCTCAGAGACTTTGGTCTGCAAGGGTTCAAAATTACTAATTATGGGTGGTCTTGCAGAGAA
```

-continued

CGAACGCCTCCCGACCGAGTTGGGCTGGACTAAGCAGGCTAATGATGTGTCTCTGGAGGTCATCCTG

GAGATCCAGGACCTCGTCCGCAACGCGACCAACCTGATCACCGATGCCCCGCTGCCGGCAGCGCCTC

ACAAGCGGGACCTGCACGCCCCTTACAGCCTCTAGATACGAATATAAAGCTGGCATGAAGATCACCA

GGGGTTTTTGAGAATTGTGTCTTCGGCGGGACGGGAGTGGTAGATTGAGCCTTGTTGGGCTTCAGGT

GTCTGGGCATGGTTTGCTTTGGTCCTTTTACATGATTTCCCTAGCACGCC

```
SEQ ID NO: 23
LENGTH: 780
TYPE: DNA
ORGANISM: M. phaseolina
FEATURE NAME/KEY: CDS
LOCATION: (1) . . . (780)
atgaagctcaccgtctgtgccacgacccttttgcttcgctttggtttatggacaaggctcc
 M   K   L   T   V   C   A   T   T   L   C   F   A   L   V   Y   G   Q   G   S tacgaggggtggaagccagctgggccagacgactttcgcggcccttgccctatgatgaat
 Y   E   G   W   K   P   A   G   P   D   D   F   R   G   P   C   P   M   M   N accttggccaaccatggctttctccccacgatggcaggaatatcacgaaagccaacgca
 T   L   A   N   H   G   F   L   P   H   D   G   R   N   I   T   K   A   N   A atccacgctctcaacacagctatcaacttcaacacttccctcgctgctatcatgtgggag
 I   H   A   L   N   T   A   I   N   F   N   T   S   L   A   A   I   M   W   E caggctatcattgcaaacccggagcccaatgctacgttcttcactcttgaccatcttaat
 Q   A   I   I   A   N   P   E   P   N   A   T   F   F   T   L   D   H   L   N cgtcacaacgtcttggagcacgatgccagcttgagccgatccgacgccttcttcggcaac
 R   H   N   V   L   E   H   D   A   S   L   S   R   S   D   A   F   F   G   N aaccacgtcttcaaccaaactatcttcgacgtctctcgcgcgtggtggacggaggaaacc
 N   H   V   F   N   Q   T   I   F   D   V   S   R   A   W   W   T   E   E   T gtagacgccaagatgctggccaacagcaagttgttccggcagatcgagtcgcgagccgcc
 V   D   A   K   M   L   A   N   S   K   L   F   R   Q   I   E   S   R   A   A aacccgaattacaccttcacccaaactaccgaggcctttagcttgggcgaggtggctgct
 N   P   N   Y   T   F   T   Q   T   T   E   A   F   S   L   G   E   V   A   A cccatcatcgtcttcggcgaccacgcggccggcaccgtcaacaggagtctggtcgagtac
 P   I   I   V   F   G   D   H   A   A   G   T   V   N   R   S   L   V   E   Y ttcttcgagaacgaacgcctcccgaccgagttgggctggactaagcaggctaatgatgtg
 F   F   E   N   E   R   L   P   T   E   L   G   W   T   K   Q   A   N   D   V tctctggaggtcatcctggagatccaggacctcgtccgcaacgcgaccaacctgatcacc
 S   L   E   V   I   L   E   I   Q   D   L   V   R   N   A   T   N   L   I   T gatgccccgctgccggcagcgcctcacaagcgggacctgcacgccccttacagcctctag
 D   A   P   L   P   A   A   P   H   K   R   D   L   H   A   P   Y   S   L   -

SEQ ID NO: 24
LENGTH: 259
TYPE: PRT
ORGANISM: M. phaseolina
MKLTVCATTLCFALVYGQGSYEGWKPAGPDDFRGPCPMMNTLANHGFLPHDGRNITKANAIHALNTA

INFNTSLAAIMWEQAIIANPEPNATFFTLDHLNRHNVLEHDASLSRSDAFFGNNHVFNQTIFDVSRA

WWTEETVDAKMLANSKLFRQIESRAANPNYTFTQTTEAFSLGEVAAPIIVFGDHAAGTVNRSLVEYF

FENERLPTELGWTKQANDVSLEVILEIQDLVRNATNLITDAPLPAAPHKRDLHAPYSL*

SEQ ID NO: 25
LENGTH: 1314 (including 150 bp 5' UTR and 150 bp 3' UTR)
TYPE: DNA
ORGANISM: M. phaseolina
GGCCCCCGAAAGGGAGACAAAATACGAGATTCTCCTATTACGCGCCCAAGAATCGACAACACCGCCC

ATCAGCTACCGCCGCCTTCGTTTACGTCGTCCGCAGCAGCAACGCCCGACGCTACAGTCAGTCAACA

GCCTCCAGCCGCCACGATGCCCAACGCAGTGCATCTGTCAATGCTCGTCCTCACGCATGCGGTGCCG

ATCGCGGGTTATCCGGGCTGGAAGCGCAGCAAGTTGTCGCAGAAGCGCCCTCCAAGCACCACAACG

ACCTCTACGTGCCCAACCCAAGCCATCCGGTGCCGGGGAAAGTGCCGTACATCCCGGACGAGGAAGA
```

-continued

```
GCACTACTTTGAGAAGCAGGTAAACGGCTCCGGCAATGGCTACTACCGGCGGTCGTCCTGCCCGGCA

GTCAACATCATGGCGAACAGGGGCTACATCAGCCGCTCGGGCCGGGACATCAGCTACGAGGAGATAG

CGATGGCATCGCGGGAGCTGTTCAACTTCGGCGACGACAACGTGAGCAGCGGCCCCTGCAGACCGGC

AAAGTAAGCGGGCTCACCAACAATTCCTTCTTGACAGATCATGATCGTGCTGGGGCCCAGCTTCGCG

GCGCACCCGGGCCGCGAGCGCATCGACCTCGACATGCTGGCCGACGACGCGGTGCAGCACATCACCA

ACTGCCCTGCGGCGCCGACGCGGACGGACCGCGCGCTGGGCGACAACGTGAACCTGAACACGACGCT

GCTGGAGCAGCTGCTGGCGACGTCCAAGGACGGCGTCACGCTGACGCTCGAAGACGCAGCCGAGCAC

CACCACCTGCGGCACAACCAGTCGCTGGCCGAGAACCCCGGCTTCCGCTTCAGCAACTCCGACGCCA

TCTGCTCGCTTGCGCAGTACGCCAACCTGTTCGGTATCCTGGGCCGGCAGGGCAAGCATGGGCTCAA

CACGCTGTATGTGGAAGACGTCAAGACCCTGTTCGTCGACGAAGACCTGCCGGACGGATACGGCCGG

AGGGAGCTGCCGTATTTCTCGACCGAGGCGAACAACTACATCGACCGTATGGCCCACCACATCGGCT

TCGAGATCGAGCGGCCGTTCCCGGCCAACGACGCCGACCTGAAGGACATCGAGCCGGTGCAAGCCAG

ATTTGAAGTGGTGGACGGATGCTGAGCGGTGCAAAATTTAAAAAAAAATTTTTTTTAGGCAGAAGTC

AAGCATTTAATCGGGCTATACACACATCATTCCGTGCAAACAAAATCATTTCTACAGCTGTACCGCC

TCGGAAAAGAATAACGGAGATTTAAAAAAAAAAAAAAAAAC
```

```
SEQ ID NO: 26
LENGTH: 951
TYPE: DNA
ORGANISM: M. phaseolina
FEATURE NAME/KEY: CDS
LOCATION: (1)...(951)
atgcccaacgcagtgcatctgtcaatgctcgtcctcacgcatgcggtgccgatcgcgggt
 M  P  N  A  V  H  L  S  M  L  V  L  T  H  A  V  P  I  A  G tatccgggctgggaagcgcagcaagttgtcgcagaagcgccctccaagcaccacaacgac
 Y  P  G  W  E  A  Q  Q  V  V  A  E  A  P  S  K  H  H  N  D ctctacgtgcccaacccaagccatccggtgccggggaaagtgccgtacatcccggacgag
 L  Y  V  P  N  P  S  H  P  V  P  G  K  V  P  Y  I  P  D  E gaagagcactactttgagaagcaggtaaacggctccggcaatggctactaccggcggtcg
 E  E  H  Y  F  E  K  Q  V  N  G  S  G  N  G  Y  Y  R  R  S tcctgcccggcagtcaacatcatggcgaacaggggctacatcagccgctcgggccgggac
 S  C  P  A  V  N  I  M  A  N  R  G  Y  I  S  R  S  G  R  D atcagctacgaggagatagcgatggcatcgcgggagctgttcaacttcggcgacgacaac
 I  S  Y  E  E  I  A  M  A  S  R  E  L  F  N  F  G  D  D  N atcatgatcgtgctggggcccagcttcgcggcgcacccgggccgcgagcgcatcgacctc
 I  M  I  V  L  G  P  S  F  A  A  H  P  G  R  E  R  I  D  L gacatgctggccgacgacgcggtgcagcacatcaccaactgccctgcggcgccgacgcgg
 D  M  L  A  D  D  A  V  Q  H  I  T  N  C  P  A  A  P  T  R acggaccgcgcgctgggcgacaacgtgaacctgaacacgacgctgctggagcagctgctg
 T  D  R  A  L  G  D  N  V  N  L  N  T  T  L  L  E  Q  L  L gcgacgtccaaggacggcgtcacgctgacgctcgaagacgcagccgagcaccaccacctg
 A  T  S  K  D  G  V  T  L  T  L  E  D  A  A  E  H  H  H  L cggcacaaccagtcgctggccgagaaccccggcttccgcttcagcaactccgacgccatc
 R  H  N  Q  S  L  A  E  N  P  G  F  R  F  S  N  S  D  A  I tgctcgcttgcgcagtacgccaacctgttcggtatcctgggccggcagggcaagcatggg
 C  S  L  A  Q  Y  A  N  L  F  G  I  L  G  R  Q  G  K  H  G ctcaacacgctgtatgtggaagacgtcaagaccctgttcgtcgacgaagacctgccggac
 L  N  T  L  Y  V  E  D  V  K  T  L  F  V  D  E  D  L  P  D ggatacggccggagggagctgccgtatttctcgaccgaggcgaacaactacatcgaccgt
 G  Y  G  R  R  E  L  P  Y  F  S  T  E  A  N  N  Y  I  D  R atggcccaccacatcggcttcgagatcgagcggccgttcccggccaacgacgccgacctg
 M  A  H  H  I  G  F  E  I  E  R  P  F  P  A  N  D  A  D  L
```

-continued

```
aaggacatcgagccggtgcaagccagatttgaagtggtggacggatgctga
 K  D  I  E  P  V  Q  A  R  F  E  V  V  D  G  C  -
```

SEQ ID NO: 27
LENGTH: 316
TYPE: PRT
ORGANISM: *M. phaseolina*

MPNAVHLSMLVLTHAVPIAGYPGWEAQQVVAEAPSKHHNDLYVPNPSHPVPGKVPYIPDEEEHYFEK

QVNGSGNGYYRRSSCPAVNIMANRGYISRSGRDISYEEIAMASRELFNFGDDNIMIVLGPSFAAHPG

RERIDLDMLADDAVQHITNCPAAPTRTDRALGDNVNLNTTLLEQLLATSKDGVTLTLEDAAEHHHLR

HNQSLAENPGFRFSNSDAICSLAQYANLFGILGRQGKHGLNTLYVEDVKTLFVDEDLPDGYGRRELP

YFSTEANNYIDRMAHHIGFEIERPFPANDADLKDIEPVQARFEVVDGC*

SEQ ID NO: 28
LENGTH: 1480 (including 150 bp 5' UTR and 150 bp 3' UTR)
TYPE: DNA
ORGANISM: *M. phaseolina*

ATCTGGCTTTTCCTCTCTTCTCTGTCGGGCGTCCCTTGCGCAACAGATACCCCATTCATCCCTTCAG

TGCTTCTtCTTATCTCTTCGCGCGCTTTTCCCCAACCACAGCCTCTTATCGCCTGTGCTCACACCAC

GTTTCCCGCACACCCAATGGCTTCCACCGCCAGGTCCGTCTTCGCCCGCAGCGCGCTTCTGCGCTCC

GCCCCGGCCTCCATCAAGTCGAATGCCGCCCGCTCATCTCGCTTCGCCGTCCCTACCCAAGCATTCC

GCCAGCAGTCTCGCCGCGGCTACTCTTCCGAGGCCGGCTCCAAGTCTAACGGCCCCAACCCCGCCAT

CTGGATTGGTGCTCTCGCCGTCCTGGGTGGCGCCGGGTACTATGCCTACAGCTCGGGTGCCGGCGCC

CAGATCGCCTCCAAGGAACCCTTCACCCCCAAGCCCGAGGACTACCAGAAGGTCTACGACGCCATCG

CCAAGGCCCTCGAAGAGCACGACGACTACGACGACGCAGCTACGGCCCTGTCCTGCTGAGACTGGC

TTGGCACGCCAGCGGAACGTGAGTGACTTCCCCAACACTTCCAGCCCACCATTGAACCACGCACTGA

CGCCCTCCCTCACAGCTACGACAAGGAAACCGGCACCGGCGGCTCCAACGGCGCCACGATGCGCTTC

GCGCCCGAGGCGGACCACGGCGCCAACGCCGGCCTCAAGGCGGCCCGCGACTTCCTCGAGCCCATCA

AGCAGCAGTTCCCGTGGATTACGTACTCGGACCTGTGGACGCTGGCAGGCGTCGCTGCGATCCAGGA

GATGCAGGGCCCCAAGGTGCCGTGGCGCCCCGGCCGCAGCGATCGCGACGTCTCCTTCTGCACGCCC

GACGGCCGCCTGCCCGACGCCTCCAAGGACCAGAACCACCTCCGCGCCATCTTCGGCCGCATGGGTT

GGAATGACCAGGAGATCGTGGCGCTGTCGGGCGCGCATGCGCTGGGGAGGTGCCATACGGATAGGAG

TGGATTCGATGGCCCGTGGACCTTCAGCCCGACGACGCTGACGAACGATTATTTCAAGTTGTTGATC

GACGAGAAGTGGCAGTGGCGGAAGTGGGATGGACCTAAGCAGTTGGAGGACAAGAAGACGAAGAGCC

TGATGATGCTGCCGACGGATTACGCGTTGGTGCAGGACAAGAAGTTTAAGCCCTGGGTCGAGAGGTA

CGCGAAGGATCAGGATGCCTTCTTCAAGGACTTCTCGAACGTGGTTATGAGGTTGTTCGAGCTGGGC

GTGCCGTTCCAGAGTGGTGAGGACTCGAGGATTGTGTTTAAGAGCAGCTTCGACTAGGCGTGCTTGG

CGGACGTTAATTCTGATCGACGGGGTTTGATGGGAAGTTGTAAAAGGTTCTATGACGATCAGTAAAG

AAGGGTTGTTTTTGCTTTTGAGTTTCGAGGACTAAAGACTAAGACAAGAGTAGCGCAAAGGTGGGAA

AGAATA

SEQ ID NO: 29
LENGTH: 1116
TYPE: DNA
ORGANISM: *M. phaseolina*
FEATURE NAME/KEY: CDS
LOCATION: (1) . . . (1116)

```
atggcttccaccgccaggtccgtcttcgcccgcagcgcgcttctgcgctccgccccggcc
 M  A  S  T  A  R  S  V  F  A  R  S  A  L  L  R  S  A  P  A tccatcaagtcgaatgccgcccgctcatctcgcttcgccgtccctacccaagcattccgc
 S  I  K  S  N  A  A  R  S  S  R  F  A  V  P  T  Q  A  F  R cagcagtctcgccgcggctactcttccgaggccggctccaagtctaacggccccaacccc
 Q  Q  S  R  R  G  Y  S  S  E  A  G  S  K  S  N  G  P  N  P
```

```
gccatctggattggtgctctcgccgtcctgggtggcgccgggtactatgcctacagctcg
 A  I  W  I  G  A  L  A  V  L  G  G  A  G  Y  Y  A  Y  S  S ggtgccggcgcccagatcgcctccaaggaaccttcaccccaagcccgaggactaccag
 G  A  G  A  Q  I  A  S  K  E  P  F  T  P  K  P  E  D  Y  Q aaggtctacgacgccatcgccaaggccctcgaagagcacgacgactacgacgacggcagc
 K  V  Y  D  A  I  A  K  A  L  E  E  H  D  D  Y  D  D  G  S tacggccctgtcctgctgagactggcttggcacgccagcggaacctacgacaaggaaacc
 Y  G  P  V  L  L  R  L  A  W  H  A  S  G  T  Y  D  K  E  T ggcaccggcggctccaacggcgccacgatgcgcttcgcgcccgaggcggaccacggcgcc
 G  T  G  G  S  N  G  A  T  M  R  F  A  P  E  A  D  H  G  A aacgccggcctcaaggcggcccgcgacttcctcgagcccatcaagcagcagttcccgtgg
 N  A  G  L  K  A  A  R  D  F  L  E  P  I  K  Q  Q  F  P  W attacgtactcggacctgtggacgctggcaggcgtcgctgcgatccaggagatgcagggc
 I  T  Y  S  D  L  W  T  L  A  G  V  A  A  I  Q  E  M  Q  G cccaaggtgccgtggcgccccggccgcagcgatcgcgacgtctccttctgcacgcccgac
 P  K  V  P  W  R  P  G  R  S  D  R  D  V  S  F  C  T  P  D ggccgcctgcccgacgcctccaaggaccagaaccacctccgcgccatcttcggccgcatg
 G  R  L  P  D  A  S  K  D  Q  N  H  L  R  A  I  F  G  R  M ggttggaatgaccaggagatcgtggcgctgtcgggcgcgcatgcgctggggaggtgccat
 G  W  N  D  Q  E  I  V  A  L  S  G  A  H  A  L  G  R  C  H acggataggagtggattcgatggcccgtggaccttcagcccgacgacgctgacgaacgat
 T  D  R  S  G  F  D  G  P  W  T  F  S  P  T  T  L  T  N  D tatttcaagttgttgatcgacgagaagtggcagtggcggaagtgggatggacctaagcag
 Y  F  K  L  L  I  D  E  K  W  Q  W  R  K  W  D  G  P  K  Q ttggaggacaagaagacgaagagcctgatgatgctgccgacggattacgcgttggtgcag
 L  E  D  K  K  T  K  S  L  M  M  L  P  T  D  Y  A  L  V  Q gacaagaagtttaagccctgggtcgagaggtacgcgaaggatcaggatgccttcttcaag
 D  K  K  F  K  P  W  V  E  R  Y  A  K  D  Q  D  A  F  F  K gacttctcgaacgtggttatgaggttgttcgagctgggcgtgccgttccagagtggtgag
 D  F  S  N  V  V  M  R  L  F  E  L  G  V  P  F  Q  S  G  E gactcgaggattgtgtttaagagcagcttcgactag
 D  S  R  I  V  F  K  S  S  F  D  -

SEQ ID NO: 30
LENGTH: 371
TYPE: PRT
ORGANISM: M. phaseolina
MASTARSVFARSALLRSAPASIKSNAARSSRFAVPTQAFRQQSRRGYSSEAGSKSNGPNPAIWIGAL

AVLGGAGYYAYSSGAGAQIASKEPFTPKPEDYQKVYDAIAKALEEHDDYDDGSYGPVLLRLAWHASG

TYDKETGTGGSNGATMRFAPEADHGANAGLKAARDFLEPIKQQFPWITYSDLWTLAGVAAIQEMQGP

KVPWRPGRSDRDVSFCTPDGRLPDASKDQNHLRAIFGRMGWNDQEIVALSGAHALGRCHTDRSGFDG

PWTFSPTTLTNDYFKLLIDEKWQWRKWDGPKQLEDKKTKSLMMLPTDYALVQDKKFKPWVERYAKDQ

DAFFKDFSNVVMRLFELGVPFQSGEDSRIVFKSSFD*

SEQ ID NO: 31
LENGTH: 1981 (including 150 bp 5' UTR and 150 bp 3' UTR)
TYPE: DNA
ORGANISM: M. phaseolina
TAGAAGGCGCATGGAGTCGCACGCAGGGACCATGCGCAACACGGTGCCTGCAGAGAGGCGAAAGCCC

ATGCATATCACATTGATTTTTAAAGAAGGAAGTGCAAGAAGCATTGAGACATCGCACTCACCCTTCA

ACACCGCTATCGCGCGATGAAAGCCATCAGCATCGCCGTGTTCGCCGCGTCAGTGGTACCTCACACT

CTGGCAGACTATGTTTGGCCCTCGCAACATGACTTGTTGGAGGATATGTTGGCCATCCAACAAGGCT

ATATTCGCATGGGCTTCACTGACTGTATGTCGACATTCACTTGAGCCTGAAGTAATGTCTCCCTACT

AAAGCATCGTCGAAGTGGTTGTTCCTTGCGGTCACGGCAGCAACAGGCCCGGAGTAAACAACGCGGC
```

-continued

```
ACAATGGATTCGGACGGGTTTCCACGACTTCGCCACCCACGACTCGGCCGCTGGGACCGGCGGCCTC

GATGCCTCCCTCCTCTACGAGGTCGAACGGCCCGAGAACGAGGGCTCAGCCTTTAACGACACCTTCG

CCGACATGCACGACTTTATCAATCCCCGATCAAGCGCCTCGGATCTGATAGCGCTGGCCGTCGTCGC

ATCGGTTGCGGCTTGCGGCGGACCCAAGATCCCCCTGCGAGCGGGACGAATTGATGCTGTGGAGGCG

GGCCCGGCCGGCGTTCCCAAGCCCGACGACTCACTGGAGAGCACGATCGATGCATTCGCGCGGACGG

GGTTCAACACCAGCGACATGATCGCCCTCGTTGCCTGTGGCCATACCGTCGGCGGCGTGCACAGCGT

AGATTTCCCCGAGATCACCGGCGGCGAGAAAGACGTCCTGGACGTGCCGCAATTTGACAGCAGCGGC

ACCATCTTCGACACCGCAGTCGTGGACGAATACCTCGACAGCAACGGCGCCAACCCCCTCGTCTTCG

GAGCCAACGACACCACGAACTCGGACAAGCGCGTCTTCAGCGCCGACGGCAACAGCACCATGGCCAA

GCTCAAAGACCCCGCCACATTCAAAGCCACCTGCGCCGCCCTCTTCGAGCGTATGATCAACACCGTC

CCCTCATCCGTCACCCTCAGCGAACCCATCGAGCTGGCCGACATCAAGCCCTACATCGACAAGCTCG

AGCTCACACCCAACGCCTCCGCCCTCGCCTTCGAAGGCCGCATCCGGCTGCGCACCTCCCCCGTCAC

CGGCCGCGACGCCGAGGGCACCAGCATCGCCCTCAATGTCACCGACCGCGCTGGCGGGCGCAAGCTG

GTGCCGGCGCCGCGCGCCGTGTTGCGCGGCGGCACCTCGTACGGCTTCTTCGACGAGCAGTTCAGCT

GGTTCGAATTTGCGACGCAGCTCGACGTCGCAGCCGGCATCCAGGCCTTTGATATCCAGCTCACGAC

GGAGGCGACCGGACACGTGGAGACGTTCGACAACGCTGGCACCGGCGGCTATCCTAGTCTCGACGAC

TTGCTATACTTGCAGTCGCAATCGTGCATGGACACGACTGCCACGGAGGGGAATATAACGGTGACGG

TTGCGGCGGCGGTGCGCGAGGATGCGGCGAAGGCGGGTGCGGCGCCAGTGGTGAGGATGGCGCATAA

GGTTCAGCAGATGGGTGTGATGTTGCCGAAGCTTGTCGTAGAGGCAGTGCCAATGGAGAGGTCAAAC

GTTTCGCAGGGCGGGTATGTATTGTACGAGGTGGACATCCCAATCGATGCCGCTGGCTGGAGCACGA

AGTTCGATGTTGTGTTGACGGCTGGGGGAGACGAGATTGTGTCTGGCCTGCACGGGACCAGCGATCT

TACCACATGTTCGGGAAACTGACCGGTTGATGGGCTTGGGGACTTGCCCTGAGTAGCATAGCATCGG

CGTGTTTTGGGTTTGTTTACAGGTGTGGAAGATCAGATGAAGGAAGAACCAACAGGTGATTGAACCT

ATGTCGCAAGTCAGCAATGCAGTGATGGTCTCGGCGTC
```

SEQ ID NO: 32
LENGTH: 1623
TYPE: DNA
ORGANISM: M. phaseolina
FEATURE NAME/KEY: CDS
LOCATION: (1)...(1623)

```
atgaaagccatcagcatcgccgtgttcgccgcgtcagtggtacctcacactctggcagac
 M   K   A   I   S   I   A   V   F   A   A   S   V   V   P   H   T   L   A   D tatgtttggccctcgcaacatgacttgttggaggatatgttggccatccaacaaggctat
 Y   V   W   P   S   Q   H   D   L   L   E   D   M   L   A   I   Q   Q   G   Y attcgcatgggcttcactgacttggttgttccttgcggtcacggcagcaacaggcccgga
 I   R   M   G   F   T   D   L   V   V   P   C   G   H   G   S   N   R   P   G gtaaacaacgcggcacaatggattcggacgggtttccacgacttcgccacccacgactcg
 V   N   N   A   A   Q   W   I   R   T   G   F   H   D   F   A   T   H   D   S gccgctgggaccggcggcctcgatgcctccctcctctacgaggtcgaacggcccgagaac
 A   A   G   T   G   G   L   D   A   S   L   L   Y   E   V   E   R   P   E   N gagggctcagcctttaacgacaccttcgccgacatgcacgactttatcaatccccgatca
 E   G   S   A   F   N   D   T   F   A   D   M   H   D   F   I   N   P   R   S agcgcctcggatctgatagcgctggccgtcgtcgcatcggttgcggcttgcggcggaccc
 S   A   S   D   L   I   A   L   A   V   V   A   S   V   A   A   C   G   G   P aagatccccctgcgagcgggacgaattgatgctgtggaggcgggcccggccggcgttccc
 K   I   P   L   R   A   G   R   I   D   A   V   E   A   G   P   A   G   V   P aagcccgacgactcactggagagcacgatcgatgcattcgcgcggacggggttcaacacc
 K   P   D   D   S   L   E   S   T   I   D   A   F   A   R   T   G   F   N   T
```

```
agcgacatgatcgccctcgttgcctgtggccataccgtcggcggcgtgcacagcgtagat
 S  D  M  I  A  L  V  A  C  G  H  T  V  G  G  V  H  S  V  D ttccccgagatcaccggcggcgagaaagacgtcctggacgtgccgcaatttgacagcagc
 F  P  E  I  T  G  G  E  K  D  V  L  D  V  P  Q  F  D  S  S ggcaccatcttcgacaccgcagtcgtggacgaatacctcgacagcaacggcgccaacccc
 G  T  I  F  D  T  A  V  V  D  E  Y  L  D  S  N  G  A  N  P ctcgtcttcggagccaacgacaccacgaactcggacaagcgcgtcttcagcgccgacggc
 L  V  F  G  A  N  D  T  T  N  S  D  K  R  V  F  S  A  D  G aacagcaccatggccaagctcaaagaccccgccacattcaaagccacctgcgccgccctc
 N  S  T  M  A  K  L  K  D  P  A  T  F  K  A  T  C  A  A  L ttcgagcgtatgatcaacaccgtccctcatccgtcaccctcagcgaacccatcgagctg
 F  E  R  M  I  N  T  V  P  S  S  V  T  L  S  E  P  I  E  L gccgacatcaagccctacatcgacaagctcgagctcacacccaacgcctccgccctcgcc
 A  D  I  K  P  Y  I  D  K  L  E  L  T  P  N  A  S  A  L  A ttcgaaggccgcatccggctgcgcacctcccccgtcaccggccgcgacgccgagggcacc
 F  E  G  R  I  R  L  R  T  S  P  V  T  G  R  D  A  E  G  T agcatcgccctcaatgtcaccgaccgcgctggcgggcgcaagctggtgccggcgccgcgc
 S  I  A  L  N  V  T  D  R  A  G  G  R  K  L  V  P  A  P  R gccgtgttgcgcggcggcacctcgtacggcttcttcgacgagcagttcagctggttcgaa
 A  V  L  R  G  G  T  S  Y  G  F  F  D  E  Q  F  S  W  F  E tttgcgacgcagctcgacgtcgcagccggcatccaggcctttgatatccagctcacgacg
 F  A  T  Q  L  D  V  A  A  G  I  Q  A  F  D  I  Q  L  T  T gaggcgaccggacacgtggagacgttcgacaacgctggcaccggcggctatcctagtctc
 E  A  T  G  H  V  E  T  F  D  N  A  G  T  G  G  Y  P  S  L gacgacttgctatacttgcagtcgcaatcgtgcatggacacgactgccacggaggggaat
 D  D  L  L  Y  L  Q  S  Q  S  C  M  D  T  T  A  T  E  G  N ataacggtgacggttgcggcggcggtgcgcgaggatgcggcgaaggcgggtgcggcgcca
 I  T  V  T  V  A  A  A  V  R  E  D  A  A  K  A  G  A  A  A  P gtggtgaggatggcgcataaggttcagcagatgggtgtgatgttgccgaagcttgtcgta
 V  V  R  M  A  H  K  V  Q  Q  M  G  V  M  L  P  K  L  V  V gaggcagtgccaatggagaggtcaaacgtttcgcagggcgggtatgtattgtacgaggtg
 E  A  V  P  M  E  R  S  N  V  S  Q  G  G  Y  V  L  Y  E  V gacatcccaatcgatgccgctggctggagcacgaagttcgatgttgtgttgacggctggg
 D  I  P  I  D  A  A  G  W  S  T  K  F  D  V  V  L  T  A  G ggagacgagattgtgtctggcctgcacgggaccagcgatcttaccacatgttcgggaaac
 G  D  E  I  V  S  G  L  H  G  T  S  D  L  T  T  C  S  G  N tga
-
SEQ ID NO: 33
LENGTH: 540
TYPE: PRT
ORGANISM: M. phaseolina
MKAISIAVFAASVVPHTLADYVWPSQHDLLEDMLAIQQGYIRMGFTDLVVPCGHGSNRPGVNNAAQW

IRTGFHDFATHDSAAGTGGLDASLLYEVERPENEGSAFNDTFADMHDFINPRSSASDLIALAVVASV

AACGGPKIPLRAGRIDAVEAGPAGVPKPDDSLESTIDAFARTGFNTSDMIALVACGHTVGGVHSVDF

PEITGGEKDVLDVPQFDSSGTIFDTAVVDEYLDSNGANPLVFGANDTTNSDKRVFSADGNSTMAKLK

DPATFKATCAALFERMINTVPSSVTLSEPIELADIKPYIDKLELTPNASALAFEGRIRLRTSPVTGR

DAEGTSIALNVTDRAGGRKLVPAPRAVLRGGTSYGFFDEQFSWFEFATQLDVAAGIQAFDIQLTTEA

TGHVETFDNAGTGGYPSLDDLLYLQSQSCMDTTATEGNITVTVAAAVREDAAKAGAAPVVRMAHKVQ

QMGVMLPKLVVEAVPMERSNVSQGGYVLYEVDIPIDAAGWSTKFDVVLTAGGDEIVSGLHGTSDLTT

CSGN*
```

SEQ ID NO: 34
LENGTH: 2012 (including 150 bp 5' UTR and 150 bp 3' UTR)
TYPE: DNA
ORGANISM: M. phaseolina

```
GGGGGAGGCCAATGCATGTCAGCAAAATACCTGTGGCTACCCCTGTTATGGCCACATCCAGCCCATT

TTGAATGGACGGTATAAAATCTCTTCTGAAACCTTCAGAAAATTAAGGCAGGGACTATTGAAGGTTT

TGCCGTATCTGCCAAAATGCGGTTTCTCGGGGGCTTCTATCTACTCCTTGCTGCCACTCGCCACACA

CCTACGGCCAGAGCTGCGCTGCACTACCCAAATGCCCTCATTTCTCGCATGGAACACCTGCTGGTTG

ATACGGACGGCTCATTCAGGTCTGGTTTCAAGGACGCCATCAACCCCTGCACGAACTACATTTCAGG

TGCCCAAACGCTGGGGCGGCAGACCTCTGCACAGTGGCTCCGAGTTGCCTTCCATGATTTCGTCACG

TGCCCAAACGCTGGGGCGGCAGACCTCTGCACAGTGGCTCCGAGTTGCCTTCCATGATTTCGTCACG

GCCCACGTCGACGAGGGCACTGGCGGGATCGACGCGTCCATCGGCTTCGAAACTCTCCGAGCAGAAG

ATTCCGGGTCCGCATTCAATGACAGTTTCGCCTTCTTTGCTCCGTTCGTGGATGCGCAAACTTCCAG

TATCACCCATCGAGCCTTCCCCGTCGAGGGCCGTGGCATGCGCTGACGTCCTTGCAGTGGCCGACCT

CGTAGCCCTCTCTGTGGTGACTTCTCTGGGCCACTGCGGTGGTCTGCATGTCCCATATCGAGCGGGC

CGTATCGATGCTACGGGCGGAGGGCCGTTCGGCGTTCCCGAACCCGAGACAAGCCTGGAAGAGACCC

TGGAAGAGTTTGCCAATGCTGGTTTCAATGCTGAAGATGCCATTGGATTAACGGCGTGCGGGCATTC

TCTCGGCCGCGTCCATCACGGCGGGTTCCCCAACGTCGTGCCCGAATCGGCCATAGCACCAAACAAC

ACCGCGGGCGGCGTGAACCTGGACTCCACACGGGATAAATTCGACATCAGCATTGTCAAAGAATACC

TCGGCAACTATGGGCAGCGCGCGGACCTCTCGTTACCAGTGACAACGTGACTGTCCGCTCGGATCT

TCGGCTGTACGAAAGCGATCAGAACAGGACAATGCAAGCTCTCGGTCAGTCAAAAGAATACTTCTTT

AGCACCTGTGGAAATCTATTTGAGAGGATGATCAACACCGTTCCGCGCGAGGTCACTTTGTCAGATG

TCATCCATCCGATGACGGTGCAGCCGGTGAATTTCACGTTCGATATCATCAATGACCAGGCGCTGAG

GTTATCAGGAGTAGTGCGGGTGAGCTTCCAAATAGAGCTGTTTCGGTCTGCACGCAACTGACCGAGC

CCCGCAGTATTTGCCCTCAGATAATGCTGCACCGTCGACGCTCGAGGTCTCACTCGCCGACAAAGCC

GGAAAGACTATGGCATCCATTACAGCAAGGGTTATTGAAGAGAAAGGGAATAGTTTCTGGGGGGCCA

CAGCTTACTACCCGGTCGTTTTTGACATAAACCTTGCTGGGATTGCTTCTCGCAACAATCTTCCTGG

GAAGCTCCAGGTTCGCACAGCATCTCCTCAGACATTTGAGCTGCAACCGGAGCTGTTTTTCATACCA

TCCCGTTCTAGCCCTGGCACGGGGATAAGTGTGGGGGCTGCCATAGGTGCTGCTGCGCGGTCCCGCA

ACTCGACTCTGAGTGTAGAGAGTGTGGAAGCCGTGGTCAGTGTGCCGGTATCCCAGACGGGAACACT

GGCACCGAAGGTCGAGAAGCATGAGTTGAATCTCGAAAGAGATCAAGATATTGGTTTGTACTCTATA

TTCAAGGGGAACCTAAGCGATGATTTGGCTTTCAACCTGCAGACGACCGTTGATATCACGGCAACTT

TTTCAGACGGCACTGTCTGGCAAGATAGTTACAACAGATTTGCAGTGCCGTAGAGCATCCTGAAAAT

GTCTTCGTCAAAATGCCTTCATAGGGCCAGCAACAAATTTTCAGGCAGATATGTAGCTAGAGAGTCA

TTCAAATACAAATGTCTTGGTTGTCGAACAAGTTCGTGAGACGCTGCTCATGCACAATACAAGTGAG

CC
```

SEQ ID NO: 35
LENGTH: 1599
TYPE: DNA
ORGANISM: M. phaseolina
FEATURE NAME/KEY: CDS
LOCATION: (1) . . . (1599)

```
atgcggtttctcgggggcttctatctactccttgctgccactcgccacacacctacggcc
 M   R   F   L   G   G   F   Y   L   L   L   A   A   T   R   H   T   P   T   A agagctgcgctgcactacccaaatgccctcatttctcgcatggaacacctgctggttgat
 R   A   A   L   H   Y   P   N   A   L   I   S   R   M   E   H   L   L   V   D
```

```
acggacggctcattcaggtctggtttcaaggacgccatcaaccctgcacgaactacatt
 T  D  G  S  F  R  S  G  F  K  D  A  I  N  P  C  T  N  Y  I tcaggtgcccaaacgctggggcggcagacctctgcacagtggctccgagttgccttccat
 S  G  A  Q  T  L  G  R  Q  T  S  A  Q  W  L  R  V  A  F  H gatttcgtcacggcccacgtcgacgagggcactggcgggatcgacgcgtccatcggcttc
 D  F  V  T  A  H  V  D  E  G  T  G  G  I  D  A  S  I  G  F gaaactctccgagcagaagattccgggtccgcattcaatgacagtttcgccttctttgct
 E  T  L  R  A  E  D  S  G  S  A  F  N  D  S  F  A  F  F  A ccgttcgtggatgcgcaaacttccatggccgacctcgtagccctctctgtggtgacttct
 P  F  V  D  A  Q  T  S  M  A  D  L  V  A  L  S  V  V  T  S ctgggccactgcggtggtctgcatgtcccatatcgagcgggccgtatcgatgctacgggc
 L  G  H  C  G  G  L  H  V  P  Y  R  A  G  R  I  D  A  T  G ggagggccgttcggcgttcccgaacccgagacaagcctggaagagaccctggaagagttt
 G  G  P  F  G  V  P  E  P  E  T  S  L  E  E  T  L  E  E  F gccaatgctggtttcaatgctgaagatgccattggattaacggcgtgcgggcattctctc
 A  N  A  G  F  N  A  E  D  A  I  G  L  T  A  C  G  H  S  L ggccgcgtccatcacggcgggttccccaacgtcgtgcccgaatcggccatagcaccaaac
 G  R  V  H  H  G  G  F  P  N  V  V  P  E  S  A  I  A  P  N aacaccgcgggcggcgtgaacctggactccacacgggataaattcgacatcagcattgtc
 N  T  A  G  G  V  N  L  D  S  T  R  D  K  F  D  I  S  I  V aaagaatacctcggcaactatgggcagcgcggcggacctctcgttaccagtgacaacgtg
 K  E  Y  L  G  N  Y  G  Q  R  G  G  P  L  V  T  S  D  N  V actgtccgctcggatcttcggctgtacgaaagcgatcagaacaggacaatgcaagctctc
 T  V  R  S  D  L  R  L  Y  E  S  D  Q  N  R  T  M  Q  A  L ggtcagtcaaaagaatacttctttagcacctgtggaaatctatttgagaggatgatcaac
 G  Q  S  K  E  Y  F  F  S  T  C  G  N  L  F  E  R  M  I  N accgttccgcgcgaggtcactttgtcagatgtcatccatccgatgacggtgcagccggtg
 T  V  P  R  E  V  T  L  S  D  V  I  H  P  M  T  V  Q  P  V aatttcacgttcgatatcatcaatgaccaggcgctgaggttatcaggagtagtgcggtat
 N  F  T  F  D  I  I  N  D  Q  A  L  R  L  S  G  V  V  R  Y ttgccctcagataatgctgcaccgtcgacgctcgaggtctcactcgccgacaaagccgga
 L  P  S  D  N  A  A  P  S  T  L  E  V  S  L  A  D  K  A  G aagactatggcatccattacagcaagggttattgaagagaaagggaatagtttctggggg
 K  T  M  A  S  I  T  A  R  V  I  E  E  K  G  N  S  F  W  G gccacagcttactacccggtcgttttttgacataaaccttgctgggattgcttctcgcaac
 A  T  A  Y  Y  P  V  V  F  D  I  N  L  A  G  I  A  S  R  N aatcttcctgggaagctccaggttcgcacagcatctcctcagacatttgagctgcaaccg
 N  L  P  G  K  L  Q  V  R  T  A  S  P  Q  T  F  E  L  Q  P gagctgttttttcataccatcccgttctagccctggcacggggataagtgtgggggctgcc
 E  L  F  F  I  P  S  R  S  S  P  G  T  G  I  S  V  G  A  A ataggtgctgctgcgcggtcccgcaactcgactctgagtgtagagagtgtggaagccgtg
 I  G  A  A  A  R  S  R  N  S  T  L  S  V  E  S  V  E  A  V gtcagtgtgccggtatcccagacgggaacactggcaccgaaggtcgagaagcatgagttg
 V  S  V  P  V  S  Q  T  G  T  L  A  P  K  V  E  K  H  E  L aatctcgaaagagatcaagatattggtttgtactctatattcaaggggaacctaagcgat
 N  L  E  R  D  Q  D  I  G  L  Y  S  I  F  K  G  N  L  S  D gatttggcttttcaacctgcagacgaccgttgatatcacggcaacttttcagacggcact
 D  L  A  F  N  L  Q  T  T  V  D  I  T  A  T  F  S  D  G  T gtctggcaagatagttacaacagatttgcagtgccgtag
 V  W  Q  D  S  Y  N  R  F  A  V  P  -
```

SEQ ID NO: 36
LENGTH: 532
TYPE: PRT
ORGANISM: M. phaseolina
MRFLGGFYLLLAATRHTPTARAALHYPNALISRMEHLLVDTDGSFRSGFKDAINPCTNYISGAQTLG
RQTSAQWLRVAFHDFVTAHVDEGTGGIDASIGFETLRAEDSGSAFNDSFAFFAPFVDAQTSMADLVA
LSVVTSLGHCGGLHVPYRAGRIDATGGGPFGVPEPETSLEETLEEFANAGFNAEDAIGLTACGHSLG
RVHHGGFPNVVPESAIAPNNTAGGVNLDSTRDKFDISIVKEYLGNYGQRGGPLVTSDNVTVRSDLRL
YESDQNRTMQALGQSKEYFFSTCGNLFERMINTVPREVTLSDVIHPMTVQPVNFTFDIINDQALRLS
GVVRYLPSDNAAPSTLEVSLADKAGKTMASITARVIEEKGNSFWGATAYYPVVFDINLAGIASRNNL
PGKLQVRTASPQTFELQPELFFIPSRSSPGTGISVGAAIGAAARSRNSTLSVESVEAVVSVPVSQTG
TLAPKVEKHELNLERDQDIGLYSIFKGNLSDDLAFNLQTTVDITATFSDGTVWQDSYNRFAVP*

SEQ ID NO: 37
LENGTH: 2401 (including 150 bp 5' UTR and 150 bp 3' UTR)
TYPE: DNA
ORGANISM: M. phaseolina
TTTTAATATATTCTGCCGCTAAAACGTTCGCCATGTGCTCCTGATTTTTCTCGACCGCCATTTCTCG
CCTCCGCATCGGCTCCCTGCTTCGGCGCGCTCGTCGCTAGCATCCAGTTTCGCCAGTCCTTCCGTTT
CTCCCGCTCTTGAACCATGGCAAGGCATCCCGGCCTGACCCTGGTGTGGGTCGCAGGCGTGGTCTAC
CACGCCATTGGCACCGCTGCTGCCCCGACATGGCCATCTTCCATGGATGAACTGGAGGACATCATGG
TCCTCAACACCGGCTACCGCGCCCGCAGCTTCGCAGTGCCCGTCACACCCTGCGGCTTCTCGTCGCA
AGGCCCCGGACGCGTCCAAGCTGCCGAATGGATACGAACCGCCTTCCACGACATGGCTCCCGGCAGC
GTGTATACCGGCGTCGGAGGACTGGACGCATCGATAGCTTACGAAACACGGAGCTTGGAAAATCTCG
GCCCCGCCTTCAACACCACACTAGCTACCTACGCGCCGTATCTGACAAGCAGATCTTCCATGGCTGA
CATCATTGCGCTAGGAGTCTACACGGCGGTGCGGTCATGCGGAGGTCCAATCGTGCCTATCCGGACA
GGCAGAGTAGACGCAAAGGCAGCAGGCCCGCAAGGTGTGCCTCTGCCGCAGAATTCTATCGGAACTT
TTCAAAACCAGTTTCTCCGTACTGGCTTCAACACGACGGAGATGATCCAAGTGGTGGCGTGTGGCCA
CACTCTGGGCGGCGTGCACGCATCTGCCAACCCGGAGATCGTGCCCGTGGGGTCGGCGGAGGACGGC
GTCGTCAAGTTCGACACGACGGACGCGTTTGACAACAAGGTTGTCACCGAGTACCTCTCGAATACAA
CCAAGAACTCGCTTGTTGTGGGCCCCTCTACTGCGAACGGCCGGAACTCGGACGCTCGTGTCTTTGC
GGCGGATGGAAATGCTACGGTCAGGGCTCTGGCTGACCCTGATACGTTCAACAGTGTTTGCGCTAGG
ATGCTGCAGAAGATGATTGATGTTGTTCCAACGGGCGTGGTGCTCACTGACCCGATTTCAATCTATG
ATGTCAAACCCAGTGGGCTGCAGCTGACATTGCTTGGTGGAGGAGAGTCGGTAAAGCTTACGGGAGA
TATCCGTGTTAGGACTACGGAGCGCTCTGCGAGCCAGATTGAGAAGGTCGAGCTTGTCTACAAGGAC
CGCGAGGGGCCGAATCCTCGACAGCTTTGAGCACCGAATCCTCAGGTTCGGCCTCTGGGTTCGATG
ACAGCTTCGAGGTATAACTCATCCTAAGCCCCTGTTGGGATGCCACACTAACGGCCGAGAAAGTTCT
ACGGGGTCTCCGCAAACATCCCCACCGACTCCGGCATCTCCTCATTCAACGTCCTCATCACCCTCAC
CAGCGGCGAAACCGAACTTCACGACAATAATGGCAGCGGTTTCCCCCTCCAAGACACCGTCATCTTT
CAAAGCCCGCAGAGCTGCCTCAGCGGCACCACCATGACCGTCGCCGCCGCCGTCCTCAATACCGCCT
CCTCCGCCCCCACCCTCAGCGTCACCCTCAAGGTCCCCAACTCCCGCTCCGTCCTCCCCGTCCTCCA
GGTCAGCACAGTCGCCATGACGAAGAGCTCGTCTGTCGGCCCGTACGACCTCTACTCAACCACATAC
ACGCTAACCTCCGCCCAACTCGCCGACACGCGCTTTGACGTCAAGCTCGGCGCTGCCGCCGCCGACG
CCTTCAAGTCCTCCGCCGACCTCGGTGATGCCTGCCAGGACCTGAGCCCCGAACCGCCCACTTCTTC
CAGCGCGCCTAGCTCCTCGAGCACGGCTGCGCCGCCGGCCTCGTCCTCCTCTGCCGCACCAAGCTCC -continued

```
TCTGACCTCCCGGCCCCCTCCCCCAGCACAACACCCACGTCCTCCCACCCAATCTCCTCATCTACAA
CATTAGCATCATCGACCACCCCAACGCCCACAACACTCGCCTGCCCCGCCGCTGACGGCGCCACCTG
GACGCTATCCGGCGGCCAGAAGTTCGCCGTCAAGTGCGGCAAGGACTACCAGGCCGGCCAGATCGGC
GTCACGTGGACGGCCAGCTTCGAGGCCTGTCTGCAGGCGTGCGTGGATACGGACACGTGCCAGGCGG
TCGCATTCGTGGGGAGTGCAGAGGCGGGCGGGCAGTGCTACTTGAAGGACCAGAGCGCGGGCAGTGT
GGATGTTGAGGGGGTGTGGGGGGCGGTTCTGGAAAGCTGAGCGGTCGGGCGATGGAGTAGGGGATAG
AGGGTTTGGGCTGGGGGGTAATGAATTACTTCTGATGAGCTTCTACTACTGCAGGTGGCACAAATCA
TGGCCTCTCATGGACCTCCGACGCCGCATGCTGCCCGCGTTTCAAGGTATTCTTGG
```

SEQ ID NO: 38
LENGTH: 2049
TYPE: DNA
ORGANISM: *M. phaseolina*
FEATURE NAME/KEY: CDS
LOCATION: (1)...(2049)

```
atggcaaggcatcccggcctgaccctggtgtgggtcgcaggcgtggtctaccacgccatt
 M  A  R  H  P  G  L  T  L  V  W  V  A  G  V  V  Y  H  A  I ggcaccgctgctgccccgacatggccatcttccatggatgaactggaggacatcatggtc
 G  T  A  A  A  P  T  W  P  S  S  M  D  E  L  E  D  I  M  V ctcaacaccggctaccgcgcccgcagcttcgcagtgcccgtcacaccctgcggcttctcg
 L  N  T  G  Y  R  A  R  S  F  A  V  P  V  T  P  C  G  F  S tcgcaaggccccggacgcgtccaagctgccgaatggatacgaaccgccttccacgacatg
 S  Q  G  P  G  R  V  Q  A  A  E  W  I  R  T  A  F  H  D  M gctcccggcagcgtgtataccggcgtcggaggactggacgcatcgatagcttacgaaaca
 A  P  G  S  V  Y  T  G  V  G  G  L  D  A  S  I  A  Y  E  T cggagcttggaaaatctcggccccgccttcaacaccacactagctacctacgcgccgtat
 R  S  L  E  N  L  G  P  A  F  N  T  T  L  A  T  Y  A  P  Y ctgacaagcagatcttccatggctgacatcattgcgctaggagtctacacggcggtgcgg
 L  T  S  R  S  S  M  A  D  I  I  A  L  G  V  Y  T  A  V  R tcatgcggaggtccaatcgtgcctatccggacaggcagagtagacgcaaaggcagcaggc
 S  C  G  G  P  I  V  P  I  R  T  G  R  V  D  A  K  A  A  G ccgcaaggtgtgcctctgccgcagaattctatcggaacttttcaaaaccagtttctccgt
 P  Q  G  V  P  L  P  Q  N  S  I  G  T  F  Q  N  Q  F  L  R actggcttcaacacgacggagatgatccaagtggtggcgtgtggccacactctgggcggc
 T  G  F  N  T  T  E  M  I  Q  V  V  A  C  G  H  T  L  G  G gtgcacgcatctgccaacccggagatcgtgcccgtggggtcggcggaggacggcgtcgtc
 V  H  A  S  A  N  P  E  I  V  P  V  G  S  A  E  D  G  V  V aagttcgacacgacggacgcgtttgacaacaaggttgtcaccgagtacctctcgaataca
 K  F  D  T  T  D  A  F  D  N  K  V  V  T  E  Y  L  S  N  T accaagaactcgcttgttgtgggcccctctactgcgaacggccggaactcggacgctcgt
 T  K  N  S  L  V  V  G  P  S  T  A  N  G  R  N  S  D  A  R gtctttgcggcggatggaaatgctacggtcagggctctggctgaccctgatacgttcaac
 V  F  A  A  D  G  N  A  T  V  R  A  L  A  D  P  D  T  F  N agtgtttgcgctaggatgctgcagaagatgattgatgttgttccaacgggcgtggtgctc
 S  V  C  A  R  M  L  Q  K  M  I  D  V  V  P  T  G  V  V  L actgacccgatttcaatctatgatgtcaaacccagtgggctgcagctgacattgcttggt
 T  D  P  I  S  I  Y  D  V  K  P  S  G  L  Q  L  T  L  L  G ggaggagagtcggtaaagcttacgggagatatccgtgttaggactacggagcgctctgcg
 G  G  E  S  V  K  L  T  G  D  I  R  V  R  T  T  E  R  S  A agccagattgagaaggtcgagcttgtctacaaggaccgcgaggggggccgaatcctcgaca
 S  Q  I  E  K  V  E  L  V  Y  K  D  R  E  G  A  E  S  S  T gctttgagcaccgaatcctcaggttcggcctctgggttcgatgacagcttcgagttctac
 A  L  S  T  E  S  S  G  S  A  S  G  F  D  D  S  F  E  F  Y ggggtctccgcaaacatccccaccgactccggcatctcctcattcaacgtcctcatcacc
 G  V  S  A  N  I  P  T  D  S  G  I  S  S  F  N  V  L  I  T
```

```
ctcaccagcggcgaaaccgaacttcacgacaataatggcagcggtttcccccctccaagac
 L  T  S  G  E  T  E  L  H  D  N  N  G  S  G  F  P  L  Q  D accgtcatctttcaaagcccgcagagctgcctcagcggcaccaccatgaccgtcgccgcc
 T  V  I  F  Q  S  P  Q  S  C  L  S  G  T  T  M  T  V  A  A gccgtcctcaataccgcctcctccgcccccaccctcagcgtcaccctcaaggtccccaac
 A  V  L  N  T  A  S  S  A  P  T  L  S  V  T  L  K  V  P  N tcccgctccgtcctccccgtcctccaggtcagcacagtcgccatgacgaagagctcgtct
 S  R  S  V  L  P  V  L  Q  V  S  T  V  A  M  T  K  S  S  S gtcggcccgtacgacctctactcaaccacatacacgctaacctccgcccaactcgccgac
 V  G  P  Y  D  L  Y  S  T  T  Y  T  L  T  S  A  Q  L  A  D acgcgctttgacgtcaagctcggcgctgccgccgccgacgccttcaagtcctccgccgac
 T  R  F  D  V  K  L  G  A  A  A  A  D  A  F  K  S  S  A  D ctcggtgatgcctgccaggacctgagccccgaaccgcccacttcttccagcgcgcctagc
 L  G  D  A  C  Q  D  L  S  P  E  P  P  T  S  S  S  A  P  S tcctcgagcacggctgcgccgccggcctcgtcctcctctgccgcaccaagctcctctgac
 S  S  S  T  A  A  P  P  A  S  S  S  S  A  A  P  S  S  S  D ctcccggcccctcccccagcacaacacccacgtcctcccacccaatctcctcatctaca
 L  P  A  P  S  P  S  T  T  P  T  S  S  H  P  I  S  S  S  T acattagcatcatcgaccaccccaacgcccacaacactcgcctgccccgccgctgacggc
 T  L  A  S  S  T  T  P  T  P  T  T  L  A  C  P  A  A  D  G gccacctggacgctatccggcggccagaagttcgccgtcaagtgcggcaaggactaccag
 A  T  W  L  S  G  G  Q  K  F  A  V  K  C  G  K  D  Y  Q gccggccagatcggcgtcacgtggacggccagcttcgaggcctgtctgcaggcgtgcgtg
 A  G  Q  I  G  V  T  W  T  A  S  F  E  A  C  L  Q  A  C  V gatacggacacgtgccaggcggtcgcattcgtggggagtgcagaggcgggcgggcagtgc
 D  T  D  T  C  Q  A  V  A  F  V  G  S  A  E  A  G  G  Q  C tacttgaaggaccagagcgcgggcagtgtggatgttgaggggtgtgggggcggttctg
 Y  L  K  D  Q  S  A  G  S  V  D  V  E  G  V  W  G  A  V  L gaaagctga
 E  S  -

SEQ ID NO: 39
LENGTH: 682
TYPE: PRT
ORGANISM: M. phaseolina
MARHPGLTLVWVAGVVYHAIGTAAAPTWPSSMDELEDIMVLNTGYRARSFAVPVTPCGFSSQGPGRV

QAAEWIRTAFHDMAPGSVYTGVGGLDASIAYETRSLENLGPAFNTTLATYAPYLTSRSSMADIIALG

VYTAVRSCGGPIVPIRTGRVDAKAAGPQGVPLPQNSIGTFQNQFLRTGFNTTEMIQVVACGHTLGGV

HASANPEIVPVGSAEDGVVKFDTTDAFDNKVVTEYLSNTTKNSLVVGPSTANGRNSDARVFAADGNA

TVRALADPDTFNSVCARMLQKMIDVVPTGVVLTDPISIYDVKPSGLQLTLLGGGESVKLTGDIRVRT

TERSASQIEKVELVYKDREGAESSTALSTESSGSASGFDDSFEFYGVSANIPTDSGISSFNVLITLT

SGETELHDNNGSGFPLQDTVIFQSPQSCLSGTTMTVAAAVLNTASSAPTLSVTLKVPNSRSVLPVLQ

VSTVAMTKSSSVGPYDLYSTTYTLTSAQLADTRFDVKLGAAAADAFKSSADLGDACQDLSPEPPTSS

SAPSSSTAAPPASSSSAAPSSSDLPAPSPSTTPTSSHPISSSTTLASSTTPTPTTLACPAADGATW

TLSGGQKFAVKCGKDYQAGQIGVTWTASFEACLQACVDTDTCQAVAFVGSAEAGGQCYLKDQSAGSV

DVEGVWGAVLES*

SEQ ID NO: 40
LENGTH: 2004 (including 150 bp 5' UTR and 150 bp 3' UTR)
TYPE: DNA
ORGANISM: M. phaseolina
CCTTCCTGAAATTTCATGGCCAGCTTCTCGGTCTTTCTAATGAATTATAAGGCTATCTTCCTGCAGC

TTGTCGTCTGCACGTTCTAGGATTCAACCACCCGTCATTCCTTCTCAAAATCTCAGTCCAGTCGTTA

CAGCTAATCACTTAATATGAAGCCCGCCGCTCTTGCAGGCATTGGCCTGCTTAATGTCCTACCCATT
```

ACCGCCGAATACGTCTGGCCTTCTAAATACGACTATTTGGAAGACCTGCTTTACCTTCAATCCGGTT

ATCTGCGTGAGGGATTTGTCGACGGTATGCATATATGAACAACTGCTGGTGTCCCCAACTAATGGC

TTTTAGGTGTGGCTCCTTGTTCGTTTTCCTCCGCTGGACCTGGCCGTCAAACCGCAGCGGAATGGGT

CCGCACTGCATACCATGATATGGCCACTCATGATGCCGATGCTGGCACTGGTGGCTTGGACGCCTCT

ATCATGTTTGAGACCGAGCGGGACGAAAACGTGGGCGATGCGTTCAATGGTACCTTCGGCTTTACAA

ACAACTACTACAACATCAAAGCATCCGCTGCTGATCTTCTTGCACTCTCCACTGTCATCGCCGTTGG

AAACTGCGGTGGCCCGAAGATTCCTTTCCGTGTCGGTCGCGTGGACGCCACGGAGGCTGGCCCTCTG

GGTGTTCCCAAGCCGGATCAAGACGTTGATACGCACATTCAAATTTTTGCCAAGGCAGGCTTTAACA

CCAGTAGGCCTTGAATTACCTGAGGTCCACCTACCAGCCGCTGACTAGAATAGGCGACATGATCACC

ATGGTGGCCTGCGGCCACACCCTTGGTGGCGTCCATGGCAAGGACTTCCCCGAGATCACTTTCAACG

ACACGGAGACCAATTTCGTCAAGTTCGAAGGCAACAACTCCTTCTCCAACTTTGATAACACCGTCGT

GACCGAGTATCTTGGCGGAAACCCCCCCAACCCCCTCGTCACCGGCAAGAACGAGACCAACAACAGC

GATAAGCGCGTCTTTGGTGCCGACAACAACGCCACAATGCACTCCCTGTCGGACCCCTCCGTCTTCC

AGTCCTCCTGCCAAGACATCCTCGCCCGCATGATCGACACCGTCCCCTCCAACGTCGCTCTCACCGA

GCCTCTCGACCCAATCCTCATCAAGCCCTACATCCAAACCTTCTCCCTCGTCAACGCCACCCACCTC

ACCCTGACCGGCCGCATCCGCGTCCGTACCGACTGGGACAGCTACACCGACCAGTCAGTCCACCTCA

CCTACAACCCGCGCACAGCGCCCGCCCAGAATGCGACCCTCAACACCACCATCCCCACCACCCGCGC

CACCTTCCAGGGCGGCACCTCCAGCGGCATCTTTGGTGAAGTCTTCGCCTGGCACGAGTTCTCCGCC

ACCCTCCCCACATCCAGCTCGATTACCGGCTTCACTGTCACCGTCACGCGCGGCTCCACGGGCGAAT

CCACCACCTACGACAACGCCGGCAGCACGAACGGCTACGCGCTCGACGCACGCTGCTCTACCAGAG

CGCGCAGTCGTGCCGCGACGTCGGCACCACAACCATCACCGCTGCTGTGCGCAAGGACTTCCTCGCC

CGAGGTGCAAAGGTCGCCGTCGAGATGGTGAACAGGGTGCCGCGCCAGGGCGTGTACGTGCCGGCGC

TAGAGGTCGAACCGTGGGGGGCGGAGACGGTCAAGGAGGTCGGCGAGTGGGTCATCGTGCAGGCTAA

GGGTGAGTTGACGATGGAGAGCTTGAGCACAACGTTTGACGTCGTTGCGGGCGAGAAAAGGGTCGAG

TTCCAAAGGACGAATGTGCTGGGGGAGGAGTGTGCGGCTCTGTGAGGCGTAACTTAAAAAAAAAAAA

AAAGGAAGGATATATCAGTTTCTGGTACATACTTCGAATGAAAGTCTATGATTCGTATGTCCATAAC

ATTACTCTAGGCTTGAAACAACAATGCTGAATGTGCTTTATTGTGAGATAAAGAGTGTCCT

SEQ ID NO: 41
LENGTH: 1605
TYPE: DNA
ORGANISM: M. phaseolina
FEATURE NAME/KEY: CDS
LOCATION: (1) . . . (1605)
atgaagcccgccgctcttgcaggcattggcctgcttaatgtcctacccattaccgccgaa
 M   K   P   A   A   L   A   G   I   G   L   L   N   V   L   P   I   T   A   E tacgtctggccttctaaatacgactatttggaagacctgctttaccttcaatccggttat
 Y   V   W   P   S   K   Y   D   Y   L   E   D   L   L   Y   L   Q   S   G   Y ctgcgtgagggatttgtcgacggtgtggctccttgttcgttttcctccgctggacctggc
 L   R   E   G   F   V   D   G   V   A   P   C   S   F   S   S   A   G   P   G cgtcaaaccgcagcggaatgggtccgcactgcataccatgatatggccactcatgatgcc
 R   Q   T   A   A   E   W   V   R   T   A   Y   H   D   M   A   T   H   D   A gatgctggcactggtggcttggacgcctctatcatgtttgagaccgagcgggacgaaaac
 D   A   G   T   G   G   L   D   A   S   I   M   F   E   T   E   R   D   E   N gtgggcgatgcgttcaatggtaccttcggctttacaaacaactactacaacatcaaagca
 V   G   D   A   F   N   G   T   F   G   F   T   N   N   Y   Y   N   I   K   A tccgctgctgatcttcttgcactctccactgtcatcgccgttggaaactgcggtggcccg
 S   A   A   D   L   L   A   L   S   T   V   I   A   V   G   N   C   G   G   P

```
aagattcctttccgtgtcggtcgcgtggacgccacggaggctggccctctgggtgttccc
 K  I  P  F  R  V  G  R  V  D  A  T  E  A  G  P  L  G  V  P aagccggatcaagacgttgatacgcacattcaaattttttgccaaggcaggctttaacacc
 K  P  D  Q  D  V  D  T  H  I  Q  I  F  A  K  A  G  F  N  T agcgacatgatcaccatggtggcctgcggccacaccctttggtggcgtccatggcaaggac
 S  D  M  I  T  M  V  A  C  G  H  T  L  G  G  V  H  G  K  D ttccccgagatcactttcaacgacacggagaccaatttcgtcaagttcgaaggcaacaac
 F  P  E  I  T  F  N  D  T  E  T  N  F  V  K  F  E  G  N  N tccttctccaactttgataacaccgtcgtgaccgagtatcttggcggaaacccccccaac
 S  F  S  N  F  D  N  T  V  V  T  E  Y  L  G  G  N  P  P  N cccctcgtcaccggcaagaacgagaccaacaacagcgataagcgcgtctttggtgccgac
 P  L  V  T  G  K  N  E  T  N  N  S  D  K  R  V  F  G  A  D aacaacgccacaatgcactccctgtcggaccctccgtcttccagtcctcctgccaagac
 N  N  A  T  M  H  S  L  S  D  P  S  V  F  Q  S  S  C  Q  D atcctgcccgcatgatcgacaccgtccctccaacgtcgctctcaccgagcctctcgac
 I  L  A  R  M  I  D  T  V  P  S  N  V  A  L  T  E  P  L  D ccaatcctcatcaagccctacatccaaaccttctccctcgtcaacgccacccacctcacc
 P  I  L  I  K  P  Y  I  Q  T  F  S  L  V  N  A  T  H  L  T ctgaccggccgcatccgcgtccgtaccgactgggacagctacaccgaccagtcagtccac
 L  T  G  R  I  R  V  R  T  D  W  D  S  Y  T  D  Q  S  V  H ctcacctacaacccgcgcacagcgcccgcccagaatgcgaccctcaacaccaccatcccc
 L  T  Y  N  P  R  T  A  P  A  Q  N  A  T  L  N  T  T  I  P accaccgcgccaccttccagggcggcacctccagcggcatctttggtgaagtcttcgcc
 T  T  R  A  T  F  Q  G  G  T  S  S  G  I  F  G  E  V  F  A tggcacgagttctccgccacccttcccacatccagctcgattaccggcttcactgtcacc
 W  H  E  F  S  A  T  L  P  T  S  S  S  I  T  G  F  T  V  T gtcacgcgcggctccacgggcgaatccaccacctacgacaacgccggcagcacgaacggc
 V  T  R  G  S  T  G  E  S  T  T  Y  D  N  A  G  S  T  N  G tacgcgctcgacgacacgctgctctaccagagcgcgcagtcgtgccgcgacgtcggcacc
 Y  A  L  D  D  T  L  L  Y  Q  S  A  Q  S  C  R  D  V  G  T acaaccatcaccgctgctgtgcgcaaggacttcctcgcccgaggtgcaaaggtcgccgtc
 T  T  I  T  A  A  V  R  K  D  F  L  A  R  G  A  K  V  A  V gagatggtgaacagggtgccgcgccagggcgtgtacgtgccggcgctagaggtcgaaccg
 E  M  V  N  R  V  P  R  Q  G  V  Y  V  P  A  L  E  V  E  P tggggggcggagacggtcaaggaggtcggcgagtgggtcatcgtgcaggctaagggtgag
 W  G  A  E  T  V  K  E  V  G  E  W  V  I  V  Q  A  K  G  E ttgacgatggagagcttgagcacaacgtttgacgtcgttgcgggcgagaaaagggtcgag
 L  T  M  E  S  L  S  T  T  F  D  V  V  A  G  E  K  R  V  E ttccaaaggacgaatgtgctggggaggagtgtgcggctctgtga
 F  Q  R  T  N  V  L  G  E  E  C  A  A  L  -

SEQ ID NO: 42
LENGTH: 534
TYPE: PRT
ORGANISM: M. phaseolina
MKPAALAGIGLLNVLPITAEYVWPSKYDYLEDLLYLQSGYLREGFVDGVAPCSFSSAGPGRQTAAEWVRTAYH

DMATHDADAGTGGLDASIMFETERDENVGDAFNGTFGFTNNYYNIKASAADLLALSTVIAVGNCGGPKIPFRV

GRVDATEAGPLGVPKPDQDVDTHIQIFAKAGFNTSDMITMVACGHTLGGVHGKDFPEITFNDTETNFVKFEGN

NSFSNFDNTVVTEYLGGNPPNPLVTGKNETNNSDKRVFGADNNATMHSLSDPSVFQSSCQDILARMIDTVPSN

VALTEPLDPILIKPYIQTFSLVNATHLTLTGRIRVRTDWDSYTDQSVHLTYNPRTAPAQNATLNTTIPTTRAT

FQGGTSSGIFGEVFAWHEFSATLPTSSSITGFTVTVTRGSTGESTTYDNAGSTNGYALDDTLLYQSAQSCRDV

GTTTITAAVRKDFLARGAKVAVEMVNRVPRQGVYVPALEVEPWGAETVKEVGEWVIVQAKGELTMESLSTTFD

VVAGEKRVEFQRTNVLGEECAAL*
```

SEQ ID NO: 43
LENGTH: 1414 (including 150 bp 5' UTR and 150 bp 3' UTR)
TYPE: DNA
ORGANISM: M. phaseolina
AGCTTGCCTCTTCTTCTGTCTTTCTGCCCCCTTCTTCTCCAGACTCCTTTCGCCGTAGATTTCTGCC

TTTTGGACCTCGTTTTCTGCCCTCCACCAATAGCAAGCCAAGAGATTAGATTAGACATCGCCATCCC

ATCGCCGACTCCAACAATGCCCAGCAACCCAGGCGACTACGACGCCGTCCGCCACGACGTCAAGAAC

CTCCTGCACCAGCCCGAGTACGACGACGGTTCCGCCGGGCCCGTCCTCGTCCGTCTCGCATGGTATG

TTACGGCTACCCGCATCCTCCAGCCCAATCCGCCGTTTATCTGCTGTTCGTGGCTCTGCCATCTTCT

CTCCAGGGGCAGCAAGTTTCCCGAGCCTTTTTTTTTGTCTTACGAACGGCATCTCGAACAGCCCGC

TGACAACCACACCAGGCATTCCGCAGGGACCTACGACGCCCACTCTGACACAGGAGGCAGCAACGGT

GCAGGCATGCGCTACGAGGCTGAAGGCGGCGACCCCGCCAATGCCGGCCTGCAGCACGCCCGCGTCT

TCCTCGAGCCCATCAAGGCCGCGCACCCCTGGATAACCTACTCTGATCTGTGGACGCTGGCGGGCGT

GGTCGCCATCAAGGAGATGGGCGGCCCGGACATCCCGTGGCAGCCCGGCCGCACCGACTTCGTCGAC

GACAGCAAGCTGCCGCCGCGGGCGCCTGCCGGACGCCGCGCAGGGCGCTGACCACATCCGCTGGA

TTTTCTACCGCATGGGCTTCAACGATCAGGAAATTGTCGCCCTCAGCGGCGCCCACAACCTCGGCCG

CTGCCACGCCGACCGCTCCGGCTTCGACGGCGCCTGGGTCAACAACCCCACCCGCTTCTCCAACCAG

TACTTTAAGCTCCTGACCTCGGTCGAGTGGAAAGAGAAGACCCTCCCCAGCGGCATCAAGCAGTTCG

CCTACTATGATGAGGACTCGGAGGAGGAGCTCATGATGCTGCCCACCGATATCGCTCTCTTGCACGA

CCCCTCCTTCCGGCCGTGGGTCGAGAAGTATGCCGAGGACAAGGATGCCTTTTTCGCAGACTTCTCA

AAGGTCTTTGCCAAGCTGATTGAGCTGGGCATAGTCAGAGATGAGAGCGGTGCGGTAATCAACACTG

ATAACGTCAAGGGCGGCTACATCTCTGCGCCCAAGAAGAGTGAGCTGCCTGGTGCTCCGGGTAAGGC

TAATGAGGAGGCTGAGCCGCTCATGAAAGAGAATGAGAGGTTCAGGGCACGTCTGTAAGCTGGTTGG

TTTAGATTTCCTTTTTTTTTTTTTCAAGACCGTTAGACTGCGCAAGCTAGAGGGGACGGATAGAT

GGACGATACCACCTAGATTCCTATGCCTTAAGAGGAGAAAGATAGTGCCTAGAGTTTTCATAGAGAA

TGCAAAC

SEQ ID NO: 44
LENGTH: 960
TYPE: DNA
ORGANISM: M. phaseolina
FEATURE NAME/KEY: CDS
LOCATION: (1)...(960)
atgcccagcaacccaggcgactacgacgccgtccgccacgacgtcaagaacctcctgcac
 M   P   S   N   P   G   D   Y   D   A   V   R   H   D   V   K   N   L   L   H cagcccgagtacgacgacggttccgccgggcccgtcctcgtccgtctcgcatggcattcc
 Q   P   E   Y   D   D   G   S   A   G   P   V   L   V   R   L   A   W   H   S gcagggacctacgacgcccactctgacacaggaggcagcaacggtgcaggcatgcgctac
 A   G   T   Y   D   A   H   S   D   T   G   G   S   N   G   A   G   M   R   Y gaggctgaaggcggcgaccccgccaatgccggcctgcagcacgcccgcgtcttcctcgag
 E   A   E   G   G   D   P   A   N   A   G   L   Q   H   A   R   V   F   L   E cccatcaaggccgcgcacccctggataacctactctgatctgtggacgctggcgggcgtg
 P   I   K   A   A   H   P   W   I   T   Y   S   D   L   W   T   L   A   G   V gtcgccatcaaggagatgggcggcccggacatcccgtggcagcccggccgcaccgacttc
 V   A   I   K   E   M   G   G   P   D   I   P   W   Q   P   G   R   T   D   F gtcgacgacagcaagctgccgccgcggggccgcctgccggacgccgcgcagggcgctgac
 V   D   D   S   K   L   P   P   R   G   R   L   P   D   A   A   Q   G   A   D cacatccgctggattttctaccgcatgggcttcaacgatcaggaaattgtcgccctcagc
 H   I   R   W   I   F   Y   R   M   G   F   N   D   Q   E   I   V   A   L   S ggcgcccacaacctcggccgctgccacgccgaccgctccggcttcgacggcgcctgggtc
 G   A   H   N   L   G   R   C   H   A   D   R   S   G   F   D   G   A   W   V

```
aacaacccccacccgcttctccaaccagtactttaagctcctgacctcggtcgagtggaaa
 N  N  P  T  R  F  S  N  Q  Y  F  K  L  L  T  S  V  E  W  K gagaagaccctccccagcggcatcaagcagttcgcctactatgatgaggactcggaggag
 E  K  T  L  P  S  G  I  K  Q  F  A  Y  Y  D  E  D  S  E  E gagctcatgatgctgcccaccgatatcgctctcttgcacgaccccctccttccggccgtgg
 E  L  M  M  L  P  T  D  I  A  L  L  H  D  P  S  F  R  P  W gtcgagaagtatgccgaggacaaggatgcctttttcgcagacttctcaaaggtcttttgcc
 V  E  K  Y  A  E  D  K  D  A  F  F  A  D  F  S  K  V  F  A aagctgattgagctgggcatagtcagagatgagagcggtgcggtaatcaacactgataac
 K  L  I  E  L  G  I  V  R  D  E  S  G  A  V  I  N  T  D  N gtcaagggcggctacatctctgcgcccaagaagagtgagctgcctggtgctccgggtaag
 V  K  G  G  Y  I  S  A  P  K  K  S  E  L  P  G  A  P  G  K gctaatgaggaggctgagccgctcatgaaagagaatgagaggttcagggcacgtctgtaa
 A  N  E  E  A  E  P  L  M  K  E  N  E  R  F  R  A  R  L  -
```

SEQ ID NO: 45
LENGTH: 319
TYPE: PRT
ORGANISM: M. phaseolina

MPSNPGDYDAVRHDVKNLLHQPEYDDGSAGPVLVRLAWHSAGTYDAHSDTGGSNGAGMRYEAEGGDPANAGLQ

HARVFLEPIKAAHPWITYSDLWTLAGVVAIKEMGGPDIPWQPGRTDFVDDSKLPPRGRLPDAAQGADHIRWIF

YRMGFNDQEIVALSGAHNLGRCHADRSGFDGAWVNNPTRFSNQYFKLLTSVEWKEKTLPSGIKQFAYYDEDSE

EELMMLPTDIALLHDPSFRPWVEKYAEDKDAFFADFSKVFAKLIELGIVRDESGAVINTDNVKGGYISAPKKS

ELPGAPGKANEEAEPLMKENERFRARL*

SEQ ID NO: 46
LENGTH: 2160 (including 150 bp 5' UTR and 150 bp 3' UTR)
TYPE: DNA
ORGANISM: M. phaseolina

CAACTCTTTGGATCATTCGCAGTTCTGCAGATTAGACTACTCTTTTCTCGCTCCACAATGAAGCTTG

CATCATGGCTGCTCCTCCCTCAAGTACTGGCAGCGCTGGGCGGGCAGGTACGTGAATATAACTTGAC

TCTTGAGGCAAGCTGGATGGCTCAAGGTAGATGTCCCCGAAGAAACAAAGTGATAGTATCTCTGCTA

ACATGGACAGACGGGAACCCTCGCGGTGTCTTAACTATCAACGGCCAGACACCTGGTCCATTGATCT

GGGGATATGAAGGAGACACACTTCGCGTCACTGTGACCAATAAAATGTTTATTGAGGCTACTATGCA

TTGGTCAGAGTGAAGTCTGTCTGGACTGGGAGAATCAACTAACGGAAAGCAGGCACGGTGTCTATCA

GGTCGACAAGTACTGGAACGACGGAGTACCTGGCGTGACTCAATGGCCCATTGAATCCAGGGATTCG

TATACTTACGAGTTTACTCTCACCAACCAAACTGGAAGCTACTTCTACCATGGCCACTTTGGACCCG

CATTCGCGGACGGCCAACGAGGCCCGCTGTGGATTGCACCGGCCCCCTGGAGACCCCGTCCGTATGA

GCTTGCGTCTGATGACCCGGCAGAGGTTGCAGCAATGCGCGCGGCCGAAGACAATCCGAGACACCTC

ATGGTTTCCGACTGGAACTATGAGGGAATGGAAGTGCTGATTGTGGGCTTCAGAGATGCAGGCATTG

CTCCGGCATGTTCTGCGTCCCTCGTGACAAATGGAAAGGGCAGGACAACTTGCCTCGGCCCAGATGA

TATCAAGAAATACGATCCCGAGGGTCGGAGGAATTCACTTGGGTGCCTTCCTCCTCCAGTCGGCGCT

GAGTTCACCAACAAGAGAGAATGCCGCGAGACTACCACCGACTTCGAGATCATTCAGGCCGAAGAAG

GGGAGAAGTATATCTACATGAACTTTATCCACCCTGGAGCCCACCATGAACTGCGAATCGCGGTGGA

CGAGCACGACATGATCATCGTGGCAGCTGACGGGGATTTTGTCATGCCGAAAAAAGTCCAGGTACGT

TAATGCGAGAACTTGCACTGAGCGGTGCTGACCTATGGCTGCAGGCAATAAACCTCAACATGGGCGA

CAGGATCAGTGTCCTGGTACCGCTAGACAAGAAGCCGGGGAATACGCCATCCGCCTGTCGTCCATT

TCCGAGGAGCAATTGATTACGGGCTTGAGCATCTTGCGCTACCCCGGTGTGCAGGAGCGCCGCAAAG

ACGGTATTATGCTGGCACCGGAAACAAAACCCCATATTGATCTGTTGGGGCGGATGGTCACTGAAGG

AGGTGTCATGATGGATGAAATGACCGATTTGGCCCCCTTTCCGCCGCGCTCACCCCCAGCGACGTCT

-continued

GATCACACGTTTCGGTTTTTATCAAACCGCACCGGCCCGAGCACATGGATGCTGTCGAGCGAGCCAC

ACCAAGGCTTCCGCCAGCAGATGCCTCCTATTATGTGGAACGAAGAGTCTCGTGGCCCTACAACCAT

TCAGGGGATGAAGAATGGATCCACCGTAGACATCATCTTCGAGAGCCGCGCATACGCCATGCACCCT

TTCCACAAACACAATCACAAGGCCTGGATTATTGGTAGAGGAAAGGGCTACTTCCGTTGGCCAGATG

TTGCTACTGCCATCTCGGAAGCTCCAGAGAATTTCAACCTGATCAACCCGCCGTTGCGAGATGGTGC

CCGGCTCGAAGCGGAAGAGGGATCCTGGACGGTGATCCGTTACACCATCACCTTTCCTGCCATGAGC

ATGCTGCACTGCCATCGTATTCAGCACTTTGCGGTAAGTGTGTGATCTAGCCACCAAACGAATGGTC

ACTGATTGAAACAGGCTGGACAACAGATAGTCCTTTTGGAGGGGCAGGATGTGATGCAAAGCCCTCC

TGAGTACATCAAAAAAATGACGCATGCGAGCTTTGTGCCGCCACTCCGATACGGCCCCCTTGACTGA

GAGTTCCCATGCGAGGCCAGAGCACGGAATTGGGTAGTTGAAGTTAAAACCTGCCACATAAAAAATA

GCTCGAATAACAGGATTTTGCTAGCTCATGGAACTAGCCACTTGTTCCTTTGCGTTCAGTCTAATGG

CTGCGGTGAAAGCGAA

SEQ ID NO: 47
LENGTH: 1713
TYPE: DNA
ORGANISM: M. phaseolina
FEATURE NAME/KEY: CDS
LOCATION: (1) . . . (1713)

```
atggctcaaggtagatgtccccgaagaaacaaagtgatagtatctctgctaacatggaca
 M   A   Q   G   R   C   P   R   R   N   K   V   I   V   S   L   L   T   W   T gacgggaaccctcgcggtgtcttaactatcaacggccagacacctggtccattgatctgg
 D   G   N   P   R   G   V   L   T   I   N   G   Q   T   P   G   P   L   I   W ggatatgaaggagacacacttcgcgtcactgtgaccaataaaatgtttattgaggctact
 G   Y   E   G   D   T   L   R   V   T   V   T   N   K   M   F   I   E   A   T atgcattggcacggtgtctatcaggtcgacaagtactggaacgacggagtacctggcgtg
 M   H   W   H   G   V   Y   Q   V   D   K   Y   W   N   D   G   V   P   G   V actcaatggcccattgaatccagggattcgtatacttacgagtttactctcaccaaccaa
 T   Q   W   P   I   E   S   R   D   S   Y   T   Y   E   F   T   L   T   N   Q actggaagctacttctaccatggccactttggacccgcattcgcggacggccaacgaggc
 T   G   S   Y   F   Y   H   G   H   F   G   P   A   F   A   D   G   Q   R   G ccgctgtggattgcaccggccccctggagaccccgtccgtatgagcttgcgtctgatgac
 P   L   W   I   A   P   A   P   W   R   P   R   P   Y   E   L   A   S   D   D ccggcagaggttgcagcaatgcgcgcggccgaagacaatccgagacacctcatggtttcc
 P   A   E   V   A   A   M   R   A   A   E   D   N   P   R   H   L   M   V   S gactggaactatgagggaatggaagtgctgattgtgggcttcagagatgcaggcattgct
 D   W   N   Y   E   G   M   E   V   L   I   V   G   F   R   D   A   G   I   A ccggcatgttctgcgtccctcgtgacaaatggaaagggcaggacaacttgcctcggccca
 P   A   C   S   A   S   L   V   T   N   G   K   G   R   T   T   C   L   G   P gatgatatcaagaaatacgatcccgagggtcggaggaattcacttgggtgccttcctcct
 D   D   I   K   K   Y   D   P   E   G   R   R   N   S   L   G   C   L   P   P ccagtcggcgctgagttcaccaacaagagagaatgccgcgagactaccaccgacttcgag
 P   V   G   A   E   F   T   N   K   R   E   C   R   E   T   T   T   D   F   E atcattcaggccgaagaaggggagaagtatatctacatgaactttatccaccctggagcc
 I   I   Q   A   E   E   G   E   K   Y   I   Y   M   N   F   I   H   P   G   A caccatgaactgcgaatcgcggtggacgagcacgacatgatcatcgtggcagctgacggg
 H   H   E   L   R   I   A   V   D   E   H   D   M   I   I   V   A   A   D   G gattttgtcatgccgaaaaaagtccaggcaataaacctcaacatgggcgacaggatcagt
 D   F   V   M   P   K   K   V   Q   A   I   N   L   N   M   G   D   R   I   S gtcctggtaccgctagacaagaagccgggggaatacgccatccgcctgtcgtccatttcc
 V   L   V   P   L   D   K   K   P   G   E   Y   A   I   R   L   S   S   I   S gaggagcaattgattacgggcttgagcatcttgcgctaccccggtgtgcaggagcgccgc
 E   E   Q   L   I   T   G   L   S   I   L   R   Y   P   G   V   Q   E   R   R
```

```
aaagacggtattatgctggcaccggaaacaaaacccatattgatcgtgggcggatg
 K  D  G  I  M  L  A  P  E  T  K  P  H  I  D  L  L  G  R  M gtcactgaaggaggtgtcatgatggatgaaatgaccgatttggccccctttccgccgcgc
 V  T  E  G  G  V  M  M  D  E  M  T  D  L  A  P  F  P  P  R tcacccccagcgacgtctgatcacacgtttcggttttttatcaaaccgcaccggcccgagc
 S  P  P  A  T  S  D  H  T  F  R  F  L  S  N  R  T  G  P  S acatggatgctgtcgagcgagccacaccaaggcttccgccagcagatgcctcctattatg
 T  W  M  L  S  S  E  P  H  Q  G  F  R  Q  Q  M  P  P  I  M tggaacgaagagtctcgtggccctacaaccattcaggggatgaagaatggatccaccgta
 W  N  E  E  S  R  G  P  T  T  I  Q  G  M  K  N  G  S  T  V gacatcatcttcgagagccgcgcatacgccatgcacccctttccacaaacacaatcacaag
 D  I  I  F  E  S  R  A  Y  A  M  H  P  F  H  K  H  N  H  K gcctggattattggtagaggaaagggctacttccgttggccagatgttgctactgccatc
 A  W  I  I  G  R  G  K  G  Y  F  R  W  P  D  V  A  T  A  I tcggaagctccagagaatttcaacctgatcaacccgccgttgcgagatggtgcccggctc
 S  E  A  P  E  N  F  N  L  I  N  P  P  L  R  D  G  A  R  L gaagcggaagagggatcctggacggtgatccgttacaccatcacctttcctgccatgagc
 E  A  E  E  G  S  W  T  V  I  R  Y  T  I  T  F  P  A  M  S atgctgcactgccatcgtattcagcactttgcggctggacaacagatagtccttttggag
 M  L  H  C  H  R  I  Q  H  F  A  A  G  Q  Q  I  V  L  L  E gggcaggatgtgatgcaaagccctcctgagtacatcaaaaaaatgacgcatgcgagcttt
 G  Q  D  V  M  Q  S  P  P  E  Y  I  K  K  M  T  H  A  S  F gtgccgccactccgatacggccccttgactga
 V  P  P  L  R  Y  G  P  L  D  -

SEQ ID NO: 48
LENGTH: 570
TYPE: PRT
ORGANISM: M. phaseolina
MAQGRCPRRNKVIVSLLTWTDGNPRGVLTINGQTPGPLIWGYEGDTLRVTVTNKMFIEATMHWHGVY

QVDKYWNDGVPGVTQWPIESRDSYTYEFTLTNQTGSYFYHGHFGPAFADGQRGPLWIAPAPWRPRPY

ELASDDPAEVAAMRAAEDNPRHLMVSDWNYEGMEVLIVGFRDAGIAPACSASLVTNGKGRTTCLGPD

DIKKYDPEGRRNSLGCLPPPVGAEFTNKRECRETTTDFEIIQAEEGEKYIYMNFIHPGAHHELRIAV

DEHDMIIVAADGDFVMPKKVQAINLNMGDRISVLVPLDKKPGEYAIRLSSISEEQLITGLSILRYPG

VQERRKDGIMLAPETKPHIDLLGRMVTEGGVMMDEMTDLAPFPPRSPPATSDHTFRFLSNRTGPSTW

MLSSEPHQGFRQQMPPIMWNEESRGPTTIQGMKNGSTVDIIFESRAYAMHPFHKHNHKAWIIGRGKG

YFRWPDVATAISEAPENFNLINPPLRDGARLEAEEGSWTVIRYTITFPAMSMLHCHRIQHFAAGQQI

VLLEGQDVMQSPPEYIKKMTHASFVPPLRYGPLD*

SEQ ID NO: 49
LENGTH: 2269 (including 150 bp 5' UTR and 150 bp 3' UTR)
TYPE: DNA
ORGANISM: M. phaseolina
AGTATGTGCGTTGATCCCGCTGTCTATTCGAGCACCAGAGCACTGTCCAGCCACCTTGAGCTATCTC

AAGGGGCTATCTCATCTGGTCATCTTCGCTGGGGCATCGGTTGCCTTCTCAACCCTTCTCAATTCCC

CTCACGCTTCTGCAACATGTTCTTCGGCTCCCTCCACTTGGGCATCGGCGCCCTATTGGTTGCCGGC

ACTCTTGCTGGCGACGACAAGTGGCTTAGCCCCGTCTACAAGAACTTTTACGAGTTCCCCCTACCTA

AGCCACCAATCAAGGAAGCGAAAGCGTAAGTCAACTGATATTTCTCTCGCTCGTCATTTGCATGCCT

AATCTTCGCAGGAAATATACCAACCCGACTACCGGTGCTGTGATCAACTACTACGAAATCACCATCT

CACCCCTGCAGCAACAGGTTTATCCTGGCCTTGGCAAGGCAAACCTCGTTGGCTACGATGGTATCTC

TCCCGGTCCCACTTTTAAGATGGAGAGGGGAGAAGAGGCTGTCGTTCGTTTCATCAACAAGGCCTCC

ATTCCCAATTCCGTCCATCTTCACGGCTCCTACTCCTTTGCCCCCTTCGATGGCTGGCGGAGGATA

CGACCAGCCCAGGCCAATACAAGGACTACTACTACCCCAATGCCCAGTCTGCCCGTACCCTCTGGTA
```

CCACGACCATGCCGTCTTCCACACTGCCGAGAACGCCTACTACGGTCAGGCAGGTTTCTACATCCTG

CACGACTCGGCTGAGGATAGTCTGGGTCTCCCGTCTGGAGACTACGACATCCCGCTCGGTCTGAGCT

CGAAGCAATACCAGTCCAACGGTGACCTTTTCAGCCCGAATGGCGAGACGGATAGCCTTTTTGGCGA

TGTTATCCATGTCAACGGCCAGCCCTGGCCGTACCTCAAGGTCGAGCCCAGGAAGTACCGCTTCCGC

CTGCTTGATACAAGCATTTCCCGTGCCTTCCAGCTGTCACTCCAAGACGATAAGAGCAAGAAGATTG

ACTTTAACGTCATCGCCTCCGATGCCGGCCTCCTGTCCAGCCCTGTTCCGACCAACCTGCTACACAT

TTCCATGGCCGAACGCTGGGAAATTGTCGTCGACTTCTCCCAGTACGCTGGCAAGAACATCACCATG

AAGAACGAGCGTGACGTGCAGGCCGATGAAGACTACAACAGCACTGACAAGGTCATGCGCTTCGTAG

TAGGCAACAAGGTTACCTCGACTGCCAACAACAACCTGCCTGGCAGCCTCCGCAGCGTGCCTTTCCC

GCCGAATAAGTCTGGTGTTGACAGGAGCTTCAAGTTCGAGCGCAAAGGCGGTGAATGGACTATCAAC

GGCGTTACCTTTGCCGACGTCGAGAACCGTATTCTAGGCAAGCCCCAACGCGGACAGGTTGAGGTCT

GGGAGCTCGAGAACTCTTCCGGCGGCTGGTCTCACCCCGTTCACATCCATCTCATCGACTTCCAGGT

TATTTCTCGCACTGGTGGCAAGCGTGATGTCCTGCCTTACGAGAAGAACGGTCTCAAAGATGTCGTC

TTGCTTGGCGTGAACGAGAAGGTCAGAGTTGTCGCTCGCTTCCAGCCCTGGGAAGGTGTCTACATGT

TCCATTGCCACAACCTGATCCACGAGGACCACGATATGGTGCGCTCCCAGCATTCCTCTGATTACTC

GCAACAAAGACTGACAAATAATTACAGATGGCCGCTTTCAATGTATCCACCCTTTCAGACTACGGCT

ACGACCAGAAGGAGACCCTTTTCATCGACCCGATGGAGTCCCGCTGGCGCGCAAAGGATGTCAAGAC

CGAAGACTTCACAACCGATGCCATCCAGTCGAAGCTTGCCGCTTTCGCTGAAATAAATCGCTACAAG

GACGTTGCGAAGATCGAAAGTGCTCTTGAAAATTATTGGAAGACCGCTCCCACCGGGTTCAAGATTA

GCACCACCTCCTCAACTCCGAGCTCAACCGCCGCCACCTCCACCGCTTCCAGCAGTGGCTCAAACAC

CTCTATTACCGCCCCCATTCAGTCCCCGGCCACTACTTCACCCGCGACCACTTCGACCAAGGCGGAT

GACAAGGGCAAGGCTAAGACTTCTACGACCAAAACGAAGTAACGAAATGGCTTTTAGATCACGCTCA

TTATAGATAAAACTTGGGAGAATTTGGGTCGGTGTTTTTGGATAGTTTGGTTCGGAGGAGCGCTCTC

TGTAAATATGGGCCTCGCGAACTCTGTGGATATTTGTTTCTCGGTGTCTGTTAATATC

SEQ ID NO: 50
LENGTH: 1860
TYPE: DNA
ORGANISM: M. phaseolina
FEATURE NAME/KEY: CDS
LOCATION: (1)...(1860)
atgttcttcggctcctccacttgggcatcggcgccctattggttgccggcactcttgct
 M  F  F  G  S  L  H  L  G  I  G  A  L  L  V  A  G  T  L  A ggcgacgacaagtggcttagcccgtctacaagaacttttacgagttccccctacctaag
 G  D  D  K  W  L  S  P  V  Y  K  N  F  Y  E  F  P  L  P  K ccaccaatcaaggaagcgaaagcgaaatataccaacccgactaccggtgctgtgatcaac
 P  P  I  K  E  A  K  A  K  Y  T  N  P  T  T  G  A  V  I  N tactacgaaatcaccatctcacccctgcagcaacaggtttatcctggccttggcaaggca
 Y  Y  E  I  T  I  S  P  L  Q  Q  Q  V  Y  P  G  L  G  K  A aacctcgttggctacgatggtatctctcccggtcccacttttaagatggagaggggagaa
 N  L  V  G  Y  D  G  I  S  P  G  P  T  F  K  M  E  R  G  E gaggctgtcgttcgtttcatcaacaaggcctccattcccaattccgtccatcttcacggc
 E  A  V  V  R  F  I  N  K  A  S  I  P  N  S  V  H  L  H  G tcctactcctttgccccttcgatggctggcggaggatacgaccagcccaggccaatac
 S  Y  S  F  A  P  F  D  G  W  A  E  D  T  T  S  P  G  Q  Y aaggactactactaccccaatgccagtctgcccgtaccctctggtaccacgaccatgcc
 K  D  Y  Y  Y  P  N  A  Q  S  A  R  T  L  W  Y  H  D  H  A gtcttccacactgccgagaacgcctactacggtcaggcaggtttctacatcctgcacgac
 V  F  H  T  A  E  N  A  Y  Y  G  Q  A  G  F  Y  I  L  H  D

```
tcggctgaggatagtctgggtctcccgtctggagactacgacatcccgctcggtctgagc
 S   A   E   D   S   L   G   L   P   S   G   D   Y   D   I   P   L   G   L   S tcgaagcaataccagtccaacggtgacctttcagcccgaatggcgagacggatagcctt
 S   K   Q   Y   Q   S   N   G   D   L   F   S   P   N   G   E   T   D   S   L tttggcgatgttatccatgtcaacggccagccctggccgtacctcaaggtcgagcccagg
 F   G   D   V   I   H   V   N   G   Q   P   W   P   Y   L   K   V   E   P   R aagtaccgcttccgcctgcttgatacaagcatttcccgtgccttccagctgtcactccaa
 K   Y   R   F   R   L   L   D   T   S   I   S   R   A   F   Q   L   S   L   Q gacgataagagcaagaagattgactttaacgtcatcgcctccgatgccggcctcctgtcc
 D   D   K   S   K   K   I   D   F   N   V   I   A   S   D   A   G   L   L   S agccctgttccgaccaacctgctacacatttccatggccgaacgctgggaaattgtcgtc
 S   P   V   P   T   N   L   L   H   I   S   M   A   E   R   W   E   I   V   V gacttctcccagtacgctggcaagaacatcaccatgaagaacgagcgtgacgtgcaggcc
 D   F   S   Q   Y   A   G   K   N   I   T   M   K   N   E   R   D   V   Q   A gatgaagactacaacagcactgacaaggtcatgcgcttcgtagtaggcaacaaggttacc
 D   E   D   Y   N   S   T   D   K   V   M   R   F   V   V   G   N   K   V   T tcgactgccaacaacaacctgcctggcagcctccgcagcgtgccttcccgccgaataag
 S   T   A   N   N   N   L   P   G   S   L   R   S   V   P   F   P   P   N   K tctggtgttgacaggagcttcaagttcgagcgcaaaggcggtgaatggactatcaacggc
 S   G   V   D   R   S   F   K   F   E   R   K   G   G   E   W   T   I   N   G gttacctttgccgacgtcgagaaccgtattctaggcaagcccaacgcggacaggttgag
 V   T   F   A   D   V   E   N   R   I   L   G   K   P   Q   R   G   Q   V   E gtctgggagctcgagaactcttccggcggctggtctcaccccgttcacatccatctcatc
 V   W   E   L   E   N   S   S   G   G   W   S   H   P   V   H   I   H   L   I gacttccaggttatttctcgcactggtggcaagcgtgatgtcctgccttacgagaagaac
 D   F   Q   V   I   S   R   T   G   G   K   R   D   V   L   P   Y   E   K   N ggtctcaaagatgtcgtcttgcttggcgtgaacgagaaggtcagagttgtcgctcgcttc
 G   L   K   D   V   V   L   L   G   V   N   E   K   V   R   V   V   A   R   F cagccctgggaaggtgtctacatgttccattgccacaacctgatccacgaggaccacgat
 Q   P   W   E   G   V   Y   M   F   H   C   H   N   L   I   H   E   D   H   D atgatggccgctttcaatgtatccaccctttcagactacggctacgaccagaaggagacc
 M   M   A   A   F   N   V   S   T   L   S   D   Y   G   Y   D   Q   K   E   T cttttcatcgacccgatggagtcccgctggcgcgcaaaggatgtcaagaccgaagacttc
 L   F   I   D   P   M   E   S   R   W   R   A   K   D   V   K   T   E   D   F acaaccgatgccatccagtcgaagcttgccgctttcgctgaaataaatcgctacaaggac
 T   T   D   A   I   Q   S   K   L   A   A   F   A   E   I   N   R   Y   K   D gttgcgaagatcgaaagtgctcttgaaaattattggaagaccgctcccaccgggttcaag
 V   A   K   I   E   S   A   L   E   N   Y   W   K   T   A   P   T   G   F   K attagcaccacctcctcaactccgagctcaaccgccgccacctccaccgcttccagcagt
 I   S   T   T   S   S   T   P   S   S   T   A   A   T   S   T   A   S   S   S ggctcaaacacctctattaccgccccattcagtcccggccactacttcacccgcgacc
 G   S   N   T   S   I   T   A   P   I   Q   S   P   A   T   T   S   P   A   T acttcgaccaaggcggatgacaagggcaaggctaagacttctacgaccaaaacgaagtaa
 T   S   T   K   A   D   D   K   G   K   A   K   T   S   T   T   K   T   K   -
```

SEQ ID NO: 51
LENGTH: 619
TYPE: PRT
ORGANISM: M. phaseolina

MFFGSLHLGIGALLVAGTLAGDDKWLSPVYKNFYEFPLPKPPIKEAKAKYTNPTTGAVINYYEITIS

PLQQQVYPGLGKANLVGYDGISPGPTFKMERGEEAVVRFINKASIPNSVHLGSYSFAPFDGWAEDT

TSPGQYKDYYYPNAQSARTLWYHDHAVFHTAENAYYGQAGFYILHDSAEDSLGLPSGDYDIPLGLSS

KQYQSNGDLFSPNGETDSLFGDVIHVNGQPWPYLKVEPRKYRFRLLDTSISRAFQLSLQDDKSKKID

FNVIASDAGLLSSPVPTNLLHISMAERWEIVVDFSQYAGKNITMKNERDVQADEDYNSTDKVMRFVV

GNKVTSTANNNLPGSLRSVPFPPNKSGVDRSFKFERKGGEWTINGVTFADVENRILGKPQRGQVEVW

ELENSSGGWSHPVHIHLIDFQVISRTGGKRDVLPYEKNGLKDVVLLGVNEKVRVVARFQPWEGVYMF

HCHNLIHEDHDMMAAFNVSTLSDYGYDQKETLFIDPMESRWRAKDVKTEDFTTDAIQSKLAAFAEIN

RYKDVAKIESALENYWKTAPTGFKISTTSSTPSSTAATSTASSSGSNTSITAPIQSPATTSPATTST

KADDKGKAKTSTTKTK*

SEQ ID NO: 52
LENGTH: 2423 (including 150 bp 5' UTR and 150 bp 3' UTR)
TYPE: DNA
ORGANISM: M. phaseolina
AAAGGCCTTTGGCTCCCGCCAAAATTGTTCATCCTCACGCTCACTCCTGCGCTCTTCCCTACAGACC

TTTTGCCTGTAGCTTTAGCTTCACGGTCTTTTCATTCCCCTTCTCTGGCATTCATCCCACCGCGGGA

AGCCTCAATTACCACAATGGTGTCCCTTAAGCAAATCGGTGCCACTCTGTTGGCACTGACTGCTCAA

ACCTTCGCTGCTGCCATCCCTGAGGCCGAACCGGTGGACCTCGTCGCCCGTCAAGCCACGACCACTA

CGTCCACCACCTCCTCAACCACCTCGAGGGTTCCCGATTCCCGATGTACTTGGGGCCCTTCGAGCAG

GGGTTGCTGGAAGAACGGCTTCAGCATTGCCACTGACTTTGACACGAAGTGGCCATCTACTGGCAAG

ACTGTCTCATATCGCTTGGAAGTTACGAATGTCACCAACTGCGAGGACTATCAAAGCAAGGGAATTG

GAGATGGCTTCTGCAGGCCGATGCTGCTCATCAACAATCAGTTCCCAGGGCCTACCAGTCAGTTTTT

CCCTCCTCGATGCCGGGTGACAAGGGCGCTAATGACTCGTACTTTCCAGTCAATGCGGAATGGGGAG

ACAACCTTGAGATTACTGTTGTCAATAGTATGCAAGACAACGGCACCTCATTCCACTGGCACGGCAT

TCGTCAGCTGAACTCATGCCAAAACGATGGTGCCAACGGCGTCACCGAGTGCCCTATTCCTCCCGGC

GGAAGCTTCACTTATAAGTTCAAGGCTACACAGTATGGTGAGTCTTTGCCTTCTCTTCTACCTTTTC

CATTTCATGCAAGCATCTTCATGTGCGTTCTGTTGAGTTTTGAGGCGGAAATACTCTTGAGCTTGCC

CCGTTCCGTTTGTGAGCCACGTGCAAGGCCACCTGCTCCCACCCTTGTCATAATACTGACCGGCCCT

TcCAGGAACAACATGGTACCATAGCCATCACTCTGCTCAGTACGGCGATGGGATCCAAGGTGCCATC

GTGATCAATGGCCCGGCAACCGCCAATTACGACGAGGATTTAGGCCCCGTTGCCCTCACCGAAACCT

ACGATGAGACGGCATGGACGAAGAACTGGCTGGCGCTGCACGTGGCATTCCCTCCTCAGCCCCTCAA

CATTCTCTTCAATGGCTCCATGGTCAACAGCACCGGCGGCGGCCGCTACAACACCATCTCAGTCAAG

CAAGGCAAGACTTACCGGCTGCGCCTGATTAACATGAGCGTCGACACTTTCTTCGTATTCTCCATGG

ACGGGCACGAGTTCCAGATCATCACGGCCGACCTCGTCCCCGTGCACCCTTACAATGCGACCTCGAT

CATGATCGGCATCGGCCAGCGCTACGACATCGTCTTCAAGGCCAACCAGCCCGCTGCCAACTACTGG

CTGCGTACCGAGATCGCCAGCTGCAGTGCCAACGCCATCACGGCCGAAGCCGACATCGTCCCCGGCG

GCATCCTGAACTACGACACCATCGACAAGACGGATCTGCCAGTCTCCACCAAGTCCGTTATCGAGAC

GACCGACTGCGCCGCCGAGCCCTACGACAAGCTGGTCCCCTGGTGGGAGACGCAGGTCCCCAAGGAC

CAGTTCCTGACCCAGCTCGAGGGCATCGACCTGACGTTCGCGGCGGGCGCCACGGTCGGCAGCGAGA

CTGGTCTTGTGCAGTGGTACCTGAACGACAGCGCCATGGTCGTCGACTGGGCCAAACCGACTCTGGA

GTACTTCTCCGAGGGAGACACTAACTATACGTCTTCAATGAACGTTTTCCAGATGCCCGCGGAGGGG

AAGTGGTCGTTCTGGATCATCCACAACAACGCGGCCGCTCTGCTCGACCACCCGATCCATCTCCACG

GCCACGACTTTTTCCACCTGGGCGCCGGCACCGGCACCTGGGACGGCAACGTGGACTCCTTGATCTT

CGACAATCCTATGCGCAGGGACGTGATGATCTTGCCCACAGGATGGCTTATTATCGCCTTTCCAGCG

GACAAcCCCGGCGCGTGGTTGATGCATTGCCACATCGTAAGTACCCAACAAGCCCCATCTCTCTCTC

TCTCTCTCATCAAAGATGACGGCAACTGACAAGCAACCAGGCATGGCACGTTACCGACGGGCTTTCC

TTGCAGTTCGTTGAAAACCCAGGCTCATTCACGCAGGACCTCTCGGGCATGAAGAGCAACTGCGCCG

CCTGGAAAGAGTACGAGGAGAAGGCTTACTATGAGAAGGAGGTTGGCGATTCCGGCTTGTAAAACCG

TGACGGCGGGGATGAGGAGTTTATGACGAGATGTTCACTTTATACCTTCTACCACCACCACCACCCT

TTTCCTCTTTCTTTTACCGACGTAGGGCTGCACTATCTGGCGCGTCTGTGGTCTGCTTTGCATATGC

ATAAATACCTT

SEQ ID NO: 53
LENGTH: 1824
TYPE: DNA
ORGANISM: M. phaseolina
FEATURE NAME/KEY: CDS
LOCATION: (1) . . . (1824)

```
atggtgtcccttaagcaaatcggtgccactctgttggcactgactgctcaaaccttcgct
 M  V  S  L  K  Q  I  G  A  T  L  L  A  L  T  A  Q  T  F  A gctgccatccctgaggccgaaccggtggacctcgtcgcccgtcaagccacgaccactacg
 A  A  I  P  E  A  E  P  V  D  L  V  A  R  Q  A  T  T  T  T tccaccacctcctcaaccacctcgagggttcccgattcccgatgtacttggggcccttcg
 S  T  T  S  S  T  T  S  R  V  P  D  S  R  C  T  W  G  P  S agcaggggttgctggaagaacggcttcagcattgccactgactttgacacgaagtggcca
 S  R  G  C  W  K  N  G  F  S  I  A  T  D  F  D  T  K  W  P tctactggcaagactgtctcatatcgcttggaagttacgaatgtcaccaactgcgaggac
 S  T  G  K  T  V  S  Y  R  L  E  V  T  N  V  T  N  C  E  D tatcaaagcaagggaattggagatggcttctgcaggccgatgctgctcatcaacaatcag
 Y  Q  S  K  G  I  G  D  G  F  C  R  P  M  L  L  I  N  N  Q ttcccagggcctaccatcaatgcggaatggggagacaaccttgagattactgttgtcaat
 F  P  G  P  T  I  N  A  E  W  G  D  N  L  E  I  T  V  V  N agtatgcaagacaacggcacctcattccactggcacggcattcgtcagctgaactcatgc
 S  M  Q  D  N  G  T  S  F  H  W  H  G  I  R  Q  L  N  S  C caaaacgatggtgccaacggcgtcaccgagtgccctattcctcccggcggaagcttcact
 Q  N  D  G  A  N  G  V  T  E  C  P  I  P  P  G  G  S  F  T tataagttcaaggctacacagtatggaacaacatggtaccatagccatcactctgctcag
 Y  K  F  K  A  T  Q  Y  G  T  T  W  Y  H  S  H  H  S  A  Q tacggcgatgggatccaaggtgccatcgtgatcaatggcccggcaaccgccaattacgac
 Y  G  D  G  I  Q  G  A  I  V  I  N  G  P  A  T  N  Y  D gaggatttaggccccgttgccctcaccgaaacctacgatgagacggcatggacgaagaac
 E  D  L  G  P  V  A  L  T  E  T  Y  D  E  T  A  W  T  K  N tggctggcgctgcacgtggcattccctcctcagcccctcaacattctcttcaatggctcc
 W  L  A  L  H  V  A  F  P  P  Q  P  L  N  I  L  F  N  G  S atggtcaacagcaccggcggcggccgctacaacaccatctcagtcaagcaaggcaagact
 M  V  N  S  T  G  G  G  R  Y  N  T  I  S  V  K  Q  G  K  T taccggctgcgcctgattaacatgagcgtcgacactttcttcgtattctccatggacggg
 Y  R  L  R  L  I  N  M  S  V  D  T  F  F  V  F  S  M  D  G cacgagttccagatcatcacggccgacctcgtccccgtgcacccttacaatgcgacctcg
 H  E  F  Q  I  I  T  A  D  L  V  P  V  H  P  Y  N  A  T  S atcatgatcggcatcggccagcgctacgacatcgtcttcaaggccaaccagcccgctgcc
 I  M  I  G  I  G  Q  R  Y  D  I  V  F  K  A  N  Q  P  A  A aactactggctgcgtaccgagatcgccagctgcagtgccaacgccatcacggccgaagcc
 N  Y  W  L  R  T  E  I  A  S  C  S  A  N  A  I  T  A  E  A gacatcgtccccggcggcatcctgaactacgacaccatcgacaagacggatctgccagtc
 D  I  V  P  G  G  I  L  N  Y  D  T  I  D  K  T  D  L  P  V tccaccaagtccgttatcgagacgaccgactgcgccgccgagccctacgacaagctggtc
 S  T  K  S  V  I  E  T  T  D  C  A  A  E  P  Y  D  K  L  V ccctggtgggagacgcaggtccccaaggaccagttcctgacccagctcgagggcatcgac
 P  W  W  E  T  Q  V  P  K  D  Q  F  L  T  Q  L  E  G  I  D ctgacgttcgcggcgggcgccacggtcggcagcgagactggtcttgtgcagtggtacctg
 L  T  F  A  A  G  A  T  V  G  S  E  T  G  L  V  Q  W  Y  L aacgacagcgccatggtcgtcgactgggccaaaccgactctggagtacttctccgaggga
 N  D  S  A  M  V  V  D  W  A  K  P  T  L  E  Y  F  S  E  G
```

```
                    D  T  N  Y  T  S  S  M  N  V  F  Q  M  P  A  E  G  K  W  S
gacactaactatacgtcttcaatgaacgttttccagatgcccgcggaggggaagtggtcg F  W  I  I  H  N  N  A  A  A  L  L  D  H  P  I  H  L  H  G
ttctggatcatccacaacaacgcggccgctctgctcgaccacccgatccatctccacggc H  D  F  F  H  L  G  A  G  T  G  T  W  D  G  N  V  D  S  L
cacgacttttccacctgggcgccggcaccggcacctgggacggcaacgtggactccttg I  F  D  N  P  M  R  R  D  V  M  I  L  P  T  G  W  L  I  I
atcttcgacaatcctatgcgcaggacgtgatgatcttgcccacaggatggcttattatc A  F  P  A  D  N  P  G  A  W  L  M  H  C  I  A  W  H  V
gcctttccagcggacaaccccggcgcgtggttgatgcattgccacatcgcatggcacgtt T  D  G  L  S  L  Q  F  V  E  N  P  G  S  F  T  Q  D  L  S
accgacgggctttccttgcagttcgttgaaaacccaggctcattcacgcaggacctctcg G  M  K  S  N  C  A  A  W  K  E  Y  E  E  K  A  Y  Y  E  K
ggcatgaagagcaactgcgccgcctggaaagagtacgaggagaaggcttactatgagaag E  V  G  D  S  G  L  -
gaggttggcgattccggcttgtaa
```

SEQ ID NO: 54
LENGTH: 607
TYPE: PRT
ORGANISM: M. phaseolina

MVSLKQIGATLLALTAQTFAAAIPEAEPVDLVARQATTTTSTTSSTTSRVPDSRCTWGPSSRGCWKN

GFSIATDFDTKWPSTGKTVSYRLEVTNVTNCEDYQSKGIGDGFCRPMLLINNQFPGPTINAEWGDNL

EITVVNSMQDNGTSFHWHGIRQLNSCQNDGANGVTECPIPPGGSFTYKFKATQYGTTWYHSHHSAQY

GDGIQGAIVINGPATANYDEDLGPVALTETYDETAWTKNWLALHVAFPPQPLNILFNGSMVNSTGGG

RYNTISVKQGKTYRLRLINMSVDTFFVFSMDGHEFQIITADLVPVHPYNATSIMIGIGQRYDIVFKA

NQPAANYWLRTEIASCSANAITAEADIVPGGILNYDTIDKTDLPVSTKSVIETTDCAAEPYDKLVPW

WETQVPKDQFLTQLEGIDLTFAAGATVGSETGLVQWYLNDSAMVVDWAKPTLEYFSEGDTNYTSSMN

VFQMPAEGKWSFWIIHNNAAALLDHPIHLHGHDFFHLGAGTGTWDGNVDSLIFDNPMRRDVMILPTG

WLIIAFPADNPGAWLMHCHIAWHVTDGLSLQFVENPGSFTQDLSGMKSNCAAWKEYEEKAYYEKEVG

DSGL*

SEQ ID NO: 55
LENGTH: 2147 (including 150 bp 5' UTR and 150 bp 3' UTR)
TYPE: DNA
ORGANISM: M. phaseolina

GCCACGGCTCCATTTGGATCGTCACTCACCACCACCACCACAACCACTCTCTACTCACCTCTTCACC

AGCCCCCTCTTTCTCCTCACTGGCATCCATTCGTTGAAGTCGCTGTCCCGTTTTCTTGTCTTTCGTC

TTCTTCCACCGTCAGAATGAGGGCTTCTTACCTCTCTGCGGCTGCCTTCCTGGGCCTCTCGGCTGCC

GCGCCGCAAGCCGCCAGCACTTCTTCTTCCTCTGCTTCAGCCAACGCCAGTTCCACCAGCTCAGCAG

CTACTTCCACTTGCACTGGCAACACTGCCGACGACCGCACTGTGTGGTGCGACTACGACATCAGCAC

CGACTACTACAACGACGGACCCGACACGGGGGTCACCCGCGAGTACTACTTCGTCGTCAGCGACGTG

ACCGTCTCGCCCGATGGCATCTCGCGCTCCGCTATGGCGGTGAACGGCAGCATCCCCGGCCCCACCA

TTTTCGCCGACTGGGGTGACACAGTGAAAGTTACTGTCTACAACGACCTCACCACGAGCGGCAACGG

CTCTTCCATCCATTGGCACGGTATCCGGCAGAACTACACGAACCAGAATGATGGTGTGGTGTCTATT

ACGCAATGCCCGATTGCGGTCGGCGAGACCTACACCTACGAGTGGAAGGCCACGCAGTACGGCTCTT

CCTGGTACCACTCTCACATTGGCCTGCAGGCCTGGGAGGGTGTTTTCGGTGGTATCATTATCAACGG

TCCCGCTACTGCAAATTACGACGAGGACCTCGGCATCATGTTTCTCAATGATTGGGATCACTCGACT

GTTGACGAGCTCTACGATTCAGCTCAGAGCAGCGGTCCTCCTACGCTTGACACCGGTCTCATTAACG

GAACCAACATCTACAATGACTCCGGAACAGTTACTGGATCTCGCTGGGAGGCCAGCCTGACCGAGGG

-continued

```
TACCAGCTACCGGCTCCGTCTTGTCAACGCTGCTGTAGACTCGCACTTCAAATTTTCGATCGATAAC

CACACCCTCCAGGTTATCGCCATGGACCTGGTCCCCATTGAGCCCTACGAGACTACTGTTCTGGACA

TTGGCATGGGTCAGCGCTACGACGTCATTGTTACGGCAGACCAGGCTTCTGTTGCTTCTGATTTCTG

GCTTCGCGCAATTCCCCAGACCGCCTGCTCGGACAACGATAACGCAGATGATATCAAGGGCATAATC

CACTACGGATCATCAACTGGTACTCCGGAAACCACTGCTTAGTAAGTTCCGATGTCCACATCTTCCG

AGCTCTCCGCTAATGATTCAACAGTGATTACACTGATGCCTGTGTCGATGAGGACAGCTCTGATCTC

GTAAGTGCTCGAGATTCACGGTCGTCTGGAAAGAGTAGGCGCGCTGACTGTGATCTTTAGGTCCCGT

ATGTCTCTAAGACTGCCACCTCCGGTACCTCCCTGGCCGAGGCTGTTTCCGTCGGCTACAACTCGGA

CAACCTCTTCCGCTGGTACATGAACGAGACCTCTATGGAGGTCGAGTGGGAGAATCCAACCCTTCTG

CAGGTCTACAACGACAATCTGACGTTCACTGACACATCGGGTGTTGTTCAACTTGACACCGCAGACC

AATGGTACTTCTTCGTCATCGAGACCGACAACGCTGTGCCACACCCAATCCATCTTCACGGCCACGA

CTTCTTCGTCCTGGCTGCGGGCACCGGCTCTTACAGTTCAGACGTTACTCTGACTCTGGATAACCCT

CCCCGCCGCGACACGGCTATGCTTGACTCCTCTGGCTACTTGGTCCTGGCTTTCGAGACCGACAACC

CAGGTGCGTGGTTGATGCACTGCCACATCGGCTGGCACACCAGCGAGGGCTTTGCCCTTCAGATCTT

GGAGCGCTACACCGAGATCCAGGATAGCCTGATCGACTACGACGTCCTCAATGACACCTGCTCGACT

TGGTCTACTTACTCCGAGGCAAACTCGATCGAGGAGGAGGACTCTGGTGTGTAAGGAAAACTCTGAG

TGACAATCCGTCTATGGCAGGTGTGCGGGGCGCTTTGGAGCTCTCTATCTCTGTGAAAGATCTTG

TATATAACGTGATGCCAGCCTCTCCCTGACATTTGGTGCTTCGGTTGATCTACATATATTTCCTTAT

TTA
```

SEQ ID NO: 56
LENGTH: 1737
TYPE: DNA
ORGANISM: *M. phaseolina*
FEATURE NAME/KEY: CDS
LOCATION: (1) . . . (1737)

```
atgagggcttcttacctctctgcggctgccttcctgggcctctcggctgccgcgccgcaa
 M  R  A  S  Y  L  S  A  A  A  F  L  G  L  S  A  A  A  P  Q gccgccagcacttcttcttcctctgcttcagccaacgccagttccaccagctcagcagct
 A  A  S  T  S  S  S  S  A  S  A  N  A  S  S  T  S  S  A  A acttccacttgcactggcaacactgccgacgaccgcactgtgtggtgcgactacgacatc
 T  S  T  C  T  G  N  T  A  D  D  R  T  V  W  C  D  Y  D  I agcaccgactactacaacgacggacccgacacgggggtcacccgcgagtactacttcgtc
 S  T  D  Y  Y  N  D  G  P  D  T  G  V  T  R  E  Y  Y  F  V gtcagcgacgtgaccgtctcgcccgatggcatctcgcgctccgctatggcggtgaacggc
 V  S  D  V  T  V  S  P  D  G  I  S  R  S  A  M  A  V  N  G agcatccccggccccaccattttcgccgactggggtgacacagtgaaagttactgtctac
 S  I  P  G  P  T  I  F  A  D  W  G  D  T  V  K  V  T  V  Y aacgacctcaccacgagcggcaacggctcttccatccattggcacggtatccggcagaac
 N  D  L  T  T  S  G  N  G  S  S  I  H  W  H  G  I  R  Q  N tacacgaaccagaatgatggtgtggtgtctattacgcaatgcccgattgcggtcggcgag
 Y  T  N  Q  N  D  G  V  V  S  I  T  Q  C  P  I  A  V  G  E acctacacctacgagtggaaggccacgcagtacggctcttcctggtaccactctcacatt
 T  Y  T  Y  E  W  K  A  T  Q  Y  G  S  S  W  Y  H  S  H  I ggcctgcaggcctgggagggtgttttcggtggtatcattatcaacggtcccgctactgca
 G  L  Q  A  W  E  G  V  F  G  G  I  I  I  N  G  P  A  T  A aattacgacgaggacctcggcatcatgtttctcaatgattgggatcactcgactgttgac
 N  Y  D  E  D  L  G  I  M  F  L  N  D  W  D  H  S  T  V  D gagctctacgattcagctcagagcagcggtcctcctacgcttgacaccggtctcattaac
 E  L  Y  D  S  A  Q  S  S  G  P  P  T  L  D  T  G  L  I  N
```

```
ggaaccaacatctacaatgactccggaacagttactggatctcgctgggaggccagcctg
 G  T  N  I  Y  N  D  S  G  T  V  T  G  S  R  W  E  A  S  L accgagggtaccagctaccggctccgtcttgtcaacgctgctgtagactcgcacttcaaa
 T  E  G  T  S  Y  R  L  R  L  V  N  A  A  V  D  S  H  F  K ttttcgatcgataaccacaccctccaggttatcgccatggacctggtccccattgagccc
 F  S  I  D  N  H  T  L  Q  V  I  A  M  D  L  V  P  I  E  P tacgagactactgttctggacattggcatgggtcagcgctacgacgtcattgttacggca
 Y  E  T  T  V  L  D  I  G  M  G  Q  R  Y  D  V  I  V  T  A gaccaggcttctgttgcttctgatttctggcttcgcgcaattccccagaccgcctgctcg
 D  Q  A  S  V  A  S  D  F  W  L  R  A  I  P  Q  T  A  C  S gacaacgataacgcagatgatatcaagggcataatccactacggatcatcaactggtact
 D  N  D  N  A  D  D  I  K  G  I  I  H  Y  G  S  S  T  G  T ccggaaaccactgcttatgattacactgatgcctgtcgatgaggacagctctgatctc
 P  E  T  T  A  Y  D  Y  T  D  A  C  V  D  E  D  S  S  D  L gtcccgtatgtctctaagactgccacctccggtacctccctggccgaggctgtttccgtc
 V  P  Y  V  S  K  T  A  T  S  G  T  S  L  A  E  A  V  S  V ggctacaactcggacaacctcttccgctggtacatgaacgagacctctatggaggtcgag
 G  Y  N  S  D  N  L  F  R  W  Y  M  N  E  T  S  M  E  V  E tgggagaatccaaccttctgcaggtctacaacgacaatctgacgttcactgacacatcg
 W  E  N  P  T  L  L  Q  V  Y  N  D  N  L  T  F  T  D  T  S ggtgttgttcaacttgacaccgcagaccaatggtacttcttcgtcatcgagaccgacaac
 G  V  V  Q  L  D  T  A  D  Q  W  Y  F  F  V  I  E  T  D  N gctgtgccacacccaatccatcttcacggccacgacttcttcgtcctggctgcgggcacc
 A  V  P  H  P  I  H  L  H  G  H  D  F  F  V  L  A  A  G  T ggctcttacagttcagacgttactctgactctggataacccctcccgccgcgacacggct
 G  S  Y  S  S  D  V  T  L  T  L  D  N  P  P  R  R  D  T  A atgcttgactcctctggctacttggtcctggctttcgagaccgacaacccaggtgcgtgg
 M  L  D  S  S  G  Y  L  V  L  A  F  E  T  D  N  P  G  A  W ttgatgcactgccacatcggctggcacaccagcgagggctttgcccttcagatcttggag
 L  M  H  C  I  G  W  H  T  S  E  G  F  A  L  Q  I  L  E cgctacaccgagatccaggatagcctgatcgactacgacgtcctcaatgacacctgctcg
 R  Y  T  E  I  Q  D  S  L  I  D  Y  D  V  L  N  D  T  C  S acttggtctacttactccgaggcaaactcgatcgaggaggaggactctggtgtgtaa
 T  W  S  T  Y  S  E  A  N  S  I  E  E  D  S  G  V  -

SEQ ID NO: 57
LENGTH: 578
TYPE: PRT
ORGANISM: M. phaseolina
MRASYLSAAAFLGLSAAAPQAASTSSSSASANASSTSSAATSTCTGNTADDRTVWCDYDISTDYYND

GPDTGVTREYYFVVSDVTVSPDGISRSAMAVNGSIPGPTIFADWGDTVKVTVYNDLTTSGNGSSIHW

HGIRQNYTNQNDGVVSITQCPIAVGETYTYEWKATQYGSSWYHSHIGLQAWEGVFGGIIINGPATAN

YDEDLGIMFLNDWDHSTVDELYDSAQSSGPPTLDTGLINGTNIYNDSGTVTGSRWEASLTEGTSYRL

RLVNAAVDSHFKFSIDNHTLQVIAMDLVPIEPYETTVLDIGMGQRYDVIVTADQASVASDFWLRAIP

QTACSDNDNADDIKGIIHYGSSTGTPETTAYDYTDACVDEDSSDLVPYVSKTATSGTSLAEAVSVGY

NSDNLFRWYMNETSMEVEWENPTLLQVYNDNLTFTDTSGVVQLDTADQWYFFVIETDNAVPHPIHLH

GHDFFVLAAGTGSYSSDVTLTLDNPPRRDTAMLDSSGYLVLAFETDNPGAWLMHCIGWHTSEGFAL

QILERYTEIQDSLIDYDVLNDTCSTWSTYSEANSIEEDSGV*

SEQ ID NO: 58
LENGTH: 2302 (including 150 bp 5' UTR and 150 bp 3' UTR)
TYPE: DNA
ORGANISM: M. phaseolina
TGCGCCCCTCCCGCGTGCTGGGCACTCTTTTATAAAGGCAGCTCTCCACTCCTGCCCTGTGAATGCT

TGCTCAAGGGCGCTCAGGCATAGGTAAGTAGGGTAAGTATTGAGGCGTCTGGCTTTGCGGCGAATCT
```

-continued

TGGGACGATTTCAGCCATGACTCGCCTTCCGTTCGTCCTCGGGCTCGTGGCTACGGCTTTGGCCAAG

ACGGTCACTGTTGACTGGGACATTGGCTGGGTTTCCAGGGCTCCCGATGGATTCGAGCGGCCTGTCA

TCGCAATCAACGGCCAATGGCCGCTCCCTGTGCTGGAGGCCGACGTCAACGACACCATCATCGCCAC

TGTCCACAATTCTCTTGGCAACGAAACGACCAGCATCCACTGGCACGGCATGTGGCAGAGAGGCACG

CCCGAGCAAGACGGCGGGGCTGGCGTCACGCAGTGTCCGATCCCGCCTGGCGAGACTTTCACGTACG

AGTTCAAAGCATACCCGGCCGGTACTTTCTGGTACCACTCGCATGACATGGGCCAGTATCCCGATGG

CCTGCGCGCACCCATGATCATCCATGACCCCGACTCCGAAACCCAGAAGAGCAGTGATGGTGAAGTC

GTGCTCTATGTGTCCGACTGGTACCACGACCAGATGCCGCCGCTTATCCACAGCTTCCTGACCACCC

CCAATTTCAACGGCGCGATGCCCAACCCGAACTCCAGCTTGATCAACGATCAGCAGTCCACGTCCAT

CAACATCCGTCCCGGCGAGAAGAAATACGTGCGCATCATCAACACGTCCGCCCTCGCCACGTACTAC

CTGCAGTTTGGTGGGTTCCGCTTCAGCCACCCCTCCCCTGCGGAAGTGACTGACGATTTCAGACCAA

CACAACATCACCGTTGTCGCAATTGACGGTGTTGACGGTCCGTACTACCCCTGTCGCTTATGCTGTG

GCTTCGTGCATACCCGTCGGCAGCTTCCCGCCGTTGCATGCCCGAGGCGATACAAGGTTTTAGTGCT

GACCGTAGTCGTGCAGTCGAACCGCAGAGCTGGAAGGCCCTGGAGATCGTCCCCGGCCAGCGGTACG

ACTTCATCATCGAAGGTCTCGAGAACCCCACAAGGAACTACGCATTCATCAACAAGATGGCTGTTCT

CGGTCTGCAGAACGTCAACAGCCTGGTCTACGACGAGTCCTTCGGCGAGCCGGAGTCGTTCAGCCTG

AGCTCTGGCGATCTCGGAAGTGATTTCACCCTGGTGCCTCTAGATCACGAGCCTCTCTTGGAATCCG

TGGACCACACCATCACGATGGAGGTCAATAATTTGAACATTGATGGCGTTGGCTTTCGGTACGGCTG

ATCCCGTGGCCGGGAGAAATCTTGCTCACATGTGCCACAGCATCACTCAAGGCCCGGACCCGTACAT

TTCACCCCGCACGCCTACCCTGTACACAGCCCTCAGCACCGGCTTCAACGCCACCGACCCAGAAATC

TACGGCCAGGTGAACCCCTACGTCGTCAACGCCGGTGAAGTCGTCCGGCTCGTCGTCAACAGCAACG

ATCTCGTCACCGCCAACAACTCTGGCCGCGGGCACCCCATGCATCTGCACGGCCACGTTTTCCAGGT

GGTCGGTCAGTTCTCCGAGCACTGGGACGGCAACACCTCGTCCTTCCCCGCCACGCCCATGAAGCGT

GACACCACCGTCCTATTCGCTGGCGGCAGCCTGGTGCTCCAGTTCCGTGCCGACAACCCCGGTGTTT

GGCTGTGTAAGTATTTTTTTTTCCGATGCCCATGGTGCCTGGACGTGAGCTGATGAGGATGGGCCTT

GCAGTTCACTGCCATATTGAGTGGCACCTAGACGCCGGCATGTCCGCTACAATCATCGAGGCGCCGC

TCGACTTGCAGCGCGAGGGCATCAAGATCCCCCAGCAGCATCTTGAATCGTGCAGAGCCTTGAACTT

GACCACTCAAGGCAATTGCGCCGGCAACACCGCCAACCTGGATGACACTGCCGCCTGCAGGGTCTAC

GACACCGATCCATGGGGGTAGGTCATATCGGAGTTTAATTGAGCTTGAAGGACATGTGCTGACCGTT

GCGTTTAGTGCGCTTATCACGGATGACGGTGGTGGAAATAGTACCCTGAACGGAACCACTTATAAGA

GAATTTAGTGTGTAATCTTAATACGTCTTCACATGTACACAACCTATGCATTGTATTCAAATTCTAC

ATAAGCACTTCGACAGTAGTCTGAGTTGACTGACTAGGCTCGTGGACGGAGGACGCCGTTTCCTCGT

CTTTGCCTGCTAAATTTTCGCGAT

SEQ ID NO: 59
LENGTH: 1665
TYPE: DNA
ORGANISM: *M. phaseolina*
FEATURE NAME/KEY: CDS
LOCATION: (1) . . . (1665)
atgactcgccttccgttcgtcctcgggctcgtggctacggctttggccaagacggtcact
 M  T  R  L  P  F  V  L  G  L  V  A  T  A  L  A  K  T  V  T gttgactgggacattggctgggtttccagggctcccgatggattcgagcggcctgtcatc
 V  D  W  D  I  G  W  V  S  R  A  P  D  G  F  E  R  P  V  I gcaatcaacggccaatggccgctccctgtgctggaggccgacgtcaacgacaccatcatc
 A  I  N  G  Q  W  P  L  P  V  L  E  A  D  V  N  D  T  I  I

```
gccactgtccacaattctcttggcaacgaaacgaccagcatccactggcacggcatgtgg
 A  T  V  H  N  S  L  G  N  E  T  T  S  I  H  W  H  G  M  W cagagaggcacgcccgagcaagacggcggggctggcgtcacgcagtgtccgatcccgcct
 Q  R  G  T  P  E  Q  D  G  G  A  G  V  T  Q  C  P  I  P  P ggcgagactttcacgtacgagttcaaagcataccggccggtacttctggtaccactcg
 G  E  T  F  T  Y  E  F  K  A  Y  P  A  G  T  F  W  Y  H  S catgacatgggccagtatcccgatggcctgcgcgcacccatgatcatccatgaccccgac
 H  D  M  G  Q  Y  P  D  G  L  R  A  P  M  I  I  H  D  P  D tccgaaacccagaagagcagtgatggtgaagtcgtgctctatgtgtccgactggtaccac
 S  E  T  Q  K  S  S  D  G  E  V  V  L  Y  V  S  D  W  Y  H gaccagatgccgccgcttatccacagcttcctgaccaccccaatttcaacggcgcgatg
 D  Q  M  P  P  L  I  H  S  F  L  T  T  P  N  F  N  G  A  M cccaacccgaactccagcttgatcaacgatcagcagtccacgtccatcaacatccgtccc
 P  N  P  N  S  S  L  I  N  D  Q  Q  S  T  S  I  N  I  R  P ggcgagaagaaatacgtgcgcatcatcaacacgtccgccctcgccacgtactacctgcag
 G  E  K  K  Y  V  R  I  I  N  T  S  A  L  A  T  Y  Y  L  Q tttgaccaacacaacatcaccgttgtcgcaattgacggtgttgacgtcgaaccgcagagc
 F  D  Q  H  N  I  T  V  V  A  I  D  G  V  D  V  E  P  Q  S tggaaggccctggagatcgtccccggccagcggtacgacttcatcatcgaaggtctcgag
 W  K  A  L  E  I  V  P  G  Q  R  Y  D  F  I  I  E  G  L  E aaccccacaaggaactacgcattcatcaacaagatggctgttctcggtctgcagaacgtc
 N  P  T  R  N  Y  A  F  I  N  K  M  A  V  L  G  L  Q  N  V aacagcctggtctacgacgagtccttcggcgagccggagtcgttcagcctgagctctggc
 N  S  L  V  Y  D  E  S  F  G  E  P  E  S  F  S  L  S  S  G gatctcggaagtgatttcaccctggtgcctctagatcacgagcctctcttggaatccgtg
 D  L  G  S  D  F  T  L  V  P  L  D  H  E  P  L  L  E  S  V gaccacaccatcacgatggaggtcaataatttgaacattgatggcgttggctttcgcatc
 D  H  T  I  T  M  E  V  N  N  L  N  I  D  G  V  G  F  R  I actcaaggcccggacccgtacatttcaccccgcacgcctaccctgtacacagccctcagc
 T  Q  G  P  D  P  Y  I  S  P  R  T  P  T  L  Y  T  A  L  S accggcttcaacgccaccgacccagaaatctacggccaggtgaaccctacgtcgtcaac
 T  G  F  N  A  T  D  P  E  I  Y  G  Q  V  N  P  Y  V  V  N gccggtgaagtcgtccggctcgtcgtcaacagcaacgatctcgtcaccgccaacaactct
 A  G  E  V  V  R  L  V  V  N  S  N  D  L  V  T  A  N  N  S ggccgcgggcaccccatgcatctgcacggccacgttttccaggtggtcggtcagttctcc
 G  R  G  H  P  M  H  L  H  G  H  V  F  Q  V  V  G  Q  F  S gagcactgggacggcaacacctcgtccttccccgccacgcccatgaagcgtgacaccacc
 E  H  W  D  G  N  T  S  S  F  P  A  T  P  M  K  R  D  T  T gtcctattcgctggcggcagcctggtgctccagttccgtgccgacaaccccggtgtttgg
 V  L  F  A  G  G  S  L  V  L  Q  F  R  A  D  N  P  G  V  W ctgtttcactgccatattgagtggcacctagacgccggcatgtccgctacaatcatcgag
 L  F  H  C  H  I  E  W  H  L  D  A  G  M  S  A  T  I  I  E gcgccgctcgacttgcagcgcgagggcatcaagatcccccagcagcatcttgaatcgtgc
 A  P  L  D  L  Q  R  E  G  I  K  I  P  Q  Q  H  L  E  S  C agagccttgaacttgaccactcaaggcaattgcgccggcaacaccgccaacctggatgac
 R  A  L  N  L  T  T  Q  G  N  C  A  G  N  T  A  N  L  D  D actgccgcctgcagggtctacgacaccgatccatggggtgcgcttatcacggatgacggt
 T  A  A  C  R  V  Y  D  T  D  P  W  G  A  L  I  T  D  D  G ggtggaaatagtaccctgaacggaaccacttataagagaatttag
 G  G  N  S  T  L  N  G  T  T  Y  K  R  I  -
```

-continued

SEQ ID NO: 60
LENGTH: 554
TYPE: PRT
ORGANISM: M. phaseolina
MTRLPFVLGLVATALAKTVTVDWDIGWVSRAPDGFERPVIAINGQWPLPVLEADVNDTIIATVHNSL

GNETTSIHWHGMWQRGTPEQDGGAGVTQCPIPPGETFTYEFKAYPAGTFWYHSHDMGQYPDGLRAPM

IIHDPDSETQKSSDGEVVLYVSDWYHDQMPPLIHSFLTTPNFNGAMPNPNSSLINDQQSTSINIRPG

EKKYVRIINTSALATYYLQFDQHNITVVAIDGVDVEPQSWKALEIVPGQRYDFIIEGLENPTRNYAF

INKMAVLGLQNVNSLVYDESFGEPESFSLSSGDLGSDFTLVPLDHEPLLESVDHTITMEVNNLNIDG

VGFRITQGPDPYISPRTPTLYTALSTGFNATDPEIYGQVNPYVVNAGEVVRLVVNSNDLVTANNSGR

GHPMHLHGHVFQVVGQFSEHWDGNTSSFPATPMKRDTTVLFAGGSLVLQFRADNPGVWLFHCHIEWH

LDAGMSATIIEAPLDLQREGIKIPQQHLESCRALNLTTQGNCAGNTANLDDTAACRVYDTDPWGALI

TDDGGGNSTLNGTTYKRI*

SEQ ID NO: 61
LENGTH: 2460 (including 150 bp 5' UTR and 150 bp 3' UTR)
TYPE: DNA
ORGANISM: M. phaseolina
CTCCGTATCTACTGCTGACTTCACATCCACAGCATGCAAGGACTCGAGGGCTTCTGATTTAACGAGC

ACTCACTTGGCTTTTGTCTGCGTTTTCTTTTCGTTTTCCTACTATTTCATCTTGATCCATTCGTTCT

CGCCGTCGCTTTCCAGATGTCTTTCGTTTCGAAAATTTTCACAGGCCTCATCGCTTTTACCGCTGGC

TTAGGCCAAGATGAGACTAATGGGTGAGTATGCTGAACCTTGCGCAGGATATCTGAATAATAGTTGT

AGGGTTTCGAAATGGGGCACGTTCGATGCACCGAGGCTCCAGAAGTTTCTGGATCGGGTGAGGTTAT

TCTGAAACATTACTGAGCTCGGCACTGATTGGTCGGCAGGGTCATGGCATTCCCTGGGGCGGTATGA

CTTGTACCAACGCCAACCCGTATACTGAGTAGGACTCGGCCCGTGGTCCACAATCTTCTCTGCGCTG

ACGTTCGGAAAGAGCTCCAGACACAGGACAGACTGTGCGGTATGATTTCACAGTCCAGCGGCATCCG

GTGTCTCCGGACGGCTACAAGAAGAACGTTTTGCTTGTGAACGGGCAATTTCCAGGCCCGCTCATGG

AAGCTAACTGGGGAGACACAATTGAAGGTAGGATGAGAGTAAATACGGGCAGCAACAACTGCTGACA

GATACAGTGACTGTGCACAACAACATAGCCGGACCTGAGGAAGGCACACAAATCCACTGGCACGGCT

TCACGCAGAGAGGGACGCCGTTCATGGATGGTATCCCTTCCGTATCAAGCTGCCCCATTGCGCCCAA

CAATACCTTTGTGTATACCTTCAAGGCAGACCTTTACGGCACTGGCTGGTACCACTCTCATTACTCT

GGGCAATCCACCGGCGGCCTCCTCGGCCCAATCGTCGTCCATGGTCCCAGTGCGCTTGACTATGATA

TTGACCTTGGCCCTGTGTTTTTGAATGACTGGTACCACAAGGACTACTTGCAGCTTATTGACGGTGG

TGAGACTTTCCCGTAGGTCAAAGGGCTCGATAGCTGAAACCTCCAACAGTCGTCGGAACGGACCCCA

GCCTATGGCATCCCAAGGCGGACAACAACATGATAAACGGGAAGATGGACTACGATTGCTCCCTTGT

CACTGACGGCACGCCTTGCGTCTCTAATGCCGGCTTGGCCACGTTCAGCTTCACCAAGGGCGCCACG

CACCGTCTCAGGCTCATAAACGGAGGATCCGCCTCCCTGCAGCACTTCAGTATCGATGGACACGAGA

TGACAGTCATTTCCAATGACTTCGTAGCCGTAGAGCCATACCAGACGAAGACAGTGACTCTTGCAGT

AAGCCGCCCGATTTTTCCAGATATCCCACATTACTAACACCCACCAGGTCGGCCAGCGGACAGACGT

CCTCGTCACGGCCAACGGCGACGCCACCGGCGCCTACTGGATGCGCAGCACCGTCGCGGACGATGAA

TCCTGCAACTGGTCCAACCAGCCCGCCGCGCTCGCCGCAGTCTACTACGACGCGGCAAACCCCACCG

TCAAGCCCAACAGCACCGGCTGGCCCCCCGTCGCCAACCAGCAAGGCAGCTGCGACAACGACCCGCT

TACCCAAACCATCCCCCTCTTCCCCATCCCCGCGGACCCCAGCCCCTCAACGACGCTTGAGCTCGAC

TTCGGCTGGACGCAAAACGCAACCGGACACCAAGTCTGGACGGTCAACGACCGCGGCTTCCGCGGCA

ACTACAACCGCCCCGTGCTGCAGCTCGCCGCGGGCTCGGACACCGCGTCGTCCGCGTACGCGTGGGA

```
GCCCGAATGGAACGTCTACGACACGGGCCGCAACCGCACCGTCCGCATCGTCATGCACAACAACTCC

TCCATGTACCACGTACGTGAGCCCTTGTCTCCCCCCCCCCCCCCCCTCCCCTCTCGCTAATGGAAAG

ACACATGCAGCCCATGCACCTCCACGGGCACAACGCGCAGATCCTCGCCGCGGGCGCCAACGGCCCC

TGGGACGGCCGCACCGTCGCGCGCCCCGCCAACCCGGCCCGCCGCGACGTCTACCAGCTCCCGCCGA

ACGGGCACCTGGTGATCCAGTACGCGCAGGACAACCCGGGCGTGTGGCCGCTGCACTGCCACATCGC

GTGGCACGCGAGCGCGGGCATGTTTGCGAGCGTGCTGGAGCGGGCGGGGGACATTGTGGGGAGCAGC

GGGGCCGGCGGGTGGAGGGAGGAGATGGCGGGCGTGTGTGCCGGGTGGGAGGCGTACACGCGGATGA

ACGTGGTGGAGCAGGTGGACAGTGGGGTGTGAGTTGGGAGCAAGGAGGGGGGTTTGAGATGCGCGTA

TATGGTAAGCGGTTGGGGTTCTTGTTTGACTCGATTTGCTCTGCAGGCGGTGTCTCTTTTCGACTGT

GGCGCGTGCAATCTCGTTTCGTGCATCCTGGGTGGATAGGGAGCGGCG
```

SEQ ID NO: 62
LENGTH: 1803
TYPE: DNA
ORGANISM: M. phaseolina
FEATURE NAME/KEY: CDS
LOCATION: (1)...(1803)

```
atgtctttcgtttcgaaaattttcacaggcctcatcgcttttaccgctggcttaggccaa
 M  S  F  V  S  K  I  F  T  G  L  I  A  F  T  A  G  L  G  Q gatgagactaatggggtttcgaaatggggcacgttcgatgcaccgaggctccagaagttt
 D  E  T  N  G  V  S  K  W  G  T  F  D  A  P  R  L  Q  K  F ctggatcggggtcatggcattccctgggcggtatgacttgtaccaacgccaacccgtat
 L  D  R  G  H  G  I  P  W  G  G  M  T  C  T  N  A  N  P  Y actgaagctccagacacaggacagactgtgcggtatgatttcacagtccagcggcatccg
 T  E  A  P  D  T  G  Q  T  V  R  Y  D  F  T  V  Q  R  H  P gtgtctccggacggctacaagaagaacgttttgcttgtgaacgggcaatttccaggcccg
 V  S  P  D  G  Y  K  K  N  V  L  L  V  N  G  Q  F  P  G  P ctcatggaagctaactggggagacacaattgaagtgactgtgcacaacaacatagccgga
 L  M  E  A  N  W  G  D  T  I  E  V  T  V  H  N  N  I  A  G cctgaggaaggcacacaaatccactggcacggcttcacgcagagagggacgccgttcatg
 P  E  E  G  T  Q  I  H  W  H  G  F  T  Q  R  G  T  P  F  M gatggtatcccttccgtatcaagctgccccattgcgcccaacaatacctttgtgtatacc
 D  G  I  P  S  V  S  S  C  P  I  A  P  N  N  T  F  V  Y  T ttcaaggcagaccctttacggcactggctggtaccactcteattactctgggcaatccacc
 F  K  A  D  L  Y  G  T  G  W  Y  H  S  H  Y  S  G  Q  S  T ggcggcctcctcggcccaatcgtcgtccatggtcccagtgcgcttgactatgatattgac
 G  G  L  L  G  P  I  V  V  H  G  P  S  A  L  D  Y  D  I  D cttggccctgtgttttttgaatgactggtaccacaaggactacttgcagcttattgacggt
 L  G  P  V  F  L  N  D  W  Y  H  K  D  Y  L  Q  L  I  D  G gtcgtcggaacggaccccagcctatggcatcccaaggcggacaacaacatgataaacggg
 V  V  G  T  D  P  S  L  W  H  P  K  A  D  N  N  M  I  N  G aagatggactacgattgctcccttgtcactgacggcacgccttgcgtctctaatgccggc
 K  M  D  Y  D  C  S  L  V  T  D  G  T  P  C  V  S  N  A  G ttggccacgttcagcttcaccaagggcgccacgcaccgtctcaggctcataaacggagga
 L  A  T  F  S  F  T  K  G  A  T  H  R  L  R  L  I  N  G  G tccgcctccctgcagcacttcagtatcgatggacacgagatgacagtcatttccaatgac
 S  A  S  L  Q  H  F  S  I  D  G  H  E  M  T  V  I  S  N  D ttcgtagccgtagagccataccagacgaagacagtgactcttgcagtcggccagcggaca
 F  V  A  V  E  P  Y  Q  T  K  T  V  T  L  A  V  G  Q  R  T gacgtcctcgtcacggccaacggcgacgccaccggcgcctactggatgcgcagcaccgtc
 D  V  L  V  T  A  N  G  D  A  T  G  A  Y  W  M  R  S  T  V gcggacgatgaatcctgcaactggtccaaccagcccgccgcgctcgccgcagtctactac
 A  D  D  E  S  C  N  W  S  N  Q  P  A  A  L  A  A  V  Y  Y
```

-continued

```
gacgcggcaaaccccaccgtcaagcccaacagcaccggctggcccccgtcgccaaccag
 D   A   A   N   P   T   V   K   P   N   S   T   G   W   P   P   V   A   N   Q caaggcagctgcgacaacgacccgcttacccaaaccatcccctcttcccatcccgcg
 Q   G   S   C   D   N   D   P   L   T   Q   T   I   P   L   F   P   I   P   A gaccccagcccctcaacgacgcttgagctcgacttcggctggacgcaaaacgcaaccgga
 D   P   S   P   S   T   T   L   E   L   D   F   G   W   T   Q   N   A   T   G caccaagtctggacggtcaacgaccgcggcttccgcggcaactacaaccgccccgtgctg
 H   Q   V   W   T   V   N   D   R   G   F   R   G   N   Y   N   R   P   V   L cagctcgccgcgggctcggacaccgcgtcgtccgcgtacgcgtgggagcccgaatggaac
 Q   L   A   A   G   S   D   T   A   S   S   A   Y   A   W   E   P   E   W   N gtctacgacacgggccgcaaccgcaccgtccgcatcgtcatgcacaacaactcctccatg
 V   Y   D   T   G   R   N   R   T   V   R   I   V   M   H   N   N   S   S   M taccacccatgcacctccacgggcacaacgcgcagatcctcgccgcgggcgccaacggc
 Y   H   P   M   H   L   H   G   H   N   A   Q   I   L   A   A   G   A   N   G ccctgggacggccgcaccgtcgcgcgccccgccaacccggcccgccgcgacgtctaccag
 P   W   D   G   R   T   V   A   R   P   A   N   P   A   R   R   D   V   Y   Q ctccccgccgaacgggcacctggtgatccagtacgcgcaggacaacccgggcgtgtggccg
 L   P   P   N   G   H   L   V   I   Q   Y   A   Q   D   N   P   G   V   W   P ctgcactgccacatcgcgtggcacgcgagcgcgggcatgtttgcgagcgtgctggagcgg
 L   H   C   H   I   A   W   H   A   S   A   G   M   F   A   S   V   L   E   R gcggggacattgtggggagcagcggggccggcgggtggaggggaggagatggcgggcgtg
 A   G   D   I   V   G   S   S   G   A   G   G   W   R   E   E   M   A   G   V tgtgccgggtgggaggcgtacacgcggatgaacgtggtggagcaggtggacagtggggtg
 C   A   G   W   E   A   Y   T   R   M   N   V   V   E   Q   V   D   S   G   V tga
 -
```

SEQ ID NO: 63
LENGTH: 600
TYPE: PRT
ORGANISM: *M. phaseolina*

MSFVSKIFTGLIAFTAGLGQDETNGVSKWGTFDAPRLQKFLDRGHGIPWGGMTCTNANPYTEAPDTG

QTVRYDFTVQRHPVSPDGYKKNVLLVNGQFPGPLMEANWGDTIEVTVHNNIAGPEEGTQIHWHGFTQ

RGTPFMDGIPSVSSCPIAPNNTFVYTFKADLYGTGWYHSHYSGQSTGGLLGPIVVHGPSALDYDIDL

GPVFLNDWYHKDYLQLIDGVVGTDPSLWHPKADNNMINGKMDYDCSLVTDGTPCVSNAGLATFSFTK

GATHRLRLINGGSASLQHFSIDGHEMTVISNDFVAVEPYQTKTVTLAVGQRTDVLVTANGDATGAYW

MRSTVADDESCNWSNQPAALAAVYYDAANPTVKPNSTGWPPVANQQGSCDNDPLTQTIPLFPIPADP

SPSTTLELDFGWTQNATGHQVWTVNDRGFRGNYNRPVLQLAAGSDTASSAYAWEPEWNVYDTGRNRT

VRIVMHNNSSMYHPMHLHGHNAQILAAGANGPWDGRTVARPANPARRDVYQLPPNGHLVIQYAQDNP

GVWPLHCHIAWHASAGMFASVLERAGDIVGSSGAGGWREEMAGVCAGWEAYTRMNVVEQVDSGV*

SEQ ID NO: 64
LENGTH: 2285 (including 150 bp 5' UTR and 150 bp 3' UTR)
TYPE: DNA
ORGANISM: *M. phaseolina*

TGAAGCCCTCTCTGACGCAGGTATCTATTTTATTAAACCAGTTTCACCCTCCGGTCGGGTAAGTATT

TGCTCAAACAAACTTGTCCAAGTGTCAGTTAGGTAAGCTAGGAGGCTCACGAATTCAAGAGACTCTC

CAGAGATATCTTCGCCATGATTCGCCTTTCTCTCGTGCTCGGCTTCATGGCCACGACACTGGCCAAG

ACCGTCACTCTTAACTGGGATATTGGGTGGGTTTCTGCGGCTCCAGATGGATTTACACGGCCCGTCA

TTGGCATCAACGGGGAGTGGCCGCCCCCcGTTTTGGAAGCCGACGTCAACGACACTATTATAGTAAT

TACGCGGAACCTCCTGCGTAACGAGACGACGAGCTTGCACTGGCATGGTATGTGGCACTATAACTCG

ACCCACATGGACGGCGGAGCCAGGATTTCACAGTGTGAAATCCCTCCGGGGGGGACATTCACGTACA

AGTTCAAGGCGTACCCGGCCGGCACCTTTTGGTATCATTCTCACGATATGGGCCAATATCCCGACGG

-continued

CCTGCGCGCCCCAATGATCATTCACGACCCTAAGGCTGCCGCGGAGCGGGACACTGATAAGGAGTAC
GTACTTACGGTCTCCGACTGGTACCGTGACCAGATGCCGTCACTTATCCACCGCTACTTGACAACTT
CCACTTATAATAGTACTATGCCAAATCCAAACTCGAGCTTGATCAACGATCAGCAGTCTACAACGCT
AAACATCCGCCCCGGGCAGAAGATATATGTTCGGATTATTAACATGTCAGCCCTCGCAACGTACTAT
CTACAGTTCGGTAGGTGTATCCATATGGCCCTGTTACACGGACGAAGCTAACGATTAAGATCAACAC
CACTTGACTGTTATTGCCATTGACGGTGTCGACGGTTGGTAACTCTATTACCTATTCTGCGCTAAGA
TGCATGTCGGCATATGTGCCGTTAGCTGCATGCAAACGCGTTACAAGGTTAAGTGCTAACAACGGGC
AGTCGATCCCCAGACTTGGGAGGCTCTGGAGATTATCCCTGGACAGCGGTACGACGTCATTATCACC
GGCCTAGAGAACCCCGAAAGGAACTATGCATTTATCAACAAGATGGCTACTCTTGGCTTCCAGAACA
ATAACGTCCTTAGTTACGATTCGTCCTGGCCTGTCCCGGAGCCGTTGAACGTGGGCAGCTTCAATCT
TAGAAGCGATTTCAACCTGACCCCGCTTGATGAGGAGCTACTACTGGAGCCCGTGGACCACACCTTC
ACCATGGAGGTCAATAACGTGAACGTCGACGGCGTAGGCTCCCGGTGAGATATTCCCTACCCCCCCG
GCCCCCGGGGCGGGTCCCGAAGTCGGTATGAGGCTTACTCACTCCAATCCGCAGCATCACGCAGGGA
CCGGACCCTTACATCGCCCCGCGTACGCCCACCCTATACACCACCCTGAGCACCGGCTCTAATGCTA
TTAACCCCGCCATATACGGCCAGGCGAACGCTTACGTAGTGGAAGCCGGCGATATTGTCCAGCTTGT
CGTCAATAGTAACGAACCCGTCACTACCAACACTTCCGGTCGTGGGCACCCTATGCACTTGCACGGC
CACACCTTCCAAGTGGTTGGCCAATATGGCAGCCCTTGGGACGGCGATGCCTCTAAATTCCCTGCTG
TTCCTATGAAGCGGGATACCACTGTTCTGTTTACTGGCGGGAGCTTGGTGATCCGGTTCCGCGCGGA
CAATCCTGGAGTTTGGATGTGTACGGCTCCGCTTTGCTCGAAGACCCGCGTTTGAAAGCGTTGACTG
ACCTGTAACTCGCAGTCCATTGCCACAACGAATGGCACCTTGACGCCGGCATGGCTGGAACGATTAT
CGAAGCGCCACTCGAGCTTCAACAAAGCGGTCTGACGATTCCGCCGCAGCACCTCGCGTCGTGCAGG
GCGTTAAACTTAACGACCCGGGGCAATTGTGCCGGTAATACTGCGAACCTAGAGGATACGGCTGCAT
GCAGAGTCTACGACACTGAGCCTTGGGGGTGAGTTACTCCATTATTGTTTTGTTGTTATAACCCTTG
CTGATGACAATACTTCTCTAGTGCACTTATCAAGAGAGATGAGGAAACAGCATATTAAATAGCACGC
TGGCATAGCACCTGTAGATGTAGACTGATTTCTAGTATTTATTACCTGTGTACACTTGAAGAAAATT
GTTGTAAAATGATATGTCCCCATGCAACTGAACATGGCCTACGTGGCGAGAGTTTATCAGGCGCCTT
CTGCTCC

SEQ ID NO: 65
LENGTH: 1635
TYPE: DNA
ORGANISM: *M. phaseolina*
FEATURE NAME/KEY: CDS
LOCATION: (1) . . . (1635)

```
atgattcgcctttctctcgtgctcggcttcatggccacgacactggccaagaccgtcact
 M  I  R  L  S  L  V  L  G  F  M  A  T  T  L  A  K  T  V  T cttaactgggatattgggtgggtttctgcggctccagatggatttacacggcccgtcatt
 L  N  W  D  I  G  W  V  S  A  A  P  D  G  F  T  R  P  V  I ggcatcaacggggagtggccgcccccgttttggaagccgacgtcaacgacactattata
 G  I  N  G  E  W  P  P  P  V  L  E  A  D  V  N  D  T  I  I gtaattacgcggaacctcctgcgtaacgagacgacgagcttgcactggcatggtatgtgg
 V  I  T  R  N  L  L  R  N  E  T  T  S  L  H  W  H  G  M  W cactataactcgacccacatggacggcggagccaggatttcacagtgtgaaatccctccg
 H  Y  N  S  T  H  M  D  G  G  A  R  I  S  Q  C  E  I  P  P gggggacattcacgtacaagttcaaggcgtacccggccggcaccttttggtatcattct
 G  G  T  F  T  Y  K  F  K  A  Y  P  A  G  T  F  W  Y  H  S cacgatatgggccaatatcccgacggcctgcgcgccccaatgatcattcacgaccctaag
 H  D  M  G  Q  Y  P  D  G  L  R  A  P  M  I  I  H  D  P  K
```

```
gctgccgcggagcgggacactgataaggagtacgtacttacggtctccgactggtaccgt
 A   A   A   E   R   D   T   D   K   E   Y   V   L   T   V   S   D   W   Y   R gaccagatgccgtcacttatccaccgctacttgacaacttccacttataatagtactatg
 D   Q   M   P   S   L   I   H   R   Y   L   T   T   S   T   Y   N   S   T   M ccaaatccaaactcgagcttgatcaacgatcagcagtctacaacgctaaacatccgcccc
 P   N   P   N   S   S   L   I   N   D   Q   Q   S   T   T   L   N   I   R   P gggcagaagatatatgttcggattattaacatgtcagccctcgcaacgtactatctacag
 G   Q   K   I   Y   V   R   I   I   N   M   S   A   L   A   T   Y   Y   L   Q ttcgatcaacaccacttgactgttattgccattgacggtgtcgacgtcgatccccagact
 F   D   Q   H   H   L   T   V   I   A   I   D   G   V   D   V   D   P   Q   T tgggaggctctggagattatccctggacagcggtacgacgtcattatcaccggcctagag
 W   E   A   L   E   I   I   P   G   Q   R   Y   D   V   I   I   T   G   L   E aaccccgaaaggaactatgcatttatcaacaagatggctactcttggcttccagaacaat
 N   P   E   R   N   Y   A   F   I   N   K   M   A   T   L   G   F   Q   N   N aacgtccttagttacgattcgtcctggcctgtcccggagccgttgaacgtgggcagcttc
 N   V   L   S   Y   D   S   S   W   P   V   P   E   P   L   N   V   G   S   F aatcttagaagcgatttcaacctgaccccgcttgatgaggagctactactggagcccgtg
 N   L   R   S   D   F   N   L   T   P   L   D   E   E   L   L   E   P   V gaccacaccttcaccatggaggtcaataacgtgaacgtcgacggcgtaggctcccgcatc
 D   H   T   F   T   M   E   V   N   N   V   N   V   D   G   V   G   S   R   I acgcagggaccggacccttacatcgccccgcgtacgccacccctatacaccaccctgagc
 T   Q   G   P   D   P   Y   I   A   P   R   T   P   T   L   Y   T   T   L   S accggctctaatgctattaaccccgccatatacggccaggcgaacgcttacgtagtggaa
 T   G   S   N   A   I   N   P   A   I   Y   G   Q   A   N   A   Y   V   V   E gccggcgatattgtccagcttgtcgtcaatagtaacgaacccgtcactaccaacacttcc
 A   G   D   I   V   Q   L   V   V   N   S   N   E   P   V   T   T   N   T   S ggtcgtgggcacccctatgcacttgcacggccacaccttccaagtggttggccaatatggc
 G   R   G   H   P   M   H   L   H   G   H   T   F   Q   V   V   G   Q   Y   G agcccttgggacggcgatgcctctaaattccctgctgttcctatgaagcgggataccact
 S   P   W   D   G   D   A   S   K   F   P   A   V   P   M   K   R   D   T   T gttctgtttactggcgggagcttggtgatccggttccgcgcggacaatcctggagtttgg
 V   L   F   T   G   G   S   L   V   I   R   F   R   A   D   N   P   G   V   W atgttccattgccacaacgaatggcaccttgacgccggcatggctggaacgattatcgaa
 M   F   H   C   H   N   E   W   H   L   D   A   G   M   A   G   T   I   I   E gcgccactcgagcttcaacaaagcggtctgacgattccgccgcagcacctcgcgtcgtgc
 A   P   L   E   L   Q   Q   S   G   L   T   I   P   P   Q   H   L   A   S   C agggcgttaaacttaacgaccggggcaattgtgccggtaatactgcgaacctagaggat
 R   A   L   N   L   T   T   R   G   N   C   A   G   N   T   A   N   L   E   D acggctgcatgcagagtctacgacactgagccttggggtgcacttatcaagagagatgag
 T   A   A   C   R   V   Y   D   T   E   P   W   G   A   L   I   K   R   D   E gaaacagcatattaa
 E   T   A   Y   -

SEQ ID NO: 66
LENGTH: 544
TYPE: PRT
ORGANISM: M. phaseolina
MIRLSLVLGFMATTLAKTVTLNWDIGWVSAAPDGFTRPVIGINGEWPPPVLEADVNDTIIVITRNLL

RNETTSLHWHGMWHYNSTHMDGGARISQCEIPPGGTFTYKFKAYPAGTFWYHSHDMGQYPDGLRAPM

IIHDPKAAAERDTDKEYVLTVSDWYRDQMPSLIHRYLTTSTYNSTMPNPNSSLINDQQSTTLNIRPG

QKIYVRIINMSALATYYLQFDQHHLTVIAIDGVDVDPQTWEALEIIPGQRYDVIITGLENPERNYAF

INKMATLGFQNNNVLSYDSSWPVPEPLNVGSFNLRSDFNLTPLDEELLLEPVDHFTMEVNNVNVDG

VGSRITQGPDPYIAPRTPTLYTTLSTGSNAINPAIYGQANAYVVEAGDIVQLVVNSNEPVTTNTSGR

GHPMHLHGHTFQVVGQYGSPWDGDASKFPAVPMKRDTTVLFTGGSLVIRFRADNPGVWMFHCHNEWH
```

LDAGMAGTIIEAPLELQQSGLTIPPQHLASCRALNLTTRGNCAGNTANLEDTAACRVYDTEPWGALI

KRDEETAY*

```
SEQ ID NO: 67
LENGTH: 2412 (including 150 bp 5' UTR and 150 bp 3' UTR)
TYPE: DNA
ORGANISM: M. phaseolina
GGGAGACGATCTGGAAGTGTTTGTTCAGAATGATTTGGCCGTTGAAACCACCATTCATTGGCACGGT

CGGTATCCATGGTATACTTTTTACGAAGGCTAGTCAGCTGAAGGAGAAGTTCGGCAGGCATCCTTCA

GCAAGGAACACCACACATGGACGGAGTTCCGGGAGTAACACAGGTTGGTTGATGACCTTCTATCGGG

ATGACTAGGGCCTAACTTTTGGCGCAGGAGCCGATCCCACCAGGAGGAAACTTCACGTACCGCTTCT

CGCTCAAAAACGAATACGGCTTCTACTGGTATCACTCGCATTTCCGAGCATACTCGGACGACGCCAT

CCGCGGACCACTAGTCATCCATCCATCCTCACAACGCCCCCGGCCATACGAGACTCTCGCGAGGAAC

CAGACTGAGCTTACTGCTTTGCAAGAAGCTGAACGCGAAGCGGTGCCTATCCTCCTATCTGACTGGT

ACCATCGCGTTTCGGACGACATCTTCAACGAATACCTAACAACAGGCGCGTTCCCCAGTTGCGTGGA

CAGTCTCCTCGCCAATGGATACGGAAGGGTGCGGTGTCTACCGGAATACATTCTGGCAGCCGGAGCT

GGGCTAGGCATGGAGCCTGCACCTGTCAATGCTACCGCGACTAGCATCGGCACAACGCCCATGTCTT

CCATGGCGATGGGTACAAAGTACATGGAGACCAATACCAAGGAGTCGATGCGTATGGAGTCTATGGC

ACTAGACACTACGTCCATGGAGCATCACATGCGACGCATGGATTCCATGTCAGCGGAGGATATGTCC

ATGAATACGATGACTGCTCATTCTACGCCTGCGGCTGCGCCCGACTCAGGCATGCCGATGGGCTCCA

TGTCAATGGCTTCTCTACCCGTATCAGGCATATCGGGCACGTCGGGCCTGTCGGGCATGTCAAATAT

GGCGAGCGGTCCCCTTGGTCCTCGCGGCTGCAGTGCTCCCATGATGTTCAGACCGGGCTACAACATC

AGCTCTCTCCCGCCAGAGACTTGCACAGACACGTCAGCGCCGCTGCTGACTGTCGATGCAAACTATA

CACGAGGCTGGCTTGCATTAAACCTAGTCAACTCCGGTTCAGTAACCAAGCTCAGCGTCTCACTAGA

CGCCCATTCGATGTTTGTCTATGCGGCCGACGGATTCTTTGTGAAACCCCAAGAAGTAGAAGTAAGT

TGCACCTCCCCCTAACTTGTCGTCGGAAGACTTACCGCGTCTAGGTATTACAAATCTCAATCGGGCA

ACGGTACTCAGTAATGATCAAACTTAATCAACGGCCCGGAAACTACACTCTACGGTTTGCGTCGTAT

CCCTACGGCGATATGCAACAGGTTATCGAAGGCCAAGCGACCGTCTCATATAAGGTAAGCAGCAAGC

TTTTCCCCCACTCGGTATAGAACTAACTTCGTTAGGTTGATGCCGCAGAGGACATTATGCCGGTGGA

CTTGACAAACGACCCTACTGCAACGTGGATGCTTGTCAACGGTTCGGCAAAGTCGAACGCTTCTGAA

TTGAAGACGGACATGCTCGCCCCGTTCGAGGCAATTGCGCCGCCATCCCAAGCGGATATAACTTACG

ACTTCACGATCAGTCAGACAGAGATCGTAACTTGGGTGTTAAACGGATATCCCTATTCGGAACCTTC

GACGCCTATTATCTACGGCAATGCGTCGGAAGCGTGGAACGCAAATACTACAATCCGCATTCCTTCC

AACTCGACCGTAGACATTATAATGCGGATTGCCAACGACTCAATGGATACGGCAAGTTGCAGTCCAG

GCCGCCGTCAAAACGCCTGCATAAGCTAACCCGATAATGCCGTAGATGGGTCATCCTATGCACCTTC

ACGGCCACCGGTTCTTCGCCCTCGGCTCTGGATCGGGCTCCTTCCCATATCAGAACGCCGTCGACGC

GCCTCCATCCCTCATTAACCTCGAAAACCCTCCGTACCGGGACACAACCGATTTACCACCTTCAGGC

TGGGCAGTCATTCGCTATGTAGCCAACAATCCAGGCGCATGGATGTTTCACTGCCACATCCAGTGGC

ACCTCGTGAGCGGCATGGCATTGGTGTTTGTCGAAGGAGAAGAGCAGCTGCCTGGTTTGGTGGGTGC

GGCTGCGAACGGAACAAGCAATGCGAATAGCGCGTCACCGGCGCGTAGCACTCGAGAGCATGCGGCC

TTTGCCGTTGTTGCTACCCTAAGCACTGTTTTCTTCGCGTATGGCTACTAATGCGCGAAGCGCCATG

TAAGAGCGCGCCTGAGGTAATAAAGGTGGCGACTGCAAAAAGCTCATGTCCCGCGAATGATGGGAGT

TCTTTGGAGATTCTGAATCAAAGACGTCGATATTCTGGGTCCAGTCGGTGCAGAACAGACCCCATGG
```

SEQ ID NO: 68
LENGTH: 1743
TYPE: DNA
ORGANISM: M. phaseolina
FEATURE NAME/KEY: CDS
LOCATION: (1) . . . (1743)

```
atggacggagttccgggagtaacacaggagccgatcccaccaggaggaaacttcacgtac
 M  D  G  V  P  G  V  T  Q  E  P  I  P  P  G  G  N  F  T  Y cgcttctcgctcaaaaacgaatacggcttctactggtatcactcgcatttccgagcatac
 R  F  S  L  K  N  E  Y  G  F  Y  W  Y  H  S  H  F  R  A  Y tcggacgacgccatccgcggaccactagtcatccatccatcctcacaacgccccggcca
 S  D  D  A  I  R  G  P  L  V  I  H  P  S  S  Q  R  P  R  P tacgagactctcgcgaggaaccagactgagcttactgctttgcaagaagctgaacgcgaa
 Y  E  T  L  A  R  N  Q  T  E  L  T  A  L  Q  E  A  E  R  E gcggtgcctatcctcctatctgactggtaccatcgcgtttcggacgacatcttcaacgaa
 A  V  P  I  L  L  S  D  W  Y  H  R  V  S  D  D  I  F  N  E tacctaacaacaggcgcgttccccagttgcgtggacagtctcctcgccaatggatacgga
 Y  L  T  T  G  A  F  P  S  C  V  D  S  L  L  A  N  G  Y  G agggtgcggtgtctaccggaatacattctggcagccggagctgggctaggcatggagcct
 R  V  R  C  L  P  E  Y  I  L  A  A  G  A  G  L  G  M  E  P gcacctgtcaatgctaccgcgactagcatcggcacaacgccatgtcttccatggcgatg
 A  P  V  N  A  T  A  T  S  I  G  T  T  P  M  S  S  M  A  M ggtacaaagtacatggagaccaataccaaggagtcgatgcgtatggagtctatggcacta
 G  T  K  Y  M  E  T  N  T  K  E  S  M  R  M  E  S  M  A  L gacactacgtccatggagcatacatgcgacgcatggattccatgtcagcggaggatatg
 D  T  T  S  M  E  H  H  M  R  R  M  D  S  M  S  A  E  D  M tccatgaatacgatgactgctcattctacgcctgcggctgcgcccgactcaggcatgccg
 S  M  N  T  M  T  A  H  S  T  P  A  A  A  P  D  S  G  M  P atgggctccatgtcaatggcttctctacccgtatcaggcatatcgggcacgtcgggcctg
 M  G  S  M  S  M  A  S  L  P  V  S  G  I  S  G  T  S  G  L tcgggcatgtcaaatatggcgagcggtccccttggtcctcgcggctgcagtgctcccatg
 S  G  M  S  N  M  A  S  G  P  L  G  P  R  G  C  S  A  P  M atgttcagaccgggctacaacatcagctctctcccgccagagacttgcacagacacgtca
 M  F  R  P  G  Y  N  I  S  S  L  P  P  E  T  C  T  D  T  S gcgccgctgctgactgtcgatgcaaactatacacgaggctggcttgcattaaacctagtc
 A  P  L  L  T  V  D  A  N  Y  T  R  G  W  L  A  L  N  L  V aactccggttcagtaaccaagctcagcgtctcactagacgcccattcgatgtttgtctat
 N  S  G  S  V  T  K  L  S  V  S  L  D  A  H  S  M  F  V  Y gcggccgacggattctttgtgaaacccaagaagtagaagtattacaaatctcaatcggg
 A  A  D  G  F  F  V  K  P  Q  E  V  E  V  L  Q  I  S  I  G caacggtactcagtaatgatcaaacttaatcaacggcccggaaactacactctacggttt
 Q  R  Y  S  V  M  I  K  L  N  Q  R  P  G  N  Y  T  L  R  F gcgtcgtatccctacggcgatatgcaacaggttatcgaaggccaagcgaccgtctcatat
 A  S  Y  P  Y  G  D  M  Q  Q  V  I  E  G  Q  A  T  V  S  Y aaggttgatgccgcagaggacattatgccggtggacttgacaaacgaccctactgcaacg
 K  V  D  A  A  E  D  I  M  P  V  D  L  T  N  D  P  T  A  T tggatgcttgtcaacggttcggcaaagtcgaacgcttctgaattgaagacggacatgctc
 W  M  L  V  N  G  S  A  K  S  N  A  S  E  L  K  T  D  M  L gccccgttcgaggcaattgcgccgccatcccaagcggatataacttacgacttcacgatc
 A  P  F  E  A  I  A  P  P  S  Q  A  D  I  T  Y  D  F  T  I agtcagacagagatcatgggtcatcctatgcaccttcacggccaccggttcttcgccctc
 S  Q  T  E  I  M  G  H  P  M  H  L  H  G  H  R  F  F  A  L ggctctggatcgggctccttcccatatcagaacgccgtcgacgcgcctccatccctcatt
 G  S  G  S  G  S  F  P  Y  Q  N  A  V  D  A  P  P  S  L  I aacctcgaaaaccctccgtaccgggacacaaccgatttaccaccttcaggctgggcagtc
 N  L  E  N  P  P  Y  R  D  T  T  D  L  P  P  S  G  W  A  V
```

```
attcgctatgtagccaacaatccaggcgcatggatgtttcactgccacatccagtggcac
 I  R  Y  V  A  N  N  P  G  A  W  M  F  H  C  H  I  Q  W  H ctcgtgagcggcatggcattggtgtttgtcgaaggagaagagcagctgcctggtttggtg
 L  V  S  G  M  A  L  V  F  V  E  G  E  E  Q  L  P  G  L  V ggtgcggctgcgaacggaacaagcaatgcgaatagcgcgtcaccggcgcgtagcactcga
 G  A  A  A  N  G  T  S  N  A  N  S  A  S  P  A  R  S  T  R gagcatgcggcctttgccgttgttgctaccctaagcactgttttcttcgcgtatggctac
 E  H  A  A  F  A  V  V  A  T  L  S  T  V  F  F  A  Y  G  Y taa
 -

SEQ ID NO: 69
LENGTH: 580
TYPE: PRT
ORGANISM: M. phaseolina
MDGVPGVTQEPIPPGGNFTYRFSLKNEYGFYWYHSHFRAYSDDAIRGPLVIHPSSQRPRPYETLARN

QTELTALQEAEREAVPILLSDWYHRVSDDIFNEYLTTGAFPSCVDSLLANGYGRVRCLPEYILAAGA

GLGMEPAPVNATATSIGTTPMSSMAMGTKYMETNTKESMRMESMALDTTSMEHHMRRMDSMSAEDMS

MNTMTAHSTPAAAPDSGMPMGSMSMASLPVSGISGTSGLSGMSNMASGPLGPRGCSAPMMFRPGYNI

SSLPPETCTDTSAPLLTVDANYTRGWLALNLVNSGSVTKLSVSLDAHSMFVYAADGFFVKPQEVEVL

QISIGQRYSVMIKLNQRPGNYTLRFASYPYGDMQQVIEGQATVSYKVDAAEDIMPVDLTNDPTATWM

LVNGSAKSNASELKTDMLAPFEAIAPPSQADITYDFTISQTEIMGHPMHLHGHRFFALGSGSGSFPY

QNAVDAPPSLINLENPPYRDTTDLPPSGWAVIRYVANNPGAWMFHCHIQWHLVSGMALVFVEGEEQL

PGLVGAAANGTSNANSASPARSTREHAAFAVVATLSTVFFAYGY*

SEQ ID NO: 70
LENGTH: 2242 (including 150 bp 5' and 150 bp 3' UTR)
TYPE: DNA
ORGANISM: M. phaseolina
AGTCCACCCTTTCCTATTTCTTTCCTCACGTCACATTCAGATACCCGGGCTCCTTTCAACTGCCAAA

TTTCCTTTTTCCCGGGACTCATTCCCTCCCCCGACTCTCTTACTCTTCTCTCAATTTCCTACCACCC

ACCGCTCGCTCTCACAATGTCTTTCGTTGCCAGGTCCGTAGTAAGCGGCCTCGCCAGCAGAGCCGCC

TTTACTAATGGATCATGGACCGGTGCCTGGGAGACTCATGGCTCCACCCAAGGTTCCATCTCACCGC

AACTACGCAACGGTACGTACCAGGTTCAGTTGTTTAAATCCCAAATTTGACTGATCTTTGTTGCAGG

CGGCGGGCCTCTTGGTACCTTGGACGCTCCAAACTTGCCTGGCTGTATTGGTTCTCCACCGTGGGGC

AACCATGACTCTCATGACCCTTTCGGCATGCCTGATACTGGCATTACTCGGGAGTATGACTTTACTC

TCACTTATCAAGACATCGCTCCCGATGGCGTCACTAAGAGGGGCGTCGTTGTCAATGGTCAATATCC

CGGGCCCACGATCGAGGCCAACTGGTGCGTACATCACTACATCACGCACATGACATCAGGCTAACAC

TTCGTTCAGGGGCGACTGGATCCAGGTCACGGTCCACAACGGTCTAGGCGAGGACGAAGGTGAGGGT

ACCGCGATGCACTGGCACGGCTTTTTGCAGAAGGAGAGCCAGTGGATGGATGGTGTCCCCGGTGTTC

AACAATGTCCTATTCCTCCCGGAGAGAGCTTCACCTACCGCTTCCGCGCTGAGCAGTATGGCACTTC

TTGGTACCACAGCCACTACAGCGCGCAGTACTCGGGCGGTGCTGCTGGTCCTCTCATCGTATACGGT

CCGGACAGCCAGAGTTACGACGTTGACCTCGGTCCCGTCATGGTATCTGACTGGTACCACTCGCAAT

ACTACGATATTGTCAAGCAGACCATGCAGGCCGACCCCACGGGCACCACCCCTCCGCCGCCGCCTCA

GTCCGACAACAACCTGATCCAGGGCTTTGGCGAATTCGACTGCTCGCTGACGACGAAGCCCTGCATT

CCTGACGCCGGTGTAGCCAAGTTCAAGTTCACTTCCGGCAAGAAGCATCGCCTCAGGCTCATCAACT

CCGGCTCCGAGGCGATGCAGAGGTTCTCTATCGACGGCCACACCATGAAGATCATCGCACACGACTT

CGTCCCGATCGAGCCCTACGAGGTCACGGCCCTGACCCTTGGCGTCGGACAGCGGGCCGACGTGGTT

GTCGAAGCCACGGGCAAGCCCTCGGACGCGTACTGGATGCGCTCAGAGATCGGGCTCAACAAGTGCA
```

-continued

```
ACGTCTTCAATGCGAACGCCTCCGAGGCCCTCGCCGTCATCCTCTACGAGGATGCAGACCTGCTGGC

CGTGCCCAGCTCCTCCGCCCAGCCCGATGCGGAGCTGACATCGTGCACCAACGACGACATCTCCGTC

GGCCTGCCGCTCCAGCACATCCTGCCCGACCCCAACCCGTCCGTCACGACCGAGCTGCACATCGAGA

ACAAGTACAACGGCACGCACTGGCTCTGGCACTTCGGCGGCCCCAGCTACCGCGCCGACTTCAACGA

CGCCCTCCTCTACCAGCTCCAACAGGGCACGCCCGACTTCGGCCCGCAGTCCAACGTGCACGACTTC

GGCGCCAACAAATCCGTCCGCTTCGTCGTCTACAACCACGTCCCGGCTCAGCATCCCATGCACTTGC

ATGGCCACAACTTCTGGGTCCTCGCCGACGGCGTCGGCACCTGGGACGGCGCCATCGCCAACCCGCA

GAACCCCCAGCGCCGCGACGTGCACGTCCTTCAGCCCGCCCAGGGCAGCACCCCGTCGTACATGGTC

GTACAGATTGAGCTGGACAACCCGGGCCTGTGGCCGTTCCACTGCCACATCGCGTGGCACGTCTCGG

CGGGGTTGTATTTGAACGTGCTGGAGCGCCCGGACGACATCAAGGCGCTGCAGATTCCGGCCGCGGT

TGGTGATCAGTGCAGGGCGTGGGCGGACTACACGGCAAAGAATACGGTGGATCAGATCGACTCGGGG

TTGAAGAAGGAGTAGAAGGCGTGATAGTTTGCTATTGTTCTTTCTCTCTCTCTTTTTTTTTTT

TTTTACACCTTCCCTTCTTGATACCAGCATGTTTTTGGGCGTTATTTACGGTCCTTCTGCGCATTTC

CAAGGCGTTATGTCTTTCCCTTGCGGATAAG
```

SEQ ID NO: 71
LENGTH: 1836
TYPE: DNA
ORGANISM: *M. phaseolina*
FEATURE NAME/KEY: CDS
LOCATION: (1) . . . (1836)

```
atgtctttcgttgccaggtccgtagtaagcggcctcgccagcagagccgcctttactaat
 M   S   F   V   A   R   S   V   V   S   G   L   A   S   R   A   A   F   T   N ggatcatggaccggtgcctgggagactcatggctccacccaaggttccatctcaccgcaa
 G   S   W   T   G   A   W   E   T   H   G   S   T   Q   G   S   I   S   P   Q ctacgcaacggcggcgggcctcttggtaccttggacgctccaaacttgcctggctgtatt
 L   R   N   G   G   G   P   L   G   T   L   D   A   P   N   L   P   G   C   I ggttctccaccgtggggcaaccatgactctcatgaccctttcggcatgcctgatactggc
 G   S   P   P   W   G   N   H   D   S   H   D   P   F   G   M   P   D   T   G attactcgggagtatgactttactctcacttatcaagacatcgctcccgatggcgtcact
 I   T   R   E   Y   D   F   T   L   T   Y   Q   D   I   A   P   D   G   V   T aagagggcgtcgttgtcaatggtcaatatcccgggcccacgatcgaggccaactggggc
 K   R   G   V   V   V   N   G   Q   Y   P   G   P   T   I   E   A   N   W   G gactggatccaggtcacggtccacaacggtctaggcgaggacgaaggtgagggtaccgcg
 D   W   I   Q   V   T   V   H   N   G   L   G   E   D   E   G   E   G   T   A atgcactggcacggcttttttgcagaaggagagccagtggatggatggtgtccccggtgtt
 M   H   W   H   G   F   L   Q   K   E   S   Q   W   M   D   G   V   P   G   V caacaatgtcctattcctcccggagagagcttcacctaccgcttccgcgctgagcagtat
 Q   Q   C   P   I   P   P   G   E   S   F   T   Y   R   F   R   A   E   Q   Y ggcacttcttggtaccacagccactacagcgcgcagtactcgggcggtgctgctggtcct
 G   T   S   W   Y   H   S   H   Y   S   A   Q   Y   S   G   G   A   A   G   P ctcatcgtatacggtccggacagccagagttacgacgttgacctcggtcccgtcatggta
 L   I   V   Y   G   P   D   S   Q   S   Y   D   V   D   L   G   P   V   M   V tctgactggtaccactcgcaatactacgatattgtcaagcagaccatgcaggccgacccc
 S   D   W   Y   H   S   Q   Y   Y   D   I   V   K   Q   T   M   Q   A   D   P acgggcaccaccccctccgccgcgcctcagtccgacaacaacctgatccagggctttggc
 T   G   T   T   P   P   P   P   P   Q   S   D   N   N   L   I   Q   G   F   G gaattcgactgctcgctgacgacgaagccctgcattcctgacgccggtgtagccaagttc
 E   F   D   C   S   L   T   T   K   P   C   I   P   D   A   G   V   A   K   F aagttccacttccggcaagaagcatcgcctcaggctcatcaactccggctccgaggcgatg
 K   F   T   S   G   K   K   H   R   L   R   L   I   N   S   G   S   E   A   M cagaggttctctatcgacggccacaccatgaagatcatcgcacacgacttcgtcccgatc
 Q   R   F   S   I   D   G   H   T   M   K   I   I   A   H   D   F   V   P   I
```

```
gagccctacgaggtcacggccctgacccttggcgtcggacagcgggccgacgtggttgtc
 E  P  Y  E  V  T  A  L  T  L  G  V  G  Q  R  A  D  V  V  V gaagccacgggcaagccctcggacgcgtactggatgcgctcagagatcgggctcaacaag
 E  A  T  G  K  P  S  D  A  Y  W  M  R  S  E  I  G  L  N  K tgcaacgtcttcaatgcgaacgcctccgaggccctcgccgtcatcctctacgaggatgca
 C  N  V  F  N  A  N  A  S  E  A  L  A  V  I  L  Y  E  D  A gacctgctggccgtgcccagctcctccgcccagcccgatgcggagctgacatcgtgcacc
 D  L  L  A  V  P  S  S  S  A  Q  P  D  A  E  L  T  S  C  T aacgacgacatctccgtcggcctgccgctccagcacatcctgcccgaccccaacccgtcc
 N  D  D  I  S  V  G  L  P  L  Q  H  I  L  P  D  P  N  P  S gtcacgaccgagctgcacatcgagaacaagtacaacggcacgcactggctctggcacttc
 V  T  T  E  L  H  I  E  N  K  Y  N  G  T  H  W  L  W  H  F ggcggcccagctaccgcgccgacttcaacgacgccctcctctaccagctccaacagggc
 G  G  P  S  Y  R  A  D  F  N  D  A  L  L  Y  Q  L  Q  Q  G acgcccgacttcggcccgcagtccaacgtgcacgacttcggcgccaacaaatccgtccgc
 T  P  D  F  G  P  Q  S  N  V  H  D  F  G  A  N  K  S  V  R ttcgtcgtctacaaccacgtcccggctcagcatcccatgcacttgcatggccacaacttc
 F  V  V  Y  N  H  V  P  A  Q  H  P  M  H  L  H  G  H  N  F tgggtcctcgccgacggcgtcggcacctgggacggcgccatcgccaacccgcagaacccc
 W  V  L  A  D  G  V  G  T  W  D  G  A  I  A  N  P  Q  N  P cagcgccgcgacgtgcacgtccttcagcccgcccagggcagcaccccgtcgtacatggtc
 Q  R  R  D  V  H  V  L  Q  P  A  Q  G  S  T  P  S  Y  M  V gtacagattgagctggacaacccgggcctgtggccgttccactgccacatcgcgtggcac
 V  Q  I  E  L  D  N  P  G  L  W  P  F  H  C  H  I  A  W  H gtctcggcggggttgtatttgaacgtgctggagcgcccggacgacatcaaggcgctgcag
 V  S  A  G  L  Y  L  N  V  L  E  R  P  D  D  I  K  A  L  Q attccggccgcggttggtgatcagtgcagggcgtgggcggactacacggcaaagaatacg
 I  P  A  A  V  G  D  Q  C  R  A  W  A  D  Y  T  A  K  N  T gtggatcagatcgactcggggttgaagaaggagtag
 V  D  Q  I  D  S  G  L  K  K  E  -

SEQ ID NO: 72
LENGTH: 611
TYPE: PRT
ORGANISM: M. phaseolina
MSFVARSVVSGLASRAAFTNGSWTGAWETHGSTQGSISPQLRNGGGPLGTLDAPNLPGCIGSPPWGN

HDSHDPFGMPDTGITREYDFTLTYQDIAPDGVTKRGVVVNGQYPGPTIEANWGDWIQVTVHNGLGED

EGEGTAMHWHGFLQKESQWMDGVPGVQQCPIPPGESFTYRFRAEQYGTSWYHSHYSAQYSGGAAGPL

IVYGPDSQSYDVDLGPVMVSDWYHSQYYDIVKQTMQADPTGTTPPPPPQSDNNLIQGFGEFDCSLTT

KPCIPDAGVAKFKFTSGKKHRLRLINSGSEAMQRFSIDGHTMKIIAHDFVPIEPYEVTALTLGVGQR

ADVVVEATGKPSDAYWMRSEIGLNKCNVFNANASEALAVILYEDADLLAVPSSSAQPDAELTSCTND

DISVGLPLQHILPDPNPSVTTELHIENKYNGTHWLWHFGGPSYRADFNDALLYQLQQGTPDFGPQSN

VHDFGANKSVRFVVYNHVPAQHPMHLHGHNFWVLADGVGTWDGAIANPQNPQRRDVHVLQPAQGSTP

SYMVVQIELDNPGLWPFHCHIAWHVSAGLYLNVLERPDDIKALQIPAAVGDQCRAWADYTAKNTVDQ

IDSGLKKE*

SEQ ID NO: 73
LENGTH: 1048 (including 150 bp 5' UTR and 150 bp 3' UTR)
TYPE: DNA
ORGANISM: M. phaseolina
GGACCGTTGCGGCGTTACTGATCTTCGGGTGAACGTCTCTCTTCGTACCAGGAAGCCGCCAACGCCG

AAGAAAGGGAGAAATACGTGTGGCTCAACTTTATCCACCCTGGCGCCCATCATGAGCTGCGGATCTC

CGTTGACGAGCACGACATGTGGATTGCGGCCGCAGATGGAGACTTCGTAAAACCaAAGAAAGTCCAA

GTAAGTTTCCACGTCTCGGTTTCGAGCACGCGCTGACAATCTCAAGGCCATCAATGTCAACATGGGC
```

```
GAGAGGATAAGCGTCCTTATTCCTCTTACCCAAAGTCCTGGAGAGTACGCCATCCGCATGGTCTCTC

TCGCGGAAGAGCAGCTCATCTGGGGCTTGGGAATTCTCCGGTACCCCGGTGTTCAAGAGAGACGAGA

TGAGAATGGCATAATGATCCTGCCAGAAAGCCAGCCACACATTGATGTTCAGGATAACCTGTTGACT

GACGGAATTGTGATGGACGAAATGACCGACCTGATCCCGTTTCCCGCGCGCCGTCCTCCAGCCAAGG

CCGACCACACCTTTCGCTTCGCCATCAAGCGGCCGAATCCAAGCACGTGGATTTTGGCATCGGAGCC

GCATCAAGGATTCAGACAACAGCTTCCGCCGGTGCTTTGGAACAAGGATTCCCGTGGCCCTACGACG

TTCGGCGGAATGAAGAACGGCTCGGTTGTGGACATCATTTATGAAAACGGAGCATTTGGGATGCATC

CGTTTCACCAGTGGATGAACGAATCGCATCACAGTATGGCAACTGCTGACATTTCATGCACAACCAC

AAAGCGTTCATCATCGGCATGGGGATGGGTTCTTCCGGTGGCCAGACGTTGCCTCGGCCCTCAAGG

AGGCCCCTGAAAACTTTAACATGGTGAACCCTCCTCTCCGTGACGGAGCACGGCTGGCAAAGGGAGA

AGGATCGTGGACTGTAATCCGCTACCAGATCACCTCTCCCGCAATGTCCATGTTACACTGTAAGCAG

CTCTCTGCAAAGTGCCTGACGGTGTAAGCACTGACGACCTCTC

SEQ ID NO: 74
LENGTH: 702
TYPE: DNA
ORGANISM: M. phaseolina
FEATURE NAME/KEY: CDS
LOCATION: (1) . . . (702)
atgtggattgcggccgcagatggagacttcgtaaaaccaaagaaagtccaagccatcaat
 M  W  I  A  A  A  D  G  D  F  V  K  P  K  K  V  Q  A  I  N gtcaacatgggcgagaggataagcgtccttattcctcttacccaaagtcctggagagtac
 V  N  M  G  E  R  I  S  V  L  I  P  L  T  Q  S  P  G  E  Y gccatccgcatggtctctctcgcggaagagcagctcatctggggcttgggaattctccgg
 A  I  R  M  V  S  L  A  E  E  Q  L  I  W  G  L  G  I  L  R taccccggtgttcaagagagacgagatgagaatggcataatgatcctgccagaaagccag
 Y  P  G  V  Q  E  R  R  D  E  N  G  I  M  I  L  P  E  S  Q ccacacattgatgttcaggataacctgttgactgacggaattgtgatggacgaaatgacc
 P  H  I  D  V  Q  D  N  L  L  T  D  G  I  V  M  D  E  M  T gacctgatcccgtttcccgcgcgccgtcctccagccaaggccgaccacacctttcgcttc
 D  L  I  P  F  P  A  R  R  P  P  A  K  A  D  H  T  F  R  F gccatcaagcggccgaatccaagcacgtggattttggcatcggagccgcatcaaggattc
 A  I  K  R  P  N  P  S  T  W  I  L  A  S  E  P  H  Q  G  F agacaacagcttccgccggtgctttggaacaaggattcccgtggccctacgacgttcggc
 R  Q  Q  L  P  P  V  L  W  N  K  D  S  R  G  P  T  T  F  G ggaatgaagaacggctcggttgtggacatcatttatgaaaacggagcatttgggatgcat
 G  M  K  N  G  S  V  V  D  I  I  Y  E  N  G  A  F  G  M  H ccgtttcaccagtggatgaacgaatcgcatcacagtatggcaactgctgacatttcatgc
 P  F  H  Q  W  M  N  E  S  H  H  S  M  A  T  A  D  I  S  C acaaccacaaagcgttcatcatcggcatggggatgggttcttccggtggccagacgttg
 T  T  T  K  R  S  S  S  A  W  G  M  G  S  S  G  G  Q  T  L cctcggccctcaaggaggcccctgaaaactttaacatggtga
 P  R  P  S  R  R  P  L  K  T  L  T  W  -

SEQ ID NO: 75
LENGTH: 233
TYPE: PRT
ORGANISM: M. phaseolina
MWIAAADGDFVKPKKVQAINVNMGERISVLIPLTQSPGEYAIRMVSLAEEQLIWGLGILRYPGVQER

RDENGIMILPESQPHIDVQDNLLTDGIVMDEMTDLIPFPARRPPAKADHTFRFAIKRPNPSTWILAS

EPHQGFRQQLPPVLWNKDSRGPTTFGGMKNGSVVDIIYENGAFGMHPFHQWMNESHHSMATADISCT

TTKRSSSAWGMGSSGGQTLPRPSRRPLKTLTW*
```

SEQ ID NO: 76
LENGTH: 2269 (including 150 bp 5' UTR and 150 bp 3' UTR)
TYPE: DNA
ORGANISM: M. phaseolina

GCTGCGAGGCATTCGAGAGGATTACCGAGTATTGGAGAGGCCGCGTGAAGGCAGCAGAGCATTAAAT

ACGTGCTTTGGAGCACGCGAATTACTTTCAAGTTGAACAAGATATCACCTGTCTTGCACGACGTTGC

AAGCTCCGCCGCAGCCATGAAGTGTGCAACTCTTTGGAGCTATCTTGCCTCTGTCCTGACCGTCGGC

GCTTCTGCGAGGTATTCCATTCAGCATAGACTTCAAACATTACCTAAATGCTGACAACTCATTTACA

GAAGCTTGACGCGGTCCTTGCCTCAGCACAAGACCAACGGAGGGTCCAATTGGGGAACTTTGGACTG

TCCAAAGTTACCCGATTTTTTGACCTCGAACCCGCTGCCCGGCGGCTTCCCGTGGGGTGACAGAAGC

GGCCTAAGCAACGATCCCTACACTGATGTGCCGAACACCGGGGTGACGAGGTACTACGATTTCAGCG

TCGCACGTGGCTATCTCGCTCCAGATGGCTACAACAAAAGTGGCATCTTCATCAACGGCGAGTTCCC

TGGGCCTGCCATTGAGGCCAATTGGGGCGACATGATTGAAGTACGAGTGCACAACAACATCGTCGGC

CCTGAAGAAGGCACTGCGTTCCACTGGCATGGCATTACTCAGAAGGGCACGCAATGGTTTGACGGCG

TTCCCGGCGTGTCCCAATGCCCCATTGCCCCTGGATCCTCTTTTACCTACCGCTTCCGTGCCGACGT

CTACGGCACTTCTTGGTGGCACTCGCACTTCTCTGCGCAATATACCGCTGGTGCTTTTGGGCCCCTC

ATTATCTACGGCCCCAAGCATGTTCCTTACGATGTTGATGTCGGCCCTGTAATTCTCGGTGATTACT

ACCACCGTGACTACTTTGATGTTCTGGAGGATGCTGCCAGCAACACCACTGACTTCAACATCTACGT

CCCTTGGTCCGACAACAATCTGATCAATGGCAAGAACAACTATAATTGCTCCATGGTAGCTGGAAAC

TCTACGAGCTTCGCCAACGCTACAAGCTCCTCGAACGCCACGTGCTTCTCCAACGCTGGCCTTGCCC

AGTTCCGTTTCGAGCCAGGCAAAGTGCACCGCCTGCGTCTGATGAACGTGGGCGCAGCAGCACTGCT

GCACTTCTCAATCGACGGGCACAAAATGCAAGTCATCGCCCACGACTTCGAACCTGTTGTCCCGTAC

GAGGCAGACGTCATCACGCTGGGCGCCGCCCAACGCACCGACATCCTCGTCACTGCAGATGCCAACC

CCAACGAGACATACTGGATCCGCTCCACCATCTCGCTCAACTGCTCTGTCTCGCACAACACCAACGC

GCTGGCCGTTCTCTCCTACGAAGGCAATGACCACATAGAAGAGCCACGCAGCCGCATTAGCGCCGCC

GCGGCCGCTGCTGACGAGAAGAGCTTCCTCTGCAAGAACGACGACCTGTCCCAGACGGTGCCCTTCT

TCCCCAAGCCCGTCGCCGAGCCCGATGTGACCGAGACGATCGAAGTCGACCTCTTCACCAATGCGAC

CGGCCACCATGTGTGGATCATGAACAACCGCACGCAGCGCACGAACTACAACGAGCCCGTCTTGCTG

CTCGCCAACCAGGGCAACAGCACCTTCCCGGACGAGTGGAACGTTTACGACTTTGGGCGCAACAAGA

CCATCCGCATCGTCCTCAACACCGTCTACCAGTCCGCCCACCCGATGCACTTGCACGGCCACTCTTT

CGTAAGACCCTTCATCCCTTCGCCACGCATGTGTGCCCACTCTGACCTCTTCCTCGCAGCAAGTCCT

CGCCGAAGGCCCCGGCGCCTGGGACGGCACGACCATCACCAACCCATCCAATCCCGCCCGCCGCGAC

ACGCACATGCAGCGCCGGTACGGGCACCTGGTAATCCAGTTCGAGGCCGACAACCCGGGCGCGTGGA

GCTACCACTGCCACATCGCCTGGCACGCCAGCATGGGCTACAACATCGAGATCCTCGAGCGCGGCGA

CGAGCTGGCGGCCGCCGGCGCTATTCCTATGGTCATGCAGCAGACGTGTGATGATTGGAAGGAGTGG

AGCGGCAGGAATGTGGTCAATCAGATCGACGCGGGCATTTAGATTATCGGCGACTTCTATGCCCGAT

GGTATAATGTTTTTACCGAGCGTGGGATGATGTGGGTTTGGGGTCGGAATTTGTAGATATGGGCGGG

GGATTGCCTGCACAAAATAGACCGATGCACATGTTTATAAAGCAAAAACTCTTCCCAT

SEQ ID NO: 77
LENGTH: 1854
TYPE: DNA
ORGANISM: M. phaseolina
FEATURE NAME/KEY: CDS
LOCATION: (1)...(1854)
atgaagtgtgcaactctttggagctatcttgcctctgtcctgaccgtcggcgcttctgcg
 M  K  C  A  T  L  W  S  Y  L  A  S  V  L  T  V  G  A  S  A

```
agaagcttgacgcggtccttgcctcagcacaagaccaacggagggtccaattggggaact
 R  S  L  T  R  S  L  P  Q  H  K  T  N  G  G  S  N  W  G  T ttggactgtccaaagttacccgattttttgacctcgaacccgctgcccggcggcttccg
 L  D  C  P  K  L  P  D  F  L  T  S  N  P  L  P  G  G  F  P tggggtgacagaagcggcctaagcaacgatccctacactgatgtgccgaacaccggggtg
 W  G  D  R  S  G  L  S  N  D  P  Y  T  D  V  P  N  T  G  V acgaggtactacgatttcagcgtcgcacgtggctatctcgctccagatggctacaacaaa
 T  R  Y  Y  D  F  S  V  A  R  G  Y  L  A  P  D  G  Y  N  K agtggcatcttcatcaacggcgagttccctgggcctgccattgaggccaattggggcgac
 S  G  I  F  I  N  G  E  F  P  G  P  A  I  E  A  N  W  G  D atgattgaagtacgagtgcacaacaacatcgtcggccctgaagaaggcactgcgttccac
 M  I  E  V  R  V  H  N  N  I  V  G  P  E  E  G  T  A  F  H tggcatggcattactcagaagggcacgcaatggtttgacggcgttcccggcgtgtcccaa
 W  H  G  I  T  Q  K  G  T  Q  W  F  D  G  V  P  G  V  S  Q tgccccattgcccctggatcctcttttacctaccgcttccgtgccgacgtctacggcact
 C  P  I  A  P  G  S  S  F  T  Y  R  F  R  A  D  V  Y  G  T tcttggtggcactcgcacttctctgcgcaatataccgctggtgcttttgggcccctcatt
 S  W  W  H  S  H  F  S  A  Q  Y  T  A  G  A  F  G  P  L  I atctacggccccaagcatgttccttacgatgttgatgtcggccctgtaattctcggtgat
 I  Y  G  P  K  H  V  P  Y  D  V  D  V  G  P  V  I  L  G  D tactaccaccgtgactactttgatgttctggaggatgctgccagcaacaccactgacttc
 Y  Y  H  R  D  Y  F  D  V  L  E  D  A  A  S  N  T  T  D  F aacatctacgtcccttggtccgacaacaatctgatcaatggcaagaacaactataattgc
 N  I  Y  V  P  W  S  D  N  N  L  I  N  G  K  N  N  Y  N  C tccatggtagctggaaactctacgagcttcgccaacgctacaagctcctcgaacgccacg
 S  M  V  A  G  N  S  T  S  F  A  N  A  T  S  S  S  N  A  T tgcttctccaacgctggccttgcccagttccgtttcgagccaggcaaagtgcaccgcctg
 C  F  S  N  A  G  L  A  Q  F  R  F  E  P  G  K  V  H  R  L cgtctgatgaacgtgggcgcagcagcactgctgcacttctcaatcgacgggcacaaaatg
 R  L  M  N  V  G  A  A  A  L  L  H  F  S  I  D  G  H  K  M caagtcatcgcccacgacttcgaacctgttgtcccgtacgaggcagacgtcatcacgctg
 Q  V  I  A  H  D  F  E  P  V  V  P  Y  E  A  D  V  I  T  L ggcgccgcccaacgcaccgacatcctcgtcactgcagatgccaaccccaacgagacatac
 G  A  A  Q  R  T  D  I  L  V  T  A  D  A  N  P  N  E  T  Y tggatccgctccaccatctcgctcaactgctctgtctcgcacaacaccaacgcgctggcc
 W  I  R  S  T  I  S  L  N  C  S  V  S  H  N  T  N  A  L  A gttctctcctacgaaggcaatgaccacatagaagagccacgcagccgcattagcgccgcc
 V  L  S  Y  E  G  N  D  H  I  E  E  P  R  S  R  I  S  A  A gcggccgctgctgacgagaagagcttcctctgcaagaacgacgacctgtcccagacggtg
 A  A  A  D  E  K  S  F  L  C  K  N  D  D  L  S  Q  T  V cccttcttccccaagcccgtcgccgagcccgatgtgaccgagacgatcgaagtcgacctc
 P  F  F  P  K  P  V  A  E  P  D  V  T  E  T  I  E  V  D  L ttcaccaatgcgaccggccaccatgtgtggatcatgaacaaccgcacgcagcgcacgaac
 F  T  N  A  T  G  H  H  V  W  I  M  N  N  R  T  Q  R  T  N tacaacgagcccgtcttgctgctcgccaaccagggcaacagcaccttcccggacgagtgg
 Y  N  E  P  V  L  L  L  A  N  Q  G  N  S  T  F  P  D  E  W aacgtttacgactttgggcgcaacaagaccatccgcatcgtcctcaacaccgtctaccag
 N  V  Y  D  F  G  R  N  K  T  I  R  I  V  L  N  T  V  Y  Q tccgccacccgatgcacttgcacggccactctttccaagtcctcgccgaaggcccccggc
 S  A  H  P  M  H  L  H  G  H  S  F  Q  V  L  A  E  G  P  G gcctgggacggcacgaccatcaccaacccatccaatcccgccgccgcgacacgcacatg
 A  W  D  G  T  T  I  T  N  P  S  N  P  A  R  R  D  T  H  M cagcgccggtacgggcacctggtaatccagttcgaggccgacaacccgggcgcgtggagc
 Q  R  R  Y  G  H  L  V  I  Q  F  E  A  D  N  P  G  A  W  S
```

```
taccactgccacatcgcctggcacgccagcatgggctacaacatcgagatcctcgagcgc
 Y  H  C  I  A  W  H  A  S  M  G  Y  N  I  E  I  L  E  R ggcgacgagctggcggccgccggcgctattcctatggtcatgcagcagacgtgtgatgat
 G  D  E  L  A  A  A  G  A  I  P  M  V  M  Q  Q  T  C  D  D tggaaggagtggagcggcaggaatgtggtcaatcagatcgacgcgggcatttag
 W  K  E  W  S  G  R  N  V  V  N  Q  I  D  A  G  I  -
```

SEQ ID NO: 78
LENGTH: 617
TYPE: PRT
ORGANISM: M. phaseolina
MKCATLWSYLASVLTVGASARSLTRSLPQHKTNGGSNWGTLDCPKLPDFLTSNPLPGGFPWGDRSGL

SNDPYTDVPNTGVTRYYDFSVARGYLAPDGYNKSGIFINGEFPGPAIEANWGDMIEVRVHNNIVGPE

EGTAFHWHGITQKGTQWFDGVPGVSQCPIAPGSSFTYRFRADVYGTSWWHSHFSAQYTAGAFGPLII

YGPKHVPYDVDVGPVILGDYYHRDYFDVLEDAASNTTDFNIYVPWSDNNLINGKNNYNCSMVAGNST

SFANATSSSNATCFSNAGLAQFRFEPGKVHRLRLMNVGAAALLHFSIDGHKMQVIAHDFEPVVPYEA

DVITLGAAQRTDILVTADANPNETYWIRSTISLNCSVSHNTNALAVLSYEGNDHIEEPRSRISAAAA

AADEKSFLCKNDDLSQTVPFFPKPVAEPDVTETIEVDLFTNATGHHVWIMNNRTQRTNYNEPVLLLA

NQGNSTFPDEWNVYDFGRNKTIRIVLNTVYQSAHPMLHGHSFQVLAEGPGAWDGTTITNPSNPARR

DTHMQRRYGHLVIQFEADNPGAWSYHCHIAWHASMGYNIEILERGDELAAAGAIPMVMQQTCDDWKE

WSGRNVVNQIDAGI*

SEQ ID NO: 79
LENGTH: 2373 (including 150 bP 5' UTR and 150 bP 3' UTR)
TYPE: DNA
ORGANISM: M. phaseolina
GACAATCCCTCCGCTAAATCCGACATCCGGTACTCTCGCCTCCCGGATCCCGAGCGGACACACAGCT

TCGCCTGTATACCACTTTCACCGGAGTCGCCTTCCCACCCCCTATAATTCTTTTCCTGTTGAGTCTA

CTCCGCGCGCGGTATCATGATAGATACCAAGAGCACAGGGTCCGGCGCAGACGGCGGTCGTTACGCC

GCCTTAAGGCAAGACGAGTCAGAGCTATACGAGCAGAAAGAACATACGCAGTGTACACAGCCCTCCG

GCGCCGCGTACCTCGGTGGAAATGGCAGAGAAGAAGCCCTGGGATTGATCGACGAAAATGTCGTCGC

TCGAACAAAAAGACGCTGTGGACCCACCCGGCGGTACTCTGTCTTCCTTGAATTTGCCATCCTCGGT

CTGGTACTCATAATCGCTCTACTCGGCGCTCTCGCTTGGTCCAGAGGCTCTCATCATCATACCGACC

CGGTATCTGGCAGTTCACAACCATCGTCCAAGGGTCGCCGCGGAAAGTATGTCCTGGACCCTGCCTG

GGATTTCGCTGCACCGCCGCAGGTCCGCAAATACCACTGGACGATCAGGGACATCGAGCTTCGCCCA

GACGGCGTGAAGCGGCCGCTGATCACCATCAATAACGAGTTCCCGGGCCGACCATCGAATGCAACC

AGGGGGATACCGTGCGGGTTGAGGTTCATAACGAAGCCGTCAATTCAACTTCCTTTCACTGGCACGG

CATTTACCAGAACGGAACCACGTACATGGATGGCACGGTCGGCATCAGCCAGTGTCCTATCACGTCT

GGGTCTAGCATGACATATGAGTTCAAAGTCGACAGAGAATCCGGCACCTATTGGTATCATGCGCACA

TGGCTATGCAGGGCTCAGATGGTCTTTTTGGTCCTCTGATCGTCCATTCGAAAAATGAGCGGAAGCT

GCAGCAACTCGAATATGCCTCCGATCAAGTCATCATGGTCCACGATTACTACCACGATCTGACCAGC

GCGCTGATACCACACTACTTAGCGCCGGATAACGAGAACACAGAGCCTGTCCCTGACGGAGGTCTCA

TCAACGGAATGAATAAGAGAAATTGCGAGCTCCTCCGTGGTCGAGACTGTGATGCCACTGATGCACA

GCTTGCCACATTCGGCCTCGAACCGAACAAGAACCACCGTCTTCGAATTATCAATACTGGAGCATTT

GCTGAATTCCAGGTGAAGATTGACGAGCACACGTTCGCTGTGACGGAGGTGGATGGGACCGAAGTTG

CTCCCGCCTACTACCACAGGCTCAACATCAATCCCGGACAGCGCTACAGCATCGTAATAAACACCAA

TGTCACGGATCGTGACTCCTTCTGGCTGAGAGCTAAGATGATTGAGGCCTGTTTCGCTGAGGAGAAC

CCAAATCTGGATCCCGAAGTGCGCGCCATTATCCAATATACTCGCAAGGACGAGGATACCCAGCCCA

-continued

```
AGGAACCTTCGAGCAGAGACTGGGACGACATCGTGGACATGCAGTGTCTCGACATGAACGTGACAGA

GCTCCAGCCCGTAGAGAAGGCAACACCTCCACCTGCAGACACCACACTATACCTCCGCTCCAACTTC

GAGATCGGCAACTGGCGTCTGAGCCGCGGCTTCTTCAACAGCTCGTCCTGGCGTCCAACACTCTCAT

CCCCAAGCCTGCACCGCATGATCGACGGCCTCCACAGCCAAAACGCCAGCTTCCTCCCCGACCGAGC

GTACCCCTTCCAGATCAACTCGGCCGGCTTCGACACTGGGCCCGAGCTGGTCTACCAGACCAGCGGC

ATCCGCACCATCGACATCCTCGTTTCCAACTTCGACGACGGCAACCACCCGCTCCACCTGCACGGCT

ACAAGTACTTCGTCCTTGCGTCGGGCCACGGCTACCCGCCCGCCGACCTCTACGCGCATCTCGACAT

CTCGAACCCGCTGCGCCGCGACACCGCCTCGATCGAGGCGTTCGGCTGGATCCTACTGCGTCTCGTC

GCCGACAACCCGGGCGTCTGGGCCTTCCACTGCCACATCGGCTGGCACACCGAGGCCGGCATGCTGA

TGCAGTTCGCCACGCGCGTCGACGTGCTCGCATCCAGCCAAATCCCGGATACGCACCTCGCGCTCTG

CGCGGCCGACGGGCTCGACCGCGGCGCGTCGCCGCCAGACTCGACGTGGTTTGGGGATTTTGGGGAT

CTAGATCCTTGAAAAGTTCTGGAGAGGAGTGGGAGTTTCACCTGGCATGCAAGCGTCTCCGTTTCTT

CAGGCCAGGCTGACCCACTTCCCGCGCACGCCGATCTCGTACTGCAGCCCGTCGCCTTCCATGTTTA

GGTCCCACCTGCGGTACTCATCTTCGAC
```

SEQ ID NO: 80
LENGTH: 2073
TYPE: DNA
ORGANISM: *M. phaseolina*
FEATURE NAME/KEY: CDS
LOCATION: (1) . . . (2073)

```
atgatagataccaagagcacagggtccggcgcagacggcggtcgttacgccgccttaagg
 M  I  D  T  K  S  T  G  S  G  A  D  G  G  R  Y  A  A  L  R caagacgagtcagagctatacgagcagaaagaacatacgcagtgtacacagccctccggc
 Q  D  E  S  E  L  Y  E  Q  K  E  H  T  Q  C  T  Q  P  S  G gccgcgtacctcggtggaaatggcagagaagaagccctgggattgatcgacgaaaatgtc
 A  A  Y  L  G  G  N  G  R  E  E  A  L  G  L  I  D  E  N  V gtcgctcgaacaaaaagacgctgtggacccacccggcggtactctgtcttccttgaattt
 V  A  R  T  K  R  R  C  G  P  T  R  R  Y  S  V  F  L  E  F gccatcctcggtctggtactcataatcgctctactcggcgctctcgcttggtccagaggc
 A  I  L  G  L  V  L  I  I  A  L  L  G  A  L  A  W  S  R  G tctcatcatcataccgacccggtatctggcagttcacaaccatcgtccaagggtcgccgc
 S  H  H  H  T  D  P  V  S  G  S  S  Q  P  S  S  K  G  R  R ggaaagtatgtcctggaccctgcctgggatttcgctgcaccgccgcaggtccgcaaatac
 G  K  Y  V  L  D  P  A  W  D  F  A  A  P  P  Q  V  R  K  Y cactggacgatcagggacatcgagcttcgcccagacggcgtgaagcggccgctgatcacc
 H  W  T  I  R  D  I  E  L  R  P  D  G  V  K  R  P  L  I  T atcaataacgagttcccggggccgaccatcgaatgcaaccaggggggataccgtgcgggtt
 I  N  N  E  F  P  G  P  T  I  E  C  N  Q  G  D  T  V  R  V gaggttcataacgaagccgtcaattcaacttcctttcactggcacggcatttaccagaac
 E  V  H  N  E  A  V  N  S  T  S  F  H  W  H  G  I  Y  Q  N ggaaccacgtacatggatggcacggtcggcatcagccagtgtcctatcacgtctgggtct
 G  T  T  Y  M  D  G  T  V  G  I  S  Q  C  P  I  T  S  G  S agcatgacatatgagttcaaagtcgacagagaatccggcacctattggtatcatgcgcac
 S  M  T  Y  E  F  K  V  D  R  E  S  G  T  Y  W  Y  H  A  H atggctatgcagggctcagatggtctttttggtcctctgatcgtccattcgaaaaatgag
 M  A  M  Q  G  S  D  G  L  F  G  P  L  I  V  H  S  K  N  E cggaagctgcagcaactcgaatatgcctccgatcaagtcatcatggtccacgattactac
 R  K  L  Q  Q  L  E  Y  A  S  D  Q  V  I  M  V  H  D  Y  Y cacgatctgaccagcgcgctgataccacactacttagcgccggataacgagaacacagag
 H  D  L  T  S  A  L  I  P  H  Y  L  A  P  D  N  E  N  T  E
```

```
cctgtccctgacggaggtctcatcaacggaatgaataagagaaattgcgagctcctccgt
 P  V  P  D  G  G  L  I  N  G  M  N  K  R  N  C  E  L  L  R ggtcgagactgtgatgccactgatgcacagcttgccacattcggcctcgaaccgaacaag
 G  R  D  C  D  A  T  D  A  Q  L  A  T  F  G  L  E  P  N  K aaccaccgtcttcgaattatcaatactggagcatttgctgaattccaggtgaagattgac
 N  H  R  L  R  I  I  N  T  G  A  F  A  E  F  Q  V  K  I  D gagcacacgttcgctgtgacggaggtggatgggaccgaagttgctcccgcctactaccac
 E  H  T  F  A  V  T  E  V  D  G  T  E  V  A  P  A  Y  Y  H aggctcaacatcaatcccggacagcgctacagcatcgtaataaacaccaatgtcacggat
 R  L  N  I  N  P  G  Q  R  Y  S  I  V  I  N  T  N  V  T  D cgtgactccttctggctgagagctaagatgattgaggcctgtttcgctgaggagaaccca
 R  D  S  F  W  L  R  A  K  M  I  E  A  C  F  A  E  E  N  P aatctggatcccgaagtgcgcgccattatccaatatactcgcaaggacgaggatacccag
 N  L  D  P  E  V  R  A  I  I  Q  Y  T  R  K  D  E  D  T  Q cccaaggaaccttcgagcagagactgggacgacatcgtggacatgcagtgtctcgacatg
 P  K  E  P  S  S  R  D  W  D  D  I  V  D  M  Q  C  L  D  M aacgtgacagagctccagcccgtagagaaggcaacacctccacctgcagacaccacacta
 N  V  T  E  L  Q  P  V  E  K  A  T  P  P  P  A  D  T  T  L tacctccgctccaacttcgagatcggcaactggcgtctgagccgcggcttcttcaacagc
 Y  L  R  S  N  F  E  I  G  N  W  R  L  S  R  G  F  F  N  S tcgtcctggcgtccaacactctcatccccaagcctgcaccgcatgatcgacggcctccac
 S  S  W  R  P  T  L  S  S  P  S  L  H  R  M  I  D  G  L  H agccaaaacgccagcttcctccccgaccgagcgtaccccttccagatcaactcggccggc
 S  Q  N  A  S  F  L  P  D  R  A  Y  P  F  Q  I  N  S  A  G ttcgacactgggcccgagctggtctaccagaccagcggcatccgcaccatcgacatcctc
 F  D  T  G  P  E  L  V  Y  Q  T  S  G  I  R  T  I  D  I  L gtttccaacttcgacgacggcaaccacccgctccacctgcacggctacaagtacttcgtc
 V  S  N  F  D  D  G  N  H  P  L  H  L  H  G  Y  K  Y  F  V cttgcgtcgggccacggctacccgcccgccgacctctacgcgcatctcgacatctcgaac
 L  A  S  G  H  G  Y  P  P  A  D  L  Y  A  H  L  D  I  S  N ccgctgcgccgcgacaccgcctcgatcgaggcgttcggctggatcctactgcgtctcgtc
 P  L  R  R  D  T  A  S  I  E  A  F  G  W  I  L  L  R  L  V gccgacaacccgggcgtctgggccttccactgccacatcggctggcacaccgaggccggc
 A  D  N  P  G  V  W  A  F  H  C  H  I  G  W  H  T  E  A  G atgctgatgcagttcgccacgcgcgtcgacgtgctcgcatccagccaaatcccggatacg
 M  L  M  Q  F  A  T  R  V  D  V  L  A  S  S  Q  I  P  D  T cacctcgcgctctgcgcggccgacgggctcgaccgcggcgcgtcgccgccagactcgacg
 H  L  A  L  C  A  A  D  G  L  D  R  G  A  S  P  P  D  S  T tggtttggggatttt ggggatctagatccttga
 W  F  G  D  F  G  D  L  D  P  -

SEQ ID NO: 81
LENGTH: 690
TYPE: PRT
ORGANISM: M. phaseolina
MIDTKSTGSGADGGRYAALRQDESELYEQKEHTQCTQPSGAAYLGGNGREEALGLIDENVVARTKRR

CGPTRRYSVFLEFAILGLVLIIALLGALAWSRGSHHHTDPVSGSSQPSSKGRRGKYVLDPAWDFAAP

PQVRKYHWTIRDIELRPDGVKRPLITINNEFPGPTIECNQGDTVRVEVHNEAVNSTSFHWHGIYQNG

TTYMDGTVGISQCPITSGSSMTYEFKVDRESGTYWYHAHMAMQGSDGLFGPLIVHSKNERKLQQLEY

ASDQVIMVHDYYHDLTSALIPHYLAPDNENTEPVPDGGLINGMNKRNCELLRGRDCDATDAQLATFG

LEPNKNHRLRIINTGAFAEFQVKIDEHTFAVTEVDGTEVAPAYYHRLNINPGQRYSIVINTNVTDRD

SFWLRAKMIEACFAEENPNLDPEVRAIIQYTRKDEDTQPKEPSSRDWDDIVDMQCLDMNVTELQPVE

KATPPPADTTLYLRSNFEIGNWRLSRGFFNSSSWRPTLSSPSLHRMIDGLHSQNASFLPDRAYPFQI
```

-continued

NSAGFDTGPELVYQTSGIRTIDILVSNFDDGNHPLHLHGYKYFVLASGHGYPPADLYAHLDISNPLR

RDTASIEAFGWILLRLVADNPGVWAFHCHIGWHTEAGMLMQFATRVDVLASSQIPDTHLALCAADGL

DRGASPPDSTWFGDFGDLDP*

```
SEQ ID NO: 82
LENGTH: 2372 (including 150 bp 5' UTR and 150 bp 3' UTR)
TYPE: DNA
ORGANISM: M. phaseolina
```
TATATGTTCCTCCGTCCTCAACGGAAATCCGGCAGTGCGCAAGACGAGCCCCCTTTTCCTTCTGCTT

CGCCTGCTTTTCGTAGTCTCGTCCTCCGCCCTAGACGTCGTCTTCTCAGACAATTTGCTCAAATCCC

CTCTCACCTCGCCGCCATGCGCTTCGCGAGCCTCGCCGTGGCATGGCTCACAACGTGCGTTGTCCAA

TCACTTGCCAACGAGCCCATCCCGTTCGACAGGATCCTCTGGGGTGAGAATGGCCCCGCCGGTAACC

ATATGGTGAAGCGTCAGGCCAGCTCCAGCTCCCCTGCCTCATCCACCACAAGGGCCCCGGATTCCGC

CTGCACAAACGGCCCTTTGACGAGGAGCTGCTGGTCCAATGGCTTTTCCATAGCCACTGACTTTGAC

GCCAAGTGGCCCAATACCGGAAAGACCGTCCATGTAAGCGCGCCTGCAGATATGCATCCGTCCTGCT

GCTGACGTGCAGCCCATAGTATGACCTGACCATCAACAACGCCACCTGCAGCCCCGACGGCGGGCCC

AGCCGCCCGTGCCTGATGTTCAACAACAAGATCCCTGGGCCTACGCTTTACGCCAATTGGGGCGACA

TGATCTCCGTTACCATCACCAACAAGATGCCCAACAACGGCACCAGCGTGCACTGGCATGGTCTGCG

TCAGTACAATACAAACACCCAGGATGGCGTCAACGGAATCACGGAATGCCCTCTGGCTCCCGGCGAT

TCCAAGACCTACCTATTCCAGGCTACACAGTTCGGCACGACCTGGTTCCACAGCCATTTCTCTGCGC

AGTATGGCGACGGTGCCGTCGGCCAGCTCATCATCAATGGCCCCGCCTCGGCGAATTACGATTTCGA

TCTCGGCACCTACACTATGACCGACTGGTACTACAGCACTGCGTTCCAGGTCGAAGATCAATTTGAT

GCCGCCCTTCAGAGGAAGGCCCCCGGCCCGCCAGGTGACACCATCCTGGTGAACGGTACGATGAAGT

CTCCGGATGGCTCTGCTGGTAGCTACAGCCAAGTCAAGGGCCTTGTCAAGGGAAAGAAGTACCGCCT

GCGTCTCATCAACACCTCGGTGGACAACAACATCCGCGTCTCGCTGGACAACCACCCATTCACCGTC

GTCACTTCCGACTTCGTCCCGAGCAAGCCTTGGACTACTGACTGGCTTCTCTTAGCCATCGGCCAGC

GCTACGATGTCATCTTCACGGCCAATCAACCCGCGGCCAATTATTGGTTCCGTGCAGAAGTTGCCAC

CGCATGTGCTAGCGCCAACAAGTACCGCGGCCGCGGTATATTCAGCTACGTTGGTGCCGATGGCAGC

GCTCCCCCAGAGACCGCCGTGACTGTTCCAGGTGGCTGTACCGAGCCTCTGCCTGCGCCTTTCGTCG

CAAACCAGGTTCCAAGCCAAGTCTTCCTCGACCAAGTGAAGACCCTTAGCGTCGATGTTTATGCGGC

AAACGTCTCGACCAACCAGAAGAACATTGTCTTCTGGGGCATCAACATGACTGCCATTGACATTGAT

TGGGAGAAGCCGACGCTGGAATACGTCAGGACAAAAAATACCAGCTACCCCCACGTTTACAACTTGA

TCGAGTTGCCCACAGAGAACATTGTAAGCGGAGTTAAGCTTCAACCCCGAGAAATGTTATTAACGAT

CGCAACAGTGGACCTACTGGATCATCCAAGAAACTCCCGGCACTCCCCCAATTCCGCATCCAATTCA

CTTGCACGGTAAGCTGCAGGTCTCAACCTTGCAACCCCGTAGAGATACTGATGGTCGCCTCTGTCCA

GGCCACGACTTCTACATCCTCGGAACCGGCTCTGGTGCCTTCGACCGCAGCACCTCGCCGTCCTCCC

TCAATTTCAATAACCCCACCCGGCGCGACGTCGCACTGGTTCCCGGCGGCGGTTGGTTGGCCATTGC

CTTCCCGACCGACAACCCAGGCGCTTGGCTCATGCACTGCCATATCGTAAGTTTACCTATCTCTCCG

ACTACGATCAATTGTGTATATTCATGCGCACGGCGCTGACACGTGGATTTCCCTCGCCACAGGCTTG

GCACATTAGCGAAGGTCTCGGAGTTCAGTTCCTCGAGGGCAAGGATAAGATCAATCTTCCCGACGCT

GCGTGGGAGACGACCTGCTCGAATTGGGACAAGTACTGGGACACCACTATCTACCCCAAGCAGGATT

CCGGTCTCTGAGGGGTGGCCGGTTTTTTTTCTTCTTTACGGGCCTGAGTTTAAGGGGGGTTTGATGT

TTTGCTGAAAAAAGACCCGTAGTGATTCTTGTATTATACTTTTCGTTTTATTCATATTGATAGGAAG

CAACCTGATCGCACTTCGTAAACCGCA

SEQ ID NO: 83
LENGTH: 1824
TYPE: DNA
ORGANISM: M. phaseolina
FEATURE NAME/KEY: CDS
LOCATION: (1)...(1824)

```
atgcgcttcgcgagcctcgccgtggcatggctcacaacgtgcgttgtccaatcacttgcc
 M   R   F   A   S   L   A   V   A   W   L   T   T   C   V   V   Q   S   L   A aacgagcccatcccgttcgacaggatcctctggggtgagaatggcccgccggtaaccat
 N   E   P   I   P   F   D   R   I   L   W   G   E   N   G   P   A   G   N   H atggtgaagcgtcaggccagctccagctcccctgcctcatccaccacaagggccccggat
 M   V   K   R   Q   A   S   S   S   S   P   A   S   S   T   T   R   A   P   D tccgcctgcacaaacggccctttgacgaggagctgctggtccaatggcttttccatagcc
 S   A   C   T   N   G   P   L   T   R   S   C   W   S   N   G   F   S   I   A actgactttgacgccaagtggcccaataccggaaagaccgtccattatgacctgaccatc
 T   D   F   D   A   K   W   P   N   T   G   K   T   V   H   Y   D   L   T   I aacaacgccacctgcagccccgacggcgggcccagccgcccgtgcctgatgttcaacaac
 N   N   A   T   C   S   P   D   G   G   P   S   R   P   C   L   M   F   N   N aagatccctgggcctacgctttacgccaattggggcgacatgatctccgttaccatcacc
 K   I   P   G   P   T   L   Y   A   N   W   G   D   M   I   S   V   T   I   T aacaagatgcccaacaacggcaccagcgtgcactggcatggtctgcgtcagtacaataca
 N   K   M   P   N   N   G   T   S   V   H   W   H   G   L   R   Q   Y   N   T aacacccaggatggcgtcaacggaatcacggaatgccctctggctcccggcgattccaag
 N   T   Q   D   G   V   N   G   I   T   E   C   P   L   A   P   G   D   S   K acctacctattccaggctacacagttcggcacgacctggttccacagccatttctctgcg
 T   Y   L   F   Q   A   T   Q   F   G   T   T   W   F   H   S   H   F   S   A cagtatggcgacggtgccgtcggccagctcatcatcaatggccccgcctcggcgaattac
 Q   Y   G   D   G   A   V   G   Q   L   I   I   N   G   P   A   S   A   N   Y gatttcgatctcggcacctacactatgaccgactggtactacagcactgcgttccaggtc
 D   F   D   L   G   T   Y   T   M   T   D   W   Y   Y   S   T   A   F   Q   V gaagatcaatttgatgccgcccttcagaggaaggcccccggcccgccaggtgacaccatc
 E   D   Q   F   D   A   A   L   Q   R   K   A   P   G   P   P   G   D   T   I ctggtgaacggtacgatgaagtctccggatggctctgctggtagctacagccaagtcaag
 L   V   N   G   T   M   K   S   P   D   G   S   A   G   S   Y   S   Q   V   K ggccttgtcaagggaaagaagtaccgcctgcgtctcatcaacacctcggtggacaacaac
 G   L   V   K   G   K   K   Y   R   L   R   L   I   N   T   S   V   D   N   N atccgcgtctcgctggacaaccacccattcaccgtcgtcacttccgacttcgtcccgagc
 I   R   V   S   L   D   N   H   P   F   T   V   V   T   S   D   F   V   P   S aagccttggactactgactggcttctcttagccatcggccagcgctacgatgtcatcttc
 K   P   W   T   T   D   W   L   L   L   A   I   G   Q   R   Y   D   V   I   F acggccaatcaacccgcggccaattattggttccgtgcagaagttgccaccgcatgtgct
 T   A   N   Q   P   A   A   N   Y   W   F   R   A   E   V   A   T   A   C   A agcgccaacaagtaccgcggccgcggtatattcagctacgttggtgccgatggcagcgct
 S   A   N   K   Y   R   G   R   G   I   F   S   Y   V   G   A   D   G   S   A cccccagagaccgccgtgactgttccaggtggctgtaccgagcctctgcctgcgcctttc
 P   P   E   T   A   V   T   V   P   G   G   C   T   E   P   L   P   A   P   F gtcgcaaaccaggttccaagccaagtcttcctcgaccaagtgaagacccttagcgtcgat
 V   A   N   Q   V   P   S   Q   V   F   L   D   Q   V   K   T   L   S   V   D gtttatgcggcaaacgtctcgaccaaccagaagaacattgtcttctggggcatcaacatg
 V   Y   A   A   N   V   S   T   N   Q   K   N   I   V   F   W   G   I   N   M actgccattgacattgattgggagaagccgacgctggaatacgtcaggacaaaaaatacc
 T   A   I   D   I   D   W   E   K   P   T   L   E   Y   V   R   T   K   N   T agctaccccacgtttacaacttgatcgagttgcccacagagaacatttggacctactgg
 S   Y   P   H   V   Y   N   L   I   E   L   P   T   E   N   I   W   T   Y   W atcatccaagaaactcccggcactcccccaattccgcatccaattcacttgcacggccac
 I   I   Q   E   T   P   G   T   P   P   I   P   H   P   I   H   L   H   G   H
```

```
gacttctacatcctcggaaccggctctggtgccttcgaccgcagcacctcgccgtcctcc
 D  F  Y  I  L  G  T  G  S  G  A  F  D  R  S  T  S  P  S  S ctcaatttcaataaccccaccggcgcgacgtcgcactggttcccggcggcggttggttg
 L  N  F  N  N  P  T  R  R  D  V  A  L  V  P  G  G  W  L gccattgccttcccgaccgacaacccaggcgcttggctcatgcactgccatatcgcttgg
 A  I  A  F  P  T  D  N  P  G  A  W  L  M  H  C  I  A  W cacattagcgaaggtctcggagttcagttcctcgagggcaaggataagatcaatcttccc
 H  I  S  E  G  L  G  V  Q  F  L  E  G  K  D  K  I  N  L  P gacgctgcgtgggagacgacctgctcgaattgggacaagtactgggacaccactatctac
 D  A  A  W  E  T  T  C  S  N  W  D  K  Y  W  D  T  T  I  Y cccaagcaggattccggtctctga
 P  K  Q  D  S  G  L  -

SEQ ID NO: 84
LENGTH: 607
TYPE: PRT
ORGANISM: M. phaseolina
MRFASLAVAWLTTCVVQSLANEPIPFDRILWGENGPAGNHMVKRQASSSSPASSTTRAPDSACTNGP

LTRSCWSNGFSIATDFDAKWPNTGKTVHYDLTINNATCSPDGGPSRPCLMFNNKIPGPTLYANWGDM

ISVTITNKMPNNGTSVHWHGLRQYNTNTQDGVNGITECPLAPGDSKTYLFQATQFGTTWFHSHFSAQ

YGDGAVGQLIINGPASANYDFDLGTYTMTDWYYSTAFQVEDQFDAALQRKAPGPPGDTILVNGTMKS

PDGSAGSYSQVKGLVKGKKYRLRLINTSVDNNIRVSLDNHPFTVVTSDFVPSKPWTTDWLLLAIGQR

YDVIFTANQPAANYWFRAEVATACASANKYRGRGIFSYVGADGSAPPETAVTVPGGCTEPLPAPFVA

NQVPSQVFLDQVKTLSVDVYAANVSTNQKNIVFWGINMTAIDIDWEKPTLEYVRTKNTSYPHVYNLI

ELPTENIWTYWIIQETPGTPPIPHPIHLHGHDFYILGTGSGAFDRSTSPSSLNFNNPTRRDVALVPG

GGWLAIAFPTDNPGAWLMHCHIAWHISEGLGVQFLEGKDKINLPDAAWETTCSNWDKYWDTTIYPKQ

DSGL*

SEQ ID NO: 85
LENGTH: 3008 (including 150 bp 5' UTR and 150 bp 3' UTR)
TYPE: DNA
ORGANISM: M. phaseolina
GAGAAGAGCTTTTCGAAGCCATGTCAGCAGGATTAGCTCCTGAGACAGCCCTGCCCCAAAGTCCCGT

ATTTCTATGGCCGCAGTTCTCTCTCCTCGCCGAACCAAAGCCTCCTCCAGTACTTTCTTCTCAAACC

TGCTCATACAAGTGCAATGGGGTTCTTCAATGCCTGCTGGGACTTGCTGCTCCACCTCCCTTTCTTT

GCTCCGCGGGGCGGCGGCTTCGAGCGGGATCGCTCGCAGCTTCCGATCTCCTCCGGTCCGAGTGGCG

GCGTAGTCATCCACCCGGAGAATGCTTCCCCTGGCTTCACCTGCTCTTACCCGAGCATGGAAGGGTG

GGAAAGCTGCAACTCACCCGACGACAGGAGCTGCTGGCTTAAAGATGGGAGGGCGAGTCAGCCTTAC

TTCTCTCAATACGATATCCACACAGACTGTAAGTCCTCGATATGGTTGCCCGCATTGCATGCTTTCA

GCTTTACCAGGCCTTCGTGCTAAATTTATGAAGACGAGACCGTCTGGCCTCAGGGTGTAACCAGAGA

AGTAAGTGTGGAAAATCAAAGCCCTGGGGCGCGGGGAACCCGGCCTCTGAGCCTTCATCTATGGCAG

CCCGTACACATCGAGAGACGAAGTATTTATCGCGAAGAGAATGCCCCTGATCTCTTTAAGCACATAC

ATCTGCATGAATATTTCAATTCCCCTTGTCATCAGGGATGATCAAGGGGCCATGCCGTTACCAAAAT

GTCTGGGCAGAGTCCCTTCTTTTCACGCTGCAGCAGATTTGCTTACTCGGTGTTTACTGAACATTTG

CAGTACTGGATCAACCTCAAGGACCAAGTGGTAAGTGCTGCCATTCCCTTGAGTCCGCTGTAGCTGC

TCATACGCCCAGCTTTTCCCCGACGGTTATTCCAAGCCTTATGGCAAAGTAATCAACGACACCTACC

CAGGTCCTTTAATCGAGGCTTGCTGGGGCGATGAAGTAGTTGTTCATGTGACAAACTACCTGCAGAC

GAATGGCACTACGTATTCACACGTCTATATCAGTTGTGCCGCGGTATGAGCTGATGATGGGCAGTA

TTCACTGGCACGGTGTGAGACAGCAGTTCAGCAACGAAATGGACGGAGTCAACGGTTTGTTCTGCAA
```

-continued

```
GATCCCACTATTTACCTCCTCGGCTCACGTCATGTAGGTATTACACAGTGTCCTATCGCTTATGGTG

ACACCTTCACCTACCGCTTTCGTGTTACTCAATATGGAACTACGTGTAAGTGTTTCCGACTCCTGAT

CTGGTCTCAGCCATTGACACGGAAGTAGGGTACCATTCACACTACTCGCTCCAATACCCAGATGGCG

TTGCTGGCCCTCTCGTATTTCACGGCCCTACAGCAGCCGATTGGGATGAAGAGTGGGAGACCCCGCT

GATGATCACTGATTGGGTTCACGATTCGGCTTTTGGGGTCTTCTCCCAGGAACTCCTCGCGTCGGAT

CCTGCCAACCGGAACGTCACACCACCCGTGGGGGACAGCATTCTGCTTAACGGACACGGACATTACA

ACTGCAGCCTTTCTCAGGACCAAAACCGCTGCGCGCCGGGATATGGATCTTACTACACGCAAAGATT

CCAAAAGGGTAAAAGGTACTTGATCAGGCTAATTAACTCCTCAGCTGGAGCAGCATTTATCTTCTCC

ATAGACGGACACAAAATGAAGGTCATCTCCACGGATCTCGTTCCCATTGAGCCGTACGAGACAAATG

CAGTGCTCCTCAACATAGGTATATAGCGTTTGGTGCTCGTCCTAGCATGTCTCCCAGACACTAACTT

CCCGCAGGCCAACGCTACAACATCATCGTCGAAGCCAACGCCGAACCCGGCGACTACTGGATCCGTA

CCGAGATACCCGGCGGGCCAGGCGGCTGTGGCAGCGTGCACGACCGGGCCGGTAACGTGACGGGCAT

CCTGCGCTACGACGGACGCAGTACCGCGCTACCGACCTCATCGAAGAATGACTACCCGTCGGACTGC

CACGATGAGCCAGCGGAGCTGCTGCACCCAATCCTGCCGTGGACGGTGGATCCGCACCCGCAGAACG

ACGTACACAACAACACGTACGAGGTCGGCATTTCAGACGCCCAGTTCCACAAGGCCTTCCGCTGGGA

CCTGACCGACACGCCCATGTGGCTCGACTTCTCAAACCCGACCATCCTCAACCTGTACAACACCACC

TGGAACCCGGAGTACGCCGTCATCGACTGTGAGTTGTCCTTCTTACCTCCCGTTCTCCCCAAAAAAC

ACTAGCAACGAGTGGATGAAGACTGACAGGTACGAAAACAGACAACTATGACCGCGGCTTCGTCTAC

CTCGTCATCACGGCCAACCTGACACGGCTGGGCGACAACAAGCGCGAGATCCCCGCCGGCCACCCCA

TCCACCTGCACGGCCACGACTTCGCCGTCCTCGCCCAGTCCAACTCGACCTATGACGAGCGCTCCGA

CCCGCTCAATTTCACCCTCGCCAACCCGCCGCCGCGATGTCGTCTTCCTGCCGAGCAACGGCTAC

GTCGCGCTGGCGTTCAAGCCGGACAATCCCGGCATATGGTTGGTGCATTGCCATATCGCTTGGCATG

CCAGTTCTGGTGAGTGTTTTTCTTTTTTCTTTTTGGTAACTTTGTTTTCTGTGGCTTTTTTAAAAGT

GTGTGAATGCATGCTGATGATTTTTATACGATGCACAGGCCTGGCACTGCAGATTCTGGAGAGGCAG

CCAGATATCCTGGATTCGATTGGCACGCTCGAGGCGACGAATAAGACGTGTGCTGGATGGGATACGT

ACGAGAGGGCGCATCCGATCGAGCAAGACGACAGCGGTATCTGATTAGACGTACCTCTGCGTCAGAT

CCGACGAGTTGGGAGTGAATGATGCCCTCTGGAAGGATTGTGAAGGATGGGGTGAGCTCTTTCTCCT

GTGCATTTTCTCTCATGTTGAGGAGCTCTGTTCGTAGCTGGAGTACGCTCATTTATTTCC
```

SEQ ID NO: 86
LENGTH: 1932
TYPE: DNA
ORGANISM: M. phaseolina
FEATURE NAME/KEY: CDS
LOCATION: (1) ... (1932)

```
atggggttcttcaatgcctgctgggacttgctgctccacctccctttctttgctccgcgg
 M  G  F  F  N  A  C  W  D  L  L  L  H  L  P  F  F  A  P  R ggcggcggcttcgagcgggatcgctcgcagcttccgatctcctccggtccgagtggcggc
 G  G  G  F  E  R  D  R  S  Q  L  P  I  S  S  G  P  S  G  G gtagtcatccacccggagaatgcttcccctggcttcacctgctcttacccgagcatggaa
 V  V  I  H  P  E  N  A  S  P  G  F  T  C  S  Y  P  S  M  E gggtgggaaagctgcaactcacccgacgacaggagctgctggcttaaagatggggaggcg
 G  W  E  S  C  N  S  P  D  D  R  S  C  W  L  K  D  G  R  A agtcagccttacttctctcaatacgatatccacacagactacgagaccgtctggcctcag
 S  Q  P  Y  F  S  Q  Y  D  I  H  T  D  Y  E  T  V  W  P  Q ggtgtaaccagagaatactggatcaacctcaaggaccaagtgcttttccccgacggttat
 G  V  T  R  E  Y  W  I  N  L  K  D  Q  V  L  F  P  D  G  Y
```

```
tccaagccttatggcaaagtaatcaacgacacctacccaggtcctttaatcgaggcttgc
 S  K  P  Y  G  K  V  I  N  D  T  Y  P  G  P  L  I  E  A  C tggggcgatgaagtagttgttcatgtgacaaactacctgcagacgaatggcactactatt
 W  G  D  E  V  V  V  H  V  T  N  Y  L  Q  T  N  G  T  T  I cactggcacggtgtgagacagcagttcagcaacgaaatggacggagtcaacggtattaca
 H  W  H  G  V  R  Q  Q  F  S  N  E  M  D  G  V  N  G  I  T cagtgtcctatcgcttatggtgacaccttcacctaccgctttcgtgttactcaatatgga
 Q  C  P  I  A  Y  G  D  T  F  T  Y  R  F  R  V  T  Q  Y  G actacgtggtaccattcacactactcgctccaatacccagatggcgttgctggccctctc
 T  T  W  Y  H  S  H  Y  S  L  Q  Y  P  D  G  V  A  G  P  L gtatttcacggccctacagcagccgattgggatgaagagtgggagacccgctgatgatc
 V  F  H  G  P  T  A  A  D  W  D  E  E  W  E  T  P  L  M  I actgattgggttcacgattcggcttttggggtcttctcccaggaactcctcgcgtcggat
 T  D  W  V  H  D  S  A  F  G  V  F  S  Q  E  L  L  A  S  D cctgccaaccggaacgtcacaccaccgtgggggacagcattctgcttaacggacacgga
 P  A  N  R  N  V  T  P  P  V  G  D  S  I  L  L  N  G  H  G cattacaactgcagcctttctcaggaccaaaaccgctgcgcgccgggatatggatcttac
 H  Y  N  C  S  L  S  Q  D  Q  N  R  C  A  P  G  Y  G  S  Y tacacgcaaagattccaaaagggtaaaaggtacttgatcaggctaattaactcctcagct
 Y  T  Q  R  F  Q  K  G  K  R  Y  L  I  R  L  I  N  S  S  A ggagcagcatttatcttctccatagacggacacaaaatgaaggtcatctccacggatctc
 G  A  A  F  I  F  S  I  D  G  H  K  M  K  V  I  S  T  D  L gttcccattgagccgtacgagacaaatgcagtgctcctcaacataggccaacgctacaac
 V  P  I  E  P  Y  E  T  N  A  V  L  L  N  I  G  Q  R  Y  N atcatcgtcgaagccaacgccgaacccggcgactactggatccgtaccgagatacccggc
 I  I  V  E  A  N  A  E  P  G  D  Y  W  I  R  T  E  I  P  G gggccaggcggctgtggcagcgtgcacgaccgggccggtaacgtgacgggcatcctgcgc
 G  P  G  G  C  G  S  V  H  D  R  A  G  N  V  T  G  I  L  R tacgacggacgcagtaccgcgctaccgacctcatcgaagaatgactaccgtcggactgc
 Y  D  G  R  S  T  A  L  P  T  S  S  K  N  D  Y  P  S  D  C cacgatgagccagcggagctgctgcacccaatcctgccgtggacggtggatccgcacccg
 H  D  E  P  A  E  L  L  H  P  I  L  P  W  T  V  D  P  H  P cagaacgacgtacacaacaacacgtacgaggtcggcatttcagacgcccagttccacaag
 Q  N  D  V  H  N  N  T  Y  E  V  G  I  S  D  A  Q  F  H  K gccttccgctgggacctgaccgacacgcccatgtggctcgacttctcaaacccgaccatc
 A  F  R  W  D  L  T  D  T  P  M  W  L  D  F  S  N  P  T  I ctcaacctgtacaacaccacctggaacccggagtacgccgtcatcgactacaactatgac
 L  N  L  Y  N  T  T  W  N  P  E  Y  A  V  I  D  Y  N  Y  D cgcggcttcgtctacctcgtcatcacggccaacctgacacggctgggcgacaacaagcgc
 R  G  F  V  Y  L  V  I  T  A  N  L  T  R  L  G  D  N  K  R gagatccccgccggccaccccatccacctgcacggccacgacttcgccgtcctcgcccag
 E  I  P  A  G  H  P  I  H  L  H  G  H  D  F  A  V  L  A  Q tccaactcgacctatgacgagcgctccgacccgctcaatttcaccctcgccaacccgccg
 S  N  S  T  Y  D  E  R  S  D  P  L  N  F  T  L  A  N  P  P cgccgcgatgtcgtcttcctgccgagcaacggctacgtcgcgctggcgttcaagccggac
 R  R  D  V  V  F  L  P  S  N  G  Y  V  A  L  A  F  K  P  D aatcccggcatatggttggtgcattgccatatcgcttggcatgccagttctggcctggca
 N  P  G  I  W  L  V  H  C  H  I  A  W  H  A  S  S  G  L  A ctgcagattctggagaggcagccagatatcctggattcgattggcacgctcgaggcgacg
 L  Q  I  L  E  R  Q  P  D  I  L  D  S  I  G  T  L  E  A  T aataagacgtgtgctggatgggatacgtacgagagggcgcatccgatcgagcaagacgac
 N  K  T  C  A  G  W  D  T  Y  E  R  A  H  P  I  E  Q  D  D agcggtatctga
 S  G  I  -
```

SEQ ID NO: 87
LENGTH: 643
TYPE: PRT
ORGANISM: M. phaseolina
MGFFNACWDLLLHLPFFAPRGGGFERDRSQLPISSGPSGGVVIHPENASPGFTCSYPSMEGWESCNS

PDDRSCWLKDGRASQPYFSQYDIHTDYETVWPQGVTREYWINLKDQVLFPDGYSKPYGKVINDTYPG

PLIEACWGDEVVVHVTNYLQTNGTTIHWHGVRQQFSNEMDGVNGITQCPIAYGDTFTYRFRVTQYGT

TWYHSHYSLQYPDGVAGPLVFHGPTAADWDEEWETPLMITDWVHDSAFGVFSQELLASDPANRNVTP

PVGDSILLNGHGHYNCSLSQDQNRCAPGYGSYYTQRFQKGKRYLIRLINSSAGAAFIFSIDGHKMKV

ISTDLVPIEPYETNAVLLNIGQRYNIIVEANAEPGDYWIRTEIPGGPGGCGSVHDRAGNVTGILRYD

GRSTALPTSSKNDYPSDCHDEPAELLHPILPWTVDPHPQNDVHNNTYEVGISDAQFHKAFRWDLTDT

PMWLDFSNPTILNLYNTTWNPEYAVIDYNYDRGFVYLVITANLTRLGDNKREIPAGHPIHLHGHDFA

VLAQSNSTYDERSDPLNFTLANPPRRDVVFLPSNGYVALAFKPDNPGIWLVHCHIAWHASSGLALQI

LERQPDILDSIGTLEATNKTCAGWDTYERAHPIEQDDSGI*

SEQ ID NO: 88
LENGTH: 2404 (including 150 bp 5' UTR and 150 bp 3' UTR)
TYPE: DNA
ORGANISM: M. phaseolina
AAATGCCATGGACAGCTCGCCCGGGATCGATGTCCTTTCTCCCCGAGCCCCCGTCGCCCGTCCAGGA GAGATAAACCTTCTCATAGGGCCTCATTCCTACTCTCTCCTTCCCTTTTtCGTTACCCTCCCCGACC

GCGGTCCACCTTCGACATGTGGTGGTTGGCATTGTTCTCATTGCTTGTGGCCGCCACGGCCTGGGCC

AAGGAGCCCTACCTCAAGGTCCACGATGATACCTTTATTCCAGATGCCGTGTTGCGGGTAACAGAGG

AGAGTGCCTCCATTGGTTGCATCGAGAGGACCTCCGCCGTGGTCAACGGCACAGTTCCGGGGCCGAT

TTTGGAATTCCAATCCGGCAGCGTGGTATGGGTTCGTGTTTACAATGATATGGCAGACAAAAACCTC

ACCATGGTAAGCCCCGACGATATGCCTGCGGTGAATCAGACTAGTCAATTAACTTCTCGGTCCACAG

CATTGGCATGGCCTCACCATGGCAGCCGCTCCATTCGCCGACGGTTCCGTTGCAGCCAGCCAGTGGG

CGATCGAGCCGTTCAAATTCTTCGACTACGAGCTCAACCTATTCGACATCAAGCCTGGGACGTATTT

CTACCACTCCCATGTCGGATTCCAGGCAATTACTGCCACGGGTCCCCTGCTCATTACCAAAAAGCCG

GGAGAGGAGCCGCCGTATGAGTACGAGGAGGAACGCATCGTCCTCTTTTCCGACCTTTACAACACGA

CGGACCACGACATTGAAACCGGACTGGTAGCCAGCCCTTTCAAATGGAGCGGTGAGGTCGGAGACGT

CCTCGTCAACGGATATGGCATATCGCAGTACCGGCCACGAACGACGCCGAGAGTTGCAACCTTGCA

CAGATTCCCGTGgAAGCTGGGAAGACGTACCGTTTGCGTTTCATTGGTGCCACTGCCCTTTCTTTCC

TCTCCGTTGGCTTTGAGAAGCACAATCTTACCATCATCGAGGCGGATGGCCACTACACGGAACCTGC

AGAAATCAGCTTCCTTCAAATCGGCGGCGGCCAACGGTATTCTGCTCTCCTAAAGACATGGACTTGC

GAGGAGCTCGCCGCCAAGACTGCTGGTCGAAACCAGTTCTACATCCAAATCGAGACTCGTGACAGGC

CCAAGAACCTCACCACCTACGCCATTCTGGACTACAGCGACAGCTGCGCCACCAATAGCATCAGCGT

CGAGGCCACCATCGGCAAGGACTCAACATCGCCCCCTTCCTACGCCCTCCTTCGCTCAGCAAACCC

GGCAACAACAACAAAAACAACAACAACACCACGCTCTCCCGCAAGACGCCGCCCAAGACCCCACCGC

TGCACCTCCCGCCCACCGTGCAAGGCTGGCTCGACCATGACCTCCACCCGCTCGAAACCTACACGGA

CTTCCCGACGGCGGACGAGGTCACGCGCACCGTCTACATGGACATCTTCCAGCTAGGGCAGGACGGC

TACGTCAAGTGGGCGCAGAACAACCTGTCGTGGTACGAGCACACGCCCAAGGTTCCCTACCTCGTCG

CGCTCTACACCAACAGCACGCAGTACCTGCCCGACTACGACTATGCCGTCGCATCGGGGACGGGCCA

CGACGACCGCGTCGGTGCCTGGCCCGCCAAGATGGGCGAGGTGCTCGAGATCATCGTCGTCAACACG

GGCAGCTACAGCGGCGGCATGGACGTGCATCCCATGCACCTGCACGGCGCGCACCCGTTCTATTTGG

-continued

```
GGAGTGGGAAGGGCACGTACAACAGAGAGGAGAACGAGAAGAAGTTGGCGGGGAGGGTGCCGGTCAC

GAGGGATTCGATGATGCTGTATCGGTATGGCGAGAAGGAGGAGCCGCACAAGGATAATAGCTGGATT

GCGCTGAGGATAAGGGTGACGCAGCCGGGGGTGTGGATGTTCCATTGCCATACGCTGGCGCATATGA

TTATGGGTGAGTTTGACCCTTTTtCCCTTTTTTTTTTTTTTtCTtATTGCGCATGTTGGTTTGAT

GAAAACCATGGTGCTGATGTGATTTGGAACAGGTATGCAAACGGTCTGGGTGTTTGGCGATTCGAAG

GATATCCTCACGCTGCCGCTGCCGATGGTGGAAGGTTACTTGGTGCCTGGCGGAGATGTGTTCGGTG

ATGATGATCATGATCCGGTGGTGGTGCACTTCTTTGACCTGGACGACGACGACGATGATGATGA

TGCCAATAAGACCGACGGGAACGGCGGGAAGAATGGCCGGTAGATGGGGGGAGGAGAGTTACTTGAT

TCGCAATGGAAGAGGTTACTGCGGAGGGGATTTGTAATGCATGCTACAGTTTTTATGTTATATGCCA

GGTATAACCAGAAGGAAAGCCGGATGATTAATCGTGGAAACAAGAGAAAGAAGCATTTA
```

SEQ ID NO: 89
LENGTH: 1950
TYPE: DNA
ORGANISM: M. phaseolina
FEATURE NAME/KEY: CDS
LOCATION: (1) . . . (1950)

```
atgtggtggttggcattgttctcattgcttgtggccgccacggcctgggccaaggagccc
 M   W   W   L   A   L   F   S   L   L   V   A   A   T   A   W   A   K   E   P tacctcaaggtccacgatgatacctttattccagatgccgtgttgcgggtaacagaggag
 Y   L   K   V   H   D   D   T   F   I   P   D   A   V   L   R   V   T   E   E agtgcctccattggttgcatcgagaggacctccgccgtggtcaacggcacagttccgggg
 S   A   S   I   G   C   I   E   R   T   S   A   V   V   N   G   T   V   P   G ccgattttggaattccaatccggcagcgtggtatgggttcgtgtttacaatgatatggca
 P   I   L   E   F   Q   S   G   S   V   V   W   V   R   V   Y   N   D   M   A gacaaaaacctcaccatgcattggcatggcctcaccatggcagccgctccattcgccgac
 D   K   N   L   T   M   H   W   H   G   L   T   M   A   A   A   P   F   A   D ggttccgttgcagccagccagtgggcgatcgagccgttcaaattcttcgactacgagctc
 G   S   V   A   A   S   Q   W   A   I   E   P   F   K   F   F   D   Y   E   L aacctattcgacatcaagcctgggacgtatttctaccactcccatgtcggattccaggca
 N   L   F   D   I   K   P   G   T   Y   F   Y   H   S   H   V   G   F   Q   A attactgccacgggtcccctgctcattaccaaaaagccgggagaggagccgccgtatgag
 I   T   A   T   G   P   L   L   I   T   K   K   P   G   E   E   P   P   Y   E tacgaggaggaacgcatcgtcctcttttccgacctttacaacacgacggaccacgacatt
 Y   E   E   E   R   I   V   L   F   S   D   L   Y   N   T   T   D   H   D   I gaaaccggactggtagccagcccttttcaaatggagcggtgaggtcggagacgtcctcgtc
 E   T   G   L   V   A   S   P   F   K   W   S   G   E   V   G   D   V   L   V aacggatatggcatatcgcagtacccggccacgaacgacgccgagagttgcaaccttgca
 N   G   Y   G   I   S   Q   Y   P   A   T   N   D   A   E   S   C   N   L   A cagattccgtggaagctgggaagacgtaccgtttgcgtttcattggtgccactgccctt
 Q   I   P   V   E   A   G   K   T   Y   R   L   R   F   I   G   A   T   A   L tctttcctctccgttggctttgagaagcacaatcttaccatcatcgaggcggatggccac
 S   F   L   S   V   G   F   E   K   H   N   L   T   I   I   E   A   D   G   H tacacggaacctgcagaaatcagcttccttcaaatcggcggcggccaacggtattctgct
 Y   T   E   P   A   E   I   S   F   L   Q   I   G   G   G   Q   R   Y   S   A ctcctaaagacatggacttgcgaggagctcgccgccaagactgctggtcgaaaccagttc
 L   L   K   T   W   T   C   E   E   L   A   A   K   T   A   G   R   N   Q   F tacatccaaatcgagactcgtgacaggcccaagaacctcaccacctacgccattctggac
 Y   I   Q   I   E   T   R   D   R   P   K   N   L   T   T   Y   A   I   L   D tacagcgacagctgcgccaccaatagcatcagcgtcgaggccaccatcggcaaggactca
 Y   S   D   S   C   A   T   N   S   I   S   V   E   A   T   I   G   K   D   S acatcgccccttcctacgcccctccttcgctcagcaaacccggcaacaacaacaaaaac
 T   S   P   P   S   Y   A   P   P   S   L   S   K   P   G   N   N   N   K   N
```

```
aacaacaacaccacgctctcccgcaagacgccgcccaagaccccaccgctgcacctcccg
 N  N  N  T  T  L  S  R  K  T  P  P  K  T  P  P  L  H  L  P cccaccgtgcaaggctggctcgaccatgacctccacccgctcgaaacctacacggacttc
 P  T  V  Q  G  W  L  D  H  D  L  H  P  L  E  T  Y  T  D  F ccgacggcggacgaggtcacgcgcaccgtctacatggacatcttccagctagggcaggac
 P  T  A  D  E  V  T  R  T  V  Y  M  D  I  F  Q  L  G  Q  D ggctacgtcaagtgggcgcagaacaacctgtcgtggtacgagcacacgcccaaggttccc
 G  Y  V  K  W  A  Q  N  N  L  S  W  Y  E  H  T  P  K  V  P tacctcgtcgcgctctacaccaacagcacgcagtacctgcccgactacgactatgccgtc
 Y  L  V  A  L  Y  T  N  S  T  Q  Y  L  P  D  Y  D  Y  A  V gcatcggggacgggccacgacgaccgcgtcggtgcctggcccgccaagatgggcgaggtg
 A  S  G  T  G  H  D  D  R  V  G  A  W  P  A  K  M  G  E  V ctcgagatcatcgtcgtcaacacgggcagctacagcggcggcatggacgtgcatcccatg
 L  E  I  I  V  V  N  T  G  S  Y  S  G  G  M  D  V  H  P  M cacctgcacggcgcgcacccgttctatttggggagtgggaagggcacgtacaacagagag
 H  L  H  G  A  H  P  F  Y  L  G  S  G  K  G  T  Y  N  R  E gagaacgagaagaagttggcggggagggtgccggtcacgagggattcgatgatgctgtat
 E  N  E  K  K  L  A  G  R  V  P  V  T  R  D  S  M  M  L  Y cggtatggcgagaaggaggagccgcacaaggataatagctggattgcgctgaggataagg
 R  Y  G  E  K  E  E  P  H  K  D  N  S  W  I  A  L  R  I  R gtgacgcagccgggggtgtggatgttccattgccatacgctggcgcatatgattatgggt
 V  T  Q  P  G  V  W  M  F  H  C  H  T  L  A  H  M  I  M  G atgcaaacggtctgggtgtttggcgattcgaaggatatcctcacgctgccgctgccgatg
 M  Q  T  V  W  V  F  G  D  S  K  D  I  L  T  L  P  L  P  M gtggaaggttacttggtgcctggcggagatgtgttcggtgatgatgatcatgatccggtg
 V  E  G  Y  L  V  P  G  G  D  V  F  G  D  D  D  H  D  P  V gtggtgcacttcttgacctggacgacgacgacgatgatgatgatgccaataagacc
 V  V  H  F  F  D  L  D  D  D  D  D  D  D  D  A  N  K  T gacgggaacggcgggaagaatggccggtag
 D  G  N  G  G  K  N  G  R  -

SEQ ID NO: 90
LENGTH: 649
TYPE: PRT
ORGANISM: M. phaseolina
MWWLALFSLLVAATAWAKEPYLKVHDDTFIPDAVLRVTEESASIGCIERTSAVVNGTVPGPILEFQS

GSVVWVRVYNDMADKNLTMHWHGLTMAAAPFADGSVAASQWAIEPFKFFDYELNLFDIKPGTYFYHS

HVGFQAITATGPLLITKKPGEEPPYEYEEERIVLFSDLYNTTDHDIETGLVASPFKWSGEVGDVLVN

GYGISQYPATNDAESCNLAQIPVEAGKTYRLRFIGATALSFLSVGFEKHNLTIIEADGHYTEPAEIS

FLQIGGGQRYSALLKTWTCEELAAKTAGRNQFYIQIETRDRPKNLTTYAILDYSDSCATNSISVEAT

IGKDSTSPPSYAPPSLSKPGNNNKNNNNTTLSRKTPPKTPPLHLPPTVQGWLDHDLHPLETYTDFPT

ADEVTRTVYMDIFQLGQDGYVKWAQNNLSWYEHTPKVPYLVALYTNSTQYLPDYDYAVASGTGHDDR

VGAWPAKMGEVLEIIVVNTGSYSGGMDVHPMHLHGAHPFYLGSGKGTYNREENEKKLAGRVPVTRDS

MMLYRYGEKEEPHKDNSWIALRIRVTQPGVWMFHCHTLAHMIMGMQTVWVFGDSKDILTLPLPMVEG

YLVPGGDVFGDDDHDPVVVHFFDLDDDDDDDDANKTDGNGGKNGR*

SEQ ID NO: 91
LENGTH: 2569 (including 150 bp 5' UTR and 150 bp 3' UTR)
TYPE: DNA
ORGANISM: M. phaseolina
CGCCCGATTCACACCATTCCTCTGACACTCTCCTCCGGAGCTCGCATCAGGGCGCTCTCTCGCCCTC

CTGACCTTCCGTCCGGCGCCGATATCGTCGTGTTCCGTATATGAGGGGTAATCGCGACGGTGCTCCC

GCCCACACTCTCAGCCATGGCCCAGTCTCTGTTCCTCCTGCTTGCTGCTGCCCTGTGCAGCCGCGCT

GCCACAGTCACGTATGACTTTAACGTGACCTGGGTCACCGCCAACCCTGATGCTGCTTTTCGTCGCA
```

```
CTACCATTGGCATCAATGGCCAGTGGCCGCTCCCTGCAATCGACGTCACCAAGGGCGACCGCGTTGT

CATCAACGTCAACAACCAGCTGGAAACGGAGAGTACCAGTTTGCATTTCCATGGAATCTACATGAAT

GGCACCAACCACATGGATGGCCCGACTGGCGTGACCCAGTGCGAGATACCGCCCGGGAGCTCATTCA

CATACAATTTTACGGTATAGCACGATCCCACCCCTTGTTTACTTATAGCTAACCGCACGCAGGTCGA

CCAACCGGGAACTTACTGGTGAGTAGCCAGCTGTTGGCGTCAAGACTGGGAAAGCTGACGTAGCTTC

AGGTATCATTCTCACAACCGCGGCCAGTATCCCGATGGATTGCGAGGGCCTTTTATTGTCAGAGACC

CCGACAATCCGTTCAAGGATGACTATGATGAGGAAGTCGTCCTGACATTCTCCGACTGGTACCACGA

CCGGATCCCCACCCTCATGAAGAGTTTCATTAGTGTCACAAACCCCACCGGCGCGGAGCCTGTCCCG

AACGCGGCACTGATGAATGACACTCAGAACCTCACCTTCCAGATGACTCCCGGGCGGAGATACATGT

TCCGACTAATAAACATTGGTGCATTTGCTGCTCAATACGTCTGGTTCGAAGGCCATACCATGCGTAT

CGTAGAAGTCGACGGCGTGTACACCGAAGCCGCAGATGCAGAGCGAATTTACATGACTGCCGCTCAA

CGCTACAGCGTAATCATCACCGCAAAGAACGAATCTACCTCAAACTTCGCCTTTGTTGGAAGCATGG

ATCAGGTCAGCTATCCTTTTACTGGGCCGACATTTTCCTTCTTCTAACATAATGCAGGATCTCTTTG

ATACTATTCCAGCAGGCCTTAATAATAACGTGACCGGGTGGCTTGTCTACAATCAACAGAACGGCTT

GTTGCCACCTTTAGCTATCGGGGACTACGATCCGTTCGATGACTTCACACTTGTGCCTCAAGATGGT

ATGGAGCTCTACGATCACGTCGATCATTCCATCACCCTCGATATGAAGATGGACAATCTCGGGGACG

GAGCAAATTAGTATGTTGACTGTAGTTGACAACGGCCAAATGCCATGACTGACGAGCGCAGTGCCTT

TTTCAACGACGTGACCTACGTCGAGCCCAAGGTGCCGACTCTGTACACGGTGTTGTCTACTGGCAAT

AATGCCACAGACTCGAGAATCTACGGTAGCAACACCAACAGCTTCATATTGGCTAAGGACGAAGTCG

TCGAGATCATCCTCAACAACAATGATCCGGGAAAGCACCCTTTCCATCTGCATGGGCACGCATTCCA

AGCAATCGTTCGCTCCGAAGAAGAAGCCGGCGCGTACGTGGCAAACGAAACCTTCCCCCAGACGCCA

ATGCGCCGCGATACAATTCTTGTCCGGCCCAATGGCAATATAGTACTGAGATTCAAGGCTGACAATC

CTGGTGTCTGGCTGTTCCATTGTCATATTGAATGGTATGCTCCTTGGTATCTTTTATCCTAGCTCTA

CTGACCTCTTACTGTTAGGCATGTTGCGTCGGGCCTTATTGCCACCATGATAGAGGCACCGCTTGAC

CTGCAATCTTCTCTCGGCAACAGCATTCCTGCTGATCACTGGCGAGCTTGTGCCGCCGCCGGCACAC

CTACTGCAGGCAACGCAGCAGGCAACACGATTGATTATCTTGACCTGACTGGTGAAAACAAGAGCCC

CGGCCCGCTTCCCTCTGGCTTTGAAGCGAAAGGCATTGTCGCGCTTGTCTTCAGTTGTATTGCTGCT

GTCTTGGGCATGGCAGCCATCGTATGGTACGGGATGGCGCCTCTGACAGATGGAACTGGTCAGCAAC

AACACGTTGTGGATCAACAGCCGCAAGGACGCTCCGCACAAGTTGGCGTCATGCCCCTAGCGGTCGC

GGCAAAACGTGAGCAAAGGATGGCCAGCCGGACTGATTTGGAGGCAGAGATGCGGCAAGAAAAGAGC

GGAGAAATTACCATGGTGGAGCAGAGGAGGAGCAGCCGTGGGTCATCGAACATGCTGGATGTCAGGA

GGAGTAGCCGCGGTTCGTCTAACATGCTAGAGACCAGAAGAAGCAGTCGTGGCAGTGAGCAGATGCT

GTCATGAGGACCAACATCATGGGTAGCAAGGTAAGTGGAAATCGGCTGTGAAGAAATACAGGGTCAGT

TGTGAGAGGGAAAGCTATCACGAATGGCTGAAGAGCTTTGGGCCTTGTTACGATGTAATGTTGTCCG

GAAATGTTGTGGTAATTATTGTA

SEQ ID NO: 92
LENGTH: 2016
TYPE: DNA
ORGANISM: M. phaseolina
FEATURE NAME/KEY: CDS
LOCATION: (1) . . . (2016)
atggcccagtctctgttcctcctgcttgctgctgccctgtgcagccgcgctgccacagtc
  M   A   Q   S   L   F   L   L   L   A   A   A   L   C   S   R   A   A   T   V
```

```
acgtatgactttaacgtgacctgggtcaccgccaaccctgatgctgcttttcgtcgcact
 T  Y  D  F  N  V  T  W  V  T  A  N  P  D  A  A  F  R  R  T accattggcatcaatggccagtggccgctccctgcaatcgacgtcaccaagggcgaccgc
 T  I  G  I  N  G  Q  W  P  L  P  A  I  D  V  T  K  G  D  R gttgtcatcaacgtcaacaaccagctggaaacggagagtaccagtttgcatttccatgga
 V  V  I  N  V  N  N  Q  L  E  T  E  S  T  S  L  H  F  H  G atctacatgaatggcaccaaccacatggatggcccgactggcgtgacccagtgcgagata
 I  Y  M  N  G  T  N  H  M  D  G  P  T  G  V  T  Q  C  E  I ccgcccgggagctcattcacatacaattttacggtcgaccaaccgggaacttactggtat
 P  P  G  S  S  F  T  Y  N  F  T  V  D  Q  P  G  T  Y  W  Y cattctcacaaccgcggccagtatcccgatggattgcgagggcctttattgtcagagac
 H  S  H  N  R  G  Q  Y  P  D  G  L  R  G  P  F  I  V  R  D cccgacaatccgttcaaggatgactatgatgaggaagtcgtcctgacattctccgactgg
 P  D  N  P  F  K  D  D  Y  D  E  E  V  V  L  T  F  S  D  W taccacgaccggatccccaccctcatgaagagtttcattagtgtcacaaaccccaccggc
 Y  H  D  R  I  P  T  L  M  K  S  F  I  S  V  T  N  P  T  G gcggagcctgtcccgaacgcggcactgatgaatgacactcagaacctcaccttccagatg
 A  E  P  V  P  N  A  A  L  M  N  D  T  Q  N  L  T  F  Q  M actcccgggcgagatacatgttccgactaataaacattggtgcatttgctgctcaatac
 T  P  G  R  R  Y  M  F  R  L  I  N  I  G  A  F  A  A  Q  Y gtctggttcgaaggccataccatgcgtatcgtagaagtcgacggcgtgtacaccgaagcc
 V  W  F  E  G  H  T  M  R  I  V  E  V  D  G  V  Y  T  E  A gcagatgcagagcgaatttacatgactgccgctcaacgctacagcgtaatcatcaccgca
 A  D  A  E  R  I  Y  M  T  A  A  Q  R  Y  S  V  I  I  T  A aagaacgaatctacctcaaacttcgcctttgttggaagcatggatcaggatctctttgat
 K  N  E  S  T  S  N  F  A  F  V  G  S  M  D  Q  D  L  F  D actattccagcaggccttaataataacgtgaccgggtggcttgtctacaatcaacgaac
 T  I  P  A  G  L  N  N  N  V  T  G  W  L  V  Y  N  Q  Q  N ggcttgttgccacctttagctatcggggactacgatccgttcgatgacttcacacttgtg
 G  L  L  P  P  L  A  I  G  D  Y  D  P  F  D  D  F  T  L  V cctcaagatggtatggagctctacgatcacgtcgatcattccatcaccctcgatatgaag
 P  Q  D  G  M  E  L  Y  D  H  V  D  H  S  I  T  L  D  M  K atggacaatctcggggacggagcaaattatgccttttcaacgacgtgacctacgtcgag
 M  D  N  L  G  D  G  A  N  Y  A  F  F  N  D  V  T  Y  V  E cccaaggtgccgactctgtacacggtgttgtctactggcaataatgccacagactcgaga
 P  K  V  P  T  L  Y  T  V  L  S  T  G  N  N  A  T  D  S  R atctacggtagcaacaccaacagcttcatattggctaaggacgaagtcgtcgagatcatc
 I  Y  G  S  N  T  N  S  F  I  L  A  K  D  E  V  V  E  I  I ctcaacaacaatgatccgggaaagcacccctttccatctgcatgggcacgcattccaagca
 L  N  N  N  D  P  G  K  H  P  F  H  L  H  G  H  A  F  Q  A atcgttcgctccgaagaagaagccggcgcgtacgtggcaaacgaaaccttcccccagacg
 I  V  R  S  E  E  E  A  G  A  Y  V  A  N  E  T  F  P  Q  T ccaatgcgccgcgatacaattcttgtccggcccaatggcaatatagtactgagattcaag
 P  M  R  R  D  T  I  L  V  R  P  N  G  N  I  V  L  R  F  K gctgacaatcctggtgtctggctgttccattgtcatattgaatggcatgttgcgtcgggc
 A  D  N  P  G  V  W  L  F  H  C  H  I  E  W  H  V  A  S  G cttattgccaccatgatagaggcaccgcttgacctgcaatcttctctcggcaacagcatt
 L  I  A  T  M  I  E  A  P  L  D  L  Q  S  S  L  G  N  S  I cctgctgatcactggcgagcttgtgccgccgccggcacacctactgcaggcaacgcagca
 P  A  D  H  W  R  A  C  A  A  A  G  T  P  T  A  G  N  A  A ggcaacacgattgattatcttgacctgactggtgaaaacaagagccccggcccgcttccc
 G  N  T  I  D  Y  L  D  L  T  G  E  N  K  S  P  G  P  L  P tctggctttgaagcgaaaggcattgtcgcgcttgtcttcagttgtattgctgctgtcttg
 S  G  F  E  A  K  G  I  V  A  L  V  F  S  C  I  A  A  V  L
```

```
ggcatggcagccatcgtatggtacgggatggcgcctctgacagatggaactggtcagcaa
 G  M  A  A  I  V  W  Y  G  M  A  P  L  T  D  G  T  G  Q  Q caacacgttgtggatcaacagccgcaaggacgctccgcacaagttggcgtcatgcccta
 Q  H  V  V  D  Q  Q  P  Q  G  R  S  A  Q  V  G  V  M  P  L gcggtcgcggcaaaacgtgagcaaggatggccagccggactgatttggaggcagagatg
 A  V  A  A  K  R  E  Q  R  M  A  S  R  T  D  L  E  A  E  M cggcaagaaaagagcggagaaattaccatggtggagcagaggaggagcagccgtgggtca
 R  Q  E  K  S  G  E  I  T  M  V  E  Q  R  R  S  S  R  G  S tcgaacatgctggatgtcaggaggagtagccgcggttcgtctaacatgctagagaccaga
 S  N  M  L  D  V  R  R  S  S  R  G  S  S  N  M  L  E  T  R agaagcagtcgtggcagtgagcagatgctgtcatga
 R  S  S  R  G  S  E  Q  M  L  S  -
```

SEQ ID NO: 93
LENGTH: 671
TYPE: PRT
ORGANISM: *M. phaseolina*
MAQSLFLLLAAALCSRAATVTYDFNVTWVTANPDAAFRRTTIGINGQWPLPAIDVTKGDRVVINVNN

QLETESTSLHFHGIYMNGTNHMDGPTGVTQCEIPPGSSFTYNFTVDQPGTYWYHSHNRGQYPDGLRG

PFIVRDPDNPFKDDYDEEVVLTFSDWYHDRIPTLMKSFISVTNPTGAEPVPNAALMNDTQNLTFQMT

PGRRYMFRLINIGAFAAQYVWFEGHTMRIVEVDGVYTEAADAERIYMTAAQRYSVIITAKNESTSNF

AFVGSMDQDLFDTIPAGLNNNVTGWLVYNQQNGLLPPLAIGDYDPFDDFTLVPQDGMELYDHVDHSI

TLDMKMDNLGDGANYAFFNDVTYVEPKVPTLYTVLSTGNNATDSRIYGSNTNSFILAKDEVVEIILN

NNDPGKHPFHLHGHAFQAIVRSEEEAGAYVANETFPQTPMRRDTILVRPNGNIVLRFKADNPGVWLF

HCHIEWHVASGLIATMIEAPLDLQSSLGNSIPADHWRACAAAGTPTAGNAAGNTIDYLDLTGENKSP

GPLPSGFEAKGIVALVFSCIAAVLGMAAIVWYGMAPLTDGTGQQQHVVDQQPQGRSAQVGVMPLAVA

AKREQRMASRTDLEAEMRQEKSGEITMVEQRRSSRGSSNMLDVRRSSRGSSNMLETRRSSRGSEQML

S*

SEQ ID NO: 94
LENGTH: 3063 (including 150 bp 5' UTR and 150 bp 3' UTR)
TYPE: DNA
ORGANISM: *M. phaseolina*
ACGCCTCGCCAACCTCATCTTCGTCGAACAGGCTTAGGTATCAAGCCTCCTTTGCAATCACTTACGC

GGCCCTCTCTACCTCCTGCTCATGTTTGAACAAATCACACCTCTTTGAAACGCTAGAAACACACTGT

TTCTATACCGTCGAGAATGGCCTGGACCTCAGCTCTAGATCGATCCTCGTGGCTTGCCCCAGCTTCC

CCACCAAGGGGGTTTGGTAAGTCGTAAAAGTTTCCTCACAGTTCGCAAATTCAGAGTACCGGTTCAG

CCTCTGATCTTTGCCACTGTCACGGCGGCAGCTGAAGCCGCGTGTACGTCGAATTCTCCCCTGAATA

CGTATGTGCCGGACTTGTATTTCTTCATACCCAGCCGTCTAGGATCGTTCGGTATCGGTCTCTGCAA

CGACTACCACTACGACCACTGGGAAATCCTCCACGTTCTCTACGCTGACCAGCACTTCATCTTCGTC

TACAGCGAAGACTAGCTCGGCCAGCTCGGCATCGCTTTCACGCACTACTCCTTCACCTGCCAGCTCT

TCTTCCGTGAGCTCTTCGTCGATCAGATCCTCTTCTGGCGGATCTTCATCTGCTGGTACTTCTTCTG

CCCGCTCATCATATGTCAGCTCTTCTTTGAGCTCGCGTTCTGCTGTTTCTTCCCTAGTGACCAGCAT

ATCCTCTTCTCTCACCTCAACTGGCACGGTATCGTCCTCGCCCGCTTCGAAGAGCTCCAGCTCTTCA

TCTTCCACTCTTTCAGCCTCTTCAACCACAAAGGTTGCTACTGGTACCCCGTGTGCTGGAAACACTG

CGGCTTCCAGGACAGCCTGGTGCGATCACACCATTGACGATGACTACTATCCCATTATCCCAGATAC

CGGAGTCACACGCGAATACTGGTTCGACCTTGTCGAGGTGACTGTTGCCCCTGATGGCATTGAGAGA

GCTGCCATGGCGGTCAACGGCAGCATCCCTGGACCCACCATTGAGGCGGATTGGGGCGATATCGCCG

TCATGCATGTGACCAACAGCTTGATCTCGAGCAAGAACGGCACTAGCATTCATTTCCACGGTATCCA

```
GCAGAACTTCACAAATCAAACGGACGGTGTTATTTCCATCACTCAGTGCCCTACCGCTCCTGGCGAG

AACTACACGTATACCTGGAGGGCTGAGCAGTACGGAACTACATGGTGAGCTTGATCCGAGGATACAG

ATGTAAAGGAGATGCTAAGATATCACAGGTACCATTCTCACTTTGCGCTTCAAGCTTGGGAAGGTGT

CTTTGGAGGTACATACATCCCCGCTCCAGGACCTCCAACATTTATTAACGAAGCCCTGCAGGTATCA

AGATCAATGGTCCGGCGAGTGCCAACTACGATTACGATCTTGGCCATGTCTTCCTGTGAGTTTCGAC

GCCCCTTTTCCACTCATTGTATAAAGTAAGCTTATGCGACAAAAGCCAACGATTGGAGCCACGAGAC

TTCGAGCTCTCTCGAGATCGTTTCTGCAATTCGAGGTCCGCCAACACTTGAGAATGCCCTTATCAAC

GGTACCAACGTGTACAACAACTCGGGAACCATAACGGGCTCTCGTTTTGAGACAACATTTGAGGAAG

GCAAATCCTACAGGTTGAGGTTGGTCAGCGGCGCCATCGACACGCATTTCAAGGTGTCATTGGGTAA

GTTGAGCCAAAACATTGAGATTTCCTGAGATCTAAAGCTGATTGTGTTGCAGATAACCACAGCATGC

TTGTCATAGCCAACGACCTTGTACCCATCGTGCCGTACAACACGACCGTCCTGAACATCGGAATGGG

TCATCCACTTTCTATCAGGAACTGGCCATCAAACTGACACTGAACCCCAGGCCAACGCTACGATGTA

ATCATCACCGCCAACCAAGCCGTAGTCGCCACCGACTTCTGGCTGCGTGCCGTCCCGCAGACGGCCT

GCTCCAATAACGCCAACCCAGACAATATCAAAGGAATAATCCGGTACAGCACCTCCACCTCCGCCTA

CGACTGGACGAACGAATGCGTCGACGAGGCCCTCACCAACCTCGTGCCATGGGTGACTAAGAACGCG

GCCTCGGGCACGAGTCTATCTGAAGTGGTGACGCTGGGTCGCAACGTTGACAACCTCAACCGCTGGA

TGATGAACAGCACATCGATGGTTGTCGAGTGGAATGATCCCTCGTTGCTGCAGGTTTGGAATAATGA

TACCAATTTCACGGATACGAGCGGCGTGGTCAGGCTTGGTACGGCGGACGAGTGGGTCATGTTTGTT

ATCGAGATGACGCTGCCGATTCCGCGTCCCATCCATCTTCACGGGCATGATGTAGATTTCTTCCAGC

CGCCCCCCCCCCCCCCCTTTTTTTTGGGCTCTACTTCCTAGAATACCGGACGGAGTCGTTGCGGAGC

GCGCCTTCGCCGACTTTTGCGTTCCGATGTCTCAAGAAAGGTGTCCATGTTGTAATGTGTATCCCAG

AGGCTTCCCGGCTGACTTGTTTTGTCAACACAGTTCAACATCCTCGCCCAAGGGACCGGCACGTACG

ATTCATCCGTGTCGCTCACCCTGTCAAACCCGCCGCGGAGGGACGTTGCGCTGCTGCCCGCAGCCGG

GTACTTGGTGATTGCATTCGCCACCGATAACCCTGGAGCCTGTGAGGACTTCTCTTTTTCTTGTGCA

TCCCTGGATGTCATCCTTGCTGTGAAATTTTTGGCTGACGCATTCGTCTCAATGCAGGGCTCATGCA

CTGCCACATCGGCCGGCGCACTACGGAGGGCTTCGCAATCCAGATCCTCGAGCGCTGGGACGAGATC

TCGCCGCTTATCGACTACGAGACGCTTGAAGGCAACTGCAACAGATGGGACGCGTACGTGTCGGTCA

GCGATGTCGTACAGGACGATTCTGGCGTATGAGCAATGAAGGTTAGAGTATTTGCGACGTGTTTTAT

CATATATACAACCTTTTTAATCGTAGTCGCTCCTTAACCATAATGTTAATCCATCACTTGGGCCATC

CAAGCACCAACAAAACATTTGAGCCTTCCCAATCAGGACTGGCACAAG

SEQ ID NO: 95
LENGTH: 2085
TYPE: DNA
ORGANISM: M. phaseolina
FEATURE NAME/KEY: CDS
LOCATION: (1) . . . (2085)
atggcctggacctcagctctagatcgatcctcgtggcttgcccagcttccccaccaagg
 M   A   W   T   S   A   L   D   R   S   S   W   L   A   P   A   S   P   P   R gggtttgctgaagccgcgtgtacgtcgaattctcccctgaatacgtatgtgccggacttg
 G   F   A   E   A   A   C   T   S   N   S   P   L   N   T   Y   V   P   D   L tatttcttcatacccagccgtctaggatcgttcggtatcggtctctgcaacgactaccac
 Y   F   F   I   P   S   R   L   G   S   F   G   I   G   L   C   N   D   Y   H tacgaccactgggaaatcctccacgttctctacgctgaccagcacttcatcttcctcttc
 Y   D   H   W   E   I   L   H   V   L   Y   A   D   Q   H   F   I   F   L   F ttccgtgagctcttcgtcgatcagatcctcttctggcggatcttcatctgctggtacttc
 F   R   E   L   F   V   D   Q   I   L   F   W   R   I   F   I   C   W   Y   F
```

-continued

```
ttctgcccgctcatcatatgtcagctcttctttgagctcgcgttctgctgtttcttccct
 F  C  P  L  I  I  C  Q  L  F  F  E  L  A  F  C  C  F  F  P agtgaccagcatatcctcttctctcacctcaactggcacggtatcgtcctcgcccgcttc
 S  D  Q  H  I  L  F  S  H  L  N  W  H  G  I  V  L  A  R  F gaagagctccagctcttcatcttccactctttcagcctcttcaaccacaaagcctggtgc
 E  E  L  Q  L  F  I  F  H  S  F  S  L  F  N  H  K  A  W  C gatcacaccattgacgatgactactatcccattatcccagataccggagtcacacgcgaa
 D  H  T  I  D  D  D  Y  Y  P  I  I  P  D  T  G  V  T  R  E tactggttcgaccttgtcgaggtgactgttgcccctgatggcattgagagagctgccatg
 Y  W  F  D  L  V  E  V  T  V  A  P  D  G  I  E  R  A  A  M gcggtcaacggcagcatccctggacccaccattgaggcggattggggcgatatcgccgtc
 A  V  N  G  S  I  P  G  P  T  I  E  A  D  W  G  D  I  A  V atgcatgtgaccaacagcttgatctcgagcaagaacggcactagcattcatttccacggt
 M  H  V  T  N  S  L  I  S  S  K  N  G  T  S  I  H  F  H  G atccagcagaacttcacaaatcaaacggacggtgttatttccatcactcagtgccctacc
 I  Q  Q  N  F  T  N  Q  T  D  G  V  I  S  I  T  Q  C  P  T gctcctggcgagaactacacgtatacctggagggctgagcagtacggaactacatggtac
 A  P  G  E  N  Y  T  Y  T  W  R  A  E  Q  Y  G  T  T  W  Y cattctcactttgcgcttcaagcttgggaaggtgtctttggaggtacatacatccccgct
 H  S  H  F  A  L  Q  A  W  E  G  V  F  G  G  T  Y  I  P  A ccaggacctccaacatttattaacgaagccctgcaggtatcaagatcaatggtccggcga
 P  G  P  P  T  F  I  N  E  A  L  Q  V  S  R  S  M  V  R  R gtgccaactacgattacgatcttggccatgtcttcctccaacgattggagccacgagact
 V  P  T  T  I  T  I  L  A  M  S  S  S  N  D  W  S  H  E  T tcgagctctctcgagatcgtttctgcaattcgaggtccgccaacacttgagaatgccctt
 S  S  S  L  E  I  V  S  A  I  R  G  P  P  T  L  E  N  A  L atcaacggtaccaacgtgtacaacaactcgggaaccataacgggctctcgttttgagaca
 I  N  G  T  N  V  Y  N  N  S  G  T  I  T  G  S  R  F  E  T acatttgaggaaggcaaatcctacaggttgaggttggtcagcggcgccatcgacacgcat
 T  F  E  E  G  K  S  Y  R  L  R  L  V  S  G  A  I  D  T  H ttcaaggtgtcattggataaccacagcatgcttgtcatagccaacgaccttgtacccatc
 F  K  V  S  L  D  N  H  S  M  L  V  I  A  N  D  L  V  P  I gtgccgtacaacacgaccgtcctgaacatcggaatgggccaacgctacgatgtaatcatc
 V  P  Y  N  T  T  V  L  N  I  G  M  G  Q  R  Y  D  V  I  I accgccaaccaagccgtagtcgccaccgacttctggctgcgtgccgtcccgcagacggcc
 T  A  N  Q  A  V  V  A  T  D  F  W  L  R  A  V  P  Q  T  A tgctccaataacgccaacccagacaatatcaaaggaataatccggtacagcacctccacc
 C  S  N  N  A  N  P  D  N  I  K  G  I  I  R  Y  S  T  S  T tccgcctacgactggacgaacgaatgcgtcgacgaggccctcaccaacctcgtgccatgg
 S  A  Y  D  W  T  N  E  C  V  D  E  A  L  T  N  L  V  P  W gtgactaagaacgcggcctcgggcacgagtctatctgaagtggtgacgctgggtcgcaac
 V  T  K  N  A  A  S  G  T  S  L  S  E  V  V  T  L  G  R  N gttgacaacctcaaccgctggatgatgaacagcacatcgatggttgtcgagtggaatgat
 V  D  N  L  N  R  W  M  M  N  S  T  S  M  V  V  E  W  N  D ccctcgttgctgcaggtttggaataatgataccaatttcacggatacgagcggcgtggtc
 P  S  L  L  Q  V  W  N  N  D  T  N  F  T  D  T  S  G  V  V aggcttggtacggcggacgagtgggtcatgtttgttatcgagatgacgctgccgattccg
 R  L  G  T  A  D  E  W  V  M  F  V  I  E  M  T  L  P  I  P cgtcccatccatcttcacgggcatgatttcaacatcctcgcccaagggaccggcacgtac
 R  P  I  H  L  H  G  H  D  F  N  I  L  A  Q  G  T  G  T  Y gattcatccgtgtcgctcaccctgtcaaaccgcgcgcggagggacgttgcgctgctgccc
 D  S  S  V  S  L  T  L  S  N  P  P  R  R  D  V  A  L  L  P gcagccgggtacttggtgattgcattcgccaccgataaccctggagcctggctcatgcac
 A  A  G  Y  L  V  I  A  F  A  T  D  N  P  G  A  W  L  M  H
```

```
tgccacatcggccggcgcactacggagggcttcgcaatccagatcctcgagcgctgggac
 C  H  I  G  R  R  T  T  E  G  F  A  I  Q  I  L  E  R  W  D gagatctcgccgcttatcgactacgagacgctgaaggcaactgcaacagatgggacgcg
 E  I  S  P  L  I  D  Y  E  T  L  E  G  N  C  N  R  W  D  A tacgtgtcggtcagcgatgtcgtacaggacgattctggcgtatga
 Y  V  S  V  S  D  V  V  Q  D  D  S  G  V  -
```

SEQ ID NO: 96
LENGTH: 694
TYPE: PRT
ORGANISM: M. phaseolina

MAWTSALDRSSWLAPASPPRGFAEAACTSNSPLNTYVPDLYFFIPSRLGSFGIGLCNDYHYDHWEILHVLYAD

QHFIFLFFRELFVDQILFWRIFICWYFFCPLIICQLFFELACCFFPSDQHILFSHLNWHGIVLARFEELQLF

IFHSFSLFNHKAWCDHTIDDDYYPIIPDTGVTREYWFDLVEVTVAPDGIERAAMAVNGSIPGPTIEADWGDIA

VMHVTNSLISSKNGTSIHFHGIQQNFTNQTDGVISITQCPTAPGENYTYTWRAEQYGTTWYHSHFALQAWEGV

FGGTYIPAPGPPTFINEALQVSRSMVRRVPTTITILAMSSSNDWSHETSSSLEIVSAIRGPPTLENALINGTN

VYNNSGTITGSRFETTFEEGKSYRLRLVSGAIDTHFKVSLDNHSMLVIANDLVPIVPYNTTVLNIGMGQRYDV

IITANQAVVATDFWLRAVPQTACSNNANPDNIKGIIRYSTSTSAYDWTNECVDEALTNLVPWVTKNAASGTSL

SEVVTLGRNVDNLNRWMMNSTSMVVEWNDPSLLQVWNNDTNFTDTSGVVRLGTADEWVMFVIEMTLPIPRPIH

LHGHDFNILAQGTGTYDSSVSLTLSNPPRRDVALLPAAGYLVIAFATDNPGAWLMHCHIGRRTTEGFAIQILE

RWDEISPLIDYETLEGNCNRWDAYVSVSDVVQDDSGV*

SEQ ID NO: 97
LENGTH: 2449 (including 150 bp 5' UTR and 150 bp 3' UTR)
TYPE: DNA
ORGANISM: M. phaseolina

GCGCACCCCGAATTTTCATGTGGCACTTTGCTGGTGGCGATGCATAAAGTCTCCCAAACTTGATCT

TCAGCGTCGAGAGCAGCTCAACGTCCGATCCGATTTTTCGTTCACCGCGCTTCTTGTCCCTCAAGCC

CCCAATACAATTCAACATGTTTTCTTTTGTCGTCCAGAAGCCTCAACTGCCGCTATGGCTGGACTTT

GGCCTTTCAATATGGTCAATGTTCGGCGGAAACAGTCAAGACTGCGTACACTCGCCCCAGAGCAGAC

ACTGCTGGCATGATGGGTTCGATATCAACACCGATTATGAAGCTAAGATACCGCCAGGGAAGCTCGT

GGAGGTAAGATAACCCAGCCACAGACGGCTCAGGCCATCGCAACTCACCTCCCTTAGTACGATTTCA

CTATCTCGGAAGCAGTCCTTGCTCCGGACGGATACTTGACGAATGTCACTCTGGTAAATGGAGTATT

CCCTGGTCCAACCCTCGAAGCTGAATGGGGAGATACGATCAGTATGCCTTCTTCATATGAAATCTTT

CTGTGTGCCTTTTGACGTGATTGCTGACATTTCCTGCCAGGGATAACGATCCACAACAACCTCACAA

ACCACAATGGCACATCCATACATTGGCATGGAATTCGCCAATTCGAGACCAATTGGCTTGATGGTGT

TCCCGGCGTCACTCAATGCCCGTCAAAGGTACTACGGCTGGTTTGCTTTGGGAGAGAAACAGGGGAG

CTAAGTGTCACCAGCCTGGAGACTCGCAAGTTGTCGAATTCCGAGCGATGCAATATGGGACCGCATG

GTATCATTCACACTACAGTCTTCAGTGTCAGTATCAATCACAGAGCTCTTGAGCGGCACTTACGCTA

ACCATGATTAGATACAAACGGAGTTCTCGGTATTTGCTATCTCCCTTCCATACAGTTCACAACCTGT

GGGCTGATCCCGTTGCAGGACCCATTCACATCAAGGGACCCTCGAGCATGAACTACGACGTGGATCT

CGGGCCACTGTTGATCAGTGATTGGTATCACCACGATGCCTTCGGCCTATTCCATTATGAGATCGCT

TCACCGCACGCGCCGCTTCCGGTCACAACTATCTTGAATGGCAAGGGAGTCTTTGATTGCGATCCAG

CCAGCGATGCTCGTTGTACGGGAGAGCACCAACGGCACGAGATAGTGTTCGAAGAGGGTAAAAGATA

CAAAATTGGACTAATAAATACCGGCAGCCTTCTGACATACAAGTTCTGGATCGATGGCCATAATTTT

ACAGTTGTGCAGACGGATTTCGTTCCCATCAAACCATACGTCACCGACGTTCTGATCGTCGGGATAG

GTATGTTCAGTGCCTACAAAGAATTGGCGGTAAACTGATCATTCCCAGCTCAACGATACGAGATCAT

TATCGAAGCAAATGTGACATTCACACGTGGCTCCAACTTCTGGATTCACGCAACGTACTGTGACGAT

```
GATGACATGTTGGACTCGAGAGTTGGCATAGTCCGCTACGACGGCAGCGACGGTCGTGATCCGCACA

CGCCGCCCAAGAGTGAGCAACACCCCGGATACGGGTGTCGTGATCCAGCCACGGAGAATCTTGTTCC

CATCGTGAAGAGGGAAGTAGGCAAGAGAGTGAACGGGCTCAGCCCTGCTGATTACCTCAGGATCGGC

CTGCAGGGCTGGCCCAACATCTCGGACACAGATTCGCTCGTACACAAATGGACACTTACCAACAGAA

CCCAGTACATTGATTGGAGGGAGCCAACAATCAAGGCGCTCACTTCGGATGTCGGGGCTGATTTTGC

GGATGAGACATGCCCCATATACCTGGACTACGAGACTGGCGAGTGGGTGTACTTCGTCATCGAGAAC

AACTACACGCTGAGCGACGCCAACACGCCCCGCACCATCCCCCGCTCGGTCCATCCCATCCACTTAC

ACGGGCATGACTTCGTGATCCTCGCCCAGGGTGACGGCATGTTCGACCCCGTCGACGTGGTGCCGAA

CCTCCACAACCCAACCAGGAGGGACGTGGTCAATTGCCCGATTGGCGGCTACGTATGGATCGCATTC

CAGGTCAACAATCCAGGAGCGTGGCTGATGCATTGCCATATCGCCTGGCATGCCAGCGCCGGACTCT

CACTGCAGTTCATTGAGCAACCTGGCCTGATCAAGGGGTTAATGGAGCAGGCAGGAGCCTTGCCGGA

GCTTGCTGATCGATGCGAGGACTGGACTGAGTACTACAATACTGTAAACATACCAAAAGGCGCACTG

CAAGATGATTCGGGCATATGAGTTGGTATTGAACTTCCGGCTGAACACGCTCAGCCACGGCTACTTG

CTTGGCCAAGATTGAGGGTTGGCCGAGAAATGAGTAGTGGGGATTATCACTTTCTTAGAATGTGCAC

GAAAGGGTAGTGTTCGGTCATGTCTCTTAGCTTGAAA

SEQ ID NO: 98
LENGTH: 1821
TYPE: DNA
ORGANISM: M. phaseolina
FEATURE NAME/KEY: CDS
LOCATION: (1)...(1821)
atgttttcttttgtcgtccagaagcctcaactgccgctatggctggactttggccttttca
 M  F  S  F  V  V  Q  K  P  Q  L  P  L  W  L  D  F  G  L  S atatggtcaatgttcggcggaaacagtcaagactgcgtacactcgcccagagcagacac
 I  W  S  M  F  G  G  N  S  Q  D  C  V  H  S  P  Q  S  R  H tgctggcatgatgggttcgatatcaacaccgattatgaagctaagataccgccaggaag
 C  W  H  D  G  F  D  I  N  T  D  Y  E  A  K  I  P  P  G  K ctcgtggagtacgatttcactatctcggaagcagtccttgctccggacggatacttgacg
 L  V  E  Y  D  F  T  I  S  E  A  V  L  A  P  D  G  Y  L  T aatgtcactctggtaaatggagtattccctggtccaaccctcgaagctgaatggggagat
 N  V  T  L  V  N  G  V  F  P  G  P  T  L  E  A  E  W  G  D acgatcaggataacgatccacaacaacctcacaaaccacaatggcacatccatacattgg
 T  I  R  I  T  I  H  N  N  L  T  N  H  N  G  T  S  I  H  W catggaattcgccaattcgagaccaattggcttgatggtgttcccggcgtcactcaatgc
 H  G  I  R  Q  F  E  T  N  W  L  D  G  V  P  G  V  T  Q  C ccgtcaaagcctggagactcgcaagttgtcgaattccgagcgatgcaatatgggaccgca
 P  S  K  P  G  D  S  Q  V  V  E  F  R  A  M  Q  Y  G  T  A tggtatcattcacactacagtcttcagtatacaaacggagttctcggacccattcacatc
 W  Y  H  S  H  Y  S  L  Q  Y  T  N  G  V  L  G  P  I  H  I aagggaccctcgagcatgaactacgacgtggatctcgggccactgttgatcagtgattgg
 K  G  P  S  S  M  N  Y  D  V  D  L  G  P  L  L  I  S  D  W tatcaccacgatgccttcggcctattccattatgagatcgcttcaccgcacgcgccgctt
 Y  H  H  D  A  F  G  L  F  H  Y  E  I  A  S  P  H  A  P  L ccggtcacaactatcttgaatggcaagggagtctttgattgcgatccagccagcgatgct
 P  V  T  T  I  L  N  G  K  G  V  F  D  C  D  P  A  S  D  A cgttgtacgggagagcaccaacggcacgagatagtgttcgaagagggtaaaagatacaaa
 R  C  T  G  E  H  Q  R  H  E  I  V  F  E  E  G  K  R  Y  K attggactaataaataccggcagccttctgacatacaagttctggatcgatggccataat
 I  G  L  I  N  T  G  S  L  L  T  Y  K  F  W  I  D  G  H  N tttacagttgtgcagacggatttcgttcccatcaaaccatacgtcaccgacgttctgatc
 F  T  V  V  Q  T  D  F  V  P  I  K  P  Y  V  T  D  V  L  I
```

-continued

```
gtcgggatagctcaacgatacgagatcattatcgaagcaaatgtgacattcacacgtggc
 V  G  I  A  Q  R  Y  E  I  I  I  E  A  N  V  T  F  T  R  G tccaacttctggattcacgcaacgtactgtgacgatgatgacatgttggactcgagagtt
 S  N  F  W  I  H  A  T  Y  C  D  D  D  D  M  L  D  S  R  V ggcatagtccgctacgacggcagcgacggtcgtgatccgcacacgccgcccaagagtgag
 G  I  V  R  Y  D  G  S  D  G  R  D  P  H  T  P  P  K  S  E caacaccccggatacggggtgtcgtgatccagccacggagaatcttgttcccatcgtgaag
 Q  H  P  G  Y  G  C  R  D  P  A  T  E  N  L  V  P  I  V  K agggaagtaggcaagagagtgaacgggctcagccctgctgattacctcaggatcggcctg
 R  E  V  G  K  R  V  N  G  L  S  P  A  D  Y  L  R  I  G  L cagggctggcccaacatctcggacacagattcgctcgtacacaaatggacacttaccaac
 Q  G  W  P  N  I  S  D  T  D  S  L  V  H  K  W  T  L  T  N agaacccagtacattgattggagggagccaacaatcaaggcgctcacttcggatgtcggg
 R  T  Q  Y  I  D  W  R  E  P  T  I  K  A  L  T  S  D  V  G gctgattttgcggatgagacatgccccatatacctggactacgagactggcgagtgggtg
 A  D  F  A  D  E  T  C  P  I  Y  L  D  Y  E  T  G  E  W  V tacttcgtcatcgagaacaactacacgctgagcgacgccaacacgccccgcaccatcccc
 Y  F  V  I  E  N  N  Y  T  L  S  D  A  N  T  P  R  T  I  P cgctcggtccatcccatccacttacacgggcatgacttcgtgatcctcgcccagggtgac
 R  S  V  H  P  I  H  L  H  G  H  D  F  V  I  L  A  Q  G  D ggcatgttcgacccccgtcgacgtggtgccgaacctccacaacccaaccaggagggacgtg
 G  M  F  D  P  V  D  V  V  P  N  L  H  N  P  T  R  R  D  V gtcaattgcccgattggcggctacgtatggatcgcattccaggtcaacaatccaggagcg
 V  N  C  P  I  G  G  Y  V  W  I  A  F  Q  V  N  N  P  G  A tggctgatgcattgccatatcgcctggcatgccagcgccggactctcactgcagttcatt
 W  L  M  H  C  H  I  A  W  H  A  S  A  G  L  S  L  Q  F  I gagcaacctggcctgatcaaggggttaatggagcaggcaggagccttgccggagcttgct
 E  Q  P  G  L  I  K  G  L  M  E  Q  A  G  A  L  P  E  L  A gatcgatgcgaggactggactgagtactacaatactgtaaacataccaaaaggcgcactg
 D  R  C  E  D  W  T  E  Y  Y  N  T  V  N  I  P  K  G  A  L caagatgattcgggcatatga
 Q  D  D  S  G  I  -
```

SEQ ID NO: 99
LENGTH: 606
TYPE: PRT
ORGANISM: *M. phaseolina*
MFSFVVQKPQLPLWLDFGLSIWSMFGGNSQDCVHSPQSRHCWHDGFDINTDYEAKIPPGKLVEYDFT

ISEAVLAPDGYLTNVTLVNGVFPGPTLEAEWGDTIRITIHNNLTNHNGTSIHWHGIRQFETNWLDGV

PGVTQCPSKPGDSQVVEFRAMQYGTAWYHSHYSLQYTNGVLGPIHIKGPSSMNYDVDLGPLLISDWY

HHDAFGLFHYEIASPHAPLPVTTILNGKGVFDCDPASDARCTGEHQRHEIVFEEGKRYKIGLINTGS

LLTYKFWIDGHNFTVVQTDFVPIKPYVTDVLIVGIAQRYEIIIEANVTFTRGSNFWIHATYCDDDDM

LDSRVGIVRYDGSDGRDPHTPPKSEQHPGYGCRDPATENLVPIVKREVGKRVNGLSPADYLRIGLQG

WPNISDTDSLVHKWTLTNRTQYIDWREPTIKALTSDVGADFADETCPIYLDYETGEWVYFVIENNYT

LSDANTPRTIPRSVHPIHLHGHDFVILAQGDGMFDPVDVVPNLHNPTRRDVVNCPIGGYVWIAFQVN

NPGAWLMHCHIAWHASAGLSLQFIEQPGLIKGLMEQAGALPELADRCEDWTEYYNTVNIPKGALQDD

SGI*

SEQ ID NO: 100
LENGTH: 2347 (including 150 bp 5' UTR and 150 bp 3' UTR)
TYPE: DNA
ORGANISM: *M. phaseolina*
GATACAACTCTTCTCCCCGCCTCTCTTTCACAAACTGTCTATCGCTCCTTTGTTTTTCTGTCCCTCC

TTAAGGTCACATACTACTGAGACTATTCGTGTCTCGTGCCTCTCATTTAGTTTTTAGTTGATTCATC

TTGCCGTTGCTGTAACATGCCGTTTTCTCCACGCCTAAGTATATGCCTTTTAGCATTTTGCTCTCAC

```
ATTGTGTTCGCACTTTCGATACCAAATGTAAAGGATAGGACCCCCCACTTAAGCCCGCGCAATTACG

GATTTCGTTTCGGCAACCTGTCTTGGGGCGGGGCGGAGCCTTCCGACCCACTCGCACAAGGTGCAGA

ACGTTTGGATGACATCAGTCTCCCGGCCCCTGAAGATGGCTGTCTTTTCTCCAAAGATGCTCGGAAC

TGCTGGCGCGATAACTTCAACATCGACACCGATTTCGACGAGCGCTTCCCCACGACCGGGAAGACGG

TCACTGTAAGGAATCATCGCACCTCTTGGAACCCTTACGCTAATACCGAGGGCAGTATAATCTGGAG

ATCACAAACACTACCATGGCCCCTGACGGAATCGAACGCGTCGTCATGGCCGTGAATGGCCAATATC

CCGGCCCGACCCTTATTGCTGATTGGGGGGACACGATGGTTATCAACGTCAAGAATAGCCTGGACCA

CAACGGTACGGGTCTCCATTTCCATGGACTGCGCCAATACAAAAGCAACGGCGCCGATGGGGCGAAC

GGTATCACAGAATGCCCAATTGCCCCCGGCGAGACCAAGACCTACACCTTTCAATGTACCCAGCACG

GTAGCTCGTGGTACCACTCGCATTACTCTGTCCAGTACTCCGACGGCGTTCTCGGCGGCATTATCAT

CAACGGCCCCGCCGACGCGCACTACGACCACGATCTTGGTGTGTACATGCTTTCTGACTGGTACCAC

ACTCCAATGTTTGAACTAGCCGAAGCTGCCAGGCATTCGACAAGGGGCCCACCGAAGGCGGATAACG

GACTCATCAACGGGACGATGAAGAGCCCTGACGGTTCTCTTGGAGCCTATGGCCAGATCCATGTGAA

GAAGGGTCTGCGGTACAGGATTCGCGTAATGAATGTTGGCACTAACGACCACTACCTCTTCTCTGTT

GATGGGCACAACCTCACCGTGATCGCAAGTGATTTCGTGCCGGTCGTGCCCTTTTCGGCGTCCAGCA

TTTCCCTCGGTGTTGGTGAGATATCCGATCTTTATGTTGTTATTTCGCTGCTGACCGTCACTTTAGG

ACAGAGGTACGACGTGATCCTTATCGCCGACCAAGACATTGACAACTACTGGATCCGCTCCGACCCG

GACTCTGCCTGTAGCGTTAACGGCAACGCCGGCAACATAAAAGCCATCCTCTCGTATGACACGGCTC

CCGCGGACGCTCAGCCGAATAGCACGCGCCACAGCATCTCCTCGGGCTGCAAGGACATGGCAGTCGT

GCCAAGAGTTGCTAATACCGTGCCCTCTGATCGCTTCGCGGACGCCGTCCAGAGCCTGGCGATGAGC

GTCAATATCACGCAGCAGAACGGCCCGCTCGTCCAGTGGTATATCAACGGCTCGGCTATGGAGGTCG

ACTGGAGCTACCCGACGGTCCAATATGTCCTAGATGGGAACACGTCGTACCCGCGTGAGCTGAACCT

AGTCCAGCTGGATGAGGCGGACCAGTGGTACTACTTCGTCATCCAGACCGTGCAAGGCTTGCGTGTC

AACCTGCCGCACCCAATTCATCTTCATGGCCACGTACGTTCCCTCCTTTCCCTTCCTCCCTAAACGA

AACAGTAAAAGAGGGACAAGTGAATGCGACGTACTGATTTGTTGTCCAATTGGTCCAGGACTTCTAC

ATCCTCGGCGCCGGTCCCGGCGAGTGGGACGGCAACATCGATGGCCTGCAGTTCGACAACCCTCCGC

GGCGCGATACGGCAATGCTACCTGCGGGTGGCTACCTCATCCTCGCCTTTCCGGCCGACAACCCTGG

CGCCTGGCTCATGCATTGCCACATCCCGTTCCACGTCCAGCAGGGCTTCGGGCTGCAGTTCTTGGAG

CGGCCGGATGAGATTGAGGGCGTCATGGGCGATACGAGCCCGTTTTACAACGAGTGTGCGGCTTGGA

AGGACTACTATGGTGGGGGCCAGGCTTTTCAGCAGTCCGATTCGGGCTTGTAATTGGTCGTGGTGGC

TTGCGCAAGAGCAAAGCGCCGTCGGTGCTCTGGCGGTGATTTTTAGTGGCACGGTTTTTGTACTCAT

CAACTCCTAATCACTAAGTCAGCCACCCTCGTTTCCGCCCACCCTGTACAGTCAGCATCATAACGTA

AC
```

```
SEQ ID NO: 101
LENGTH: 1854
TYPE: DNA
ORGANISM: M. phaseolina
FEATURE NAME/KEY: CDS
LOCATION: (1) . . . (1854)
atgccgttttctccacgcctaagtatatgccttttagcattttgctctcacattgtgttc
 M   P   F   S   P   R   L   S   I   C   L   L   A   F   C   S   H   I   V   F gcactttcgataccaaatgtaaaggataggaccccccacttaagcccgcgcaattacgga
 A   L   S   I   P   N   V   K   D   R   T   P   H   L   S   P   R   N   Y   G tttcgtttcggcaacctgtcttggggcggggcggagccttccgacccactcgcacaaggt
 F   R   F   G   N   L   S   W   G   G   A   E   P   S   D   P   L   A   Q   G
```

```
gcagaacgtttggatgacatcagtctcccggccctgaagatggctgtcttttctccaaa
 A  E  R  L  D  D  I  S  L  P  A  P  E  D  G  C  L  F  S  K gatgctcggaactgctggcgcgataacttcaacatcgacaccgatttcgacgagcgcttc
 D  A  R  N  C  W  R  D  N  F  N  I  D  T  D  F  D  E  R  F cccacgaccgggaagacggtcacttataatctggagatcacaaacactaccatggcccct
 P  T  T  G  K  T  V  T  Y  N  L  E  I  T  N  T  T  M  A  P gacggaatcgaacgcgtcgtcatggccgtgaatggccaatatcccggcccgaccccttatt
 D  G  I  E  R  V  V  M  A  V  N  G  Q  Y  P  G  P  T  L  I gctgattgggggacacgatggttatcaacgtcaagaatagcctggaccacaacggtacg
 A  D  W  G  D  T  M  V  I  N  V  K  N  S  L  D  H  N  G  T ggtctccatttccatggactgcgccaatacaaaagcaacggcgccgatggggcgaacggt
 G  L  H  F  H  G  L  R  Q  Y  K  S  N  G  A  D  G  A  N  G atcacagaatgcccaattgccccggcgagaccaagacctacacctttcaatgtacccag
 I  T  E  C  P  I  A  P  G  E  T  K  T  Y  T  F  Q  C  T  Q cacggtagctcgtggtaccactcgcattactctgtccagtactccgacggcgttctcggc
 H  G  S  S  W  Y  H  S  H  Y  S  V  Q  Y  S  D  G  V  L  G ggcattatcatcaacggccccgcgacgcgcactacgaccacgatcttggtgtgtacatg
 G  I  I  I  N  G  P  A  D  A  H  Y  D  H  D  L  G  V  Y  M ctttctgactggtaccacactccaatgtttgaactagccgaagctgccaggcattcgaca
 L  S  D  W  Y  H  T  P  M  F  E  L  A  E  A  A  R  H  S  T aggggcccaccgaaggcggataacggactcatcaacgggacgatgaagagccctgacggt
 R  G  P  P  K  A  D  N  G  L  I  N  G  T  M  K  S  P  D  G tctcttggagcctatggccagatccatgtgaagaagggtctgcggtacaggattcgcgta
 S  L  G  A  Y  G  Q  I  H  V  K  K  G  L  R  Y  R  I  R  V atgaatgttggcactaacgaccactacctcttctctgttgatgggcacaacctcaccgtg
 M  N  V  G  T  N  D  H  Y  L  F  S  V  D  G  H  N  L  T  V atcgcaagtgatttcgtgccggtcgtgcccttttcggcgtccagcatttccctcggtgtt
 I  A  S  D  F  V  P  V  V  P  F  S  A  S  S  I  S  L  G  V ggacagaggtacgacgtgatccttatcgccgaccaagacattgacaactactggatccgc
 G  Q  R  Y  D  V  I  L  I  A  D  Q  D  I  D  N  Y  W  I  R tccgacccggactctgcctgtagcgttaacggcaacgccggcaacataaaagccatcctc
 S  D  P  D  S  A  C  S  V  N  G  N  A  G  N  I  K  A  I  L tcgtatgacacggctcccgcggacgctcagccgaatagcacgcgccacagcatctcctcg
 S  Y  D  T  A  P  A  D  A  Q  P  N  S  T  R  H  S  I  S  S ggctgcaaggacatggcagtcgtgccaagagttgctaataccgtgccctctgatcgcttc
 G  C  K  D  M  A  V  V  P  R  V  A  N  T  V  P  S  D  R  F gcggacgccgtccagagcctggcgatgagcgtcaatatcacgcagcagaacggcccgctc
 A  D  A  V  Q  S  L  A  M  S  V  N  I  T  Q  Q  N  G  P  L gtccagtggtatatcaacggctcggctatggaggtcgactggagctacccgacggtccaa
 V  Q  W  Y  I  N  G  S  A  M  E  V  D  W  S  Y  P  T  V  Q tatgtcctagatgggaacacgtcgtacccgcgtgagctgaacctagtccagctggatgag
 Y  V  L  D  G  N  T  S  Y  P  R  E  L  N  L  V  Q  L  D  E gcggaccagtggtactacttcgtcatccagaccgtgcaaggcttgcgtgtcaacctgccg
 A  D  Q  W  Y  Y  F  V  I  Q  T  V  Q  G  L  R  V  N  L  P cacccaattcatcttcatggccacgacttctacatcctcggcgccggtcccggcgagtgg
 H  P  I  H  L  H  G  H  D  F  Y  I  L  G  A  G  P  G  E  W gacggcaacatcgatggcctgcagttcgacaaccctccgcggcgcgatacggcaatgcta
 D  G  N  I  D  G  L  Q  F  D  N  P  P  R  R  D  T  A  M  L cctgcgggtggctacctcatcctcgcctttccggccgacaaccctggcgcctggctcatg
 P  A  G  G  Y  L  I  L  A  F  P  A  D  N  P  G  A  W  L  M cattgccacatcccgttccacgtccagcagggcttcgggctgcagttcttggagcggccg
 H  C  H  I  P  F  H  V  Q  Q  G  F  G  L  Q  F  L  E  R  P gatgagattgagggcgtcatgggcgatacgagcccgttttacaacgagtgtgcggcttgg
 D  E  I  E  G  V  M  G  D  T  S  P  F  Y  N  E  C  A  A  W
```

-continued

```
aaggactactatggtgggggccaggcttttcagcagtccgattcgggcttgtaa
 K  D  Y  Y  G  G  G  Q  A  F  Q  Q  S  D  S  G  L  -
```

```
SEQ ID NO: 102
LENGTH: 617
TYPE: PRT
ORGANISM: M. phaseolina
MPFSPRLSICLLAFCSHIVFALSIPNVKDRTPHLSPRNYGFRFGNLSWGGAEPSDPLAQGAERLDDI

SLPAPEDGCLFSKDARNCWRDNFNIDTDFDERFPTTGKTVTYNLEITNTTMAPDGIERVVMAVNGQY

PGPTLIADWGDTMVINVKNSLDHNGTLHFHGLRQYKSNGADGANGITECPIAPGETKTYTFQCTQH

GSSWYHSHYSVQYSDGVLGGIIINGPADAHYDHDLGVYMLSDWYHTPMFELAEAARHSTRGPPKADN

GLINGTMKSPDGSLGAYGQIHVKKGLRYRIRVMNVGTNDHYLFSVDGHNLTVIASDFVPVVPFSASS

ISLGVGQRYDVILIADQDIDNYWIRSDPDSACSVNGNAGNIKAILSYDTAPADAQPNSTRHSISSGC

KDMAVVPRVANTVPSDRFADAVQSLAMSVNITQQNGPLVQWYINGSAMEVDWSYPTVQYVLDGNTSY

PRELNLVQLDEADQWYYFVIQTVQGLRVNLPHPIHLHGHDFYILGAGPGEWDGNIDGLQFDNPPRRD

TAMLPAGGYLILAFPADNPGAWLMHCHIPFHVQQGFGLQFLERPDEIEGVMGDTSPFYNECAAWKDY

YGGGQAFQQSDSGL*
```

```
SEQ ID NO: 103
LENGTH: 2415 (including 150 bp 5' UTR and 150 bp 3' UTR)
TYPE: DNA
ORGANISM: M. phaseolina
TCGAGCAAGATGAATGTATCCTCCGTGGAAAGTCTTTTTTCTCAGGGCGGCCGTCCGCTTTGACCTC

TGCCCTCTTGCTGGATTATAGAATACCCAGACGCCCATGTAGTGCATGGCCTTGTGAACTTACCCAC

CACCTCTCTCGCGAAGATGATTGGCCATTCTCTCGTAGCTGTAGCACTCGGCAGCGCAGCCATGGCA

CTGGCTCTTCCTCAGAGCCACGTCCCCGCTGCTTGCATGAACGGTCCGCACTCTCGGAAGTGCTGGG

GCAACTACTCCATCGACACGGACTGGTACACCGAAACTCCATACACGGGCGTGGTGAGAGAATACTG

GTTCCTGGTCGAGAATACCACCGTAGCACCAGATGTACACGCCCCTCTGGGTTGCGCCATTGGCAAC

GCATGGCAGGCTGACTTGGGGTGGCAGGGATATGAGACATGGGCTCTCACGGTAAACCGCTCGATTC

CTGGACCAACAATCGAGGCCAACTGGGGCGACGAAGGTAAAGTTGTTTCGACTGGGATTCGCCGGCC

GATAATGCTTACTGCTACGCAGTAATCGTTCATGTCACCAATGGCATGGAGCGGAATGGTACCGCAA

TCCATTTCCACGGCCTAAGGCAGCTGGGAGCCCACGAAATGGATGGTGTCCCTGGGGTTACGCAGTG

TCCTATAGTACGCCCGTACCCTCTCTCTCTCGCACTGCTGCGCGCAAGCTATTGATACTTCTCAGGC

TCCCGGACACTCCTACACATACAAGTGGCGAGCTACTCAATACGGAACGGTGAATCCCCCCTCGAGG

CAGAATCGGCCATACTTTAACTGACGGGTCTGAAAGAGCTGGTATCATTCCCACTTCAGCATGCAAT

ACTCGGTCGGTCTACAGGGCCCGATCGTCATTCACGGACCTGCTACGGCAGACTATGACGAGGACCT

GGGAACGGTCGTCTTGCAGGACTGGAGTCACACCTCTCCGTTCGCCATGTGGTGGTACGCACGTGTG

CCTTCCGGACCGCCCTCGCTCTCAAACTCGCTCATCAACGGCAAAAACGTCTTCTATTGCGACAGTA

CGACCGATTCGAGATGCTACGGTAACGGCACACGGTCGGAGTGGCGCTTTGAGCAGGGGAAAAAGTA

TCGAATGAGGCTCATCAATACAGGCCTCTACTCAAACTTCCGTTTTGCCATTGACAACCACAACCTC

ACCGTTATTGCGACCGACTTTGTTCCTATCAAACCCTACACCACAGATAACGTGAGTCACCAACCCC

TTGCTTTCGTGCACTCTAACGAGACATTTCTCCCAGGTGGCAATTTCAATGGGGCAACGCTACGACA

TCGTCGTTGAGGCAAATCAACCGGAAGGTGATTACTGGCTGCGGTAAGGCTCTAATGAATTGATCAG

ACATTGAAAAAAAGGGGGGCGGGGGAACCCCATCAACTGACATTCAACCCTACCTAGGGCTATAT

GGCAAACATCCTGCTGCCCGAACGACTACTCAAACAATACCCTTGGCATAATCCGCTACACAGCAAA

CTCCACTGCCGAACCAAACACAACAAGTCCTGCACTATCCTACCCGGACACATGCGGCGACGAGCCG

GCAGCGAGCCTCGTGCCGCACCTGGCCCTCAACGCGAGCACGCCGGCCGTCGTGCGCACCTACGACC
```

-continued

```
TGTCCAAAGTCACACTCGAGCTGCCAAAGGGCTTCCTCTGGACACTGAACGACACCTACCTCTGGAT

CAACTGGTCGTCGCCAACGAACTTGAGGCTGGCCGAGGGCGGCGCCGCCGCTGCGGCGAGCCTGCCC

GCCGAATATCTCGCCGTCGACAGCCGGGCCGGCAACGAGGGACGCTGGGCGTATCTCGTGTTCAACG

ACGTCTCCGCCCGCAATCGCTCGCACCCGATGCACCTGCACGGCCACGACTTCTTCCTGCTCGGCAC

CGGCCCTGGCTATTTTGAGTACGGCAGCAACAGCAGCAGCCTGGCGATGCTCAACCTGCACAACCCG

CCTCGTCGCGACACGGCGACCTGGCCCGAGTCTGGCTGGATGGTCGTCGCGTTCCTCATGGACAACC

CGGGGAGCTGGCTGATCCACTGCCACATCGCCTGGCACTCGAGCGAGTCGCTCGGCCTGCAGTTCCT

GGAGAGCCCTGAGACGTATGTCCCTCGATTGGAAGGCCAGAGATTGCGGGAGACGTGCGAGGCGTGG

GATGCATTCTGGAATCGCCACGACTCATACGAGCAAGAGGATGCGGGGATATAAGGGCCGCGAGGAC

TGCATGAACGCATGCTTTGGTCCTGCATGGAGGCTTCGTGAATTGGCGGGAAAGATGTGACTAACTT

CTTCCTCGCATGTTCTTGGCTCTCTCCTTCTCTACACTCTCTAAATAATCCGCAAATTTCCATGTGC

GTA
```

SEQ ID NO: 104
LENGTH: 1815
TYPE: DNA
ORGANISM: M. phaseolina
FEATURE NAME/KEY: CDS
LOCATION: (1) . . . (1815)

```
atgattggccattctctcgtagctgtagcactcggcagcgcagccatggcactggctctt
 M  I  G  H  S  L  V  A  V  A  L  G  S  A  A  M  A  L  A  L cctcagagccacgtccccgctgcttgcatgaacggtccgcactctcggaagtgctgggc
 P  Q  S  H  V  P  A  A  C  M  N  G  P  H  S  R  K  C  W  G aactactccatcgacacggactggtacaccgaaactccatacacgggcgtggtgagagaa
 N  Y  S  I  D  T  D  W  Y  T  E  T  P  Y  T  G  V  V  R  E tactggttcctggtcgagaataccaccgtagcaccagatgtacacgcccctctgggttgc
 Y  W  F  L  V  E  N  T  T  V  A  P  D  V  H  A  P  L  G  C gccattggcaacgcatggcaggctgacttggggtggcagggatatgagacatgggctctc
 A  I  G  N  A  W  Q  A  D  L  G  W  Q  G  Y  E  T  W  A  L acggtaaaccgctcgattcctggaccaacaatcgaggccaactggggcgacgaagtaatc
 T  V  N  R  S  I  P  G  P  T  I  E  A  N  W  G  D  E  V  I gttcatgtcaccaatggcatggagcggaatggtaccgcaatccatttccacggcctaagg
 V  H  V  T  N  G  M  E  R  N  G  T  A  I  H  F  H  G  L  R cagctgggagcccacgaaatggatggtgtccctggggttacgcagtgtcctatagctccc
 Q  L  G  A  H  E  M  D  G  V  P  G  V  T  Q  C  P  I  A  P ggacactcctacacatacaagtggcgagctactcaatacggaacgagctggtatcattcc
 G  H  S  Y  T  Y  K  W  R  A  T  Q  Y  G  T  S  W  Y  H  S cacttcagcatgcaatactcggtcggtctacagggcccgatcgtcattcacggacctgct
 H  F  S  M  Q  Y  S  V  G  L  Q  G  P  I  V  I  H  G  P  A acggcagactatgacgaggacctgggaacggtcgtcttgcaggactggagtcacacctct
 T  A  D  Y  D  E  D  L  G  T  V  V  L  Q  D  W  S  H  T  S ccgttcgccatgtggtggtacgcacgtgtgccttccggaccgccctcgctctcaaactcg
 P  F  A  M  W  W  Y  A  R  V  P  S  G  P  P  S  L  S  N  S ctcatcaacggcaaaaacgtcttctattgcgacagtacgaccgattcgagatgctacggt
 L  I  N  G  K  N  V  F  Y  C  D  S  T  T  D  S  R  C  Y  G aacggcacacggtcggagtggcgctttgagcaggggaaaaagtatcgaatgaggctcatc
 N  G  T  R  S  E  W  R  F  E  Q  G  K  K  Y  R  M  R  L  I aatacaggcctctactcaaacttccgttttgccattgacaaccacaacctcaccgttatt
 N  T  G  L  Y  S  N  F  R  F  A  I  D  N  H  N  L  T  V  I gcgaccgactttgttcctatcaaaccctacaccacagataacgtggcaatttcaatgggg
 A  T  D  F  V  P  I  K  P  Y  T  T  D  N  V  A  I  S  M  G caacgctacgacatcgtcgttgaggcaaatcaaccggaaggtgattactggctgcgggct
 Q  R  Y  D  I  V  V  E  A  N  Q  P  E  G  D  Y  W  L  R  A
```

```
atatggcaaacatcctgctgcccgaacgactactcaaacaatacccttggcataatccgc
 I  W  Q  T  S  C  C  P  N  D  Y  S  N  N  T  L  G  I  I  R tacacagcaaactccactgccgaaccaaacacaacaagtcctgcactatcctacccggac
 Y  T  A  N  S  T  A  E  P  N  T  T  S  P  A  L  S  Y  P  D acatgcggcgacgagccggcagcgagcctcgtgccgcacctggccctcaacgcgagcacg
 T  C  G  D  E  P  A  A  S  L  V  P  H  L  A  L  N  A  S  T ccggccgtcgtgcgcacctacgacctgtccaaagtcacactcgagctgccaaagggcttc
 P  A  V  V  R  T  Y  D  L  S  K  V  T  L  E  L  P  K  G  F ctctggacactgaacgacacctacctctggatcaactggtcgtcgccaacgaacttgagg
 L  W  T  L  N  D  T  Y  L  W  I  N  W  S  S  P  T  N  L  R ctggccgagggcggcgccgccgctgcggcgagcctgcccgccgaatatctcgccgtcgac
 L  A  E  G  G  A  A  A  A  A  S  L  P  A  E  Y  L  A  V  D agccgggccggcaacgagggacgctgggcgtatctcgtgttcaacgacgtctccgcccgc
 S  R  A  G  N  E  G  R  W  A  Y  L  V  F  N  D  V  S  A  R aatcgctcgcacccgatgcacctgcacggccacgacttcttcctgctcggcaccggccct
 N  R  S  H  P  M  H  L  H  G  H  D  F  F  L  L  G  T  G  P ggctattttgagtacggcagcaacagcagcagcctggcgatgctcaacctgcacaacccg
 G  Y  F  E  Y  G  S  N  S  S  S  L  A  M  L  N  L  H  N  P cctcgtcgcgacacggcgacctggcccgagtctggctggatggtcgtcgcgttcctcatg
 P  R  R  D  T  A  T  W  P  E  S  G  W  M  V  V  A  F  L  M gacaacccggggagctggctgatccactgccacatcgcctggcactcgagcgagtcgctc
 D  N  P  G  S  W  L  I  H  C  H  I  A  W  H  S  S  E  S  L ggcctgcagttcctggagagccctgagacgtatgtccctcgattggaaggccagagattg
 G  L  Q  F  L  E  S  P  E  T  Y  V  P  R  L  E  G  Q  R  L cgggagacgtgcgaggcgtgggatgcattctggaatcgccacgactcatacgagcaagag
 R  E  T  C  E  A  W  D  A  F  W  N  R  H  D  S  Y  E  Q  E gatgcggggatataa
 D  A  G  I  -

SEQ ID NO: 105
LENGTH: 604
TYPE: PRT
ORGANISM: M. phaseolina
MIGHSLVAVALGSAAMALALPQSHVPAACMNGPHSRKCWGNYSIDTDWYTETPYTGVVREYWFLVEN

TTVAPDVHAPLGCAIGNAWQADLGWQGYETWALTVNRSIPGPTIEANWGDEVIVHVTNGMERNGTAI

HFHGLRQLGAHEMDGVPGVTQCPIAPGHSYTYKWRATQYGTSWYHSHFSMQYSVGLQGPIVIHGPAT

ADYDEDLGTVVLQDWSHTSPFAMWWYARVPSGPPSLSNSLINGKNVFYCDSTTDSRCYGNGTRSEWR

FEQGKKYRMRLINTGLYSNFRFAIDNHNLTVIATDFVPIKPYTTDNVAISMGQRYDIVVEANQPEGD

YWLRAIWQTSCCPNDYSNNTLGIIRYTANSTAEPNTTSPALSYPDTCGDEPAASLVPHLALNASTPA

VVRTYDLSKVTLELPKGFLWTLNDTYLWINWSSPTNLRLAEGGAAAAASLPAEYLAVDSRAGNEGRW

AYLVFNDVSARNRSHPMHLHGHDFFLLGTGPGYFEYGSNSSSLAMLNLHNPPRRDTATWPESGWMVV

AFLMDNPGSWLIHCHIAWHSSESLGLQFLESPETYVPRLEGQRLRETCEAWDAFWNRHDSYEQEDAG

I*

SEQ ID NO: 106
LENGTH: 2275 (including 150 bp 5' UTR and 150 bp 3' UTR)
TYPE: DNA
ORGANISM: M. phaseolina
TCGATGCATCCCTCTCTGACGCAGATCTCTTTTATAAAACCGACTGTCATCCTCGATTGAGTCAGTC

TTTGCTCAAACGGACTTATTCAAAGGTCAGTTGGGTGAGTTGGGAGGCTGATGGATTCAGGATACTC

TCCGGGCACGTTCGCCATGATTCGCCTTTTTCTCGTGCTCGGCTTTGTGGCCACGACATTGGCCAAG

ACTGTTACTTTTAACTGGAACATCGGCTGGGTTTCTGCGGCTCCAGATGGATTTACACGGCCCGTCA

TCGGCATCAACGGGCTGTGGCCGCCTCCCGTCTTAGAAGCCGACGTTAACGACACCATTATCGTAAC
```

-continued

```
CGCGCATAACTCGCTAGGCAATGAGACGACGAGCTTGCACTGGCATGGCATGTGGCAGAACAACTCG

ACTCATATAGACGGCGGAAGTAGAGTCTCGCAGTGCGAAATCCCTCTAGGGGGCACCTTTACGTACA

GGTTTAAGGCATACCCGGCAGGCACTTTTTGGTACCATTCTCACGCTATGGGCCAATATCCCGACGG

CCTACGGGCCCCGATGATTATTCACGACCCTGATTCTGCTGCGGAGCAGGACGCCGATGAGCAGCAT

ATACTTACGGTCTCGGACTGGTACCGTAACCAGATGCCGCCGCTTATCCACCGCTATCTAACTACTC

CTAACTATAACGGCGCCATGCCGAAACCCAACTCGAGCTTAGTTAACGACCAGCAGTCCAAGAGGCT

AAACATCCGCCCGGGGCAGAAGAGCTATATCCGCATTATTAATATATCAGCGCTAGCAACGTTCTAT

CTACAGTTCGGTAGGTACATCCCCCTTGTTGTACAGACAAAGCTAACGATTTAGATCAACACAACAT

GACTGTCGTTTCTATCGACGATGTTAACGGTTGGTAATCCTGTTACTTATGCTACGCTAAGATGCAT

GTCGGCATATAAGCCGTAGTCGTATGCAAACACGTAAGATTAAAGTGCTAACGACAGGTAGTCGAGC

CCCAGAGTTGGGAGGCCCTAGAGATTACCCCCGGACAACGGTACGACGTTATCATCACCGGTCTAGA

GAACCCCCAAAGAAACTATGCATTTATCAATAAGATGGCCGTTCTCGGCTTGCAGAACAACAACATC

CTCAGTTATAATTCGTCCTGGCCTGACCCAGAGCCATTGGCCGTGAGTAGGTTCAACCTCGGAAGCG

ATATCAATCTAACTCCGCTTGACCACGAGCCACTGCTGGAGCCCGTGGACAAAACCTTCACCATGGA

GGTCAACAACCTCAACATCGACGGCGTAGGCTACCGGTGAGATTGCCCCGCGGCCCTTAATCCGCAT

GCCGCTTGCTAACTTCGATACACAGCATCACGCAAGGCCCGTACCCCTACATTACCCCGCGCACACC

CACTCTGTACACTGCCCTAACCACCGGCTTTAATGCTACCAACCCCGCCATCTACGGCCAGACCAAC

TCTTACATCGTAGAAGCCGGCGATATCGTCCAGCTCGTTGTCAACAGCAACGACCTTGTCACAACTA

ACACCTCCGGCCGCGGGCACCCCATGCACTTGCACGGCCACACCTTCCAAGTCGTGGGCCAATACGG

CACCCACTGGGACGGCGACACCGCAAAATTCCCTACCGTTCCAATGAAGCGGGACACGACCGTTCTC

TTCGCCGGCGGGAGCTTGGTCATTCGGTTCCAGGCGAACAATCCTGGTGTCTGGATGTGTACGGCTC

TCCTCCACTTTGCACGAAAACCCCAGTCCCCGGCTGCTTGAAAAGCTTTTTGAACTGACCTTGTGA

GTCGCGCAGTCCACTGCCATATCGAATGGCATCTCGACGCCGGCATGGCCGCCACAATCATCGAAGC

GCCGCTCGAGTTCCAGCGAAGCGGTCTGCGGATCCCGCCACAGCACCTCGCGGCGTGCCGGGCATTA

AACTTAACGACCCGGGGCAATTGTGCCGGCAACACCGTTAACCTGGAGGATACGGCTGCGTGCAGAA

TCTACGACACTGATCCTTGGGGGTGAGTTGCTCTGATTTCGCGTTAACGCAGCCTTTGCTGACGACT

ACCGCTTTCTGCAGTGCGCTTATCGGGGAACGTGAGACAGCACGTTGAATAACACGCTGGCGTAGCA

CCGTATTTTGTATAGACTACTTTTCCATGTTAAATTTTTCTGTATACAGTTCGAAATAGATTCATTT

AGGGACAAATACCAGAAACAGGCTCATCCGCAACTCATGTGCACCCTGCGTAGATCGTTATGCT

SEQ ID NO: 107
LENGTH: 1632
TYPE: DNA
ORGANISM: M. phaseolina
FEATURE NAME/KEY: CDS
LOCATION: (1) . . . (1632)
atgattcgcctttttctcgtgctcggctttgtggccacgacattggccaagactgttact
 M   I   R   L   F   L   V   L   G   F   V   A   T   T   L   A   K   T   V   T tttaactggaacatcggctgggtttctgcggctccagatggatttacacggcccgtcatc
 F   N   W   N   I   G   W   V   S   A   A   P   D   G   F   T   R   P   V   I ggcatcaacgggctgtggccgcctccgtcttagaagccgacgttaacgacaccattatc
 G   I   N   G   L   W   P   P   P   V   L   E   A   D   V   N   D   T   I   I gtaaccgcgcataactcgctaggcaatgagacgacgagcttgcactggcatggcatgtgg
 V   T   A   H   N   S   L   G   N   E   T   T   S   L   H   W   H   G   M   W cagaacaactcgactcatatagacggcggaagtagagtctcgcagtgcgaaatccctcta
 Q   N   N   S   T   H   I   D   G   G   S   R   V   S   Q   C   E   I   P   L gggggcacctttacgtacaggtttaaggcatacccggcaggcacttttggtaccattct
 G   G   T   F   T   Y   R   F   K   A   Y   P   A   G   T   F   W   Y   H   S
```

```
cacgctatgggccaatatcccgacggcctacgggccccgatgattattcacgaccctgat
 H   A   M   G   Q   Y   P   D   G   L   R   A   P   M   I   I   H   D   P   D tctgctgcggagcaggacgccgatgagcagcatatacttacggtctcggactggtaccgt
 S   A   A   E   Q   D   A   D   E   Q   H   I   L   T   V   S   D   W   Y   R aaccagatgccgccgcttatccaccgctatctaactactcctaactataacggcgccatg
 N   Q   M   P   P   L   I   H   R   Y   L   T   T   P   N   Y   N   G   A   M ccgaaacccaactcgagcttagttaacgaccagcagtccaagaggctaaacatccgcccg
 P   K   P   N   S   S   L   V   N   D   Q   Q   S   K   R   L   N   I   R   P gggcagaagagctatatccgcattattaatatatcagcgctagcaacgttctatctacag
 G   Q   K   S   Y   I   R   I   I   N   I   S   A   L   A   T   F   Y   L   Q ttcgatcaacacaacatgactgtcgtttctatcgacgatgttaacgtcgagccccagagt
 F   D   Q   H   N   M   T   V   V   S   I   D   D   V   N   V   E   P   Q   S tgggaggccctagagattaccccggacaacggtacgacgttatcatcaccggtctagag
 W   E   A   L   E   I   T   P   G   Q   R   Y   D   V   I   I   T   G   L   E aaccccaaagaaactatgcatttatcaataagatggccgttctcggcttgcagaacaac
 N   P   Q   R   N   Y   A   F   I   N   K   M   A   V   L   G   L   Q   N   N aacatcctcagttataattcgtcctggcctgacccagagccattggccgtgagtaggttc
 N   I   L   S   Y   N   S   S   W   P   D   P   E   P   L   A   V   S   R   F aacctcggaagcgatatcaatctaactccgcttgaccacgagccactgctggagcccgtg
 N   L   G   S   D   I   N   L   T   P   L   D   H   E   P   L   L   E   P   V gacaaaaccttcaccatggaggtcaacaacctcaacatcgacggcgtaggctaccgcatc
 D   K   T   F   T   M   E   V   N   N   L   N   I   D   G   V   G   Y   R   I acgcaaggcccgtacccctacattaccccgcgcacacccactctgtacactgccctaacc
 T   Q   G   P   Y   P   Y   I   T   P   R   T   P   T   L   Y   T   A   L   T accggctttaatgctaccaaccccgccatctacggccagaccaactcttacatcgtagaa
 T   G   F   N   A   T   N   P   A   I   Y   G   Q   T   N   S   Y   I   V   E gccggcgatatcgtccagctcgttgtcaacagcaacgaccttgtcacaactaacacctcc
 A   G   D   I   V   Q   L   V   V   N   S   N   D   L   V   T   T   N   T   S ggccgcgggcacccccatgcacttgcacggccacaccttccaagtcgtgggccaatacggc
 G   R   G   H   P   M   H   L   H   G   H   T   F   Q   V   V   G   Q   Y   G acccactgggacgcgacaccgcaaaattccctaccgttccaatgaagcgggacacgacc
 T   H   W   D   G   D   T   A   K   F   P   T   V   P   M   K   R   D   T   T gttctcttcgccggcgggagcttggtcattcggttccaggcgaacaatcctggtgtctgg
 V   L   F   A   G   G   S   L   V   I   R   F   Q   A   N   N   P   G   V   W atgttccactgccatatcgaatggcatctcgacgccggcatggccgccacaatcatcgaa
 M   F   H   C   H   I   E   W   H   L   D   A   G   M   A   A   T   I   I   E gcgccgctcgagttccagcgaagcggtctgcggatcccgccacagcacctcgcggcgtgc
 A   P   L   E   F   Q   R   S   G   L   R   I   P   P   Q   H   L   A   A   C cgggcattaaacttaacgacccggggcaattgtgccggcaacaccgttaacctggaggat
 R   A   L   N   L   T   T   R   G   N   C   A   G   N   T   V   N   L   E   D acggctgcgtgcagaatctacgacactgatccttggggtgcgcttatcggggaacgtgag
 T   A   A   C   R   I   Y   D   T   D   P   W   G   A   L   I   G   E   R   E acagcacgttga
 T   A   R   -

SEQ ID NO: 108
LENGTH: 543
TYPE: PRT
ORGANISM: M. phaseolina
MIRLFLVLGFVATTLAKTVTFNWNIGWVSAAPDGFTRPV -continued

VGYRITQGPYPYITPRTPTLYTALTTGFNATNPAIYGQTNSYIVEAGDIVQLVVNSNDLVTTNTSGR

GHPMHLHGHTFQVVGQYGTHWDGDTAKFPTVPMKRDTTVLFAGGSLVIRFQANNPGVWMFHCHIEWH

LDAGMAATIIEAPLEFQRSGLRIPPQHLAACRALNLTTRGNCAGNTVNLEDTAACRIYDTDPWGALI

GERETAR*

SEQ ID NO: 109
LENGTH: 2052 (including 150 bp 5' UTR and 150 bp 3' UTR)
TYPE: DNA
ORGANISM: M. phaseolina

GCAGCAACTACATCCGGGTAGGCATCAAACGCAAAGATGGTACGGAGGGAGCACTGATGCGCTTTTA

TAGCTCATATCAGCACAGCTGCGTGTAGTTGAATGGGACCGACCGAGTTTTTTTGTAGCCTCAATCT

TTCCACGCTCCGAACCATGTCCTCAGATTCTCAGAAGCATGGCGCTGTGCTCCGTAGGCGCAGCATA

CCACAGCAACCAGAAGAAGAAACCCCGCCTTCAACAACCCGGAAGTCATCGGAAAATCGACATAGCG

TTCTATCATGGTTTCTCTTTGTCCTTTCATGCGCCATCTTCGCGACGTTTATTTCCTATCTCAATAG

CGCAACGGCATACCAAACTGCGGGGTCTTATTACACAATAACTGGCCTCAAGGCTTTTCTGTCCCAT

GGGAACTCTGACAACAATTTCGACAGTCATCCTGGCAAGGGCCCATACGGCGGATCTCTGGGCCAGA

ACTTGCATCCTCGAGAGCACGTGGTCCGTGCTCCTAGTGTCAGGCACTACAGTTGGAAGGTTACCAA

GGCTTTTCGATACCCAGATGGGGTGAAAAAGGCTGTTTATCTGATTAACGACGGCTTTCTGGGACCC

ACAGTCGAAGCTCGTTCTGGCGATAGACTGGTGATTGAGGTCCAAAATGCGTTGGAAGACGAAGGTC

TCTCCTTCCACTGGCACGGTCTTTTAATGAGAGGTGCCAACTACATGGACGGTGCCGTCGGATTTAC

GCAAGACGCCATTCACCCGGGCGCCAACTTCACGTATGAGTTCGATATCGCGGATGACCAAGCCGGC

ACATTTTGGTATCACGCTCATGACCAAGTGCAGCGGGCGGATGGCCTGTTCGGAGGACTGATCATCC

ATCGCCCGGAAACCGCAACTGGAGTCGCCGATTTGGATAGATATGGGTACGATGAAGAGAGATTGCT

GCTTATCGGACACTGGTACCATCGTTCCGCACAAGATGTCCTAGCGTGGTACATCAGTGCTGGGTCC

TTTGGAAATGAGCCTGTGCCGGATTCACTCCTCATCAATGGAATGGGAGCATTCAATTGCTCAAAAG

CTATTCCTGCGAGACCTGTGGAATGCATTAACTTTGAAGGAACTGCCACACCTAATCTACAGTTCAA

CTTCACCAGACGTCACCGGCTGAGACTCGTCAACACTGGTACATTGGCTGGATTCACCTTGAGCATT

CCGGGTGCGGCCATGCAGGTCATCGAAGTTGACGGCGGCAATGCCGTTACCAGCGACTCTGAGAACG

ACACTTCAGTAGGGAGCTTATATCCAGGCCAACGTGCCGACCTAATCCTCTCTTGGCCAGAGGATAC

TCTAGAAGCCTCAAAAATTTCAATCACCCTTGACGGGGAGGACTTCAAGTACCCCAATCCAGCCCTG

ACTCGCACTCAGCACTTCTCCATATTTCGCTCTGCCCCTGTCCCGAAGGAAAAGAGCGAAGCCTCTG

CCTCTTCGGAACAAGGCAGGCCAGAAAGCCACGCACCACAAACCCTCATCGACCTCAATGCCCTTGT

CAGCGCAGATATCATCACCCCATCACTGCCCCCTGCCACTGAACACACTCTCGTTCTATACGCCAAC

ACCCTCAAACTCTCCCACCGCGGCAACAAACCCCACGGCTACATGAACCAAACCAGCTGGTCGCCGC

AATCCTCTCCGCCCCGTCCGCTCATCGCGCTGCCGCGCTCCTCTTGGGACGCCAACCAGTTCGTCCC

GCGCATCCCTCTTCCCAACGGCACCTCAGACGCGCCCTGGGTCACCATCGTCCTCAACAACCTGGAC

GACGGCTCGCACCCCTTCCACCTACATGGCCACGCGTTCTGGGTGCTCCAAACCCACGCCGCAGGGT

GGGGCTGGGGGTCGTGGAATCCATGAGCGGAGGAGCAGCCGCCGGGCGGCCCACTGGAGCTGCAGCG

CGCGGTGACGAGGGATACGGTCATGGTGCCGCGGAGGGGGTATGCGGTGCTGCGATTTAGAGCGGAC

AATGAGGGGCTCTGGATGCTGCACTGCCACAATTTGTGGCAT

SEQ ID NO: 110
LENGTH: 1752
TYPE: DNA
ORGANISM: M. phaseolina
FEATURE NAME/KEY: CDS
LOCATION: (1)...(1752)

```
atgtcctcagattctcagaagcatggcgctgtgctccgtaggcgcagcataccacagcaa
 M   S   S   D   S   Q   K   H   G   A   V   L   R   R   R   S   I   P   Q   Q ccagaagaagaaacccgccttcaacaacccggaagtcatcggaaaatcgacatagcgtt
 P   E   E   E   T   P   P   S   T   T   R   K   S   S   E   N   R   H   S   V ctatcatggtttctctttgtcctttcatgcgccatcttcgcgacgtttatttcctatctc
 L   S   W   F   L   F   V   L   S   C   A   I   F   A   T   F   I   S   Y   L aatagcgcaacggcataccaaactgcggggtcttattacacaataactggcctcaaggct
 N   S   A   T   A   Y   Q   T   A   G   S   Y   Y   T   I   T   G   L   K   A tttctgtcccatgggaactctgacaacaatttcgacagtcatcctggcaagggcccatac
 F   L   S   H   G   N   S   D   N   N   F   D   S   H   P   G   K   G   P   Y ggcggatctctgggccagaacttgcatcctcgagagcacgtggtccgtgctcctagtgtc
 G   G   S   L   G   Q   N   L   H   P   R   E   H   V   V   R   A   P   S   V aggcactacagttggaaggttaccaaggcttttcgatacccagatggggtgaaaaaggct
 R   H   Y   S   W   K   V   T   K   A   F   R   Y   P   D   G   V   K   K   A gtttatctgattaacgacggctttctgggacccacagtcgaagctcgttctggcgataga
 V   Y   L   I   N   D   G   F   L   G   P   T   V   E   A   R   S   G   D   R ctggtgattgaggtccaaaatgcgttggaagacgaaggtctctccttccactggcacggt
 L   V   I   E   V   Q   N   A   L   E   D   E   G   L   S   F   H   W   H   G cttttaatgagaggtgccaactacatggacggtgccgtcggatttacgcaagacgccatt
 L   L   M   R   G   A   N   Y   M   D   G   A   V   G   F   T   Q   D   A   I cacccgggcgccaacttcacgtatgagttcgatatcgcggatgaccaagccggcacattt
 H   P   G   A   N   F   T   Y   E   F   D   I   A   D   D   Q   A   G   T   F tggtatcacgctcatgaccaagtgcagcgggcggatggcctgttcggaggactgatcatc
 W   Y   H   A   H   D   Q   V   Q   R   A   D   G   L   F   G   G   L   I   I catcgcccggaaaccgcaactggagtcgccgatttggatagatatgggtacgatgaagag
 H   R   P   E   T   A   T   G   V   A   D   L   D   R   Y   G   Y   D   E   E agattgctgcttatcggacactggtaccatcgttccgcacaagatgtcctagcgtggtac
 R   L   L   L   I   G   H   W   Y   H   R   S   A   Q   D   V   L   A   W   Y atcagtgctgggtcctttggaaatgagcctgtgccggattcactcctcatcaatggaatg
 I   S   A   G   S   F   G   N   E   P   V   P   D   S   L   L   I   N   G   M ggagcattcaattgctcaaaagctattcctgcgagacctgtggaatgcattaactttgaa
 G   A   F   N   C   S   K   A   I   P   A   R   P   V   E   C   I   N   F   E ggaactgccacacctaatctacagttcaacttcaccagacgtcaccggctgagactcgtc
 G   T   A   T   P   N   L   Q   F   N   F   T   R   R   H   R   L   R   L   V aacactggtacattggctggattcaccttgagcattccgggtgcggccatgcaggtcatc
 N   T   G   T   L   A   G   F   T   L   S   I   P   G   A   A   M   Q   V   I gaagttgacggcggcaatgccgttaccagcgactctgagaacgacacttcagtagggagc
 E   V   D   G   G   N   A   V   T   S   D   S   E   N   D   T   S   V   G   S ttatatccaggccaacgtgccgacctaatcctctcttggccagaggatactctagaagcc
 L   Y   P   G   Q   R   A   D   L   I   L   S   W   P   E   D   T   L   E   A tcaaaaatttcaatcacccttgacggggaggacttcaagtaccccaatccagccctgact
 S   K   I   S   I   T   L   D   G   E   D   F   K   Y   P   N   P   A   L   T cgcactcagcacttctccatatttcgctctgcccctgtcccgaaggaaaagagcgaagcc
 R   T   Q   H   F   S   I   F   R   S   A   P   V   P   K   E   K   S   E   A tctgcctcttcggaacaaggcaggccagaaagccacgcaccacaaacccctcatcgacctc
 S   A   S   S   E   Q   G   R   P   E   S   H   A   P   Q   T   L   I   D   L aatgcccttgtcagcgcagatatcatcacccccatcactgcccctgccactgaacacact
 N   A   L   V   S   A   D   I   I   T   P   S   L   P   P   A   T   E   H   T ctcgttctatacgccaacaccctcaaactctcccaccgcggcaacaaacccacggctac
 L   V   L   Y   A   N   T   L   K   L   S   H   R   G   N   K   P   H   G   Y
```

```
atgaaccaaaccagctggtcgccgcaatcctctccgccccgtccgctcatcgcgctgccg
 M  N  Q  T  S  W  S  P  Q  S  S  P  P  R  P  L  I  A  L  P cgctcctcttgggacgccaaccagttcgtcccgcgcatccctcttcccaacggcacctca
 R  S  S  W  D  A  N  Q  F  V  P  R  I  P  L  P  N  G  T  S gacgcgccctgggtcaccatcgtcctcaacaacctggacgacggctcgcaccccttccac
 D  A  P  W  V  T  I  V  L  N  N  L  D  D  G  S  H  P  F  H ctacatggccacgcgttctgggtgctccaaacccacgccgcagggtggggctggggtcg
 L  H  G  H  A  F  W  V  L  Q  T  H  A  A  G  W  G  W  G  S tggaatccatga
 W  N  P  -

SEQ ID NO: 111
LENGTH: 583
TYPE: PRT
ORGANISM: M. phaseolina
MSSDSQKHGAVLRRRSIPQQPEEETPPSTTRKSSENRHSVLSWFLFVLSCAIFATFISYLNSATAYQTAGSYYTITGL

KAFLSHGNSDNNFDSHPGKGPYGGSLGQNLHPREHVVRAPSVRHYSWKVTKAFRYPDGVKKAVYLINDGFLGP

TVEARSGDRLVIEVQNALEDEGLSFHWHGLLMRGANYMDGAVGFTQDAIHPGANFTYEFDIADDQAGTFWY

HAHDQVQRADGLFGGLIIHRPETATGVADLDRYGYDEERLLLIGHWYHRSAQDVLAWYISAGSFGNEPVPDSLLI

NGMGAFNCSKAIPARPVECINFEGTATPNLQFNFTRRHRLRLVNTGTLAGFTLSIPGAAMQVIEVDGGNAVTSD

SENDTSVGSLYPGQRADLILSWPEDTLEASKISITLDGEDFKYPNPALTRTQHFSIFRSAPVPKEKSEASASSEQGRP

ESHAPQTLIDLNALVSADIITPSLPPATEHTLVLYANTLKLSHRGNKPHGYMNQTSWSPQSSPPRPLIALPRSSWD

ANQFVPRIPLPNGTSDAPWVTIVLNNLDDGSHPFHLHGHAFWVLQTHAAGWGWGSWNP*
```

INCORPORATION BY REFERENCE

All of the U.S. patents, U.S. published patent applications, and published PCT applications that cited herein are hereby incorporated by reference.

EQUIVALENTS

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practiced otherwise than as specifically described and claimed.

What is claimed is:

1. A polynucleotide comprising a coding nucleotide sequence (cDNA) which is at least 80% identical to the nucleotide sequence set forth in SEQ ID No. 2, 5, or 8, or any combination thereof, wherein said cDNA encodes a lignin peroxidase.

2. An expression construct comprising a polynucleotide which is at least 80% identical to the nucleotide sequence set forth in SEQ ID NO. 1, 2, 4, 5, 7, or 8, or any combinations thereof, wherein said polynucleotide is operably linked to at least one translational regulatory sequence, said translational regulatory sequence comprises a ribosomal binding site, translational start sequence, or translation stop sequence, or combination thereof, and said polynucleotide encodes a lignin peroxidase.

3. A recombinant gene construct comprising the polynucleotide of claim 1, wherein the polynucleotide is expressible in a host cell to produce an enzyme which degrades lignin.

4. A recombinant gene construct according to claim 3, further comprising a promoter region operably-linked to enhance expression of the polynucleotide template.

5. An isolated transformed host cell comprising the recombinant gene construct of claim 3, wherein said transformant produces an enzyme which accelerates lignin degradation.

6. A transgenic fungi of *M. phaseolina* with enhanced lignin degradation, comprising the recombinant gene construct of claim 3.

7. An isolated transformed host cell comprising the expression construct of claim 2, wherein said transformant produces an enzyme which accelerates lignin degradation.

8. A transgenic fungi of *M. phaseolina* with enhanced lignin degradation, comprising the expression construct of claim 2.

9. The polynucleotide of claim 1, wherein said cDNA has at least 85% sequence identity to said nucleotide sequence.

10. The polynucleotide of claim 1, wherein said cDNA has at least 90% sequence identity to said nucleotide sequence.

11. The polynucleotide of claim 1, wherein said cDNA has at least 95% sequence identity to said nucleotide sequence.

12. The polynucleotide of claim 1, wherein said cDNA has at least 98% sequence identity to said nucleotide sequence.

13. The polynucleotide of claim 1, wherein said cDNA has at least 99% sequence identity to said nucleotide sequence.

14. The polynucleotide of claim 1, wherein said cDNA has 100% sequence identity to said nucleotide sequence.

15. The expression construct of claim 2, wherein said polynucleotide has at least 85% sequence identity to said nucleotide sequence.

16. The expression construct of claim 2, wherein said polynucleotide has at least 90% sequence identity to said nucleotide sequence.

17. The expression construct of claim 2, wherein said polynucleotide has at least 95% sequence identity to said nucleotide sequence.

18. The expression construct of claim 2, wherein said polynucleotide has at least 98% sequence identity to said nucleotide sequence.

19. The expression construct of claim 2, wherein said polynucleotide has at least 99% sequence identity to said nucleotide sequence.

20. The expression construct of claim 2, wherein said polynucleotide has 100% sequence identity to said nucleotide sequence.

* * * * *